United States Patent
Blackwell, III et al.

(10) Patent No.: US 12,427,212 B2
(45) Date of Patent: Sep. 30, 2025

(54) NECTIN-4 BINDING MINIPROTEINS, CONJUGATES AND USES THEREOF

(71) Applicant: Aktis Oncology, Inc., Boston, MA (US)

(72) Inventors: William C. Blackwell, III, Raleigh, NC (US); Michael Lawrence Doligalski, Chapel Hill, NC (US); Paul L. Feldman, Durham, NC (US); Isaiah Nathaniel Gober, Durham, NC (US); Brian Scott Goodman, Boston, MA (US); Hyun Joo Kil, Cary, NC (US); Jeff Kovacs, Raleigh, NC (US); Dasa Lipovsek, Pepperell, MA (US); Trevor Price, Durham, NC (US); Matthew Roden, Princeton, NJ (US); James M. Way, Raleigh, NC (US); Ved Srivastava, Cary, NC (US)

(73) Assignee: Aktis Oncology, Inc., Boston, MA (US)

( * ) Notice: Subject to any disclaimer, the term of this patent is extended or adjusted under 35 U.S.C. 154(b) by 0 days.

(21) Appl. No.: 19/067,809

(22) Filed: Feb. 28, 2025

(65) Prior Publication Data
US 2025/0242065 A1 Jul. 31, 2025

Related U.S. Application Data

(63) Continuation of application No. PCT/US2024/049013, filed on Sep. 27, 2024.

(60) Provisional application No. 63/636,078, filed on Apr. 18, 2024, provisional application No. 63/618,228, filed on Jan. 5, 2024, provisional application No. 63/598,874, filed on Nov. 14, 2023, provisional application No. 63/587,042, filed on Sep. 29, 2023.

(51) Int. Cl.
*A61K 51/08* (2006.01)
*A61K 38/00* (2006.01)
*A61P 35/00* (2006.01)
*C07K 14/00* (2006.01)

(52) U.S. Cl.
CPC ............ *A61K 51/088* (2013.01); *A61P 35/00* (2018.01); *C07K 14/001* (2013.01); *A61K 38/00* (2013.01); *A61K 2121/00* (2013.01)

(58) Field of Classification Search
CPC ....... A61K 51/088; A61K 38/00; A61P 35/00; C07K 14/001
See application file for complete search history.

(56) References Cited

U.S. PATENT DOCUMENTS

| | | | |
|---|---|---|---|
| 7,521,541 B2 * | 4/2009 | Eigenbrot | A61K 47/6817 424/133.1 |
| 2020/0046843 A1 | 2/2020 | Tsien et al. | |
| 2020/0197545 A1 | 6/2020 | Wurzer et al. | |
| 2020/0353105 A1 | 11/2020 | Salter et al. | |
| 2021/0017099 A1 | 1/2021 | Dudkin et al. | |

FOREIGN PATENT DOCUMENTS

| | | | | |
|---|---|---|---|---|
| WO | WO-2021151984 A1 | | 8/2021 | |
| WO | WO2021257525 | * | 12/2021 | ............. C07K 16/28 |
| WO | 2022098745 A1 | | 5/2022 | |
| WO | WO-2023169584 A1 | | 9/2023 | |
| WO | 2024010957 A2 | | 1/2024 | |
| WO | 2024107762 A2 | | 5/2024 | |

OTHER PUBLICATIONS

Khosravanian et al. Nectin-4-directed antibody-drug conjugates (ADCs): Spotlight on preclinical and clinical evidence, Life Sciences, 352, 122610, 2024. https://doi.org/10.1016/j.lfs.2024.122910. (Year: 2024).*
Anonymous https://en.wikipedia.org/wiki/List_of_cancer_types—accessed May 22, 2020. (Year: 2020).*
Anonymous. https://www.cancer.gov/about-cancer/understanding/what-is-cancer accessed May 22, 2020. (Year: 2020).*
Bellmunt, et al., "Pembrolizumab as Second-Line Therapy for Advanced Urothelial Carcinoma", N Engl J Med., Mar. 2017, vol. 376, No. 11: pp. 1015-1026.
Berger, et al., "Computationally designed high specificity inhibitors delineate the roles of BCL2 family proteins in cancer", Elife, Nov. 2016, vol. 5, Article e20352: pp. 1-31.
Challita-Eid, et al., "Enfortumab Vedotin Antibody-Drug Conjugate Targeting Nectin-4 Is a Highly Potent Therapeutic Agent in Multiple Preclinical Cancer Models", Cancer Res., May 2016, vol. 76, No. 10: pp. 3003-3013. doi: 10.1158/0008-5472.CAN-15-1313. Epub Mar. 24, 2016.
Fabre, et al., "Prominent role of the Ig-like V domain in trans-interactions of nectins. NECTIN3 and NECTIN4 bind to the predicted C—C'—C"—D beta-strands of the NECTIN1 V domain", J Biol Chem, Jul. 2002, vol. 277, No. 30: pp. 27006-27013. doi: 10.1074/jbc.M203228200. Epub May 14, 2002.
Fabre-Lafay, et al., "Nectin-4 is a new histological and serological tumor associated marker for breast cancer", BMC Cancer, May 2007, vol. 7: Article 73: pp. 1-16. doi: 10.1186/1471-2407-7-73.
Fujiyuki, et al., "Recombinant SLAMblind Measles Virus Is a Promising Candidate for Nectin-4-Positive Triple Negative Breast Cancer Therapy", Mol Ther Oncolytics, Sep. 2020, vol. 19: pp. 127-135. doi: 10.1016/j.omto.2020.09.007.
Geenen, et al., "Overcoming nephrotoxicity in peptide receptor radionuclide therapy using [177Lu]Lu-DOTA-TATE for the treatment of neuroendocrine tumours", Nucl Med Biol, Nov.-Dec. 2021, vol. 102-103: pp. 1-11. doi: 10.1016/j.nucmedbio.2021.06.006. Epub Jul. 1, 2021.
Hoffman-Censits, et al., "New and topics: enfortumab vedotin mechanisms of response and resistance in urothelial cancer—What do we understand so far?", Urol Oncol, Oct. 2021, vol. 39, No. 10: pp. 619-622. doi: 10.1016/j.urolonc.2021.05.013. Epub Jun. 18, 2021.

(Continued)

Primary Examiner — Elly-Gerald Stoica
(74) Attorney, Agent, or Firm — Goodwin Procter LLP

(57) ABSTRACT

Provided herein are polypeptides and conjugates thereof, including radionuclide conjugates, useful in compositions and methods of treating, diagnosing, monitoring, and/or imaging a disease, disorder, or condition associated with expression of one or more targets, including Nectin-4.

30 Claims, 41 Drawing Sheets

Specification includes a Sequence Listing.

(56) References Cited

OTHER PUBLICATIONS

Ma, et al., "Expression and clinical significance of Nectin-4 in hepatocellular carcinoma", Onco Targets Ther, Jan. 2016, vol. 9: pp. 183-190. doi: 10.2147/OTT.S96999.
Nishiwada, et al., "Nectin-4 expression contributes to tumor proliferation, angiogenesis and patient prognosis in human pancreatic cancer", J Exp Clin Cancer Res, Mar. 2015, vol. 34, Issue 1, Article 30: pp. 1-9. doi: 10.1186/s13046-015-0144-7.
PCT/US2023/027173—International Preliminary Report on Patentability, Jan. 16, 2025, 9 pages.
PCT/US2023/027173—International Search Report and Written Opinion, Jan. 25, 2024, 14 pages.
PCT/US2023/079693—International Search Report and Written Opinion, Jun. 12, 2024, 19 pages.
Powles, et al., "Enfortumab Vedotin and Pembrolizumab in Untreated Advanced Urothelial Cancer", N Engl J Med, Mar. 2024, vol. 390, No. 10: pp. 875-888. doi: 10.1056/NEJMoa2312117. Includes Supplemental Information. 459 pages total.
Ramonaheng, K., et al., "Allometric scaling of preclinical dosimetry for the Nectin-4 miniprotein binders AKY-807 and AKY-1189 accurately predicts human absorbed dose to major organs", Poster session presented at the EORTC-NCI-AACR Symposium on Molecular Targets and Cancer Therapeutics, Barcelona, Spain. Abstract 308. The European Journal of Cancer, vol. 211S1, p. S116, Oct. 2024.
Rigby, et al., "BT8009; A Nectin-4 Targeting Bicycle Toxin Conjugate for Treatment of Solid Tumors", Mol Cancer Ther, Dec. 2022, vol. 21, No. 12: pp. 1747-1756. doi: 10.1158/1535-7163.MCT-21-0875.
Rosenberg, et al., "EV-101: A Phase I Study of Single-Agent Enfortumab Vedotin in Patients With Nectin-4-Positive Solid Tumors, Including Metastatic Urothelial Carcinoma", J Clin Oncol, Apr. 2020, vol. 38, No. 10: pp. 1041-1049. doi: 10.1200/JCO.19.02044. Epub Feb. 7, 2020. Erratum in: J Clin Oncol, May 2022, vol. 40, No. 15: p. 1711. doi: 10.1200/JCO.22.00785.
Sathekge, M., et al., "AKY-1189, a novel, first-in-class miniprotein radiopharmaceutical designed to deliver Actinium-225 (225Ac) to Nectin-4 expressing tumors with broad therapeutic applications in metastatic urothelial carcinoma (mUC) and other Nectin-4 expressing tumors", Poster session presented at the EORTC-NCI-AACR Symposium on Molecular Targets and Cancer Therapeutics, Barcelona, Spain. Abstract 10. The European Journal of Cancer, vol. 211, 81, p. 87, Oct. 2024.
Scheinberg, et al., "Actinium-225 in targeted alpha-particle therapeutic applications", Curr Radiopharm, Oct. 2011, vol. 4, No. 4: pp. 306-320. doi: 10.2174/1874471011104040306.
Tafreshi, et al., "Lipophilicity Determines Routes of Uptake and Clearance, and Toxicity of an Alpha-Particle-Emitting Peptide Receptor Radio", ACS Pharmacology & Translational Science, Mar. 2021, vol. 4, Issue 2: pp. 953-965.
Takano, et al., "Identification of nectin-4 oncoprotein as a diagnostic and therapeutic target for lung cancer", Cancer Res, Aug. 2009, vol. 69, No. 16: pp. 6694-6703. doi: 10.1158/0008-5472.CAN-09-0016. Includes Supplemental Material. 15 pages total.
UniProt Accession A0A5M9NQK0_QCLOT, *Clostridium* sp. HV4-5-AiG peptidylprolyl isomerase, Feb. 26, 2020 [online]. [Retrieved on Nov. 18, 2023]. Retrieved from the internet: <URL: <https://www.uniprot.org/uniprotkb/A0A5M9NQK0/entry>> Entire document.
Way, J., et al., "Discovery and pre-clinical development of AKY-1189, a potent and selective Nectin-4 miniprotein binder optimized for use as a targeted radiopharmaceutical", Poster session presented at the EORTC-NCI-AACR Symposium on Molecular Targets and Cancer Therapeutics, Barcelona, Spain. Abstract 117. The European Journal of Cancer, vol. 211, 81, p. 849, Oct. 2024.
Yu, et al., "Enfortumab vedotin after PD-1 or PD-L1 inhibitors in cisplatin-ineligible patients with advanced urothelial carcinoma (EV-201): a multicentre, single-arm, phase 2 trial", Lancet Oncol, Jun. 2021, vol. 22, No. 6: pp. 872-882. doi: 10.1016/81470-2045(21)00094-2. Epub May 12, 2021. Erratum in: Lancet Oncol, Jun. 2021, vol. 22, No. 6, Article 239. doi: 10.1016/81470-2045(21)00300-4.
Zhang, et al., "High expression of Nectin-4 is associated with unfavorable prognosis in gastric cancer", Oncol Lett, Jun. 2018, vol. 15, No. 6: pp. 8789-8795. doi: 10.3892/ol.2018.8365. Epub Mar. 28, 2018.
Zhang, et al., "Upregulation of nectin-4 is associated with ITGB1 and vasculogenic mimicry and may serve as a predictor of poor prognosis in colorectal cancer", Oncol Lett, Aug. 2019, vol. 18, No. 2: pp. 1163-1170. doi: 10.3892/ol.2019.10417. Epub May 30, 2019.
Reches Adi, et al., Nectin4 is a novel TIGIT ligand which combines checkpoint inhibition and tumor specificity, J. Immunother Cancer, 8(1):e000266 (2020).
PCT/US2024/049013 International Search Report and Written Opinion mailed Jun. 2, 2025.

\* cited by examiner

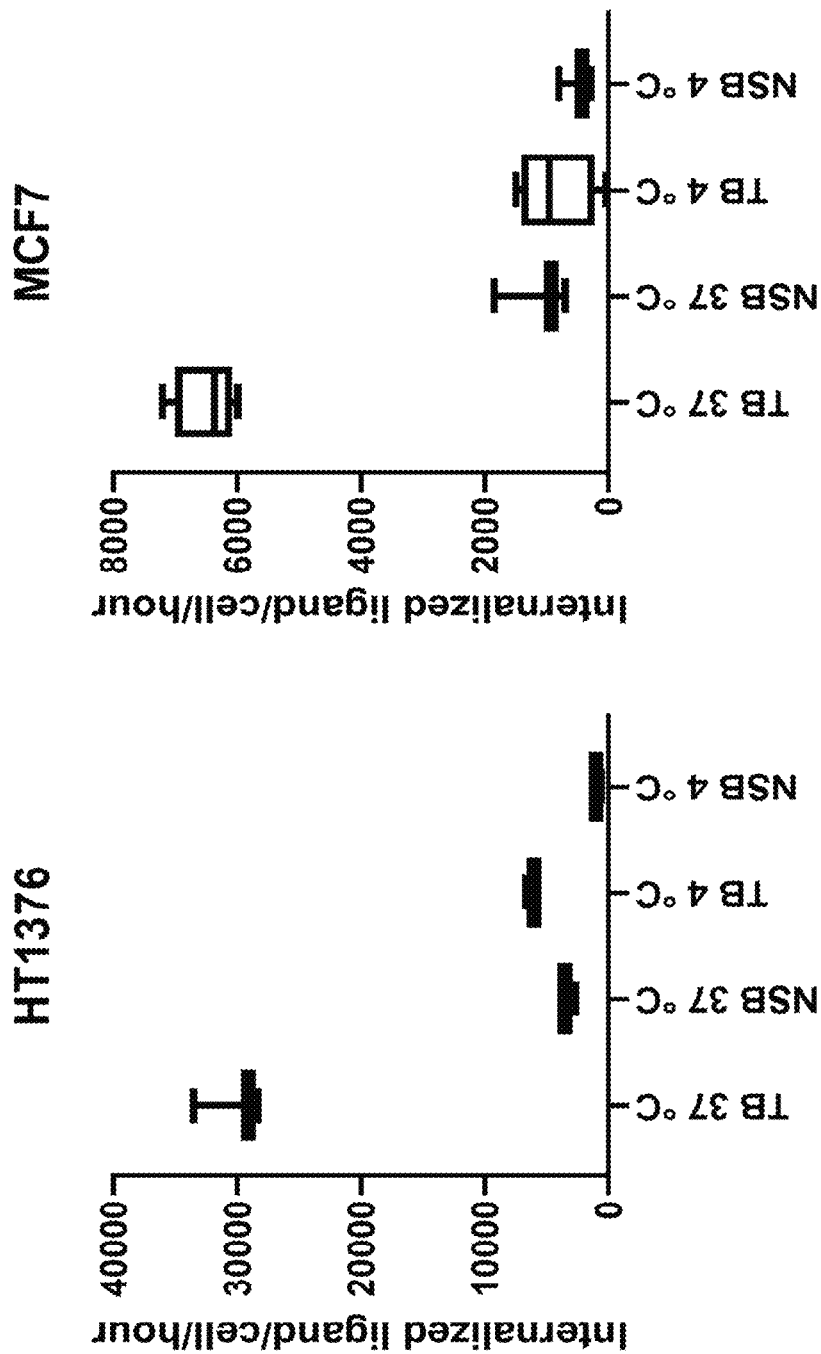

NECTIN-4 BINDING MINIPROTEINS, CONJUGATES AND USES THEREOF

CROSS-REFERENCE TO RELATED APPLICATIONS

This application is a continuation of International Application No. PCT/US2024/049013, filed on Sep. 27, 2024, which claims the benefit of and priority to U.S. Provisional Patent Application Nos. 63/587,042, filed on Sep. 29, 2023; 63/598,874, filed on Nov. 14, 2023; 63/618,228, filed on Jan. 5, 2024; and 63/636,078, filed on Apr. 18, 2024, the disclosures of each of which are incorporated by reference herein in their entireties for all purposes.

SEQUENCE LISTING

This application contains a Sequence Listing that has been submitted electronically in XML format and is hereby incorporated by reference in its entirety. The XML file, created on Sep. 17, 2024, is named AKT-031WO_SL.xml, and is 488.567 bytes in size.

BACKGROUND

Cancer is a leading cause of death worldwide. Classical cancer therapies such as radiotherapy, chemotherapy, and surgical procedures can be accompanied by severe side effects including those due to killing of healthy non-cancerous cells. Newer therapeutics enhance the targeting of cytotoxic drugs to tumor cells, relative to earlier therapies, including those that use biologics conjugates.

SUMMARY

The present disclosure provides technologies such as compositions and methods of use and manufacture thereof to address needs in the field of cancer. For example, in contrast to classical cancer diagnostics or therapies, targeted molecules can be designed to increase specificity and decrease toxicity of, e.g., imaging or therapeutic modalities. For instance, delivery of a therapeutic having a chelator and/or radionuclide (e.g., alpha emitter) using a polypeptide to specifically target the therapeutic to the tumor microenvironment provides focused treatment to tumor cells and avoids or reduces risk of toxicity to surrounding healthy tissues.

In contrast to classical cancer therapies, radionuclide therapies are more targeted and less toxic. For instance, delivery of a radionuclide specifically to a tumor microenvironment allows for selective radiation of tumor tissue, effectively killing malignant cells while preserving the surrounding healthy tissue. For example, a radionuclide can employ a targeting molecule that specifically binds to an antigen expressed at an increased level and/or density on the surface of tumor cells relative to non-tumor cells. Binding of the radionuclide to the antigen-positive tumor cells targets radiation to those cells without targeting healthy tissue. Full-length antibodies have previously been evaluated as targeting moieties; however, due to considerations such as their large size, full-length antibodies, or even antibody fragments (e.g., fragments larger than polypeptides provided herein) can have several challenges such as having poor tumor tissue penetration, longer circulating half-life which leads to normal tissue irradiation, as well as challenges such as manufacturing, and storage, among other things. Accordingly, a need remains for new approaches to specifically target tumors, and particularly solid tumors. The present disclosure provides technologies that meet this and other needs. Among other things, the present disclosure provides compositions comprising polypeptides and conjugates thereof with improved tumor penetration, decreased off-target toxicity and/or accumulation, and improved affinity for Nectin-4, as compared to currently existing technologies (e.g., antibodies, e.g., antibody-drug conjugates, polypeptides, etc.). In addition, the disclosure provides the insight that compositions and conjugates provided herein can be even further improved. Contemplated herein, in some embodiments, conjugates, such as radionuclide conjugates of the disclosure may be improved, such as improvement on one or more measures, such as efficacy and/or reduction in toxicity grade and/or off-target effects, by modification of one or more amino acids in a polypeptide sequence of the conjugate and/or addition of one or more decoys.

In some aspects, the present disclosure provides polypeptides comprising certain amino acid sequences. In some embodiments, these polypeptides bind to Nectin-4 with certain affinities.

In one aspect, the disclosure provides a composition, comprising a polypeptide of at least 44 amino acids in length and having an amino sequence comprising that set forth in SEQ ID NO: 171, wherein X2 is E or D; X6 is E or Q; X17 is G or A; X21 is Q, Y, or E; X26 is Kme3, Kme2, Kme, K, Kipr, or S; X32 is A, G, or D; X41 is N or K; and X45 is S or absent.

In one aspect, the disclosure provides a composition, comprising a polypeptide of at least 44 amino acids in length and having an amino acid sequence comprising that set forth in SEQ ID NO: 176, wherein X2 is E or D; X6 is E or Q; X9 is T or A; X10 is A or G; X12 is A, Kme3, Kme2, Kme, Kipr or K; X13 is R or (Cit) X17 is G or A; X21 is Q, Y, or E; X24 is Q or K, X25 is A or K; X26 is Kme3, Kme2, Kme, K, Kipr, or S; X28 is Q or K; X29 is Y or K; X30 is L or V; X32 is A, G, or D; X41 is N or K, and X45 is S or absent.

In another aspect, the disclosure provides a composition, comprising a Nectin-4 binding polypeptide having an amino acid sequence comprising at least 44 amino acids, wherein the amino acids include (i) a cysteine at each of four positions corresponding to 1, 20, 34, and 44 of SEQ ID NO: 195; (ii) SEQ ID NO: 169 at positions corresponding to positions 9-15 of SEQ ID NO: 195; (iii) QKKme3 at positions corresponding to positions 24, 25, and 26 of SEQ ID NO: 195; and (iv) QYL at positions corresponding to positions 28, 29, and 30 of SEQ ID NO: 195.

In one aspect, the disclosure provides a composition, comprising a Nectin-4 binding polypeptide having an amino acid sequence comprising at least 44 amino acids, wherein the amino acids include (i) a cysteine at each of four positions corresponding to 1, 20, 34, and 44 of SEQ ID NO: 200; (ii) SEQ ID NO: 247 at positions corresponding to positions 9-15 of SEQ ID NO: 200; (iii) QKKme3 at positions corresponding to positions 24, 25, and 26 of SEQ ID NO: 200; and (iv) QYL at positions corresponding to positions 28, 29, and 30 of SEQ ID NO: 200.

In another aspect, the disclosure provides a composition, comprising a Nectin-4 binding polypeptide having an amino acid sequence, wherein the amino acid sequence comprises: at least four cysteines, which form two disulfide bonds; at least one modified lysine residue at a position corresponding to X12 and/or X26 of SEQ ID NO: 195, wherein the modification comprises at least one small alkyl group attached to the nitrogen of the lysine side chain, optionally comprising a methyl, dimethyl, trimethyl, or isopropyl group; at least 44 amino acids in length; and has a binding affinity for Nectin-4 stronger than 100 nM in a cell-based assay.

In some embodiments, the polypeptide is at least 40 amino acids in length, but no greater than 100 amino acids in length.

In some embodiments, the polypeptide binds to Nectin-4 with an affinity of stronger than 10 nM in a cell-based assay.

In some embodiments, the amino acid sequence of the polypeptide shares at least 90% identity to any one of SEQ ID NOs: 3-158, 161-168, 177-208, or 212-215, but includes at least one lysine with at least one modification comprising at least one small alkyl group bonded to the nitrogen of the side chain, optionally selected from: trimethyl, dimethyl, monomethyl, and isopropyl.

In some embodiments, the amino acid sequence of the polypeptide shares at least 90% identity to at least 44 amino acids of a reference polypeptide, which reference polypeptide is longer than 44 amino acids in length and binds to Nectin-4 with a strength of at least 10 nM on a cell-based assay, and/or has an inhibition constant of no greater than 10 nM.

In some embodiments, the amino acid sequence of the polypeptide shares at least 90% identity to at least 40 amino acids of any one of SEQ ID NOs: 3-158, 161-168, 177-208, or 212-215, provided that the 40 amino acids includes at least four cysteine residues that form two disulfide bridges.

In some embodiments, the amino acid sequence of the polypeptide shares at least 90% identity to at least 35 contiguous amino acids of any one of SEQ ID NOs: 3-158, 161-168, 177-208, or 212-215, provided that the 40 amino acids includes at least four cysteine residues that form two disulfide bridges.

In some embodiments, the amino acid sequence of the poly peptide shares 100% identity to at least 44 amino acids of a reference polypeptide, which reference polypeptide is longer than 44 amino acids in length.

In certain embodiments, the amino acid sequence shares 90% identity to at least 44 amino acids as set forth in any one of SEQ ID NO: 78, 83, 85, 99, 103, 162-168, 195, or 200.

In certain embodiments, the amino acid sequence shares 100% identity to at least 44 amino acids as set forth in any one of SEQ ID NO: 78, 83, 85, 99, 103, 162-168, 195, or 200.

In one aspect, the disclosure provides a composition comprising a polypeptide having an amino acid sequence comprising SEQ ID NO: 195.

In another aspect, the disclosure provides a composition comprising a compound as set forth in C251 of Table 2A, having an amino acid sequence comprising SEQ ID NO: 195

In one aspect, the disclosure provides a composition comprising a polypeptide having an amino acid sequence comprising SEQ ID NO: 200.

In one aspect, the disclosure provides a composition comprising a compound as set forth in C260 of Table 2A, having an amino acid sequence comprising SEQ ID NO: 200.

In some embodiments, the composition further comprises a radionuclide.

In some embodiments, the radionuclide is Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In one aspect, the disclosure provides a composition comprising a polypeptide having an amino acid sequence of at least 44 amino acids in length, but with four amino acid substitutions at positions corresponding to 12, 21, 26, and 32 of SEQ ID NO: 78, wherein the substitutions correspond to K12A, Y21Q, S26Kme3, and G32A.

In some embodiments, the C-terminus has an —OH or an —NH2.

In certain embodiments, the binding affinity for Nectin-4 is stronger than 100 nM.

In certain embodiments, the inhibition constant is no greater than 100 nM.

In some embodiments, the composition further comprises one or more of a linker, chelator, and radionuclide.

In some embodiments, the linker comprises or consists of a polyethylene glycol (PEG) linker of PEG4, PEG2, PEG, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- or (PEG)n, wherein n is from 1 to 10. (Gly)1-10, or any fragment or combination via covalent bond thereof.

In some embodiments, the chelator comprises or consists of DOTA, Crown. NOPO, Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, the radionuclide is selected from Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, if the polypeptide comprises any one of SEQ ID NO: 83, 85, 93, 99, 134, 138, 145, 155, 162-168, or 195 the polypeptide further comprises a linker, wherein the linker is PEG4, and an optional chelator, wherein the chelator is DOTA.

In certain embodiments, when present, the linker is attached to the N-terminus of the polypeptide. In certain embodiments, the C-terminal amino acid of the polypeptide is not a cysteine. In some embodiments, when present, the chelator is attached to either the polypeptide or the linker. In some embodiments, when present, the radionuclide is attached to the chelator.

In one aspect, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M). L comprises a linker (L), C comprises a chelator (C), R comprises a radionuclide (R), and x is 1, 2, 3, or 4, wherein M comprises an amino acid sequence of any one of SEQ ID NO: 162-176, 178-208, or 212-215.

In certain embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- or (PEG)n, wherein n is from 1 to 10, (Gly)1-10, or any fragment or combination via covalent bond thereof.

In some embodiments, the chelator comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, the radionuclide Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225. Tb-165, or At-211.

In one aspect, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M), L comprises a linker (L), C comprises a chelator (C). R comprises a radionuclide (R), and x is 1, 2, 3, or 4, wherein M has an amino acid sequence comprising any one of those set forth in SEQ ID NOs: 162-176, 178-208, or 212-215.

In some embodiments, when L is present, L comprises or consists of a polyethylene glycol (PEG) linker of PEG4, PEG, PEG2, PEG6, PEG8, PEG12, PEG24, lys(MPB)-PEG4, PEG36, an ester linker, an amide linker, a maleimide linker a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a dTyr-Gly-Phe (yGF) linker, a caproleic acid linker, or (Gly)n-(gGlu)n- or (PEG)n, wherein n is from 1 to 10, (Gly)1-10, or any fragment or combination via covalent bond thereof.

In some embodiments, when C is present. C comprises or consists of DOTA, Crown, NOPO, Macropa, lead-specific chelator (PSC), N-succinimidyl 3-(tri-n-butylstannyl)benzoate (BuSTB), or N-succinimidyl 3-trimethylstannylbenzoate (MeSTB).

In some embodiments, when R is present. R comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In certain embodiments, when present, the linker is attached to the N-terminus of the polypeptide. In certain embodiments, the C-terminal amino acid of the polypeptide is not a cysteine. In some embodiments, when present, the chelator is attached to either the polypeptide or the linker. In some embodiments, when present, the radionuclide is attached to the chelator.

In some embodiments, the polypeptide comprises at least one disulfide bridge.

In some embodiments, the polypeptide comprises at least two disulfide bridges.

In some embodiments, the composition and/or polypeptide thereof selectively binds to Nectin-4 or a portion thereof.

In certain embodiments, the polypeptide has a binding affinity for Nectin-4 or a portion thereof of 10 pM to 200 nM, 10 pM to 100 nM, or 10 nM to 100 nM, in vivo, ex vivo, or in vitro and/or as measured in a cell-based assay.

In some embodiments, the polypeptide has a binding inhibition constant of no greater than 100 nM.

In one aspect, the disclosure provides a composition comprising a polypeptide-drug conjugate, comprising a polypeptide and at least one drug moiety, wherein the polypeptide comprises an amino acid sequence having at least 90% identity to at least 44 amino acids a polypeptide having an amino acid sequence set forth in any one of SEQ ID NOs: 3-158, 162-208, or 212-237.

In certain embodiments, the drug moiety is selected from a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRMI, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a topoisomerase inhibitor, an auristatin (e.g., monomethyl auristatin E), and an immunotoxin.

In one aspect, the disclosure provides a composition comprising an isolated compound or pharmaceutically acceptable salt thereof comprising an optional linker (L), and one or more of a polypeptide (M), chelator (C) or radionuclide (R), wherein M has an amino acid sequence comprising any one of SEQ ID NOs: 3-158, 161-168, 171-208, 212-215, or 216-237, including amino acid substitutions as set forth in Table 1C, Table 1D, Table 2C, Table 2D, Table 2E, Table 2F, or Table 2G.

In another aspect, the disclosure provides a composition comprising, a compound designed to bind to Nectin-4, which compound comprises or consists of a polypeptide having an amino acid sequence comprising any one of SEQ ID NOs: 3-158, 161-168, 171-208, 212-215, or 216-237, including amino acid substitutions as set forth in Table 1C, Table 1D, Table 2C, Table 2D, Table 2E, Table 2F, or Table 2G, and further comprises a modified N and/or C-terminus.

In certain embodiments, the modified N-terminus comprises one or more of an NH2-, Acetyl-, PEGn-, wherein n=0-10, DOTA-, or Biotin-. In some embodiments, the C terminus comprises an —NH2 or an —OH. In some embodiments, the polypeptide selectively binds to Nectin-4 or a portion thereof. In some embodiments, the polypeptide has a binding affinity of stronger than about 100 nM to Nectin-4, or a portion thereof, in vivo or in a cell-based assay.

In one aspect, the disclosure provides a compound comprising a miniprotein having an amino acid sequence with 90% identity to SEQ ID NO: 195, and further comprising one or more additional components according to a formula M-L-C-R, wherein L is a linker, C is a chelator, and R is a radionuclide.

In some embodiments, L comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, any linker set forth in Table 2A, or (Gly)n-(gGlu)n- or (PEG)n, wherein n is from 1 to 10. (Gly)1-10, or any fragment or combination via covalent bond thereof. In some embodiments, C comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB). In some embodiments, R comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In one aspect, the disclosure provides a compound comprising a miniprotein 90% identical to at least 40 amino acids of the amino acid sequence of SEQ ID NO: 195, wherein the N and/or C-terminus comprise between one and thirty additional amino acids, and/or wherein the C-terminus comprises one fewer amino acids or up to 30 additional amino acids, provided that the entire miniprotein is no greater than about 100 amino acids in length.

In one aspect, the disclosure provides a method of improving binding affinity strength of a polypeptide to Nectin-4, the improvement comprising modifying four amino acid residues of a polypeptide, which polypeptide has at least 44 amino acids in length and has substitutions at positions corresponding to 12, 21, 26, and 32 of SEQ ID NO: 78, wherein the substitutions correspond to K12A, Y21Q, S26Kme3, and G32A.

In some embodiments, the disclosure provides a pharmaceutical composition comprising a polypeptide or compound as provided herein; and a pharmaceutically acceptable excipient.

In one aspect, the disclosure provides a method of treating cancer, the method comprising administering to a subject in need thereof, a composition comprising a conjugate comprising a polypeptide having at least 90% identity to at least 40 amino acids of an amino acid sequence as set forth in any one of SEQ ID NOs: 3-158, 161-168, 171-208, 212-215, or 216-237 and a radionuclide.

In some embodiments, the radionuclide is associated with the polypeptide with a linker and/or chelator according to a formula M-L-C-R, wherein M is the polypeptide, L is a linker, C is a chelator, and R is the radionuclide. In some embodiments, the polypeptide has an amino acid sequence comprising or consisting of SEQ ID NO: 195 or SEQ ID NO: 200.

In some embodiments, L comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, any linker set forth in Table 2A, or (Gly)n-(gGlu)n- or (PEG)n, wherein n is from 1 to 10, (Gly)1-10, or any fragment or combination via covalent bond thereof. In some embodiments, C comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB). In some embodiments, R is Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In certain embodiments, R is a therapeutic agent and/or an imaging agent. In some such embodiments, R is Cu-64, Ga-68, Lu-177, In-111, Cu-67, La-132, or F-18.

In one aspect, the disclosure provides a method of reducing kidney cell uptake of a composition comprising administering to a subject a Nectin-4 binding protein having an amino acid sequence comprising at least one modified lysine residue at a position corresponding to X12 and/or X26 of SEQ ID NO: 195, wherein the modification comprises at least small alkyl group attached to the nitrogen of the lysine side chain, optionally comprising a monomethyl, dimethyl, trimethyl, or isopropyl group and the reduction is as compared to administration to the subject or a control subject an otherwise identical composition but not comprising the modified lysine residue at the position corresponding to X12 and/or X26.

In another aspect, the disclosure provides a method of treating cancer, the improvement comprising administering a composition comprising a Nectin-4 binding protein having an amino acid sequence comprising at least one modified lysine residue at a position corresponding to X12 and/or X26 of SEQ ID NO: 195, wherein the modification comprises at least one carbon attached to the nitrogen of the lysine side chain, optionally comprising a methyl, dimethyl, trimethyl, or isopropyl group as compared to a composition not comprising a modified lysine residue at a position corresponding to X12 and/or X26.

In one aspect, the disclosure provides a method of treating a subject with refractory or recurrent cancer comprising administering a composition, compound, or pharmaceutical composition as provided herein, wherein the treatment treats the cancer.

In one aspect, the disclosure provides a method of improving biodistribution of a pharmaceutical composition for a Nectin-4 positive population of cancer cells in a subject having a Nectin-4-positive cancer, comprising contacting the population with a polypeptide that has a modified lysine at a position corresponding to X12 and/or X26 of SEQ ID NO: 195, wherein the lysine is modified by adding at least one small alkyl group to a lysine side chain and wherein the biodistribution is improved as compared to contacting the population without the modified lysine at a position corresponding to X12 and/or X26 of SEQ ID NO: 195.

In another aspect, the disclosure provides a method of diagnosing presence of a Nectin-4 positive population of cancer cells comprising:
  contacting a population of cells with a composition, compound, or pharmaceutical composition as provided herein; detecting the presence of the composition, compound, or pharmaceutical composition of step (a) by measuring a signal; and comparing the detection in step (b) to a control signal; and diagnosing cancer if the composition, compound, or pharmaceutical composition of step (a) is detected above the control.

In some embodiments, the contacting is performed by administering to a subject in need thereof. In some embodiments, the administering is intravenous or subcutaneous. In some embodiments, the contacting is outside of the subject, optionally in vitro with a biopsy sample.

In one aspect, the disclosure provides a method of treating a cancer in a subject using an immunotherapy, the method comprising administering to the subject a composition comprising a composition, compound, or pharmaceutical composition as provided herein.

In another aspect, the disclosure provides a use of a composition, compound, or pharmaceutical composition as provided herein to treat cancer in a subject.

In one aspect, the disclosure provides a method of treating a subject in need thereof comprising administering to the subject in need thereof a composition, compound, or pharmaceutical composition as provided herein.

In some embodiments, the subject is diagnosed as having cancer. In some embodiments, a cancer cell from the subject expresses Nectin-4, or a portion thereof. In some embodiments, the expression of Nectin-4 is higher in the cancer cell than in a non-cancer cell, which expression can be measured by protein and/or nucleic acid levels.

In some embodiments, the composition, compound, or pharmaceutical composition is not taken up and/or retained in the kidney as compared to a compound that does not comprise a composition, compound, or pharmaceutical composition as provided herein. In some embodiments, the composition, compound, or pharmaceutical composition is internalized in a cell expressing human Nectin-4.

In some embodiments, the cancer is selected from breast cancer, ovarian cancer, melanoma, pancreatic cancer, peripheral neuroma, glioblastoma, adrenocortical carcinoma, AIDS-related lymphoma, anal cancer, urothelial cancer, bladder cancer, meningioma, glioma, astrocytoma, cervical cancer, chronic myeloproliferative disorders, colon cancer, endometrial cancer, ependymoma, esophageal cancer. Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, the composition, compound, or pharmaceutical composition is administered intravenously or subcutaneously.

In one aspect, the disclosure provides a method of targeting cancer cells expressing Nectin-4, the method comprising: determining or having determined a level of expression of Nectin-4 in a population of cancer cells, administering to a subject in need thereof a composition comprising a composition, compound, or pharmaceutical composition as provided herein, wherein the polypeptide of the composition, compound, or pharmaceutical composition is designed to specifically bind to human Nectin-4 and (iii) wherein the composition, compound, or pharmaceutical composition is attached to the surface and/or internalized into one or more Nectin-4 expressing cancer cells.

In some embodiments, the subject is treated after the administering as compared to prior to the administering.

In one aspect, the disclosure provides a method of targeting a population of cancer cells expressing Nectin-4, the improvement comprising contacting the population with a composition, compound, or pharmaceutical composition as provided herein, wherein X12 and/or X26 comprise a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at positions X12 and/or X26, wherein, optionally, the small alkyl group is part of a monomethyl, dimethyl, trimethyl, or isopropyl group.

In one aspect, the disclosure provides a conjugate comprising: a polypeptide (M) that specifically binds to Nectin-4; a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Actinium-225.

In one aspect, the disclosure provides a conjugate comprising: a polypeptide (M) that specifically binds to Nectin-4; a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Copper-64.

In one aspect, the disclosure provides a conjugate comprising: a polypeptide (M) that specifically binds to Nectin-4; a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Gallium-68.

In another aspect, the disclosure provides a conjugate comprising: a polypeptide (M) that specifically binds to Nectin-4; a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Indium-111.

In one aspect, the disclosure provides a conjugate comprising: a polypeptide (M) that specifically binds to Nectin-4; a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Lead-212.

In another aspect, the disclosure provides a conjugate comprising: a polypeptide (M) that specifically binds to Nectin-4; a chelator (C) conjugated to (M) through an optional linker (L), wherein (C) comprises DOTA, and (L), when present, comprises PEG, wherein the PEG is optionally PEG-4; and (iii) a radionuclide (R) chelated to (C), wherein (R) is Lutetium-177.

In one aspect, the disclosure provides a conjugate comprising: a miniprotein (M) that specifically binds to Nectin-4; an N-terminal modification, conjugated to (M) through an optional linker (L), wherein (L), when present, comprises PEG, wherein the PEG is optionally PEG-4; and the N-terminal modification comprises a biotin.

In some embodiments, M of the conjugate has an amino acid sequence comprising any one of the amino acid sequences set forth in SEQ ID NOs: 3-158, 161-168, 171-208, or 212-215. In some embodiments, the amino acid sequence has at least 90% identity to that of at least 40 amino acids of SEQ ID NO: 176, wherein X2 is E or D; X6 is E or Q; X9 is T or A; X10 is A or G; X12 is A, Kme3, Kme2, Kme, Kipr or K; X13 is R or (Cit) X17 is G or A. X21 is Q, Y, or E; X24 is Q or K; X25 is A or K; X26 is Kme3, Kme2, Kme, K, Kipr, or S; X28 is Q or K; X29 is Y or K; X30 is L or V; X32 is A, G, or D; X41 is N or K; and X45 is S or absent.

In certain embodiments, M has an amino acid sequence comprising or consisting of SEQ ID NO: 195.

In certain embodiments, M has an amino acid sequence comprising or consisting of SEQ ID NO: 200.

In one aspect, the disclosure provides an isolated polynucleotide comprising one or more nucleic acid sequences encoding a poly peptide selected from any one of SEQ ID NOs: 3-158, 161-208, and 212-215; or a nucleic acid sequence encoding a polypeptide comprising at least 90%, 95%, 96%, 97%, 98%, 99% or greater identity to any one of SEQ ID NOs: 3-158, 161-168, 171-208, or 212-215.

In some embodiments, the disclosure provides a vector comprising an isolated polynucleotide provided herein. In some embodiments, the disclosure provides a host cell transformed with an isolated polynucleotide provided herein or a vector provided herein.

In one aspect, the disclosure provides a method of evaluating locations of one or more populations of cancerous cells in a subject, the method comprising administering to the subject a composition, compound, or pharmaceutical composition as provided herein and detecting to determine location of the composition in the subject.

In one aspect, the disclosure provides a method of decreasing kidney uptake of a composition administered to detect and/or treat one or more populations of cancer cells, the improvement comprising administering to a subject in need thereof a composition, compound, or pharmaceutical composition as provided herein, wherein X12 and/or X26 comprise a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at positions X12 and/or X26, wherein, optionally, the small alkyl group is part of a monomethyl, dimethyl, trimethyl, or isopropyl group.

In some embodiments, the detecting comprises an imaging procedure allows for selecting subjects, monitoring subjects, and/or treating subjects with a therapeutic comprising a miniprotein designed to bind to Nectin-4 expressed on one or more cancer cells in the one or more populations of cancer cells. In some embodiments, the therapeutic comprises a composition, compound, pharmaceutical composition, or conjugate as provided herein.

In one aspect, the disclosure provides a method of improving delivery of a radionuclide to a population of cancer cells in a subject, the method comprising administering a composition, compound, pharmaceutical composition, or conjugate as provided herein, wherein the amino acid sequences of the polypeptide comprise amino acids corresponding to positions X12 and/or X26 of SEQ ID NO: 195, and wherein X12 and/or X26 comprise a lysine with at least one additional small alkyl group attached to the nitrogen in the side chain, wherein uptake by kidney cells is less than with a polypeptide having an amino acid sequence that does not comprise an additional small alkyl group attached to a nitrogen on the side chain of a lysine at positions X12 and/or X26.

In some embodiments, the small alkyl group comprises a monomethyl, dimethyl, trimethyl, or isopropyl group.

In one aspect, the disclosure provides a method of treating an individual with cancer, the improvement comprising reducing one or more off-target effects or toxicity measures by administering composition, compound, pharmaceutical composition, or conjugate as provided herein, wherein the amino acid sequences of the polypeptide comprise amino acids corresponding to positions X12 and/or X26 of SEQ ID NO: 195, and wherein X12 and/or X26 comprise a lysine with at least one additional small alkyl group attached to the nitrogen in the side chain, wherein uptake by kidney cells is less than with a polypeptide having an amino acid sequence that does not comprise an additional small alkyl group attached to a nitrogen on the side chain of a lysine at positions X12 and/or X26.

In another aspect, the disclosure provides a method of treating an individual with cancer, the improvement comprising achieving a reduction in concentration of R in a kidney tissue in the presence of composition, compound, pharmaceutical composition, or conjugate as provided herein, wherein the amino acid sequences of the polypeptide comprise amino acids corresponding to positions X12 and/or X26 of SEQ ID NO: 195, and wherein X12 and/or X26 comprise a lysine with at least one additional small alkyl group attached to the nitrogen in the side chain, wherein uptake by kidney cells is less than with a polypeptide having an amino acid sequence that does not comprise a small alkyl group attached to a nitrogen on the side chain of a lysine at positions X12 and/or X26, as compared to the concentration of R in the kidney tissue in the absence of the composition, compound, pharmaceutical composition, or conjugate.

In some embodiments, the reduction in concentration of R in the kidney tissue is measured by urine output of R as measured by percent of administered radiation recovered or by detection as measured by a cell-based in vitro assay, or an in vivo detection assay.

In some embodiments, the administration of the composition can be repeated at least 2, 3, 4, 5, 6, or 7 times more in the presence of the composition having 90% identity to at least 40 amino acids of SEQ ID NO: 195 including a modified lysine at positions corresponding to X12 and/or X26 of SEQ ID NO: 195 than in the presence of an A or K at positions corresponding to X12 and/or X26.

In one aspect, the disclosure provides a method of reducing uptake by a kidney tissue of a composition, the improvement comprising administering a composition comprising (a) a radionuclide therapeutic comprising at least a polypeptide and a radionuclide (R); wherein the polypeptide has at least 90% identity to 40 amino acids of SEQ ID NO: 195 and/or has a modified lysine at positions corresponding to X12 and/or X26 of SEQ ID NO: 195, such that in the presence of the modified lysine, the radionuclide is less concentrated in the kidney tissue than in the absence of the polypeptide.

In another aspect, the disclosure provides a method comprising administering to a subject in need thereof a compound that binds to Nectin-4 and includes one or two modified lysines at positions corresponding to X12 and/or X26, respectively, of SEQ ID NO: 195, wherein administration of the compound having a miniprotein with the one or two modified lysines reduces one or more off target effects, toxicity grades, and/or uptake and/or retention in a kidney tissue as compared to a compound having an alanine or unmodified lysine at a position corresponding to X12 and an unmodified lysine at a position corresponding to X26.

In one aspect, the disclosure provides a method of treating an individual having or suspected of having a Nectin-4-positive cancer, the method comprising administering to the individual: a means for blocking uptake and/or retention of a radiotherapeutic to kidney tissue, and a linker, a chelator, and a radionuclide.

In some embodiments, the means for blocking uptake and/or retention of a radiotherapeutic to kidney tissue binds to Nectin-4 and includes one or two modified lysines at positions corresponding to X12 and/or X26, respectively, of SEQ ID NO: 195 and/or has at least 90% identity to 40 amino acids of SEQ ID NO: 195 and/or has a modified lysine at positions corresponding to X12 and/or X26 of SEQ ID NO: 195.

In some embodiments, the means for blocking uptake and/or retention of a radiotherapeutic to kidney tissue binds to Nectin-4 and includes one or two modified lysines at positions corresponding to X12 and/or X26, respectively, of SEQ ID NO: 195 and/or has at least 90% identity to 35 contiguous amino acids of SEQ ID NO: 195 and/or has a modified lysine at positions corresponding to X12 and/or X26 of SEQ ID NO: 195.

In some embodiments, the means for blocking uptake and/or retention of a radiotherapeutic to the kidney tissue blocks uptake and/or retention to the kidney tissue greater than as compared to the blocking of uptake and/or retention to the kidney tissue by a means that does not include one or two modified lysines at positions corresponding to X12 and/or X26, respectively, of SEQ ID NO: 195 and/or has at least 90% identity to 40 amino acids of SEQ ID NO: 195 and/or has a modified lysine at positions corresponding to X12 and/or X26 of SEQ ID NO: 195.

In some embodiments, the means for blocking uptake and/or retention of a radiotherapeutic to the kidney tissue blocks uptake and/or retention to the kidney tissue greater than as compared to the blocking of uptake and/or retention to the kidney tissue by a means that does not include one or two modified lysines at positions corresponding to X12 and/or X26, respectively, of SEQ ID NO: 195 and/or has at least 90% identity to 35 contiguous amino acids of SEQ ID NO: 195 and/or has a modified lysine at positions corresponding to X12 and/or X26 of SEQ ID NO: 195.

In some embodiments, the means for blocking uptake and/or retention of a radiotherapeutic to the kidney tissue is a radiotherapeutic. In some embodiments, the radiotherapeutic is targeted to a tumor or a population of cancer cells. In some embodiments, the radiotherapeutic targeted to the tumor or the population of cancer cells is at a greater concentration than in the absence of the means for binding to kidney tissue. In some embodiments, the radiotherapeutic comprises a polypeptide that targets Nectin-4.

In some embodiments, the radiotherapeutic comprises or consists of a compound selected from C3-C293 or C298-C307. In some embodiments, the radionuclide of the radiotherapeutic is selected from Ac-225, Cu-64, Ga-68, In-111, Lu-177, or Pb-212.

In one aspect, the disclosure provides a kit comprising a polypeptide and instructions for use, wherein the polypeptide has an amino acid sequence as set forth in a polypeptide of any one of a composition, compound, pharmaceutical composition, or conjugate as provided herein.

In some embodiments, the kit further comprises one or more of a linker, chelator, and radionuclide. In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- or (PEG)n, wherein n is from 1 to 10, (Gly)1-10, or any fragment or combination via covalent bond thereof. In some embodiments, the chelator comprises or consists of DOTA, NOPO, Crown, Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, prior to use, the compound is labeled with a radionuclide, wherein the radionuclide is chelated to the chelator to produce a composition with a formula M-L-C-R.

In some embodiments, the radionuclide is selected from Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. In some embodiments, the radionuclide is Ac-225, Cu-64, Ga-68, In-111, Lu-177, or Pb-212.

In some embodiments, if the polypeptide has an amino acid comprising any of those set forth in any one of SEQ ID NOs: 83, 85, 93, 99, 134, 138, 145, 155, 161-176, 195, or 200 the polypeptide further comprises a linker, wherein the linker is PEG4, and a chelator, wherein the chelator is DOTA. In some embodiments, when present, the linker is attached to the N-terminus amino acid of the polypeptide. In some embodiments, the C-terminal amino acid of the polypeptide is not cysteine. In some embodiments, when present, the chelator is attached to either the polypeptide or the linker. In some embodiments, when present, the radionuclide is attached to the chelator. In some embodiments, when present, the radionuclide is attached to the N-terminus amino acid of the polypeptide.

BRIEF DESCRIPTION OF FIGURES

FIGS. 6A and 6B are graphs showing internalization of an exemplary radioconjugate in HT-1376 (FIG. 6A) and MCF7 (FIG. 6B) cell lines at 37° C., and 4° C. TB=total binding, NSB=non-specific binding.

FIG. 17A is a line graph showing % ID/g in kidney of an exemplary Nectin-4-targeting miniprotein conjugate ($^{111}$In-C109) alone/without a decoy (circles) or in combination with an exemplary decoy (C295; squares). FIG. 17B is a line graph showing % ID/g in tumor of an exemplary Nectin-4-targeting miniprotein conjugate ($^{111}$In-C109) alone/without a decoy (circles) or in combination with an exemplary decoy (C295; squares). FIG. 17C is a line graph showing % ID/g in kidney of an exemplary Nectin-4-targeting miniprotein conjugate ($^{111}$In-C251) alone/without a decoy (circles) or in combination with an exemplary decoy (C296; squares). FIG. 17D is a line graph showing % ID/g in tumor of an exemplary Nectin-4-targeting miniprotein conjugate ($^{111}$In-C251) alone/without a decoy (circles) or in combination with an exemplary decoy (C296; squares).

FIG. 18A) and body weight (% of initial weight; FIG. 18B) measurements in an exemplary mouse xenograft model, treated at Day 0 with: (i) vehicle (solid circles); (ii) an exemplary decoy (C296; 1 mg; 1000× of C251 dose, solid triangles); (iii) an $^{225}$Ac-labeled exemplary Nectin-4-targeting radionuclide conjugate ($^{225}$Ac-C251; 1 mg; 1,000 nCi; open circles); or (iv) a combination of the exemplary decoy (C296; 1000× of C251 dose) and the exemplary Nectin-4-targeting radionuclide conjugate ($^{225}$Ac-C251; 1,000 nCi) (open triangles). In FIG. 18A, the dotted line at 2,000 mm$^3$ marks the maximum tumor growth threshold for the pre-defined humane endpoint of experimental mice. In FIG. 18B, the dotted line at 80% of initial body weight marks the body weight decrease threshold for the pre-defined humane endpoint for the experimental mice. Error bars represent standard error of the mean (SEM).

FIG. 19A) and body weight (% of initial weight; FIG. 19B) measurements in an exemplary mouse xenograft model, treated at Day 0 with: (i) vehicle (circles; single dose); an $^{225}$Ac-labeled exemplary Nectin-4-targeting radionuclide conjugate ($^{225}$Ac-C251) at two different doses ((ii) 0.5 mg; 1,000 nCi; single dose; triangles, or (iii) 1 mg; 2,000 nCi; single dose; inverted triangles); or (iv) an anti-Nectin-4 antibody-drug conjugate (ADC) control (enfortumab vedotin (EV); 3 mg/kg; three doses; squares). Black arrowheads under the x-axis indicate dosing of $^{225}$Ac-C251 at Day 0. Gray arrowheads under the x-axis indicate dosing of EV at Days 0, 8, and 15. In FIG. 19A, the dotted line at 1.500 mm$^3$ marks the maximum tumor growth threshold for the pre-defined humane endpoint of experimental mice. In FIG. 19B, the dotted line at 80% of initial body weight marks the body weight decrease threshold for the pre-defined humane endpoint of experimental mice. Error bars represent standard error of the mean (SEM).

FIG. 20A) and body weight (% of initial weight; FIG. 20B) measurements in an exemplary patient-derived mouse xenograft model, treated at Day 0 with: (i) vehicle (circles); (ii) an $^{225}$Ac-labeled exemplary Nectin-4-targeting radionuclide conjugate ($^{225}$Ac-C251; 1 mg; 2,000 nCi; single dose; inverted triangles), or (iii) an anti-Nectin-4 ADC control (enfortumab vedotin (EV); 3 mg/kg; three doses; squares). Black arrowheads under the x-axis indicate dosing of $^{225}$Ac-C251 at Day 0. Gray arrowheads under the x-axis indicate dosing of EV at Days 0, 8, and 15. Error bars represent standard error of the mean (SEM).

FIG. 23A shows the percentage of cells normalized to the mode (on y-axis) identified to express Nectin-4 after incubation with 100 nM of C253, as measured by the mean fluorescence intensity (MFI; on x-axis). FIG. 23B shows the difference in mean fluorescence intensity (Delta MFI; y-axis) of HT-1376-P (circles) and HT-1376-KO (inverted triangles) cells incubated with C253 and cells incubated with vehicle, as a measurement of Nectin-4 binding at 0.0) 1 nM, 0.01 nM, 0.1 nM, 1 nM, 10 nM, 100 nM, and 100) nM of C253 (on x-axis).

DETAILED DESCRIPTION

Figure 1A:
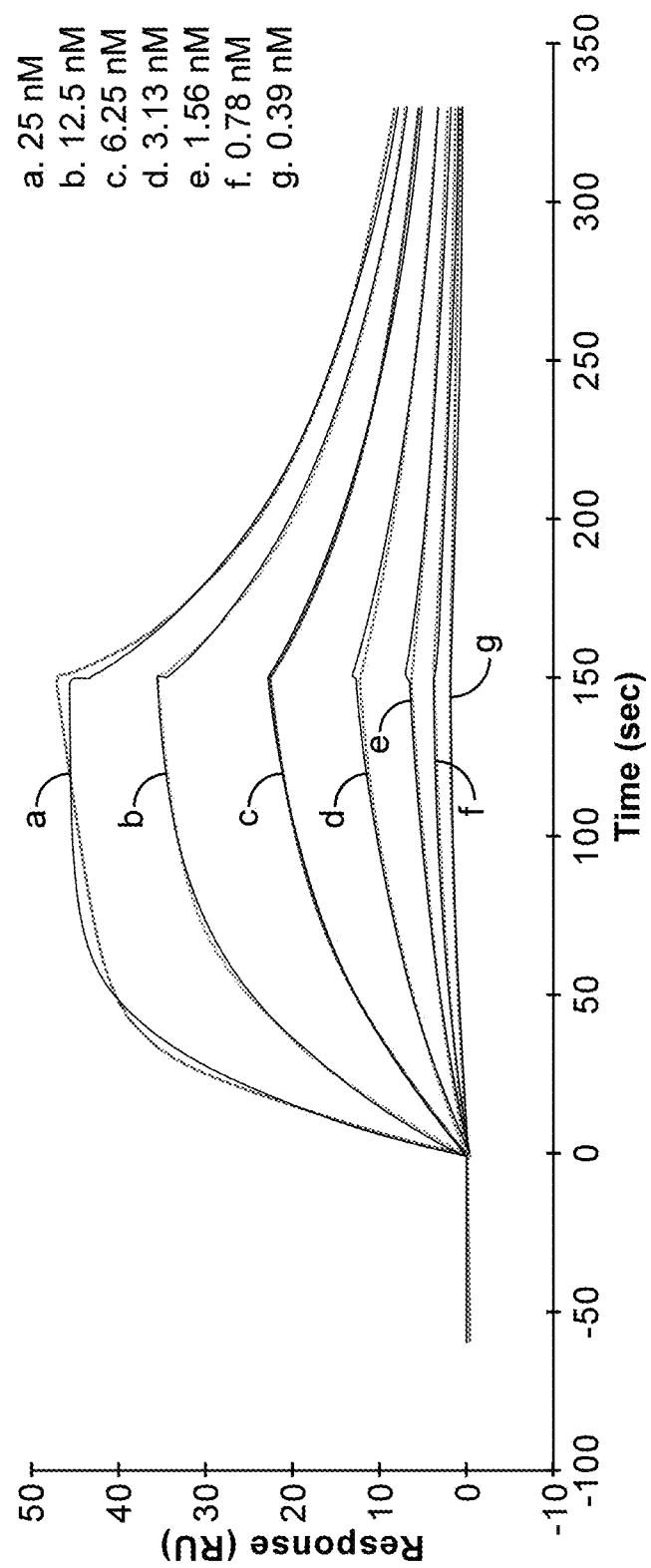
FIGS. 1A and 1B are fitted sensorgrams (SPR) of an exemplary Nectin-4 peptide binding to mouse and human Nectin-4, respectively.

Among other things, the disclosure provides compositions and methods of use thereof. In some embodiments, a composition selectively binds to a target (e.g., Nectin-4). In some embodiments, the target is on a tumor cell. In some such embodiments, the tumor cell is part of a population of tumor cells (e.g., a solid tumor). In some embodiments, the tumor cells are circulating (e.g., a hematologic cancer, circulating tumor cells, etc.). In some embodiments the composition comprises one or more additional agents (e.g., a chelator, a radionuclide), which agents may be used as therapeutics (e.g., a radionuclide to kill a cancer cell) wherein the therapeutic agent is selectively targeted to a cell, e.g., a cell expressing Nectin-4, e.g., a cancer cell expressing Nectin-4, by a miniprotein that is part of the composition. In some embodiments the composition comprises one or more therapeutic agents (e.g., a chelator, a radionuclide), wherein the therapeutic agent is selectively targeted to a cell expressing Nectin-4 such that the Nectin-4-expressing cell is treated and cells not expressing Nectin-4 are not treated. The disclosure recognizes that a source of a problem in treating cells expressing a target (e.g., cancer cells) is that traditional therapies are not selective enough to specifically target cells (e.g., tumor cells) and to deliver a therapeutic in a way that minimizes damage to surrounding cells (e.g., non-tumor cells). Surrounding cells (e.g., as in one or more non-tumor tissues) may also express the target at lower amounts or levels than target cells. The present disclosure provides the insight that a combination of selective targeting with a specific therapeutic such as a chelator and/or radionuclide (e.g., an alpha emitter) provides an advantage over previously used therapeutics (e.g., antibodies, beta-emitters, etc.).

Furthermore, the disclosure provides the insight that even a therapeutic such as those provided herein is designed to be more specific for Nectin-4 and/or a tissue such as a tumor tissue), challenges can still arise. When Nectin-4 is expressed by a non-tumor cell and/or when a therapeutic (e.g., a radiotherapeutic) is taken up by an organ system, such as involved in clearance of systemically administered agents (e.g., kidney), efficacy can decrease and toxicity can increase. The disclosure contemplates that uptake to a tumor may be challenged by uptake, retention, and/or clearance by one or more non-target (e.g., non-tumor) tissues. For example, kidney can play a role in clearance of administered therapeutics. In addition, such therapeutics can be taken up and/or retained in the kidney. For example, uptake of a therapeutic intended for a tumor can also be taken up, retained, and/or cleared by the kidney resulting in (1) faster clearance from a subject to whom it has been administered; (2) reduced tumor targeting (including because therapeutic is taken up and/or retained in a non-target tissue), and/or cleared; and/or (3) non-target tissue (e.g., kidney, etc.) damage.

The disclosure recognizes that any or all of these challenges may be mitigated or prevented by combining administration of a Nectin-4 targeting therapeutic with administration of a decoy. In some embodiments, the decoy blocks uptake by a kidney of a composition comprising a polypeptide as provided herein (e.g., a radionuclide conjugate). Without wishing to be bound by theory, the disclosure contemplates that improvement in treatment efficacy is at least maintained while reducing damage to one or more non-tumor tissues (e.g., kidney) and, in some embodiments, treatment efficacy is improved while simultaneously reducing risk of harm or actual harm to non-tumor tissue (e.g., kidney tissue and/or renal system tissues such as ureters, bladder, etc.).

Unless otherwise defined herein, scientific and technical terms used in connection with the present disclosure shall have the meanings that are commonly understood by those of ordinary skill in the art. Furthermore, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art.

The methods and techniques of the present disclosure are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor. N.Y. (1990); Wittrup and VanAntwerp, *Fine Affinity Discrimination by Yeast Surface Display and Flow Cytometry*, Biotechnol. Prog. 2002. (16) 31-37; C. Queen et al., A humanized antibody that binds to the interleukin 2 receptor, Proc. Natl. Acad. Sci. USA 1989, 86 (24) 10029-10033; Scheinberg D A and McDevitt M R. *Actinium*-225 *in targeted alpha-particle therapeutic applications*. Curr Radiopharm. 2011; 4(4):306-320.

All publications, patents, and other references mentioned herein are hereby incorporated by reference in their entireties. In case of conflict, the present specification, including definitions, will control. Materials, methods, and examples as disclosed herein are illustrative only and not intended to be limiting.

Unless otherwise defined, all technical and scientific terms used herein have the same meaning as commonly understood by one of ordinary skill in the art to which this present disclosure pertains. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art.

Throughout this specification and claims, the word "comprise" or variations such as "comprises" or "comprising," will be understood to imply the inclusion of a stated integer or group of integers but not the exclusion of any other integer or group of integers.

As used herein, ranges and amounts can be expressed as "about" a particular value or range, e.g., "about" one particular value, and/or to "about" another particular value. About also includes the exact amount. Hence "about 100 nucleotides" means "about 100 nucleotides" and also "100 nucleotides." Given context, the term "about" as used herein also includes an amount that would be expected to be within experimental error. If "about" appears before a quantitative value, the present disclosure also includes the specific quantitative value itself, unless specifically stated otherwise. In such instances "about" can also refer to a ±10% variation from the nominal value unless otherwise indicated or inferred. When values are expressed as approximations by use of the antecedent "about," it is understood that the disclosure also contemplates embodiments that specify the particular values and ranges of values without the approximations.

As used herein, the singular forms "a." "an" and "the" include plural referents unless context clearly dictates otherwise. Thus, for example, in some embodiments, reference to, e.g., decoys includes a plurality of decoys, a single decoy, etc.

As used herein, the expression "and/or" in connection with two or more recited objects includes individually each of the recited objects and the various combinations of two or more of the recited objects, unless otherwise understood from the context and use.

Unless otherwise indicated, and as an example for all sequences described herein under the general format "SEQ ID NO:", "nucleic acid comprising SEQ ID NO: 1" refers to a nucleic acid, at least a portion of which has either (i) the sequence of SEQ ID NO: 1, or (ii) a sequence complementary to SEQ ID NO: 1. The choice between the two is dictated by the context. For instance, if the nucleic acid is used as a probe, the choice between the two is dictated by the requirement that the probe be complementary to the desired target.

As used herein, the term "administration" refers providing a composition to a subject or system. Administration to a subject may be by any appropriate route, dose and/or dose schedule.

As used herein, the term "affibody" refers to a subgenus of miniproteins. An affibody is a molecule derived from the Z-domain of staphylococcal protein A that consists of three alpha helices with 58 amino acids and has a molar mass of about 6 kDa. See, for exemplary details of affibody structures and uses, Orlova, A; Magnusson, M; Eriksson, T L; Nilsson, M; Larsson, B; Höidén-Guthenberg, I; Widström, C; Carlsson, J et al. (2006). "Tumor imaging using a picomolar affinity HER2 binding affibody molecule", Cancer Res. 66 (8): 4339-48. Exemplary Affibody) Molecules are commercially available from Abcam Corp. Cambridge Mass. An affibody is stable at high temperatures and under acidic or alkaline conditions. Target specificity is obtained by randomization of 13 amino acids located in two alpha-helices involved in the binding activity of the parent protein domain (Feldwisch J. Tolmachev V.; (2012) Methods Mol Biol. 899:103-26).

As used herein, the term "affinity maturation" generally refers to a process whereby successive changes to a sequence (e.g., successive mutations) are made and selection of the polypeptide sequences are performed to choose one or more sequences with increased affinity relative to the "starting" sequence or another sequence with less affinity as compared to one with greater affinity.

As used herein, the terms "amino acid sequence" and "polypeptide" refer to a polymer of amino acids connected by one or more peptide bonds. A polypeptide of the present disclosure encompasses both naturally occurring and non-naturally occurring proteins, and any fragments, portions, peptides, mutants, derivatives, and analogs thereof. A polypeptide may be monomeric or polymeric. Further, a polypeptide may comprise a number of different domains each of which has one or more distinct activities. A polypeptide may be fully or partially synthetic or otherwise modified (i.e., comprising one or more synthetically produced amino acids and/or modifications thereof). The term "peptide" may be used to refer to a short polypeptide, such as one comprising fewer than about 70 amino acids (e.g., between about 5, 10, 15, 20, 25, 30, 35, 40, 45, 50, 55, 60, 65, or 70 amino acids).

As used herein, the term "anticalin" refers to a subgenus of miniproteins. An anticalin is an engineered protein derived from a lipocalin (Beste G. Schmidt F S, Stibora T, Skerra A. (1999) Proc Natl Acad Sci USA. 96(5): 1898-903; Gebauer and Skerra (2009) Curr Opinion in Chemical Biology 13:245-255). Anticalins possess an eight-stranded b-barrel which forms a highly conserved core unit among the lipocalins and naturally forms binding sites for ligands by means of four structurally variable loops at the open end. Anticalins, although not homologous to the IgG superfamily, show features that so far have been considered typical for the binding sites of antibodies: (i) high structural plasticity as a consequence of sequence variation and (ii) elevated conformational flexibility, allowing induced fit to targets with differing shape.

As used herein, the term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances, a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

As used herein, the term "avimer" refers to a subgenus of miniproteins. An avimer is a class of antibody mimetics which consist of two or more peptide sequences of preferably to 35 amino acids each, which are derived from A-domains of various membrane receptors, and which are connected by linker peptides. Binding of target molecules occurs via the A-domain and domains with the desired binding specificity can be selected, for example, by phage display techniques. The binding specificity of the different A-domains contained in an avimer may but does not have to be identical (Weidle U H, et al., (2013). Cancer Genomics Proteomics 10(4): 155-68). For further details see Nature Biotechnology 23(12). 1556-1561 (2005) and Expert Opinion on Investigational Drugs 16(6), 909-917 (June 2007). As used herein, the term "binder" refers to a subgenus of miniprotein. A binder is characterized in that it comprises or consists of a polypeptide that is capable of binding or has known ability to engage and associate a target or a portion thereof. Binders generally comprise a cysteine-containing peptide comprising one or more disulfide bonds, though some binders do not comprise cysteine-residues and/or disulfide bonds. Binders are preferably cleared rapidly from circulation when administered systemically to a mammalian subject. As will be understood, given context, reference to a binder may be or include its nucleic acid sequence or amino acid sequence encoding it. A binder may be provided, for instance, as a polynucleotide, polypeptide, using a vector, host cell, etc., and/or any combination of modalities. A binder may be derived or manufactured using any method known to those of skill in the art. For instance, in some embodiments, a binder can be recombinant (i.e., produced using recombinant nucleic acids encoding a polypeptide). In some embodiments, a binder can be synthetic (e.g., synthesized such as using standard solid phase synthesis methods, such as solid phase peptide synthesis, known to those of skill in the art (see, e.g., Palomo, *J. RSC Adv.,* 2014.4, 32658-32672) and described herein).

As used herein, the term "block" refers to preventing, slowing, suppressing, or otherwise reducing or decreasing uptake and/or retention of a compound into a tissue (e.g., a non-tumor tissue, e.g., a kidney tissue). In some embodiments, a decoy blocks, suppresses, reduces, or otherwise decreases uptake of a conjugate or compound of the disclosure into a non-tumor tissue, such as kidney tissue. In some embodiments, a decoy reduces retention of a compound (e.g., a radiotherapeutic compound, e.g., comprising a miniprotein) in a non-tumor tissue (e.g., kidney).

As used herein, the term "chelator" refers to any molecule or moiety that is capable of forming a complex (i.e., "chelates") with a metal ion. Chelators generally have two or more unshared electron pairs that can be used to donate to a metal ion. Metal ions are usually coordinated to the chelator by two or more pairs of electrons.

As used herein, the term "conjugated" refers to the joining by covalent or noncovalent means of two compounds or agents.

As used herein, a "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, Methods Mol. Biol. 24:307-31 and 25:365-89 (herein incorporated by reference). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y). Tryptophan (W).

As used herein the terms "cysteine-dense peptide" and "CDP" are used interchangeably and refer to a subgenus of miniproteins that generally comprise a high density of cysteines (e.g., at least one, two, three, four, or more cysteines in a span of about to about 90 amino acids, or about 13 to 80 amino acids in a polypeptide). In some embodiments, such a CDP may comprise at least two independent folding domains. In some embodiments, the CDP comprises at least one, two, three, four, or more cysteine residues in a span of from about 10 to about 90 amino acid residues, preferably 13 to 80 amino acid residues. (pubmed.ncbi.nlm.nih.gov/29483648/). In some embodiments, the CDP comprises a constrained distribution of cysteines, Cys-$X_{[0-15]}$-Cys-$X_{[0-15]}$-Cys-$X_{[0-15]}$-Cys-$X_{[0-15]}$-Cys-$X_{[0-15]}$-Cys (wherein X represents any amino acid) (SEQ ID NO: 241).

As used herein, a "compound" refers at least to a miniprotein with an amino acid sequence. Compounds may include miniproteins with different modifications, such as a N-terminal modification or a C-terminal modification. In various embodiments, a "compound" can include a miniprotein and one or more additional elements, examples of which include a linker, a chelator, and/or a radionuclide. For example, a compound may include a miniprotein conjugated to a chelator and/or a radionuclide e.g., via a linker. As denoted herein, compounds are identified with a specific compound number e.g., "C1," "C2," C3", etc. Different compounds may have different sequences. In various embodiments, different compounds may have the same sequence (e.g., assigned the same SEQ ID NO), but may have one or more of different modifications (e.g., different N-terminal or C-terminal modifications), different linkers, different chelators, and/or different radionuclides. N- and C-terminal modifications may include but not be limited to acetyl, acid, or amide (e.g., Acetyl, NH2, OH), such as provided in exemplary compounds and miniproteins of TABLE 2A. In some embodiments, a polypeptide according to the disclosure may have various modifications to its N-terminus (e.g., such as set forth in exemplary compounds in TABLE 2A), and can have an acid or amide group on its C-terminus (see, e.g., TABLE 2A). A given polypeptide having a particular amino acid sequence can have one or more N-terminal and/or C-terminal differences without materially changing the utility or function of the polypeptide, such as for binding to Nectin-4 (e.g., for detection and/or treatment of cancer).

As used herein, the term "deletion" generally refers to the removal of one or more nucleotides from a nucleic acid molecule or one or more amino acids from a protein, the regions on either side being joined together.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

As used herein, the term "derived from," with reference to a nucleic acid sequence refers to a nucleic acid sequence that has at least 85% sequence identity to a reference naturally occurring nucleic acid sequence from which it is derived. The term "derived from," with reference to an amino acid sequence refers to an amino acid sequence that has at least 85% sequence identity to a reference naturally occurring amino acid sequence from which it is derived. The term "derived from" as used herein does not denote any specific process or method for obtaining the nucleic acid or amino acid sequence. For example, the nucleic acid or amino acid sequence can be chemically synthesized.

As used herein, the term "designed ankyrin repeat domain (DARPin)" refers to a subgenus of miniproteins. A DARPin is a peptide derived from Ankyrin which is a family of proteins that mediate attachment of integral membrane proteins to the cytoskeleton. A single ankyrin repeat is preferably a 33-residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1. DARPins typically provide a rigid interface and lack structural flexibility (Gebauer and Skerra, 2009).

As used herein, the term "domain" as used herein refers to a structure of a biomolecule that contributes to a known or suspected function of the biomolecule. Domains may be co-extensive with regions or portions thereof: domains may also include distinct, non-contiguous regions of a biomolecule. Examples of protein domains include, but are not limited to, an Ig domain, an extracellular domain, a transmembrane domain, and a cytoplasmic domain.

As used herein, the term "engineered Kunitz domain" refers to a subgenus of miniproteins. An engineered Kunitz domain is preferably a peptide derived from the Kunitz domain of a Kunitz-type protease inhibitor such as bovine pancreatic trypsin inhibitor (BPTI), amyloid precursor protein (APP) or tissue factor pathway inhibitor (TFPI). Kunitz domains have a molecular weight of approximately 6 kDa and domains with the required target specificity can be selected by display techniques such as phage display (Weidle et al., (2013), Cancer Genomics Proteomics; 10(4): 155-68).

As used herein, the term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

As used herein, the term "functional variant" refers to a polypeptide that comprises or consists of a portion of a sequence of a polypeptide provided herein, and still retains one or more functions of a polypeptide comprising or consisting of an entire amino acid sequence as provided herein (e.g., still binds to a target, e.g., Nectin-4).

As used herein, the term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present disclosure have particular utility. The heterologous polypeptide included within the fusion protein of the present disclosure is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, when referring to a protein, "homology" to a second protein can exist if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) Homology between two regions of amino acid sequences (especially with respect to predicted structural similarities) can be interpreted as implying similarity in function. Homologous proteins or peptides with residue positions that are not identical are often recognized to differ by conservative amino acid substitutions.

As used herein the term "identical" refers to a nucleic acid sequence or amino acid sequence of at least two nucleic acid or at least two amino acid sequences or subsequences that have a specified percentage of nucleotides or amino acids, respectively, that are the same, when compared and aligned for maximum correspondence, as measured using a sequence comparison algorithm or by visual inspection. For sequence comparison, typically one sequence acts as a reference sequence, to which test (i.e. query) sequences are compared. A length of sequence identity comparison may be over a stretch of any number of nucleotides or amino acids. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. A number of algorithms are known in the art. Non-limiting examples of algorithms that are suitable for determining percent sequence identity and sequence similarity are the BLAST and BLAST 2.0 algorithms, which are described in, e.g., Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information. Additionally, or alternatively, sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity can be determined using FASTA with its default parameters (a word size of 6 and the NOPAM factor for the scoring matrix) or using Gap with its default parameters as provided in GCG Version 6.1, herein incorporated by reference. Percent identity is not necessarily determined over the entire length of two sequences. That is, for example, with a reference sequence and a query sequence, one may be longer or shorter than the other and percent identity is determined based on match over the length of a particular stretch of nucleic acids or amino acids. For example, if a sequence disclosed herein is compared to a query sequence and the query is shorter, a percent identity is determined by aligning the reference and query and determining the percent identity as between the query and the portion of the reference sequence over which it aligns. If the query is longer than the disclosed sequence, percent identity is identity over an aligned portion with the reference sequence (e.g., over 5, 10, 15, 20, 25, 30, 35 or more amino acids of a miniprotein).

As used herein, the term "isolated" polynucleotide or polypeptide is one which is substantially separated from other cellular components that naturally accompany the native polynucleotide in its natural host cell, e.g., ribosomes, polymerases and genomic sequences with which it is naturally associated. For instance, an isolated molecule is one that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polynucleotide or polypeptide found in nature or it includes amino acid analogs or derivatives not found in nature or linkages other than standard peptide bonds). Thus, a polynucleotide or polypeptide that is chemically synthesized or synthesized in a cellular system different from the cell from which it naturally originates will be "isolated" from its naturally associated components. A polynucleotide or polypeptide may also be rendered substantially free of naturally associated components by isolation, using protein purification techniques well known in the art. As thus defined, "isolated" does not necessarily require that any molecule so described has been physically removed from its native environment. In some embodiments, as used in reference to an isolated construct, isolated means in the absence of a pharmaceutically acceptable salt.

As used herein, the term "Ki" (M) refers to the binding inhibition constant of a given entity and a target (e.g., a particular polypeptide-target interaction).

As used herein, the term "$k_d$" ($s^{-1}$) refers to the dissociation rate constant between a given entity and a target (e.g., of a particular polypeptide-target interaction). This value is also referred to as the $k_{off}$ value.

As used herein, the term "$k_a$" ($M^{-1} \times s^{-1}$) refers to the association rate constant of a given entity and a target (e.g., a particular polypeptide-target interaction). This value is also referred to as the $k_{on}$ value.

As used herein, the term "$K_D$" (M) refers to the dissociation equilibrium constant of a given entity and a target (particular interaction between an entity and its target (e.g. a polypeptide-target interaction). $K_D = k_d/k_a$.

As used herein, the term "$K_A$" ($M^{-1}$) refers to the association equilibrium constant of a given entity and a target (e.g., a particular polypeptide-target interaction). $K_A = k_a/k_d$.

The affinity of a molecule X for its target Y can be represented by the dissociation equilibrium constant ($K_D$). The kinetic components that contribute to the dissociation equilibrium constant are as described above. For clarity, as known in the art, a smaller $K_D$ value indicates a higher affinity interaction, while a larger $K_D$ value indicates a lower affinity interaction. Affinity can be measured by common methods known in the art, including those described herein, such as surface plasmon resonance (SPR) technology (e.g., BIACORE®) or biolayer interferometry (e.g., FORTEBIO®).

In some embodiments, the peptide or miniprotein (e.g., targeting miniprotein, e.g., Nectin-4-binding miniprotein) of the present disclosure binds to Nectin-4 with a dissociation equilibrium constant ($K_D$) of less than about $10^{-7}$ M, such as less than about $10^{-8}$ M, $10^{-9}$ M, or $10^{-10}$ M or less, for example, as determined using surface plasmon resonance (SPR) techniques in an SPR machine, such as a BIACORE T200 instrument.

As used herein, the term "knock out" generally refers to a gene whose level of expression or activity has been reduced to zero. In some examples, a gene is knocked out via deletion of some or all of its coding sequence. In other examples, a gene is knocked out via introduction of one or more nucleotides into its open reading frame, which results in translation of a nonsense or otherwise nonfunctional protein product.

As used herein, the term "knottin" refers to a structural motif of a miniprotein containing three disulfide bridges.

As used herein, the term "knottin peptide" refers to a subgenus of miniproteins that comprises at least one knottin.

As used herein, the term "linker" refers to a moiety that is used to conjugate a miniprotein to a chelator.

As used herein, the term "miniprotein" refers to short proteins of less than or equal to about 100 amino acids with well-defined folds comprising two or more secondary structure elements, a sequestered hydrophobic core, and/or cooperative folding. CDPs, knottins, affibodies, engineered Kunitz domains, monobodies (adnectins), anticalins, designed ankyrin repeat domains (DARPins), and avimers, as disclosed herein are all examples of miniproteins. Further, a miniprotein can refer to a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer.

As used herein, the term "modification," with reference to a nucleic acid sequence, refers to a nucleic acid sequence that comprises at least one substitution, alteration, inversion, addition, or deletion of nucleotide compared to a reference nucleic acid sequence. As used herein, the term "modification," with reference to an amino acid sequence refers to an amino acid sequence that comprises at least one substitution, alteration, inversion, addition, or deletion of an amino acid residue compared to a reference amino acid sequence. An alteration can include but is not limited to a change to or of one or more atoms of a side chain, such as, for example addition of a methyl-group (e.g., methylated versions of lysine). In some embodiments, a natural amino acid is modified such as set forth herein.

As used herein, the term "modified derivative" refers to polypeptides or fragments thereof that are substantially homologous in primary structural sequence, but which include e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as 125I, 32P, 35S, and 3H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. &e, e.g., Ausubel et a, Current Protocols in Molecular Biology, Greene Publishing Associates (1992, and Supplements to 2002).

As used herein, the term "molecule" means any compound, including, but not limited to, a miniprotein, a small molecule, peptide, protein, sugar, nucleotide, nucleic acid, lipid, etc., and such a molecule (e.g., miniprotein, compound, etc.) can be natural or synthetic or a combination of natural and synthetic.

As used herein, the term "monobody" or "adnectin" are used interchangeably and refer to a subgenus of miniproteins. A monobody relates to a molecule, preferably based on the 10th extracellular domain of human fibronectin III (10Fn3), which adopts an Ig-like b-sandwich fold of preferably 94 residues with 2 to 3 exposed loops but lacks the central disulfide bridge (Gebauer and Skerra (2009) Curr Opinion in Chemical Biology 13:245-255). Adnectins with the desired target specificity can be genetically engineered by introducing modifications in specific loops of the protein.

As used herein, the term "mutein" or "mutant protein" or "Variant" means a protein comprising an amino acid sequence with at least one variation (e.g., an insertion, a deletion, or a substitution, which can be a conservative or non-conservative substitution) compared to a reference sequence. When applied to sequences (e.g., nucleic acid sequences, amino acid sequences) "mutated" means that nucleotides in a nucleic acid sequence or amino acids in an amino acid sequence may be inserted, deleted or changed compared to a reference sequence. A single alteration may be made at a locus (a point mutation) or multiple nucleotides or amino acids may be inserted, deleted or changed at a single locus. In addition, one or more alterations may be made at any number of loci within a nucleic acid or amino acid sequence. A nucleic acid or amino acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., Technique, 1:11-15 (1989) and Caldwell and Joyce, PCR Methods Applic. 2:28-33 (1992)); "oligonucleotide-directed mutagenesis" (a process which enables the generation of site-specific mutations in any cloned DNA segment of interest, see, e.g., Reidhaar-Olson and Sauer, Science 241.53-57 (1988)); directed evolution (e.g., exposing a polypeptide to differing sets of conditions resulting in production of different polypeptides with one or more amino acid changes that may or may not confer greater fitness upon the polypeptide); and site-directed mutagenesis (e.g., specifically directed changes in a sequence).

As used herein, the terms "polypeptide mutant" or "mutein" refer to a polypeptide whose sequence contains an insertion, duplication, deletion, rearrangement, or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein. A mutein has at least 85% overall sequence homology to its wild-type counterpart. Even more preferred are muteins having at least 90% overall sequence homology to the wild-type protein. In an even more preferred embodiment, a mutein exhibits at least 95% sequence identity, even more preferably 98%, even more preferably 99% and even more preferably 99.9% overall sequence identity. Sequence homology may be measured by any common sequence analysis algorithm, such as Gap or Bestfit. Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the term "non-disulfide sequence" refers to an amino acid sequence encoding a polypeptide that does not comprise more than one cysteine residue and/or disulfide bonds in its folded and active form. For example, in some embodiments, a miniprotein may comprise or consist of a non-disulfide sequence.

As used herein, the term "non-peptide analog" refers to a compound with properties that are analogous to those of a reference polypeptide. A non-peptide compound may also be termed a "peptide mimetic" or a "peptidomimetic." See, e.g., Jones, Amino Acid and Peptide Synthesis, Oxford University Press (1992); Jung, Combinatorial Peptide and Nonpeptide Libraries: A Handbook, John Wiley (1997); Bodanszky et al., Peptide Chemistry-A Practical Textbook, Springer Verlag (1993); Synthetic Peptides: A Users Guide, (Grant, ed., W. H. Freeman and Co., 1992), Evans et al., J. Med. Chem. 30:1229 (1987); Fauchere, J. Adv. Drug Res. 15:29 (1986); Veber and Freidinger, Trends Neurosci., 8:392-396 (1985); and references sited in each of the above, which are incorporated herein by reference. Such compounds are often developed with the aid of computerized molecular modeling. Peptide mimetics that are structurally similar to useful peptides of the present disclosure may be used to produce an equivalent effect and are therefore envisioned to be part of the present disclosure.

As used herein, the terms "nucleic acid sequence" and "polynucleotide" are used interchangeably to refer to a polymer of nucleotides. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The nucleic acid sequence can contain natural, non-natural, or altered nucleotides; and contain a natural, non-natural, or altered internucleotide linkage, such as a phosphoramidate linkage or a phosphorothioate linkage, instead of the phosphodiester found between the nucleotides of an unmodified nucleic acid sequence. Nucleic acid sequences include, but are not limited to, all nucleic acid sequences which are obtained by any means available in the art, including, without limitation, recombinant means, e.g., the cloning of nucleic acid sequences from a recombinant library or a cell genome, using ordinary cloning technology and polymerase chain reaction, and the like, and by synthetic means. Polynucleotides of the present disclosure may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., poly peptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

As used herein, the terms "operatively linked" or "operably linked" expression control sequences refer to a linkage in which the expression control sequence is contiguous with the gene of interest to control the gene of interest, as well as expression control sequences that act in trans or at a distance to control the gene of interest.

As used herein, the term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

As used herein, the term "radionuclide" refers to an atom capable of undergoing radioactive decay.

As used herein, the term "radiotherapeutic" refers to a radionuclide-labeled miniprotein or compound as provided herein, comprising a radionuclide. A radiotherapeutic may be administered to a subject, such as a test subject (e.g., a mouse or rat, e.g., a non-human primate, e.g., a healthy volunteer), and/or a subject in need of radiotherapy, e.g., a subject with a cancer.

As used herein, the term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, and/or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it. A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

As used herein, the term "region" as used herein refers to a physically contiguous portion of the primary structure of a biomolecule. In the case of proteins, a region is defined by a contiguous portion of the amino acid sequence of that protein.

As used herein the phrase "secondary structure elements" refers to local folded structures that form within a polypeptide due to interactions between atoms of its backbone. Examples of secondary structure elements can include an alpha helix, a beta sheet, a 310 helix, a pi helix, and a random coil. A miniprotein of the present disclosure may comprise one or more of any of such secondary structures (e.g., one or more alpha helix, one or more alpha helices and one or more beta sheets). It will be understood by those of skill in the art that secondary structure elements may be joined by loop regions, which may or may not be modified to change the interactions of secondary structure elements of the polypeptide. As will be understood to those of skill in the art, in some embodiments, loops may be secondary structural elements. In some embodiments, loops may, be interstructural elements that are not necessarily considered secondary structural elements.

As used herein, "sequence homology" for polypeptides, also referred to as "percent sequence identity." is typically measured using sequence analysis software. See, e.g., the Sequence Analysis Software Package of the Genetics Computer Group (GCG), University of Wisconsin Biotechnology Center, 910 University Avenue. Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1. A preferred algorithm when comparing a particular polypeptide sequence to a database containing a large number of sequences from different organisms is the computer program BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)). Preferred parameters for BLASTp are: Expectation value: 10 (default); Filter: seg (default); Cost to open a gap: 11 (default); Cost to extend a gap: 1 (default); Max, alignments: 100 (default); Word size: 11 (default); No, of descriptions: 100 (default); Penalty Matrix: BLOSUM62. The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson. Methods Enzymol. 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

As used herein, the term "specific activity" generally refers to the activity per unit mass of a radionuclide. The unity of specific activity may include units of becquerel per kilogram (Bq/kg) or curie per gram (Ci/g).

As used herein, the term "specificity" generally refers to a sequence (e.g., of a protein, e.g. of a miniprotein, e.g. a miniprotein having certain amino acids) that, when in a conformation that can bind, selectively or "specifically" binds to a specific target (e.g., an antigen, such as expressed on a tumor, e.g., Nectin-4, e.g., certain cell types, e.g., kidney cells, e.g., kidney proximal tubule cells, etc.).

As used herein, "specifically binds" means that the binding of a polynucleotide, polypeptide, or protein is selective for a specified antigen (e.g., target) and can be discriminated from unwanted or non-specific interactions. For example, the ability of a protein (e.g., cysteine-dense peptides) to bind to a specific antigenic determinant can be measured techniques familiar to one of skill in the art, for example through an enzyme-linked immunosorbent assay (ELISA) or surface plasmon resonance. Between two molecules (e.g., entities such as miniproteins), "specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold, or even 1,000-fold. Typically, the affinity or avidity of a specific binding reaction, as quantified by a dissociation constant, is about $10^{-7}$ M or stronger (e.g., about $10^{-8}$ M, $10^{-9}$ M or even stronger). Specific-binding requires specificity of a particular first entity (e.g., a polypeptide) for a particular second entity (e.g., an antigen binding sequence).

As used herein, the term "stabilizer" in the context of a pharmaceutical composition refers to an agent, molecule, or compound that may act to impact the active pharmaceutical ingredient or ingredients to maintain desirable properties (e.g., therapeutic properties or properties that allow therapeutic effect to be achieved) until it is administered to a subject.

As used herein "stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization. In general, "stringent hybridization" is performed at about 25° C. below the thermal melting It (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press. Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 h, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

As used herein, the term "synthetic" is used to refer to an entity that is made is lab-created and not naturally produced or isolated, without modification, from a naturally occurring source. A recombinant polymer, such as a recombinant polynucleotide or polypeptide, may be synthetic. Synthetic polymers such as polynucleotides or polypeptides may be produced by any method known to those of skill in the art, including but not limited to solid phase synthesis, solution phase synthesis, biological synthesis by, e.g., host cells, etc.

As used herein, the term "subject" is a mammal. A subject may be a human or non-human mammal. Given context, a subject may be used interchangeably with patient, individual, donor, etc. In some embodiments, a subject is a healthy subject without a disease that is contemplated for treatment by a composition of the disclosure (e.g., a healthy volunteer being administered one or more compositions provided herein). In some embodiments, a subject is one suspected or diagnosed as having a disease, disorder, or condition, such as a cancer and/or tumor, as provided herein. In some such embodiments, such a subject is considered for treatment by a composition of the disclosure. In some embodiments, analyses of results achieved with technologies disclosed herein are evaluated in a population comprising a plurality of subjects.

As used herein, the terms "substantial homology" or "substantial similarity," when referring to a polynucleotide or polypeptide, indicate that, when optimally aligned with appropriate nucleotide or amino acid insertions or deletions with another reference molecule (or its complementary strand when appropriate), there is sequence identity in at least about 70%, 75%, 80%, 85%, preferably at least about 90%, and more preferably at least about 95%, 96%, 97%, 98% or 99% or more of the nucleic acid or amino acid residues, as measured by any well-known algorithm of sequence identity, such as, e.g., FASTA, BLAST, Gap, etc. Alternatively or additionally, substantial homology or similarity exists when, for example, a nucleic acid or fragment thereof hybridizes to another nucleic acid, to a strand of another nucleic acid, or to the complementary strand thereof, under stringent hybridization conditions.

As used herein, the term "target" refers to a protein or functional portion or variant thereof. A target is a protein to which another protein (e.g. a miniprotein) is designed to bind. A target may be or comprise a binding region, such as an epitope, to which a miniprotein (e.g., CDP, knottin, binder, affibody, engineered Kunitz domain, monobody, anticalin, designed ankyrin repeat domain (DARPin), avimer) of the present disclosure binds. Further, the term "antigen" refers to a protein or functional portion or variant thereof to which a polypeptide (e.g., a miniprotein, etc.) or variant thereof binds to. A target may be or comprise an antigen. A target may be expressed on the surface of a particular cell (a "target cell") or expressed within (e.g., on the surfaces of) cells in a population of cells. A target may have a certain percent identity to a reference protein and still be referred to as a target by a particular name (e.g., Nectin-4). In certain embodiments that will be clear from context, a target may also refer to a protein in a pathway related to another protein. For example, if a target is Nectin-4, a target may also be a protein in a pathway that is necessary for Nectin-4 activity. A target may be or comprise a binding region, such as an epitope, to which a miniprotein of the present disclosure binds. In certain embodiments that will be clear given context, a target may also be a particular cell type (or be localized to a particular cell type) characterized by expression of particular surface entities such as receptors (e.g., a cell in a tissue, e.g., a proximal tubule cell in a kidney). Such targets may be different or the same as a target to which a miniprotein (M) is designed to bind; in some embodiments, a target (e.g., a non-tumor cell, e.g., a kidney cell, etc.) is bound by a decoy rather than a polypeptide (e.g., a miniprotein) of a composition (e.g., a radiotherapeutic composition) provided herein.

As used herein "thermal stability" refers to the ability of a miniprotein to remain stable (e.g., not unfolded, e.g., structurally intact) over a period of time. In some embodiments, a mini protein of the present disclosure retains at least 95% of its stability for at least one hour.

As used herein, a treatment that is "tolerable" to a subject refers to a therapeutic administration and/or regimen that is not terminated because of dose-limiting toxicity.

As used herein, the term "treatment" (as well as "treat" or "treating") refers to partial or complete alleviation, amelioration, mitigation, prevention, reduction in risk of onset, relief, inhibition, delay in onset of, reduction in severity of, reduction in frequency or incidence of one or more causes, features, and/or symptoms of or associated with a particular disease, disorder, and/or condition.

As used herein, the term "vector" is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell and are thereby replicated along with the host genome. Moreover, certain preferred vectors are capable of directing the expression of genes to which they are operatively linked. Such vectors are referred to herein as "recombinant expression vectors" (or simply "expression vectors").

As used herein, the term "decoy peptides" or "decoys" refers to a subgenus of miniproteins specifically designed to (i) decrease accumulation of a compound (e.g., a miniprotein, e.g., a radiolabeled miniprotein, e.g., a radiotherapeutic as provided herein) in a non-tumor tissue (e.g., kidney tissue when the tumor is elsewhere); and/or (ii) have substantially no impact to minimal impact on compound uptake by a tumor (e.g., a tumor expressing a target, e.g., Nectin-4); and/or (iii) decrease adverse (e.g., toxic) accumulation in a non-tumor containing organ (e.g., kidney, etc.) of a subject. To give but one example, an exemplary decoy may be combined with a composition of the disclosure (e.g., comprising a miniprotein and a radionuclide) to block uptake and/or retention of the radioactive composition in kidney tissue, as compared to uptake and/or retention in kidney tissue in the absence of the decoy. Certain decoys are provided herein, such as C295-C297 (SEQ ID NOs: 209-211). Decoys of the disclosure may bind to a target protein (e.g., Nectin-4) with an affinity of about $10^{-6}$ M, $10^{-5}$ M, $10^{-4}$ M, $10^{-3}$ M, or greater (e.g., $10^{-2}$ M, etc.), or may have binding that is not detectable using measures including those provided herein. Without wishing to be bound by theory, the disclosure describes, in some embodiments, a decoy peptide (or decoy) that decoys a composition such as a radiotherapeutic, which means that presence of the decoy in a non-tumor tissue (e.g., kidney) blocks uptake and/or retention of the radiotherapeutic into the non-tumor tissue (e.g., kidney). For clarity, when a decoy peptide is referred to as "decoying," e.g., a composition, e.g., a compound, e.g., a miniprotein that binds to a target (e.g., Nectin-4), the decoy is not acting on the composition (or compound or miniprotein), rather, it is acting on its own and, for example, even in the absence of a composition that it is decoying, if administered alone, would still be present in the non-tumor tissue (e.g., kidney).

As used herein, the term "scaffold" is used to describe miniproteins that share a general set of structural characteristics (e.g., certain constraints, secondary structures, tertiary structures, etc.). Any individual scaffold may include varying amounts of alpha helix, turn, and/or beta sheet, e.g. all alpha helix proteins ("a"), all beta sheet proteins ("b"), blended alpha helix/beta sheet proteins ("a/b"), blended alpha and beta proteins ("a+b"), and small proteins. Examples and features of certain scaffolds are provided herein, for example, as in compounds of TABLE 2A, e.g., C1-C293, e.g., C294.

Compositions

Provided herein are compositions comprising one or more of a polypeptide (e.g., miniprotein), linker, chelator, and/or radionuclide. In some embodiments, a composition comprises a linker and a chelator. In some such embodiments, the composition is metalated (e.g., with a cold-metal form of an elemental label, such as provided herein). In some embodiments, the composition is radiolabeled (e.g., with a radionuclide such as provided herein). In some embodiments, a composition comprises a linker, chelator, and radionuclide. In some embodiments, a composition comprises or consists of a polypeptide (i.e., miniprotein), an optional linker, and a chelator and/or radionuclide. In some embodiments, a chelator and/or radionuclide are conjugated to a miniprotein via a linker. In some embodiments, a miniprotein of the present disclosure comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer. In some embodiments, a radionuclide of the present disclosure is an alpha emitter. In some such embodiments, a chelator and/or radionuclide are conjugated to a miniprotein via a linker.

Without wishing to be bound by any particular theory, the present disclosure contemplates that compositions of the present disclosure are more effective than previously described compositions (e.g., such as those comprising antibodies and/or beta-emitter radionuclides). Such miniproteins or compositions comprising miniproteins can be used to treat subjects in need thereof with improved target specificity, increased speed of clearance, and decreased off-target effects (e.g., as compared to conjugates with non-alpha emitter radionuclides, e.g., as compared to compositions comprising antibodies or antibody-drug-conjugates, etc.) For example, while miniproteins (e.g., to be used in compositions as provided herein) have several key features of antibody-based therapeutics (e.g., affinity, potency, specificity, and ability to disrupt protein:protein interactions), they can avoid undesirable limitations such as, e.g., large size, expensive manufacturing, and the necessity of chimerization or humanization. For instance, in some embodiments, a miniprotein (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) of the present disclosure is no more than about 100 amino acids in length. In some embodiments, such a miniprotein may be or comprise a cysteine dense peptide. In some embodiments, a miniprotein comprises one or more disulfide bridges. In some embodiments, a miniprotein comprises at least two disulfide bridges. In some embodiments, a miniprotein comprises no more than two disulfide bridges. In some embodiments, a miniprotein comprises multiple cysteine residues that crosslink to maintain a very stable, folded state for a peptide of its length (e.g., relative to a peptide of the same length without as many cysteine residues). Without wishing to be bound by theory, the disclosure contemplates that in some embodiments, a miniprotein does not comprise multiple cysteine residues such as, for example, a miniprotein comprising a single cysteine residue. In some such embodiments, the miniprotein may form a dimer, such as with another miniprotein (e.g., self-dimerization). In some embodiments, two miniproteins are linked together to form a dimer. In other embodiments, two miniproteins are each linked to a linker to form a dimer. In other embodiments, two different miniproteins are each linked to a linker to form a dimer. The present disclosure contemplates that stability conferred by crosslinked cysteines contributes to reduced immunogenicity of miniproteins or comprising such miniproteins. In some embodiments, such stability may also confer resistance to harsher conditions provided for efficient chelation (e.g., high temperature, low pH incubations, etc.), while continuing to retain biological activity (e.g., capability of binding a target).

In some embodiments, miniproteins as provided herein function as targeting moieties, e.g., specifically binding to a target expressed on the surface of a tumor cell. In some such embodiments, a miniprotein is designed such that it may be joined to one or more additional components. For example, without being bound by any particular theory, miniproteins of the present disclosure may be formulated such that they are combined with other components such as a therapeutic molecule (e.g., chelator compositions and/or radionuclide) and/or a detectable agent (e.g., a visualizable agent, e.g., a metabolizable and visualizable agent). In some such embodiments, such miniproteins conjugated to one or more additional components may be used, for example, in diagnosis, prognosis, monitoring, and/or treatment of one or more diseases, disorders or conditions such as those with expression of particular targets on particular populations of cells.

In some embodiments a miniprotein (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) has low immunogenicity relative to a larger protein. In some such embodiments, the lower immunogenicity increases amenability to harsher environmental conditions (e.g., high temperature and low pH incubations) while retaining biological activity. Thus, in some embodiments, a conjugate comprising a miniprotein has lower immunogenicity than a composition comprising a larger protein or different targeting moiety (i.e., other than a miniprotein).

In some embodiments, a composition comprising a linker, chelator, and/or radionuclide can efficiently penetrate a tumor.

In some embodiments, miniproteins) have superior penetration efficiency relative to larger proteins. That is, in some embodiments, a miniprotein or composition comprising a miniprotein can penetrate a solid tumor better than a larger protein or composition comprising a protein larger than a miniprotein. For example, in some embodiments, a binder has superior tumor penetration efficiency with a hydrodynamic radius on the order of about 1 nm-25 nm. In some embodiments, the hydrodynamic radius is between about 1 nm-5 nm. In some embodiments, the hydrodynamic radius is between about 1 nm-3 nm. In some embodiments, the hydrodynamic radius is about 1, 2, 3, 4, 5, 6, 7, 8, 9, 10, 11, 12, 13, 14, 15, 16, 17, 18, 19, 20, 21, 22, 23, 24, or 25 nm.

As described herein, miniproteins are conjugated to a chelator. In some embodiments, the chelator binds a radionuclide (e.g., an alpha-emitter radionuclide, e.g., actinium). In some such embodiments, such radionuclide conjugates combine specific-binding capabilities and properties of a miniprotein with a radionuclide. That is, without being bound by any particular theory, the present disclosure provides a conjugate wherein, in some embodiments, a miniprotein targets a radioisotope to which it's conjugated to a cell expressing a target. In some embodiments, the target is expressed on the surface of a cell. In some embodiments, the target is Nectin-4. In some embodiments, the cell is a tumor cell. In some embodiments, the conjugate binds to the Nectin-4 on the surface of the tumor cell. In some such embodiments, the radionuclide is targeted to the tumor cell. In some embodiments, the radionuclide is an alpha-emitter radionuclide and when internalized, serves to specifically target (e.g., without damaging surrounding tissue/cells) the tumor cell.

Targets

Any cell expressing a target may be targeted by a miniprotein as provided herein.

In some embodiments, a cell is a mammalian cell. In some embodiments, a cell is a human cell. In some embodiments, a cell is from a cell line. In some embodiments, a cell is a primary cell. In some embodiments, a primary cell is from a sample from a subject such as from a tumor or from corresponding tissue without a tumor (e.g., from another area of an organ or from a healthy donor). In some embodiments, a cell is in vitro (e.g., a primary cell, a cell line, etc.).

In some embodiments, a cell is in vivo (e.g., in a subject, e.g., in a human subject, e.g., in a tumor of a human subject.) In some embodiments, a cell expresses or has been induced to express (e.g., via recombinant technology) a target. In some embodiments, the target is expressed on the surface of a cell. In some embodiments, a cell is contacted by a composition binding to a target expressed on its surface. In some embodiments, upon binding (e.g., upon binding of a miniprotein provided by the present disclosure), a target and any bound proteins and/or payloads is/are internalized into the cell. In some embodiments, a cell is killed by a payload (e.g., a radionuclide and/or chelator, etc.) after internalization.

In some embodiments, a target is a protein or portion thereof that is upregulated or overexpressed on cancer cells as compared to non-cancer cells. That is, in some embodiments, a target is expressed or overexpressed in a tumor or in a tumor microenvironment relative to a level of the target in non-diseased tissue (e.g., tissue without a tumor or tumor microenvironment). In some such embodiments, the target is absent or non-detectable in non-diseased (e.g., healthy) tissue. In some embodiments, a target is a biomarker for cancer (e.g., for cancer cells, for a tumor).

In some embodiments, a target may be related to a protein such as, for example, a protein in a pathway activated or acted upon by another protein. For instance, in some embodiments, a protein may be expressed on the surface of a cancer cell and a target may be a pathway that the surface-cell protein acts upon. In some embodiments, a protein may be expressed on a cancer cell and a target may be a protein on a different cell that causing a cancer cell to proliferate or otherwise be refractory to a treatment. In some embodiments, a tumor-associated cell surface molecule or tumor-specific cell surface molecule may be targeted by a miniprotein or composition comprising a miniprotein as provided herein.

In some embodiments, the miniprotein or composition comprising a miniprotein specifically binds a target expressed on the surface of a cell. In some embodiments, a target is cleaved from a cell surface. In some such embodiments, if the target is in an organism, cleavage of the target results in circulation of the target throughout the system of the organism. In some such embodiments, a target is found at a particular level in, e.g., blood, serum, plasma. In some embodiments, however, a substantial portion of expressed target is localized to cell surfaces, thus, in some embodiments, measurements of a level of a target may not accurately reflect the amount of target in a population of cells (e.g., a tumor). In some embodiments, a target is a secreted protein. In some such embodiments, a target is found at a particular level in, e.g., blood, serum, plasma. In some such embodiments, the miniprotein binds to a region of a target such as, for example, an epitope. In some embodiments, a miniprotein or composition comprising a miniprotein specifically binds a target expressed on the surface of a cancer cell. In some embodiments, the cancer cell is in, on, or near a solid tumor. In some embodiments, the cancer cell is a circulating cancer cell. In some embodiments, a miniprotein or composition comprising a miniprotein specifically binds a target or expressed at a higher level on a cancer cell than a reference cell. In some embodiments, the cell is a mammalian cell. In some embodiments, the cell is a human cell.

In some embodiments, the miniprotein or composition comprising a miniprotein specifically binds to Nectin-4. In some embodiments, the target comprises or consists of Nectin-4. In some embodiments, the miniprotein specifically binds to a target comprising an amino acid sequence or portion thereof as set forth in TABLE 1A.

In some embodiments, the disclosure provides a composition, comprising a polypeptide of at least 44 amino acids in length and having an amino sequence comprising that set forth in SEQ ID NO: 171, wherein X2 is E or D; X6 is E or Q; X17 is G or A; X21 is Q, Y, or E; X26 is Kme3, Kme2, Kme, K, Kipr, or S; X32 is A, G, or D; X41 is N or K; and X45 is S or absent.

In certain embodiments, the disclosure provides a composition, comprising a polypeptide of at least 44 amino acids in length and having an amino acid sequence comprising that set forth in SEQ ID NO: 176, wherein X2 is E or D; X6 is E or Q; X9 is T or A; X10 is A or G; X12 is A, Kme3, Kme2, Kme, Kipr or K; X13 is R or (Cit) X17 is G or A; X21 is Q, Y, or E; X24 is Q or K; X25 is A or K; X26 is Kme3, Kme2, Kme, K, Kipr, or S; X28 is Q or K; X29 is Y or K; X30 is L or V; X32 is A, G, or D; X41 is N or K; and X45 is S or absent.

In some embodiments, the disclosure provides a composition, comprising a Nectin-4 binding polypeptide having an amino acid sequence comprising at least 44 amino acids, wherein the amino acids include (i) a cysteine at each of four positions corresponding to 1, 20, 34, and 44 of SEQ ID NO: 195; (ii) TALARLR (SEQ ID NO: 169) at positions corresponding to positions 9-15 of SEQ ID NO: 195; (iii) QKKme3 at positions corresponding to positions 24, 25, and 26 of SEQ ID NO: 195; and (iv) QYL at positions corresponding to positions 28, 29, and 30 of SEQ ID NO: 195.

In some embodiments, the disclosure provides a composition, comprising a Nectin-4 binding polypeptide having an amino acid sequence comprising at least 44 amino acids, wherein the amino acids include (i) a cysteine at each of four positions corresponding to 1, 20, 34, and 44 of SEQ ID NO: 200; (ii) TALA(Cit)LR (SEQ ID NO:247) at positions corresponding to positions 9-15 of SEQ ID NO: 200; (iii) QKKme3 at positions corresponding to positions 24, 25, and 26 of SEQ ID NO: 200; and (iv) QYL at positions corresponding to positions 28, 29, and 30 of SEQ ID NO: 200.

In some embodiments, the disclosure provides a composition, comprising a Nectin-4 binding polypeptide having an amino acid sequence, wherein the amino acid sequence comprises: at least four cysteines, which form two disulfide bonds; at least one modified lysine residue at a position corresponding to X12 and/or X26 of SEQ ID NO: 195, wherein the modification comprises at least one small alkyl group attached to the nitrogen of the lysine side chain, optionally comprising a methyl, dimethyl, trimethyl, or isopropyl group; at least 44 amino acids in length; and has a binding affinity for Nectin-4 stronger than 100 nM in a cell-based assay.

In some embodiments, the polypeptide is at least 40 amino acids in length, but no greater than 100 amino acids in length. In some embodiments, the polypeptide binds to Nectin-4 with an affinity of stronger than 10 nM in a cell-based assay.

In some embodiments, the amino acid sequence of the polypeptide shares at least 90% identity to any one of SEQ ID NOs: 3-158, 161-168, 177-208, or 212-215, but includes at least one lysine with at least one modification comprising at least one small alkyl group bonded to the nitrogen of the side chain, optionally selected from: trimethyl, dimethyl, monomethyl, and isopropyl. In some embodiments, the amino acid sequence of the polypeptide shares at least 90% identity to at least 44 amino acids of a reference polypeptide, which reference polypeptide is longer than 44 amino acids in length and binds to Nectin-4 with a strength of at least 10 nM on a cell-based assay, and/or has an inhibition constant of no greater than 10 nM.

In some embodiments, the amino acid sequence of the polypeptide shares at least 90% identity to at least 40 amino acids of any one of SEQ ID NOs: 3-158, 161-168, 177-208, or 212-215, provided that the 40 amino acids includes at least four cysteine residues that form two disulfide bridges.

In some embodiments, the amino acid sequence of the polypeptide shares at least 90% identity to at least 35 contiguous amino acids of any one of SEQ ID NOs: 3-158, 161-168, 177-208, or 212-215, provided that the 40 amino acids includes at least four cysteine residues that form two disulfide bridges. In some embodiments, the amino acid sequence of the polypeptide shares 100% identity to at least 44 amino acids of a reference polypeptide, which reference polypeptide is longer than 44 amino acids in length.

In some embodiments, the amino acid sequence shares 90% identity to at least 44 amino acids as set forth in any one of SEQ ID NO: 78, 83, 85, 99, 103, 162-168, 195, or 200.

In some embodiments, the amino acid sequence shares 100% identity to at least 44 amino acids as set forth in any one of SEQ ID NO: 78, 83, 85, 99, 103, 162-168, 195, or 200.

In some embodiments, the disclosure provides composition comprising a polypeptide having an amino acid sequence comprising SEQ ID NO: 195.

In some embodiments, the disclosure provides a composition comprising a compound as set forth in C251 of Table 2A, having an amino acid sequence comprising SEQ ID NO: 195

In some embodiments, the disclosure provides a composition comprising a polypeptide having an amino acid sequence comprising SEQ ID NO: 200.

In some embodiments, the disclosure provides a composition comprising a compound as set forth in C260 of Table 2A, having an amino acid sequence comprising SEQ ID NO: 200.

In some embodiments, the composition further comprises a radionuclide. In some embodiments, the radionuclide is Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, the disclosure provides a composition comprising a polypeptide having an amino acid sequence of at least 44 amino acids in length, but with four amino acid substitutions at positions corresponding to 12, 21, 26, and 32 of SEQ ID NO: 78, wherein the substitutions correspond to K12A. Y21Q, S26Kme3, and G32A.

In some embodiments, the C-terminus has an —OH or an —NH2.

In some embodiments, the binding affinity of the composition (e.g., the polypeptide) for Nectin-4 is stronger than 100 nM.

In some embodiments, the inhibition constant is no greater than 100 nM.

In some embodiments, the composition further comprises one or more of a linker, chelator, and radionuclide.

In some embodiments, the linker comprises or consists of a polyethylene glycol (PEG) linker of PEG4, PEG2, PEG, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- or (PEG)n, wherein n is from 1 to 10, (Gly)1-10, or any fragment or combination via covalent bond thereof.

In some embodiments, the chelator comprises or consists of DOTA, Crown. NOPO, Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, the radionuclide is selected from Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, if the polypeptide comprises any one of SEQ ID NO: 83, 85, 93, 99, 134, 138, 145, 155, 162-168, or 195 the polypeptide further comprises a linker, wherein the linker is PEG4, and an optional chelator, wherein the chelator is DOTA.

In some embodiments, when present, the linker is attached to the N-terminus of the polypeptide. In some embodiments, when present, the linker is attached to the C-terminus of the polypeptide.

In some embodiments, the C-terminal amino acid of the polypeptide is not a cysteine.

In some embodiments, when present, the chelator is attached to either the polypeptide or the linker.

In some embodiments, when present, the radionuclide is attached to the chelator.

In some embodiments, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M), L comprises a linker (L), C comprises a chelator (C), R comprises a radionuclide (R), and x is 1, 2, 3, or 4, wherein M comprises an amino acid sequence of any one of SEQ ID NO: 162-176, 178-208, or 212-215.

In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- or (PEG)n, wherein n is from 1 to 10, (Gly)1-10, or any fragment or combination via covalent bond thereof.

In some embodiments, the chelator comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, the radionuclide Ac-225, Cu-64, Ga-68, Lu-177, Pb-212, In-111, Cu-67, La-132, La-135, Ce-134, F-18, I-131, I-124, Pb-203. Th-232, Bi-123, Sm-153, Ra-225, Tb-165, or At-211.

In some embodiments, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a polypeptide (M), L comprises a linker (L), C comprises a chelator (C), R comprises a radionuclide (R), and x is 1, 2, 3, or 4, wherein M has an amino acid sequence comprising any one of those set forth in SEQ ID NOs: 162-176, 178-208, or 212-215.

In some embodiments, when L is present, L comprises or consists of a polyethylene glycol (PEG) linker of PEG4, PEG, PEG2, PEG6, PEG8, PEG12, PEG24, lys(MPB)-PEG4, PEG36, an ester linker, an amide linker, a maleimide linker a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a dTyr-Gly-Phe (yGF) linker, a caproleic acid linker, or (Gly)n-(gGlu)n- or (PEG)n, wherein n is from 1 to 10, (Gly)1-10, or any fragment or combination via covalent bond thereof.

In some embodiments, when C is present, C comprises or consists of DOTA, Crown, NOPO. Macropa, lead-specific chelator (PSC), N-succinimidyl 3-(tri-n-butylstannyl)benzoate (BuSTB), or N-succinimidyl 3-trimethylstannylbenzoate (MeSTB).

In some embodiments, when R is present, R comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, when present, the linker is attached to the N-terminus of the polypeptide. In some embodiments, when present, the linker is attached to the C-terminus of the polypeptide.

In some embodiments, the C-terminal amino acid of the polypeptide is not a cysteine.

In some embodiments, when present, the chelator is attached to either the polypeptide or the linker.

In some embodiments, when present, the radionuclide is attached to the chelator.

In some embodiments, the polypeptide comprises at least one disulfide bridge.

In some embodiments, the polypeptide comprises at least two disulfide bridges.

In some embodiments, the composition and/or polypeptide thereof selectively binds to Nectin-4 or a portion thereof.

In some embodiments, the polypeptide has a binding affinity for Nectin-4 or a portion thereof of 10 pM to 200 nM. 10 pM to 100 nM, or 10 nM to 100 nM, in vivo, ex vivo, or in vitro and/or as measured in a cell-based assay.

In some embodiments, the polypeptide has a binding inhibition constant of no greater than 100 nM.

A composition comprising a polypeptide-drug conjugate, comprising a polypeptide and at least one drug moiety, wherein the polypeptide comprises an amino acid sequence having at least 90% identity to at least 44 amino acids a polypeptide having an amino acid sequence set forth in any one of SEQ ID NOs: 3-158, 162-208, or 212-237.

In some embodiments, the drug moiety is selected from a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRMI, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a topoisomerase inhibitor, an auristatin (e.g., monomethyl auristatin E), and an immunotoxin.

In some embodiments, the disclosure provides a composition comprising an isolated compound or pharmaceutically acceptable salt thereof comprising an optional linker (L), and one or more of a polypeptide (M), chelator (C) or radionuclide (R), wherein M has an amino acid sequence comprising any one of SEQ ID NOs: 3-158, 161-168, 171-208, 212-215, or 216-237, including amino acid substitutions as set forth in Table 1C, Table 1D, Table 2C, Table 2D, Table 2E, Table 2F, or Table 2G.

In some embodiments, the disclosure provides a composition comprising, a compound designed to bind to Nectin-4, which compound comprises or consists of a polypeptide having an amino acid sequence comprising any one of SEQ ID NOs: 3-158, 161-168, 171-208, 212-215, or 216-237, including amino acid substitutions as set forth in Table 1C, Table 1D, Table 2C, Table 2D, Table 2E, Table 2F, or Table 2G, and further comprises a modified N and/or C-terminus.

In some embodiments, the modified N-terminus comprises one or more of an NH2, Acetyl, PEGn, wherein n=0-10, DOTA, or Biotin.

In some embodiments, the C terminus comprises an —NH2 or an —OH.

In some embodiments, the polypeptide selectively binds to Nectin-4 or a portion thereof.

In some embodiments, the polypeptide has a binding affinity of stronger than about 100 nM to Nectin-4, or a portion thereof, in vivo or in a cell-based assay.

Nectin-4

Nectin proteins are involved in cellular adhesion, migration, and polarization. Nectin-4 in most human organs was found to be homogenously expressed at weak to moderate levels, but specifically overexpressed in a majority of samples from metastatic urothelial, breast, lung, head/neck, and cervical tumors. One antibody-drug conjugate (ADC), enfortumab vedotin ("EV". Padcev; Astellas; Tokyo, Japan; and Seattle Genetics; Bothell, WA, USA), specifically targets Nectin-4 that is overexpressed on the surface of bladder tumor cells. EV is conjugated to a microtubule inhibitor (monomethyl auristatin E), which causes G2/M cell cycle arrest and apoptosis. In some embodiments, a miniprotein of the present disclosure targets Nectin-4 on tumor cells. (Bednova O. & Leyton J V. Int J Mol Sci. 2020 Oct. 1; 21(19): 7268).

Clinical trials with EV suggest that, in some embodiments, depending on context (e.g., type of cancer), targeting of Nectin-4 can be all or part of a successful therapeutic strategy for treatment of cancer. For example, EV approval in the United States followed PhI and II clinical trial results. In the PhI study, patients who had previously been treated with ICI therapy had an overall tumor objective response rate (ORR) of 42% and patients with particularly high tumor burden (e.g., liver metastases) has a 36% ORR. Furthermore, in the EV PhiI trial, patients with locally advanced or metastatic bladder cancer who had been previously treated with platinum-containing chemotherapy or ICI therapy were treated with EV and all tumors were positive for Nectin-4 and all characterized as having a "strong" level of expression. PD-L1 expression was also evaluated but results of EV therapy showed that at 10.2 months (median follow up time), the ORR was 44%, with a 12% complete response rate (CRR); PD-L1 status had no impact on ORR or CRR. This study showed that Nectin-4 is a relevant target in bladder cancer, PD-L1 status or therapy does not negatively impact efficacy of Nectin-4-based therapy and provides a targeted alternative or addition to ICI-based therapy.

EV is currently being explored in a Phase III study, as well as developed for a PhiI combination study with ICI therapy in cisplatin-ineligible patients. (Bednova O. & Leyton J V. Int J Mol Sci. 2020 Oct. 1; 21(19): 7268).

In some embodiments, Nectin-4 is an important target, alone or in conjunction with one or more therapies, for use with a miniprotein of the present disclosure.

In some embodiments, compositions provided by the present disclosure more specifically and effectively target a cell overexpressing Nectin-4 (e.g., a cancer cell) while minimizing or eliminating damage to surrounding cells not expressing or overexpressing Nectin-4 by providing a targeted composition including, in some embodiments, a chelator and/or alpha-emitter, which when combined with a miniprotein as provided herein provide specific, efficient and effective approaches to target cells overexpressing Nectin-4.

Importantly, novel compositions provided by the present disclosure are capable of specifically, efficiently, and effectively targeting Nectin-4 overexpressing cells with reduced toxicity as compared to presently available treatments. That is, in some embodiments, a composition targeting Nectin-4 as provided by the present disclosure provides improved treatment as compared to presently available treatments.

In some embodiments, a target of compositions of the present disclosure comprises or consists of Nectin-4. In some embodiments, a material change in a basic and novel characteristic of a polypeptide provided herein is the ability to strongly and specifically bind to its intended target (e.g., Nectin-4, e.g., Nectin-4 on a cancer cell) with minimal or no off-target effects and minimal kidney uptake (e.g., as compared to kidney uptake of previously developed Nectin-4 binding molecules). In some embodiments, Nectin-4 is expressed on the surface of a cell. In some embodiments, the cell is a cancer cell. In some such embodiments, the cancer cell is a tumor cell and the tumor is a solid tumor. In some embodiments, a level of Nectin-4 expressed in a tumor cell or population of tumor cells is higher than that expressed in non-tumor cells. In some embodiments, targeting of Nectin-4 by a miniprotein or composition comprising a miniprotein as provided by the present disclosure specifically targets a composition or one or more components thereof (e.g., a chelator and/or radionuclide) to a cancer cell or a tumor microenvironment (e.g., a location comprising a population of cancer cells or cells at risk of becoming cancer cells).

In some embodiments, miniproteins in accordance with the present disclosure specifically bind to Nectin-4. Without limitation, exemplary Nectin-4 miniproteins are provided in TABLE 2A and exemplary Nectin-4 sequences are shown in TABLE 1A.

In some embodiments, a miniprotein of the present disclosure comprises or consists of a polypeptide sequence corresponding to a poly peptide sequence shown in the TABLES 1B, 1C, and/or 2A or binding to a polypeptide as shown in TABLE 1A. In some embodiments, a miniprotein comprises or consists of an amino acid sequence having sequence at least 85% identical to a polypeptide sequence shown in the TABLE(s). In some embodiments, a miniprotein of the present disclosure has at least 70%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or higher identity to a polypeptide sequence according to TABLES 2A, 1B, 1C and/or 1D.

In some embodiments, compositions in accordance with the present disclosure specifically bind to Nectin-4 (e.g., through a miniprotein that specifically binds to Nectin-4). In some embodiments, a target is Nectin-4. In some such embodiments, a compound targeting Nectin-4 is disclosed in TABLE 1B.

In some embodiments, a composition comprising a miniprotein comprises or consists of a protein comprising a specific an amino acid sequence that binds to Nectin-4 or a portion thereof. In some embodiments, certain exemplary Nectin-4 binding miniproteins are In some such embodiments, such a Nectin-4 miniprotein comprises or consists of an amino acid sequence selected from any of SEQ ID NOs: 93, 99, 134, 138, 145, 155, and 178-215 or a functional variant or portion thereof (e.g., a functional fragment, e.g., a miniprotein that folds and binds to Nectin-4 or a portion thereof). In some embodiments, such a Nectin-4 miniprotein is a binding protein or part of a conjugate comprising such a binding protein as set forth in TABLE 2A. In particular embodiments, such a Nectin-4 miniprotein comprises or consists of an amino acid sequence selected from any of SEQ ID NOs: 99, 195, or 200 or a functional variant or portion thereof (e.g., a functional fragment, e.g., a miniprotein that folds and binds to Nectin-4 or a portion thereof). In some embodiments a Nectin-4 miniprotein comprises or consists of an amino acid sequence that is 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or more identical to any one of SEQ ID NOs: 93, 99, 134, 138, 145, 155, or 178-215 or a functional variant or portion thereof. In some embodiments a Nectin-4 miniprotein comprises or consists of an amino acid sequence that is 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or more identical to any one of SEQ ID NOs: 99, 195, or 200 or a functional variant or portion thereof.

In some embodiments, a Nectin-4 miniprotein comprises or consists of an amino acid sequence according to SEQ ID NO: 3. In some embodiments, a Nectin-4 miniprotein comprises or consists of an amino acid sequence according to SEQ ID NO: 4. In some embodiments, a Nectin-4 miniprotein comprises or consists of an amino acid sequence according to SEQ ID NO: 5. In some embodiments, a Nectin-4 miniprotein comprises or consists of an amino acid sequence according to SEQ ID NO: 6. In some embodiments, a Nectin-4 miniprotein comprises or consists of an amino acid sequence according to SEQ ID NO: 7. In some embodiments, a Nectin-4 miniprotein comprises or consists of an amino acid sequence according to SEQ ID NO: 8. In some embodiments, a Nectin-4 miniprotein comprises or consists of an amino acid sequence according to SEQ ID NO: 9. In some embodiments, a Nectin-4 miniprotein comprises or consists of an amino acid sequence according to SEQ ID NO: 10. In some embodiments, a Nectin-4 miniprotein comprises or consists of an amino acid sequence according to SEQ ID NO: 11. In some embodiments, a Nectin-4 miniprotein comprises or consists of an amino acid sequence according to SEQ ID NO: 12. In some embodiments, a Nectin-4 miniprotein comprises or consists of an amino acid sequence according to SEQ ID NO: 13. In some embodiments, a Nectin-4 miniprotein comprises or consists of an amino acid sequence according to SEQ ID NO: 14. In some embodiments, a Nectin-4 miniprotein comprises or consists of an amino acid sequence according to SEQ ID NO: 15. In some embodiments, a Nectin-4 miniprotein comprises or consists of an amino acid sequence according to SEQ ID NO: 16. In some embodiments, a Nectin-4 miniprotein comprises or consists of an amino acid sequence according to SEQ ID NO: 17. In some embodiments, a Nectin-4 miniprotein comprises or consists of an amino acid sequence according to SEQ ID NO: 18. In some embodiments, a Nectin-4 miniprotein comprises or consists of an amino acid sequence according to SEQ ID NO: 19. In some embodiments, a Nectin-4 miniprotein comprises or consists of an amino acid sequence according to SEQ ID NO: 20. In some embodiments, a Nectin-4 miniprotein comprises or consists of an amino acid sequence according to SEQ ID NO: 21. In some embodiments, a Nectin-4 miniprotein comprises or consists of an amino acid sequence according to SEQ ID NO: 22. In some embodiments, a Nectin-4 miniprotein comprises or consists of an amino acid sequence according to SEQ ID NO: 23. In some embodiments, a Nectin-4 miniprotein comprises or consists of an amino acid sequence according to SEQ ID NO: 24. In some embodiments, a Nectin-4 miniprotein comprises or consists of an amino acid sequence according to SEQ ID NO: 25. In some embodiments, a Nectin-4 miniprotein comprises or consists of an amino acid sequence according to SEQ ID NO: 26. In some embodiments, a Nectin-4 miniprotein comprises or consists of an amino acid sequence according to SEQ ID NO: 27. In some embodiments, a Nectin-4 miniprotein comprises or consists of an amino acid sequence according to SEQ ID NO: 28. In some embodiments, a Nectin-4 miniprotein comprises or consists of an amino acid sequence according to SEQ ID NO: 29. In some embodiments, a Nectin-4 miniprotein comprises or consists of an amino acid sequence according to SEQ ID NO: 30. In some embodiments, a Nectin-4 miniprotein comprises or consists of an amino acid sequence according to SEQ ID NO: 31. In some embodiments, a Nectin-4 miniprotein comprises or consists of an amino acid sequence according to SEQ ID NO: 32. In some embodiments, a Nectin-4 miniprotein comprises or consists of an amino acid sequence according to SEQ ID NO: 33. In some embodiments, a Nectin-4 miniprotein comprises or consists of an amino acid sequence according to SEQ ID NO: 34. In some embodiments, a Nectin-4 miniprotein comprises or consists of an amino acid sequence according to SEQ ID NO: 35. In some embodiments, a Nectin-4 miniprotein comprises or consists of an amino acid sequence according to SEQ ID NO: 36. In some embodiments, a Nectin-4 miniprotein comprises or consists of an amino acid sequence according to SEQ ID NO: 37. In some embodiments, a Nectin-4 miniprotein comprises or consists of an amino acid sequence according to SEQ ID NO: 38. In some embodiments, a Nectin-4 miniprotein comprises or consists of an amino acid sequence according to SEQ ID NO: 39. In some embodiments, a Nectin-4 miniprotein comprises or consists of an amino acid sequence according to SEQ ID NO: 40. In some embodiments, a Nectin-4 miniprotein comprises or consists of an amino acid sequence according to SEQ ID NO: 41. In some embodiments, a Nectin-4 miniprotein comprises or consists of an amino acid sequence according to SEQ ID NO: 42. In some embodiments, a Nectin-4 miniprotein comprises or consists of an amino acid sequence according to SEQ ID NO: 43. In some embodiments, a Nectin-4 miniprotein comprises or consists of an amino acid sequence according to SEQ ID NO: 44. In some embodiments, a Nectin-4 miniprotein comprises or consists of an amino acid sequence according to SEQ ID NO: 45. In some embodiments, a Nectin-4 miniprotein comprises or consists of an amino acid sequence according to SEQ ID NO: 46. In some embodiments, a Nectin-4 miniprotein comprises or consists of an amino acid sequence according to SEQ ID NO: 47. In some embodiments, a Nectin-4 miniprotein comprises or consists of an amino acid sequence according to SEQ ID NO: 48. In some embodiments, a Nectin-4 miniprotein comprises or consists of an amino acid sequence according to SEQ ID NO: 49. In some embodiments, a Nectin-4 miniprotein comprises or consists of an amino acid sequence according to SEQ ID NO: 50. In some embodiments, a Nectin-4 miniprotein comprises or consists of an amino acid sequence according to SEQ ID NO: 51. In some embodiments, a Nectin-4 miniprotein comprises or consists of an amino acid sequence according to SEQ ID NO: 52. In some embodiments, a Nectin-4 miniprotein comprises or consists of an amino acid sequence according to SEQ ID NO: 53. In some embodiments, a Nectin-4 miniprotein comprises or consists of an amino acid sequence according to SEQ ID NO: 54. In some embodiments, a Nectin-4 miniprotein comprises or consists of an amino acid sequence according to SEQ ID NO: 55. In some embodiments, a Nectin-4 miniprotein comprises or consists of an amino acid sequence according to SEQ ID NO: 56. In some embodiments, a Nectin-4 miniprotein comprises or consists of an amino acid sequence according to SEQ ID NO: 57. In some embodiments, a Nectin-4 miniprotein comprises or consists of an amino acid sequence according to SEQ ID NO: 58. In some embodiments, a Nectin-4 miniprotein comprises or consists of an amino acid sequence according to SEQ ID NO: 59. In some embodiments, a Nectin-4 miniprotein comprises or consists of an amino acid sequence according to SEQ ID NO: 60. In some embodiments, a Nectin-4 miniprotein comprises or consists of an amino acid sequence according to SEQ ID NO: 61. In some embodiments, a Nectin-4 miniprotein comprises or consists of an amino acid sequence according to SEQ ID NO: 62. In some embodiments, a Nectin-4 miniprotein comprises or consists of an amino acid sequence according to SEQ ID NO: 63. In some embodiments, a Nectin-4 miniprotein comprises or consists of an amino acid sequence according to SEQ ID NO: 64. In some embodiments, a Nectin-4 miniprotein comprises or consists of an amino acid sequence according to SEQ ID NO: 65. In some embodiments, a Nectin-4 miniprotein comprises or consists of an amino acid sequence according to SEQ ID NO: 66. In some embodiments, a Nectin-4 miniprotein comprises or consists of an amino acid sequence according to SEQ ID NO: 67. In some embodiments, a Nectin-4 miniprotein comprises or consists of an amino acid sequence according to SEQ ID NO: 68. In some embodiments, a Nectin-4 miniprotein comprises or consists of an amino acid sequence according to SEQ ID NO: 69. In some embodiments, a Nectin-4 miniprotein comprises or consists of an amino acid sequence according to SEQ ID NO: 70. In some embodiments, a Nectin-4 miniprotein comprises or consists of an amino acid sequence according to SEQ ID NO: 71. In some embodiments, a Nectin-4 miniprotein comprises or consists of an amino acid sequence according to SEQ ID NO: 72. In some embodiments, a Nectin-4 miniprotein comprises or consists of an amino acid sequence according to SEQ ID NO: 73. In some embodiments, a Nectin-4 miniprotein comprises or consists of an amino acid sequence according to SEQ ID NO: 74. In some embodiments, a Nectin-4 miniprotein comprises or consists of an amino acid sequence according to SEQ ID NO: 75. In some embodiments, a Nectin-4 miniprotein comprises or consists of an amino acid sequence according to SEQ ID NO: 76. In some embodiments, a Nectin-4 miniprotein comprises or consists of an amino acid sequence according to SEQ ID NO: 77. In some embodiments, a Nectin-4 miniprotein comprises or consists of an amino acid sequence according to SEQ ID NO: 78. In some embodiments, a Nectin-4 miniprotein comprises or consists of an amino acid sequence according to SEQ ID NO: 79. In some embodiments, a Nectin-4 miniprotein comprises or consists of an amino acid sequence according to SEQ ID NO: 80. In some embodiments, a Nectin-4 miniprotein comprises or consists of an amino acid sequence according to SEQ ID NO: 81. In some embodiments, a Nectin-4 miniprotein comprises or consists of an amino acid sequence according to SEQ ID NO: 82. In some embodiments, a Nectin-4 miniprotein comprises or consists of an amino acid sequence according to SEQ ID NO: 83. In some embodiments, a Nectin-4 miniprotein comprises or consists of an amino acid sequence according to SEQ ID NO: 84. In some embodiments, a Nectin-4 miniprotein comprises or consists of an amino acid sequence according to SEQ ID NO: 85. In some embodiments, a Nectin-4 miniprotein comprises or consists of an amino acid sequence according to SEQ ID NO: 86. In some embodiments, a Nectin-4 miniprotein comprises or consists of an amino acid sequence according to SEQ ID NO: 87. In some embodiments, a Nectin-4 miniprotein comprises or consists of an amino acid sequence according to SEQ ID NO: 88. In some embodiments, a Nectin-4 miniprotein comprises or consists of an amino acid sequence according to SEQ ID NO: 89. In some embodiments, a Nectin-4 miniprotein comprises or consists of an amino acid sequence according to SEQ ID NO: 90. In some embodiments, a Nectin-4 miniprotein comprises or consists of an amino acid sequence according to SEQ ID NO: 91. In some embodiments, a Nectin-4 miniprotein comprises or consists of an amino acid sequence according to SEQ ID NO: 92. In some embodiments, a Nectin-4 mini protein comprises or consists of an amino acid sequence according to SEQ ID NO: 93. In some embodiments, a Nectin-4 miniprotein comprises or consists of an amino acid sequence according to SEQ ID NO: 94. In some embodiments, a Nectin-4 miniprotein comprises or consists of an amino acid sequence according to SEQ ID NO: 95. In some embodiments, a Nectin-4 miniprotein comprises or consists of an amino acid sequence according to SEQ ID NO: 96. In some embodiments, a Nectin-4 miniprotein comprises or consists of an amino acid sequence according to SEQ ID NO: 97. In some embodiments, a Nectin-4 mini protein comprises or consists of an amino acid sequence according to SEQ ID NO: 98. In some embodiments, a Nectin-4 miniprotein comprises or consists of an amino acid sequence according to SEQ ID NO: 99. In some embodiments, a Nectin-4 miniprotein comprises or consists of an amino acid sequence according to SEQ ID NO: 100. In some embodiments, a Nectin-4 miniprotein comprises or consists of an amino acid sequence according to SEQ ID NO: 101. In some embodiments, a Nectin-4 miniprotein comprises or consists of an amino acid sequence according to SEQ ID NO: 102. In some embodiments, a Nectin-4 miniprotein comprises or consists of an amino acid sequence according to SEQ ID NO: 103. In some embodiments, a Nectin-4 miniprotein comprises or consists of an amino acid sequence according to SEQ ID NO: 104. In some embodiments, a Nectin-4 miniprotein comprises or consists of an amino acid sequence according to SEQ ID NO: 105. In some embodiments, a Nectin-4 miniprotein comprises or consists of an amino acid sequence according to SEQ ID NO: 106. In some embodiments, a Nectin-4 miniprotein comprises or consists of an amino acid sequence according to SEQ ID NO: 107. In some embodiments, a Nectin-4 miniprotein comprises or consists of an amino acid sequence according to SEQ ID NO: 108. In some embodiments, a Nectin-4 miniprotein comprises or consists of an amino acid sequence according to SEQ ID NO: 109. In some embodiments, a Nectin-4 miniprotein comprises or consists of an amino acid sequence according to SEQ ID NO: 110. In some embodiments, a Nectin-4 miniprotein comprises or consists of an amino acid sequence according to SEQ ID NO: 111. In some embodiments, a Nectin-4 miniprotein comprises or consists of an amino acid sequence according to SEQ ID NO: 112. In some embodiments, a Nectin-4 miniprotein comprises or consists of an amino acid sequence according to SEQ ID NO: 113. In some embodiments, a Nectin-4 miniprotein comprises or consists of an amino acid sequence according to SEQ ID NO: 114. In some embodiments, a Nectin-4 miniprotein comprises or consists of an amino acid sequence according to SEQ ID NO: 115. In some embodiments, a Nectin-4 miniprotein comprises or consists of an amino acid sequence according to SEQ ID NO: 116. In some embodiments, a Nectin-4 miniprotein comprises or consists of an amino acid sequence according to SEQ ID NO: 117. In some embodiments, a Nectin-4 miniprotein comprises or consists of an amino acid sequence according to SEQ ID NO: 118. In some embodiments, a Nectin-4 miniprotein comprises or consists of an amino acid sequence according to SEQ ID NO: 119. In some embodiments, a Nectin-4 miniprotein comprises or consists of an amino acid sequence according to SEQ ID NO: 120. In some embodiments, a Nectin-4 miniprotein comprises or consists of an amino acid sequence according to SEQ ID NO: 121. In some embodiments, a Nectin-4 miniprotein comprises or consists of an amino acid sequence according to SEQ ID NO: 122. In some embodiments, a Nectin-4 miniprotein comprises or consists of an amino acid sequence according to SEQ ID NO: 123. In some embodiments, a Nectin-4 miniprotein comprises or consists of an amino acid sequence according to SEQ ID NO: 124. In some embodiments, a Nectin-4 miniprotein comprises or consists of an amino acid sequence according to SEQ ID NO: 125. In some embodiments, a Nectin-4 miniprotein comprises or consists of an amino acid sequence according to SEQ ID NO: 126. In some embodiments, a Nectin-4 miniprotein comprises or consists of an amino acid sequence according to SEQ ID NO: 127. In some embodiments, a Nectin-4 miniprotein comprises or consists of an amino acid sequence according to SEQ ID NO: 128. In some embodiments, a Nectin-4 miniprotein comprises or consists of an amino acid sequence according to SEQ ID NO: 129. In some embodiments, a Nectin-4 miniprotein comprises or consists of an amino acid sequence according to SEQ ID NO: 130. In some embodiments, a Nectin-4 miniprotein comprises or consists of an amino acid sequence according to SEQ ID NO: 131. In some embodiments, a Nectin-4 miniprotein comprises or consists of an amino acid sequence according to SEQ ID NO: 132. In some embodiments, a Nectin-4 miniprotein comprises or consists of an amino acid sequence according to SEQ ID NO: 133. In some embodiments, a Nectin-4 miniprotein comprises or consists of an amino acid sequence according to SEQ ID NO: 134. In some embodiments, a Nectin-4 miniprotein comprises or consists of an amino acid sequence according to SEQ ID NO: 135. In some embodiments, a Nectin-4 miniprotein comprises or consists of an amino acid sequence according to SEQ ID NO: 136. In some embodiments, a Nectin-4 miniprotein comprises or consists of an amino acid sequence according to SEQ ID NO: 137. In some embodiments, a Nectin-4 miniprotein comprises or consists of an amino acid sequence according to SEQ ID NO: 138. In some embodiments, a Nectin-4 miniprotein comprises or consists of an amino acid sequence according to SEQ ID NO: 139. In some embodiments, a Nectin-4 miniprotein comprises or consists of an amino acid sequence according to SEQ ID NO: 140. In some embodiments, a Nectin-4 miniprotein comprises or consists of an amino acid sequence according to SEQ ID NO: 141. In some embodiments, a Nectin-4 miniprotein comprises or consists of an amino acid sequence according to SEQ ID NO: 142. In some embodiments, a Nectin-4 miniprotein comprises or consists of an amino acid sequence according to SEQ ID NO: 143. In some embodiments, a Nectin-4 miniprotein comprises or consists of an amino acid sequence according to SEQ ID NO: 144. In some embodiments, a Nectin-4 miniprotein comprises or consists of an amino acid sequence according to SEQ ID NO: 145. In some embodiments, a Nectin-4 miniprotein comprises or consists of an amino acid sequence according to SEQ ID NO: 146. In some embodiments, a Nectin-4 miniprotein comprises or consists of an amino acid sequence according to SEQ ID NO: 147. In some embodiments, a Nectin-4 miniprotein comprises or consists of an amino acid sequence according to SEQ ID NO: 148. In some embodiments, a Nectin-4 miniprotein comprises or consists of an amino acid sequence according to SEQ ID NO: 149. In some embodiments, a Nectin-4 miniprotein comprises or consists of an amino acid sequence according to SEQ ID NO: 150. In some embodiments, a Nectin-4 miniprotein comprises or consists of an amino acid sequence according to SEQ ID NO: 151. In some embodiments, a Nectin-4 miniprotein comprises or consists of an amino acid sequence according to SEQ ID NO: 152. In some embodiments, a Nectin-4 miniprotein comprises or consists of an amino acid sequence according to SEQ ID NO: 153. In some embodiments, a Nectin-4 miniprotein comprises or consists of an amino acid sequence according to SEQ ID NO: 154. In some embodiments, a Nectin-4 miniprotein comprises or consists of an amino acid sequence according to SEQ ID NO: 155. In some embodiments, a Nectin-4 miniprotein comprises or consists of an amino acid sequence according to SEQ ID NO: 156. In some embodiments, a Nectin-4 miniprotein comprises or consists of an amino acid sequence according to SEQ ID NO: 157. In some embodiments, a Nectin-4 miniprotein comprises or consists of an amino acid sequence according to SEQ ID NO: 158. In some embodiments, a Nectin-4 miniprotein comprises or consists of an amino acid sequence according to SEQ ID NO: 161. In some embodiments, a Nectin-4 miniprotein comprises or consists of an amino acid sequence according to SEQ ID NO: 162. In some embodiments, a Nectin-4 miniprotein comprises or consists of an amino acid sequence according to SEQ ID NO: 163. In some embodiments, a Nectin-4 miniprotein comprises or consists of an amino acid sequence according to SEQ ID NO: 164. In some embodiments, a Nectin-4 miniprotein comprises or consists of an amino acid sequence according to SEQ ID NO: 165. In some embodiments, a Nectin-4 miniprotein comprises or consists of an amino acid sequence according to SEQ ID NO: 166. In some embodiments, a Nectin-4 miniprotein comprises or consists of an amino acid sequence according to SEQ ID NO: 167. In some embodiments, a Nectin-4 miniprotein comprises or consists of an amino acid sequence according to SEQ ID NO: 168. In some embodiments, a Nectin-4 miniprotein comprises or consists of an amino acid sequence according to SEQ ID NO: 177. In some embodiments, a Nectin-4 miniprotein comprises or consists of an amino acid sequence according to SEQ ID NO: 178. In some embodiments, a Nectin-4 miniprotein comprises or consists of an amino acid sequence according to SEQ ID NO: 179. In some embodiments, a Nectin-4 miniprotein comprises or consists of an amino acid sequence according to SEQ ID NO: 180. In some embodiments, a Nectin-4 miniprotein comprises or consists of an amino acid sequence according to SEQ ID NO: 181. In some embodiments, a Nectin-4 miniprotein comprises or consists of an amino acid sequence according to SEQ ID NO: 182. In some embodiments, a Nectin-4 miniprotein comprises or consists of an amino acid sequence according to SEQ ID NO: 183. In some embodiments, a Nectin-4 miniprotein comprises or consists of an amino acid sequence according to SEQ ID NO: 184. In some embodiments, a Nectin-4 miniprotein comprises or consists of an amino acid sequence according to SEQ ID NO: 185. In some embodiments, a Nectin-4 miniprotein comprises or consists of an amino acid sequence according to SEQ ID NO: 186. In some embodiments, a Nectin-4 miniprotein comprises or consists of an amino acid sequence according to SEQ ID NO: 187. In some embodiments, a Nectin-4 miniprotein comprises or consists of an amino acid sequence according to SEQ ID NO: 188. In some embodiments, a Nectin-4 miniprotein comprises or consists of an amino acid sequence according to SEQ ID NO: 189. In some embodiments, a Nectin-4 miniprotein comprises or consists of an amino acid sequence according to SEQ ID NO: 190. In some embodiments, a Nectin-4 miniprotein comprises or consists of an amino acid sequence according to SEQ ID NO: 191. In some embodiments, a Nectin-4 miniprotein comprises or consists of an amino acid sequence according to SEQ ID NO: 192. In some embodiments, a Nectin-4 miniprotein comprises or consists of an amino acid sequence according to SEQ ID NO: 193. In some embodiments, a Nectin-4 miniprotein comprises or consists of an amino acid sequence according to SEQ ID NO: 194. In some embodiments, a Nectin-4 miniprotein comprises or consists of an amino acid sequence according to SEQ ID NO: 195. In some embodiments, a Nectin-4 miniprotein comprises or consists of an amino acid sequence according to SEQ ID NO: 196. In some embodiments, a Nectin-4 miniprotein comprises or consists of an amino acid sequence according to SEQ ID NO: 197. In some embodiments, a Nectin-4 miniprotein comprises or consists of an amino acid sequence according to SEQ ID NO: 198. In some embodiments, a Nectin-4 miniprotein comprises or consists of an amino acid sequence according to SEQ ID NO: 199. In some embodiments, a Nectin-4 miniprotein comprises or consists of an amino acid sequence according to SEQ ID NO: 200. In some embodiments, a Nectin-4 miniprotein comprises or consists of an amino acid sequence according to SEQ ID NO: 201. In some embodiments, a Nectin-4 miniprotein comprises or consists of an amino acid sequence according to SEQ ID NO: 202. In some embodiments, a Nectin-4 miniprotein comprises or consists of an amino acid sequence according to SEQ ID NO: 203. In some embodiments, a Nectin-4 miniprotein comprises or consists of an amino acid sequence according to SEQ ID NO: 204. In some embodiments, a Nectin-4 miniprotein comprises or consists of an amino acid sequence according to SEQ ID NO: 205. In some embodiments, a Nectin-4 miniprotein comprises or consists of an amino acid sequence according to SEQ ID NO: 206. In some embodiments, a Nectin-4 miniprotein comprises or consists of an amino acid sequence according to SEQ ID NO: 207. In some embodiments, a Nectin-4 miniprotein comprises or consists of an amino acid sequence according to SEQ ID NO: 208. In some embodiments, a Nectin-4 miniprotein comprises or consists of an amino acid sequence according to SEQ ID NO: 212. In some embodiments, a Nectin-4 miniprotein comprises or consists of an amino acid sequence according to SEQ ID NO: 213. In some embodiments, a Nectin-4 miniprotein comprises or consists of an amino acid sequence according to SEQ ID NO: 214. In some embodiments, a Nectin-4 miniprotein comprises or consists of an amino acid sequence according to SEQ ID NO: 215.

In some embodiments, a Nectin-4 binding miniprotein comprises or consists of an amino acid sequence according to any one of SEQ ID NOs: 3-158, 161-168, 177-208, or 212-215 and can have different N- and/or C-terminal ends, such as, for example, an Acetyl. NH2, Biotin-PEG4, DOTA-PEG4, radiolabel, etc. on its N-terminus and an —OH or —NH2 on its C-terminus. N- and/or C-termini of Nectin-4 binding miniproteins of the disclosure can include but are not limited to acetyl, acid, or amide (e.g., Acetyl, NH2, OH), such as provided in exemplary compounds and miniproteins of TABLE 2A. In some embodiments, a polypeptide according to the disclosure may have various modifications to its N-terminus (e.g., a linker, chelator, and/or radionuclide, e.g., such as set forth in exemplary compounds in TABLE 2A) or its C-terminus (e.g., a linker, chelator, and/or radionuclide). In some embodiments, the C-terminus of a given polypeptide can have an acid or amide group on its C-terminus (see, e.g., TABLE 2A). A given polypeptide having a particular amino acid sequence can have one or more N-terminal and/or C-terminal differences without materially changing the utility or function of the polypeptide, such as for binding to Nectin-4 (e.g., for detection and/or treatment of cancer).

In some embodiments, a decoy comprises or consists of an amino acid sequence according to SEQ ID NO: 209. In some embodiments, a decoy comprises or consists of an amino acid sequence according to SEQ ID NO: 210. In some embodiments, a decoy comprises or consists of an amino acid sequence according to SEQ ID NO: 211.

In some embodiments a Nectin-4 miniprotein comprises or consists of an amino acid sequence that is 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or more identical to any one of SEQ ID NOs: 78, 93, 99, 134, 138, 145, 155, 161-168, 177-208, or 212-215 or a functional variant or portion thereof. In some embodiments a Nectin-4 miniprotein comprises or consists of an amino acid sequence that is 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or more identical to any one of SEQ ID NOs: 78, 93, 99, 134, 138, 145, 155, 194, 195, 200, 203, or 204 or a functional variant or portion thereof. In some embodiments a Nectin-4 miniprotein comprises or consists of an amino acid sequence that is 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or more identical to any one of SEQ ID NOs: 99, 195, and 200 or a functional variant or portion thereof. In some embodiments, a miniprotein of SEQ ID NOs: 216-237 has one or more substitutions as set forth in TABLE 1C. In some embodiments, a miniprotein of SEQ ID NOs: 170-176 or 243-246 and has one or more substitutions as set forth in TABLE 1D. In some embodiments, a Nectin-4 miniprotein comprises or consists of an amino acid sequence that is 80%, 85%, 90%, 95%, 96%, 97%, 98%, 98.1%, 98.2%, 98.3%, 98.4%, 98.5%, 98.6%, 98.7%, 98.8%. 98.9%, 99%, 99.1%, 99.2%, 99.3%, 99.4%, 99.5%, 99.6%, 99.7%, 99.8%, 99.9% or more identical to any one of SEQ ID NOs: 216-237 or a functional variant or portion thereof having one or more substitutions as set forth in TABLE 1C, TABLE 2C. TABLE 2D, TABLE 2E, TABLE 2E. TABLE 2F, or TABLE 2G.

In some embodiments, the present disclosure provides a polynucleotide encoding a polypeptide that comprises or consists of one or more portions of a composition as provided herein. In some embodiments, the present disclosure provides a vector and/or host cell comprising a sequence encoding one or more components of a composition as provided herein. In some embodiments, the present disclosure provides methods of detecting a target. In some embodiments, a method as provided herein comprises detecting presence of a target for, e.g., imaging, e.g., diagnostic, prognostic, and/or monitoring purposes, e.g., treatment. In some embodiments, the present disclosure provides methods of treatment and/or methods of manufacturing using composition as provided herein (e.g., a miniprotein, e.g., a linker-chelator, e.g., a miniprotein comprising one or more of a linker, chelator, and radionuclide, etc.). In some embodiments, a method of treatment comprises administering a composition as provided herein to a subject in need thereof.

Polypeptides

Among other things, the present disclosure provides polypeptides. In some embodiments a polypeptide is assembled using solid phase synthesis methods. In some embodiments, a polypeptide is recombinant. In some embodiments, a polypeptide comprises or consists of a miniprotein. In some such embodiments, a miniprotein comprises or consists of a binder. In some embodiments, polypeptides of the present disclosure (including muteins, allelic variants, fragments, derivatives, and analogs) are encoded by polynucleotides as described and provided herein.

In some embodiments, a polypeptide has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to a portion of an amino acid sequence set forth in TABLE 2A. For example, in some embodiments, a polypeptide has an amino acid sequence that is 75%, 80%, 85%, 901%, 95%, 96%, 97%, 98%, 98, 1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to 30, 31, 32, 33, 34, 35, 36, 37, 38, 39, 40, 41, 42, 43, or 44 amino acids of a given polypeptide such as those set forth in TABLE 2A. In some embodiments, a polypeptide has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 contiguous amino acids of a given polypeptide such as those set forth in TABLE 2A.

In some embodiments, a polypeptide is a miniprotein. In some such embodiments, the mini protein is capable of binding to a target (e.g., Nectin-4 or a portion thereof) as provided herein.

In some embodiments, a miniprotein of the present disclosure comprises or consists of a polypeptide capable of binding to target as shown in TABLE 1A.

In some embodiments, the present disclosure provides binders comprising or consisting of a fragment of a polypeptide as provided herein. In some such embodiments, fragments include at least 20 contiguous amino acids, more preferably at least 25, 30, 35, 40, 45, 50, 55, 60, 65, 70, 75, 80, 85, 90, 95 or more contiguous amino acids.

In some embodiments, miniproteins of the present disclosure can also include fusions or conjugates with one or more other components, such as heterologous polypeptides. For example, in some embodiments, heterologous sequences can comprise or consist of sequences designed to facilitate purification, e.g., histidine tags, and/or visualization of recombinantly-expressed proteins. Other non-limiting examples of such fusions or conjugates include those that permit display of the encoded protein on the surface of a phage or a cell, including any detectable or visualizable component such as, e.g., green fluorescent protein (GFP), and fusions to the IgG Fc region.

In some embodiments, a miniprotein comprises or consists of a specific amino acid sequence. In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%. 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 3-158, 161-168, 170-208, 212-237, 243-246, 248 and/or according to TABLES 1B and/or 1C, 1D and/or 2A.

In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any amino acid sequences set forth in TABLE 2A.

In some embodiments, a miniprotein has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to a portion or all of an amino acid sequence set forth in TABLE 2A. For example, in some embodiments, a miniprotein has an amino acid sequence that is 75%, 80%, 85%, 90%, 95%, 96% 97%, 98%, 98.1%, 98.2%, 98.3%, 98.4%, 98.5%, 98.6%. 98.7%, 98.8%, 98.9%, 99%, 99.1%, 99.2%, 99.3%, 99.4%, 99.5%, 99.6%, 99.7%, 99.8%, 999%, or 100% identical to 30, 31, 32, 33, 34, 35, 36, 37, 38, 39, 40, 41, 42, 43, or 44 amino acids of a given polypeptide such as those set forth in TABLE 2A. In some embodiments, a miniprotein has an amino acid sequence that is 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 contiguous amino acids of a given polypeptide such as those set forth in TABLE 2A.

In some embodiments, a polypeptide (e.g., a miniprotein) has an amino acid sequence with a certain percent identity over a certain percent coverage (e.g., of a reference sequence). That is, a Nectin-4 binding polypeptide (e.g., a reference molecule) as provided herein can have 70, 75, 80, 85, 90, 95, 99, or 100 percent identity to a given query but over a percent coverage of that molecule (e.g., 10, 20, 30, 40, 50, 60, 70, 80, 90, 100%), where if the query molecule is shorter it may have a percent identity and a percent coverage that are different (e.g., 100% identity and 90% coverage). If the query molecule is longer, than the percent identity and coverage could each be 100% with respect to the reference molecule, and the reference molecule would have a percent identity over a length (e.g., at least 20, 25, 30, amino acids) of the query molecule. For example, in some embodiments, if a reference sequence (e.g., a miniprotein as provided herein) is shorter than a query sequence, such a query sequence is within the scope of the present disclosure if it has a length of reference sequence that aligns with the query sequence, wherein the percent identity is determined over at least a minimum length of the alignment between the two sequences (query and reference). That is, if a polypeptide disclosed herein is longer than a query sequence, a percent identity is determined by aligning the reference and query and determining the percent identity as between the query and the portion of the reference sequence over which it aligns. Conversely, where a query sequence is longer than a reference sequence, percent identity equals an identity over an aligned portion with the reference sequence. That is, if the reference sequence is shorter, the query sequence can fall within the scope of a reference sequence if it aligns at a claimed percent identity over the aligned portion between the two polypeptides (reference and query).

As used herein and known to those of skill in the art, the twenty conventional amino acids and their abbreviations follow conventional usage. See Immunology-A Synthesis (Golub and Gren eds., Sinauer Associates, Sunderland. Mass., 2nd ed. 1991), which is incorporated herein by reference. In some embodiments, an amino acid of the present disclosure may be a stereoisomer (e.g., D-amino acids) of the twenty conventional amino acids. In some embodiments, an amino acid in a polypeptide of the present disclosure may be a non-natural amino acid. For example, amino acids such as α-, α-disubstituted amino acids, N-alkyl amino acids, and other unconventional amino acids may also be suitable components for polypeptides of the present disclosure. Examples of unconventional amino acids include: 4-hydroxyproline, γ-carboxyglutamate, ε-N-monomethyllysine, ε-N,N-dimethyllysine, ε-N,N,N-trimethyllysine, ε-N-acetyllysine, ε-N-isopropyl-lysine, O-phosphoserine, N-acetylserine, N-formylmethionine, 3-methylhistidine, 5-hydroxylysine, N-methylarginine, and other similar amino acids and imino acids (e.g., 4-hydroxyproline). Arrangements of polypeptide sequence notations used herein have a left-side end corresponding to the amino terminal and a right-side end corresponding to the carboxy-terminal end, in accordance with standard usage and convention.

In some embodiments, miniproteins of the present disclosure comprising two or more cysteine residues, such as those set forth in TABLE 2A, have cysteine residues connected via disulfide bridges (e.g., via natural folding).

In some embodiments, cysteine connections are between positions corresponding to Cys1 and Cys34; and Cys20 and Cys44 of a reference sequence such as set forth in TABLE 2A (e.g., SEQ ID NO: 195). In some embodiments, cysteine connections are between Cys1 and Cys20, and Cys34 and Cys44. In some embodiments, cysteine connections are between Cys1 and Cys44; and Cys20 and Cys34.

In some embodiments, In some embodiments, the disulfide bridge or bridges comprise two or four cysteines at positions corresponding to 1, 20, 34, and 44 of SEQ ID NO: 195, wherein the cysteine corresponding to position 1 can form a disulfide bridge with the cysteine corresponding to position 20, 34, or 44. In some embodiments, the cysteine corresponding to position 20 can form a disulfide bridge with the cysteine corresponding to position 1, 34, or 44. In some embodiments, the cysteine corresponding to position 34 can form a disulfide bridge with the cysteine corresponding to position 1, 20, or 44. In some embodiments, the cysteine corresponding to position 44 can form a disulfide bridge with the cysteine corresponding to position 1, 20, or 44. In some embodiments, where four cysteines are present and correspond to positions 1, 20, 34, and 44 of SEQ ID NO: 195, pairings can comprise 1 paired with 34 and 20 paired with 44, 1 paired 20 and 34 paired with 44, or 1 paired with 44 and 20 paired with 34 (e.g. disulfide bridges between the two cysteines of the pair).

In some embodiments, the present disclosure provides a miniprotein comprising or consisting of an amino acid sequence set forth in SEQ ID NO: 3-158, 161-168, 170-208, 212-237, 243-246, 248 and/or as set forth in TABLES 1B, 1C, 1D, and/or 2A or a portion or functional variant thereof. In some embodiments, a miniprotein comprises or consists of an amino acid sequence having at least 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or greater sequence identity to SEQ ID NO: 3-158, or 177-237 and/or as set forth in TABLES 1B, 1C, 1D, and/or 2A or a portion or functional variant thereof. In some embodiments, the miniprotein comprises or consists of an amino acid sequence having at least 2, at least 3, at least 4, at least 5, at least 6, at least 7, at least 8, at least 9, at least 10, at least 15, at least 20 or more amino acid residue differences from SEQ ID NO: 3-158, 161-168, 170-208, 212-237, 243-246, 248 and/or as set forth in TABLES 1B, 1C, 1D, and/or 2A or a portion or functional variant thereof. In some embodiments, the miniprotein comprises or consists of an amino acid sequence having no more than 2, 3, 4, 5, 6, 7, 8, 9, 10, 11, 12, 13, 14, 15, 16, 17, 18, 19, or 20 amino acid residue differences from SEQ ID NO: 3-158, 161-168, 170-208, 212-237, 243-246, 248 and/or as set forth in TABLES 1B, 1C, 1D, and/or 2A or a portion or functional variant thereof. In some embodiments, the miniprotein comprising or consisting of SEQ ID NOs: 3-158, 161-168, 170-208, 212-237, 243-246, 248 and/or as set forth in TABLES IB, 1C, 1D, and/or 2A or a portion or functional variant thereof selectively binds to the target Nectin-4.

Polypeptides of the disclosure may have one or more modifications. A modification can refer to an amino acid sequence that comprises at least one substitution, alteration, inversion, addition, or deletion of an amino acid residue compared to a reference amino acid sequence. An alteration can include but is not limited to a change to or of one or more atoms of a side chain, such as, for example addition of a methyl-group (e.g., methylated versions of lysine). In some embodiments, a natural amino acid is modified such as set forth herein. In some embodiments, a modification includes addition of at least one small alkyl group attached to the nitrogen of an amino acid side chain, such as, for example, a lysine side chain. As used herein, a "small alkyl group" refers to an alkyl group with a short carbon chain, typically having one to four carbon atoms, such as methyl, ethyl, propyl, or butyl, and also including, for example, dimethyl, trimethyl, isopropyl, etc. In some embodiments, for example, one or more small alkyl groups can be added to the nitrogen of a lysine side chain to produce monomethyl, dimethyl, or trimethyllysine. In some embodiments, one, two, three, four or more small alkyl groups may be added to a given amino acid (e.g., through attachment to the nitrogen of the side chain). In some embodiments no more than five, four, three, two, or one small alkyl groups are added. Miniproteins Provided herein are novel polypeptides (i.e., miniproteins) and methods of use thereof. In some embodiments, a polypeptide comprises or consists of a miniprotein. In some such embodiments, the miniprotein comprises or consists of a CDP, knottin, and/or binder. In some embodiments the miniprotein is designed to be linked to one or more other components. For example, in some embodiments, a miniprotein may be linked (conjugated) to another component such as a chelator and/or a radionuclide. In some embodiments, conjugation is via a lysine or cysteine residue. For example, in some embodiments, a miniprotein is engineered to remove all lysine residues except for one, which is, in some embodiments, used for conjugation. In some embodiments, conjugation occurs via an optional linker. In some embodiments, conjugation between a miniprotein and a chelator and/or radionuclide is direct.

Without wishing to be bound by any particular theory, the present disclosure contemplates that therapeutics comprising compositions provided by the present disclosure are characterized by several features relative to other (e.g., antibody-based) therapeutics. For example, in some embodiments, miniproteins display several key features of antibody-based therapeutics (e.g., affinity, potency, specificity, and ability to disrupt protein:protein interactions) but also have several advantages as compared to antibody-based therapeutics such as smaller size, cheaper manufacturing, and elimination of need to chimerize or humanize the proteins. In addition, the size and specificity of binding increases tumor penetrance and uptake into cells expressing the target of the miniprotein or composition (e.g., conjugate) comprising a miniprotein.

In some embodiments, a miniprotein of the present disclosure is no more than about 100 amino acids in length. In some embodiments, a miniprotein is about 20, 25, 30, 35, 40, 45, 50, 55, 60, 65, 70, 75, 80, 85, 90, 95 or more amino acids in length, up to about 100 amino acids in length. In some such embodiments, however, a miniprotein of the present disclosure does not exceed about 100 amino acids in length. In some embodiments a miniprotein is between about 20 to about 40, about 30 to about 50, about 40 to about 60, about 45 to about 65, about 50 to about 70, about 55 to about 75, about 65 to about 85 or more amino acids in length, but not exceeding about 100 amino acids in length. In some preferred embodiments, a miniprotein is about 65 amino acids or less. In some preferred embodiments, a mini protein is about 50 amino acids or less.

In some embodiments, a miniprotein of the present disclosure is not larger than about 12 kDa. In some embodiments, a miniprotein of the present disclosure is about 2, 2.5, 3, 3.5, 4, 4.5, 5, 5.5, 6, 6.5, 7, 7.5, 8, 8.5, 9, 9.5, 10, 10.5, 11, 11.5 or more kDa. In some such embodiments, however, a miniprotein of the present disclosure does not exceed about 12 kDa.

In some embodiments, a miniprotein comprises one or more disulfide bridges. In some embodiments, a miniprotein comprises at least two disulfide bridges. In some embodiments, a miniprotein comprises at least three cysteine residues. In some embodiments, a miniprotein comprises multiple (e.g., more than three) cysteine residues. In some such embodiments, cysteine residues crosslink to maintain a very stable, folded state for a peptide of its length (e.g., relative to a peptide of the same length without as many cysteine residues). The present disclosure contemplates that such crosslinking confers improved stability with reduced (i.e., very low to no) immunogenicity and/or sustains or improves ability to maintain biological activity in harsh but efficient chelation conditions (e.g., high temperature and low pH).

In some embodiments a miniprotein or composition comprising a miniprotein (e.g., a radionuclide conjugate) has low immunogenicity relative to a larger protein or composition comprising or consisting of a larger protein (e.g., an antibody).

In some embodiments, miniproteins (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) have superior penetration efficiency relative to larger proteins. That is, in some embodiments, a miniprotein or composition comprising a miniprotein can penetrate a solid tumor better than a larger protein or composition comprising a protein larger than a miniprotein. For example, in some such embodiments, a miniprotein or composition comprising a miniprotein has a hydrodynamic radius of about 1 to about 25 nm. In some embodiments, a hydrodynamic radius is in a range of about 1-25 nm. 10-20 nm, 5-15 nm. 1-5 nm, 2-4 nm, or 1-3 nm. In some embodiments, hydrodynamic radius is measured using light scatter methods known to those of skill in the art.

In some embodiments, a miniprotein of the present disclosure is characterized in that it has one or more properties relative to a protein larger than 100 amino acids like an antibody, antibody fragment. VHH domain, single chain antibody, or other protein or binder greater than 12 kDa. In some embodiments a property is selected from increased protein expression, increased thermoactivity, increased thermostability, increased pH activity, increased stability, increased activity, increased receptor binding specificity and/or affinity, increased specific activity, increased resistance to substrate and/or end-product inhibition, increased chemical stability, improved chemoselectivity, improved solvent stability, increased tolerance to acidic pH, increased tolerance to proteolytic activity (i.e., reduced sensitivity to proteolysis), reduced aggregation, increased solubility, reduced immunogenicity, and altered temperature profile, increased resistance to liver uptake, kidney uptake or healthy tissue binding, decreased binding to megalin and/or cubulin, increased tumor penetration, and/or increased volume of distribution.

In some embodiments, a miniprotein or composition comprising a miniprotein (e.g., conjugate, e.g., radionuclide conjugate) provided by the present disclosure exhibits binding affinity to Nectin-4. In some embodiments, the Nectin-4 is human Nectin-4. In some embodiments, the human Nectin-4 is on a cell. In some embodiments, the cell is a cell line, a primary cell, or a cell in a human (e.g., in a tumor).

In some embodiments, a miniprotein or composition comprising a miniprotein (e.g., conjugate, e.g., radionuclide conjugate) displays nM or sub-nM binding affinity to Nectin-4. In some embodiments, the affinity is measured in an in vitro assay. In some embodiments, the in vitro assay is a cell-based assay. In some embodiments, affinity is measured in an in vivo assay (e.g., a PET scan) or using a sample from a subject (e.g., an in vitro assay using a biological specimen such as blood or a cell biopsy from a subject).

In some embodiments, a miniprotein or conjugate thereof displays a binding affinity to Nectin-4 (KD or Kd). In some embodiments, the binding affinity of a miniprotein or conjugate thereof to human Nectin-4 is about 500 nM, 400 nM, 300 nM, 200 nM, 100 nM, or stronger (e.g., 90 nM, 75 nM, 50 nM, 25 nM, 10 nM, 5 nM, etc.). In some embodiments, the miniprotein comprises picomolar binding affinity. In some embodiments, the miniprotein or conjugate thereof comprises a binding affinity characterized by a dissociation constant ranging from about 900 nM to about 1 nM, e.g., 900, 800, 700, 600, 500, 400, 300, 200, 100, 90, 80, 70, 60, 50, 40, 30, 20, 10, 9, 8, 7, 6, 5, 4, 3, 2, 1, 0.9, 0.8, 0.7, 0.6, 0.5, 0.4 nM or stronger (e.g., 0.3, 0.2, 0.1 nM, etc.) binding affinity to human Nectin-4. In some embodiments, the binding is selective to human Nectin-4 and, not, e.g., non-human Nectin-4.

In some embodiments, a miniprotein or conjugate thereof displays a binding inhibition constant. In some embodiments, the binding inhibition constant (Ki) to human Nectin-4 is about 300 nM, 200 nM, 100 nM. 50 nM, 25 nM, 10 nM, 5 nM, or less (e.g., 1 nM, etc.). In some embodiments, the miniprotein comprises picomolar binding affinity. In some embodiments, the miniprotein or conjugate thereof comprises a binding affinity characterized by a dissociation constant ranging from about 900 nM to about 1 nM, e.g., 900, 800, 700, 600, 500, 400, 300, 200, 100, 90, 80, 70, 60, 50, 40, 30, 20, 10, 9, 8, 7, 6, 5, 4, 3, 2, 1, 0.9, 0.8, 0.7, 0.6, 0.5, 0.4 nM or stronger (e.g., 0.3, 0.2, 0.1 nM, etc.) binding affinity to human Nectin-4. In some embodiments, the binding is selective to human Nectin-4 and, not, e.g., non-human Nectin-4.

In some embodiments, a miniprotein or conjugate thereof provided by the present disclosure has high affinity for Nectin-4 (e.g., as measured by binding affinity and/or inhibition constant, etc.). In some such embodiments, the Nectin-4 is human Nectin-4. In some embodiments, a miniprotein of the present disclosure is stable, including in the presence of one or more additional molecules (e.g., a cytotoxic molecule, e.g., radiation).

In some embodiments, binding ability of a miniprotein or conjugate thereof to a target is improved by one or more modifications. For example, in some embodiments, binding ability of a miniprotein or conjugate thereof as provided herein to Nectin-4, is improved using chemical crosslinking. In some embodiments, binding can be enhanced by using one or more of lysine residues, fusion proteins, non-natural amino acids, or other chemical moieties to enhance binding and/or functional activity.

In some embodiments, to ensure proper folding and connectivity, selected cysteine pairs can be replaced with selenocysteines. It is contemplated that, in some embodiments, diselenide crosslinks can form more readily than disulfide crosslinks due to their lower redox potential and such a replacement may cross-couple remaining cysteine residues.

In some embodiments, a miniproteins or conjugates thereof provided by the present disclosure comprises or consists of monomers that make up a dimer, polymer or a multimer. In some such embodiments, the monomers all bind to the same target. For example, in some embodiments, where more than one miniprotein is present, each miniprotein is no greater than about 30-40 amino acids in length or a total of about 8 kDa in size (with both miniproteins). In some embodiments, the monomers each bind to a different target. In some embodiments, some monomers bind to one target and others bind to one or more additional targets.

In some embodiments, a miniprotein of the present disclosure comprises or consists of an antigen for use in generating an antibody that specifically binds to at least one epitope on Nectin-4. In some embodiments, such an antibody may be used for, e.g., diagnostic purposes, blocking (e.g., antagonism), etc.

In some embodiments, the miniprotein comprises one or more disulfide bridges. In some embodiments, the miniprotein comprises at least two disulfide bridges.

In some embodiments, a miniprotein or conjugate thereof as provided herein does not comprise one or more cysteine residues. In some embodiments, the miniprotein does not comprise one or more disulfide bridges.

In some embodiments, a miniprotein or conjugate thereof as provided herein is specific for a target. In some embodiments, a miniprotein is specific for Nectin-4 or a fragment thereof.

In some embodiments, a miniprotein or conjugate thereof as provided herein comprises or consists of a specific amino acid sequence.

In some embodiments, miniproteins or compositions comprising miniproteins (e.g., radionuclide conjugates) are conjugated to a chelator that optionally binds a radionuclide (e.g., actinium). In some embodiments, the conjugation is via a linker. In some embodiments, conjugation is direct conjugation. In some embodiments, such radionuclide conjugates combine and synergize to provide target specificity (e.g., via the miniprotein) and superior treatment (e.g., via directed radioisotope delivery to the cell expressing the target).

In some embodiments, miniproteins or compositions comprising miniproteins are conjugated to a chelator that optionally binds a cold-metal surrogate. In some embodiments, a cold-metal surrogate is a natural isotope of an element that is not radioactive. In some embodiments, an element may have more than one natural isotope that is not radioactive. In some embodiments, "cold" is used to refer to an isotype of an element that is not radioactive. In some embodiments, "hot" refers to an isotope of an element that is radioactive.

As used herein and known to those of skill in the art, the twenty conventional amino acids and their abbreviations follow conventional usage. See Immunology-A Synthesis (Golub and Gren eds., Sinauer Associates, Sunderland, Mass., 2nd ed. 1991), which is incorporated herein by reference. In some embodiments, an amino acid of the present disclosure may be a stereoisomer (e.g., D-amino acids) of the twenty conventional amino acids. In some embodiments, an amino acid in a polypeptide of the present disclosure may be a non-natural amino acid. For example, amino acids such as α-, α-disubstituted amino acids, N-alkyl amino acids, and other unconventional amino acids may also be suitable components for polypeptides of the present disclosure. Examples of unconventional amino acids include: 4-hydroxyproline, γ-carboxyglutamate, trimethyllysine, ε-N,N,N-trimethyllysine, ε-N-acetyllysine (Lys(Ac)), O-phosphoserine, N-acetylserine, N-formylmethionine, 3-methylhistidine, 5-hydroxylysine, N-methylarginine, norleucine, citrulline, L-citrulline, symmetrically dimethylated arginine (sRme2, Rme2s, or SDMA) nitroarginine (Arg (NO2)). Leu-13C6,15N (an enriched stable isotope version of Leucine), and other similar amino acids and imino acids (e.g., 4-hydroxyproline). Arrangements of polypeptide sequence notations used herein have a left-side end corresponding to the amino terminal and a right-side end corresponding to the carboxy-terminal end, in accordance wvith standard usage and convention. In some embodiments, a miniprotein disclosed herein has one or more of the following unconventional amino acids: trimethyllysine, dimethyllysine, monomethyllysine, isopropyl-lysine, Lys(Ac), norleucine, citrulline, L-citrulline, symmetrically dimethylated arginine (sRme2, Rme2s, or SDMA), nitroarginine (Arg (NO2)), or Leu-13C6,15N.

In some embodiments, a miniprotein as provided herein is specific for a polypeptide or portion thereof having an amino acid sequence or portion or functional variant thereof as set forth in TABLE 1A.

TABLE 1A

Exemplary Target Protein Amino Acid Sequences

| Target Protein (Uniprot Acc. No.) | Amino Acid Sequence | SEQ ID NO: |
|---|---|---|
| Human Nectin-4 (Q96NY8) | MPLSLGAEMWGPEAWLLLLLLLASFTGRCPAGELETSDVVTVVL<br>GODAKLPCFYRGDSGEQVGQVAWARVDAGEGAQELALLHSKYGL<br>HVSPAYEGRVEQPPPPRNPLDGSVLLRNAVQADEGEYECRVSTE<br>PAGSFQARLRLRVLVPPLPSLNPGPALEEGOGLTLAASCTAEGS<br>PAPSVTWDTEVKGTTSSRSFKHSRSAAVTSEFHLVPSRSMNGQP<br>LTCVVSHPGLLQDORITHILHVSFLAEASVRGLEDQNLWHIGRE<br>GAMLKCLSEGOPPPSYNWTRLDGPLPSGVRVDGDTLGFPPLTTE<br>HSGIYVCHVSNEFSSRDSQVTVDVLDPQEDSGKQVDLVSASVVV<br>VGVIAALLFCLLVVVVVLMSRYHRRKAQQMTQKYEEELTLTREN<br>SIRRIHSHHTDPRSQPEESVGLRAEGHPDSLKDNSSCSVMSEEP<br>EGRSYSTLTTVREIETQTELLSPGSGRAEEEEDQDEGIKQAMNH<br>FVQENGTLRAKPTGNGIYINGRGHLV | 159 |
| Murine Nectin-4 (Q8R007) | MPLSLGAEMWGPEAWIRLLFLASFTGQYSAGELETSDVVTVVLG<br>QDAKLPCFYRGDPDEQVGQVAWARVDPNEGIRELALLASKYGLH<br>VNPAYEDRVEQPPPPRDPLDGSVLLRNAVQADEGEYECRVSTEP<br>AGSFOARMRLRVLVPPLPSLNPGPPLEEGOGLTLAASCTAEGSP<br>APSVTWDTEVKGTQSSRSFTHPRSAAVTSEFHLVPSRSMNGQPL<br>TCVVSHPGLLQDRRITHTLQVAFLAEASVRGLEDONLWQVGREG<br>ATLKCLSEGOPPPKYNWTRLDGPLPSGVRVKGDTLGFPPLTTEH<br>SGVYVCHVSNELSSRDSQVTVEVLDPEDPGKQVDLVSASVIIVG<br>VIAALLFCLLVVVVVLMSRYHRRKAQQMTQKYEEELTLTRENSI<br>RRIHSHHSDPRSQPEESVGLRAEGHPDSLKDNSSCSVMSEEPEG<br>RSYSTLTTVREIETQTELLS PGSGRTEEDDDQDEGIKQAMNHFV<br>QENGTLRAKPTGNGIYINGRGHLV | 160 |

Certain Nectin-4 binding miniproteins are known in the art. See, e.g., SEQ ID NO: 1 and SEQ ID NO: 2, as set forth below. Molecular weights (calculated and observed) are also provided herein.

| Compound Name | N-terminus | SEQ ID NO | Sequence | C-terminus |
|---|---|---|---|---|
| C1 | NH2 | 1 | CEDDGEYFAGLQRLYGGDICYY<br>IKLKFPKVPDLCIKEILDKIGC | OH |
| C2 | Biotin-PEG4 | 2 | CEDDEEFFADLKRLRGGDICYY<br>IKLKFDKVPDLCIKEILDKLGC | OH |

| Compound Name | SEQ ID NO: | Parent MW | Calculated Mass (M + 4/4) | Observed Mass (M + 4/4) |
|---|---|---|---|---|
| C1 | 1 | 5042.88 | 1261.72 | Not observed |
| C2 | 2 | 5641.6 | 1411.40 | 1412.5 |

The present disclosure recognizes that a source of a problem in therapeutics binding Nectin-4 is lack of sufficient specificity and affinity. Thus, provided herein are miniproteins that bind strongly, efficiently, and specifically to Nectin-4 (e.g., on a cell, e.g., on a cancer cell).

Another source of a problem includes toxicity (e.g., renal toxicity). In some embodiments, specificity and strength of binding for Nectin-4 in cancer cells reduces uptake into kidney.

In some embodiments, a miniprotein comprises or consists of a specific amino acid sequence. In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 3-158, 161-168, 170-208, 212-237, 243-246 and 248.

In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%. 98.7%, 98.8%, 98.9%, 99%, 99.1%, 99.2%, 99.3%, 99.4%, 99.5%, 99.6%, 99.7%, 99.8%, 99.9%, or 100% identical to at least 30, 31, 32, 33, 34, 35, 36, 37, 38, 39, 40, 41, 42, 43, 44 or 45 amino acids of any one of SEQ ID NOs 3-158, 161-168, 170-208, 212-237, 243-246 and 248. In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 contiguous amino acids of any one of SEQ ID NOs: 3-158, 161-168, 170-208, 212-237, 243-246 and 248. In some embodiments, a miniprotein comprises or consists of a specific amino acid sequence. In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to the amino acid sequence set forth in any of SEQ ID NOs: 170-176, 216-237, or 243-246.

In some embodiments, a miniprotein has an amino acid sequence that is 70%, 75%, 80%, 85%, 90%, 95%, 96% 97%, 98%, 98.1%, 98.2%, 98.3%, 98.4%, 98.5%, 98.6%. 98.7%, 98.8%, 98.9%, 99%, 99.1%, 99.2%, 99.3%, 99.4%, 99.5%, 99.6%, 99.7%, 99.8%, 99.9%, or 100% identical to at least 30, 31, 32, 33, 34, 35, 36, 37, 38, 39, 40, 41, 42, 43, 44, or 45 amino acids of any one of SEQ ID NOs: 170-176, 216-237, or 243-246.

In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%. 98.7%, 98.8%, 98.9%, 99%, 99.1%, 99.2%, 99.3%, 99.4%, 99.5%, 99.6%, 99.7%, 99.8%, 99.9%, or 100% identical to at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 contiguous amino acids of any one of SEQ ID NOs: 170-176, 216-237 or 243-246.

In some embodiments, a miniprotein comprises or consists of a specific amino acid sequence. In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%. 98.7%, 98.8%, 98.9%, 99%, 99.1%, 99.2%, 99.3%, 99.4%, 99.5%, 99.6%, 99.7%, 99.8%, 99.9%, or 100% identical to an amino acid sequence set forth in any of TABLES 1B, 1C, 1D, and/or 2A.

In some embodiments, a miniprotein has an amino acid sequence that is 70%, 75%, 8(0%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to at least 30, 31, 32, 33, 34, 35, 36, 37, 38, 39, 40, 41, 42, 43, 44, or 45 amino acids of any one of the amino acid sequences set forth in any of TABLES 1B, 1C, 1D, and/or 2A.

In some embodiments, a miniprotein has an amino acid sequence that is 70%, 75%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% identical to at least 5, 6, 7, 8, 9, 10, 1, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 contiguous amino acids of any one of the amino acid sequences set forth in any of TABLES 1B, 1C, 1 D, and/or 2A.

As used herein and known to those of skill in the art, the twenty conventional amino acids and their abbreviations follow conventional usage. See Immunology-A Synthesis (Golub and Gren eds., Sinauer Associates, Sunderland, Mass., 2nd ed. 1991), which is incorporated herein by reference. In some embodiments, an amino acid of the present disclosure may be a stereoisomer (e.g., D-amino acids) of the twenty conventional amino acids. In some embodiments, an amino acid in a polypeptide of the present disclosure may be a non-natural amino acid. For example, amino acids such as α-, α-disubstituted amino acids, N-alkyl amino acids, and other unconventional amino acids may also be suitable components for polypeptides of the present disclosure. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). Arrangements of polypeptide sequence notations used herein have a left-side end corresponding to the amino terminal and a right-side end corresponding to the carboxy-terminal end, in accordance with standard usage and convention.

In some embodiments, a miniprotein provided by the present disclosure is set forth in one or more consensus sequences provided in TABLE 1B.

In some embodiments, a miniprotein with a sequence set forth in TABLE 1B has amino acid substitutions as provided in TABLE 1C.

TABLE 1B

Consensus Sequences of Exemplary Nectin-4 Miniproteins

| SEQ ID NO | Formula | Consensus Sequence[1] |
|---|---|---|
| 216 | III | CX2YX4X5X6FFTX10LX12X13LX15GX17DICX21YIX24X25X26FX28X29X30X31X32X33CIX36EIX39X40X41LGCX45 |
| 217 | III-A | CEYX4X5X6FFTX10LX12X13LX15GX17DICX21YIX24X25X26FX28X29X30X31X32X33CIX36EIX39X40X41LGCS |
| 218 | III-B | CDYX4X5X6FFTX10LX12X13LX15GX17DICX21YIX24X25X26FX28X29X30X31X32X33CIX36EIX39X40X41LGCS |
| 219 | III-C | CEYX4X5X6FFTX10LX12X13LX15GGDICX21YIX24X25X26FX28X29X30X31X32X33CIX36EIX39X40X41LGCS |
| 220 | III-D | CDYDX5X6FFTX10LX12X13LX15GGDICX21YIX24X25X26FX28X29X30X31X32X33CIX36EIX39X40X41LGCS |
| 221 | III-E | CEYDX5X6FFTX10LX12X13LX15GADICX21YIX24X25X26FX28X29X30X31X32X33CIX36EIX39X40NLGCS |
| 222 | III-F | CEYX4X5X6FFTX101X12X13LX15GGDICX21YIX24X25X26FX28X29X30X31X32X33CIKEIX39X40DKGC |
| 223 | III-G | CEYDX5X6FFTALKX13LX15GGDICEYIX24X25X26FX28X29X30X31X32X33CIEEIX39X40NLGCS |
| 224 | III-H | CEYDX5X6FFTALKX13LX15GGDICYYIX24X25X26FX28X29X30X31X32X33CIEEIX39X40NLGCS |
| 225 | III-I | CEYDX5X6FFTALKX13LX15GGDICEYIQAX26FQX29X30X31X32X33CIEEILX40NIGCS |
| 226 | III-J | CEYDX5X6FFTALKX13LX15GGDICYYIQASFQX29X30X31X32X33CIEEILX40NLGCS |
| 227 | III-K | CDYDX5X6FFTX10LX12X13LX15GGDICX21YIX24X25X26FX28X29X30X31X32X33CIEEILDNIGCS |
| 228 | III-I | CEYKX5X6FFTELX12X13LX15GGDICYYIX24X25X26FX28X29X30X31X32X33CIEEILDNLGC |
| 229 | III-M | CEYDEX6FFTALX12RLRGGDICEYIX24AX26FQX29X30X31X32X33CIEEILX40NLGCS |
| 230 | III-N | CDYDEX6FFTALAX13LX15GGDICX21YIX24X25X26FX28X29X30X31X32LCIEEILDNIGCS |
| 231 | III-O | CEYDEQFFTALX12RLRGGDICEYIQAX26FQYX30X31X32LCIEEILDNIGCS |
| 232 | III-P | CEYDEEFFTALX12RLRGGDICEYIQAX26FQYX30X31X32LCIEEILDNLGCS |

[1] In consensus sequences of the present application, each X is followed by a number indicating its linear position along a miniprotein, where amino acid position I is the N-terminal amino acid of a particular sequence and 45 is the C-terminal amino acid of a particular amino acid sequence. For example, X2 is a substitutable position at the second amino acid, X28 is a substitutable amino acid at the 28th amino acid, and so on. Amino acid positions can be determined relative to, for example, SEQ ID NO: 78. The numbering system in the present application has been updated from provisional priority applications US 63/587,042, US 63/598,874, US 63/618,228, and US 63/636,078, each of which is incorporated by reference in its entirety for all purposes.

TABLE 1C

Consensus Sequences Substitutions

| SEQ ID NO | Position | Amino Acids |
|---|---|---|
| 216 | X2 | D, E |
| 216-219 and 222 | X4 | D, K |
| 216-228 | X5 | E, G |
| 216-230 | X6 | Q, E |
| 216-222 and 227 | X10 | A, E |
| 216-222, 227-229, and 231-232 | X12 | A, K, E, S |
| 216-228 and 230 | X13 | A, R, Q, K, S, Cit |
| 216-228 and 230 | X15 | Y, R, K |
| 216-218 | X17 | A, D, G, S |
| 216-222, 227, and 230 | X21 | D, Q, E, L, S, Y |
| 216-224 and 227-230 | X24 | Q, L, K, S |
| 216-224, 227, 228, and 230 | X25 | A, Q, E, K |
| 216-225 and 227-232 | X26 | A, Q, K, S, Y, T, D, R, (Kme3), (sRme2), Cit, Arg(NO2), OH-Norleu, Norleu |
| 216-224, 227, 228, and 230 | X28 | A, N, Q, D, K, S |
| 216-230 | X29 | N, T, Y |
| 216-232 | X30 | L, Y, V |
| 216-232 | X31 | P, E |
| 216-232 | X32 | A, D, Q, G, K |
| 216-229 | X33 | D, Q, E, I, L |

TABLE 1C-continued

Consensus Sequences Substitutions

| SEQ ID NO | Position | Amino Acids |
|---|---|---|
| 216-221 | X36 | Q, K, E |
| 216-224 | X39 | L, R |
| 216-226 and 229 | X40 | D, Q, E |
| 216-220 | X41 | N, K, Q |
| 216 | X45 | Absent or S |

"Kme3" refers to trimethyllysine, "sRme2" refers to symmetrically dimethylated arginine, "Cit" refers to citrulline, "Arg(NO2)" refers to nitroarginine, "Norleu" refers to Norleucine, "OH-Norleu" refers to OH-Norleucine.

TABLE 1D

Consensus Sequences of Exemplary Nectin-4 Miniproteins

| SEQ ID NO: | CONSENSUS | SUBSTITUTIONS |
|---|---|---|
| 176 | CX2YDEX6

TABLE ID-continued

Consensus Sequences of Exemplary Nectin-4 Miniproteins

| SEQ ID NO: | CONSENSUS | SUBSTITUTIONS |
|---|---|---|
| | | K, K(Ac), S, R, or L; X25 is A, Q, K, K(Ac), L, or E; X26 is Kme3, Kme2, Kme, Kipr, K, K(Ac), S, Q, R, NI, Nle, T, D, SRme2, Cit, RNO2, A, or N; X28 is Q, K, D, K (Ac), N, P, S, or A; X29 is Y, K, K(Ac), T, or N; X30 is L, V, Y, or LCN; X31 is P or E; X32 is A, D, G, K, E, K(Ac), Q, or R; X33 is L, E, I, Q, D, Or LCN; X36 is E, K, Q, or A; X39 is L, R, or LCN; X40 is D, K, E, or Q; X41 is N, K, K(Ac), or Q; X42 is L or LCN; X45 is S or absent |

"dD" refers to D-aspartic acid; "hR" refers to homo-arginine; "hyP" refers to hydroxyproline; "lNal" refers to 1-naphthylamine; "sRme2" refers to symmetric dimethyl arginine; "Cit" refers to citrulline; "Kme" refers to methyl lysine; "Kme2" refers to dimethyl lysine; "Kme3" refers to trimethyl lysine; "Kipr" refers to Ne-isopropyl-L-Lysine; "Dap" refers to diaminopimelic acid; "K(Ac)" refers to acetylated lysine; "RNO2" or "Arg(NO2)" refer to nitroarginine; "LCN" refers to Leu-13C6,15N; "NI" refers to hydroxynorleucine, "Nle" refers to Norleucine.

In some embodiments, the present disclosure provides a miniprotein. In some embodiments, the miniprotein is or comprises a polypeptide, comprising: an amino acid sequence, wherein the amino acid sequence comprises Formula III:

(SEQ ID NO: 216)
CX2YX4X5X6FFTX10LX12X131X15GX17DICK21YIX24X25X26F
X28X29X30X31X32X33CIX36EIX39X40X41LGCX45 wherein X45 is an optional amino acid or carboxy terminus comprising an —OH and wherein X2 is D or E; X4 is D or K, X5 is E or GX6 is Q or E; X10 is A or E, X12 is A, K, E, or S; X13 is A, R, Q, K, S, or Cit; X15 is Y, R, or K, X17 is A, D, G, or S; X21 is D, Q, E, L, S, or Y; X24 is Q, L, K, or S; X25 is A, Q, E, K; X26 is A, Q, K, S, Y, T, D, R, (Kme3), (sRme2), Cit, Arg (NO2), OH-Norleu, or Norleu; X28 is A, N, Q, D, K, or S; X29 is N, T, or Y; X30 is L, Y, or V; X31 is P or E; X32 is A, D, Q, G, or K; X33 is D, Q, E, I, or L; X36 is Q, K or E; X39 is L or R; X40 is D, Q, or E; X41 is N, K or Q; and X45, when present as an amino acid is S.

In some embodiments, the amino acid sequence satisfies one or more of: wherein if X4 is K, then X26 is K and X15 is Y, wherein if X4 is D, then X26 is one of N, T. D, R. (Kme3), (sRme2), Cit, or Arg(NO2), or X26 is K, X10 is E, X36 is K, and X39 is R, or wherein if the amino acid is leucine, then leucine can be L-leucine.

In some embodiments, a polypeptide according to Formula III or any of Formula IIIA-IIIP further comprises one or more of a linker, chelator, and radionuclide. In some embodiments, the linker can be or comprise linker comprises or consists of a polyethylene glycol (PEG) linker of PEG4, PEG, PEG2, PEG6, PEG8, PEG12, PEG24, lys (MPB)-PEG4, PEG36, an ester linker, an amide linker, a maleimide linker, a, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- (SEQ ID NO: 239) or (PEG)n, wherein n is from 1 to 10, (Gly)1-10 (SEQ ID NO: 240), or any fragment or combination via covalent bond thereof. In some embodiments, the chelator comprises or consists of DOTA, DOPA, Macropa, PSC, N-succinimidyl 3-(tri-n-butylstannyl)benzoate (BuSTB), N-succinimidyl 3-trimethylstannyl-benzoate (MeSTB), and Crown. In some embodiments, the radionuclide is Ac-225, Cu-CA, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, when present, the linker is attached to the C-terminal end of the polypeptide. In some embodiments, when present, the chelator is attached to either the polypeptide or the linker. In some embodiments, when present, the radionuclide is attached to the chelator. In some embodiments, the polypeptide comprises one or more additional N-terminal amino acids. In some embodiments, the one or more amino acids on the N-terminal and/or the C-terminal end of the polypeptide.

In some embodiments, a miniprotein comprising an amino acid sequence of any of SEQ ID NOs: 170-176, 216-237, or 243-246 and/or according to any of TABLES 1B, 1C, 1D, and/or 2A has at least one disulfide bridge.

In some embodiments, a miniprotein comprising an amino acid sequence of any of SEQ ID NOs: 170-176, 216-237, or 243-246 and/or according to any of TABLES 1B, 1C, 1D, and/or 2A has at least two disulfide bridges.

In some embodiments, the miniprotein has at least two disulfide bridges.

In some embodiments, disulfide bridges are formed between cysteines 1 and 34 and between cysteines 20 and 44. In some embodiments, a miniprotein comprising four cysteines has two disulfide bridges and Cys 1 is connected to Cys 34 and Cys 20 is connected to Cys 44. In some embodiments, a cysteine is at a position with reference to a reference sequence having a certain length (e.g., SEQ ID NO: 195 having 45 amino acids). For example, in some embodiments, the cysteine corresponding to position 1 connects with 20 and the 34 connects with 44, etc. as provided herein.

In some embodiments, the miniprotein has one or more additional amino acids inserted into amino acids within CDP loop regions (amino acids in loops of secondary structures between cysteines connected to one another, e.g., amino acids in structures formed between Cys 1 and Cys 34 and Cys 20 and Cys 44). As will be understood to those in the art, retention of conformation is key to binding affinity and behavior; accordingly, in some embodiments, any additions within CDP loop regions can be made in a way that preserves proper conformation and stability such that binding affinity is not reduced and/or conformation or stability is not impaired or destroyed.

In some embodiments, the polypeptide is a monomer. In some embodiments, the polypeptide is a dimer, trimer, or tetramer. In some embodiments, the polypeptide comprises an amino acid sequence with at least 80% sequence identity to that of SEQ ID NO: 78. In some embodiments, the polypeptide comprises an amino acid sequence with at least 80% sequence identity to that of any of SEQ ID NOs: 3-158 or 177-215. In some embodiments, the polypeptide comprises a consensus sequence according to any of Formulas IIIA-IIIP (SEQ ID NOs: 216-237) according to TABLE 1B, further comprising a substitution in accordance with those set forth in TABLE 1C. In some embodiments, the polypeptide has an amino acid sequence that meets the definitions as set forth in TABLE 1D. In some embodiments, the polypeptide has an amino acid sequence that meets a definition of any one or more of SEQ ID NOs: 170-176, 216-237, or 243-246.

In some embodiments, a sequence comprising a variable position (e.g., as in TABLE 1B, can also include a substitution with any cognate amino acid. As used herein, a cognate amino acid is one with one or more similar characteristics to another amino acid, such as, for example, a similar charge (e.g., a negatively charged amino acid, in reference to charge at physiologic pH), or, in some embodiments, a set of substitutions (e.g., more than one amino acid) that creates a similar charge profile to the polypeptide as prior to the substitution or set of substitutions, etc.

TABLE 2A

Exemplary Miniprotein Sequences and Compound Structures

| Compound Name[2] | N-terminus | SEQ ID NO[3] | Sequence[4] | C-terminus |
|---|---|---|---|---|
| C3 | NH2 | 3 | CEYDEEFFAGLKRLRGGDICYYIKKKKFDKVPDLCIKEILDKLGC | OH |
| C4 | NH2 | 4 | CEDDFQFFADLKRLRGGDICYYIRLKFDKVPDLCIKEILDKLGC | OH |
| C5 | ACETYL | 3 | CEYDEEFFAGLKRLRGGDICYYIKKKKFDKVPDLCIKEILDKLGC | OH |
| C6 | ACETYL | 4 | CEDDFQFFADLKRLRGGDICYYIRLKFDKVPDLCIKEILDKLGC | OH |
| C7 | NH2 | 5 | CEYDEEFFAGLKRLRGGDICYYIKKKKFDKVPDLCIEEILDKLGC | OH |
| C8 | Biotinylated | 5 | CEYDEEFFAGLKRLRGGDICYYIKKKKFDKVPDLCTEEILDKLGC | OH |
| C9 | ACETYL | 5 | CEYDEEFFAGLKRLRGGDICYYIKKKKFDKVPDLCIEEILDKLGC | OH |
| C10 | FITC | 5 | CEYDEEFFAGLKRLRGGDICYYIKKKKFDKVPDLCIEEILDKLGC | OH |
| C11 | DTPA-PEG4 | 5 | CEYDEEFFAGLKRLRGGDICYYIKKKKFDKVPDLCIEEILDKLGC | OH |
| C12 | DOTA-PEG4 | 5 | CEYDEEFFAGLKRLRGGDICYYIKKKKFDKVPDLCIEEILDKLGC | OH |
| C13 | ACETYL | 6 | CEYDEEFFNGLKRLRGGDICYYIKKKKFDKVPDLCIEEILDKLGC | OH |
| C14 | ACETYL | 7 | CEYDEEFFAGLKRLRRGGDICYYIKKKKFDKVPDLCIEEILDKLGC | OH |
| C15 | ACETYL | 8 | CEYDEEFFNGLKRLRGGDICYYIKKKKFDKVPDLCIEEILDKLGC | OH |
| C16 | ACETYL | 9 | CEYDEEFFAGLKRLRGGDICYYIKKKKFKKVPDLCIEEILDKLGC | OH |
| C17 | ACETYL | 10 | CEYDEEFFNGLKRLRGGDICYYIKKKKFKKVPDLCIEEILDKLGC | OH |
| C18 | ACETYL | 11 | CEYDEEFFNGLHRLRRGGDICYYIKKKKFKKVPDLCIEEILDKLGC | OH |
| C19 | ACETYL | 12 | CEYDEEFFAGLKRLRGGDICYYIKKKKFPKVPDLCIEEILDKLGC | OH |
| C20 | ACETYL | 13 | CEYDEEFFAGLHRLRGGDICYYIKKKKFDKVPDLCIEEILDKLGC | OH |
| C21 | ACETYL | 14 | CEYDEEFFAGLHRLRGGDICYYIKKKKFPKVPDLCIEEILDKLGC | OH |
| C22 | ACETYL | 15 | CEYDEEFFAGLKRLRGTDICYYIKKKKFDKVPDLCIEEILDKLGC | OH |
| C23 | ACETYL | 16 | CEYDEEFFAGLHRLRGTDICYYIKKKKFDKVPDLCIEEILDKLGC | OH |
| C24 | ACETYL | 17 | CEYDEEFFAGLHRLRGTDICYYIKKKKFPKVPDLCIEEILDKLGC | OH |
| C25 | ACETYL | 18 | CEYDEEFFKGLKRLRGGDICYYIKKKKFKKVPDLCIEEILDKLGC | OH |
| C26 | ACETYL | 19 | CEYDEEFFEGLKRLRGGDICYYIKKKKFKKVPDLCIEEILDKLGC | OH |
| C27 | ACETYL | 20 | CEYDEEFFDGLKRLRGGDICYYIKKKFKKVPDLCIEEILDKLGC | OH |
| C28 | ACETYL | 21 | CEYDEEFFSGLKRLRGGDICYYIKKKKFKKVPDLCIEEILDKLGC | OH |
| C29 | ACETYL | 22 | CEYDEEFFTGLKRLRGGDICYYIKKKKFKKVPDLCIEEILDKLGC | OH |
| C30 | ACETYL | 23 | CEYDEEFFEGLKKLRGGDICYYIKKKKFKKVPDLCIEEILDKLGC | OH |
| C31 | ACETYL | 24 | CEYDEEFFTGLKRLRGGDICYYIKKKKFKKVPKLCIEEILDKLGC | OH |
| C32 | ACETYL | 25 | CEYDEEFFTGLKRLRGGDICYYIKKKKFKKVPELCIEEILDKLGC | OH |
| C33 | ACETYL | 26 | CEYDEEFFQGLKRLRGGDICYYIKKKKFKKVPDLCIEEILDKLGC | OH |
| C34 | ACETYL | 27 | CEYDEEFFLGLKRLRGGDICYYIKKKKFKKVPDLCIEEILDKLGC | OH |
| C35 | ACETYL | 28 | CEYKEEFFTGLKRLRGGDICYYIKKKKFKKVPDLCIEEILDKLGC | OH |
| C36 | ACETYL | 29 | CEYEEEFFTGLKRLRGGDICYYIKKKKFKKVPDLCIEEILDKLGC | OH |
| C37 | ACETYL | 30 | CEYDEEFFTGLKRLRGGKICYYIKKKKFKKVPDLCIEEILDKLGC | OH |
| C38 | ACETYL | 31 | CEYDEEFFTGLKRLRGGEICYYIKKKKFKKVPDLCIEEILDKLGC | OH |
| C39 | ACETYL | 32 | CEYDEEFFTGLKRLRGGNICYYIKKKKFKKVPDLCIEEILDKLGC | OH |
| C40 | ACETYL | 33 | CEYDEEFFTGLKRLRGGSICYYIKKKKFKKVPDLCIEEILDKLGC | OH |
| C41 | ACETYL | 34 | CEYDEEFFTGLKRLRGGTICYYIKKKKFKKVPDLCIEEILDKLGC | OH |
| C42 | ACETYL | 35 | CEYDEEFFTGLKRLRGGQICYYIKKKKFKKVPDLCIEEILDKLGC | OH |
| C43 | ACETYL | 36 | CEYDEEFFDapGLKRLRGGDICYYIKKKEKKVPDLCIEEILDKLGC | OH |
| C44 | ACETYL | 37 | CEYDEEFFTGLKRLRGGDICYYIKKKKFKKVPDLCIEEILKKLGC | OH |
| C45 | ACETYL | 38 | CEYDEEFFTGLKRLRGGDICYYIKKKKFKKVPDLCIEEILEKLGC | OH |
| C46 | ACETYL | 39 | CEYDEKFFTGLKRLRGGDICYYIKKKKFKKVPDLCIEEILDKLGC | OH |
| C47 | ACETYL | 40 | CEYDKEFFTGLKRLRGGDICYYIKKKKFKKVPDLCIEEILDKLGC | OH |
| C48 | ACETYL | 41 | CKYDEEFFTGLKRLRGGDICYYIKKKKFKKVPDLCIEEILDKLGC | OH |
| C49 | ACETYL | 42 | CEYDEQFFTGLKRLRGGDICYYIKKKKFKKVPDLCIEEILDKLGC | OH |
| C50 | DOTA-PEG8 | 5 | CEYDEEFFAGLKRLRGGDICYYIKKKKFDKVPDLCIEEILDKLGC | OH |
| C51 | DOTA-PEG12 | 5 | CEYDEEFFAGLKRLRGGDICYYIKKKKFDKVPDLCIEEILDKLGC | OH |
| C52 | ACETYL | 43 | CEYDEEFFTDLKRLRGGDICYYIKKKKFKKVPKLCIEEILDKLGC | OH |
| C53 | ACETYL | 44 | CEYDEEFFTELKRLRGGDICYYIKKKKFKKVPKLCIEEILDKLGC | OH |
| C54 | ACETYL | 45 | CEYDEEFFTKLKRLRGGDICYYIKKKKFKKVPKLCIEEILDKLGC | OH |
| C55 | ACETYL | 46 | CEYDEEFFTTLKRLRGGDICYYIKKKKFKKVPKLCIEEILDKLGC | OH |
| C56 | ACETYL | 47 | CEYDEEFFTTLKRLRGGDICYYIKKKKFKKVPKLCIEEILDKLGC | OH |
| C57 | ACETYL | 48 | CEYDEEFFTALKRLRGGDICYYIKKKKFKKVPKLCIEEILDKLGC | OH |

TABLE 2A-continued

| | | | | |
|---|---|---|---|---|
| C58 | ACETYL | 49 | CEYDEEFFLGLKRLRGGDICYYIKKKFKKVPKLCIEEILDKLGC | OH |
| C59 | ACETYL | 50 | CEYDEEFFTGLKRLRGGDICYYIKKKFKKVPKLCIEEILEKLGC | OH |
| C60 | ACETYL | 51 | CEYDEEFFLGLKRLRGGDICYYIKKKFKKVPDLCIEEILEKLGC | OH |
| C61 | ACETYL | 52 | CEYDEEFFLGLKRLRGGDICYYIKKKFKKVPKLCIEEILEKLGC | OH |
| C62 | ACETYL | 53 | CEYDEEFFTGLKRLRGGDICYYIKKKFKKVPKLCIEEILKKLGC | OH |
| C63 | ACETYL | 54 | CEYDEEFFLGLKRLRGGDICYYIKKKFKKVPKLCIEEILKKLGC | OH |
| C64 | ACETYL | 55 | CEYDEEFFLGLKRLRGGDICYYIKKKFKKVPDLCIEEILKKLGC | OH |
| C65 | ACETYL | 56 | CEYDEEFFTGLKRLRGGDICYYIKKKFKKVPELCIEEILKKLGC | OH |
| C66 | ACETYL | 57 | CEYDEEFFTGLKRLRGGDICYYIKKKFKKVPELCIEEILEKLGC | OH |
| C67 | ACETYL | 58 | CEYDEEFFLGLKRLRGGDICYYIKKKFKKVPELCIEEILKKLGC | OH |
| C68 | ACETYL | 59 | CEYDEEFFLGLKRLRGGDICYYIKKKFKKVPELCIEEILEKLGC | OH |
| C69 | ACETYL | 60 | CEYDEEFFKGLKRLRGGDICYYIKKKFKKVPKLCIEEILEKLGC | OH |
| C70 | ACETYL | 61 | CEYDEKFFTGLKRLRGGDICYYIKKKFKKVPKLCIEEILDKLGC | OH |
| C71 | ACETYL | 62 | CEYDEQFFTGLKRLRGGDICYYIKKKFKKVPKLCIEEILDKLGC | OH |
| C72 | ACETYL | 63 | CEYDEKFFLGLKRLRGGDICYYIKKKFKKVPKLCIEEILKKLGC | OH |
| C73 | ACETYL | 64 | CEYDEQFFLGLKRLRGGDICYYIKKKFKKVPKLCIEEILKKLGC | OH |
| C74 | ACETYL | 65 | CEYDEKFFTGLKRLRGGDICYYIKKKFKKVPKLCIEEILKKLGC | OH |
| C75 | ACETYL | 66 | CEYDEQFFTGLKRLRGGDICYYIKKKFKKVPKLCIEEILKKLGC | OH |
| C76 | ACETYL | 67 | CEYDEEFFKALKRLRGGDICYYIKKKFKKVPKLCIEEILEKLGC | OH |
| C77 | ACETYL | 68 | CEYDEEFFLALKRLRGGDICYYIKKKFKKVPKLCIEEILEKLGC | OH |
| C78 | ACETYL | 69 | CEYDEEFFLALKRLRGGDICYYIKKKFKKVPKLCIEEILDKLGC | OH |
| C79 | ACETYL | 70 | CEYDEEFFTALKRLRGGDICYYIKKKFKKVPKLCIEEILEKLGC | OH |
| C80 | ACETYL | 71 | CEYDEEFFKGLKRLRGGDICYYIKKKFKKVPKLCIEEILDKLGC | OH |
| C81 | ACETYL | 72 | CEYDEEFFKALKRLRGGDICYYIKKKFKKVPKLCIEEILDKLGC | OH |
| C82 | DOTA-PEG4 | 48 | CEYDEEFFTALKRLRGGDICYYIKKKFKKVPKLCIEEILDKLGC | NH2 |
| C83 | ACETYL | 48 | CEYDEEFFTALKRLRGGDICYYIKKKFKKVPKLCIEEILDKLGC | NH2 |
| C84 | DOTA-PEG4 | 73 | CEYDEEFFTALLys(Ac)CitrullineLCitrullineGGDICYYIKKKFKKVPKLCIEEILDLys(Ac)LGC | NH2 |
| C85 | FITC-PEG4 | 73 | CEYDEEFFTALLys(Ac)CitrullineLCitrullineGGDICYYIKKKFKKVPKLCIEEILDLys(Ac)LGC | NH2 |
| C86 | DOTA-PEG4 | 74 | CEYDEEFFTALLys(Ac)CitrullineLCitrullineGGDICYYILys(Ac)Lys(Ac)Lys(Ac)FLys(Ac)Lys(Ac)VPLys(Ac)LCIEEILDLys(Ac)LGC | NH2 |
| C87 | FITC-PEG4 | 74 | CEYDEEFFTALLys(Ac)CitrullineLCitrullineGGDICYYILys(Ac)Lys(Ac)Lys(Ac)FLys(Ac)Lys(Ac)VPLys(Ac)LCIEEILDLys(Ac)LGC | NH2 |
| C88 | DOTA-PEG4 | 75 | CEYDEEFFTALKRLRGGDICYYILys(Ac)Lys(Ac)Lys(Ac)FLys(Ac)Lys(Ac)VPLys(Ac)LCIEEILDKLGC | NH2 |
| C89 | FITC-PEG4 | 75 | CEYDEEFFTALKRLRGGDICYYILys(Ac)Lys(Ac)Lys(Ac)FLys(Ac)Lys(Ac)VPLys(Ac)LCIEEILDKLGC | NH2 |
| C90 | $^{151}$Eu-DOTA-PEG4 | 5 | CEYDEEFFAGLKRLRGGDICYYIKKKFDKVPDLCIEEILDKLGC | OH |
| C91 | $^{138}$La-DOTA-PEG4 | 5 | CEYDEEFFAGLKRLRGGDICYYIKKKFDKVPDLCIEEILDKLGC | OH |
| C92 | $^{nat}$In-DOTA-PEG4 | 5 | CEYDEEFFAGLKRLRGGDICYYIKKKFDKVPDLCIEEILDKLGC | OH |
| C93 | $^{69}$Ga-DOTA-PEG4 | 5 | CEYDEEFFAGLKRLRGGDICYYIKKKFDKVPDLCIEEILDKLGC | OH |
| C94 | $^{63}$Cu-DOTA-PEG4 | 5 | CEYDEEFFAGLKRLRGGDICYYIKKKFDKVPDLCIEEILDKLGC | OH |
| C95 | $^{151}$Eu-DOTA-PEG4 | 48 | CEYDEEFFTALKRLRGGDICYYIKKKFKKVPKLCIEEILDKLGC | OH |
| C96 | $^{138}$La-DOTA-PEG4 | 48 | CEYDEEFFTALKRLRGGDICYYIKKKFKKVPKLCIEEILDKLGC | OH |
| C97 | $^{138}$La-DOTA-PEG4 | 48 | CEYDEEFFTALKRLRGGDICYYIKKKFKKVPKLCIEEILDKLGC | NH2 |
| C98 | $^{nat}$In-DOTA-PEG4 | 48 | CEYDEEFFTALKRLRGGDICYYIKKKFKKVPKLCIEEILDKLGC | NH2 |
| C99 | $^{225}$Ac-DOTA-PEG4 | 5 | CEYDEEFFAGLKRLRGGDICYYIKKKFDKVPDLCIEEILDKLGC | OH |
| C100 | Acetyl | 76 | CEYDEQFFTALKRLRGGDICYYISAQFNTLPDLCIEEILENLGC | OH |
| C101 | DOTA-PEG4 | 76 | CEYDEQFFTALKRLRGGDICYYISAQFNTLPDLCIEEILENLGC | OH |
| C102* | In:DOTA-PEG4 | 76 | CEYDEOFFTALKRLRGGDICYYISAQFNTLPDLCIEEILENLGC | OH |
| C103 | Biotin-PEG4 | 76 | CEYDEQFFTALKRLRGGDICYYISAQFNTLPDLCIEEILENLGC | OH |
| C104 | Acetyl | 77 | CEYDEEFFTALKKLRGGDICYYIQQAFNYLPGICIEEILDNLGC | OH |
| C105 | DOTA-PEG4 | 77 | CEYDEEFFTALKKLRGGDICYYIQQAFNYLPGICIEEILDNLGC | OH |
| C106* | In:DOTA-PEG4 | 77 | CEYDEEFFTALKKLRGGDICYYIQQAFNYLPGICIFEILDNLGC | OH |
| C107 | Biotin-PEG4 | 77 | CEYDEEFFTALKKLRGGDICYYIQQAFNYLPGICIEEILDNLGC | OH |
| C108 | Acetyl | 78 | CEYDEEFFTALKRLRGGDICYYIQASFQYLPGLCIEEILDNLGCS | OH |
| C109 | DOTA-PEG4 | 78 | CEYDEEFFTALKRLRGGDICYYIQASFQYLPGLCIEEILDNLGCS | OH |
| C110* | In:DOTA-PEG4 | 78 | CEYDEEFFTALKRLRGGDICYYIQASFQYLPGLCIEEILDNLGCS | OH |
| C111 | Biotin-PEG4 | 78 | CEYDEEFFTALKRLRGGDICYYIQASFQYLPGLCIEEILDNLGCS | OH |
| C112 | Acetyl | 79 | CEYDEQFFTALKALRGGDICYYIQASFNYLPDLCIEEILDNLGC | NH2 |
| C113 | DOTA-PEG4 | 80 | CEYDEQFFTALKALRGGDICYYIQASFNYLPDLCIEEILDNLGCS | OH |
| C114* | In:DOTA-PEG4 | 80 | CEYDEQFFTALKALRGGDICYYIQASFNYLPDLCIEEILDNLGCS | OH |
| C115 | Biotin-PEG4 | 80 | CEYDEQFFTALKALRGGDICYYIQASFNYLPDLCIEEILDNLGCS | OH |
| C116 | Acetyl | 81 | CEYDEEFFTALKRLRGGDICYYIQAKFQYLPKLCIEEILDNLGCS | OH |
| C117 | DOTA-PEG4 | 81 | CEYDEEFFTALKRLRGGDICYYIQAKFQYLPKLCIEEILDNLGCS | OH |
| C118* | In:DOTA-PEG4 | 81 | CEYDEEFFTALKRLRGGDICYYIQAKFQYLPKLCIEEILDNLGCS | OH |
| C119 | Biotin-PEG4 | 81 | CEYDEEFFTALKRLRGGDICYYIQAKFQYLPKLCIEEILDNLGCS | OH |
| C120 | Acetyl | 82 | CEYDEEFFTALKRLRGGDICYYIQKAFQYLPGLCIEEILDNLGCS | OH |
| C121 | DOTA-PEG4 | 82 | CEYDEEFFTALKRLRGGDICYYIQKAFQYLPGLCIEEILDNLGCS | OH |
| C122* | In:DOTA-PEG4 | 82 | CEYDEEFFTALKRLRGGDICYYIQKAFQYLPGLCIEEILDNLGCS | OH |
| C123 | Biotin-PEG4 | 82 | CEYDEEFFTALKRLRGGDICYYIQKAFQYLPGLCIEEILDNLGCS | OH |
| C124 | Acetyl | 83 | CEYDEEFFTALARLRGGDICYYIQAKFQYLPGLCIEEILDNLGCS | OH |
| C125 | DOTA-PEG4 | 83 | CEYDEEFFTALARLRGGDICYYIQAKFQYLPGLCIEEILDNLGCS | OH |
| C126* | In:DOTA-PEG4 | 83 | CEYDEEFFTALARLRGGDICYYIQAKFQYLPGLCIEEILDNLGCS | OH |
| C127 | Biotin-PEG4 | 83 | CEYDEEFFTALARLRGGDICYYIQAKFQYLPGLCIEEILDNLGCS | OH |
| C128 | Acetyl | 84 | CEYDEQFFTALARLRGGDICYYIQEQFATVPGLCIEEILDQLGC | NH2 |
| C129 | DOTA-PEG4 | 85 | CEYDEQFFTALARLRGGDICYYIQEQFATVPGLCIEEILDQLGCS | OH |
| C130* | In:DOTA-PEG4 | 85 | CEYDEQFFTALARLRGGDICYYIQEQFATVPGLCIEEILDQLGCS | OH |
| C131 | Biotin-PEG4 | 85 | CEYDEQFFTALARLRGGDICYYIQEQFATVPGLCIEEILDQLGCS | OH |

TABLE 2A-continued

| | | | | |
|---|---|---|---|---|
| C132 | Acetyl | 86 | CEYDEEFFTALSRLRGGDICYYIQQAFQYLPGLCIEEILDNLGC | NH2 |
| C133 | DOTA-PEG4 | 87 | CEYDEEFFTALSRLRGGDICYYIQQAFQYLPGLCIEEILDNLGCS | OH |
| C134* | In:DOTA-PEG4 | 87 | CEYDEEFFTALSRLRGGDICYYIQQAFQYLPGLCIFEILDNLGCS | OH |
| C135 | Biotin-PEG4 | 87 | CEYDEEFFTALSRLRGGDICYYIQQAFQYLPGLCIEEILDNLGCS | OH |
| C136 | Acetyl | 88 | CEYDEQFFTALSSLRGGDICYYIQEQFANVPGICIEEILDNLGC | OH |
| C137 | DOTA-PEG4 | 89 | CEYDEQFFTALSSLRGGDICYYIQEQFANVPGICIEEILDNLGCS | OH |
| C138* | In:DOTA-PEG4 | 89 | CEYDEQFFTALSSLRGGDICYYIQEQFANVPGICIEEILDNLGCS | OH |
| C139 | Biotin-PEG4 | 89 | CEYDEQFFTALSSLRGGDICYYIQEQFANVPGICIEEILDNLGCS | OH |
| C140 | Biotin-PEG4 | 90 | CEYDEEFFTALARLRGADICYYIQAKFQYLPGDCIEEILDNLGCS | OH |
| C141 | Biotin-PEG4 | 91 | CDYDEEFFTALARLRGGDICEYIQAKFQYLPGLCIEEILDNLGCS | OH |
| C142 | Biotin-PEG4 | 92 | CEYDEEFFTALARLRGGDICYYIQAKFQYLPGECIEEILQNLGCS | OH |
| C143 | Biotin-PEG4 | 93 | CEYDEEFFTALARLRGDDICSYIQAKFQYLPGLCIEEILDNLGCS | OH |
| C144 | Biotin-PEG4 | 94 | CEYDGEFFTALARLRGADICEYIQAKFQYYPGLCIEEILDNLGCS | OH |
| C145 | Biotin-PEG4 | 95 | CEYDEEFFTALARLRGGDICYYILAKFQYLPGECIEEILDNLGCS | OH |
| C146 | Biotin-PEG4 | 96 | CEYDEQFFTALARLRGGDICEYIQAKFQYLPGLCIEEILDNLGCS | OH |
| C147 | Biotin-PEG4 | 97 | CEYDEEFFTALARLRGADICDYIQAKFQYLPGLCIEEILDNLGCS | OH |
| C148 | Biotin-PEG4 | 98 | CEYDEEFFTALARLRGGDICEYIQAKFQYLPGLCIQEILDNLGCS | OH |
| C149 | Biotin-PEG4 | 99 | CEYDEEFFTALARLRGGDICQYIQAKFQYLPGQCIEEILDNLGCS | OH |
| C150 | Biotin-PEG4 | 100 | CEYDEEFFTALARLRGGDICEYIQAKFQYLEGLCIEEILDNLGCS | OH |
| C151 | Biotin-PEG4 | 101 | CEYDEAFFTALARLRGGDICQYIQAKFQYLPGLCIEEILDNLGCS | OH |
| C152 | Biotin-PEG4 | 102 | CEYDEQFFTALARLRGGDICYYILAKFQYLPQLCIEEILDNLGCS | OH |
| C153 | Biotin-PEG4 | 103 | CEYDEEFFTALARLRGGDICQYIQAKFQYLPALCIEEILDNLGCS | OH |
| C154 | Biotin-PEG4 | 104 | CEYDEEFFTALARLRGGDICYYIQAKFAYLPALCIEEILDNLGCS | OH |
| C155 | Biotin-PEG4 | 105 | CEYDEEFFTALARLRGGDICQYIQAKFAYVPGLCIEEILDNLGCS | OH |
| C156 | Biotin-PEG4 | 106 | CEYDEEFFTALARLRGSDICLYIQAKFQYLPGLCIEEILDNLGCS | OH |
| C157 | Biotin-PEG4 | 107 | CEYDEEFFTALARLRGGDICDYIQAKFQYLPGLCIAEILDNLGCS | OH |
| C158 | Biotin-PEG4 | 108 | CEYDGEFFTALARLRGGDICQYIQAKFQYLPGLCIEEILDNLGCS | OH |
| C159 | Biotin-PEG4 | 109 | CDYDEEFFTALARLRGGDICYYIQAKFSYLPGLCIEEILDNLGCS | OH |
| C160 | Biotin-PEG4 | 110 | CDYDEEFFTALARLRGGDICQYIQAKFQYLPGLCIEEILDNLGCS | OH |
| C161 | Biotin-PEG4 | 111 | CEYDEEFFTALASLRGGDICYYIQAKFQYLPGLCIEEILDNLGCS | OH |
| C162 | Biotin-PEG4 | 112 | CEYDEEFFTALAQLRGGDICYYIQAKFQYLPGLCIEEILDNLGCS | OH |
| C163 | Biotin-PEG4 | 113 | CEYDEEFFTALA(Cit)LRGGDICYYIQAKFQYLPGLCIEEILDNLGCS | OH |
| C164 | Biotin-PEG4 | 114 | CEYDEEFFTALARLRGGDICYYIQA(hydroxy-norleucine)FQYLPGLCIEE-ILDNLGCS | OH |
| C165 | Biotin-PEG4 | 115 | CEYDEEFFTALARLRGGDICYYIQAYFQYLPGLCIEEILDNLGCS | OH |
| C166 | Biotin-PEG4 | 116 | CEYDEEFFTALARLRGGDICYYIQAKFQYLPKLCIEEILDNLGCS | OH |
| C167 | Biotin-PEG4 | 117 | CEYDEEFFTALARLRGGDICEYIQAKFQYLPKLCIEEILDNLGCS | OH |
| C168 | Biotin-PEG4 | 118 | CEYDEEFFTALARLRGGDICSYIQAKFQYLPKLCIEEILDNLGCS | OH |
| C169 | Biotin-PEG4 | 119 | CEYDEEFFTALARLRGGDICDYIQAKFQYLPKLCIEEILDNLGCS | OH |
| C170 | Biotin-PEG4 | 120 | CEYDEEFFTALACitLRGDDICSYIQA(hydroxy-norleucine)FQYLPGLCIEEILDNLGCS | OH |
| C171 | Biotin-PEG4 | 121 | CEYDEEFFTALA(Cit)LRGGDICEYIQAKFQYLPGLCIEEILDNLGCS | OH |
| C172 | Biotin-PEG4 | 122 | CEYDEEFFTALA(Cit)LRGGDICSYIQAKFQYLPGLCIEEILDNLGCS | OH |
| C173 | Biotin-PEG4 | 123 | CEYDEEFFTALARLRGGDICYYIQA(hydroxy-norleucine)FQYLPGLCIEE-ILDNLGCS | OH |
| C174 | Biotin-PEG4 | 115 | CEYDEEFFTALARLRGGDICYYIQAYFQYLPGLCIEEILDNLGCS | OH |
| C175 | Biotin-PEG4 | 124 | CEYDEEFFTALA(Cit)LRGGDICSYIQAKFQYLPGLCIEEILDNLGCS | OH |
| C176 | Biotin-PEG4 | 125 | CDYDEEFFTALA(Cit)LRGGDICEYIQAKFQYLPGLCIEEILDNLGCS | OH |
| C177 | Biotin-PEG4 | 126 | CEYDEEFFTALKRLRGGDICYYIQASFQYLPGECIEEILDNLGCS | OH |
| C178 | Biotin-PEG4 | 127 | CEYDEEFFTALKRLRGGDICEYIQASFQYLPGLCIEEILDNLGCS | OH |
| C179 | Biotin-PEG4 | 128 | CEYDEEFFTALKRLRGGDICSYIQASFQYLPGLCIEEILDNLGCS | OH |
| C180 | Biotin-PEG4 | 129 | CEYDEEFFTALKRLRGDDICYYIQASFQYLPGLCIEEILDNLGCS | OH |
| C181 | Biotin-PEG4 | 130 | CEYDEEFFTALKRLRGDDICSYIQASFQYLPGLCIEEILDNLGCS | OH |
| C182 | Biotin-PEG4 | 131 | CEYDEEFFTALKRLRGDDICSYIQASFQYLPGLCIEEILDNLGCS | OH |
| C183 | Biotin-PEG4 | 132 | CEYDEQFFTALKRLRGADICEYIQASFQYLPGLCIEEILDNLGCS | OH |
| C184 | Biotin-PEG4 | 133 | CEYDEQFFTALKRLRGGDICSYIQASFQYLPGLCIEEILDNLGCS | OH |
| C185 | Biotin-PEG4 | 134 | CEYDEQFFTALKRLRGADICSYIQASFQYLPGLCIEEILDNLGCS | OH |
| C186 | Biotin-PEG4 | 135 | CEYDEQFFTALKRLRGDDICSYIQASFQYLPGLCIEEILDNLGCS | OH |
| C187 | natIn-DOTA-PEG4 | 93 | CEYDEEFFTALARLRGDDICSYIQAKFQYLPGLCIEEILDNLGCS | OH |
| C188 | Biotin-PEG4 | 136 | CDYDEEFFTALKRLRGGDICEYIQASFQYLPGLCIEEILDNLGCS | OH |
| C189 | Biotin-PEG4 | 137 | CDYDEEFFTALKRLRGGDICSYIQASFQYLPGLCIEEILDNLGCS | OH |
| C190 | Biotin-PEG4 | 138 | CDYDEQFFTALKRLRGGDICEYIQASFQYLPGLCIEEILDNLGCS | OH |
| C191 | Biotin-PEG4 | 139 | CDYDEEFFTALKRLRGDDICEYIQASFQYLPGLCIEEILDNLGCS | OH |
| C192 | Biotin-PEG4 | 140 | CDYDEQFFTALKRLRGDDICSYIQASFQYLPGLCIEEILDNLGCS | OH |
| C193 | Biotin-PEG4 | 141 | CDYDEQFFTALKRLRGDDICEYIQASFQYLPGLCIEEILDNLGCS | OH |
| C194 | Biotin-PEG4 | 142 | CEYDEQFFTALKRLRGADICEYIQASFQYLPGLCIEEILDNLGCS | OH |
| C195 | Biotin-PEG4 | 143 | CEYDEEFFTALKRLRGADICDYIQASFQYLPGLCIEEILDNLGCS | OH |
| C196 | Biotin-PEG4 | 144 | CEYDEQFFTALKRLRGGDICDYIQASFQYLPGLCTEEILDNLGCS | OH |
| C197 | Biotin-PEG4 | 145 | CEYDEQFFTALKRLRGGDICDYIQASFQYLPGLCIEEILDNLGCS | OH |
| C198 | Biotin-PEG4 | 146 | CEYDEEFFTALKRLRGGDICEYIQAAFQYLPGLCIEEILDNLGCS | OH |
| C199 | Biotin-PEG4 | 147 | CEYDEEFFTALKRLRGGDICEYIQANleFQYLPGLCIEEILDNLGCS | OH |
| C200 | Biotin-PEG4 | 148 | CEYDEEFFTALKRLRGGDICDYIQASFQYLPGLCIEEILDNLGCS | OH |
| C201 | Biotin-PEG4 | 149 | CEYDEEFFTALKRLRGGDICEYIQAKme3FQYLPGLCIEEILDNLGCS | OH |
| C202 | Biotin-PEG4 | 150 | CEYDEEFFTALKRLRGGDICEYIQASFQYLPGECIEEILDNLGCS | OH |
| C203 | Biotin-PEG4 | 151 | CEYDEEFFTALKRLRGGDICDYIQASFQYLPGECIEEILDNLGCS | OH |
| C204 | Biotin-PEG4 | 152 | CEYDEEFFTALKRLRGGDICEYIQASFQYLPGECIEEILQNLGCS | OH |
| C205 | Biotin-PEG4 | 153 | CEYDEEFFTALKRLRGGDICDYIQASFQYLPGECIEEILQNLGCS | OH |
| C207 | Biotin-PEG4 | 154 | CDYDEQFFTALKRLRGADICEYIQASFQYLPGLCIEEILDNLGCS | OH |
| C208 | Biotin-PEG4 | 155 | CDYDEQFFTALKRLRGADICEYIQASFQYLPGECIEEILDNLGCS | OH |
| C209 | Biotin-PEG4 | 156 | CDYDEQFFTALKRLRGADICEYIQASFQYLPGQCIEEILDNLGCS | OH |

TABLE 2A-continued

| | | | | |
|---|---|---|---|---|
| C210 | Biotin-PEG4 | 157 | CDYDEQFFTALKRLRGGDICEYIQASFQYLPGECIEEILDNLGCS | OH |
| C211 | Biotin-PEG4 | 158 | CDYDEQFFTALKRLRGGDICEYIQASFQYLPGQCIEEILDNLGCS | OH |
| C212 | ACETYL | 177 | CEYDEEFFTALKRLRGGDICYYIKKKFDYLPKLCIEEILDNLGC | NH2 |
| C213 | ACETYL | 177 | CEYDEEFFTALKRLRGGDICYYIKKKFDYLPKLCIEEILDNLGC | OH |
| C214 | DOTA-PEG4 | 177 | CEYDEEFFTALKRLRGGDICYYIKKKFDYLPKLCIEEILDNLGC | NH2 |
| C215 | DOTA-PEG4 | 48 | CEYDEEFFTALKRLRGGDICYYIKKKFKKVPKLCIEEILDKLGC | NH2 |
| C216 | $^{nat}$In-DOTA-PEG4 | 75 | CEYDEEFFTALKRLRGGDICYYILys(Ac)Lys(Ac)Lys(Ac)FLys(Ac)Lys(Ac)VPLys(Ac)LCIEEILDKLGC | NH2 |
| C217 | $^{nat}$In-DOTA-PEG4 | 73 | CEYDEEFFTALLys(Ac)CitrullineLCitrullineGGDICYYIKKKFKKVPKLCIEEILDLys(Ac)LGC | NH2 |
| C218 | DOTA-lys(MPB)-PEG4 | 96 | CEYDEQFFTALARLRGGDICEYIQAKFQYLPGLCIEEILDNLGCS | OH |
| C219 | In-DOTA-PEG4 | 96 | CEYDEQFFTALARLRGGDICEYIQAKFQYLPGLCIEEILDNLGCS | OH |
| C220 | Biotin-PEG4 | 178 | CEYDEEFFTALKRLRGGDICQYIQASFQYLPGQCIEEILDNLGCS | OH |
| C221 | Biotin-PEG4 | 179 | CEYDEQFFTALKRLRGGDICQYIQASFQYLPGQCIEEILDNLGCS | OH |
| C222 | Biotin-PEG4 | 180 | CDYDEQFFTALKRLRGGDICQYIQASFQYLPGQCIEEILDNLGCS | OH |
| C223 | Biotin-PEG4 | 181 | CEYDEEFFTALKRLRGADICQYIQASFQYLPGQCIEEILDNLGCS | OH |
| C224 | Biotin-PEG4 | 182 | CDYDEEFFTALKRLRGADICQYIQASFQYLPGQCIEEILDNLGCS | OH |
| C225 | Biotin-PEG4 | 183 | CEYDEQFFTALKRLRGGDICEYIQASFQYLPGLCIEEILDNLGCS | OH |
| C226 | Biotin-PEG4 | 184 | CDYDEQFFTALKRLRGADICSYIQASFQYLPGLCIEEILDNLGCS | OH |
| C227 | Biotin-PEG4 | 185 | CEYDEQFFTALARLRGGDICEYIQASFQYLPGLCIEEILDNLGCS | OH |
| C228 | Biotin-PEG4 | 186 | CEYDEEFFTALARLRGADICEYIQASFQYLPGLCIEEILDNLGCS | OH |
| C229 | Biotin-PEG4 | 187 | CDYDEEFFTALARLRGGDICEYIQASFQYLPGLCIEEILDNLGCS | OH |
| C230 | Biotin-PEG4 | 188 | CDYDEQFFTALA(Cit)LRGGDICYYIQAKFQYLPGLCIFEILDNLGCS | OH |
| C231 | Biotin-PEG4 | 189 | CDYDEQFFTALA(Cit)LRGGDICEYIQAKFQYLPGLCIEEILDNLGCS | OH |
| C232 | Biotin-PEG4 | 190 | CDYDEQFFTALA(Cit)LRGADICEYIQAKFQYLPGLCIEEILDNLGCS | OH |
| C233 | Biotin-PEG4 | 191 | CDYDEQFFTALA(Cit)LRGADICYYIQAKFQYLPGLCIEEILDNLGCS | OH |
| C234 | Biotin-PEG4 | 192 | CDYDEQFFTALACitLRGGDICEYIQA(hydroxy-norleucine)FQYLPGLCIEEILDNLGCS | OH |
| C235 | Biotin-PEG4 | 193 | CDYDEQFFTALA(Cit)LRGGDICEYIQAYFQYLPGLCIEEILDNLGCS | OH |
| C236 | DOTA-PEG4 | 145 | CEYDEQFFTALKRLRGDDICDYIQASFQYLPGLCIEEILDNLGCS | OH |
| C237 | In-DOTA-PEG4 | 145 | CEYDEQFFTALKRLRGDDICDYIQASFQYLPGLCIEEILDNLGCS | OH |
| C238 | NH2 | 145 | CEYDEQFFTALKRLRGDDICDYIQASFQYLPGLCIEEILDNLGCS | OH |
| C239 | NH2 | 138 | CDYDEQFFTALKRLRGGDICEYIQASFQYLPGLCIEEILDNLGCS | OH |
| C240 | In-DOTA-PEG4 | 138 | CDYDEQFFTALKRLRGGDICEYIQASFQYLPGLCIEEILDNLGCS | OH |
| C241 | DOTA-PEG4 | 138 | CDYDEQFFTALKRLRGGDICEYIQASFQYLPGLCIEEILDNLGCS | OH |
| C242 | In-DOTA-PEG4 | 99 | CEYDEEFFTALARLRGGDICQYIQAKFQYLPGQCIEEILDNLGCS | OH |
| C243 | NH2 | 99 | CEYDEEFFTALARLRGGDICQYIQAKFQYLPGQCIEEILDNLGCS | OH |
| C244 | DOTA-PEG4 | 99 | CEYDEEFFTALARLRGGDICQYIQAKFQYLPGQCIEEILDNLGCS | OH |
| C245 | DOTA-PEG4 | 194 | CDYDEQFFTALARLRGADICEYIQASFQYLPGECIEEILDNLGCS | OH |
| C246 | In-DOTA-PEG4 | 194 | CDYDEQFFTALARLRGADICEYIQASFQYLPGECIEEILDNLGCS | OH |
| C247 | Biotin-PEG4 | 194 | CDYDEQFFTALARLRGADICEYIQASFQYLPGECIEEILDNLGCS | OH |
| C248 | In-DOTA-PEG4 | 134 | CEYDEQFFTALKRLRGADICSYIQASFQYLPGLCIEEILDNLGCS | OH |
| C249 | NH2 | 134 | CEYDEQFFTALKRLRGADICSYIQASFQYLPGLCIEEILDNLGCS | OH |
| C250 | DOTA-PEG4 | 134 | CEYDEQFFTALKRLRGADICSYIQASFQYLPGLCIEEILDNLGCS | OH |
| C251 | DOTA-PEG4 | 195 | CEYDEEFFTALARLRGGDICQYIQA(Kme3)FQYLPALCIEEILDNLGCS | OH |
| C252 | Biotin-PEG4 | 161 | CEYDEEFFTALARLRGADICQYIQA(Kme3)FQYLPALCIEEILDNLGCS | OH |
| C253 | Biotin-PEG4 | 195 | CEYDEEFFTALARLRGGDICQYIQA(Kme3)FQYLPALCIEEILDNLGCS | OH |
| C254 | In-DOTA-PEG4 | 195 | CEYDEEFFTALARLRGGDICQYIQA(Kme3)FQYLPALCIEEILDNLGCS | OH |
| C255 | Biotin-PEG4 | 196 | CDYDEQFFTALKRLRGGDICEYIQA(Kme3)FQYLPGECIEEILDNLGCS | OH |
| C256 | Biotin-PEG4 | 197 | CDYDEQFFTALKRLRGGDICEYIQA(Kme3)FQYLPGLCIEEILDNLGCS | OH |
| C257 | Biotin-PEG4 | 198 | CDYDEQFFTALKRLRGADICEYIQA(Kme3)FQYLPGECIEEILDNLGCS | OH |
| C258 | Biotin-PEG4 | 199 | CDYDEQFFTALKRLRGADICEYIQA(Kme3)FQYLPGLCIEEILDNLGCS | OH |
| C259 | Biotin-PEG4 | 200 | CDYDEQFFTALA(Cit)LRGGDICEYIQA(Kme3)FQYLPGLCIEEILDNLGCS | OH |
| C260 | DOTA-PEG4 | 200 | CDYDEQFFTALA(Cit)LRGGDICEYIQA(Kme3)FQYLPGLCIEEILDNLGCS | OH |
| C261 | In-DOTA-PEG4 | 200 | CDYDEQFFTALA(Cit)LRGGDICEYIQA(Kme3)FQYLPGLCIEEILDNLGCS | OH |
| C262 | Biotin-PEG4 | 201 | CEYDEQFFTALARLRGADICEYIQA(Kme3)FQYLPGLCIEEILDNLGCS | OH |
| C263 | Biotin-PEG4 | 202 | CEYDEQFFTALARLRGGDICEYIQA(Kme3)FQYLPGLCIEEILDNLGCS | OH |
| C264 | Biotin-PEG4 | 203 | CEYDEQFFTALARLRGGDICEYIQARFQYLPGLCIEEILDNLGCS | OH |
| C265 | DOTA-PEG4 | 203 | CEYDEQFFTALARLRGGDICEYIQARFQYLPGLCIEEILDNLGCS | OH |
| C266 | In:DOTA-PEG4 | 203 | CEYDEQFFTALARLRGGDICEYIQARFQYLPGLCIEEILDNLGCS | OH |
| C267 | Biotin-PEG4 | 204 | CEYDEQFFTALARLRGGDICEYIQA(sRme2)FQYLPGLCIEEILDNLGCS | OH |
| C268 | DOTA-PEG4 | 204 | CEYDEQFFTALARLRGGDICEYIQA(sRme2)FQYLPGLCIEEILDNLGCS | OH |
| C269 | In:DOTA-PEG4 | 204 | CEYDEQFFTALARLRGGDICEYIQA(sRme2)FQYLPGLCIEEILDNLGCS | OH |
| C270 | In-DOTA-PEG4 | 155 | CDYDEQFFTALKRLRGADICEYIQASFQYLPGECIEEILDNLGCS | OH |
| C271 | DOTA-PEG4 | 155 | CDYDEQFFTALKRLRGADICEYIQASFQYLPGECIEEILDNLGCS | OH |
| C272 | NH2 | 155 | CDYDEQFFTALKRLRGADICEYIQASFQYLPGECIEEILDNLGCS | OH |
| C273 | Biotin-PEG4 | 205 | CEYDEQFFTALKRLRGGDICEYIQANFQYLPGLCIEEILDNLGCS | OH |
| C274 | Biotin-PEG4 | 206 | CEYDEQFFTALKRLRGGDICEYIQATFQYLPGLCIEEILDNLGCS | OH |
| C275 | Biotin-PEG4 | 207 | CEYDEQFFTALKRLRGGDICEYIQADFQYLPGLCIEEILDNLGCS | OH |
| C276 | Biotin-PEG4 | 208 | CEYDEQFFTALKRLRGGDICEYIQARFQYLPGLCTEEILDNLGCS | OH |
| C277 | Biotin-PEG4 | 209 | CEYDEEFFTELERLKGGDICYYIKKKFDKVPRLCIKEIRDKLGC | OH |
| C278 | Biotin-PEG4 | 210 | CEYKEEFFTELKRLYGGDICYYIKKKFKKVPDLCIEEILDKLGC | NH2 |
| C279 | Biotin-PEG4 | 211 | CEYKEEFFTELERLKGGDICYYIKKKFDKVPDLCIKEIRDKLGC | NH2 |
| C280 | Biotin-PEG4 | 212 | CEYDEQFFTALARLRGADICEYIQARFQYLPGLCIEEILDNLGCS | OH |
| C281 | Biotin-PEG4 | 213 | CEYDEEFFTELERLKGGDICEYIQA-Cit-FQYLPGLCIEEILDNLGCS | OH |
| C282 | Biotin-PEG4 | 214 | CEYDEQFFTALARLRGGDICEYIQA(Arg(NO2))FQYLPGLCIEEILDNLGCS | OH |
| C283 | La-DOTA-PEG4 | 78 | CEYDEEFFTALKRLRGGDICYYIQASFQYLPGLCIEEILDNLGCS | OH |
| C284 | Ga-DOTA-PEG4 | 78 | CEYDEEFFTALKRLRGGDICYYIQASFQYLPGLCIEEILDNLGCS | OH |
| C285 | Cu-DOTA-PEG4 | 78 | CEYDEEFFTALKRLRGGDICYYIQASFQYLPGLCIEEILDNLGCS | OH |
| C286 | Ac-DOTA-PEG4 | 78 | CEYDEEFFTALKRLRGGDICYYIQASFOYLPGLCIEEILDNLGCS | OH |

TABLE 2A-continued

| | | | | |
|---|---|---|---|---|
| C287 | NH2 | 78 | CEYDEEFFTALKRLRGGDICYYIQASFQYLPGLCIEEILDNLGCS | OH |
| C288 | DOTA-PEG4 | 215 | CEYDEEFFTA(Leu-13C6,15N)KR(Leu-13C6,15N)RGGDICYYIQASFQY(Leu-13C6,15N)PG(Leu-13C6,15N)CIEEI(Leu-13C6,15N)DN(Leu-13C6,15N)GCS-OH | OH |
| C289 | NH2 | 93 | CEYDEEFFTALARLRGDDICSYIQAKFQYLPGLCIEEILDNLGCS | OH |
| C290 | NH2 | 194 | CDYDEQFFTALARLRGADICEYIQASFQYLPGECIEEILDNLGCS | OH |
| C291 | NH2 | 195 | CEYDEEFFTALARLRGGDICQYIQA(Kme3)FQYLPALCIEEILDNLGCS | OH |
| C292 | NH2 | 200 | CDYDEQFFTALA(Cit)LRGGDICEYIQA(Kme3)FQYLPGLCIEEILDNLGCS | OH |
| C293 | DOTA-PEG4 | 93 | CEYDEEFFTALARLRGGDICSYIQAKFQYIPGLCIEEILDNLGCS | OH |
| C298 | Biotin-PEG4 | 162 | CEYDEEFFTALARLRGGDICQYIQAKFQYLPALCIEEILDNLGCS | OH |
| C299 | Biotin-PEG4 | 163 | CEYDEEFFTALARLRGGDICQYIQA(Kme)FQYLPALCIEEILDNLGCS | OH |
| C300 | Biotin-PEG4 | 164 | CEYDEEFFTALARLRGGDICQYIQA(Kme2)FQYLPALCIEEILDNLGCS | OH |
| C301 | Biotin-PEG4 | 165 | CEYDEEFFTALARLRGGDICQYIQA(Kipr)FQYLPALCIEEILDNLGCS | OH |
| C302 | Biotin-PEG4 | 166 | CEYDEEFFTAL(Kme)RLRGGDICQYIQA(Kme3)FQYLPALCIEEILDNLGCS | OH |
| C303 | Biotin-PEG4 | 167 | CEYDEEFFTAL(Kme2)RLRGGDICQYIQA(Kme3)FQYLPALCIEEILDNLGCS | OH |
| C304 | Biotin-PEG4 | 168 | CEYDEEFFTAL(Kipr)RLRGGDICQYIQA(Kme3)FQYLPALCIEEILDNLGCS | OH |
| C305 | | 248 | CEYDEEFFTA(Leu-13C6,15N)AR(Leu-13C6,15N)RGGDICQYIQA(Kme3)FQY(Leu-13C6,15N)PA(Leu-13C6,15N)CIEEI(Leu-13C6,15N)DN(Leu-13C6,15N)GCS | OH |
| C306 | Biotin-PEG4 | 48 | CEYDEEFFTALKRLRGGDICYYIKKKFKKVPKLCIEEILDKLGC | NH2 |
| C307 | Eu:DOTA:PEG4 | 48 | CEYDEEFFTALKRLRGGDICYYIKKKFKKVPKLCIEEILDKLGC | NH2 |

| Compound Name[2] | Parent MW | Calculated Mass (M + 4/4) | Observed Mass (M + 4/4) |
|---|---|---|---|
| C3 | 5173.08 | 1294.27 | 1295.2 |
| C4 | 5213.1 | 1304.28 | 1305.1 |
| C5 | 5215.12 | 1304.78 | 1305.6 |
| C6 | 5255.14 | 1314.79 | 1315.9 |
| C7 | 5174.02 | 1294.51 | 1296.0 |
| C8 | 5647.6 | 1412.90 | 1413.2 |
| C9 | 5216.06 | 1305.02 | 1305.5 |
| C10 | 5809.75 | 1453.44 | 1454.1 |
| C11 | 5796.64 | 1450.16 | 1450.8 |
| C12 | 5806.7 | 1452.68 | 1454.1 |
| C13 | 5259.08 | 1315.77 | 1316.6 |
| C14 | 5315.19 | 1329.80 | 1330.5 |
| C15 | 5358.22 | 1340.56 | 1341.4 |
| C16 | 5233.17 | 1309.29 | 1309.3 |
| C17 | 5272.17 | 1319.04 | 1320.2 |
| C18 | 5384.3 | 1347.08 | 1347.0 |
| C19 | 5198.08 | 1300.52 | 1301.2 |
| C20 | 5225.02 | 1307.26 | 1307.9 |
| C21 | 5207.05 | 1302.76 | 1303.2 |
| C22 | 5260.11 | 1316.03 | 1317.1 |
| C23 | 5269.08 | 1318.27 | 1319.3 |
| C24 | 5251.1 | 1313.78 | 1315.0 |
| C25 | 5286.24 | 1322.56 | 1323.2 |
| C26 | 5287.18 | 1322.80 | 1324.1 |
| C27 | 5273.15 | 1319.29 | 1320.1 |
| C28 | 5245.14 | 1312.29 | 1314.5 |
| C29 | 5259.17 | 1315.79 | 1316.4 |
| C30 | 5228.06 | 1308.02 | 1308.8 |
| C31 | 5272.26 | 1319.07 | 1320.3 |
| C32 | 5273.2 | 1319.30 | 1320.3 |
| C33 | 5286.19 | 1322.55 | 1323.9 |
| C34 | 5271.22 | 1318.81 | 1319.6 |
| C35 | 5272.26 | 1319.07 | 1320.3 |
| C36 | 5273.20 | 1319.30 | 1320.3 |
| C37 | 5272.26 | 1319.07 | 1320.3 |
| C38 | 5273.2 | 1319.30 | 1320.3 |
| C39 | 5258.18 | 1315.55 | 1316.5 |
| C40 | 5231.16 | 1308.79 | 1309.8 |
| C41 | 5248.22 | 1313.06 | 1313.7 |
| C42 | 5276.24 | 1320.06 | 1320.2 |
| C43 | 5249.17 | 1313.29 | 1313.2 |
| C44 | 5258.27 | 1315.57 | 1316.7 |
| C45 | 5273.2 | 1319.30 | 1316.7 |
| C46 | 5258.23 | 1315.56 | 1316.6 |
| C47 | 5258.23 | 1315.56 | 1316.5 |
| C48 | 5258.23 | 1315.56 | 1316.7 |
| C49 | 5258.18 | 1315.55 | 1316.5 |
| C50 | 5983.93 | 1496.98 | 1498.4 |
| C51 | 6160.14 | 1541.04 | 1542.1 |
| C52 | 5330.29 | 1333.57 | 1334.6 |
| C53 | 5344.32 | 1337.08 | 1338.3 |
| C54 | 5343.38 | 1336.85 | 1338.2 |
| C55 | 5316.31 | 1330.08 | 1331.2 |
| C56 | 5328.36 | 1333.09 | 1334.0 |
| C57 | 5286.28 | 1322.57 | 1324.0 |
| C58 | 5284.31 | 1322.08 | 1323.2 |

TABLE 2A-continued

| | | | |
|---|---|---|---|
| C59 | 5286.28 | 1322.57 | 1323.7 |
| C60 | 5285.25 | 1322.31 | 1323.2 |
| C61 | 5298.34 | 1325.59 | 1326.7 |
| C62 | 5285.34 | 1322.34 | 1323.2 |
| C63 | 5297.4 | 1325.35 | 1326.6 |
| C64 | 5284.31 | 1322.08 | 1323.2 |
| C65 | 5286.28 | 1322.57 | 1323.7 |
| C66 | 5287.22 | 1322.81 | 1324.1 |
| C67 | 5284.31 | 1322.08 | 1326.8 |
| C68 | 5299.28 | 1325.82 | 1327.2 |
| C69 | 5313.35 | 1329.34 | 1329.8 |
| C70 | 5271.32 | 1318.83 | 1319.8 |
| C71 | 5271.27 | 1318.82 | 1319.6 |
| C72 | 5296.46 | 1325.12 | 1326.5 |
| C73 | 5296.41 | 1325.10 | 1326.6 |
| C74 | 5284.4 | 1322.10 | 1323.1 |
| C75 | 5284.36 | 1322.09 | 1323.1 |
| C76 | 5327.38 | 1332.85 | 1333.9 |
| C77 | 5312.36 | 1329.09 | 1329.9 |
| C78 | 5298.34 | 1325.59 | 1327.1 |
| C79 | 5300.31 | 1326.08 | 1327.7 |
| C80 | 5299.33 | 1325.83 | 1327.4 |
| C81 | 5313.35 | 1329.34 | 1329.9 |
| C82 | 5880.99 | 1471.25 | 1471.6 |
| C83 | 5286.28 | 1322.57 | 1323.4 |
| C84 | 5963 | 1491.75 | 1492.3 |
| C85 | 5965.98 | 1492.495 | 1493.7 |
| C86 | 6215.22 | 1554.805 | 1556.5 |
| C87 | 6218.2 | 1555.55 | 1556.8 |
| C88 | 6129.18 | 1533.295 | 1534.2 |
| C89 | 6132.16 | 1534.04 | 1534.7 |
| C90 | 5956.65 | — | 1193.6 |
| C91 | 5943.6 | — | 1191.3 |
| C92 | 5919.51 | — | 1185.9 |
| C93 | 5874.41 | — | 1176.8 |
| C94 | 5869.24 | — | 1175.8 |
| C95 | 6027.84 | — | 1207.6 |
| C96 | 6013.82 | — | 1205.1 |
| C97 | 6012.83 | — | 1204.9 |
| C98 | 5988.75 | — | 1199.3 |
| C99 | — | | |
| C100 | 5146.84 | 1287.71 | 1287.35 |
| C101 | 5738.50 | 1435.63 | 1435.68 |
| C102* | 5850.30 | 1463.57 | 1463.02 |
| C103 | 5578.409 | 1395.60 | 1395.17 |
| C104 | 5150.88 | 1288.72 | 1288.26 |
| C105 | 5742.53 | 1436.63 | 1436.6 |
| C106* | 5854.33 | 1464.58 | 1464.01 |
| C107 | 5582.43 | 1396.61 | 1395.56 |
| C108 | 5238.94 | 1310.74 | 1309.96 |
| C109 | 5830.6 | 1458.65 | 1458.12 |
| C110* | 5942.39 | 1486.60 | 1486.06 |
| C111 | 5670.50 | 1418.62 | 1417.98 |
| C112 | 5109.78 | 1278.44 | — |
| C113 | 5788.52 | 1448.13 | 1447.66 |
| C114* | 5904.34 | 1477.09 | 1475.39 |
| C115 | 5628.41 | 1408.10 | 1407.69 |
| C116 | 5351.16 | 1338.79 | 1337.78 |
| C117 | 5942.82 | 1486.71 | 1486.25 |
| C118* | 6050.738 | 1513.68 | 1514.03 |
| C119 | 5782.72 | 1446.68 | 1446.55 |
| C120 | 5280.04 | 1321.01 | 1320.52 |
| C121 | 5871.70 | 1468.92 | 1468.34 |
| C122* | 5983.69 | 1496.92 | 1496.26 |
| C123 | 5711.59 | 1428.90 | 1428.33 |
| C124 | 5222.94 | 1306.74 | 1306.24 |
| C125 | 5814.6 | 1454.65 | 1454.19 |
| C126* | 5926.39 | 1482.60 | 1482.09 |
| C127 | 5654.50 | 1414.62 | 1414.15 |
| C128 | 5073.75 | 1269.44 | — |
| C129 | 5752.49 | 1439.12 | 1438.7 |
| C130* | 5864.28 | 1467.07 | 1466.58 |
| C131 | 5592.38 | 1399.10 | 1398.69 |
| C132 | 5150.84 | 1288.71 | 1288.35 |
| C133 | 5,830.56 | 1458.64 | 1457.92 |
| C134* | 5942.35 | 1486.59 | 1486.11 |
| C135 | 5670.45 | 1418.61 | 1417.98 |
| C136 | 5019.61 | 1255.90 | — |
| C137 | 5698.35 | 1425.59 | 1425.09 |
| C138* | 5810.14 | 1453.54 | 1453.08 |

TABLE 2A-continued

| | | | |
|---|---|---|---|
| C139 | 5538.24 | 1385.56 | — |
| C140 | 5,670.45 | 1418.61 | 1418.11 |
| C141 | 5606.4 | 1402.60 | 1402.2 |
| C142 | 5683.49 | 1421.87 | 1421.36 |
| C143 | 5636.43 | 1410.11 | 1409.7 |
| C144 | 5612.41 | 1404.10 | 1403.7 |
| C145 | 5655.48 | 1414.87 | 1414.35 |
| C146 | 5619.45 | 1405.86 | 1405.29 |
| C147 | 5620.44 | 1406.11 | 1405.7 |
| C148 | 5619.45 | 1405.86 | 1405.48 |
| C149 | 5634.42 | 1409.61 | 1408.83 |
| C150 | 5652.4 | 1414.10 | 1412.93 |
| C151 | 5561.38 | 1391.35 | 1390.75 |
| C152 | 5709.59 | 1428.40 | 1428.28 |
| C153 | 5633.44 | 1409.36 | 1409 |
| C154 | 5611.44 | 1403.86 | 1403.55 |
| C155 | 5548.34 | 1388.09 | 1387.71 |
| C156 | 5634.47 | 1409.62 | 1409.2 |
| C157 | 5548.34 | 1388.09 | 1387.65 |
| C158 | 5547.35 | 1387.84 | 1387.45 |
| C159 | 5599.41 | 1400.85 | 1400.36 |
| C160 | 5605.42 | 1402.36 | 1402 |
| C161 | 5585.38 | 1397.35 | 1396.9 |
| C162 | 5626.43 | 1407.61 | 1406.98 |
| C163 | 5661.48 | 1416.37 | 1414.47 |
| C164 | 5655.48 | 1414.87 | 5655.481 |
| C165 | 5689.50 | 1423.37 | 1422.94 |
| C166 | 5725.62 | 1432.41 | 1432.17 |
| C167 | 5691.55 | 1423.89 | 1424.3 |
| C168 | 5649.52 | 1413.38 | 1413.82 |
| C169 | 5677.53 | 1420.38 | 1419.95 |
| C170 | 5638.40 | 1410.60 | 1410.24 |
| C171 | 5621.42 | 1406.36 | 1410.24 |
| C172 | 5637.41 | 1410.35 | 1409.93 |
| C173 | 5655.48 | 1414.87 | 1414.46 |
| C174 | 5,689.49 | 1423.37 | 1422.94 |
| C175 | 5579.38 | 1395.85 | 1395.34 |
| C176 | 5607.39 | 1402.85 | 1402.35 |
| C177 | 5686.45 | 1422.61 | 1422.15 |
| C178 | 5,636.43 | 1410.11 | 1409.9 |
| C179 | 5,594.39 | 1399.60 | 1399.24 |
| C180 | 5,728.53 | 1433.13 | 1432.7 |
| C181 | 5,694.47 | 1424.62 | 1424.07 |
| C182 | 5,652.43 | 1414.11 | 1413.13 |
| C183 | 5,649.47 | 1413.37 | 1413.07 |
| C184 | 5,593.41 | 1399.35 | 1398.93 |
| C185 | 5,607.44 | 1402.86 | 1402.32 |
| C186 | 5,651.45 | 1413.86 | 1413.43 |
| C187 | 5908.33 | 1478.08 | 1477.66 |
| C188 | 5,622.40 | 1406.60 | 1406.18 |
| C189 | 5,580.37 | 1396.09 | 1395.63 |
| C190 | 5,621.42 | 1406.36 | 1405.57 |
| C191 | 5,680.44 | 1421.11 | 1420.73 |
| C192 | 5,638.40 | 1410.60 | 1410.18 |
| C193 | 5,679.46 | 1420.87 | 1420.48 |
| C194 | 5635.45 | 1409.86 | 1409.74 |
| C195 | 5636.44 | 1410.11 | 1409.68 |
| C196 | 5621.42 | 1406.36 | 1405.95 |
| C197 | 5679.46 | 1420.87 | 1420.52 |
| C198 | 5620.44 | 1406.11 | 1405.45 |
| C199 | 5662.52 | 1416.63 | 1416.22 |
| C200 | 5622.41 | 1406.60 | 1406.12 |
| C201 | 5720.62 | 1431.16 | 1430.4 |
| C202 | 5652.39 | 1414.10 | 1413.65 |
| C203 | 5638.36 | 1410.59 | 1410.22 |
| C204 | 5665.43 | 1417.36 | 1417.02 |
| C205 | 5651.4 | 1413.85 | 1413.71 |
| C207 | 5635.45 | 1409.86 | 1409.62 |
| C208 | 5651.41 | 1413.85 | 1413.38 |
| C209 | 5650.42 | 1413.61 | 1413.25 |
| C210 | 5637.38 | 1410.34 | 1409.92 |
| C211 | 5636.40 | 1410.10 | 1409.69 |
| C212 | 5307.196 | 1327.79 | 1328.8 |
| C213 | — | — | — |
| C214 | 5899.863 | 1475.96 | 1476.9 |
| C215 | 5876.985 | 1470.24 | 1471.6 |
| C216 | 6160.166 | 1541.04 | 1542.1 |
| C217 | 6074.821 | 519.7 | 1520.4 |
| C218 | 6067.947 | 1517.99 | 1517.46 |
| C219 | 5908.333 | 1478.08 | 1477.66 |

TABLE 2A-continued

| | | | |
|---|---|---|---|
| C220 | 5,650.42 | 1413.61 | 1413.21 |
| C221 | 5,649.44 | 1413.36 | 1413.1 |
| C222 | 5,635.41 | 1409.85 | 1409.43 |
| C223 | 5,664.45 | 1417.11 | 1416.73 |
| C224 | 5,650.42 | 1413.61 | 1413.23 |
| C225 | 5,635.45 | 1409.86 | 1409.48 |
| C226 | 5,593.41 | 1399.35 | 1399 |
| C227 | 5,578.36 | 1395.59 | 1395.38 |
| C228 | 5,592.38 | 1399.10 | 1398.8 |
| C229 | 5,564.33 | 1392.08 | 1391.63 |
| C230 | 5,640.47 | 1411.12 | 1410.48 |
| C231 | 5,606.41 | 1402.60 | 1402.24 |
| C232 | 5,619.45 | 1405.86 | 1405.59 |
| C233 | 5,654.50 | 1414.62 | 1414.29 |
| C234 | 5,607.39 | 1402.85 | 1402.65 |
| C235 | 5,641.41 | 1411.35 | 1410.94 |
| C236 | 5,839.56 | 1460.89 | 1460.05 |
| C237 | 5,951.36 | 1488.84 | 1488.58 |
| C238 | 5,205.87 | 1302.47 | N/A |
| C239 | 5,147.83 | 1287.96 | N/A |
| C240 | 5,893.32 | 1474.33 | 1473.96 |
| C241 | 5,781.53 | 1446.38 | 1445.93 |
| C242 | 5,906.32 | 1477.58 | 1477.19 |
| C243 | 5,160.83 | 1291.21 | N/A |
| C244 | 5,794.53 | 1449.63 | 1449.32 |
| C245 | 5,754.41 | 1439.60 | 1439.25 |
| C246 | 5,866.21 | 1467.55 | 1467.22 |
| C247 | 5,594.31 | 1399.58 | 1399.17 |
| C248 | 5,879.34 | 1470.83 | 1470.41 |
| C249 | 5,133.85 | 1284.46 | N/A |
| C250 | 5,767.55 | 1442.89 | 1442.97 |
| C251 | 5,836.67 | 1460.17 | 1459.52 |
| C252 | 5,690.60 | 1423.65 | 1423.6 |
| C253 | 5,676.57 | 1420.14 | 1418.17 |
| C254 | 5,948.47 | 1488.12 | 1487.67 |
| C255 | 5,721.57 | 1431.39 | 1431.48 |
| C256 | 5,705.61 | 1427.40 | 1426.8 |
| C257 | 5,735.59 | 1434.90 | 1434.31 |
| C258 | 5,719.64 | 1430.91 | 1430.29 |
| C259 | 5,649.50 | 1413.37 | 1412.79 |
| C260 | 5,809.60 | 1453.40 | 1452.97 |
| C261 | 5,921.40 | 1481.35 | 1480.89 |
| C262 | 5,676.57 | 1420.14 | 1419.61 |
| C263 | 5,662.54 | 1416.64 | 1416.12 |
| C264 | 5,647.47 | 1412.87 | 1412.59 |
| C265 | 5,807.57 | 1452.89 | 1452.74 |
| C266 | 5919.364 | 1480.84 | 1480.57 |
| C267 | 5,675.52 | 1419.88 | 1419.53 |
| C268 | 5,835.62 | 1459.91 | 1459.7 |
| C269 | 5947.41 | 1487.85 | 1487.50 |
| C270 | 5,923.30 | 1481.83 | 1281.49 |
| C271 | 5,811.51 | 1453.88 | 1453.52 |
| C272 | 5,177.81 | 1295.45 | N/A |
| C273 | 5,662.48 | 1416.62 | 1416.2 |
| C274 | 5,649.48 | 1413.37 | 1413.62 |
| C275 | 5,663.46 | 1416.87 | 1416.51 |
| C276 | 5,704.56 | 1427.14 | 1426.68 |
| C277 | 5,557.57 | 1390.39 | 1390.15 |
| C278 | 5,535.60 | 1384.90 | 1384.44 |
| C279 | 5,517.45 | 1380.36 | 1379.7 |
| C280 | 5,661.49 | 1416.37 | 1416.32 |
| C281 | 5,648.45 | 1413.11 | 1412.86 |
| C282 | 5,692.46 | 1424.12 | 1423.8 |
| C283 | 5,966.48 | 1492.62 | N/A |
| C284 | 5,897.30 | 1475.32 | N/A |
| C285 | 5,892.13 | 1474.03 | 1474.37 |
| C286 | 6,052.60 | 1514.15 | N/A |
| C287 | 5,200.94 | 1301.23 | N/A |
| C288 | 5,872.28 | 1469.07 | 1469.47 |
| C289 | 5,162.84 | 1291.71 | N/A |
| C290 | 5,120.72 | 1281.18 | N/A |
| C291 | 5,202.98 | 1301.74 | N/A |
| C292 | 5,132.82 | 1284.20 | N/A |
| C293 | 5796.539 | 1450.13 | 1449.79 |
| C298 | 5,633.47 | 1409.36 | 1409.29 |
| C299 | 5,647.50 | 1412.87 | 1413.03 |
| C300 | 5,662.54 | 1416.63 | 1416.58 |
| C301 | 5,675.56 | 1419.89 | 1419.74 |
| C302 | 5,747.69 | 1437.92 | 1437.60 |
| C303 | 5,761.71 | 1441.42 | 1441.16 |

TABLE 2A-continued

| | | | |
|---|---|---|---|
| C304 | 5,775.74 | 1444.93 | 1444.50 |
| C305 | — | — | — |
| C306 | 5716.881 | 1430.22 | 1430.01 |
| C307 | — | — | — |

[2] Each compound is identified via a compound # (e.g., "C1", "C2", "C3", etc.) and refers to the combination of the N-terminal, Linker (if present), Sequence, and C-terminal.
[3] Refers to sequences in the "Sequence" column.
[4] "dD" refers to D-aspartic acid; "hR" refers to homo-arginine; "hyP" refers to hydroxyproline; "1Nal" refers to 1-naphthylamine; "sRme2" refers to symmetric dimethyl arginine; "Cit" refers to citrulline; "Kme" refers to methyllysine; "Kme2" refers to dimethyllysine; "Kme3" refers to trimethyllysine; "Kipr" refers to Nε-isopropyl-L-Lysine.
NOTE:
In all sequences shown, Cys1 is connected to Cys34 and Cys20 is connected to Cys44.
*Compounds designated In-labeled in TABLE 2A are cold-metal labeled, using "natural abundance" Indium, also known as $^{nat}$In. This Indium-may comprise a combination of 113-In and 115-In, and distinguished from 111-In, which can be used as a radiolabel for conjugates provided herein.
DOTA-PEG4: alpha-(1,4,7,10-tetraazacyclododecan-1,4,7,10-tetraacetate)-4(ethylene glycol)
DOTA-PEG8: alpha-(1,4,7,10-tetraazacyclododecan-1,4,7,10-tetraacetate)-8(ethylene glycol)
DOTA-PEG12: alpha-(1,4,7,10-tetraazacyclododecan-1,4,7,10-tetraacetate)-12(ethylene glycol)
Biotin-PEG4:

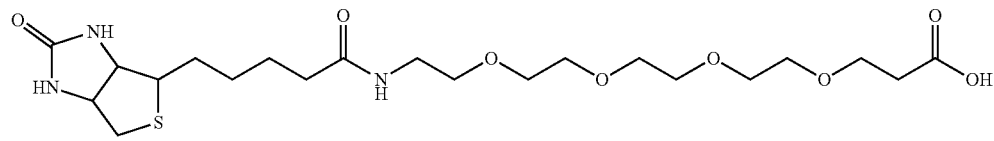 [SMILES: O=C(O)CCOCCOCCOCCOCCNC(=O)CCCCC1SCC2NC(=O)NC21]

FITC1-PEG4: Fluorescein isothiocyanate-4(ethylene glycol)

TABLE 2B

Binding Affinities of Exemplary Compounds to Nectin-4

| SEQ ID NO: OF POLYPEPTIDE TESTED | Compound Name | Binding Affinity ($K_D$, nM) |
|---|---|---|
| 1 | C1 | 184.20 |
| 2 | C2 | 58.92 |
| 3 | C3 | 9.68 |
| 4 | C4 | 14.40 |
| 3 | C5 | 18.93 |
| 4 | C6 | 17.09 |
| 5 | C7 | 5.50 |
| 5 | C8 | 9.77 |
| 5 | C9 | 7.50 |
| 5 | C10 | 37.58 |
| 5 | C11 | 6.86 |
| 5 | C12 | 10.50 |
| 6 | C13 | 6.01 |
| 7 | C14 | 14.11 |
| 8 | C15 | 12.17 |
| 9 | C16 | 4.34 |
| 10 | C17 | 4.16 |
| 11 | C18 | 38.16 |
| 12 | C19 | 10.81 |
| 13 | C20 | 22.08 |
| 14 | C21 | 49.39 |
| 15 | C22 | 12.83 |
| 16 | C23 | 18.51 |
| 17 | C24 | 84.39 |
| 18 | C25 | 3.745 |
| 19 | C26 | 5.04 |
| 20 | C27 | 9.85 |
| 21 | C28 | 5.29 |
| 22 | C29 | 3.91 |
| 23 | C30 | 24.92 |
| 24 | C31 | 1.31 |
| 25 | C32 | 3.26 |
| 26 | C33 | 3.47 |
| 27 | C34 | 3.17 |
| 34 | C41 | 5.60 |
| 36 | C43 | 3.97 |
| 37 | C44 | 3.14 |
| 38 | C45 | 3.29 |
| 39 | C46 | 2.28 |
| 42 | C49 | 1.93 |
| 5 | C51 | 8.37 |
| 43 | C52 | 5.24 |
| 46 | C55 | 3.39 |
| 47 | C56 | 3.88 |
| 48 | C57 | 0.29 |
| 49 | C58 | 1.81 |
| 51 | C60 | 3.17 |
| 52 | C61 | 1.79 |
| 54 | C63 | 1.97 |
| 55 | C64 | 3.80 |
| 56 | C65 | 2.21 |
| 57 | C66 | 2.63 |
| 58 | C67 | 2.64 |
| 59 | C68 | 2.66 |
| 60 | C69 | 1.86 |
| 61 | C70 | 2.20 |
| 62 | C71 | 2.85 |
| 67 | C76 | 0.52 |
| 68 | C77 | 0.58 |
| 69 | C78 | 0.49 |
| 70 | C79 | 0.38 |
| 71 | C80 | 2.70 |
| 72 | C81 | 0.43 |
| 76 | C100 | 4.80 |
| 76 | C102 | 6.40 |
| 76 | C103 | 6.60 |
| 77 | C104 | 3.70 |
| 77 | C106 | 4.38 |
| 77 | C107 | 3.38 |
| 78 | C108 | 5.78 |
| 78 | C111 | 4.32 |
| 79 | C112 | 6.24 |
| 80 | C115 | 6.46 |
| 81 | C116 | 0.78 |
| 81 | C119 | 0.95 |
| 82 | C120 | 2.11 |
| 82 | C123 | 1.43 |
| 83 | C124 | 1.10 |
| 83 | C127 | 1.27 |
| 84 | C128 | 10.10 |
| 85 | C131 | 12.40 |
| 86 | C132 | 30.10 |
| 87 | C135 | 5.42 |
| 88 | C136 | 36.50 |
| 89 | C139 | 25.20 |
| 90 | C140 | 1.10 |
| 91 | C141 | 0.64 |
| 92 | C142 | 0.81 |
| 93 | C143 | 0.55 |
| 94 | C144 | 3.70 |
| 95 | C145 | 1.30 |
| 96 | C146 | 0.54 |

TABLE 2B-continued

Binding Affinities of Exemplary Compounds to Nectin-4

| SEQ ID NO: OF POLYPEPTIDE TESTED | Compound Name | Binding Affinity ($K_D$, nM) |
|---|---|---|
| 97 | C147 | 0.69 |
| 98 | C148 | 0.82 |
| 99 | C149 | 0.75 |
| 100 | C150 | 1.00 |
| 101 | C151 | 0.68 |
| 102 | C152 | 0.85 |
| 103 | C153 | 0.56 |
| 104 | C154 | 0.94 |
| 105 | C155 | 1.10 |
| 106 | C156 | 1.10 |
| 107 | C157 | 1.10 |
| 108 | C158 | 1.10 |
| 111 | C161 | 7.50 |
| 112 | C162 | 8.80 |
| 113 | C163 | 1.90 |
| 114 | C164 | 5.00 |
| 115 | C165 | 4.10 |
| 116 | C166 | 0.75 |
| 117 | C167 | 1.20 |
| 118 | C168 | 0.90 |
| 119 | C169 | 0.74 |
| 120 | C170 | 8.80 |
| 121 | C171 | 2.20 |
| 122 | C172 | 1.80 |
| 123 | C173 | 5.00 |
| 115 | C174 | 4.10 |
| 124 | C175 | 2.30 |
| 125 | C176 | 1.30 |
| 126 | C177 | 2.00 |
| 127 | C178 | 1.40 |
| 128 | C179 | 1.80 |
| 129 | C180 | 2.70 |
| 130 | C181 | 3.00 |
| 131 | C182 | 3.00 |
| 132 | C183 | 1.20 |
| 133 | C184 | 2.50 |
| 134 | C185 | 1.00 |
| 135 | C186 | 1.70 |
| 136 | C188 | 1.60 |
| 137 | C189 | 1.10 |
| 138 | C190 | 0.71 |
| 139 | C191 | 1.40 |
| 140 | C192 | 1.30 |
| 141 | C193 | 1.00 |
| 142 | C194 | 1.10 |
| 143 | C195 | 2.30 |
| 144 | C196 | 1.60 |
| 145 | C197 | 0.97 |
| 146 | C198 | 2.30 |
| 147 | C199 | 3.50 |
| 148 | C200 | 2.00 |
| 149 | C201 | 0.68 |
| 150 | C202 | 2.20 |
| 151 | C203 | 2.30 |
| 152 | C204 | 1.98 |
| 153 | C205 | 2.10 |
| 154 | C207 | 1.08 |
| 155 | C208 | 1.02 |
| 156 | C209 | 1.25 |
| 157 | C210 | 1.54 |
| 158 | C211 | 1.19 |

In some embodiments, a miniprotein of the present disclosure exhibits binding specificity to human Nectin-4. For example, in some embodiments a miniprotein provided by the present disclosure, such as, for example, those represented by any one of SEQ ID NOs: 3-158, 161-168, 170-208, 212-237, 243-246 and 248, demonstrates binding when expressed on the surface of yeast and binding to Nectin-4 tested by flow cytometry. In some embodiments, a miniprotein provided by the present disclosure, such as, for example, those represented by any one of SEQ ID NOs: 3-158, 161-168, 170-208, 212-237, 243-246 and 248 or in accordance with TABLES 1B, 1 C, 1D, and/or 2A, demonstrates binding specificity via flow cytometry when, for example, such a Nectin-4 miniprotein (e.g., as represented by any of SEQ ID NOs: 3-158, 161-168, 170-208, 212-237, 243-246 and 248 or in accordance with any of TABLES 1B, 1C, 1D and/or 2A) only binds to Nectin-4 and not to other antigens.

In some embodiments, a miniprotein of the present disclosure such as, for example, any of those represented by SEQ ID NOs: 3-158, 161-168, 170-208, 212-237, 243-246 and 248 or in accordance with TABLES 1B, 1C, 1D, 2A, 2B, and/or 2C shows greater than 10 nM potency. In some embodiments, a miniprotein shows potency greater than 1, 2, 3, 4, 5, 6, 7, 8, 9 nM or more.

In some embodiments, a miniprotein is part of a conjugate comprising one or more modifications or components, for example, as provided herein (see, e.g., TABLE 2A).

In some embodiments, a miniprotein provided by the present disclosure is set forth in the consensus sequences provided as Formula IV:

(SEQ ID NO: 233)
CX2X3X4X5X6X7X8X9X10X11X12X13X14X15X16X17X18X19C

X21X22X23X24X25X26X27X28X29X30X31X32X33CX35X36X37

X38X39X40X41X42X43CS wherein
X2 is E, G, A, S, T, D, N, K, R, Y, F, V, I, or W; X3 is Y, P, G, A, S, T, Q, K, H, F, W, V, M, D, E, L, or 1; X4 is D, S, N, R, Y, L, M, G, T, or I; X5 is E, G, D, Q, F, W, V, L, I, M, K, or R; X6 is E, P, G, D, Q, N, K, Y, F, W, or V; X7 is F, Y, or W; X8 is F, Y, W, 1, or M; X9 is T, P, A, S, D, Q, N, K, Y, F, V, M, E, R, or L; X10 is A, S, E, N, K, F, W, V, L, I, G, T, D, Q, R, or H; X11 is L, T, I, or M; X12 is K, L, G, A, S, T, N, R, H, F, W, V. I, or M; X13 is R, G, A, S, E, N, K, Y, W, L, I, or M; X14 is L, T, V, I, or M; X15 is R, T, Q, K, L, I, M, or V; X16 is G, D, N, K, R, H, Y, W, V, L, I, or M; X17 is G, P, A, S, T, D, Q, N, R, H, Y, F, W, V, L, or M; X18 is D, P, G, A, T, E, Q, N, K, Y, F, W, V, I, M, or S; X19 is I, P, A, T, D, N, Y, V, M, G, or Q; X21 is Y, S, T, D, E, K, F, W, L, I, or V; X22 is Y or E; X23 is I, A, T, Y, V, L, M, or F; X24 is Q, P, G, D, K, R, H, F, V, L, I, M. or N; X25 is A, P, S, D, E, Q, K, R, H, Y, F, W, V, I, M, or T; X26 is S, P, G, A, D, Q, N, R, F, V, L, I, T, E, or W; X27 is F, P, A, S, K, H, Y, W, M, E, or V; X28 is Q, P, G, A, S, D, E, K, R, H, Y, W, V, L, F, or I; X29 is Y, P, A, S, E, Q, N, K, F, W, L, I, M, T, or V; X30 is L, P, G, A, S, T, E, N, R, H, F, W, V, I, M, Q, or K; X31 is P, G, A, T, D, E, Q, N, K, R, H, Y, V, S, W, L, or I; X32 is G, A, S, D, N, R, H, Y, L, I, or V; X33 is L, P, G, A, S, D, E, N, K, R, H, Y, F, W, V, I, or M; X35 is I, P, S, D, E, N, K, R, Y, F, W, L, or M; X36 is E, G, A, S, T, D, Q, K, R, H, Y, W, L, I, or M; X37 is E, P, G, A, S, T, N, K, R, H, Y, F, W, V, or D; X38 is I, A, S, E, Y, F, W, V, L, T, or H; X39 is L, S, T, E, N, R, H, Y, F, W, V, M, D, or I; X40 is D, G, A, S, E, Q, R, H, F, W, V, L, I, M, N, or K; X41 is N. G, A, S, D, Q, R, H, Y, F, V, L, I, M, P, or K; X42 I, L, P, G, Q, N, H, F, W, I, M, or S; and X43 is G, P, A, T, D, N, K, R, Y, F, W, V, 1, or Q.

In some embodiments, the consensus sequence of Formula IV is summarized in TABLE 2C. In some embodiments, a miniprotein provided by the present disclosure is set forth in the consensus sequences provided as Formula IV, wherein X2-X43 comprise amino acid residues of SEQ ID NO: 78 or any one of the amino acids of the allowed substitutions in TABLE 2C, and/or any one of the preferred substitutions in TABLE 2C. In some embodiments, a miniprotein provided by the present disclosure is set forth in the consensus sequences provided as Formula IV, wherein X2-X43 comprise amino acid residues of SEQ ID NO: 78 and/or any one of the preferred substitutions in TABLE 2C. In some embodiments, a miniprotein provided by the present disclosure comprises SEQ ID NO: 78 comprising a single allowed substitution shown in TABLE 2C. In some embodiments, a miniprotein provided by the present disclosure comprises SEQ ID NO: 78 comprising a single preferred substitution shown in TABLE 2C. In some embodiments, a miniprotein provided by the present disclosure comprises SEQ ID NO: 78 comprising 2 or more allowed substitution shown in TABLE 2C. In some embodiments, a miniprotein provided by the present disclosure comprises SEQ ID NO: 78 comprising 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, or 42 or more allowed substitution shown in TABLE 2C. In some embodiments, a miniprotein provided by the present disclosure comprises SEQ ID NO: 78 comprising a single preferred substitution shown in TABLE 2C. In some embodiments, a miniprotein provided by the present disclosure comprises SEQ ID NO: 78 comprising two preferred substitutions, three preferred substitutions, four preferred substitutions, or five preferred substitutions shown in TABLE 2C.

TABLE 2C

| Formula IV Consensus and Substitutions | | | |
|---|---|---|---|
| Formula IV Consensus sequence (SEQ ID NO: 233) | SEQ ID NO: 78 | Allowed substitutions | Preferred substitutions |
| C | C | | |
| X2 | E | G, A, S, T, D, N, K, R, Y, F, V, I | W |
| X3 | Y | P, G, A, S, T, Q, K, H, F, W, V, M | D, E, L, I |
| X4 | D | S, N, R, Y, L, M | G, T, I |
| X5 | E | G, D, Q, E, W, V, L, I, M | K, R |
| X6 | E | P, G, D, Q, N, K, Y, F, W, V | |
| X7 | E | Y, W | |
| X8 | E | Y, W, I, M | |
| X9 | T | P, A, S, D, Q, N, K, Y, F, V, M | E, R, L |
| X10 | A | S, B, N, K, F, W, V, L, I | G, T, D, Q, R, H |
| X11 | L | T, I | M |
| X12 | K | G, A, S, T, N, R, H, F, W, V, I, M | |
| X13 | R | G, A, S, E, N, K, Y, W, L, I, M | |
| X14 | L | T, V, I | M |
| X15 | R | T, Q, K, L, I, M | V |
| X16 | G | D, N, K, R, H, Y, W, V, L, I, M | |
| X17 | G | P, A, S, T, D, Q, N, R, H, Y, F, W, V, L, M | |
| X18 | D | P, G, A, T, E, Q, N, K, Y, F, W, V, I, M | S |
| X19 | I | P, A, T, D, N, Y, V, M | G, Q |
| C | C | | |
| X21 | Y | S, T, D, E, K, F, W, L, I | V |
| X22 | Y | E | |
| X23 | I | A, T, Y, V, L, M | F |
| X24 | Q | P, G, D, K, R, H, F, V, L, I, M | N |
| X25 | A | P, S, D, E, Q, K, R, H, Y, F, W, V, I, M | T |
| X26 | S | P, G, A, D, Q, N, R, F, V, L, I | T, E, W |
| X27 | F | P, A, S, K, H, Y, W, M | E, V |
| X28 | Q | P, G, A, S, D, E, K, R, H, Y, W, V, L | F, I |
| X29 | Y | P, A, S, E, Q, N, K, F, W, L, I, M | T, V |
| X30 | L | P, G, A, S, T, E, N, R, H, E, W, V, I, M | Q, K |
| X31 | P | G, A, T, D, E, Q, N, K, R, H, Y, V | S, W, L, I |
| X32 | G | A, S, D, N, R, H, Y, L, I | V |
| X33 | L | P, G, A, S, D, E, N, K, R, H, Y, F, W, V, I | M |
| C | C | | |
| X35 | I | P, S, D, E, N, K, R, Y, F, W, L, M | |
| X36 | E | G, A, S, T, D, Q, K, R, H, Y, W, L, I, M | |
| X37 | E | P, G, A, S, T, N, K, R, H, Y, F, W, V | D |
| X38 | I | A, S, E, Y, F, W, V, L | T, H |
| X39 | L | S, T, E, N, R, H, Y, F, W, V, M | D, I |
| X40 | D | G, A, S, E, Q, R, H, F, W, V, L, I, M | N, K |
| X41 | N | G, A, S, D, Q, R, H, Y, F, V, L, I, M | P, K |
| X42 | I | P, G, Q, N, H, F, W, I, M | S |
| X43 | G | P, A, T, D, N, K, R, Y, F, W, V, I | Q |
| C | C | | |
| S | S | | |

In some embodiments, a miniprotein provided by the present disclosure is set forth in the consensus sequences provided as Formula V:

(SEQ ID NO: 234)
CX2X3X4X5X6X7X8X9X10X11X12X13X14X15X16X17X18X19C

X21X22X23X24X25X26X27X28X29X30X31X32X33CX35X36X37

X38X39X40X41X42X43CS wherein X2 is E. P, G, A, S. T, Q, N, K, R, H. Y. F, W, V. L, I, or M; X3 is Y, P, G, A. S. T, D, E, Q, N, K, R, H, F, W, V, L, I, or M, X4 is D, P, G, A, S, T, E. Q, N, K, R, H, Y F, W. V, L, I, or M; X5 is E. P, G, S, T. D, Q, N, K, R, H, F, W, V, L, I, M, or Y; X6 is E, P. G. A, S, T. D, Q, N, K, R, H. F. W, V, L, I, M, or Y; X7 is F. Y, or W. X8 is F, T. Y. W, V, L, I, or M; X9 is T, P, G, S, D, E, N, K, R, H, Y, F, V, L, I, M, A, Q, or W; X10 is A, P, G, S, T, D, E, Q, N, K, R, H, Y, F, W, V, L, I, or M; X11 is L, A, V, I, or M; X12 is A, G, S, D, E, Q, N, K, R, H, Y, F, W, V, L, I, M, or T; X13 is R, P, S, T, D, E, Q, K, H, Y, F, V, L, M, G, A, N, W, or I; X14 is L, A, T, F, V, I, or M; X15 is R, Q, Y, F, W, V, L, I, M, or K; X16 is G, P, A, S, T, D, E, Q, N, K, R, H, Y, F, W, V, L, M, or I; X17 is G, P, A, S, T, D, E, Q, N, K, R, H, Y, W, V, L, I, M, or F; X18 is D, P, G, A, S, T, E, Q, N, K, R, H, Y, W, V, I, M, F, or L; X19 is I, P, G, A, S, T, D, E, Q, N, K, R, Y, F, W, V, L, M, or H; X21 is Y, P, G, A, S, T, D, E, Q, N, K, R, H, F, W, V, L, I, or M; X22 is Y, H, or F; X23 is I, G, A, S, T, Y, W, V, L, M, or F; X24 is Q, G, S, T, D, E, N, K, R, H, F, W, V, L, I, M, P, A, or Y; X25 is A, G, S, T, D, E, Q, N, K, R, H, Y, F, W, V, M, P, L, or I; X26 is K, P, G, A, S, T, D, E, Q, N, R, H, Y, F, W, V, L, I, or M; X27 is F, P, G, A, S, T, D, E, Q, N, K, R, H, Y, W, V, L, I, or M; X28 is Q, P, G, A, S, T, D, E, N, K, R, H, Y, F, W, V, L, I, or M; X29 is Y, P, G, A, S, T, D, E, N, K, R, H, F, W, V, L, I, M, or Q; X30 is L, P, G, A, S, T, D, E, Q, N, K, R, H, Y, F, W, V, I, or M; X31 is P, G, A, S, T, D, Q, N, K, R, H, Y, F, V, 1, M, E, W, or L; X32 is G, P, A, S, T, D, E, Q, N, K, R, H, Y, F, W, V, L, I, or M; X33 is L, P, G, A, S, T, D, E, Q, N, K, R, H, Y, F, W, V, I, or M; X35 is I, P, G, A, S, T, D, E, Q, N, K, R, Y, F, W, V, L, M, or H; X36 is E, P, G, A, S, D, Q, N, R, H, F, V, L, I, M, T, K, Y, or W; X37 is E, P, G, A, S, T, D, N, K, H, Y, F, W, V, L, I, M, Q, or R; X38 is 1, P, G, A, S, T, E, Q, N, K, H, Y, F, W, V, L, or M; X39 is L, G, A, S, T, D, E, Q, N, K, R, H, Y, W, V, I, M, or F; X40 is D, P, G, A, S, E, Q, N, K, R, H, Y, F, W, V, L, I, M, or T; X41 is N, P, G, A, S, T, D, E, Q, K, R, H, Y, F, W, V, L, I, or M; X42 is L, G, A, S, T, E, Q, N, K, R, H, Y, F, W, V, I, or M; and X43 is G, P, A, S, T, D, E, Q, N, K, R, H, Y, F, W, V, L, M, or 1.

In some embodiments, the consensus sequence of Formula V is summarized in TABLE 2D. In some embodiments, a miniprotein provided by the present disclosure is set forth in the consensus sequences provided as Formula V, wherein X2-X43 comprise amino acid residues of SEQ ID NO: 83, any one of the amino acids of the allowed substitutions in TABLE 2D, and/or any one of the preferred substitutions in TABLE 2D. In some embodiments, a miniprotein provided by the present disclosure is set forth in the consensus sequences provided as Formula V, wherein X2-X43 comprise amino acid residues of SEQ ID NO: 83 or any one of the preferred substitutions in TABLE 2D. In some embodiments, a miniprotein provided by the present disclosure comprises SEQ ID NO: 83 comprising a single allowed substitution shown in TABLE 2D. In some embodiments, a miniprotein provided by the present disclosure comprises SEQ ID NO: 83 comprising a single preferred substitution shown in TABLE 2D. In some embodiments, a miniprotein provided by the present disclosure comprises SEQ ID NO: 83 comprising 2 or more allowed substitution shown in TABLE 2D. In some embodiments, a miniprotein provided by the present disclosure comprises SEQ ID NO: 83 comprising 3 or more, 4 or more, 5 or more, 6 or more, 7 or more, 8 or more, 9 or more, 10 or more, 11 or more, 12 or more, 13 or more, 14 or more, or more, 16 or more, 17 or more, 18 or more, 19 or more, 20 or more, 21 or more, 22 or more, 23 or more, 24 or more, 25 or more, 26 or more, 27 or more, 28 or more, 29 or more, or more, 31 or more, 32 or more, 33 or more, 34 or more, 35 or more, 36 or more, 37 or more, 38 or more, 39 or more, 40 or more, 41 or more, or 42 or more allowed substitution shown in TABLE 2D. In some embodiments, a miniprotein provided by the present disclosure comprises SEQ ID NO: 83 comprising a single preferred substitution shown in TABLE 2D. In some embodiments, a miniprotein provided by the present disclosure comprises SEQ ID NO: 83 comprising two preferred substitutions, three preferred substitutions, four preferred substitutions, or five preferred substitutions shown in TABLE 2D.

TABLE 2D

Formula V Consensus and Substitutions

| Formula V Consensus sequence (SEQ ID NO: 234) | SEQ ID NO: 83 | Allowed substitutions | Preferred substitutions |
|---|---|---|---|
| C | C | | |
| X2 | | P, G, A, S, T, Q, N, K, R, H, Y, F, W, V, L, I, M | |
| X3 | Y | P, G, A, S, T, D, E, Q, N, K, R, H, F, W, V, L, I, M | |
| X4 | D | P, G, A, S, T, E, Q, N, K, R, H, Y, F, W, V, L, I, M | |
| X5 | E | P, G, S, T, D, Q, N, K, R, H, F, W, V, L, I, M | Y |
| X6 | E | P, G, A, S, T, D, Q, N, K, R, H, F, W, V, L, I, M | Y |
| X7 | E | Y, W | |
| X8 | E | T, Y, W, V, L, I, M | |
| X9 | T | P, G, S, D, E, N, K, R, H, Y, E, V, L, I, M | A, Q, W |
| X10 | A | P, G, S, T, D, E, Q, N, K, R, H, Y, E, W, V, L, I, M | |
| X11 | L | A, V, I, M | |
| X12 | A | G, S, D, E, Q, N, K, R, H, Y, F, W, V, L, I, M | T |
| X13 | R | P, S, T, D, E, Q, K, H, Y, F, V, L, M | G, A, N, W, I |
| X14 | L | A, T, F, V, I, M | |
| X15 | R | Q, Y, E, W, V, L, I, M | K |
| X16 | G | P, A, S, T, D, E, Q, N, K, R, H, Y, F, W, V, L, M | I |
| X17 | G | P, A, S, T, D, E, Q, N, K, R, H, Y, W, V, L, I, M | E |
| X18 | D | P, G, A, S, T, E, Q, N, K, R, H, Y, W, V, I, M | F, L |
| X19 | I | P, G, A, S, T, D, E, Q, N, K, R, Y, F, W, V, L, M | H |
| C | C | | |
| X21 | Y | P, G, A, S, T, D, E, Q, N, K, R, H, F, W, V, L, I, M | |
| X22 | Y | H, F | |
| X23 | I | G, A, S, T, Y, W, V, L, M | F |
| X24 | Q | G, S, T, D, E, N, K, R, H, F, W, V, L, I, M | P, A, Y |
| X25 | A | G, S, T, D, E, Q, N, K, R, H, F, W, V, M | P, L, I |
| X26 | K | P, G, A, S, T, D, E, Q, N, R, H, Y, F, W, V, L, I, M | |
| X27 | F | P, G, A, S, T, D, E, Q, N, K, R, H, Y, W, V, L, I, M | |
| X28 | Q | P, G, A, S, T, D, E, N, K, R, H, Y, F, W, V, L, M | |
| X29 | Y | P, G, A, S, T, D, E, N, K, R, H, F, W, V, L, I, M | Q |
| X30 | I | P, G, A, S, T, D, E, Q, N, K, R, H, Y, F, W, V, I, M | |
| X31 | P | G, A, S, T, D, Q, N, K, R, H, Y, F, V, I, M | E, W, L |

TABLE 2D-continued

Formula V Consensus and Substitutions

| Formula V Consensus sequence (SEQ ID NO: 234) | SEQ ID NO: 83 | Allowed substitutions | Preferred substitutions |
|---|---|---|---|
| X32 | G | P, A, S, T, D, E, Q, N, K, R, H, Y, F, W, V, L, I, M | |
| X33 | L | P, G, A, S, T, D, E, Q, N, K, R, H, Y, F, W, V, I, M | |
| C | C | | |
| X35 | I | P, G, A, S, T, D, E, Q, N, K, R, Y, F, W, V, L, M | H |
| X36 | E | P, G, A, S, D, Q, N, R, H, F, V, L, I, M | T, K, Y, W |
| X37 | E | P, G, A, S, T, D, N, K, H, Y, F, W, V, L, I, M | Q, R |
| X38 | I | P, G, A, S, T, E, Q, N, K, H, Y, F, W, V, L | M |
| X39 | I | G, A, S, T, D, E, Q, N, K, R, H, Y, W, V, I, M | F |
| X40 | D | P, G, A, S, E, Q, N, K, R, H, Y, F, W, V, L, I, M | T |
| X41 | N | P, G, A, S, T, D, E, Q, K, R, H, Y, E, W, V, L, I, M | |
| X42 | I | G, A, S, T, E, Q, N, K, R, H, Y, E, W, V, I, M | |
| X43 | G | P, A, S, T, D, E, Q, N, K, R, H, Y, E, W, V, L, M | I |
| C | C | | |
| S | S | | |

In some embodiments, a miniprotein provided by the present disclosure is set forth in the consensus sequences provided as Formula VI:

```
                                                (SEQ ID NO: 235)
CX2X3X4X5X6X7X8X9X10X11X12X13X14X15X16X17X18X19C

X21X22X23X24X25X26X27X28X29X30X31X32X33CX35X36X37

X38X39X40X41X42X43CS
``` wherein X2 is E, P, G, A, S, T, D, Q, N, K, R, H, Y, W, V, L, I, M, or F; X3 is Y, P, G, A, 5, T, D, E, Q, K, RH, F, W, V, L, I, M, or N, X4 is D, P, A, S, E, Q, N, or H; X5 is E, P, G, A, T, Q, N, K, R, H, Y, F, W, V, L, I, M, S, or D; X6 is Q, P, G, A, S, T, D, E, N, K, R, H, Y, F, W, V, L, I, or M, X7 is F, Y, or W; X8 is F, Y, W, V, 1, or M, X9 is T, P, G, A, S, D, Q, N, R, H, Y, F, V, L, I, M, E, K, or W, X10 is A, G, T, D, E, Q, N, K, R, H, W, L, I, M, S, Y, F, or V, X11 is L, V, I, or M, X12 is A, G, 5, T, D, K, LY, F, W, V, L, I, M, E, Q, N, or H; X13 is R, G, A, S, T, D, Q, N, K, H, Y, F, W, V, L, M, E, or I; X14 is L, T, V, I, or M; X15 is R, Q, K, I, or M; X16 is G, A, T, D, E, Q, N, K, R, H, Y, W, V, L, I, M, P, S, or F; X17 is G, P, A, S, T, D, E, Q, N, K, R, H, Y, F, W, V, L, I, or M, X18 is D, P, G, A, S, T, E, N, K, H, Y, F, L, M, Q, or K; X19 is 1, G, A, S, T, E, Q, N, K, R, H, Y, F, W, V, L, or M; X21 is Y, P, G, A, S, D, E, Q, N, K, R, H, F, W, V, L, I, M, or T; X22 is Y; X23 is 1, A, T, Y, F, W, V, L, or M; X24 is Q, P, A, S, D, E, N, K, H, Y, F, W, V, L, I, G, T, R, or M; X25 is E, P, G, A, S, T, D, Q, N, R, H, Y, F, W, V, L, I, M, or K; X26 is Q, G, A, S, T, E, N, K, R, H, F, W, V, L, I, M, D, or Y; X27 is F, Y, W, L, I, M, or V; X28 is A, P, G, S, T, D, E, Q, N, K, R, H, Y, W, V, L, I, M, or F; X29 is T, P, G, A, S, D, E, Q, K, R, H, Y, F, W, V, L, I, M, or N; X30 is V, P, G, A, T, D, E, N, K, R, H, Y, F, W, I, M, S, Q, or L; X31 is P, G, A, S, T, D, E, Q, N, K, R, H, Y, F, W, V, L, I, or M; X32 is G, P, A, T, D, E, Q, N, K, R, H, Y, F, W, V, L, I, M, or S; X33 is L, P, G, A, S, T, D, E, Q, K, R, H, Y, F, W, V, I, M, or N; X35 is I, P, G, A, S, T, D, E, Q, N, K, R, H, Y, F, W, L, M, or V; X36 is E, P, G, A, S, T, D, N, R, H, F, W, V, L, I, M, K, or Y; X37 is E, P, G, A, S, T, D, N, R, H, Y, W, V, L, I, M, Q, K, or F; X38 is I, G, A, S, E, Q, H, Y, W, V, L, M, P, or F; X39 is L, G, A, S, T, D, E, Q, N, K, H, Y, F, W, V, I, M, or R; X40 is D, P, G, A, S, T, E, Q, N, R, H, Y, F, W, L, I, M, or K; X41 is Q, P, G, A, S, T, D, E, N, K, R, H, Y, F, W, V, L, I, or M; X42 is L, G, A, S, T, E, Q, R, H, Y, F, V, I, M, N, or W; and X43 is G, P, A, S, T, D, E, Q, N, K, F, W, V, L, I, M, R, H, or Y.

In some embodiments, the consensus sequence of Formula VI is summarized in TABLE 2E. In some embodiments, a miniprotein provided by the present disclosure is set forth in the consensus sequences provided as Formula VI, wherein X2-X43 comprise amino acid residues of SEQ ID NO: 85, any one of the amino acids of the allowed substitutions in TABLE 2E, and/or any one of the preferred substitutions in TABLE 2E. In some embodiments, a miniprotein provided by the present disclosure is set forth in the consensus sequences provided as Formula VI, wherein X2-X43 comprise amino acid residues of SEQ ID NO: 85 and/or any one of the preferred substitutions in TABLE 2E. In some embodiments, a miniprotein provided by the present disclosure comprises SEQ ID NO: 85 comprising a single allowed substitution shown in TABLE 2E. In some embodiments, a miniprotein provided by the present disclosure comprises SEQ ID NO: 85 comprising a single preferred substitution shown in TABLE 2E. In some embodiments, a miniprotein provided by the present disclosure comprises SEQ ID NO: 85 comprising 2 or more allowed substitution shown in TABLE 2E. In some embodiments, a miniprotein provided by the present disclosure comprises SEQ ID NO: 85 comprising 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more 25 or more, 26 or more, 27 or more, 28 or more. 29 or more, 30 or more, 31 or more, 32 or more, 33 or more, 34 or more, 35 or more, 36 or more, 37 or more, 38 or more, 39 or more, 40) or more, 41 or more, or 42 or more allowed substitution shown in TABLE 2E. In some embodiments, a miniprotein provided by the present disclosure comprises SEQ ID NO: 85 comprising a single preferred substitution shown in TABLE 2E. In some embodiments, a miniprotein provided by) the present disclosure comprises SEQ ID NO: 85 comprising two preferred substitutions, three preferred substitutions, four preferred substitutions, or five preferred substitutions shown in TABLE 2E.

TABLE 2E

Formula VI Consensus and Substitutions

| Formula VI Consensus sequence (SEQ ID NO: 235) | SEQ ID NO: 85 | Allowed substitutions | Preferred substitutions |
|---|---|---|---|
| C | C | | |
| X2 | E | P, G, A, S, T, D, Q, N, K, R, H, Y, W, V, L, I, M | F |
| X3 | Y | P, G, A, S, T, D, E, Q, K, R, H, E, W, V, L, I, M | N |
| X4 | D | P, A, S, E, Q, N, H | |
| X5 | E | P, G, A, T, Q, N, K, R, H, Y, F, W, V, L, I, M | S, D |
| X6 | Q | P, G, A, S, T, D, E, N, K, R, H, Y, E, W, V, L, I, M | |
| X7 | F | Y, W | |
| X8 | F | Y, W, V, I, M | |
| X9 | T | P, G, A, S, D, Q, N, R, H, Y, E, V, L, I, M | E, K, W |
| X10 | A | G, T, D, E, Q, N, K, R, H, W, L, I, M | S, Y, F, V |
| X11 | L | V, I, M | |
| X12 | A | G, S, T, D, K, R, Y, F, W, V, L, I, M | E, Q, N, H |
| X13 | R | G, A, S, T, D, Q, N, K, H, Y, F, W, V, L, M | E, I |
| X14 | | T, V, I, M | |
| X15 | R | Q, K, I, M | |
| X16 | G | A, T, D, E, Q, N, K, R, H, Y, W, V, L, I, M | P, S, F |
| X17 | G | P, A, S, T, D, E, Q, N, K, R, H, Y, F, W, V, L, I, M | |
| X18 | D | P, G, A, S, T, E, N, K, H, Y, F, L, M | Q, K |
| X19 | I | G, A, S, T, E, Q, N, K, R, H, Y, E, W, V, L, M | |
| C | C | | |
| X21 | Y | P, G, A, S, D, E, Q, N, K, R, H, E, W, V, L, I, M | T |
| X22 | Y | | |
| X23 | I | A, T, Y, F, W, V, L | M |
| X24 | O | P, A, S, D, E, N, K, H, Y, F, W, V, L, I | G, T, R, M |
| X25 | E | P, G, A, S, T, D, Q, N, R, H, Y, F, W, V, L, I, M | K |
| X26 | Q | G, A, S, T, E, N, K, R, H, F, W, V, L, I, M | D, Y |
| X27 | F | Y, W, L, I, M | V |
| X28 | A | P, G, S, T, D, E, Q, N, K, R, H, Y, W, V, L, I, M | E |
| X29 | T | P, G, A, S, D, E, Q, K, R, H, Y, F, W, V, L, I, M | N |
| X30 | V | P, G, A, T, D, E, N, K, R, H, Y, F, W, I, M | S, Q, L |
| X31 | P | G, A, S, T, D, E, Q, K, R, H, Y, F, W, V, I, M | |
| X32 | G | P, A, T, D, E, Q, N, K, R, H, Y, F, W, V, L, I, M | S |
| X33 | L | P, G, A, S, T, D, E, Q, K, R, H, Y, E, W, V, I, M | N |
| C | C | | |
| X35 | I | P, G, A, S, T, D, E, Q, N, K, R, H, Y, F, W, L, M | V |
| X36 | E | P, G, A, S, T, D, N, R, H, F, W, V, L, I, M | K, Y |
| X37 | E | P, G, A, S, T, D, N, R, H, Y, W, V, L, I, M | Q, K, F |
| X38 | H | G, A, S, E, Q, H, Y, W, V, L, M | P, F |
| X39 | | G, A, S, T, D, E, Q, N, K, H, Y, E, W, V, I, M | R |
| X40 | D | P, G, A, S, T, E, Q, N, R, H, Y, F, W, L, I, M | K |
| X41 | 2 | P, G, A, S, T, D, E, N, K, R, H, Y, F, W, V, L, I, M | |
| X42 | | G, A, S, T, E, Q, R, H, Y, F, V, I, M | N, W |
| X43 | G | P, A, S, T, D, E, Q, N, K, F, W, V, L, I, M | R, H, Y |
| C | C | | |
| S | S | | |

In some embodiments, the consensus sequence of Formula VII is summarized in TABLE 2F. In some embodiments, a miniprotein provided by the present disclosure is set forth in the consensus sequences provided as Formula VII, wherein X2-X43 comprise amino acid residues of SEQ ID NO: 195, any one of the amino acids of the allowed substitutions in TABLE 2F, and/or any one of the preferred substitutions in TABLE 2F. In some embodiments, a miniprotein provided by the present disclosure is set forth in the consensus sequences provided as Formula VII, wherein X2-X43 comprise amino acid residues of SEQ ID NO: 195 and/or any one of the preferred substitutions in TABLE 2F. In some embodiments, a miniprotein provided by the present disclosure comprises SEQ ID NO: 195 comprising a single allowed substitution shown in TABLE 2F. In some embodiments, a miniprotein provided by the present disclosure comprises SEQ ID NO: 195 comprising a single preferred substitution shown in TABLE 2F. In some embodiments, a miniprotein provided by the present disclosure comprises SEQ ID NO: 195 comprising 2 or more allowed substitution shown in TABLE 2F. In some embodiments, a miniprotein provided by the present disclosure comprises SEQ ID NO: 195 comprising 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, or 42 or more allowed substitution shown in TABLE 2F. In some embodiments, a miniprotein provided by the present disclosure comprises SEQ ID NO: 195 comprising a single preferred substitution shown in TABLE 2F. In some embodiments, a miniprotein provided by the present disclosure comprises SEQ ID NO: 195 comprising two preferred substitutions, three preferred substitutions, four preferred substitutions, or five preferred substitutions shown in TABLE 2F.

TABLE 2F

Formula VII Consensus and Substitutions

| Formula VII Consensus sequence (SEQ ID NO: 236) | SEQ ID NO: 195 | Allowed substitutions | Preferred substitutions |
|---|---|---|---|
| C | C | | |
| X2 | E | P, G, A, S, T, D, Q, N, K, R, H, Y, W, V, L, I, M | F |
| X3 | Y | P, G, A, S, T, D, E, Q, N, K, H, W, V, L, I, M | R, F |
| X4 | D | P, G, A, T, Q, N, K, R, H, Y, F, W, V, L, M | S, E, I |
| X5 | E | P, G, A, S, T, D, N, K, R, H, Y, F, W, V, L | Q, I, M |
| X6 | E | P, G, A, D, Q, N, R, H, Y, F, W, V, L, M | S, K, I |
| X7 | F | Y | W |
| X8 | F | H, Y, W, V, L, I, M | |
| X9 | T | P, G, S, D, E, Q, N, K, R, H, Y, E, W, V, L, I, M | A |
| X10 | A | P, G, T, D, E, Q, N, K, R, H, Y, F, W, V, L, M | S, I |
| X11 | L | A, V, I, M | |
| X12 | A | P, G, S, T, D, E, K, R, H, Y, F, W, V, L, I, M | Q, N |
| X13 | R | P, A, S, T, D, E, Q, N, K, H, Y, F, W, V, L, I, M | G |
| X14 | L | T, F, V, M | I |
| X15 | R | Q, N, K, H, F, W, V, L, I, M | Y |
| X16 | G | P, A, T, D, E, Q, N, K, R, H, Y, F, W, V, L, I, M | S |
| X17 | G | A, S, D, E, Q, N, K, R, H, Y, F, W, V, L, I, M | P |
| X18 | D | P, G, A, S, T, E, Q, N, K, R, Y, F, W, V, L, I, M | H |
| X19 | I | P, G, A, S, T, D, E, Q, N, K, R, H, Y, F, W, V, L, M | |
| C | C | | |
| X21 | Q | P, G, A, S, D, E, N, R, H, Y, F, W, V, I, M | T, K, L |
| X22 | Y | H, F | |
| X23 | I | G, A, S, T, Y, F, V, L, M | |
| X24 | Q | P, G, A, S, E, N, K, R, H, Y, F, W, V, L, I, M | T, D |
| X25 | A | P, G, S, T, D, E, Q, N, K, H, Y, F, W, V, L, I, M | R |
| X26 | Kme 3 | P, G, S, T, D, E, Q, N, K, R, H, Y, F, W, V, L, M | A, I |
| X27 | F | P, G, A, S, D, E, Q, N, K, Rs Y, W, V, L, I, M | |
| X28 | Q | P, G, A, S, T, D, E, N, K, R, H, Y, F, W, V, L, I, M | |
| X29 | Y | P, G, A, S, T, D, E, Q, N, K, R, H, F, W, V, L, I, M | |
| X30 | T | P, G, A, T, D, E, Q, N, K, R, H, Y, F, W, V, I, M | S |
| X31 | P | G, S, T, D, E, Q, N, K, R, H, Y, W, V, L, I, M | A, F |
| X32 | A | P, G, S, T, D, Q, N, K, R, H, Y, F, W, V, I, M | E, L |
| X33 | L | P, G, A, S, T, D, E, Q, N, K, R, H, Y, E, W, V, I, M | |
| C | C | | |
| X35 | I | P, G, A, S, T, D, E, Q, N, R, H, Y, W, V, L, M | K, E |
| X36 | E | P, A, S, T, D, Q, N, K, R, H, Y, F, W, V, L, I, M | G |
| X37 | E | G, A, S, D, Q, N, K, R, H, Y, F, W, V, L, I, M | T |
| X38 | I | P, G, A, S, T, D, E, Q, N, H, Y, E, W, V, L, M | K, R |
| X39 | L | G, A, S, T, D, E, Q, N, R, H, Y, W, V, I, M | K, F |
| X40 | D | P, G, A, S, T, E, Q, K, R, H, Y, W, V, L, I, M | N, F |
| X41 | N | P, G, A, S, T, D, E, Q, K, R, H, Y, E, W, V, L, I, M | |
| X42 | L | G, A, S, D, E, Q, N, K, R, H, Y, F, W, V, I | M |
| X43 | G | P, A, S, T, D, E, Q, N, K, R, H, Y, F, W, V, L, I, M | |
| C | C | | |
| S | S | | |

In some embodiments, the consensus sequence of Formula VIII is summarized in TABLE 2G. Here, TABLE 2G differs from TABLE 2F in that the substitutable amino acid at position X24 of Formula VIII in TABLE 2G is a trimethyllysine (Kme3) whereas the substitutable amino acid at position X26 of Formula VII in TABLE 2F is a lysine (K).

In some embodiments, a miniprotein provided by the present disclosure is set forth in the consensus sequences provided as Formula VIII, wherein X2-X43 comprise amino acid residues of SEQ ID NO. 103, any one of the amino acids of the allowed substitutions in TABLE 2G, and/or any one of the preferred substitutions in TABLE 2G. In some embodiments, a miniprotein provided by the present disclosure is set forth in the consensus sequences provided as Formula VIII, wherein X2-X43 comprise amino acid residues of SEQ ID NO: 103 and/or any one of the preferred substitutions in TABLE 2G. In some embodiments, a miniprotein provided by the present disclosure comprises SEQ ID NO: 103 comprising a single allowed substitution shown in TABLE 2G. In some embodiments, a miniprotein provided by the present disclosure comprises SEQ ID NO: 103 comprising a single preferred substitution shown in TABLE 2G. In some embodiments, a miniprotein provided by the present disclosure comprises SEQ ID NO: 103 comprising 2 or more allowed substitution shown in TABLE 2G. In some embodiments, a miniprotein provided by the present disclosure comprises SEQ ID NO: 103 comprising 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, or 42 or more allowed substitution shown in TABLE 2G. In some embodiments, a miniprotein provided by the present disclosure comprises SEQ ID NO: 103 comprising a single preferred substitution shown in TABLE 2G. In some embodiments, a miniprotein provided by the present disclosure comprises SEQ ID NO: 103 comprising two preferred substitutions, three preferred substitutions, four preferred substitutions, or five preferred substitutions shown in TABLE 2G.

TABLE 2G

Formula VIII Consensus and Substitutions

| Formula VIII Consensus sequence (SEQ ID NO: 237) | SEQ ID NO: 103 | Allowed substitutions | Preferred substitutions |
|---|---|---|---|
| C | C | | |
| X2 | E | P, G, A, S, T, D, Q, N, K, R, H, Y, W, V, L, I, M | F |
| X3 | Y | P, G, A, S, T, D, E, Q, N, K, H, W, V, L, I, M | R, F |
| X4 | D | P, G, A, T, Q, N, K, R, H, Y, F, W, V, L, M | S, E, I |
| X5 | E | P, G, A, S, T, D, N, K, R, H, Y, E, W, V, L | Q, I, M |
| X6 | E | P, G, A, D, Q, N, R, H, Y, F, W, V, L, M | S, K, I |
| X7 | F | Y | W |
| X8 | F | H, Y, W, V, L, I, M | |
| X9 | T | P, G, S, D, E, Q, N, K, R, H, Y, E, W, V, L, I, M | A |
| X10 | A | P, G, T, D, E, Q, N, K, R, H, Y, F, W, V, L, M | S, I |
| X11 | L | A, V, I, M | |
| X12 | A | P, G, S, T, D, E, K, R, H, Y, F, W, V, L, I, M | Q, N |
| X13 | R | P, A, S, T, D, E, Q, N, K, H, Y, F, W, V, L, I, M | G |
| X14 | L | T, F, V, M | I |
| X15 | R | Q, N, K, H, F, W, V, L, I, M | Y |
| X16 | G | P, A, T, D, E, Q, N, K, R, H, Y, F, W, V, L, I, M | S |
| X17 | G | A, S, D, E, Q, N, K, R, H, Y, F, W, V, L, I, M | P |
| X18 | D | P, G, A, S, T, E, Q, N, K, R, Y, F, W, V, L, I, M | H |
| X19 | I | P, G, A, S, T, D, E, Q, N, K, R, H, Y, E, W, V, L, M | |
| C | C | | |
| X21 | Q | P, G, A, S, D, E, N, R, H, Y, F, W, V, I, M | T, K, L |
| X22 | Y | H, F | |
| X23 | I | G, A, S, T, Y, E, V, L, M | |
| X24 | Q | P, G, A, S, E, N, K, R, H, Y, F, W, V, L, I, M | T, D |
| X25 | A | P, G, S, T, D, E, Q, N, K, H, Y, F, W, V, L, I, M | R |
| X26 | K | P, G, S, T, D, E, Q, N, R, H, Y, E, W, V, L, M | A, I |
| X27 | F | P, G, A, S, D, E, Q, N, K, R, H, Y, W, V, L, I, M | |
| X28 | Q | P, G, A, S, T, D, E, N, K, R, H, Y, F, W, V, L, I, M | |
| X29 | Y | P, G, A, S, T, D, E, Q, N, K, R, H, F, W, V, L, I, M | |
| X30 | L | P, G, A, T, D, E, Q, N, K, R, H, Y, F, W, V, I, M | S |
| X31 | P | G, S, T, D, E, Q, N, K, R, H, Y, W, V, L, I, M | A, F |
| X32 | A | P, G, S, T, D, Q, N, K, R, H, Y, F, W, V, I, M | E, L |
| X33 | L | P, G, A, S, T, D, E, Q, N, K, R, H, Y, E, W, V, I, M | |
| C | C | | |
| X35 | I | P, G, A, S, T, D, E, Q, N, R, H, Y, W, V, L, M | K, F |
| X36 | E | P, A, S, T, D, Q, N, K, R, H, Y, F, W, V, L, I, M | G |
| X37 | E | G, A, S, D, Q, N, K, R, H, Y, F, W, V, L, I, M | T |
| X38 | I | P, G, A, S, T, D, E, Q, N, H, Y, E, W, V, L, M | K, R |
| X39 | L | G, A, S, T, D, E, Q, N, R, H, Y, W, V, I, M | K, F |
| X40 | D | P, G, A, S, T, E, Q, K, R, H, Y, W, V, L, I, M | N, F |
| X41 | N | P, G, A, S, T, D, E, Q, K, R, H, Y, E, W, V, L, I, M | |
| X42 | L | G, A, S, D, E, Q, N, K, R, H, Y, E, W, V, I | M |
| X43 | G | P, A, S, T, D, E, Q, N, K, R, H, Y, F, W, V, L, I, M | |
| C | C | | |
| S | S | | |

In some embodiments, a miniprotein in accordance with the present disclosure displays a binding specificity to human Nectin-4. In some embodiments, the miniprotein comprises a binding affinity characterized by a dissociation constant ranging from about 500 nM to about 1 pM, e.g., 500, 400, 300, 20, 100, 90, 80, 70, 60, 50, 40, 30, 20, 10, 9, 8, 7, 6, 5, 4, 3, 2, 1 nM, 100, 90, 80, 70, 60, 50, 40, 30, 20, 10, 9, 8, 7, 6, 5, 4, 3, 2, or 1 pM binding affinity to human Nectin-4. Without being bound by theory, the present disclosure contemplates that, in some embodiments, a preferred dissociation constant of a miniprotein is about 10 nM or less, about 7.5 nM, about 5 nM or less, about 2.5 nM or less, about 1 nM or less (i.e., in the picomolar range). For clarity, a stronger binder can be one that has a binding affinity of 2.5 nM as compared to one with 5 nM to Nectin 4, and a weaker binder one with a binding affinity of 5 nM to Nectin-4 as compared to a binder with a binding affinity of 2.5 nM to Nectin-4.

In some embodiments, a miniprotein of the present disclosure binds to Nectin-4 with a binding affinity of about 1 pM to 100 nM.

In some embodiments, a miniprotein in accordance with the present disclosure binds to Nectin-4 with a binding affinity of about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 pM; 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 1000 nM. In some embodiments, a miniprotein in accordance with the present disclosure binds to Nectin-4 with a binding affinity of about 1 pM to 100 pM, 10 pM to 1 nM, 100 pM to 10 nM, or 1 nM to 100 nM.

In some embodiments, the binding affinity ($K_D$ of Kd) of a polypeptide (or composition comprising such polypeptide, e.g., a miniprotein) as provided herein is in a range of about 1 pM to 100 nM.

In some embodiments, a binding affinity is between about 1 pM to 100 nM, 1 pM to 100 pM, 10 pM to 1 nM, 100 pM to 10 nM, or 1 nM to 100 nM. In some embodiments, a binding affinity is between about 1 pM to 5 pM, 1 pM to 10 pM, 1 pM to 15 pM, 1 pM to 20 pM, 1 pM to 25 pM, 1 pM to 30 pM, 1 pM to 35 pM, 1 pM to 40 pM, 1 pM to 45 pM, 1 pM to 50 pM, 1 pM to 55 pM, 1 pM to 60 pM, 1 pM to 65 pM, 1 pM to 70 pM, 1 pM to 75 pM, 1 pM to 80 pM, 1 pM to 85 pM, 1 pM to 90 pM, 1 pM to 95 pM, or 1 pM to 100 pM. In some embodiments, a binding affinity is between about 25 pM to 30 pM, 25 pM to 35 pM, 25 pM to 40 pM, 25 pM to 45 pM, 25 pM to 50 pM, 25 pM to 55 pM, 25 pM to 60 pM, 25 pM to 65 pM, 25 pM to 70 pM, 25 pM to 75 pM, 25 pM to 80 pM, 25 pM to 85 pM, 25 pM to 90 pM, pM to 95 pM, or 25 pM to 100 pM. In some embodiments, a binding affinity is between about 50 pM to 55 pM, 50 pM to 60 pM, 50 pM to 65 pM, 50 pM to 70 pM, 50 pM to 75 pM. 50 pM to 80 pM, 50 pM to 85 pM, 50 pM to 90 pM, 50 pM to 95 pM, or 50 pM to 100 pM. In some embodiments, a binding affinity is between about 75 pM to 80 pM, 75 pM to 85 pM, 75 pM to 90 pM, 75 pM to 95 pM, or 75 pM to 100 pM. In some embodiments, a binding affinity is between about 10 pM to 1 nM, 100 pM to 1 nM, 200 pM to 1 nM 300 pM to 1 nM, 400 pM to 1 nM, 500 pM to 1 nM, 600 pM to 1 nM, 700 pM to 1 nM, 800 pM to 1 nM, or 900 pM to 1 nM. In some embodiments, a binding affinity is between about 1 nM to 100) nM, 10 nM to 100 nM, 20 nM to 100 nM, 30 nM to 100) nM, 40 nM to 100 nM, 50 nM to 100 nM, 60 nM to 100 nM. 70 nM to 100 nM, 80 nM to 100 nM, or 90 nM to 100 nM. In some embodiments, a binding affinity is between about 5 nM to 100 nM, 10 nM to 100 nM, 15 nM to 100 nM, 20 nM to 100 nM, 25 nM to 100 nM, 30 nM to 100 nM, 35 nM to 100 nM, 40 nM to 100 nM, 45 nM to 100 nM, 50 nM to 100 nM, 55 nM to 100 nM, 60 nM to 100 nM, 65 nM to 100 nM, 70 nM to 100 nM, 75 nM to 100 nM, 80 nM to 100 nM, 85 nM to 100 nM, 90 nM to 100 nM, or 95 nM to 100 nM.

In some embodiments, a binding affinity is about 5 pM, 10 pM, 15 pM, 20 pM, 25 pM, 30 pM, 35 pM, 40 pM, 45 pM, 50 pM, 55 pM, 60 pM, 65 pM, 70 pM, 75 pM, 80 pM, 85 pM, 90 pM, 95 pM, or 100 pM. In some embodiments, a binding affinity is about 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, or 1 nM. In some embodiments, a binding affinity is about 1 nM, 2 nM, 3 nM, 4 nM, 5 nM, 6 nM, 7 nM, 8 nM, 9 nM, or 10 nM. In some embodiments, a binding affinity is about 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM. 90 nM, 95 nM, or 10) nM.

In some embodiments, a binding affinity is about 1 pM. In some embodiments, a binding affinity is about 2 pM. In some embodiments, a binding affinity is about 3 pM. In some embodiments, a binding affinity is about 4 pM. In some embodiments, a binding affinity is about 5 pM. In some embodiments, a binding affinity is about 10 pM. In some embodiments, a binding affinity is about 15 pM. In some embodiments, a binding affinity is about 20 pM. In some embodiments, a binding affinity is about 25 pM. In some embodiments, a binding affinity is about 30 pM. In some embodiments, a binding affinity is about 35 pM. In some embodiments, a binding affinity is about 40 pM. In some embodiments, a binding affinity is about 45 pM. In some embodiments, a binding affinity is about 50 pM. In some embodiments, a binding affinity is about 55 pM. In some embodiments, a binding affinity is about 60 pM. In some embodiments, a binding affinity is about 65 pM. In some embodiments, a binding affinity is about 70 pM. In some embodiments, a binding affinity is about 75 pM. In some embodiments, a binding affinity is about 80 pM. In some embodiments, a binding affinity is about 85 pM. In some embodiments, a binding affinity is about 90 pM. In some embodiments, a binding affinity is about 95 pM. In some embodiments, a binding affinity is about 100 pM. In some embodiments, a binding affinity is about 150 pM. In some embodiments, a binding affinity is about 200 pM. In some embodiments, a binding affinity is about 250 pM. In some embodiments, a binding affinity is about 300 pM. In some embodiments, a binding affinity is about 350 pM. In some embodiments, a binding affinity is about 400 pM. In some embodiments, a binding affinity is about 450 pM. In some embodiments, a binding affinity is about 500 pM. In some embodiments, a binding affinity is about 550 pM. In some embodiments, a binding affinity is about 600 pM. In some embodiments, a binding affinity is about 650 pM. In some embodiments, a binding affinity is about 700 pM. In some embodiments, a binding affinity is about 750 pM. In some embodiments, a binding affinity is about 800 pM. In some embodiments, a binding affinity is about 850 pM. In some embodiments, a binding affinity is about 900 pM. In some embodiments, a binding affinity is about 950 pM. In some embodiments, a binding affinity is about 1 nM. In some embodiments, a binding affinity is about 2 nM. In some embodiments, a binding affinity is about 3 nM. In some embodiments, a binding affinity is about 4 nM. In some embodiments, a binding affinity is about 5 nM. In some embodiments, a binding affinity is about 6 nM. In some embodiments, a binding affinity is about 7 nM. In some embodiments, a binding affinity is about 8 nM. In some embodiments, a binding affinity is about 9 nM. In some embodiments, a binding affinity is about 10 nM. In some embodiments, a binding affinity is about 15 nM. In some embodiments, a binding affinity is about 20 nM. In some embodiments, a binding affinity is about 25 nM. In some embodiments, a binding affinity is about 30 nM. In some embodiments, a binding affinity is about 35 nM. In some embodiments, a binding affinity is about 40 nM. In some embodiments, a binding affinity is about 45 nM. In some embodiments, a binding affinity is about 50 nM. In some embodiments, a binding affinity is about 55 nM. In some embodiments, a binding affinity is about 60 nM. In some embodiments, a binding affinity is about 65 nM. In some embodiments, a binding affinity is about 70 nM. In some embodiments, a binding affinity is about 75 nM. In some embodiments, a binding affinity is about 80 nM. In some embodiments, a binding affinity is about 85 nM. In some embodiments, a binding affinity is about 90 nM. In some embodiments, a binding affinity is about 95 nM. In some embodiments, a binding affinity is about 100 nM.

In some embodiments, a binding affinity is stronger than about 100 nM (e.g., 90 nM, 80 nM, etc.). In some embodiments, a binding affinity is no weaker than about 0.5 nM, 1 nM, 5 nM, 10 nM, 15 nM, 20 nM, 25 nM, 30 nM, 35 nM 40 nM, 45 nM. 50 nM, 55 nM, 60 nM, 65 nM, 70 nM, 75 nM, 80 nM, 85 nM, 90 nM, 95 nM, or 100 nM. In some embodiments, a binding affinity is no weaker than about 0.5 nM. In some embodiments, a binding affinity is no greater than about 1 nM. In some embodiments, a binding affinity is no weaker than about 5 nM. In some embodiments, a binding affinity is no weaker than about 10 nM. In some embodiments, a binding affinity is no weaker than about 15 nM. In some embodiments, a binding affinity is no weaker than about 20 nM. In some embodiments, a binding affinity is no weaker than about 25 nM. In some embodiments, a binding affinity is no weaker than about 30 nM. In some embodiments, a binding affinity is no weaker than about 35 nM. In some embodiments, a binding affinity is no weaker than about 40 nM. In some embodiments, a binding affinity is no weaker than about 45 nM. In some embodiments, a binding affinity is no weaker than about 50 nM. In some embodiments, a binding affinity is no weaker than about 55 nM. In some embodiments, a binding affinity is no weaker than about 60 nM. In some embodiments, a binding affinity is no weaker than about 65 nM. In some embodiments, a binding affinity is no weaker than about 70 nM. In some embodiments, a binding affinity is no weaker than about 75 nM. In some embodiments, a binding affinity is no weaker than about 80 nM. In some embodiments, a binding affinity is no weaker than about 85 nM. In some embodiments, a binding affinity is no weaker than about 90 nM. In some embodiments, a binding affinity is no weaker than about 95 nM. In some embodiments, a binding affinity is no weaker than 100 nM.

In some embodiments, an inhibition constant (Ki) of a polypeptide (or composition comprising such polypeptide) as provided herein is in a range of about 1 pM to about 100 nM.

In some embodiments, an inhibition constant (Ki) is between about 1 pM to 100 nM, 1 pM to 100 pM, 10 pM to 1 nM, 100 pM to 10 nM, or 1 nM to 100 nM. In some embodiments, an inhibition constant is between about 1 pM to 5 pM, 1 pM to 10 pM, 1 pM to pM, 1 pM to 20 pM, 1 pM to 25 pM, 1 pM to 30 pM, 1 pM to 35 pM, 1 pM to 40 pM, 1 pM to 45 pM, 1 pM to 50 pM, 1 pM to 55 pM, 1 pM to 60 pM, 1 pM to 65 pM, 1 pM to 70 pM, 1 pM to 75 pM, 1 pM to 80 pM, 1 pM to 85 pM, 1 pM to 90 pM, 1 pM to 95 pM, or 1 pM to 100 pM. In some embodiments, an inhibition constant is between about 25 pM to 30 pM, 25 pM to 35 pM, 25 pM to 40 pM, 25 pM to 45 pM, 25 pM to 50 pM, 25 pM to 55 pM, pM to 60 pM, 25 pM to 65 pM, 25 pM to 70 pM, 25 pM to 75 pM, 25 pM to 80 pM, 25 pM to 85 pM, 25 pM to 90 pM, 25 pM to 95 pM, or 25 pM to 100 pM. In some embodiments, an inhibition constant is between about 50 pM to 55 pM, 50 pM to 60 pM, 50 pM to 65 pM, 50 pM to 70 pM, 50 pM to 75 pM, 50 pM to 80 pM, 50 pM to 85 pM, 50 pM to 90 pM, 50 pM to 95 pM, or 50 pM to 100 pM. In some embodiments, an inhibition constant is between about 75 pM to 80 pM, 75 pM to 85 pM, 75 pM to 90 pM, 75 pM to 95 pM, or 75 pM to 100 pM. In some embodiments, an inhibition constant is between about 10 pM to 1 nM, 100 pM to 1 nM, 200 pM to 1 nM, 300 pM to 1 nM, 400 pM to 1 nM, 500 pM to 1 nM, 600 pM to 1 nM, 700 pM to 1 nM, 800 pM to 1 nM, or 900 pM to 1 nM. In some embodiments, an inhibition constant is between about 1 nM to 100 nM, 10 nM to 100 nM, 20 nM to 10 nM, 30 nM to 100 nM, 40 nM to 100 nM, 50 nM to 100 nM 60 nM to 100 nM, 70 nM to 100 nM, 80 nM to 100 nM, or 90 nM to 100 nM. In some embodiments, an inhibition constant is between about 5 nM to 100 nM, 10 nM to 100 nM, 15 nM to 100 nM, 20 nM to 100 nM, 25 nM to 100 nM, 30 nM to 100 nM, 35 nM to 100 nM, 40 nM to 100 nM, 45 nM to 100 nM, 50 nM to 100 nM, 55 nM to 100 nM, 60 nM to 100 nM. 65 nM to 100 nM, 70 nM to 100 nM, 75 nM to 100 nM, 80 nM to 100 nM, 85 nM to 100 nM, 90 nM to 100 nM, or 95 nM to 100 nM.

In some embodiments, an inhibition constant is about 5 pM, 10 pM, 15 pM, 20 pM, pM, 30 pM, 35 pM, 40 pM, 45 pM, 50 pM, 55 pM, 60 pM, 65 pM, 70 pM, 75 pM, 80 pM, 85 pM, 90 pM, 95 pM, or 100 pM. In some embodiments, an inhibition constant is about 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, or 1 nM. In some embodiments, an inhibition constant is about 1 nM, 2 nM, 3 nM, 4 nM, 5 nM, 6 nM, 7 nM, 8 nM, 9 nM, or 10 nM. In some embodiments, an inhibition constant is about 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, or 100 nM.

In some embodiments, an inhibition constant is about 1 pM. In some embodiments, an inhibition constant is about 2 pM. In some embodiments, an inhibition constant is about 3 pM. In some embodiments, an inhibition constant is about 4 pM. In some embodiments, an inhibition constant is about 5 pM. In some embodiments, an inhibition constant is about 10 pM. In some embodiments, an inhibition constant is about 15 pM. In some embodiments, an inhibition constant is about 20 pM. In some embodiments, an inhibition constant is about 25 pM. In some embodiments, an inhibition constant is about 30 pM. In some embodiments, an inhibition constant is about 35 pM. In some embodiments, an inhibition constant is about 40 pM. In some embodiments, an inhibition constant is about 45 pM. In some embodiments, an inhibition constant is about 50 pM. In some embodiments, an inhibition constant is about 55 pM. In some embodiments, an inhibition constant is about 60 pM. In some embodiments, an inhibition constant is about 65 pM. In some embodiments, an inhibition constant is about 70 pM. In some embodiments, an inhibition constant is about 75 pM. In some embodiments, an inhibition constant is about 80 pM. In some embodiments, an inhibition constant is about 85 pM. In some embodiments, an inhibition constant is about 90 pM. In some embodiments, an inhibition constant is about 95 pM. In some embodiments, an inhibition constant is about 100 pM. In some embodiments, an inhibition constant is about 150 pM. In some embodiments, an inhibition constant is about 200 pM. In some embodiments, an inhibition constant is about 250 pM. In some embodiments, an inhibition constant is about 300 pM. In some embodiments, an inhibition constant is about 350 pM. In some embodiments, an inhibition constant is about 400 pM. In some embodiments, an inhibition constant is about 450 pM. In some embodiments, an inhibition constant is about 500 pM. In some embodiments, an inhibition constant is about 550 pM. In some embodiments, an inhibition constant is about 600 pM. In some embodiments, an inhibition constant is about 650 pM. In some embodiments, an inhibition constant is about 700 pM. In some embodiments, an inhibition constant is about 750 pM. In some embodiments, an inhibition constant is about 800 pM. In some embodiments, an inhibition constant is about 850 pM. In some embodiments, an inhibition constant is about 900 pM. In some embodiments, an inhibition constant is about 950 pM. In some embodiments, an inhibition constant is about 1 nM. In some embodiments, an inhibition constant is about 2 nM. In some embodiments, an inhibition constant is about 3 nM. In some embodiments, an inhibition constant is about 4 nM. In some embodiments, an inhibition constant is about 5 nM. In some embodiments, an inhibition constant is about 6 nM. In some embodiments, an inhibition constant is about 7 nM. In some embodiments, an inhibition constant is about 8 nM. In some embodiments, an inhibition constant is about 9 nM. In some embodiments, an inhibition constant is about 10 nM. In some embodiments, an inhibition constant is about 15 nM. In some embodiments, an inhibition constant is about 20 nM. In some embodiments, an inhibition constant is about 25 nM. In some embodiments, an inhibition constant is about 30 nM. In some embodiments, an inhibition constant is about 35 nM. In some embodiments, an inhibition constant is about 40 nM. In some embodiments, an inhibition constant is about 45 nM. In some embodiments, an inhibition constant is about 50 nM. In some embodiments, an inhibition constant is about 55 nM. In some embodiments, an inhibition constant is about 60 nM. In some embodiments, an inhibition constant is about 65 nM. In some embodiments, an inhibition constant is about 70 nM. In some embodiments, an inhibition constant is about 75 nM. In some embodiments, an inhibition constant is about 80 nM. In some embodiments, an inhibition constant is about 85 nM. In some embodiments, an inhibition constant is about 90 nM. In some embodiments, an inhibition constant is about 95 nM. In some embodiments, an inhibition constant is about 100 nM.

In some embodiments, an inhibition constant is no greater than about 0.5 nM, 1 nM, nM, 10 nM, 15 nM, 20 nM, 25 nM, 30 nM, 35 nM, 40 nM, 45 nM, 50 nM, 55 nM, 60 nM, 65 nM. 70 nM, 75 nM, 80 nM, 85 nM, 90 nM, 95 nM, or 100 nM.

In some embodiments, an inhibition constant is no greater than about 0.5 nM. In some embodiments, an inhibition constant is no greater than about 1 nM. In some embodiments, an inhibition constant is no greater than about 5 nM. In some embodiments, an inhibition constant is no greater than about 10 nM. In some embodiments, an inhibition constant is no greater than about 15 nM. In some embodiments, an inhibition constant is no greater than about 20 nM. In some embodiments, an inhibition constant is no greater than about 25 nM. In some embodiments, an inhibition constant is no greater than about 30 nM. In some embodiments, an inhibition constant is no greater than about 35 nM. In some embodiments, an inhibition constant is no greater than about 40 nM. In some embodiments, an inhibition constant is no greater than about 45 nM. In some embodiments, an inhibition constant is no greater than about 50 nM. In some embodiments, an inhibition constant is no greater than about 55 nM. In some embodiments, an inhibition constant is no greater than about 60 nM. In some embodiments, an inhibition constant is no greater than about 65 nM. In some embodiments, an inhibition constant is no greater than about 70 nM. In some embodiments, an inhibition constant is no greater than about 75 nM. In some embodiments, an inhibition constant is no greater than about 80 nM. In some embodiments, an inhibition constant is no greater than about 85 nM. In some embodiments, an inhibition constant is no greater than about 90 nM. In some embodiments, an inhibition constant is no greater than about 95 nM. In some embodiments, an inhibition constant is no greater than about 100 nM.

CDPs

In some embodiments, miniproteins of the present disclosure comprise or consist of a cysteine-dense peptides (CDPs). In some embodiments, conjugates provided herein comprise a CDP. In some embodiments, a CDP functions as a targeting moiety, e.g., specifically binding to a protein target or antigen expressed on the surface of a target tumor cell. In some embodiments, a CDP comprises or consists of at least two independent folding domains and a high density of cysteines. In some embodiments, the CDP comprises at least one, two, three, four, five, six, or more than six cysteine residues in a span of from about 10 to about 90 amino acid residues, preferably 13 to 80 amino acid residues. (See, e.g., Correnti et al., Nat Struct Mol Biol. 2018 March; 25(3):270-278, for exemplary CDPs and characteristics thereof). In some embodiments, the CDP comprises a constrained distribution of cysteines, Cys-X[0-15]-Cys-X[0-15]-Cys-X[I-15]-Cys-X[0-15]-Cys-X[0-15]-Cys (wherein X represents any amino acid) (SEQ ID NO: 241). In some embodiments, a CDP comprises one or more cysteine dense regions comprising at least one cysteine residue, preferably at least two, three, four, or more cysteine residues in a span of from about 10 to 80 amino acid residues. In some embodiments, a CDP can be further engineered to modify binding, folding, and/or related properties.

In some embodiments, a CDP specifically binds to a target. In some embodiments, the target is located in, on, or near a cell. In some embodiments, the CDP specifically binds to Nectin-4 or a fragment thereof. In some embodiments, a CDP is conjugated to a chelator and/or radionuclide. In some embodiments, conjugation is via a linker. It will be understood by those of skill in the art, that in some embodiments, the particular CDP employed in a conjugate of the present disclosure may vary depending on the target protein or antigen of interest.

In some embodiments, in miniproteins having cysteine residues, to ensure proper folding and connectivity, selected cysteine pairs can be replaced with selenocysteines. In some embodiments, diselenide crosslinks may form more readily than disulfide crosslinks due to their lower redox potential. In some such embodiments, such replacement can lead to cross-coupling of remaining cysteines.

Knottins

In some embodiments, miniproteins of the present disclosure comprise or consist of knottin peptides. In some embodiments, conjugates provided herein comprise a knottin peptide. In some embodiments, a knottin peptide functions as a targeting moiety, e.g., specifically binding to an antigen expressed on the surface of a target tumor cell. In some embodiments, a knottin comprises at least three disulfide bonds connected in an arrangement that generates the so-called "cysteine-knot" for which knottins are named. (See, e.g., Kintzing & Cochran et al., Curr Opin Chem Biol. 2016 October; 34:143-150). In some embodiments, knottins have high stability (e.g., thermal, proteolytic, chemical, etc.). In some embodiments, a knottin can be further engineered to modify binding, folding, and/or related properties.

In some embodiments, a given knottin is highly specific for a given target. In some embodiments, a knottin specifically binds to a target. In some embodiments, the target is located in, on, or near a cell. In some embodiments, the knottin specifically binds to Nectin-4 or a fragment thereof. In some embodiments, a knottin is conjugated to a chelator and/or radionuclide. In some embodiments, conjugation is via a linker. It will be understood by those of skill in the art, that in some embodiments, the particular knottin employed in a conjugate of the present disclosure may vary depending on the target protein or antigen of interest.

In some embodiments, folded structures of miniproteins (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) make them rigid, providing for very tight and potent binding to the target protein or antigen (relative to less structured peptides). In some such embodiments, a minprotein exhibits extraordinary stability with resistance to heat, peptidase cleavage, and pH.

Binders

In some embodiments, a miniprotein of the present disclosure comprises or consists of a binder. In some embodiments, the binder functions as a targeting moiety, e.g., specifically binding to a target expressed on the surface of a tumor cell.

In some embodiments, a binder has certain structural features; for example, in some embodiments, a binder may be rich in alpha-helices, such as a helix-helix-helix structure (see, e.g., Crook et al., Nat Commun. (2017) 8, 2244; Berger et al. Elife (2016) 5, e20352; and Procko et al., Cell (2014), 157, 1644-1656). In some embodiments, a binder comprises sufficient surface to functionalize the molecule on a disparate surface to a binding surface. In some embodiments, a binder comprises a sequestered hydrophobic core. In some embodiments, a binder displays cooperative folding. In some embodiments, a binder has two or more of the following features: (i) represented by an amino acid sequence of 100 amino acids or fewer; (ii) at least two secondary structure elements; (iii) a sequestered hydrophobic core; and/or (iv) cooperative folding.

In some embodiments, a given binder is highly specific for a given target. In some embodiments, a binder specifically binds to a target. In some embodiments, the target is located in, on, or near a cell. In some embodiments, the binder specifically binds to Nectin-4 or a fragment thereof. In some embodiments, a binder is conjugated to a chelator and/or radionuclide. In some embodiments, conjugation is via a linker. It will be understood by those of skill in the art, that in some embodiments, the particular binder employed in a conjugate of the present disclosure may vary depending on the target protein or antigen of interest.

Affibodies

In some embodiments, miniproteins of the present disclosure comprise or consist of affibodies. In some embodiments, conjugates provided herein comprise an affibody. In some embodiments, an affibody functions as a targeting moiety, e.g., specifically binding to a protein target or antigen expressed on the surface of a target tumor cell. In some embodiments, an affibody comprises or consists of no more than 100 amino acids, 90 amino acids, 80 amino acids, 70 amino acids, 60 amino acids, 50 amino acids, 40 amino acids, 30 amino acids, 20 amino acids, or 10 amino acids. In some embodiments, an affibody comprises or consists of at least three alpha helices with 58 amino acids. In some embodiments, the affibody comprises target specificity that is obtained by randomization of 13 amino acids located in two alpha-helices involved in the binding activity of the parent protein domain (Feldwisch J, Tolmachev V.; (2012) Methods Mol Biol. 899:103-26). In some embodiments, an affibody can be further engineered to modify binding, folding, and/or related properties.

In some embodiments, an affibody specifically binds to a target. In some embodiments, the target is located in, on, or near a cell. In some embodiments, the affibody specifically binds to Nectin-4 or a fragment thereof. In some embodiments, an affibody is conjugated to a chelator and/or radionuclide. In some embodiments, conjugation is via a linker. It will be understood by those of skill in the art, that in some embodiments, the particular affibody employed in a conjugate of the present disclosure may vary depending on the target protein or antigen of interest.

Engineered Kunitz Domains

In some embodiments, miniproteins of the present disclosure comprise or consist of engineered Kunitz domains. In some embodiments, conjugates provided herein comprise an engineered Kunitz domain. In some embodiments, an engineered Kunitz domain functions as a targeting moiety, e.g., specifically binding to a protein target or antigen expressed on the surface of a target tumor cell. In some embodiments, an engineered Kunitz domain comprises or consists of at least one peptide derived from the Kunitz domain of a Kunitz-type protease inhibitor such as bovine pancreatic trypsin inhibitor (BPTI), amyloid precursor protein (APP) or tissue factor pathway inhibitor (TFPI). In some embodiments, an engineered Kunitz domain can be further engineered to modify binding, folding, and/or related properties.

In some embodiments, an engineered Kunitz domain specifically binds to a target. In some embodiments, the target is located in, on, or near a cell. In some embodiments, the engineered Kunitz domain specifically binds to Nectin-4 or a fragment thereof. In some embodiments, an engineered Kunitz domain is conjugated to a chelator and/or radionuclide. In some embodiments, conjugation is via a linker. It will be understood by those of skill in the art, that in some embodiments, the particular engineered Kunitz domain employed in a conjugate of the present disclosure may vary depending on the target protein or antigen of interest.

Monobodies

In some embodiments, miniproteins of the present disclosure comprise or consist of monobodies. In some embodiments, conjugates provided herein comprise a monobody. In some embodiments, a monobody functions as a targeting moiety, e.g., specifically binding to a protein target or antigen expressed on the surface of a target tumor cell. In some embodiments, a monobody comprises or consists of a molecule based on the 10th extracellular domain of human fibronectin III (10Fn3), which adopts an Ig-like b-sandwich fold of about 94 residues with 2 to 3 exposed loops but lacks the central disulfide bridge. In some embodiments, a monobody can be further engineered to modify binding, folding, and/or related properties.

In some embodiments, a monobody specifically binds to a target. In some embodiments, the target is located in, on, or near a cell. In some embodiments, the monobody specifically binds to Nectin-4 or a fragment thereof. In some embodiments, a monobody is conjugated to a chelator and/or radionuclide. In some embodiments, conjugation is via a linker. It will be understood by those of skill in the art, that in some embodiments, the particular monobody employed in a conjugate of the present disclosure may vary depending on the target protein or antigen of interest.

Anticalins

In some embodiments, miniproteins of the present disclosure comprise or consist of anticalins. In some embodiments, conjugates provided herein comprise an anticalin. In some embodiments, an anticalin functions as a targeting moiety, e.g., specifically binding to a protein target or antigen expressed on the surface of a target tumor cell. In some embodiments, an anticalin comprises or consists of an eight-stranded p-barrel which forms a highly conserved core unit among the lipocalins and naturally forms binding sites for ligands by means of four structurally variable loops at the open end. In some embodiments, an anticalin can be further engineered to modify binding, folding, and/or related properties.

In some embodiments, an anticalin specifically binds to a target. In some embodiments, the target is located in, on, or near a cell. In some embodiments, the anticalin specifically binds to Nectin-4 or a fragment thereof. In some embodiments, an anticalin is conjugated to a chelator and/or radionuclide. In some embodiments, conjugation is via a linker. It will be understood by those of skill in the art, that in some embodiments, the particular anticalin employed in a conjugate of the present disclosure may vary depending on the target protein or antigen of interest.

Designed Ankyrin Repeat Domains

In some embodiments, miniproteins of the present disclosure comprise or consist of designed Ankyrin repeat domains. In some embodiments, conjugates provided herein comprise a designed Ankyrin repeat domain. In some embodiments, a designed Ankyrin repeat domain functions as a targeting moiety, e.g., specifically binding to a protein target or antigen expressed on the surface of a target tumor cell. In some embodiments, a designed Ankyrin repeat domain comprises a peptide derived from Ankyrin. In some embodiments, a designed Ankyrin repeat domain comprises a single ankyrin repeat, preferably comprising a 33-residue motif comprising two alpha-helices and a beta-turn. In some embodiments a designed Ankyrin repeat domain provides a rigid interface and lacks structural flexibility. In some embodiments, a designed Ankyrin repeat domain can be further engineered to modify binding, folding, and/or related properties.

In some embodiments, a designed Ankyrin repeat domain specifically binds to a target. In some embodiments, the target is located in, on, or near a cell. In some embodiments, the designed Ankyrin repeat domain specifically binds to Nectin-4 or a fragment thereof. In some embodiments, a designed Ankyrin repeat domain is conjugated to a chelator and/or radionuclide. In some embodiments, conjugation is via a linker. It will be understood by those of skill in the art, that in some embodiments, the particular designed Ankyrin repeat domain employed in a conjugate of the present disclosure may vary depending on the target protein or antigen of interest.

Avimers

In some embodiments, miniproteins of the present disclosure comprise or consist of avimers. In some embodiments, conjugates provided herein comprise an avimer. In some embodiments, an avimer functions as a targeting moiety, e.g., specifically binding to a protein target or antigen expressed on the surface of a target tumor cell. In some embodiments, an avimer comprises a peptide of about 10 amino acids, 20 amino acids, 30 amino acids, 40 amino acids, 50 amino acids, 60 amino acids, 70 amino acids, 80 amino acids, 90 amino acids, or 100 amino acids. In some embodiments, an avimer comprises at least one peptide sequence of about 30 to 35 amino acids. In some embodiments, an avimer comprises two or more of two peptide sequences of about 30 to 35 amino acids. In some embodiments, an avimer comprises one or more peptide sequences derived from A-domains of various membrane receptors. (Weidle U H, et al., (2013), Cancer Genomics Proteomics; 10(4): 155-68). For further details see Nature Biotechnology 23(-2), 1556-1561 (2005) and Expert Opinion on Investigational Drugs 16(6), 909-917 (June 2007). In some embodiments, an avimer can be further engineered to modify binding, folding, and/or related properties.

In some embodiments, an avimer specifically binds to a target. In some embodiments, the target is located in, on, or near a cell. In some embodiments, the avimer specifically binds to Nectin-4 or a fragment thereof. In some embodiments, an avimer is conjugated to a chelator and/or radionuclide. In some embodiments, conjugation is via a linker. It will be understood by those of skill in the art, that in some embodiments, the particular avimer employed in a conjugate of the present disclosure may vary depending on the target protein or antigen of interest.

Linkers

In some embodiments the present disclosure provides linkers for use in one or more conjugates. In some embodiments, a linker is attached to the N-terminus of a miniprotein provided herein. In some embodiments, a linker is attached to the C-terminus of a miniprotein provided herein. For example, in some embodiments, a linker is linked to a chelator. In some embodiments, a linker is linked to a chelator, which itself is coupled to a radionuclide. In some embodiments, a miniprotein is conjugated to a chelator and/or radionuclide. In some embodiments, a miniprotein is conjugated to a chelator, optionally, through a linker. In some embodiments, a composition as provided herein comprises one or more linkers. In some embodiments, a miniprotein is conjugated to a chelator and/or a cold-metal surrogate.

As described herein, in some embodiments, a miniprotein conjugate comprises a linker. In some embodiments, the linker functions to connect the chelator to miniprotein. In some embodiments, a linker is non-cleavable. In some embodiments, a linker is cleavable. In some embodiments, selection and placement of one or more linkers and chelators on a miniprotein aids to maintain desired potency and receptor engagement profile, enhance binder affinity and optimize physicochemical and pharmacokinetic properties of a miniprotein or conjugate thereof. Any suitable linker known in the art can be utilized. Exemplary linkers include, but are not limited to polyethylene glycol (PEG) linkers, an ester linker, an amide linker, a maleimide linker, a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a dTyr-Gly-Phe (yGF) linker, a caproleic acid linker, or a linker including any combination thereof. One or more additional linkers may be contemplated as will be known to those of skill in the art and chosen given the context and components of a given composition. In some embodiments, the linker is a PEG linker. In some embodiments, the linker is a non-cleavable PEG linker. In some embodiments, the PEG linker is any of PEGs (2-24). In some embodiments, a linker is a PEG4, PEG, PEG2, PEG6, or PEG8 linker. In some embodiments, a linker is a PEG4 linker.

In some embodiments, linkers are used to assess lead polypeptide sequences binding to a target, a target expressed on cells, and target selectivity and/or affinity. For instance, in some embodiments, confirmation of in vitro on-target binding and affinity for lead polypeptide sequences and lead polypeptide sequences-linker-fluorophore reagent can be assessed using an SPR machine, such as a Biacore. In some embodiments, other linkers such as a fast clear linker or a halogen linker are also contemplated.

Chelators

In some embodiments, a composition (e.g., conjugate) as provided herein comprises a linker. In some embodiments, a composition comprises a linker and a chelator. In some embodiments, a composition comprises a linker, a chelator, and a radionuclide. In some embodiments, a composition comprises a miniprotein, optional linker, chelator, and/or radionuclide. In some embodiments, a chelator is covalently attached to a miniprotein. In some embodiments, a chelator binds to a radionuclide. In some embodiments, a chelator binds to a cold-metal surrogate. In some embodiments, a chelator refers to any molecule or moiety that "binds" to a metal ion, in solution (effectively collecting/binding up metal ions so that they may, e.g., no longer participate in one or more cellular activities or processes). In some embodiments a chelator chelates one or more components of a metabolic pathway in a cell (e.g., metal ions, e.g., copper, iron, zinc, etc.). In some such embodiments, a chelator disrupts a life-cycle of a cancer cell and may, in some embodiments, reduce its viability, function, and/or ability to grow or proliferate. In some embodiments, a chelator chelates one or more toxins that are produced as a result of targeted radiotherapy (e.g., to reduce toxicity of the therapy).

In some embodiments, a chelator comprises or consists of, but is not limited to tetrazacyclododecane-1,4,7,10-tetraacetic acid (DOTA), diethylenetriamine pentaacetic acid (DTPA), ethylenediaminetetraacetic acid (EDTA), 1,4,7-triazacyclo'on"ne-N,N',N"-triacetic acid (NOTA), ethylenediaminetetraacetic acid (EDTA), diethylenetriaminepentaacetic acid (DTPA), 1,4,7-triazacyclo'on"ne-N,N',N"-triacetic acid (NOTA), ({4-[2-(bis-carboxymethyl-amino)-ethyl]-7-carboxymethyl-[1,4,7]triazonan-1-yl}acetic acid (NETA), Macropa, lead specific chelator (PSC) (e.g., a cyclen-based Pb specific chelator), N-succinimidyl 3-(tri-n-butylstannyl)benzoate (BuSTB), N-succinimidyl 3-trimethylstannylbenzoate (MeSTB), p-bromoacetamidobenzyl-tetraethylaminetetraacetic acid (TETA), porphyrins, polyanunes, crown ethers, bis-thiosemicarbazones, or polyoximes. In some embodiments, the chelator is 1,4,7,10-tetraazacyclododecane-1,4,7,10-tetraacetic acid (DOTA). In some embodiments, the chelator is lead specific chelator (PSC). In some embodiments, the chelator is N-succinimidyl 3-(tri-n-butylstannyl)benzoate (BuSTB). In some embodiments, the chelator is N-succinimidyl 3-trimethylstannylbenzoate (MeSTB), In some embodiments, the chelator is Macropa. In some embodiments, a chelator comprises or consists of:

(i) DOTA

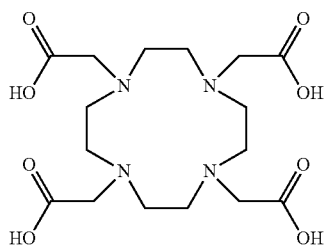

(ii) CROWN

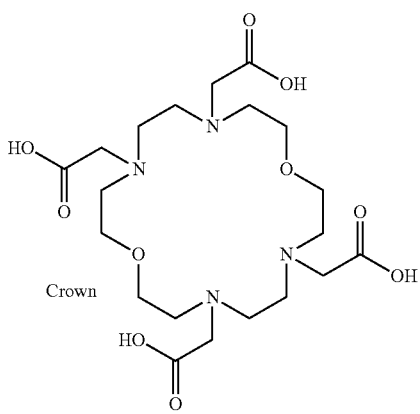

(iii) NOPO

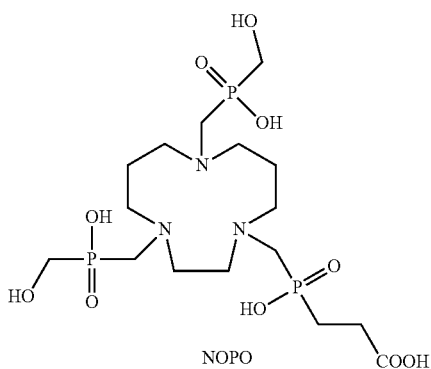

(iv) Macropa

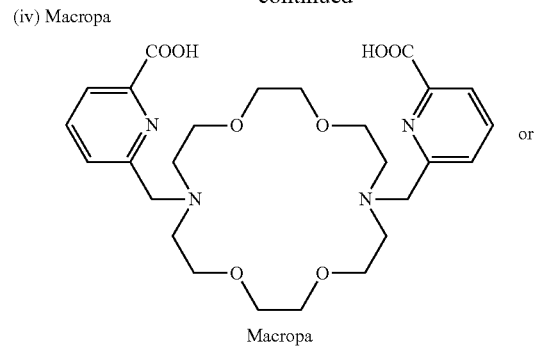

(v) lead-specific chelator (PSC)

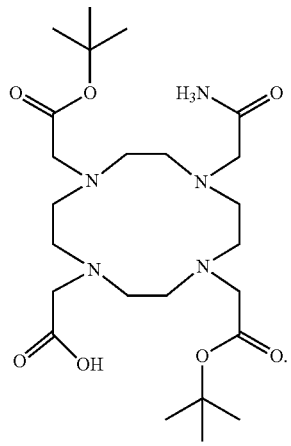

In some embodiments, a chelator comprises or consists of, but is not limited to diethylenetriamine pentaacetic acid (DTPA), tetrazacyclododecane-1,4,7,10-tetraacetic acid (DOTA), ethylenediaminetetraacetic acid (EDTA), 1,4,7-triazacyclo'on"ne-N,N',N"-triacetic acid (NOTA), ethylenediaminetetraacetic acid (EDTA), diethylenetriaminepentaacetic acid (DTPA), 1,4,7-triazacyclo'on"ne-N,N',N"-triacetic acid (NOTA), ({4-[2-(bis-carboxymethyl-amino)-ethyl]-7-carboxymethyl-[1,4,7] triazonan-1-yl}acetic acid (NETA), Macropa, p-bromoacetamidobenzyl-tetraethylaminetetraacetic acid (TETA), PSC, N-succinimidyl 3-(tri-n-butylstannyl)benzoate (BuSTB), N-succinimidyl 3-trimethylstannylbenzoate (MeSTB), porphyrins, polyamines, crown ethers, bis-thiosemicarbazones, or polyoximes. In some embodiments, the chelator is 1,4,7,10-tetraazacyclododecane-1,4,7,10-tetraacetic acid (DOTA). In some embodiments, the chelator is Macropa.

In additional embodiments, the chelation conditions are optimized using methods known to those of skill in the art (see, e.g., J Nucl Med. 1998 December; 39(12):2105-10). In some embodiments, chelation efficiency is about >99%, >98%, >97%, >96%, >95%, >94%, >93%, >92%, >91%, >90%, >89%, >88%, >87%, >86%, >85%, >84%, >83%, >82%, >81%, or >80%.

In some embodiments, a chelator for use in a composition as described herein is chosen based on if and which radionuclide is present. As provided herein, in some embodiments, a chelator is DOTA, NOPO, Crown, PSC, N-succinimidyl 3-(tri-n-butylstannyl)benzoate (BuSTB), N-succinimidyl 3-trimethylstannylbenzoate (MeSTB), or Macropa. In some embodiments, DOTA is the chelator and the radionuclide is Ac-225, In-111, Ga-68, Pb-212, Lu-177, Cu-67, Cu-64, La-132, La-135, Ce-134, F-18, I-131, I-124, Pb-203, Th-232, Bi-123, or At-211. In some embodiments, Crown is the chelator and the radionuclide is Ac-225, In-111, Ga-68, Pb-212, Lu-177, Cu-67, Cu-64, La-132, La-135, Ce-134, F-18, I-131, I-124, Pb-203, Th-232, Bi-123, or At-211. In some embodiments, NOPO is the chelator, and the radionuclide is Ac-225, In-111, Ga-68, Pb-212, Lu-177, Cu-67, Cu-6A, La-132, La-135, Ce-134, F-18, I-131, I-124, Pb-203, Th-232, Bi-123, or At-211. In some embodiments, Macropa is the chelator, and the radionuclide is Ac-225, In-111, Ga-68, Pb-212, Lu-177, Cu-67, Cu-64, La-132, La-135, Ce-134, F-18, I-131, I-124, Pb-203, Th-232, Bi-123, or At-211.

In some embodiments, a particular chelator or type of chelator may be chosen for certain applications. In some embodiments, DOTA is used for diagnostic, theranostic, and/or therapeutic applications. For instance, in some embodiments, NOPO is used in diagnostic or theranostic applications. In some embodiments, Crown is used for therapeutic applications. In some embodiments. Macropa is used for diagnostic, theranostic, and/or therapeutic applications.

It is recognized that screening chelators for certain characteristics is within the scope of this disclosure and methods for such screening are known to those of skill in the art. For example, in some embodiments, chelators are screened for their ability to bind radionuclides (e.g., Ac-225 and daughter(s) of Ac-225 (Bi213), In-111, Ga-68) and display serum stability.

In some embodiments, a miniprotein conjugate described herein comprises a chelator. Any suitable chelator known in the art can be utilized. In some embodiments the chelator is directly conjugated to the miniprotein. In some embodiments, the chelator is indirectly connected to the miniprotein through a linker. In some embodiments, the chelator is indirectly connected to the miniprotein through a linker (e.g., a linker described herein).

Radionuclides

In some embodiments the present disclosure provides one or more radionuclides for use in a composition (e.g., conjugate).

In some embodiments, miniprotein conjugates comprise a radionuclide bound to a chelator. In some embodiments, the radionuclide is on the N-terminal side of the miniprotein and, optionally includes a linker and chelator, wherein the linker is attached to the N-terminus of the miniprotein and the chelator is attached to the linker (see, e.g., compounds as set forth in TABLE 2A). In some embodiments, the radionuclide is on the C-terminal side of the miniprotein, and, optionally includes a linker and chelator, wherein the linker is attached to the C-terminus of the miniprotein and the chelator is attached to the linker. As will be understood to those of skill in the art, any suitable radionuclide known in the art may be used. In some embodiments, a radionuclide is selected for imaging of a tumor within a human having cancer. In some embodiments, a radionuclide is selected for its inability to kill cells in vivo. In some embodiments, the radionuclide is selected for its ability to kill cells in vivo.

In some embodiments, a composition of the present disclosure comprises one or more cytotoxic payloads including particle-emitting isotopes such as alpha-, beta-particles, and Auger electrons in radiotherapeutic applications. In some embodiments, a radionuclide of the present disclosure is an alpha emitter. In some embodiments, a radionuclide of the present disclosure is a beta emitter. As will be known to those of skill in the art, in some embodiments, an alpha emitter has a more localized area of impact such that when internalized into a cell it will act to, e.g., kill a cancer cell, but will spare surrounding tissue from extensive damage such as could occur with use of a beta or gamma emitter.

Studies have evaluated alpha nuclide therapy versus beta nuclide therapy with the stronger clinical results pointing to alpha nuclides. In some embodiments, a benefit of alpha therapy is that the short path length means patients do not have to physically distance themselves from family and health care providers making treatment more tolerable. Further, in some embodiments, alpha therapy exhibits better cell killing potency due to its ability to induce double stranded DNA breaks.

In some embodiments, a composition comprises a linker, chelator, and radionuclide. In some embodiments, a composition comprises a miniprotein, optional linker, chelator, and a radionuclide. Without being bound by any particular theory, the present disclosure contemplates that a wide variety of radionuclides can be used in the pharmaceutical composition or as a diagnostic. Exemplary radionuclides, include but are not limited to, Actinium-225, Indium-111, Astatine-211, Bismuth-212, Bismuth-213, Cesium-137, Chromium-51, Cobalt-60, Copper-64 Dysprosium-165, Erbium-169, Fermium-255, Fluor-18, Gallium-67, Gallium-68, Gold-198, Holmium-166, Iodine-123, Iodine-124, Iodine-125, Iodine-131, Iridium-192, Iron-59. Lead-212, Lead-203, Lutetium-177, Molybdenum-99, Palladium-103, Phosphorus-32, Potassium-42, Rhenium-186, Rhenium-188, Samarium-153, Technetium-99m, Radium-223, Ruthenium-106, Sodium-24, Strontium-89, Terbium-149, Thorium-227, Thorium-232, Xenon-133, Ytterbium-169, Ytterbium-177, Yttrium-90, and Zirconium-89. Accordingly, in some embodiments, a radionuclide is selected from: actinium (225Ac), indium (111 In), iodine (131I or 125I), yttrium (90Y), lutetium (177Lu), praseodymium, astatine (211 At), rhenium (186Re), bismuth (212Bi or 213Bi), technetium (99Tc), phosphorus (32P), rhodium (I88Rh), sulfur (35S), carbon (14C), tritium (3H), chromium (51Cr), chlorine (36C1), cobalt (57Co or 58Co), iron (59Fe), selenium (75Se), or gallium (67Ga) or (68Ga). In some embodiments, the present disclosure contemplates that certain radioisotopes may be useful in or as therapeutic agents including but not limited to yttrium (90Y), lutetium (177Lu), actinium (225Ac), praseodymium, astatine (211At), rhenium (I86Re), bismuth (212 Bi or 213Bi), and rhodium (188Rh). In some embodiments, radioisotopes are useful as labels, e.g., for use in diagnostics. In some such embodiments, such radioisotopes may include but are not limited to iodine (131I or 125I), technetium (99Tc), phosphorus (32P), carbon (14C), lead (203Pb or 212Pb), thorium (232Th), bismuth (213Bi), or tritium (3H). See, e.g., U.S. Pat. No. 7,514,078.

In some embodiments, radionuclides are conjugated to different complexing agents and chelators. In some embodiments, chelators are identified and attached/bound to miniproteins through a linker or by acyclic, cyclic and macrocyclic chelates such as, for example, 1,4,7,10,13,16-hexaazacyclohexadecane-N,N',N'',N''',N'''',N''''' -hexaacetic acid (HEHA), 1,4,7,10-tetraazacyclododecane-N,N',N'',N'''-tetraacetic acid (DOTA), NOPO, Crown, lead-specific chelator (PSC) (e.g., a cyclen-based Pb specific chelator), N-succinimidyl 3-(tri-n-butylstannyl)benzoate (BuSTB), N-succinimidyl 3-trimethylstannylbenzoate (MeSTB), etc. In some embodiments, certain chelators may be preferred for certain radionuclides such as, for example, Ac-225 with DOTA or Crown, Ga-68 with NOPO, etc. In some embodiments, preferred combinations of chelators and radionuclides comprise one or more of the following: DOTA and Ac-225, In-111, Ga-68, Pb-212, Lu-177, Cu-67, Cu-64, La-132, La-135, Ce-134, F-18, I-131, I-124, Pb-203. Th-232, Bi-123, or At-211; Crown and Ac-225, In-111, Ga-68, Pb-212, Lu-177, Cu-67, Cu-64, La-132, La-135, Ce-134, F-18, I-131, I-124, Pb-203, Th-232, Bi-123, or At-211; NOPO and Ac-225, In-111, Ga-68, Pb-212, Lu-177, Cu-67, Cu-64, La-132, La-135, Ce-134, F-18, I-131, I-124. Pb-203, Th-232, Bi-123, or At-211; and/or Macropa and Ac-225, In-111, Ga-68, Pb-212, Lu-177, Cu-67, Cu-64, La-132, La-135, Ce-134, F-18, I-131, I-124, Pb-203, Th-232, Bi-123, or At-211.

Preferably, in some embodiments, a preferred radionuclide complex comprises Ac-225, In-111, Ga-68, Pb-212, Lu-177, Cu-67, Cu-64, La-132, La-135, Ce-134, F-18, I-131, I-124, Pb-203, Th-232, Bi-123, or At-211. In some such embodiments, such a complex with desired stability is selected. That is, in some embodiments, a complex comprising Ac-225, In-111, Ga-68, Pb-212, Lu-177, Cu-67, Cu-64, La-132, La-135, Ce-134, F-18, I-131, I-124, Pb-203, Th-232, Bi-123, or At-211 is characterized as having better stability in vivo in comparison to other complexes. Without being bound by any particular theory, the present disclosure contemplates that, in some embodiments, a radionuclide complex comprising a miniprotein forms with the miniprotein target (e.g., Nectin-4 or a fragment thereof). In some such embodiments, such a complex is internalized in the target cell.

In some embodiments, a radionuclide complex forms with a chelator (e.g., DOTA, NOPO, Crown, lead-specific chelator (PSC) (e.g., a cyclen-based Pb specific chelator), N-succinimidyl 3-(tri-n-butylstannyl)benzoate (BuSTB), N-succinimidyl 3-trimethylstannylbenzoate (MeSTB), Macropa, etc.) and is considerably more stable in vivo. In some embodiments, a miniprotein forms internalizing complexes with targets (e.g., Nectin-4).

In some embodiments, a composition provided by the present disclosure comprises Actinium-225 (Ac-225). In some embodiments, a composition provided by the present disclosure comprises indium (In-111). In some embodiments, a composition provided by the present disclosure comprises gallium (Ga-68). In some embodiments, a composition provided by the present disclosure comprises copper (Cu-6A). In some embodiments, a composition provided by the present disclosure comprises lutetium (Lu-177). In some embodiments, a composition provided by the present disclosure comprises lead (Pb-212). In some embodiments, a composition provided by the present disclosure comprises copper (Cu-67). In some embodiments, a composition provided by the present disclosure comprises lanthanum (La-132). In some embodiments, a composition provided by the present disclosure comprises lanthanum (La-135). In some embodiments, a composition provided by the present disclosure comprises cerium (Ce-134). In some embodiments, a composition provided by the present disclosure comprises iodine (I-131). In some embodiments, a composition provided by the present disclosure comprises iodine (I-124). In some embodiments, a composition provided by the present disclosure comprises lead (Pb-203). In some embodiments, a composition provided by the present disclosure comprises thorium (Th-232). In some embodiments, a composition provided by the present disclosure comprises bismuth (Bi-213). For example, in some embodiments, radioimmunotherapy comprising Ac-225 may provide i) limited range in tissue of a few cell diameters; ii) high linear energy transfer leading to dense radiation damage along each alpha track; iii) a 10-day half-life; and/or iv) four net alpha particles emitted per decay (see, e.g., as described in Scheinberg, David A, and Michael R McDevitt. "Actinium-225 in targeted alpha-particle therapeutic applications." Current radiopharmaceuticals vol. 4,4 (2011): 306-20).

In some embodiments, targeting constructs (e.g., 225-Ac-drug constructs, e.g., 68-Ga-constructs) have potential for use in cancer. For example, in some such embodiments, such constructs may be used in the treatment of cancer, such as, for example 225-Ac-drug constructs. In some embodiments, such constructs may be used in imaging, such as for prognostics, diagnostics, and/or monitoring, such as Ga-68 or Cu-64-based constructs.

In some embodiments, Ac-225 is conjugated to a miniprotein as provided herein. In some embodiments, the actinium is conjugated onto a chelator and may include an optional linker to link it to a miniprotein, which miniprotein targets the conjugate to a cell expressing the target (e.g., Nectin-4).

In some embodiments, Ga-68 is conjugated to a miniprotein as provided herein. In some embodiments, the gallium is conjugated onto a chelator and may include an optional linker to link it to a miniprotein, which miniprotein targets the conjugate to a cell expressing the target (e.g., Nectin-4).

In some embodiments, Cu-64 is conjugated to a miniprotein as provided herein. In some embodiments, the copper is conjugated onto a chelator and may include an optional linker to link it to a miniprotein, which miniprotein targets the conjugate to a cell expressing the target (e.g., Nectin-4).

In some embodiments, In-111 is conjugated to a miniprotein as provided herein. In some embodiments, the indium is conjugated onto a chelator and may include an optional linker to link it to a miniprotein, which miniprotein targets the conjugate to a cell expressing the target (e.g., Nectin-4).

In some embodiments, Lu-177 is conjugated to a miniprotein as provided herein. In some embodiments, the lutetium is conjugated onto a chelator and may include an optional linker to link it to a miniprotein, which miniprotein targets the conjugate to a cell expressing the target (e.g., Nectin-4).

In some embodiments, Pb-212 is conjugated to a miniprotein as provided herein. In some embodiments, the lead is conjugated onto a chelator and may include an optional linker to link it to a miniprotein, which miniprotein targets the conjugate to a cell expressing the target (e.g., Nectin-4).

In some embodiments, Cu-67 is conjugated to a miniprotein as provided herein. In some embodiments, the copper is conjugated onto a chelator and may include an optional linker to link it to a miniprotein, which miniprotein targets the conjugate to a cell expressing the target (e.g., Nectin-4).

In some embodiments, La-132 is conjugated to a miniprotein as provided herein. In some embodiments, the lanthanum is conjugated onto a chelator and may include an optional linker to link it to a miniprotein, which miniprotein targets the conjugate to a cell expressing the target (e.g., Nectin-4).

In some embodiments, La-135 is conjugated to a miniprotein as provided herein. In some embodiments, the lanthanum is conjugated onto a chelator and may include an optional linker to link it to a miniprotein, which miniprotein targets the conjugate to a cell expressing the target (e.g., Nectin-4).

In some embodiments, Ce-134 is conjugated to a miniprotein as provided herein. In some embodiments, the cerium is conjugated onto a chelator and may include an optional linker to link it to a miniprotein, which miniprotein targets the conjugate to a cell expressing the target (e.g., Nectin-4).

In some embodiments, I-131 is conjugated to a miniprotein as provided herein. In some embodiments, the iodine is conjugated onto a chelator and may include an optional linker to link it to a miniprotein, which miniprotein targets the conjugate to a cell expressing the target (e.g., Nectin-4).

In some embodiments, I-124 is conjugated to a miniprotein as provided herein. In some embodiments, the iodine is conjugated onto a chelator and may include an optional linker to link it to a miniprotein, which miniprotein targets the conjugate to a cell expressing the target (e.g., Nectin-4).

In some embodiments, Pb-203 is conjugated to a miniprotein as provided herein. In some embodiments, the lead is conjugated onto a chelator and may include an optional linker to link it to a miniprotein, which miniprotein targets the conjugate to a cell expressing the target (e.g., Nectin-4).

In some embodiments, Th-232 is conjugated to a miniprotein as provided herein. In some embodiments, the thorium is conjugated onto a chelator and may include an optional linker to link it to a miniprotein, which miniprotein targets the conjugate to a cell expressing the target (e.g., Nectin-4).

In some embodiments, Bi-123 is conjugated to a miniprotein as provided herein. In some embodiments, the bismuth is conjugated onto a chelator and may include an optional linker to link it to a miniprotein, which miniprotein targets the conjugate to a cell expressing the target (e.g., Nectin-4).

In some embodiments, alpha particles (e.g., of Actinium-225, etc.) are positively charged. In some such embodiments, the range of penetration in tissue varies between 5 and cell diameters (40 to 100 μm) depending on their energy (Radiobiologic principles in radionuclide therapy. Kassis A I, Adelstein S J J Nucl Med. 2005 January, 46 Suppl 1:4S-12S). In some such embodiments, such penetration allows for localized irradiation of target cells with minimal toxicity on surrounding normal cells, and internalization by cancer cells with as few as 1-3 tracks across the cell nucleus resulting in cell death (Humm 1987; Macklis et al 1988; Humm and Chin 1993; Couturier et al 2005) causing single- and double-stranded DNA breaks. See, e.g., Sofou S. Radionuclide carriers for targeting of cancer. Int J Nanomedicine. 2008; 3(2):181-199, doi:10.2147/ijn.s2736.

Radionuclides and Chelation

A radionuclide can be bound to a chelator through any method known in the art. In some embodiments, chelation methods may differ based on the radionuclide and chelator selected. For example, in some embodiments, chelation can be carried out in one step by incubating the miniprotein-chelator conjugate with the radionuclide for a predetermined period at a predetermined temperature to achieve a sufficient amount of chelation. In some embodiments, a miniprotein-chelator conjugate comprises a chelator or variant thereof as provided herein (e.g., DOTA, e.g., NOPO, e.g., Crown, e.g., Macropa, e.g., PSC, e.g., N-succinimidyl 3-(tri-n-butylstannyl)benzoate (BuSTB), e.g., N-succinimidyl 3-trimethylstannylbenzoate (MeSTB), etc.). In some embodiments, miniprotein-chelator conjugates can be chelated to a radionuclide (e.g., Actinium-225, Indium-111, Gallium-68, Copper-64, Lutetium-177, Lead-212, etc.) by incubation with the radionuclide for about 1 hour at 70° C. In some embodiments, miniprotein-chelator conjugates can be chelated to a radionuclide (e.g., Actinium-225, Indium-111, Gallium-68, Copper-64, Lutetium-177, Lead-212, etc.) by incubation with the radionuclide for about 1 hour at 70° C.

In some embodiments, the chelation process yields a preparation in which at least 90%, 91%, 92%, 93%, 94%, 95%, 96%, 97%, 98%, or 99% of the miniprotein-chelator is bound to a radionuclide. In some embodiments, the chelation process yields a preparation in which more than 90%, 91%, 92%, 93%, 94%, 95%, 96%, 97%, 98%, or 99% of the miniprotein-chelator is bound to a radionuclide. Excess radionuclide can be removed from the preparation by purification methods known in the art.

Conjugates and Compounds

The disclosure provides conjugates and compounds that comprise a polypeptide as provided herein. Exemplary conjugates are provided, for example, in TABLE 2A (e.g., C2-C208, C212-C215, etc.). For example, in certain embodiments, the disclosure provides a compound comprising a miniprotein having an amino acid sequence with 90% identity to SEQ ID NO: 195, and further comprising one or more additional components according to a formula M-L-C-R, wherein L is a linker, C is a chelator, and R is a radionuclide. In some embodiments. L comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, any linker set forth in TABLE 2A, or (Gly)n-(gGlu)n- or (PEG)n, wherein n is from 1 to 10, (Gly)1-10, or any fragment or combination via covalent bond thereof. In some embodiments, C comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB). In some embodiments, R comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some aspects, the disclosure provides a compound comprising a miniprotein 90% identical to at least 40 amino acids of the amino acid sequence of SEQ ID NO: 195, wherein the N and/or C-terminus comprise between one and thirty additional amino acids, and/or wherein the C-terminus comprises one fewer amino acids or up to 30 additional amino acids, provided that the entire miniprotein is no greater than about 100 amino acids in length.

In some embodiments, the disclosure provides a miniprotein conjugate comprising one or more components including a miniprotein and one or more of a linker, chelator, and/or radionuclide.

In some embodiments, a miniprotein conjugate comprises: (i) miniprotein (M) that specifically binds to Nectin-4; (ii) a chelator (C) conjugated to (M) through an optional linker (L), wherein (C) comprises DOTA, and (L), when present, comprises PEG; and (ii) a radionuclide (R) chelated to (C), wherein (R) is Actinium-225.

In some embodiments, a miniprotein conjugate comprises: (i) miniprotein (M) that specifically binds to Nectin-4; (ii) a chelator (C) conjugated to (M) through an optional linker (L), wherein (C) comprises DOTA, and (L), when present, comprises PEG; and (ii) a radionuclide (R) chelated to (C), wherein (R) is Copper-64.

In some embodiments, a miniprotein conjugate comprises: (i) miniprotein (M) that specifically binds to Nectin-4; (ii) a chelator (C) conjugated to (M) through an optional linker (L), wherein (C) comprises DOTA, and (L), when present, comprises PEG; and (ii) a radionuclide (R) chelated to (C), wherein (R) is Indium-111.

In some embodiments, a miniprotein conjugate comprises: (i) miniprotein (M) that specifically binds to Nectin-4; (ii) a chelator (C) conjugated to (M) through an optional linker (L), wherein (C) comprises DOTA, and (L), when present, comprises PEG; and (ii) a radionuclide (R) chelated to (C), wherein (R) is Lead-212.

In some embodiments, a miniprotein conjugate comprises: (i) miniprotein (M) that specifically binds to Nectin-4; (ii) a chelator (C) conjugated to (M) through an optional linker (L), wherein (C) comprises DOTA, and (L), when present, comprises PEG; and (ii) a radionuclide (R) chelated to (C), wherein (R) is Lutetium-177.

In some embodiments, a miniprotein conjugate comprises: (i) miniprotein (M) that specifically binds to Nectin-4; (ii) a chelator (C) conjugated to (M) through an optional linker (L), wherein (C) comprises DOTA, and (L), when present, comprises PEG; and (ii) a radionuclide (R) chelated to (C), wherein (R) is Gallium-68.

In some embodiments, the PEG linker is PEG (2-24).

In some embodiments, a conjugate of the disclosure comprises a polypeptide. M, which has an amino acid sequence comprising any one of the amino acid sequences set forth in SEQ ID NOs: 3-158, 161-168, 171-208, or 212-215.

In some embodiments, the amino acid sequence has at least 90% identity to that of at least 40 amino acids of SEQ ID NO: 176, wherein X2 is E or D; X6 is E or Q; X9 is T or A; X10 is A or G; X12 is A, Kme3, Kme2, Kme, Kipr or K; X13 is R or (Cit) X17 is G or A; X21 is Q, Y, or E; X24 is Q or K; X25 is A or K; X26 is Kme3, Kme2, Kme, K, Kipr, or S; X28 is Q or K; X29 is Y or K; X30 is L or V; X32 is A, G, or D; X41 is Nor K; and X45 is S or absent.

In some embodiments, M has an amino acid sequence comprising or consisting of SEQ ID NO: 195. In some embodiments, M has an amino acid sequence comprising or consisting of SEQ ID NO: 200.

Decoys and Co-Administration

In some embodiments, a composition provided herein is co-administered with one or more additional proteins such as a decoy peptide. As used herein the term "co-administration" refers to delivering a composition provided herein at substantially the same time (e.g. concomitant, e.g., sequential) as one or more additional proteins such as a decoy peptide. Co-administration can also be used to refer to co-treatment (e.g., in vitro, e.g., in vivo, e.g., of a population of cells, e.g., of a test subject, e.g., of a patient, etc.) or co-incubation (e.g., in vitro by contacting a population of cells with two components (1) a composition provided herein and (2) one or more additional proteins, such as a decoy.

Decoys of the disclosure can be monomeric or multimeric. For example, in some embodiments, a decoy is a monomer. In some embodiments, a decoy is a multimer of one or more monomers of the same or different miniprotein. A multimer may have one or more monomers attached to one another by one or more linkers, such as peptide linkers, covalent bonds, non-covalent linkages, etc.

Without wishing to be limited by theory, the disclosure contemplates that, in some embodiments, co-administration of the composition with a decoy results in reduced or substantially no kidney uptake due to inhibition of proximal tubule cell surface entities (e.g., cell surface transporter(s)). See Xiong. C, et, al. Mol. Pharmaceutics 2019, 16, 808-15; Melis, M, et, al. Eur J Nucl Med Imaging, 2009, 36, 1968-76. In some embodiments, uptake is blocked. In some embodiments, retention is blocked. In some embodiments, decoys can block uptake of a composition of the disclosure (e.g., a radiotherapeutic).

Decoys of the disclosure may be based on a particular scaffold (e.g., type A, a scaffold that is not a scaffold A, etc.). The scaffold of a given decoy may be the same or different from a polypeptide of the disclosure (e.g., a miniprotein, e.g., a Nectin-4-targeting miniprotein) with which it can be combined (co-administered, such as in the same vial, or serially administered vials, etc.), in order to act as a decoy (e.g., block uptake into kidney tissue). For example, a scaffold A polypeptide that binds to a target (e.g., Nectin-4) can be used for co-administration with a scaffold A decoy (e.g., concomitantly, sequentially, etc.). In some embodiments, a scaffold A decoy can be used for co-administration with polypeptide of a different scaffold (e.g., such as in C294, etc.) (e.g. concomitantly, sequentially, etc.). The present disclosure contemplates that compositions (e.g., comprising a miniprotein) do not need to be combined with a decoy of the same scaffold in order for the decoy to block uptake and/or retention of the miniprotein (e.g., a cold-labeled miniprotein, e.g., a radionuclide-labeled miniprotein) into kidney tissue.

Furthermore, the disclosure contemplates that decoys provided herein can decoy compositions (e.g., comprising polypeptides as provided herein) that have one or more modifications to an N-terminus and/or C-terminus, and/or, one or more positions on a polypeptide backbone (e.g., the polypeptide of the composition, e.g., the target-binding polypeptide). That is, a polypeptide that binds to a target (e.g., Nectin-4) can be modified by one or more N- and/or C-terminal modifications and/or one or more poly peptide backbone modifications and, in addition, decoys such as disclosed herein, can still block uptake and/or retention into a kidney tissue when co-administered with one or more such polypeptides. Compositions that can be combined with decoys of the disclosure include, for example, polypeptides modified on N- and/or C-termini and/or their polypeptide backbones such as to include one or more modifications and/or payloads (e.g. radionuclide payloads, e.g., antimitotic payloads, etc.).

Without wishing to be limited by theory, the disclosure contemplates that, in some embodiments, co-administration of the composition with a decoy results in reduced or substantially no kidney uptake due to competitive inhibition of the proximal tubule cell receptors. In some embodiments, co-administration with a functional inhibitor results in reduced or substantially no kidney uptake. See Xiong, C, et, al. Mol. Pharmaceutics 2019, 16, 808-15; Melis, M, et, al. Eur J Nucl Med Imaging, 2009, 36, 1968-76. In some embodiments, uptake is blocked. In some embodiments, retention is reduced or otherwise mitigated. In some embodiments, decoys can block retention and/or uptake of a composition of the disclosure (e.g., a radiotherapeutic).

Decoys of the disclosure may be based on a particular scaffold (e.g., a particular miniprotein scaffold, e.g., a binder scaffold, such as in the Nectin-4 targeting miniproteins provided herein, e.g., C1-C293, e.g., a scaffold such as in a bicyclic Nectin-4 binding protein, e.g., C294). The scaffold of a given decoy may be the same or different from a polypeptide of the disclosure (e.g., a miniprotein, e.g., a Nectin-4 targeting miniprotein). Such a decoy can be combined (co-administered, such as in the same vial, or serially administered vials, etc.) with a composition (e.g., as in TABLES 2A-2G) that targets a Nectin-4 expressing cell (e.g., a tumor cell), in order to act as a decoy (e.g. to block uptake and/or retention into a tissue, such as a kidney tissue). In some embodiments, a polypeptide that binds to a target (e.g., Nectin-4) and has the same (e.g., C1-C293) or a different (e.g., C294) scaffold as a decoy can be used for co-administration with a decoy (e.g., concomitantly, sequentially, etc.). The present disclosure contemplates that compositions (e.g., comprising a miniprotein) do not need to be combined with a decoy of the same scaffold in order for the decoy to block uptake and/or retention of the miniprotein (e.g., a cold-labeled mini protein, e.g., a radionuclide-labeled miniprotein) into a kidney tissue.

In certain embodiments, the decoy comprises or consists of a miniprotein having an amino acid sequence comprising, consisting essentially of, or consisting of any of SEQ ID NOs: 209-211. In some embodiments, the decoy comprises or consists any of compounds C295-C297, as set forth in TABLE 2H.

TABLE 2H

Decoys

| Compound | SEQ ID NO: | N-term | Sequence | C-term |
|---|---|---|---|---|
| C295 | 209 | Acetyl | CEYDEEFFTELERLKGGDICYYIKKK EDKVPRICIKEIRDKLGC | NH2 |
| C296 | 211 | Acetyl | CEYDEEFFTELERLKGGDICYYIKKK EDKVPDLCIKEIRDKLGC | NH2 |
| C297 | 210 | Acetyl | CEYKEEFFTELKRLYGGDICYYIKKK FKKVPDLCIEEILDKLGC | NH2 |

The disclosure contemplates that the combination of reduction in kidney retention and/or uptake at the same time as successful uptake and/or retention in tumor tissue may represent an improvement in a therapeutic index (TI), including while reducing kidney tissue uptake and/or retention. Therapeutic index, as used herein, refers to a ratio that compares blood concentration at which an agent (e.g., a compound as provided herein, e.g., a radionuclide conjugate as provided herein) becomes toxic versus the concentration at which the drug is effective. Typically, a quantitative measure of TI is LD50 (median lethal dose) over ED50 (median effective dose). When TI is quantified by LD50/ED50, improvement in TI is characterized by a decrease in LD50/ED50 due to a decrease in LD50, an increase in ED50, or a combination of both.

In some embodiments, the decoy has an amino acid sequence comprising any one of SEQ ID NOs: 209-211. In some embodiments, the decoy is a compound selected from any of C295-C297. In some embodiments, the decoy is present at a concentration of about 2×, 5×, 10×, 20×, 30×, 40×, 50×, 60×, 70×, 80×, 90×, 100×, 250×, 500×, 750×, 1000×, 2500×, 5000×, 7500×, 10000×, or greater as compared to the concentration of M. Examples 26, 27, and 32 each provide data on levels of kidney retention measured in mice treated with radioactively-labeled peptides and imaged via SPECT/CT, as provided herein. In some embodiments, the decoy blocks uptake of M (e.g., of a composition of the disclosure) in the kidney, such as shown in, e.g., FIG. 16 and FIG. 17A.

In certain embodiments, the decoy comprises or consists of an amino acid sequence selected from any of compounds C295-C297. In certain embodiments, the miniprotein comprises or consists of any compound or amino acid sequence selected from TABLE 2A.

In some embodiments, the decoy comprises or consists of an amino acid sequence selected from any of compounds C295-C297.

In certain embodiments, the decoy comprises or consists of a decoy having the same scaffold as a miniprotein comprising or consisting of an amino acid sequence as set forth in TABLE 2A. In certain embodiments, the decoy comprises or consists of a decoy having a different scaffold as a miniprotein comprising or consisting of an amino acid sequence as set forth in TABLE 2A. In some embodiments, the decoy is selected from C295-C297 or a miniprotein comprising or consisting of any of SEQ ID NOs: 209-211 and the Nectin-4-binding miniprotein comprises or consists of any of C3-C293. C298-C307 and/or has an amino acid sequence comprising, consisting essentially of, or consisting of any of SEQ ID NOs: 3-158, 161-168, 170-208, 212-237, 243-246 and 248. In some embodiments, the decoy is selected from C295-C297 or a miniprotein comprising, consisting essentially of, or consisting of any of SEQ ID NOs: 209-211 and the Nectin-4-binding miniprotein comprises or consists of C294 and/or an amino acid sequence comprising or consisting of an amino acid sequence of SEQ ID NO: 238. In some embodiments, the Nectin-4 binding miniprotein comprises [TATA(1,5,15)]SCBiot-(dPEG4) CP(1Nal)(dD)CM(hR)DWSTP(hyP)WC (SEQ ID NO: 238). In some embodiments, the Nectin-4 binding miniprotein comprises, consists essentially of, or consists of an amino acid sequence CP(1Nal)(dD)CM(hR)DWSTP(hyP) (SEQ ID NO: 242).

The present disclosure contemplates that, in some embodiments, the decoy reduces the uptake of M (e.g., of a composition of the disclosure, e.g., of a cold-metal labeled compound of the disclosure, e.g., of a radionuclide composition of the disclosure) in the kidney by competitive inhibition. In some embodiments, the decoy can be of a desirable length. In some such embodiments, the desirable length is about the same length as that of the M portion of a composition for which uptake by the kidney is being reduced or prevented. In some aspects, amino acid residues added to the N-terminal end or the C-terminal end of the decoys disclosed herein may prevent ubiquitination, improve stability, help maintain the three dimensional structure of the peptide, or a combination thereof. In some embodiments, a given decoy has similar features (e.g., length, secondary structure, charge, etc.) and/or is of the same scaffold (e.g., a binder scaffold, e.g., a scaffold that is the same as a Nectin-4 binding protein as set forth in TABLE 2A, e.g., a scaffold such as in C294, etc.) of a target-binding composition that it is being co-administered with, and, in some embodiments, a given decoy has different features than the target-binding composition. In such embodiments, regardless of the scaffold of the miniprotein of the composition or the decoy, the decoy is able to block or reduce uptake and/or retention of the composition comprising the miniprotein (e.g., labeled miniprotein, e.g., cold-labeled, e.g., radiolabeled, etc.) in kidney tissue.

In some aspects, the decoys disclosed herein can further comprise a peptide or polypeptide having one or more amino acid residues with a modified side chain. In some aspects, one or more amino acids of any of the decoys disclosed here can have a modified side chain. Examples of side chain modifications include but are not limited to modifications of amino acid groups, such as reductive alkylation; amidination with methylacetimidate; acylation with acetic anhydride; carbamolyation of amino groups with cynate; trinitrobenzylation of amino acid with 2,4,6-trinitrobenzene sulfonic acid (TNBS); alkylation of amino groups with succinic anhydride; and pyridoxylation with pridoxal-5-phosphate followed by reduction with NaBH4.

In some aspects, the decoys described herein can be further modified to improve stability. In some aspects, any of the amino acid residues of the decoys described herein can be modified to improve stability. In some aspects, decoy can have at least one amino acid residue that has an acetyl group, a fluorenylmethoxy carbonyl group, a formyl group, a palmitoyl group, a myristyl group, a stearyl group, or polyethylene glycol. In some aspects, an acetyl protective group can be bound to the decoy described herein.

In some aspects, the amino acid sequence of the decoys described herein can include a peptide sequence that has substantial identity to any of the sequences of the decoys disclosed herein. As used herein, the term "substantial identity" means that two amino acid sequences, when optimally aligned and then analyzed by an algorithm normally used in the art, such as BLAST, GAP, or BESTFIT, or by visual inspection, share at least about 60%, 70%, 80%, 85%, 90%, or 95% sequence identity. Methods of alignment for sequence comparison are known in the art.

In some aspects, the amino acid sequence of the decoys described herein can include a sequence (e.g., a nucleic acid sequence, an amino acid sequence) that has some degree of identity or homology to a sequence of any decoy disclosed herein. The degree of identity can vary and be determined by methods known to one of ordinary skill in the art. The terms "homology" and "identity" each refer to sequence similarity between two polypeptide or polynucleotide sequences. Homology and identity can each be determined by comparing a position in each sequence which can be aligned for purposes of comparison. When a position in the compared sequence is occupied by the same amino acid residue or nucleic acid, then the polypeptides or polynucleotides can be referred to as identical at that position; when the equivalent site is occupied by the same amino acid or nucleic acid (e.g., identical) or a similar amino acid or nucleic acid (e.g., similar in steric and/or electronic nature), then the molecules can be referred to as homologous at that position. A percentage of homology or identity between sequences is a function of the number of matching or homologous positions shared by the sequences. The decoys disclosed herein can have at least or about 25%, 50%, 65%, 75%, 80%, 85%, 90%, 95%, 96%, 97%, 98%, or 99% identity or homology to a reference decoy.

Dose Calculation

In some embodiments, a dose of a radiotherapeutic is calculated. In some such embodiments, calculation of an absorbed dose (D) is necessary to quantitatively correlate tumor response to a particular radiotherapeutic modality and to project on the potential effect of other radiotherapeutic modalities or administration strategies. That is, in some embodiments, the absorbed dose from a target site is defined as the energy (E) absorbed by a particular mass of tissue, normalized by the tissue mass (M): D=E/M (Sgouros 2005). The absorbed energy is defined as a function of three parameters: the number of disintegrations within the particular volume of interest ($\delta$), the energy emitted per disintegration ($\varepsilon$), and the fraction of emitted energy that is absorbed by the particular volume of interest (the target mass)(f): E=$\delta \times \varepsilon \times f$. For the relatively long-range beta emitters, the dose evaluation at a target site includes not only the energy emitted by radionuclides localized within the target volume, but also the energy emitted by radionuclides accumulated in neighboring organs or areas whose emissions cross along their path the target volume of interest (Kolbert et al 2003). In other words, in some embodiments, the calculated total absorbed dose is the sum of the dose contributions from all regions containing radionuclides that act as secondary sources. In some embodiments, the adsorbed dose due to photon emissions is usually calculated separately and added to the dose due to alpha or beta particles. In some embodiments, where a composition comprises an alpha particle emitter, such cross organ absorbed doses may be of no significance due to their short recoil distances. In some embodiments, given appropriate context, at the micron-scale and at distances comparable to a few cells, microdosimetric evaluations are used to evaluate dose or 'hits' acquired by cancer cells within micrometastatic clusters (Palm et al 2002).

In some embodiments, a miniprotein conjugate comprising a radionuclide displays binding specificity to human Nectin-4. In some embodiments, the miniprotein comprises a binding affinity characterized by a dissociation constant ranging from about 500 nM to about 1 pM, e.g., 500, 400, 300, 200, 100, 90, 80, 70, 60, 50, 40, 30, 20, 10, 9, 8, 7, 6, 5, 4, 3, 2, 1 nM, 100, 90, 80, 70, 60, 50, 40, 30, 20, 10, 9, 8, 7, 6, 5, 4, 3, 2, or 1 pM binding affinity to human Nectin-4. Without being bound by any particular theory, the present disclosure contemplates that, in some embodiments, a preferred dissociation constant of a miniprotein is about 10 nM or less, about 7.5 nM, about 5 nM or less, about 2.5 nM or less, about 1 nM or less (i.e., in the picomolar range).

In some embodiments, a miniprotein comprising a radionuclide in accordance with the present disclosure binds to Nectin-4 with a binding affinity of about 1 pM to 100 nM. In some embodiments, a miniprotein in accordance with the present disclosure binds to Nectin-4 with a binding affinity of about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 pM; 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 30, 350, 400, 450, 500, 550, 600, 650, 700, 750, 800, 850, 900, 950, or 1000 nM. In some embodiments, a miniprotein in accordance with the present disclosure binds to Nectin-4 with a binding affinity of about 1 pM to 1 W pM, 10 pM to 1 nM, 100 pM to 10 nM, or 1 nM to 100 nM.

In some embodiments, compositions as provided herein are characterized for one or more of absorbed dose, dose rate, tumor penetration profile of radionuclides, intracellular localization profiles of radionuclides of shorter range, and tumor radiosensitivity (see, e.g., Sofou S. Radionuclide carriers for targeting of cancer. Int J Nanomedicine. 2008: 3(2):181-199).

As is known to those of skill in the art, due to toxicity of radionuclides, dose needs to be carefully controlled and considered. Accordingly, in some embodiments, compositions comprising radionuclides of the present disclosure address dose-limiting toxicity of compositions such that radionuclides do not accumulate significantly (e.g., in a toxicity—limiting manner) in vital organs.

In some embodiments, alpha particle-emitting isotopes engage in on-target cell killing while minimizing toxic effects (e.g., to surrounding tissue, e.g., as compared to, e.g., beta emitters, etc.).

In some embodiments, compositions provided herein (comprising a radionuclide) are administered in a single step such as, e.g., using a ligand, e.g., a miniprotein resulting in improved biodistributions (e.g., specific targeting), pK with partial and acceptable damage or no damage to normal tissues, enhanced penetration of the pharmaceutical composition into the tumor heterogeneous interstitial space.

In some embodiments, one or more radionuclides is conjugated to a miniprotein. Relatedly, in some embodiments, radiolabeling efficiency of a miniprotein is optimized to radiolabel a desired number of radionuclides. In some embodiments, a ratio of radionuclides conjugated to a miniprotein is 1:1, 2:1, 3:1, 4:1, 5:1, 6:1, 7:1, 8:1, 9:1, 10:1. In some embodiments, radionuclides conjugated to a miniprotein does not present toxicity. In some embodiments, a composition comprising a miniprotein and radionuclide does not accumulate in the liver, spleen, and/or pancreas and is cleared rapidly when administered to a subject. For instance, in some embodiments, after administration to a subject, biodistribution in the kidney is >100% of the injected dose per gram (% ID/g) at 24 h and in tumors is >3% ID/g at 24 h.

In some embodiments, after administration to a subject, t1n is shorter than that of, e.g., a Nectin-4 ADC, e.g., enfortumab vedotin.

In some embodiments, a dose calculation comprises or consists of a dose calculation for a compound comprising a radionuclide and/or a compound comprising a decoy. In some embodiments, a decoy dose calculation depends on a dose of a radionuclide (e.g., nCi). In some embodiments, a decoy, when administered (e.g., co-administered, e.g., before, concomitant with, after administration of a radionuclide) is dosed at an excess (a mass or molar excess) as compared to the radionuclide dose. For example, in some embodiments, a dose excess may be 1, 2, 3, 4, 5, 10, 25, 50, 100, 250, 50, 750, 1,000, 1,250, 1,500, 1,750, 2,000, 2,250, 2,500, 2,750, 3,000, 3,250, 3,500, 3,750, 4,000, 4,250, 4,500, 4,750, 5,000, 7,500, 10,000-fold excess, or greater. In some embodiments, the excess is a fold-excess based on molarity of the concentration of a compound and/or radionuclide. In some embodiments, the excess is a fold-excess based on mass of the concentration of a compound and/or radionuclide.

In some embodiments, a dose calculation may include more than one administration of a given compound (e.g., a radioactive compound, e.g., a radionuclide-labeled compound of the disclosure, etc.). For example, in some embodiments, dose is measured as absorbed dose to a location (e.g., a tissue, e.g., an organ, e.g., kidney). In some such embodiments, dose can be measured using methods know to those of skill in the art, such as in RBE5Gy/MBq, and dose limits, such as for a particular organ, are determined by guidelines, such as accepted clinical guidelines known to those of ordinary skill in the art. Without wishing to be bound by theory, the disclosure contemplates that co-administration (e.g., of a radionuclide compound of the disclosure and a decoy of the disclosure) can allow a greater number of administrations of the radionuclide-labeled compound as compared to the radionuclide compound alone (in the absence of a decoy). In some embodiments, a number of administrations increases while absorbed dose (e.g., to kidneys) decreases. In some embodiments, co-administration of a decoy with a target-binding radionuclide of the disclosure reduces an absorbed dose to the kidney by 5, 10, 15, 20, 25, 30, 35, 40, 45, 50, 55, 60, 65% or more. In some embodiments, number of administrations achieved with co-administration increases by 5, 10, 15, 20, 25, 30, 35, 40, 45, 50, 55, 60, 65% or more. In some embodiments, absorbed dose to the kidney decreases while number of administrations increases. In some embodiments, administration of the decoy will enable higher dosing with one or more radiotherapeutic treatments, as compared to dosing in the absence of a decoy with no change in toxicity grade of the therapeutic.

Kidney Uptake and/or Retention

Among other things, the disclosure provides the insight that administration of a conjugate (e.g., a radiotherapeutic conjugate) of the disclosure in combination with a decoy can reduce uptake and/or retention of a radioactive compound in kidney tissue. Without being limited by theory, the disclosure contemplates that administration of a decoy along with a therapeutic molecule, such as a radiotherapeutic for use in targeting tumor cells (e.g., in a tumor) can be improved including by (1) decreasing off-target uptake, accumulation, retention excretion, and/or kidney tissue toxicity; and/or (2) improving uptake and/or retention in a tumor tissue comprising tumor cells. In some embodiments, kidney uptake and/or retention is blocked by a decoy.

In some aspects, provided herein are methods and compositions to address undesirable effects of radionuclide therapy upon transit through the kidney. Accordingly, disclosed herein are compositions (e.g., comprising target-binding miniproteins) characterized to exhibit reduced kidney retention, and/or, compositions characterized to bind to a target and used in combination with one or more additional proteins such as decoy peptides provided to block uptake of compositions into kidney.

The disclosure contemplates that, for example, kidney retention and/or absorption of peptide-based radiopharmaceuticals may be attributed as a result of target expression in protein conservation from ultrafiltration and reuptake into the proximal tubule cells, or expression of one or more receptors or co-receptors that uptakes proteins and/or molecules into the kidney for clearance through the body. Reuptake in the proximal tubule cells is thought to occur through protein or peptide cleavable by the kidney brush border peptidases and reuptake of short peptides, as well as receptor mediated reuptake. Without wishing to be bound by theory, in receptor mediated reuptake, a peptide-based radiopharmaceutical may bind to the megalin/cubulin receptor complex of the kidney, undergo receptor mediated endocytosis, and get degraded and retained in lysosomes, which can result in extended retention of radioactivity in the proximal tubules of the kidneys and dose-limiting toxicity of the radiopharmaceutical. Geenen et al., Nucl. Med. Biol, 2021, 102-103: 1-11. The disclosure provides decoys and uses thereof to block uptake and/or retention in kidney tissue by a radionuclide-labeled target-binding miniprotein.

Thus, among other things, provided herein, are improvements in methods of use or treatment of compositions comprising a target-binding miniprotein (e.g., to kidney tissue. e.g., a miniprotein or compound of TABLE 2A). Improvements can be achieved, for example, by co-administration of a decoy with a target-binding miniprotein (e.g., a radionuclide labeled miniprotein, e.g., a miniprotein or compound as provided in TABLE 2A, e.g., a miniprotein that binds to Nectin-4). In some embodiments, an improvement comprises blocking absorption, uptake, and/or retention of a compound into the kidney by co-administration with a decoy. In some embodiments, the scaffold of the Nectin-4-binding miniprotein or compound is the same or is different from the co-administered decoy.

In some embodiments, the disclosure provides a method comprising means for blocking uptake and/or retention into kidney tissue of a target-binding miniprotein or compound provided herein. In some such embodiments, the means for blocking comprises or consists of a decoy. In some embodiments, the decoy is selected from any of C295-C297 and/or has an amino acid sequence comprising, consisting essentially of, or consisting of any of SEQ ID NOs: 209-211. In some embodiments, the decoy is a miniprotein of the same scaffold as a Nectin-4 targeting miniprotein such as provided herein (see, e.g., TABLE 2A, e.g., C1-C293 or C297-C307) or a different scaffold (e.g., C294, etc.).

Nucleic Acids

Among other things, the present disclosure provides herein polynucleotides and methods of use thereof. In some embodiments, all or a portion of the polynucleotides encode a polypeptide (e.g., a miniprotein) that specifically binds to Nectin-4. In some embodiments, the Nectin-4 is murine or human Nectin-4. In some embodiments, the nucleic acid sequence has a specific sequence. In some embodiments, a polynucleotide of the present disclosure is codon-optimized (i.e., the nucleic acid sequence is codon-optimized).

In some embodiments, a polynucleotide of the present disclosure comprises or consists of a nucleic acid sequence encoding a polypeptide that is or comprises a miniprotein that specifically binds To Nectin-4 or any portion, fragment, or variant thereof.

In some embodiments, a miniprotein is represented by a nucleic acid molecule encoding an amino acid that, when folded, comprises one or more disulfide bridges.

In some embodiments, for example, a nucleic acid molecule (i.e., a polynucleotide) may be non-identical to a reference sequence as provided herein, but still encode a binder as provided by the present disclosure. In some such embodiments, such as provided polynucleotide (i.e., encoding a miniprotein or analog thereto) hybridizes under stringent conditions as disclosed herein.

In some embodiments, the present disclosure provides nucleic acid molecules comprising a fragment of any polynucleotide as provided herein. In some embodiments, a polynucleotide fragment comprises or consists of a portion of contiguous nucleic acid residues. For instance, in some embodiments, a polynucleotide fragment comprises or consists of 20, 25, 30, 35, 40, 45, 50, 55, 60, 65, 70, 75, 80, 85, 100 or more nucleic acid residues.

In some embodiments, fragments of the present disclosure display utility in a variety of systems and methods. For example, the fragments may be used as probes in various assays. For instance, in some embodiments, fragments may be used in hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. In some embodiments, fragments may be used as probes, e.g., such as when immobilized on a microarray. Methods for creating microarrays by deposition and fixation of nucleic acids onto support substrates are well known in the art. Reviewed in DNA Microarrays: A Practical Approach (Practical Approach Series), Schena (ed.), Oxford University Press (1999) (ISBN: 0199637768); Nature Genet. 21(1)(suppl):1-60 (1999); Microarray Biochip: Tools and Technology, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., Trends Biochem. Sci. 24:168-173 (1999) and Zweiger, Trends Biotechnol. 17:429436 (1999); DNA Microarrays: A Practical Approach (Practical Approach Series), Schena (ed.), Oxford University Press (1999) (ISBN: 0199637768); Nature Genet. 21(1)(suppl):1-60 (1999); Microarray Biochip: Tools and Technology, Schena (ed.), Eaton Publishing Company/BioTechniques Books Division (2000) (ISBN: 1881299376).

In some embodiments, a polynucleotide of the present disclosure comprises or consists of a nucleic acid sequence encoding up to 100 amino acids of SEQ ID NO: 159 or SEQ ID NO: 160.

In some embodiments, a polynucleotide of the present disclosure comprises or consists of a sequence that encodes a polypeptide of SEQ ID NOs: 3-158, 161-168, 170-208, 212-237, 243-246 and 248 and/or as set forth in TABLES 1B, 1C, 1D, and/or 2A or a portion or functional variant thereof. In some such embodiments, a polynucleotide encodes a polypeptide, such as those set forth in SEQ ID NOs: 3-158, 161-168, 170-208, 212-237, 243-246 and 248 and/or as set forth in TABLES 1B, 1C, 1D, and/or 2A or a portion or functional variant thereof, that binds to a target represented by SEQ ID NOs 159 or 160.

In some embodiments, a polynucleotide of the present disclosure comprises or consists of a nucleic acid sequence encoding a polypeptide that is or comprises a miniprotein that binds to Nectin-4 or any portion, fragment, or variant thereof. In some embodiments, the polynucleotide encodes a polypeptide that comprises or consists of the amino acid sequence set forth in any one of SEQ ID NOs: 3-158, 161-168, 170-208, 212-237, 243-246 and 248 and/or as set forth in TABLES 1B, 1C, 1D, and/or 2A or a portion or functional variant thereof. In some embodiments, the polynucleotide encodes a polypeptide sequence having at least 70%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%. 99.8%, 99.9%, or more identity to the amino acid sequences provided in a polypeptide according to those set forth in TABLES 1B and/or 1C or a polypeptide of a compound of TABLE 2A.

In some embodiments, the disclosure provides an isolated polynucleotide comprising one or more nucleic acid sequences encoding a polypeptide selected from any one of SEQ ID NOs: 3-158, 161-168, 170-208, 212-237, 243-246 and 248; or a nucleic acid sequence encoding a polypeptide comprising at least 90%, 95%, 96%, 97%, 98%, 99% or greater identity to any one of SEQ ID NOs: 3-158, 161-168, 170-208, 212-237, 243-246 and 248.

In some embodiments, a miniprotein comprises one or more disulfide bridges. In some embodiments, a miniprotein is represented by a nucleic acid sequence encoding a polypeptide that, when folded, comprises one or more disulfide bridges.

In some embodiments, the present disclosure provides nucleic acid molecules comprising or consisting of a sequence as set forth in SEQ ID NO: 159 or SEQ ID NO: 160, or variations (e.g., codon-optimized) thereof.

In some embodiments, for example, a nucleic acid molecule (i.e., a polynucleotide) may be non-identical to a reference sequence as provided herein, but still encode a miniprotein or close analog as provided by the present disclosure (e.g., a miniprotein in accordance with any one of SEQ ID NOs: 3-158, 161-168, 170-208, 212-237, 243-246 and 248 and/or as set forth in TABLES 1B. 1C, 1D, and/or 2A or a portion or functional variant thereof as provided for herein). In some such embodiments, such as provided polynucleotide (i.e., encoding a miniprotein or analog thereto) hybridizes under stringent conditions as disclosed herein.

In some embodiments, the present disclosure provides nucleic acid molecules comprising a fragment of any polynucleotide as provided herein. In some embodiments, a polynucleotide fragment comprises or consists of a portion of contiguous nucleic acid residues identical to that of a polynucleotide of any of SEQ ID NOs: 3-158, 161-168, 170-208, 212-237, 243-246 and 248 and/or as set forth in TABLES 1B, 1C, 1D, and/or 2A or a portion or functional variant thereof. For instance, in some embodiments, a polynucleotide fragment comprises or consists of 20, 25, 30, 35, 40, 45, 50, 55, 60, 65, 70, 75, 80, 85, 100 or more nucleic acid residues encoding some or all of a polypeptide or fragment thereof as set forth in any one of SEQ ID NOs: 3-158, 161-168, 170-208, 212-237, 243-246 and 248, and/or as set forth in TABLES 1B, 1C, ID, and/or 2A or a portion or functional variant thereof.

One of skill in the art will appreciate that the nucleic acid fragments of the present disclosure may be used in a wide variety of techniques capture and/or detection techniques not specifically described herein.

Vectors

Also provided herein are vectors, including expression vectors, which comprise, among other things, nucleic acids comprising or consisting of sequences encoding miniproteins that specifically bind to Nectin-4. In some embodiments, a vector is used to produce a polypeptide encoding a binder that binds to Nectin-4. In some embodiments, the Nectin-4 is murine or human Nectin-4. In some embodiments, given appropriate contexts, a miniprotein is represented by an amino acid sequence with a corresponding nucleic acid sequence that has been codon-optimized. In some such embodiments, one of skill in the art is capable of designing and optimizing polynucleotides that correspond to amino acids of miniproteins that bind to a target (e.g., Nectin-4), for which exemplary amino acid sequences are set forth in TABLE 1A. In some embodiments, a vector comprises a nucleic acid sequence that comprises or consists of a sequence encoding Nectin-4. In some embodiments, the disclosure provides a vector encoding a polypeptide or portion thereof as provided herein.

In some embodiments, the vector comprises a nucleic acid sequence encoding Nectin-4 or a fragment or variant thereof, wherein the polynucleotide is codon-optimized (i.e., the nucleic acid sequence is codon-optimized). In some embodiments, the vector comprises a nucleic acid sequence encoding up to 100 amino acids. In some embodiments, a vector of the present disclosure comprises or consists of a nucleic acid sequence that encodes an amino acid sequence of a miniprotein. In some embodiments, the vectors of the present disclosure further comprise a nucleic acid sequence as provided herein operably linked to one or more expression control sequences.

Also provided herein are vectors, including expression vectors, which comprise, among other things, nucleic acids comprising or consisting of those described herein. In some embodiments, a vector is used to produce a polypeptide encoding a miniprotein that binds to Nectin-4. In some embodiments, the Nectin-4 is murine or human Nectin-4. In some embodiments, given appropriate contexts, a Nectin-4 miniprotein (e.g., as provided in TABLE 2A) has a corresponding nucleic acid sequence that has been codon-optimized. In some such embodiments, one of skill in the art is capable of designing and optimizing polynucleotides that correspond to amino acids of particular Nectin-4 miniproteins such as, for example, polynucleotides comprising nucleic acid sequences that correspond to amino acid sequences of TABLE 2A. In some embodiments, a vector comprises a nucleic acid sequence encoding the amino acid sequence set forth in SEQ ID NO: 159. In some embodiments, a vector comprises a nucleic acid sequence encoding the amino acid sequence set forth in SEQ ID NO: 160. In some embodiments, a vector comprises a nucleic acid sequence that comprises or consists of a sequence having 70%, 80%, 85%, 90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or more identity to wild type Nectin-4. In some embodiments, the vector comprises a nucleic acid sequence encoding Nectin-4 or a fragment or variant thereof, wherein the polynucleotide is codon-optimized (i.e., the nucleic acid sequence is codon-optimized). In some embodiments, the vector comprises a nucleic acid sequence encoding up to 50, 55, 60, 65, 70, 75, 80, 85, 90, 95, or 100 amino acids of any one of SEQ ID NOs: 3-158, 161-168, 170-237 and/or as set forth in TABLES 1B. 1C, 1D, and/or 2A or a portion or functional variant thereof. In some embodiments, a vector of the present disclosure comprises or consists of a nucleic acid sequence, wherein the nucleic acid sequence encodes an amino acid sequence comprising those as set forth in in TABLES 1B, 1C, 1D, and/or 2A or a portion or functional variant thereof. In some embodiments, the nucleic acid sequence is a codon-optimized nucleic acid sequence. In some embodiments, the vectors of the present disclosure further comprise a nucleic acid sequence as provided herein operably linked to one or more expression control sequences.

Host Cell Transformants

In some embodiments, the present disclosure provides host cells transformed with polynucleotides, polypeptides, and/or vectors of the present disclosure, and any combinations as well as any descendants thereof. In some embodiments host cells comprise and carry nucleic acid sequences of the present disclosure on vectors. In some embodiments, a host cell is a cell line. In some embodiments, a host cell is a primary cell, such as an immune cell. In some embodiments, such a primary cell is derived from or made compatible with a subject. In some embodiments, a subject is a mammal. In some embodiments, a mammal is a human. In some embodiments, a human is at risk of having or has been diagnosed as having cancer.

In some embodiments, the disclosure provides a host cell transformed with an isolated polypeptide or vector as provided herein.

In some such embodiments, such vectors may but need not be freely replicating vectors. In some embodiments, nucleic acid sequences or polynucleotides provided by the present disclosure have been integrated into a genome of a host cell.

In some embodiments, host cells of the present disclosure can be mutated by recombination with a disruption, deletion, or mutation of the isolated nucleic acid of the present disclosure so that the activity of one or more functional activities in the host cell is reduced or eliminated compared to a host cell lacking the mutation.

Without limitation, and as will be appreciated by those of skill in the art, a wide variety of host cells is contemplated in various embodiments in order to express binders of the present disclosure (via use of, e.g., nucleic acid sequences, amino acid sequences, and/or additional components as provided here).

Combination Compositions

The disclosure provides an insight that a combination of one or more components provided herein may confer one or more advantages, such as improvement in treatment, for a subject or group of subjects in need thereof. For example, a combination composition may comprise a radionuclide therapeutic as provided herein and a decoy as provided herein. Such compositions may each be provided in a different container, but administered "together" which can be concomitant or serial administration. Without wishing to be bound by theory, the disclosure contemplates that a combination composition provides one or more positive effects on a disease, disorder, or condition as disclosed herein that is at least as good or better, relative to either composition of the combination alone.

Combination compositions can include miniproteins (e.g., in a fusion, as a decoy) having the same or different scaffolds as one another. For example, a combination composition may comprise a compound or miniprotein as provided herein, such as a radionuclide conjugate comprising a miniprotein (M), and a decoy, where the miniprotein of the conjugate is a Nectin-4 targeting miniprotein and the decoy is of the same scaffold.

In one aspect, the disclosure provides a combination composition comprising. (i) a radionuclide therapeutic comprising a composition represented by the formula selected from one or more of M-L-C-R, M-L-C, M-C-R, M-L-R, M-C, M-L, and M-R, wherein M comprises a miniprotein (M), L comprises a linker (L), C comprises a chelator (C), and R comprises a radionuclide (R), wherein the M is of a particular scaffold; and (ii) a decoy comprising or consisting of an amino acid sequence selected from SEQ ID NOs: 209-211. In some embodiments, the decoy does not comprise the same scaffold as the M. In some embodiments, the decoy comprises the same scaffold as any of C3-C293.

In another aspect, the disclosure provides a combination composition comprising a conjugate comprising miniprotein (M) or compound selected from any of TABLE 2A and a decoy. In some embodiments, the decoy is of a scaffold that is the same scaffold or a different scaffold as a Nectin-4 binding protein as provided herein (e.g., TABLE 2A, e.g., C1-C293, e.g., C294, etc.). In some embodiments, the decoy is selected from any of compounds C295-C297, and/or has an amino acid sequence comprising, consisting essentially of, or consisting of any of SEQ ID NOs: 209-211. In certain embodiments, the decoy is administered together or separately from a conjugate as provided herein (e.g., a radioactive conjugate, e.g., a radionuclide therapeutic as provided herein). In certain embodiments, the decoy is administered prior to or after the conjugate. In certain embodiments, administration of a therapeutic compound (e.g., comprising a miniprotein, e.g., a radionuclide therapeutic) is administered concomitant with the decoy. In certain embodiments, the sequential administering comprises administering the decoy followed by administering the composition comprising the miniprotein (M) (e.g., a radionuclide therapeutic as disclosed herein). In certain embodiments, the sequential administering comprises administering the composition comprising the miniprotein (e.g., a radionuclide therapeutic as disclosed herein) followed by administering the decoy.

Pharmaceutical Compositions

The present disclosure provides, among other things, pharmaceutical compositions comprise a polypeptide, polynucleotide, vector and/or host cell encoding a miniprotein (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) as provided herein. It is to be understood that a pharmaceutical composition comprising a miniprotein is interpreted as a pharmaceutical composition comprising a miniprotein per se and/or one or more components encoding a miniprotein (e.g., a vector, e.g., a host cell). In some embodiments, a pharmaceutical composition comprises a linker and a chelator. In some embodiments, a pharmaceutical composition comprises a linker, chelator, and radionuclide. In some embodiments, a composition comprises a miniprotein, optional linker, and chelator. In some embodiments, a composition comprises a miniprotein, optional linker, chelator, and radionuclide. In some embodiments, a pharmaceutical composition provided by the present disclosure comprises a miniprotein that selectively binds to Nectin-4. In some embodiments, the Nectin-4 is human Nectin-4.

In some embodiments, a pharmaceutical composition comprises a combination of miniprotein conjugate that is radiolabeled as provided herein and a miniprotein that is not conjugated.

In some embodiments, the present disclosure provides pharmaceutical compositions comprising a conjugate in accordance with the present disclosure and a pharmaceutically acceptable excipient.

In some embodiments, the composition is formulated for intravenous administration. In some embodiments, the composition is formulated for subcutaneous administration. In some embodiments, the composition is formulated for parenteral or oral administration.

In some embodiments, a pharmaceutical composition comprises a combination of a miniprotein conjugate that is conjugated to a radionuclide as provided herein and a miniprotein conjugate that is conjugated to a cold-metal surrogate as provided herein.

In some embodiments, a pharmaceutical composition comprises a combination of miniprotein conjugate that is radiolabeled with an alpha emitter radionuclide as provided herein and a miniprotein that is radiolabeled with a beta emitter radionuclide.

In various embodiments, compositions disclosed herein comprise a plurality of miniprotein conjugates, wherein each miniprotein conjugate is represented by a formula selected from one or more of (M)x-L-C-R, (M)x-L-C, (M)x-C-R, (M)x-L-R, (M)x-C, (M)x-L, and (M)x-R, wherein M comprises a miniprotein (M), L comprises a linker (L), C comprises a chelator (C). R comprises a radionuclide (R), and x is 1, 2, 3, or 4, wherein M comprises an amino acid sequence of any one of SEQ ID NOs: 3-158, 161-168, 170-237 and/or as set forth in TABLES 1B, 1C, ID, and/or 2A. In various embodiments, the plurality of miniprotein conjugates comprise at least a first subset and a second subset. For example, a first subset of the plurality of miniprotein conjugates comprise radionuclides (R) comprising a hot radionuclide and a second subset of the plurality of miniprotein conjugates comprise radionuclides (R) comprising a cold-metal surrogate of a radionuclide.

In various embodiments, the first subset accounts for less than 10%, less than 20%, less than 30%, less than 40%, less than 50%, less than 60%, less than 70%, less than 80%, or less than 90% of miniprotein conjugates in the plurality of miniprotein conjugates. In various embodiments, the second subset accounts for less than 10%, less than 20%, less than 30%, less than 40%, less than 50%, less than 60%, less than 70%, less than 80%, or less than 90% of miniprotein conjugates in the plurality of miniprotein conjugates.

In various embodiments, the first subset of the plurality of miniprotein conjugates comprise radionuclides (R) comprises an alpha emitter and a second subset of the plurality of miniprotein conjugates comprise radionuclides (R) comprises a beta emitter. In various embodiments, the first subset accounts for less than 10%, less than 20%, less than 30%, less than 40%, less than 50%, less than 60%, less than 70%, less than 80%, or less than 90% of miniprotein conjugates in the plurality of miniprotein conjugates. In various embodiments, the second subset accounts for less than 10%, less than 20%, less than 30%, less than 40%, less than 50%, less than 60%, less than 70%, less than 80%, or less than 90% of miniprotein conjugates in the plurality of miniprotein conjugates.

In various embodiments, compositions disclosed herein comprise one or more isolated polypeptides comprising an amino acid sequence of any one of SEQ ID NOs: 3-158, 161-168, 170-208, 212-237, 243-246 and 248 and/or as set forth in TABLES 1B, 1C, 1D, and/or 2A. For example, such isolated polypeptides can be mixed in the composition with a plurality of miniprotein conjugates. In various embodiments, the miniprotein conjugates have an amino acid sequence selected from SEQ ID NOs: 3-158, 161-168, 170-208, 212-237, 243-246 and 248 and/or as set forth in TABLES 1B, 1C, 1D, and/or 2A and the isolated polypeptides have the same amino acid sequence selected from SEQ ID NOs: 3-158, 161-168, 170-208, 212-237, 243-246, 248 and/or as set forth in TABLES 1B, 1C, 1D, and/or 2A. An example of an isolated polypeptide is a polypeptide that is not conjugated to a linker, a chelator, or a radionuclide. For example, an isolated polypeptide may, in various embodiments, consist of an amino acid sequence selected from SEQ ID NOs: 3-158, 161-168, 170-208, 212-237, 243-246 and 248 and/or as set forth in TABLES 1B, 1C, 1D, and/or 2A.

In certain embodiments, a pharmaceutical composition comprises a miniprotein comprising one or more cysteine-rich domains. In some embodiments, the pharmaceutical composition comprises a miniprotein having one or more disulfide bonds. In some embodiments, the pharmaceutical composition comprises a miniprotein represented or encoded by an amino acid sequence having about <100 amino acids (AAs), <90 AAs, <80 AAs, <85 AAs, <75 AAs, <70 AAs, <65 AAs, <60 AAs, <55 AAs, <50 AAs, <45 AAs, <40 AAs, <35 AAs, <30 AAs, <25 AAs, <20 AAs, <15 AAs, <10 AAs, or <5 AAs.

In some embodiments, a pharmaceutical composition comprising a miniprotein as provided herein is characterized as having a molecule weight equal to or less than 12 kDa.

In some embodiments, a pharmaceutical composition comprising a miniprotein does not elicit an undesirable immune response or elicits a tolerable immune response. In some embodiments, a pharmaceutical composition of the present disclosure comprises a miniprotein having high tissue penetrating properties.

In some embodiments, a pharmaceutical composition comprising a miniprotein comprises acceptable half-life and/or stability. In some such embodiments, acceptable stability is between about 30 minutes to 48 hours in serum and 1-4 days or more in a tumor or tumor microenvironment. By way of non-limiting example, for instance, in some embodiments, a miniprotein of the present disclosure has stability of about 2.5 hours in serum. In some embodiments, stability of a miniprotein is about 30 minutes, 60 minutes. 1, 2, 3, 4, 5, 6, 7, 8, 9, 10, 11, 12, 13, 14, 15, 16, 17, 18, 19, 20, 21, 22, 23, 24, 30, 36, 40, or 48 hours in serum. In some embodiments, stability in a tumor or tumor microenvironment is 24, 36, 48, 60, 72, 84, 96 hours or more.

In some embodiments, the pharmaceutical composition is characterized as stable in vivo. In some embodiments, a pharmaceutical composition provided herein is not taken up in kidney or liver. In some embodiments, a pharmaceutical composition provided herein is taken up and/or retained in a tissue, such as a non-tumor tissue, for example, kidney or liver. In some such embodiments, where a pharmaceutical composition is taken up and/or retained in a tissue, the uptake and/or retention is blocked by co-administration with a decoy as provided herein. In some embodiments, a pharmaceutical composition provided herein does not bind megalin and/or cubulin. In some embodiments, a pharmaceutical composition provided herein, when taken up in kidney or liver, clears kidney and/or liver faster than a pharmaceutical composition not comprising a polypeptide as provided herein. In some such embodiments, such clearance is improved by co-administration of a decoy. In some embodiments, biodistribution may be measured at a timepoint in accordance with the percent injected dose per gram of a tissue (% ID/g). For example, biodistribution in a tumor in a subject (e.g., a murine subject, e.g., a human subject) of a pharmaceutical composition can be measured in accordance with % ID/g of the tumor tissue. In some embodiments, biodistribution of a composition disclosed herein in a tumor in a subject (e.g., a murine subject, e.g., a human subject) is between about 1 and about 300% ID/g, between about 1.5 and about 200% ID/g, between about 2 and about 100% ID/g, between about 2.5 and about 50% ID/g, between about 3 and about 40% ID/g, between about 3.5 and about 30%1D/g, between about 4 and about 20% ID/g, between about 4.5 and about 10% ID/g, or between about 5 and about 8% ID/g. In some embodiments, biodistribution of a composition disclosed herein in a tumor in a subject (e.g., a murine subject, e.g., a human subject) is between about and about 300% ID/g, between about 30 and about 250% ID/g, between about 50 and about 200% ID/g, between about 75 and about 180% ID/g, between about 85 and about 160% ID/g, between about 100 and about 150% ID/g, between about 110 and about 140% ID/g, between about 120 and about 130% ID/g, or between about 124 and about 126% ID/g. In some embodiments biodistribution in a tumor in a subject (e.g., a murine subject, e.g., a human subject) of a pharmaceutical composition as provided herein four and/or 24 h after administration is greater than 5% ID/g, 10% ID/g, 15% ID/g, 20% ID/g, 40% ID/g, 60% ID/g, 80% ID/g, 100% ID/g, 120% ID/g, 140% D/g, 160% ID/g, 180% ID/g, or 200% ID/g.

In some embodiments, biodistribution in a tumor in a subject (e.g., a murine subject, e.g., a human subject) of a pharmaceutical composition as provided herein is measured at four hours after administration and is between about 1 and about 10 (% ID/g), between about 1 and about 9 (% ID/g), between about 1 and about 8 (% ID/g), between about 1 and about 7 (% ID/g), between about 1 and about 6 (% ID/g), between about 1 and about 5 (% ID/g), between about 1 and about 4 (% ID/g), between about 1 and about 3 (% ID/g), or between about 1 and about 2 (% ID/g). In some embodiments, concentration in a tumor is greater than concentration in a kidney of a subject to whom a pharmaceutical composition comprising a polypeptide provided herein is administered. In some such embodiments, concentration in a tumor is even greater than in a kidney when the pharmaceutical composition is co-administered with a decoy.

In some embodiments, a pharmaceutical composition as provided herein has a positive tumor/kidney (T/K) % ID/g ratio. In some embodiments, a pharmaceutical composition as provided herein achieves a T/K ratio greater than 0.5% ID/g, 1% ID/g, 1.5% ID/g, 2% ID/g, 2.5% ID/g, 3% ID/g, 3.5% ID/g, 4% ID/g, 4.5% ID/g, 5% ID/g, 5.5% ID/g, 6% ID/g, 6.5% ID/g, 7% ID/g, 7.5% ID/g, 8% ID/g, 8.5% ID/g, 9% ID/g, 9.5% ID/g, or 10% ID/g.

In some embodiments, a pharmaceutical composition as provided herein achieves a T/K ratio greater than 5% ID/g, 10% ID/g, 15% ID/g, 20% ID/g, 25% ID/g, 30% ID/g, 35% ID/g, 40% ID/g, 45% ID/g, 50% ID/g, 55% ID/g, 60% ID/g, 65% ID/g, 70% ID/g, 75% ID/g, 80% ID/g, 85% ID/g, 90% ID/g, 95% ID/g, or 100% ID/g.

In some embodiments, a pharmaceutical composition of the present disclosure exhibits solubility of >0.05 mg/mL, >0.1 mg/mL, >0.2 mg/mL, >0.3 mg/mL, >0.4 mg/mL, >0.5 mg/mL, >0.6 mg/mL, >0.7 mg/mL, >0.8 mg/mL, >0.9 mg/mL, >1 mg/mL, >2 mg/mL, >3 mg/mL, >4 mg/mL, >5 mg/mL, >6 mg/mL, >7 mg/mL, >8 mg/mL, >9 mg/mL, or >10 mg/mL.

In some embodiments, a pharmaceutical composition provided by the present disclosure exhibits stability of >80%, >81%, >82%, >83%, >84%, >85%, >86%, >87%, >88%, >89%, >90%, >91%, >92%, >93%, >94%, >95%, >96%, >97%, >98%, or >99%.

In some embodiments, a pharmaceutical composition of the present disclosure is characterized as comprising a certain purity, represented as a percentage of parent molecule still intact. In some embodiments, a pharmaceutical composition of the present disclosure comprises about 85% purity or greater at 5 days at room temperature. In some embodiments, a pharmaceutical composition of the present disclosure is characterized as having about 90% purity or greater at 40° C. for 4 h. In some embodiments, a pharmaceutical composition of the present disclosure comprises cyclic or acyclic sequence.

In some embodiments, a pharmaceutical composition in accordance with the present disclosure comprises a miniprotein (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) and one or more additional components. For example, in some embodiments, one or more additional components may be a linker and/or a conjugate such as a cytotoxic payload or detectable moiety for use in diagnosis and/or imaging. In some such embodiments, a pharmaceutical composition comprises a linker, chelator, and/or radionuclide as provided herein.

In some embodiments, pharmaceutical compositions modulating, binding, or inhibiting human Nectin-4 (or any related activity thereto) are provided. In some embodiments, a pharmaceutical composition is or comprises a therapeutic. In some embodiments, a pharmaceutical composition is or comprises a detectable moiety (e.g., as used for imaging such as MRI, CT, PET, etc.).

In preferred embodiments, one or more characteristics of the pharmaceutical compositions are identified for optimized administration parameters including but not limited to dose, effective dose, dose rate, tumor penetration profile, intracellular localization profile, binding specificity, etc. See Sofou S. Radionuclide carriers for targeting of cancer. Int J Nanomedicine. 2008:3(2); 181-199, doi:10.2147/ijn.s2736.

In some embodiments, a pharmaceutical composition of the present disclosure does not present toxicity or presents less toxicity than a composition comprising one or more different components such as a larger targeting peptide, or a different radionuclide (e.g., beta emitter, etc.).

In some embodiments, a pharmaceutical composition of the present disclosure does not accumulate in the liver, spleen, and/or pancreas and is cleared rapidly. For instance, the biodistribution in some embodiments, after administration to a subject, biodistribution in the kidney is >10% of the injected dose/g (% ID/g) at 24 h and in tumors is >3% ID/g at 24 h. In some embodiments, after administration to a subject, $t_{1/2}$ is shorter than that of, e.g., a Nectin-4 ADC, e.g., enfortumab vedotin.

Theranostic Compositions

In some embodiments, theranostic compositions are provided. In some embodiments, the present disclosure provides a diagnostic or a screening to detect the presence or absence, and/or the level of Nectin-4 in a subject or sample. In some embodiments, the subject is a mammal. In some embodiments, the subject is a rodent (e.g., mouse) subject and the Nectin-4 is a rodent (e.g., murine) Nectin-4. In some embodiments, the subject is a human subject, and the Nectin-4 is a human Nectin-4. In some embodiments, presence of Nectin-4 in a subject is related to a risk of developing a disease, disorder, or condition. In some embodiments, presence of a particular level of Nectin-4 indicates an increased risk of developing or diagnosis of a disease, disorder, or condition. In some embodiments, a reduction in a level of Nectin-4 (e.g., as compared to a prior measurement) is associated with treatment of a diagnosed disease.

In certain aspects, theranostic compositions are provided. In some embodiments, the present disclosure provides a diagnostic or a screening to detect the presence or absence, and/or the level of human Nectin-4 in a subject or sample.

In certain aspects, the present disclosure provides methods for defining the structure activity relationship of a pharmaceutical composition comprising: (i) a Nectin-4-specific miniprotein; (ii) an optional linker; (iii) a chelator; and (iv) a radioactive molecule, wherein the modified polypeptide sequence modulates human Nectin-4 activity.

Methods of Screening and Development

In some embodiments, directed evolution and computational folding algorithms can be combined for de novo creation of miniproteins (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer). For example, in some embodiments, hundreds of miniprotein backbones with various secondary structure elements, orientations, and loop lengths can be matched with hotspot binding motifs on a protein target or antigen of interest (e.g., Nectin-4). In some such embodiments, if the binding motifs of the miniprotein do not clash with the backbone of the target, the monomer and interaction energies are optimized with programs known to those of skill in the art such as, e.g., AlphaFold, Rosetta combinatorial sequence optimization, etc.

In some embodiments, oligonucleotide pools encoding design sequences selected through the computational approach can be synthesized, amplified, and co-transformed into yeast. The resulting yeast libraries displaying the design sequences can be incubated with fluorescently labeled target protein or antigen. Cells that display the designs that bind the target can be retrieved by fluorescence-activated cell sorting (FACS) and deep sequenced. Once miniproteins are identified either through affinity-maturation or original designs, they can be chemically synthesized or expressed, e.g., in *Escherichia coli*, and purified, and characterized in solution.

In some embodiments, libraries of stable miniproteins may be developed to allow for screening against specific chosen targets. Such a library designs a hydrophobic core to the miniprotein to enable folding in addition to cysteine crosslinking, improving the number of folded structures in a library.

In some embodiments, once miniprotein are identified or engineered, they may be produced via chemical synthesis or recombinant expression. In some embodiments, a miniprotein may be produced by solid phase peptide synthesis followed by in vitro folding. Standard 9-fluorenylmethyl-oxycarbonyl (Fmoc)-based solid phase peptide chemistry may be employed. In some such embodiments, the linear peptide may then be folded under conditions that promote oxidation of cysteine side chain thiols to form disulfide bonds, followed by purification, e.g., by reversed-phase high-performance liquid chromatography (RP-HPLC). An approach using recombinant DNA may also be employed to produce a miniprotein as provided herein.

Iterations between data-driven model improvement and experimental testing with miniproteins is likely to optimize the folding and binding abilities of miniproteins, to develop pharmaceutically superior specific molecules,
Characterization, Analysis & Synthesis In some embodiments, a miniprotein (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) of the present disclosure is characterized. For example, in some embodiments, binding specificity, binding affinity, binding localization, etc. are performed using methods known to those of skill in the art. For instance, in some embodiments, binding localization is performed using one or more techniques such as immunohistochemistry/immunocytochemistry (e.g., using cell lines or tissue biopsy samples). In some embodiments, binding affinity is performed using surface plasmon resonance measurements. In some such embodiments, binding affinity (e.g., dissociation constant expressed as $K_D$ or Kd) is measured in one or more assays (e.g., a yeast-based assay where the target is recombinantly expressed in yeast and exposed to a miniprotein provided by the present disclosure).

In some embodiments, synthesis and analysis techniques including, without limitation, HPLC, LCMS, CD, quantitative thin layer chromatography and others known to those of skill in the art are used to efficiently synthesize via solid phase peptide synthesis methods, characterize miniproteins and fully optimized clinical pharmaceutical composition candidates.

In some embodiments, internalization assays can be performed. For example, in some embodiments, labeled miniproteins (e.g., radiolabeled, e.g., fluorescently labeled, etc.) can be used to assay internalization of Nectin-4 miniproteins. In some embodiments, miniproteins may be coupled to detectable labels (e.g., pH-sensitive fluorescent dye, e.g., radiolabels). Cells can then be examined. In some embodiments, cells can be labeled with an antibody for the target and/or one or more antibodies to endocytic or lysosomal markers (e.g., clathrin, LAMP-1, etc.) after fixation and permeabilization, followed by microscopic analysis.

In some embodiments, internalization assays may be conducted using other methods known to those of skill in the art and provided herein such as, e.g., in Examples 13A and 13B.
Modifications to Miniproteins In some embodiments, the present disclosure further provides one or more modifying components. In some embodiments, a modifying component comprises or consists of an inducible or repressible promoter that is operably linked to the coding sequence of a miniprotein as provided herein. In some embodiments, expression profile of a miniprotein or its underlying amino acid sequence can be altered via the promoter of a nucleic acid sequence encoding it. In some embodiments, the expression profile of the miniprotein can be temporally altered or controlled by temporally altering or controlling promoter function. In some embodiments, a promoter may be spatially and/or environmentally controlled. In some embodiments, a modifying component comprises or consists of an enhancer. In some such embodiment, an enhancer is used to modify expression profile of a binder but not necessarily operably linked to the coding sequence of the binder, rather, in some embodiments, an enhancer is located upstream or downstream of a coding sequence of a binder of the present disclosure. In some embodiments, an enhancer may be temporally controlled. In some embodiments, an enhancer may be spatially and/or environmentally controlled.

In some embodiments, an expression profile of a binder and/or a sequence encoding it (e.g., a nucleic acid sequence, e.g., an amino acid sequence such as, e.g., a gene or portion thereof) of the present disclosure can be altered via one or more modifications. In some such embodiments, the one or more modifications comprise one or more mutations in a sequence (e.g., nucleic acid sequence, e.g., amino acid sequence) provided by the present disclosure. In some embodiments, a sequence of the present disclosure comprises a deletion relative to a parental sequence or portion thereof.

Modifications may also be made using changes to amino acid sequences and bonds. For example, chemical crosslinking can be used to improve binding ability or affinity of a miniprotein for a target. In some embodiments, changes such as amino acid residues (e.g., lysine, etc., e.g., non-natural amino acids, etc.) fusion proteins, or other chemical moieties can be used to generate miniproteins with enhanced binding and functional activity, e.g., as compared to those without modifications. In some embodiments, miniproteins can be characterized as having small disulfide-rich peptide scaffolds and can have difficulties folding. For example, in some embodiments, miniproteins can form various isomers (e.g., a miniprotein with three core disulfide bonds can, in some embodiments, form at least 15 different isomers). In some such embodiments, such a variety of isomers can impact yield. In some embodiments, miniproteins without cysteine residues (e.g., two or more cysteines, e.g., at least one disulfide bridge) may be modified to improve stability without need for additional chemical crosslinking by increased numbers of disulfide bonds.

A modification (e.g., to a polypeptide amino acid sequence) can refer to an amino acid sequence that comprises at least one substitution, alteration, inversion, addition, or deletion of an amino acid residue compared to a reference amino acid sequence. An alteration can include but is not limited to a change to or of one or more atoms of a side chain, such as, for example addition of a small alkyl group (e.g., a methyl-group) onto the nitrogen of the side chain (e.g., addition of a small alkyl group (e.g., methyl) onto lysine to generate monomethylated lysine). In some embodiments, a natural amino acid is modified such as set forth herein. In some embodiments, a modification includes addition of at least one small alkyl group attached to the nitrogen of an amino acid side chain, such as, for example, a lysine side chain. As used herein, a "small alkyl group" refers to an alkyl group with a short carbon chain, typically having one to four carbon atoms, such as methyl, ethyl, propyl, or butyl, and also including, for example, dimethyl, trimethyl, isopropyl, etc. In some embodiments, for example, one or more small alkyl groups can be added to the nitrogen of a lysine side chain to produce monomethyl, dimethyl, or trimethyllysine. In some embodiments, one, two, three, four or more small alkyl groups may be added to a given amino acid (e.g., through attachment to the nitrogen of the side chain).

In some embodiments no more than five, four, three, two, or one small alkyl groups are added. In some embodiments, for example, binding affinity of miniproteins can be improved using an SAR approach. For instance, various amino acid residues within the mini protein structures can be replaced with optimal substitutions, resulting in improved binding affinity. In some embodiments, these substitutions can include natural and/or non-natural amino acids, conjugated chemical moieties, and/or other small molecule attachments.

In some embodiments, chemical crosslinking can be used to provide proper structural conformation and stability. Proper structural conformation can be critical to retention of certain binding affinity (e.g., in an improved Nectin-4 miniprotein, e.g., as compared to a miniprotein that has not been improved using an SAR or other approach). In some embodiments, miniproteins have small disulfide-rich peptide scaffolds and difficulties folding. In some such embodiments, using techniques and approaches known to those of ordinary skill in the art, optimized conditions for folding and purification via reverse-phase HPLC can be used to ensure final (e.g., optimized) compounds (comprising miniproteins as provided herein) have correct structure, conformation, and purity.

Constraints

Modifications, such as constraints, can be introduced (e.g., engineered) into proteins, such as any miniprotein provided herein. A constraint can alter function (e.g., binding) and/or structure (e.g., folding) of a protein. For example, constraints can assist in maintaining secondary structure of a given protein (e.g., a miniprotein as provided herein, e.g., a conjugate as provided herein). A common protein secondary structure is an α-helix. These helices can play key roles in not only structure of a protein, but also function, impacting how a particular protein can interact with a binding partner. For example, alpha helices can mediate protein-protein interactions (PPIs) by serving as recognition motifs. Introducing a constraint in a protein, such as a miniprotein, on an alpha-helix can, in some embodiments, change one or more features of a protein such as affinity of a protein for a target (e.g., increase affinity), cell penetration (e.g., increased cell penetration), resistance to proteolysis (e.g., increased resistance to proteolytic degradation). Examples of constraints (e.g., α-helix constraints) can include, but are not limited to disulfide bridges/bonds, staples (e.g., hydrocarbon staples), salt bridges between charged amino acid side chain residues, lactam bridges, disulfide bridges, hydrogen bond surrogates, hydrophobic interactions, metal ligation, triazole staples synthesized from alkenyl and azido side chain residues, photocontrollable macrocycles, and introduction amino acids, such as, e.g., α,α-disubstituted amino acids. As will be known to those of skill in the art, a staple can refer to a synthetic constraint (e.g., a brace) between two previously independent entities. For example, a staple can be formed via covalent linkage between two previously independent entities such as, for example, amino acid side-chains (e.g., forming, for example, a peptide macrocycle).

In some embodiments, miniproteins provided herein comprise one or more constraints (e.g., disulfide bridge, e.g., staple). In some embodiments, a miniprotein of the present disclosure comprises one or more disulfide bridges. In some embodiments, a miniprotein provided by the present disclosure comprises two or more disulfide bridges. For example, miniproteins of the present disclosure herein may contain a set of amino acids that together support formation of or are part of a constraint (e.g., a disulfide bridge, e.g., a staple). In some embodiments, a structural feature of a miniprotein is having at least two cysteine residues, positioned relative to one another so that disulfide bridge can be formed (e.g., as provided herein, see, e.g., TABLE 2A). In some embodiments, a miniprotein provided by the present disclosure has at least three, or at least four cysteine residues, which form one or two disulfide bridges. In some embodiments, the disulfide bridge or bridges comprise two or four cysteines at positions corresponding to 1, 20, 34, and 44 of SEQ ID NO: 195, wherein the cysteine corresponding to position 1 can form a disulfide bridge with the cysteine corresponding to position 20, 34, or 44. In some embodiments, the cysteine corresponding to position 20 can form a disulfide bridge with the cysteine corresponding to position 1, 34, or 44. In some embodiments, the cysteine corresponding to position 34 can form a disulfide bridge with the cysteine corresponding to position 1, 20, or 44. In some embodiments, the cysteine corresponding to position 44 can form a disulfide bridge with the cysteine corresponding to position 1, 20, or 44. In some embodiments, where four cysteines are present and correspond to positions 1, 20, 34, and 44 of SEQ ID NO: 195, pairings can comprise 1 paired with 34 and 20 paired with 44, 1 paired 20 and 34 paired with 44, or 1 paired with 44 and 20 paired with 34 (e.g., disulfide bridges between the two cysteines of the pair). In some such embodiments, such a miniprotein further comprises one or more additional constraints (e.g., staples).

In some embodiments, a miniprotein of the present disclosure comprises a staple. In some embodiments, the present disclosure provides stapled miniproteins that bind to Nectin-4, wherein presence of the staple changes at least one binding characteristic relative to the miniprotein without the staple (e.g., increased binding affinity for Nectin-4, e.g., a change in avidity for Nectin-4). Those skilled in the art, reading the present disclosure, will appreciate that, a stapled miniprotein may be prepared using any desired stapling technology.

Binding Assays

In some embodiments, binding assays are used to determine binding affinities and/or binding/dissociation constants or a composition or one or more components thereof (e.g., of a miniprotein with or without one or more additional components as provided herein). For example, in some embodiments, a dissociation equilibrium constant ($K_D$) is determined using fluorescent labeling and detection methods. In some embodiments, a cell population (e.g., yeast cells) engineered to express a library of miniproteins (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) (e.g., binders that bind to a target) is produced. In some embodiments, the cells express a target. Depending on whether a set of cells expresses targets or miniproteins, in some embodiments, a cell library is incubated with a target (e.g., Nectin-4) or with a miniprotein or set of miniproteins as provided herein. In some such embodiments, cells and miniproteins are assessed using flow cytometry and/or FACS analysis to determine binding affinity using methods known to those of skill in the art. (See. e.g., "Chapter Nine—Engineering CDPs as Novel Binding Agents." Methods in Enzymology, edited by K. Dane Wittrup and Gregory L. Verdine, vol. 503, Academic Press, 2012, pp. 223-51. ScienceDirect, doi: 10.1016/B978-0-12-396962-0,00009-4).

Affinity Maturation In some embodiments, a miniprotein of the present disclosure comprises or consists of a sequence that exhibits certain desired affinity ranges for a target. In some embodiments, affinity maturation is performed on a sequence as provided by the present disclosure wherein the affinity matured sequence displays the same or better selectivity and/or affinity for Nectin-4 as compared to the starting sequence or another sequence with "less" affinity as compared to the affinity matured sequence. In some embodiments, affinity maturation is performed using a Nectin-4 antigen and a sequence that binds to the antigen is that of a miniprotein as provided herein.

In some embodiments, affinity maturation is performed on a sequence that selectively binds to Nectin-4. In some embodiments, the Nectin-4 is human Nectin-4.

In preferred aspects of the present disclosure, the modified polypeptide sequence of the pharmaceutical composition comprises nM or sub-nM binding affinity to a target on a cell line expressing human Nectin-4, binding potency on protein target or in a cell-based assay.

In certain embodiments, the modified polypeptide sequence comprises a binding affinity stronger than about 1 mM (e.g., 900, 800, 700, 600, 500, 400, 300, 200, 100, 90, 80, 70, 60, 50, 40, 30, 20, 10, 9, 8, 7, 6, 5, 4, 3, 2, 1 nM) to human Nectin-4.

In one embodiment, the modified polypeptide sequence comprises a binding affinity of 500 nM binding affinity to human Nectin-4.

In more preferred embodiments, the modified polypeptide sequence comprises a picomolar binding affinity.

In other preferred embodiments, the modified polypeptide sequence exhibits selectivity with which the sequence binds to only the Nectin-4 protein target.

In some embodiments, affinity maturation is performed using magnetic-based assays. In some embodiments, affinity maturation is performed using flow cytometry/FACS-based assays in accordance with procedures known to those of skill in the art.

Methods of Miniprotein Manufacturing

In some embodiments, synthesis of a miniprotein comprises solid phase synthesis. In some embodiments, miniproteins are synthesized using standard solid phase peptide synthesis as is known to those of skill in the art. (See, e.g., Johannes Meienhofer, Hormonal Proteins and Peptides, Volume 11, 1973, Pages 45-267). In some embodiments. SPS comprises synthesis using methods known to those of skill in the art including, for example, Fmoc or Boc amino protecting groups. In some embodiments, synthesis comprises protection from reaction with incoming N-protected amino acids. In some embodiments, synthesized polypeptides are analyzed to determine sequence, structure, and related properties using HPLC/LC-MS.

In some embodiments, a miniprotein is manufactured using recombinant production methods as are known to those of skill in the art including, for example, yeast-based approaches and chemical synthesis.

Methods of Conjugation

In some embodiments, conjugates of the present disclosure comprise a linker and a chelator. In some embodiments, the chelator has a bound radionuclide. In some embodiments, a linker and chelator, or a linker, chelator, and radionuclide are conjugated to a miniprotein. In some embodiments, a chelator and/or radionuclide are conjugated to a miniprotein. In some embodiments, a miniprotein is conjugated to a chelator either directly or through a linker (e.g., a linker described herein). Any known conjugation chemistry can be utilized to conjugate a miniprotein directly to a chelator or to conjugate a linker to the miniprotein and to the chelator.

In some embodiments, a miniprotein comprises a surface exposed functional group to allow for site specific conjugation. In some embodiments, a miniprotein comprises a surface exposed lysine or cysteine residue that can serve for site specific conjugation. In some embodiments, a miniprotein conjugate comprises one or more non-naturally occurring amino acids that can serve for site specific conjugation.

A person of ordinary skill in the art will recognize that numerous chemical conjugation strategies provide ready access to present technology, whereby exposed amino acid residues on a protein undergo well-known reactions with reactive moieties on a chelator.

A person of ordinary skill in the art will recognize that cysteine coupling reactions may be employed to conjugate chelators with thiol-reactive termini to protein surfaces through exposed thiol side chains on cysteine residues on the protein surface. (See generally Tsuchikama & An, supra, at 36-37; see also, e.g., Pierre Adumeau et al., Thiol-Reactive Bifunctional Chelators for the Creation of Site-Selectively Modified Radioimmuno conjugates with Improved Stability, 29 Bioconjugate Chem. 1364 (2018)). In some embodiments, because cysteine residues readily form disulfide linkages with nearby cysteine residues under physiological conditions, rather than existing as free thiols, some cysteine coupling strategies may rely upon selective reduction of disulfides to generate a higher number of reactive free thiols. Cysteine coupling techniques known in the art include, but are not limited to, cys alkylation reactions, cysteine rebridging reactions, and cys-aryl coupling using organometallic palladium reagents. See, e.g., C. R. Behrens et al., Antibody-Drug Conjugates (ADCs) Derived from Interchain Cysteine Cross-Linking Demonstrates Improved Homogeneity and Other Pharmacological Properties Over Conventional Heterogeneous ADCs, 12 Mol. Pharm. 3986 (2015); Vinogradova et al., Organometallic Palladium Reagents for Cysteine Bioconjugation, 526 Nature 687 (2015); see also Tsuchikama, supra, at 37.

Protein conjugation strategies using non-natural amino acid side chains are also well known in the art. For example, in some embodiments, "click chemistries" provide access to conjugated proteins, by rapid and selective chemical transformations under a diverse range of reaction conditions. In some embodiments, click chemistries are known to yield peptide conjugates with limited by-product formation, despite the presence of unprotected functional groups, in aqueous conditions. For instance, in some embodiments, a click reaction in the formation of conjugated peptides is the copper(I)-catalyzed azide-alkyne 1,3-dipolar cycloaddition reaction (CuAAC). (See Liyuan Liang & Didier Astruc, The Copper(I)-CatalysedAlkyne-Azide Cycloaddition (CuAAC) "Click" Reaction and Its Applications: An Oveniew, 255 COORD. CHEM. Rev 2933 (2011); see also, e.g., Herman S. Gill & Jan Marik, Preparation of 18F-labeled Peptides using the Copper(I)-Catalyzed Azide-Alkyne 1,3-Dipolar Cycloaddition, 6 Nature Protocols 1718 (2011)). In some embodiments, a CuAAC click reaction may be carried out in the presence of ligands to enhance reaction rates. In some such embodiments, such ligands may include, for example, polydentate nitrogen donors, including amines (e.g., tris (triazolyl)methyl amines) and pyridines. (See Liang & Astruc, supra, at 2934 (collecting examples), P. L. Goias et al., 39 Macromolecules 6451 (2006)). In some embodiments, other widely utilized click reactions include, but are not limited to, thiol-ene, oxime, Diels-Alder. Michael addition, and pyridyl sulfide reactions.

In some embodiments, copper-free (Cu-free) click methods are also known in the art for delivery of therapeutic and/or diagnostic agents, such as radionuclides (e.g., 18F), chemotherapeutic agents, dyes, contrast agents, fluorescent labels, chemiluminescent labels, or other labels, to protein surfaces. In some embodiments, Cu-free click methods may permit stable covalent linkage between target molecules and prosthetic groups. In some embodiments, Cu-free click chemistry may include reacting an antibody or antigen binding fragment, which has been modified with a non-natural amino acid side chain that includes an activating moiety such as a cyclooctyne (e.g., dibenzocyclooctyne (DBCO)), a nitrone or an azide group, wvith a prosthetic group that presents a corresponding or complementary reactive moiety, such as an azide, nitrone or cyclooctyne (e.g., DBCO). (See, e.g., David. J. Donnelly et al., Synthesis and Biologic Evaluation of a Novel 18F-Labeled Adnectin as a PET Radio ligand for Imaging PD-L 1 Expression, 59 J. NUCL. MED. 529 (2018)). For instance, in some embodiments, where a targeting molecule comprises a cyclooctyne, the prosthetic group may include an azide, nitrone, or similar reactive moiety. In some embodiments, where a targeting molecule includes an azide or nitrone, the prosthetic group may present a complementary cyclooctyne, alkyne, or similar reactive moiety. In some embodiments. Cu-free click reactions may be carried out at room temperature, in aqueous solution, in the presence of phosphate-buffered saline (PBS). In some such embodiments, prosthetic group may be radiolabeled (e.g., with 18F) or may be conjugated to any alternative diagnostic and/or therapeutic agent (e.g., a chelator). (See id, at 531.)

In some embodiments, conjugation chemistries such as the Huisgen cyclo-addition ("click" reaction) are available for synthesis of chelates and peptides. In some embodiments, an efficient, high-yielding three-step synthesis of a versatile monofluoro-substituted cyclooctyne (MFCO) has been shown to facilitate a variety of bioconjugation processes (M. Martin et al., 2013). In some embodiments. MFCO can be utilized to prepare a DOTA derivative for copper-free click chemical addition at an internal azide-modified lysine residue of the CDP or knottin peptide.

In some embodiments, a miniprotein conjugate provided herein has a lysine at a specific position (e.g., in a cysteine knot, or cysteine-dense region) and can be replaced with an azide derivative for "click" chemistry with DOTA-MFCO.

In some embodiments, a DOTA-MFCO-CDP conjugate can be prepared by first coupling an amine-modified DOTA to MFCO, then conjugating the DOTA-MFCO to the azide on the desired lysine of the miniprotein.

In some embodiments, the chelator and miniprotein are joined together by a cycloaddition reaction in the presence of a transition metal catalyst. In some embodiments, a metal catalyst is based on Cu or Rh.

In some embodiments, utilizing solution phase conjugation, a chelator (DOTA) and a miniprotein are joined with 1-ethyl-3-[3-(dimethylamino)propyl](EDC) and N-hydroxysulfonosuccinimide (SNHS) in water (pH 5.5) for 40 min at room temperature using a 1:1:1 molar ratio of DOTA: EDC:SNHS. In some such embodiments, peptides are dissolved in sodium phosphate buffer and added to the above sulfosuccinimidyl ester of DOTA (DOTA-OSSu). In some such embodiments, a molar excess of DOTA-OSSu is used to drive the conjugation on the N-termini of the peptide (See, e.g., Kimura. Richard H et al. "Engineered knottin peptides: a new class of agents for imaging integrin expression in living subjects." Cancer research vol. 69, 6 (2009): 2435-42, doi:10.1158/0008-5472.CAN-08-2495).

In some embodiments, a new DOTA derivative, α-amino-DOTA is prepared with the objective of attaching DOTA to the C-terminus of a peptide, since in some scenarios, the peptide function might be compromised because of DOTA conjugation to the N-terminus or to lysine side chains.

In some embodiments, a miniprotein is generated by solid-phase peptide synthesis (SPPS). The tris-tert-butyl ester of DOTA, a bifunctional ligand (in the salt free, zwitterionic form), is readily soluble in most organic solvents and the tert-butyl ester protection is fully compatible with standard SPPS techniques. The most convenient way of conjugation comprises the addition of DOTA to the N-terminus of the protected peptide chain as the last amino acid in an automated peptide synthesizer followed by cleavage from the resin and removal of the acid-labile protecting groups. It can also be attached to Lys side chains. The preformed activated NHS ester of DOTA-tris(tert-butyl ester) has also been synthesized, and this reagent does not require a coupling agent to couple DOTA to free amino groups. The DOTA unit is linked to peptides through one of the acetate sidearms, and the conjugate has four amino, three carboxylates, and one amide group available for metal binding. See, e.g., De León-Rodriguez LM. Kovacs Z. The synthesis and chelation chemistry of DOTA-peptide conjugates. Bioconjug Chem. 2008 February; 19(2):391-402, doi: 10.1021/bc700328s. Epub 2007 Dec. 12. PMID: 18072717.

In some embodiments, a more general method involves the use of preformed DOTA-amino acid derivatives which allows the introduction of a DOTA unit into any desired position in the peptide sequence without the need of orthogonal protection. Protected DOTA-Lys and DOTA-Phe derivatives that are fully compatible with standard SPPS conditions (N-R-Fmoc protection, free carboxyl for the coupling, and acid-labile tert-butyl protection of the remaining acetate sidearms of the DOTA unit) have been synthesized. These DOTA-amino acids can be used in SPPS to build peptides that incorporate the DOTA moiety in any desired position. See, e.g., De León-Rodriguez L M, Kovacs Z. The synthesis and chelation chemistry of DOTA-peptide conjugates. Bioconjug Chem. 2008 February; 19(2):391-402, doi: 10.1021/bc700328s. Epub 2007 Dec. 12. PMID: 18072717.

General methods for coupling DOTA-type macrocycles to targeting groups through a linker (e.g., by activation of one of the carboxylates of the DOTA to form an active ester, which is then reacted with an amino group on the linker to form a stable amide bond), are known to those skilled in the art. See, e.g., Tweedle et al. U.S. Pat. No. 4,885,363.

A linker may be incorporated between the chelator and the targeting vector to influence the pharmacokinetic properties of the conjugate. Hydrocarbon. PEG, or polypeptide linkers can alter the pharmacokinetics and biodistribution by changing the overall charge and hydrophilicity of the radiopharmaceutical. &e, e.g., De Leon-Rodriguez L M, Kovacs Z. The synthesis and chelation chemistry of DOTA-peptide conjugates. Bioconjug Chem. 2008 February; 19(2):391-402, doi: 10.1021/bc700328s. Epub 2007 Dec. 12. PMID: 18072717.

Miniprotein Conjugate Orientation

In some embodiments, a conjugate has the following orientation; linker-chelator, linker-chelator-radionuclide, linker-radionuclide, chelator-radionuclide. In some such embodiments a conjugate has the following orientation: miniprotein-linker-radionuclide, miniprotein-chelator, chelator-miniprotein, miniprotein-linker-chelator, chelatorlinker-miniprotein, miniprotein-chelator-radionuclide, radionuclide-chelator-miniprotein, miniprotein-linker-chelator-radionuclide, or radionuclide-chelator-linker-miniprotein.

In some embodiments, a conjugate provided by the present disclosure comprises a miniprotein. In some such embodiments, the miniprotein functions as a targeting moiety, e.g., specifically binding to a target, e.g., a protein expressed on the surface of a target tumor cell. Accordingly, in some embodiments, the miniprotein in the conjugates of the present disclosure may vary depending on the target of interest.

Exemplary Miniprotein Conjugates

The following provides exemplary embodiments of miniprotein conjugates as provided herein. In some such embodiments, such miniproteins specifically bind to Nectin-4 expressed on the surface of a cancer cell (e.g., a solid tumor cell). In some embodiments, a conjugate comprises a linker, a chelator, and/or a radionuclide.

In some embodiments, a conjugate comprises a miniprotein, optional linker, chelator, and radionuclide. In some embodiments, a miniprotein comprises or consists of a linear poly peptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer In some embodiments, a chelator comprises or consists of DOTA, Crown, NOPO, PSC, N-succinimidyl 3-(tri-n-butylstannyl)benzoate (BuSTB), N-succinimidyl 3-trimethylstannylbenzoate (MeSTB), or Macropa. In some embodiments, a radionuclide comprises or consists of an alpha emitter. In some embodiments, a radionuclide comprises or consists of a beta emitter. In some embodiments, a radionuclide comprises or consists of Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211.

In some embodiments, the linker, chelator, and/or radionuclide are connected to the N-terminus of the miniprotein. In some embodiments, the linker, chelator, and/or radionuclide are connected to the C-terminus of the miniprotein. In some embodiments, when present, a linker is attached to the N- and/or C-terminus of the polypeptide, and the chelator, when present, can be attached to the linker, or directly to the polypeptide. In some embodiments, a conjugate comprises or consists of a miniprotein that specifically binds to Nectin-4, an optional PEG linker, a DOTA chelator, and Ac-225.

In some embodiments, a conjugate comprises or consists of a miniprotein that specifically binds to Nectin-4, an optional PEG linker, a DOTA chelator, and In-111.

In some embodiments, a conjugate comprises or consists of a miniprotein that specifically binds to Nectin-4, an optional PEG linker, a DOTA chelator, and Lu-177.

In some embodiments, a conjugate comprises or consists of a miniprotein that specifically binds to Nectin-4, an optional PEG linker, a DOTA chelator, and Ga-68.

In some embodiments, a conjugate comprises or consists of a miniprotein that specifically binds to Nectin-4, an optional PEG linker, a DOTA chelator, and La-132.

In some embodiments, a conjugate comprises or consists of a miniprotein that specifically binds to Nectin-4, an optional PEG linker, a DOTA chelator, and La-135.

In some embodiments, a conjugate comprises or consists of a miniprotein that specifically binds to Nectin-4, an optional PEG linker, a DOTA chelator, and Cu-64.

In some embodiments, a conjugate comprises or consists of a miniprotein that specifically binds to Nectin-4, an optional PEG linker, a DOTA chelator and Cu-67.

In some embodiments, a conjugate comprises or consists of a miniprotein that specifically binds to Nectin-4, an optional PEG linker, a DOTA chelator, and Ce-134.

In some embodiments, a conjugate comprises or consists of a miniprotein that specifically binds to Nectin-4, an optional PEG linker, a DOTA chelator, and I-131.

In some embodiments, a conjugate comprises or consists of a miniprotein that specifically binds to Nectin-4, an optional PEG linker, a DOTA chelator, and I-124.

In some embodiments, a conjugate comprises or consists of a miniprotein that specifically binds to Nectin-4, an optional PEG linker, a DOTA chelator, and Pb-203.

In some embodiments, a conjugate comprises or consists of a miniprotein that specifically binds to Nectin-4, an optional PEG linker, a DOTA chelator, and Th-232

In some embodiments, a conjugate comprises or consists of a miniprotein that specifically binds to Nectin-4, an optional PEG linker, a DOTA chelator, and Bi-123.

In some embodiments, a conjugate comprises or consists of a miniprotein that specifically binds to Nectin-4, an optional PEG linker, a DOTA chelator, and Sm-153.

In some embodiments, a conjugate comprises or consists of a miniprotein that specifically binds to Nectin-4, an optional PEG linker, a DOTA chelator, and Ra-225.

In some embodiments, a conjugate comprises or consists of a miniprotein that specifically binds to Nectin-4, an optional PEG linker, a DOTA chelator, and Tb-165.

In some embodiments, a conjugate comprises or consists of a miniprotein that specifically binds to Nectin-4, an optional PEG linker, a Crown chelator, and Ac-225.

In some embodiments, a conjugate comprises or consists of a miniprotein that specifically binds to Nectin-4, an optional PEG linker, a Crown chelator, and In-111.

In some embodiments, a conjugate comprises or consists of a miniprotein that specifically binds to Nectin-4, an optional PEG linker, a Crown chelator, and Lu-177.

In some embodiments, a conjugate comprises or consists of a miniprotein that specifically binds to Nectin-4, an optional PEG linker, a Crown chelator, and Ga-68.

In some embodiments, a conjugate comprises or consists of a miniprotein that specifically binds to Nectin-4, an optional PEG linker, a Crown chelator, and La-132.

In some embodiments, a conjugate comprises or consists of a miniprotein that specifically binds to Nectin-4, an optional PEG linker, a Crown chelator, and La-135.

In some embodiments, a conjugate comprises or consists of a miniprotein that specifically binds to Nectin-4, an optional PEG linker, a Crown chelator, and Cu-64.

In some embodiments, a conjugate comprises or consists of a miniprotein that specifically binds to Nectin-4, an optional PEG linker, a Crown chelator, and Cu-67.

In some embodiments, a conjugate comprises or consists of a miniprotein that specifically binds to Nectin-4, an optional PEG linker, a Crown chelator, and Ce-134.

In some embodiments, a conjugate comprises or consists of a miniprotein that specifically binds to Nectin-4, an optional PEG linker, a Crown chelator, and I-131.

In some embodiments, a conjugate comprises or consists of a miniprotein that specifically binds to Nectin-4, an optional PEG linker, a Crown chelator, and I-124.

In some embodiments, a conjugate comprises or consists of a miniprotein that specifically binds to Nectin-4, an optional PEG linker, a Crown chelator, and Pb-203.

In some embodiments, a conjugate comprises or consists of a miniprotein that specifically binds to Nectin-4, an optional PEG linker, a Crown chelator, and Th-232

In some embodiments, a conjugate comprises or consists of a miniprotein that specifically binds to Nectin-4, an optional PEG linker, a Crown chelator, and Bi-123.

In some embodiments, a conjugate comprises or consists of a miniprotein that specifically binds to Nectin-4, an optional PEG linker, a Crown chelator, and Sm-153.

In some embodiments, a conjugate comprises or consists of a miniprotein that specifically binds to Nectin-4, an optional PEG linker, a Crown chelator, and Ra-225.

In some embodiments, a conjugate comprises or consists of a miniprotein that specifically binds to Nectin-4, an optional PEG linker, a Crown chelator, and Tb-165.

In some embodiments, a conjugate comprises or consists of a miniprotein that specifically binds to Nectin-4, an optional PEG linker, a NOPO chelator, and Ac-225.

In some embodiments, a conjugate comprises or consists of a miniprotein that specifically binds to Nectin-4, an optional PEG linker, a NOPO chelator, and In-111.

In some embodiments, a conjugate comprises or consists of a miniprotein that specifically binds to Nectin-4, an optional PEG linker, a NOPO chelator, and Ga-68.

In some embodiments, a conjugate comprises or consists of a miniprotein that specifically binds to Nectin-4, an optional PEG linker, a NOPO chelator, and La-132.

In some embodiments, a conjugate comprises or consists of a miniprotein that specifically binds to Nectin-4, an optional PEG linker, a NOPO chelator, and La-135.

In some embodiments, a conjugate comprises or consists of a miniprotein that specifically binds to Nectin-4, an optional PEG linker, a NOPO chelator, and Cu-64.

In some embodiments, a conjugate comprises or consists of a miniprotein that specifically binds to Nectin-4, an optional PEG linker, a NOPO chelator, and Cu-67.

In some embodiments, a conjugate comprises or consists of a miniprotein that specifically binds to Nectin-4, an optional PEG linker, a NOPO chelator, and Ce-134.

In some embodiments, a conjugate comprises or consists of a miniprotein that specifically binds to Nectin-4, an optional PEG linker, a NOPO chelator, and I-131.

In some embodiments, a conjugate comprises or consists of a miniprotein that specifically binds to Nectin-4, an optional PEG linker, a NOPO chelator, and I-124.

In some embodiments, a conjugate comprises or consists of a miniprotein that specifically binds to Nectin-4, an optional PEG linker, a NOPO chelator, and Pb-203.

In some embodiments, a conjugate comprises or consists of a miniprotein that specifically binds to Nectin-4, an optional PEG linker, a NOPO chelator, and Th-232

In some embodiments, a conjugate comprises or consists of a miniprotein that specifically binds to Nectin-4, an optional PEG linker, a NOPO chelator, and Bi-123.

In some embodiments, a conjugate comprises or consists of a miniprotein that specifically binds to Nectin-4, an optional PEG linker, a NOPO chelator, and Sm-153.

In some embodiments, a conjugate comprises or consists of a miniprotein that specifically binds to Nectin-4, an optional PEG linker, a NOPO chelator, and Ra-225.

In some embodiments, a conjugate comprises or consists of a miniprotein that specifically binds to Nectin-4, an optional PEG linker, a NOPO chelator, and Tb-165.

In some embodiments, a conjugate comprises or consists of a miniprotein that specifically binds to Nectin-4, an optional PEG linker, a Macropa chelator, and Ac-225.

In some embodiments, a conjugate comprises or consists of a miniprotein that specifically binds to Nectin-4, an optional PEG linker, a Macropa chelator, and In-111.

In some embodiments, a conjugate comprises or consists of a miniprotein that specifically binds to Nectin-4, an optional PEG linker, a Macropa chelator, and Lu-177.

In some embodiments, a conjugate comprises or consists of a miniprotein that specifically binds to Nectin-4, an optional PEG linker, a Macropa chelator, and Ga-68.

In some embodiments, a conjugate comprises or consists of a miniprotein that specifically binds to Nectin-4, an optional PEG linker, a Macropa chelator, and La-132.

In some embodiments, a conjugate comprises or consists of a miniprotein that specifically binds to Nectin-4, an optional PEG linker, a Macropa chelator, and La-135.

In some embodiments, a conjugate comprises or consists of a miniprotein that specifically binds to Nectin-4, an optional PEG linker, a Macropa chelator, and Cu-64.

In some embodiments, a conjugate comprises or consists of a miniprotein that specifically binds to Nectin-4, an optional PEG linker, a Macropa chelator, and Cu-67.

In some embodiments, a conjugate comprises or consists of a miniprotein that specifically binds to Nectin-4, an optional PEG linker, a Macropa chelator, and Ce-134.

In some embodiments, a conjugate comprises or consists of a miniprotein that specifically binds to Nectin-4, an optional PEG linker, a Macropa chelator, and I-131.

In some embodiments, a conjugate comprises or consists of a miniprotein that specifically binds to Nectin-4, an optional PEG linker, a Macropa chelator, and I-124.

In some embodiments, a conjugate comprises or consists of a miniprotein that specifically binds to Nectin-4, an optional PEG linker, a Macropa chelator, and Pb-203.

In some embodiments, a conjugate comprises or consists of a miniprotein that specifically binds to Nectin-4, an optional PEG linker, a Macropa chelator, and Th-232

In some embodiments, a conjugate comprises or consists of a miniprotein that specifically binds to Nectin-4, an optional PEG linker, a Macropa chelator, and Bi-123.

In some embodiments, a conjugate comprises or consists of a miniprotein that specifically binds to Nectin-4, an optional PEG linker, a Macropa chelator, and Sm-153.

In some embodiments, a conjugate comprises or consists of a miniprotein that specifically binds to Nectin-4, an optional PEG linker, a Macropa chelator, and Ra-225.

In some embodiments, a conjugate comprises or consists of a miniprotein that specifically binds to Nectin-4, an optional PEG linker, a DOTA chelator, and Tb-165.

In some embodiments, a conjugate comprises or consists of a miniprotein that specifically binds to Nectin-4, an optional PEG linker, a lead-specific chelator, and Ac-225.

In some embodiments, a conjugate comprises or consists of a miniprotein that specifically binds to Nectin-4, an optional PEG linker, a lead-specific chelator, and In-111.

In some embodiments, a conjugate comprises or consists of a miniprotein that specifically binds to Nectin-4, an optional PEG linker, a lead-specific chelator, and Lu-177.

In some embodiments, a conjugate comprises or consists of a miniprotein that specifically binds to Nectin-4, an optional PEG linker, a lead-specific chelator, and Ga-68.

In some embodiments, a conjugate comprises or consists of a miniprotein that specifically binds to Nectin-4, an optional PEG linker, a lead-specific chelator, and La-132.

In some embodiments, a conjugate comprises or consists of a miniprotein that specifically binds to Nectin-4, an optional PEG linker, a lead-specific chelator, and La-135.

In some embodiments, a conjugate comprises or consists of a miniprotein that specifically binds to Nectin-4, an optional PEG linker, a lead-specific chelator, and Cu-64.

In some embodiments, a conjugate comprises or consists of a miniprotein that specifically binds to Nectin-4, an optional PEG linker, a lead-specific chelator, and Cu-67.

In some embodiments, a conjugate comprises or consists of a miniprotein that specifically binds to Nectin-4, an optional PEG linker, a lead-specific chelator, and Ce-134.

In some embodiments, a conjugate comprises or consists of a miniprotein that specifically binds to Nectin-4, an optional PEG linker, a lead-specific chelator, and I-131.

In some embodiments, a conjugate comprises or consists of a miniprotein that specifically binds to Nectin-4, an optional PEG linker, a lead-specific chelator, and I-124.

In some embodiments, a conjugate comprises or consists of a miniprotein that specifically binds to Nectin-4, an optional PEG linker, a lead-specific chelator, and Pb-203.

In some embodiments, a conjugate comprises or consists of a miniprotein that specifically binds to Nectin-4, an optional PEG linker, a lead-specific chelator, and Th-232

In some embodiments, a conjugate comprises or consists of a miniprotein that specifically binds to Nectin-4, an optional PEG linker, a lead-specific chelator, and Bi-123.

In some embodiments, a conjugate comprises or consists of a miniprotein that specifically binds to Nectin-4, an optional PEG linker, lead-specific chelator, and Sm-153.

In some embodiments, a conjugate comprises or consists of a miniprotein that specifically binds to Nectin-4, an optional PEG linker, lead-specific chelator, and Ra-225.

In some embodiments, a conjugate comprises or consists of a miniprotein that specifically binds to Nectin-4, an optional PEG linker, lead-specific chelator, and Tb-165.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and Ac-225.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and In-111.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and Lu-177.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and Ga-68.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and La-132.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and La-135.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and Cu-64.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and Cu-67.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and Ce-134.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and I-131.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and I-124.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and Pb-203.

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and Th-232

In some embodiments, a conjugate comprises or consists of a miniprotein that specifically binds to Nectin-4, an optional PEG linker, a N-succinimidyl 3-(tri-n-butylstannyl) benzoate (BuSTB) chelator, and Bi-123.

In some embodiments, a conjugate comprises or consists of a miniprotein that specifically binds to Nectin-4, an optional PEG linker, a N-succinimidyl 3-trimethylstannylbenzoate (MeSTB) chelator, and Ac-225.

In some embodiments, a conjugate comprises or consists of a miniprotein that specifically binds to Nectin-4, an optional PEG linker, a N-succinimidyl 3-trimethylstannylbenzoate (MeSTB) chelator, and In-111.

In some embodiments, a conjugate comprises or consists of a miniprotein that specifically binds to Nectin-4, an optional PEG linker, a N-succinimidyl 3-trimethylstannylbenzoate (MeSTB) chelator, and Lu-177.

In some embodiments, a conjugate comprises or consists of a miniprotein that specifically binds to Nectin-4, an optional PEG linker, a N N-succinimidyl 3-trimethylstannylbenzoate (MeSTB) chelator, and Ga-68.

In some embodiments, a conjugate comprises or consists of a miniprotein that specifically binds to Nectin-4, an optional PEG linker, a N-succinimidyl 3-trimethylstannylbenzoate (MeSTB) chelator, and La-132.

In some embodiments, a conjugate comprises or consists of a miniprotein that specifically binds to Nectin-4, an optional PEG linker, a N N-succinimidyl 3-trimethylstannylbenzoate (MeSTB) chelator, and La-135.

In some embodiments, a conjugate comprises or consists of a miniprotein that specifically binds to Nectin-4, an optional PEG linker, N-succinimidyl 3-trimethylstannylbenzoate (MeSTB) chelator, and Cu-64.

In some embodiments, a conjugate comprises or consists of a miniprotein that specifically binds to Nectin-4, an optional PEG linker, a N N-succinimidyl 3-trimethylstannylbenzoate (MeSTB) chelator, and Cu-67.

In some embodiments, a conjugate comprises or consists of a miniprotein that specifically binds to Nectin-4, an optional PEG linker, a N-succinimidyl 3-trimethylstannylbenzoate (MeSTB) chelator, and Ce-134.

In some embodiments, a conjugate comprises or consists of a miniprotein that specifically binds to Nectin-4, an optional PEG linker, a N-succinimidyl 3-trimethylstannylbenzoate (MeSTB) chelator, and I-131.

In some embodiments, a conjugate comprises or consists of a miniprotein that specifically binds to Nectin-4, an optional PEG linker, a N-succinimidyl 3-trimethylstannylbenzoate (MeSTB) chelator, and I-124.

In some embodiments, a conjugate comprises or consists of a miniprotein that specifically binds to Nectin-4, an optional PEG linker, a N-succinimidyl 3-trimethylstannyl-benzoate (MeSTB) chelator, and Pb-203.

In some embodiments, a conjugate comprises or consists of a miniprotein that specifically binds to Nectin-4, an optional PEG linker, a N-succinimidyl 3-trimethylstannyl-benzoate (MeSTB) chelator, and Th-232

In some embodiments, a conjugate comprises or consists of a miniprotein that specifically binds to Nectin-4, an optional PEG linker, a N-succinimidyl 3-trimethylstannyl-benzoate (MeSTB) chelator, and Bi-123.

In some embodiments, a conjugate comprises or consists of a miniprotein that specifically binds to Nectin-4, an optional PEG linker, a N-succinimidyl 3-trimethylstannyl-benzoate (MeSTB) chelator, and Sm-153.

In some embodiments, a conjugate comprises or consists of a miniprotein that specifically binds to Nectin-4, an optional PEG linker, a N-succinimidyl 3-trimethylstannyl-benzoate (MeSTB) chelator, and Ra-225.

In some embodiments, a conjugate comprises or consists of a miniprotein that specifically binds to Nectin-4, an optional PEG linker, a N-succinimidyl 3-trimethylstannyl-benzoate (MeSTB) chelator, and Tb-165.

In some embodiments, an exemplary imaging/diagnostic miniprotein conjugate described herein comprises a miniprotein that specifically binds to Nectin-4 or a fragment or portion thereof (e.g., expressed on the surface of a solid tumor cell), a PEG linker, a DOTA chelator, and Ac-225 (or a cold-metal surrogate thereof).

In some embodiments, an exemplary imaging/diagnostic miniprotein conjugate described herein comprises a miniprotein that specifically binds to Nectin-4 or a fragment or portion thereof (e.g., expressed on the surface of a solid tumor cell), a PEG linker, a DOTA chelator, and Indium-111 (or a cold-metal surrogate thereof).

In some embodiments, an exemplary imaging/diagnostic miniprotein conjugate described herein comprises a miniprotein that specifically binds to Nectin-4 or a fragment or portion thereof (e.g., expressed on the surface of a solid tumor cell), a PEG linker, a DOTA chelator, and Gallium-68 (or a cold-metal surrogate thereof).

In some embodiments, an exemplary imaging/diagnostic miniprotein conjugate described herein comprises a miniprotein that specifically binds to Nectin-4 or a fragment or portion thereof (e.g., expressed on the surface of a solid tumor cell), a PEG linker, a DOTA chelator, and Copper-64 (or a cold-metal surrogate thereof).

In some embodiments, an exemplary imaging/diagnostic miniprotein conjugate described herein comprises a miniprotein that specifically binds to Nectin-4 or a fragment or portion thereof (e.g., expressed on the surface of a solid tumor cell), a PEG linker, a DOTA chelator, and Lutetium-177 (or a cold-metal surrogate thereof).

In some embodiments, exemplary imaging/diagnostic CDP conjugate described herein comprises a miniprotein that specifically binds to Nectin-4 or a fragment or portion thereof (e.g., expressed on the surface of a solid tumor cell), a PEG linker, a DOTA chelator, and Lead-212 (or a cold-metal surrogate thereof).

In some embodiments, exemplary imaging/diagnostic CDP conjugate described herein comprises a miniprotein that specifically binds to Nectin-4 or a fragment or portion thereof (e.g., expressed on the surface of a solid tumor cell), a PEG linker, a DOTA chelator, and Cerium-134 (or a cold-metal surrogate thereof).

In some embodiments, exemplary imaging/diagnostic CDP conjugate described herein comprises a miniprotein that specifically binds to Nectin-4 or a fragment or portion thereof (e.g., expressed on the surface of a solid tumor cell), a PEG linker, a DOTA chelator, and Iodine-131 (or a cold-metal surrogate thereof).

In some embodiments, exemplary imaging/diagnostic CDP conjugate described herein comprises a miniprotein that specifically binds to Nectin-4 or a fragment or portion thereof (e.g., expressed on the surface of a solid tumor cell), a PEG linker, a DOTA chelator, and Iodine-124 (or a cold-metal surrogate thereof).

In some embodiments, exemplary imaging/diagnostic CDP conjugate described herein comprises a miniprotein that specifically binds to Nectin-4 or a fragment or portion thereof (e.g., expressed on the surface of a solid tumor cell), a PEG linker, a DOTA chelator, and Lead-203 (or a cold-metal surrogate thereof).

In some embodiments, exemplary imaging/diagnostic CDP conjugate described herein comprises a miniprotein that specifically binds to Nectin-4 or a fragment or portion thereof (e.g., expressed on the surface of a solid tumor cell), a PEG linker, a DOTA chelator, and Thorium-232 (or a cold-metal surrogate thereof).

In some embodiments, exemplary imaging/diagnostic CDP conjugate described herein comprises a miniprotein that specifically binds to Nectin-4 or a fragment or portion thereof (e.g., expressed on the surface of a solid tumor cell), a PEG linker, a DOTA chelator, and Bismuth-213 (or a cold-metal surrogate thereof).

In some embodiments, an exemplary imaging/diagnostic miniprotein conjugate described herein comprises a miniprotein that specifically binds to Nectin-4 or a fragment or portion thereof (e.g., expressed on the surface of a solid tumor cell), a PEG linker, a DOTA chelator, and Sm-153 (or a cold-metal surrogate thereof).

In some embodiments, an exemplary imaging/diagnostic miniprotein conjugate described herein comprises a miniprotein that specifically binds to Nectin-4 or a fragment or portion thereof (e.g., expressed on the surface of a solid tumor cell), a PEG linker, a DOTA chelator, and Ra-225 (or a cold-metal surrogate thereof).

In some embodiments, an exemplary imaging/diagnostic miniprotein conjugate described herein comprises a miniprotein that specifically binds to Nectin-4 or a fragment or portion thereof (e.g., expressed on the surface of a solid tumor cell), a PEG linker, a DOTA chelator, and Tb-165 (or a cold-metal surrogate thereof).

In some embodiments, a pharmaceutical composition comprising the radionuclide is employed in imaging scans to detect or diagnosis one or more diseases. Further embodiments include use as companion diagnostics.

In some embodiments, one or more different linkers and different chelators for different radionuclides and their respective chelators are operably linked to the same miniprotein.

In some embodiments, one or more different linkers and different chelators for Ga-68 (e.g., NOPO) and Ac-225 (e.g., Crown or DOTA) for both are operably linked to the same miniprotein.

Methods of Use

In some embodiments, the present disclosure provides methods of treating or preventing disease or disorder in a subject, the method comprising administering to the subject the pharmaceutical composition in an amount effective that modulates, binds, or inhibits human Nectin-4 to treat or prevent disease or disorder in the subject. In preferred embodiments, the disease or disorder associated with Nectin-4 is treated (e.g., prevented, progression is slowed, symptoms are relieved, tumor size reduced to improve overall survival, etc.).

In some embodiments, subjects, e.g., patient or patients' inclusion criteria include, without limitation, Nectin-4 positive candidates shown via imaging (e.g., DOTA PET/CT), candidates with progressive disease, advanced or metastatic disease, candidates who are not candidates for surgery, refractory or relapsed candidates.

In some embodiments, possible certain side effects including nausea, suppression of blood cell counts are managed through one or more medications. In some embodiments, side effects may include renal toxicity, myelodysplastic syndrome, however, it is contemplated that the pharmaceutical compositions are manageable, and treatment is generally well-tolerated.

Treatment, Imaging, and Diagnostic/Prognostic Methods of Use

In some embodiments, the present disclosure provides methods of treating cancer in a human subject by administering a miniprotein conjugate described herein. In some embodiments, the cancer expresses the target (e.g., Nectin-4) specifically bound by the miniprotein of the conjugate. As provided herein, a Nectin-4 positive cancer is a cancer having cancer cells expressing Nectin-4, but does not explicitly require assaying a tumor prior to treatment to determine if the tumor expresses Nectin-4. In some embodiments, the target protein is expressed on the surface of malignant cells with limited expression on cells of normal tissues, and/or expressed at much higher density on malignant versus normal cells. In some embodiments, a method of treating includes a method of targeting and/or contacting a population of cancer cells. In some embodiments, a malignant cell is part of a population of cells, wherein the population is heterogenous and only a portion expresses a target (e.g., Nectin-4). Without wishing to be bound by theory, the disclosure contemplates that, in some such embodiments, a heterogenous population of cancer cells including cells that express the target and cells that do not express the target can be treated by a composition provided herein. For example, if a Nectin-4-expressing cell internalizes a composition provided herein, cells apposed to but not expressing Nectin-4 can also be treated (e.g., killed) by uptake of the composition into the Nectin-4 cell, thereby treating a heterogenous tumor by targeting the target (e.g., Nectin-4).

In some embodiments, the cancer is a solid tumor. In some embodiments, the cancer is characterized by presence of one or more tumor cells. In some embodiments, the cancer is characterized by one or more cancer cells (e.g., but not necessarily a cancer cell in a tumor such as a solid tumor). In some embodiments, the cancer is metastatic. In some embodiments, the cancer is recurrent. In some embodiments, the cancer is remitting. In some embodiments, the cancer is selected from the group consisting of bladder, breast, pancreas, ovary, stomach, gastrointestinal tract, liver, lung, prostate, skin, colon, rectum, colon and rectum, skin.

In some embodiment, miniprotein conjugates provided herein can be used for imaging and treating a wide variety of cancers, including, but not limited to, breast cancer, ovarian cancer, melanoma, pancreatic cancer, peripheral neuroma, glioblastoma, adrenocortical carcinoma, AIDS-related lymphoma, anal cancer, bladder cancer, urothelial cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma. Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

As will be known to those of skill in the art, determination of the appropriate dose and regimen of a composition provided by the present disclosure can be made by the clinician, e.g., using parameters or factors known or suspected in the art to affect treatment or predicted to affect treatment. In some embodiments, actual dosage levels of the active ingredients in compositions provided by the present disclosure may be varied so as to obtain an amount of the active ingredient which is effective to achieve the desired therapeutic response for a particular patient, composition, and mode of administration, without being toxic to the patient. In some embodiments, the selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

In some embodiments, the present disclosure provides methods of imaging, diagnosing and/or monitoring (including determining prognosis) of presence of a target in a subject. In some embodiments, a conjugate (e.g., a miniprotein conjugate comprising, e.g., a chelator and/or radionuclide) of the present disclosure is useful for PET, SPECT, or MRI imaging.

In some embodiments, conjugates (e.g., miniprotein conjugates comprising a chelator and/or radionuclide) of the present disclosure can be used in image-guided surgery. For example, in some embodiments, tissue of interest suspected of containing cancerous cells or a tumor can be contacted with a Nectin-4-targeted miniprotein, such that the Nectin-4-targeted miniprotein or component(s) thereof (chelator, radionuclide) accumulates in metastatic cancerous cells. Imaging of tissues labeled with the Nectin-4 miniprotein conjugate wherein the conjugate comprises more additional detectable components (e.g., chelator, e.g., radionuclide, e.g., other detectable imaging moiety) can be used, for example, for detection of metastatic cells, tumor margin delineation, evaluation of the completeness of resection, and evaluation of the efficacy of treatment.

In some embodiments, the present disclosure provides methods of imaging a cancer in a subject. In some embodiments, miniprotein conjugates of the present disclosure are useful for PET, SPECT, or MRI imaging. In some embodiments, a detectably effective amount of a miniprotein conjugate is administered to a subject; that is, an amount that is sufficient to yield an acceptable image using the imaging equipment that is available for clinical use. In some embodiments, a detectably effective amount of a miniprotein conjugate may be administered in more than one injection if needed. In some such embodiments, a detectably effective amount of miniprotein conjugate needed for an individual may vary according to factors such as the degree of uptake of miniprotein conjugates into cancerous tissue, the age, sex, and weight of the individual, and the particular medical imaging method used. Optimization of such factors is within the level of skill in the art.

In some embodiments, imaging with miniprotein conjugates can be used in assessing efficacy of therapeutic drugs in treating cancer. For example, images can be acquired after treatment with an anti-cancer therapy to determine if the individual is responding to treatment. In some embodiments, in a subject with cancer, imaging with miniprotein conjugate can be used to evaluate whether a tumor is shrinking or growing. Further, the extent of cancerous disease (how far and where the cancer has spread) can be determined to aid in determining prognosis and evaluating optimal strategies for treatment (e.g., surgery, radiation, or chemotherapy).

In some embodiments, miniprotein conjugates can be used in image-guided surgery. Tissue of interest suspected of containing cancerous cells or a tumor can be contacted with a miniprotein conjugate, such that the miniproteins or components thereof (e.g., chelator, e.g., radionuclide) accumulate in metastatic cancerous cells. In some embodiments, imaging of tissues labeled with miniprotein conjugate in this way can be used, for example, for detection of metastatic cells, tumor margin delineation, evaluation of the completeness of resection, and evaluation of the efficacy of treatment.

In another aspect, the disclosure provides a method of treating an individual, a group of individuals, or a population of individuals that are diagnosed with a cancer, the method comprising administering to the individual a means for blocking uptake and/or retention of a radiotherapeutic to kidney tissue, and a radionuclide therapeutic comprising a composition represented by the formula selected from one or more of M-L-C-R, M-L-C, M-C-R, M-L-R. M-C, M-L, and M-R, wherein M comprises a miniprotein (M), L comprises a linker (L), C comprises a chelator (C), and R comprises a radionuclide (R), wherein the M is of a particular scaffold. In some embodiments, the means for binding to kidney tissue blocks uptake of the radiotherapeutic into the kidney. In some embodiments, the radiotherapeutic is targeted to a tumor. In some embodiments, the radiotherapeutic targeted to the tumor is at a greater concentration than in the absence of the means for blocking uptake and/or retention by kidney tissue.

In another aspect, the disclosure provides a method of improving a cancer treatment in an individual or group or population of individuals experiencing one or more off-target effects, the method comprising administering: (a) a decoy, and (b) a radionuclide therapeutic, wherein the one or more off-target effects is prevented or reduced as compared to administering the radiotherapeutic in the absence of the decoy. In some embodiments, the radionuclide therapeutic comprises a miniprotein that targets a protein (e.g. Nectin-4). In some embodiments, the radionuclide therapeutic comprises a miniprotein that targets Nectin-4. In some embodiments, the radionuclide therapeutic comprises a compound selected from TABLE 2A.

In some embodiments, the one or more off-target effects includes uptake, accumulation, and/or retention of a radiotherapeutic in kidney tissue. In some embodiments, off-target effects can also include, but are not limited to, symptoms such as nausea, fatigue, muscle wasting, one or more indicators of toxicity, such as set forth in regulatory agency guidance for toxicity, such as, e.g., at the United States FDA website, fda.gov/media/73679/download.

In some embodiments, the disclosure provides a method for treatment comprising administering a pharmaceutical composition as provided herein in the absence of administering targeted conditioning or pre-conditioning regimens where conditioning is necessary prior to administration of therapies, e.g., adoptive cell therapies and gene therapies to ablate certain cells.

In some embodiments, methods and compositions of the present disclosure include multistep or pre-targeting approaches. For instance, in some embodiments, a radionuclide can be decoupled to a provided composition and may be subsequently administered after an initial step of administering a miniprotein or an antibody (e.g., a first ligand binding moiety). In such embodiments, the first ligand binding moiety is not conjugated to a radionuclide and has the desired affinity and specificity for the tumor cells. The first ligand binding moiety is then targeted by a second moiety carrying the radionuclide. For instance, the first ligand binding moiety may comprise an antibody to the target protein (e.g., Nectin-4) and the second moiety may be the pharmaceutical composition comprising the miniprotein, linker, chelator and the radionuclide wherein the miniprotein may exhibit a desired avidity to the first ligand binding moiety.

In some embodiments, the present disclosure provides methods of use (e.g., treatment, manufacture, etc.) of miniproteins (e.g., CDPs, knottins, binders, affibodies, engineered Kunitz domains, monobodies, anticalins, designed ankyrin repeat domains (DARPins), avimers) as provided herein.

In some embodiments, anti-target protein (e.g., Nectin-4) compositions and pharmaceutical compositions are produced, e.g., using miniproteins (e.g., CDPs, knottins, binders, affibodies, engineered Kunitz domains, monobodies, anticalins, designed ankyrin repeat domains (DARPins), avimers), as provided herein.

In some embodiments, miniproteins of the target (e.g., Nectin-4) proteins (e.g. CDPs, knottins, binders, affibodies, engineered Kunitz domains, monobodies, anticalins, designed ankyrin repeat domains (DARPins), avimers) provided by the present disclosure are formatted to generate peptides, antibodies, antibody and antibody fragments, ADCs, BiTEs, CAR-Ts, and TRuCs, Fc-domain components, portions, or modifications, bispecific antibodies etc. In some such embodiments, such compositions and pharmaceutical compositions are used in treatment of a disease, disorder, or condition wherein expression of the target proteins (e.g., Nectin-4) is suspected or detected. In some such embodiments, the disease, disorder, or condition is related to overexpression and/or aberrant expression the target proteins (e.g., Nectin-4). In some embodiments, the disease, disorder and/or condition is cancer. Accordingly, the present disclosure provides various anti-target (e.g., Nectin- 4) protein compositions and pharmaceutical compositions for the treatment of disease related to the target proteins (e.g., Nectin-4).

Among other things, the present disclosure provides methods of treating a subject in need thereof by administering a composition as provided herein. In some such embodiments, a composition is or comprises a miniprotein (e.g., CDP, knottin, binder, affibody, engineered Kunitz domain, monobody, anticalin, designed ankyrin repeat domain (DARPin), avimer). In some embodiments, the composition is a miniprotein conjugate comprising a miniprotein and one or more of a chelator and radionuclide, as well as, optionally, a linker (e.g., linking the chelator to the miniprotein).

In some embodiments, a subject treated herein is at risk of having or has been diagnosed as having a cancer. In some embodiments, the subject is a mammal. In some embodiments, the mammal is a human. In some embodiments, the human is a fetus, infant, child, adolescent, adult, or elderly adult. In some embodiments, a human subject having a cancer is treated by administering a miniprotein (e.g., CDP, knottin, binder, affibody, engineered Kunitz domain, monobody, anticalin, designed ankyrin repeat domain (DARPin), avimer) as described herein.

In some embodiments, the cancer expresses a target protein (e.g., Nectin-4) specifically bound by a miniprotein (e.g., CDP, knottin, binder, affibody, engineered Kunitz domain, monobody, anticalin, designed ankyrin repeat domain (DARPin), avimer) of the present disclosure. In some embodiments, the target protein (e.g., Nectin-4) or portion thereof is expressed on the surface of a cancer cell of the subject. In some such embodiments, the target protein (e.g., Nectin-4) is expressed on the cancer cell and has lower or non-detectable expression on cells of normal tissues, and/or is expressed at much higher density on cancer cells versus normal cells.

In some embodiments, the cancer is a solid tumor. In some embodiments, the cancer is metastatic. In some embodiments, the cancer is recurrent. In some embodiments, the cancer is remitting. In some embodiments, the cancer is selected from bladder, breast, pancreas, ovary, stomach, gastrointestinal tract, liver, lung, prostate, skin, colon, rectum, colon and rectum, and/or skin.

In some embodiments, miniproteins (e.g., CDPs, knottins, binders, affibodies, engineered Kunitz domains, monobodies, anticalins, designed ankyrin repeat domains (DARPins), avimers) provided herein can be used in conjunction with one or more additional components. For example, in some embodiments, a miniprotein (e.g., CDP, knottin, binder affibody, engineered Kunitz domain, monobody, anticalin, designed ankyrin repeat domain (DARPin), avimer) may be combined with one or more other components for use in imaging, diagnosis, prognosis/monitoring and/or treating a disease, disorder or condition. In some embodiments, the disease is cancer. In some embodiments, a miniprotein (e.g., CDP, knottin, binder, affibody, engineered Kunitz domain, monobody, anticalin, designed ankyrin repeat domain (DARPin), avimer) of the present disclosure may be used in a wide variety of cancers, including, but not limited to, breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma. Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, treatment (e.g., including with a miniprotein (e.g., CDP, knottin, binder affibody, engineered Kunitz domain, monobody, anticalin, designed ankyrin repeat domain (DARPin), avimer) of the present disclosure), diagnosis, prognosis/monitoring, or imaging is in a subject who does not exhibit signs or symptoms of a disease, disorder, and/or condition. In some embodiments, treatment is in a subject who exhibits one or more signs or symptoms of a disease, disorder, or condition even if, for example, such signs or symptoms are not objectively observable without further testing such as laboratory diagnostics. In some embodiments, a subject is susceptible to having or at risk of developing a disease, disorder, or condition (e.g., cancer), based on one or more factors (e.g., level of the target protein (e.g., Nectin-4), etc.) that are related to increased risk of developing of the disease, disorder or condition. In some embodiments, a subject has been diagnosed as having a disease, disorder, or condition (e.g., cancer).

In some embodiments, present disclosure provides methods of treating or preventing disease or disorder in a subject, the method comprising administering to the subject a pharmaceutical composition comprising a miniprotein (e.g., CDP, knottin, binder affibody, engineered Kunitz domain, monobody, anticalin, designed ankyrin repeat domain (DARPin), avimer) of the present disclosure in an amount effective that modulates, binds or inhibits human isoform of the target protein (e.g., Nectin-4) to treat or prevent disease or disorder in the subject. In some embodiments, the disease or disorder is cancer. In some embodiments, the cancer is treated (e.g., resolved, prevented, progression is slowed, symptoms are relieved, tumor size reduced to improve overall survival, etc.).

In some embodiments, the method comprises further administering a decoy. A decoy can be selected from compounds C295-C297 and/or a miniprotein comprising, consisting essentially of, or consisting of an amino acid sequence of any of SEQ ID NOs: 209-211. In certain embodiments, administration of the decoy reduces one or more off target effects and/or reduces uptake and/or retention of the polypeptide or composition in kidney tissue.

In another aspect, the disclosure provides a method of treating an individual with a cancer, the method comprising administering to the individual a means for blocking uptake and/or retention of a radiotherapeutic to kidney tissue, and a radionuclide therapeutic comprising a composition represented by the formula selected from one or more of M-L-C-R, M-L-C, M-C-R, M-L-R, M-C, M-L, and M-R, wherein M comprises a miniprotein (M), L comprises a linker (L), C comprises a chelator (C), and R comprises a radionuclide (R), wherein the M is of a particular scaffold. In some embodiments, the means for binding to kidney tissue blocks uptake and/or retention of the radiotherapeutic into the kidney. In some embodiments, the radiotherapeutic is targeted to a tumor. In some embodiments, the radiotherapeutic targeted to the tumor is at a greater concentration than in the absence of the means for binding to kidney tissue.

In another aspect, the disclosure provides a method of improving a cancer treatment in an individual experiencing one or more off-target effects, the method comprising administering: (a) a decoy; and (b) a radionuclide therapeutic, wherein the one or more off-target effects is prevented or reduced as compared to administering the radiotherapeutic in the absence of the decoy. In some embodiments, the radionuclide therapeutic comprises a miniprotein that targets Nectin-4. In some embodiments, the radionuclide therapeutic comprises a compound selected from TABLE 2A.

In some embodiments, methods and compositions of the present disclosure include multistep or pre-targeting approaches. For instance, in some embodiments, a radionuclide can be decoupled to a provided composition and may be subsequently administered after an initial step of administering a miniprotein or an antibody (e.g., a first ligand binding moiety). In such embodiments, the first ligand binding moiety is not conjugated to a radionuclide and has the desired affinity and specificity for the tumor cells. The first ligand binding moiety is then targeted by a second moiety carrying the radionuclide. For instance, the first ligand binding moiety may comprise an antibody to the Nectin-4 and the second moiety may be the pharmaceutical composition comprising the miniprotein, linker, chelator and the radionuclide wherein the miniprotein may exhibit a desired avidity to the first ligand binding moiety.

In some embodiments, the present disclosure provides methods of use (e.g., treatment, manufacture, etc.) of miniproteins (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) as provided herein.

In some embodiments, anti-Nectin-4 compositions and pharmaceutical compositions are produced, e.g., using miniproteins, as provided herein.

In some embodiments, Nectin-4 miniproteins provided by the present disclosure are formatted to generate peptides. In some such embodiments, such compositions and pharmaceutical compositions are used in treatment of a disease, disorder, or condition wherein Nectin-4 expression is suspected or detected. In some such embodiments, the disease, disorder, or condition is related to overexpression and/or aberrant expression of Nectin-4. In some embodiments, the disease, disorder and/or condition is cancer. Accordingly, the present disclosure provides various anti-Nectin-4 compositions and pharmaceutical compositions for the treatment of disease related to Nectin-4.

Among other things, the present disclosure provides methods of treating a subject in need thereof by administering a composition as provided herein. In some such embodiments, a composition is or comprises a miniprotein. In some embodiments, the composition is a miniprotein conjugate comprising a miniprotein and one or more of a chelator and radionuclide, as well as, optionally, a linker (e.g., linking the chelator to the miniprotein).

In some embodiments, a subject treated herein is at risk of having or has been diagnosed as having a cancer. In some embodiments, the subject is a mammal. In some embodiments, the mammal is a human. In some embodiments, the human is a fetus, infant, child, adolescent, adult, or elderly adult. In some embodiments, a human subject having a cancer is treated by administering a miniprotein as described herein.

In some embodiments, the cancer expresses a target protein (e.g., Nectin-4) specifically bound by a miniprotein of the present disclosure. In some embodiments, the Nectin-4 or portion thereof is expressed on the surface of a cancer cell of the subject. In some such embodiments, the Nectin-4 is expressed on the cancer cell and has lower or non-detectable expression on cells of normal tissues, and/or is expressed at much higher density on cancer cells versus normal cells.

In some embodiments, the cancer is a solid tumor. In some embodiments, the cancer is metastatic. In some embodiments, the cancer is recurrent. In some embodiments, the cancer is remitting. In some embodiments, the cancer is selected from the group consisting of bladder, breast, pancreas, ovary, stomach, gastrointestinal tract, liver, lung, prostate, skin, colon, rectum, colon and rectum, skin.

In some embodiments, miniproteins provided herein can be used in conjunction with one or more additional components. For example, in some embodiments, a miniprotein (e.g., that targets Nectin-4, e.g., that binds to cells expressing Nectin-4, etc.) may be combined with one or more other components for use in imaging, diagnosis, prognosis/monitoring and/or treating a disease, disorder or condition. In some embodiments, a miniprotein or composition of the present disclosure maybe administered in combination with one or more treatment or components for use in monoclonal antibody therapy, immunotherapy, chemotherapy, radiotherapy, gene therapy, or RNA therapy.

In some embodiments, the miniprotein or composition is administered in combination with an immunotherapy treatment. In some embodiments, a miniprotein or composition of the present disclosure is administered in combination with an immune checkpoint inhibitors. Exemplary immune checkpoint inhibitors include agents that inhibit one or more of (i) cytotoxic T lymphocyte-associated antigen 4 (CTLA4), (ii) programmed cell death protein 1 (PD1), (iii) PDL1, (iv) LAG3, (v) B7-H3, (vi) B7-H4, and (vii) TIM3.

In some embodiments, the miniprotein or composition is administered in combination with monoclonal antibody agents that target non-checkpoint targets (e.g., herceptin) and non-cytotoxic agents (e.g., tyrosine-kinase inhibitors).

In some embodiments, the miniprotein or composition is administered in combination with other anti-cancer agents, including, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK inhibitor, an inhibitor of both DNA-PK and mTOR, a DNMT1 Inhibitor, a DNMT1 Inhibitor plus 2-chloro-deoxyadenosine, an HD AC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

In some embodiments, the miniprotein or composition is administered in combination with a radiotherapy treatment. Examples of radiotherapy treatment include external beam radiation therapy and internal radiation therapy.

In some embodiments, the disease is cancer. In some embodiments, a miniprotein of the present disclosure may be used in a wide variety of cancers, including, but not limited to, breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma. Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, a miniprotein or composition of the present disclosure is administered in combination with a second therapeutic agent, including, for example, a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRMI, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a topoisomerase inhibitor, an auristatin (e.g., monomethyl auristatin E), and/or an immunotoxin.

In some embodiments, a miniprotein or composition of the present disclosure is administered in combination with a second therapeutic agent that is a DNA damage response (DDR) inhibitor. A DDR inhibitor may be an inhibitor of Serine-protein kinase ATM (ATM), Serine/threonine-protein kinase ATR (ATR), Serine/threonine-protein kinase Chk1 (CHK1/2), DNA-dependent protein kinase catalytic subunit (DNA-PK), Poly [ADP-ribose] polymerase (PARP), Membrane-associated tyrosine- and threonine-specific CDC2-inhibitory kinase (PKMYT1), RNA-directed DNA polymerase (POLO), and/or DNA repair protein RAD51 homolog 1 (RAD51).

In some embodiments, treatment (e.g., including with a miniprotein (e.g., a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer) of the present disclosure), diagnosis, prognosis/monitoring, or imaging is in a subject who does not exhibit signs or symptoms of a disease, disorder, and/or condition. In some embodiments, treatment is in a subject who exhibits one or more signs or symptoms of a disease, disorder, or condition even if, for example, such signs or symptoms are not objectively observable without further testing such as laboratory diagnostics. In some embodiments, a subject is susceptible to having or at risk of developing a disease, disorder, or condition (e.g., cancer), based on one or more factors (e.g., level of Nectin-4, etc.) that are related to increased risk of developing of the disease, disorder or condition. In some embodiments, a subject has been diagnosed as having a disease, disorder, or condition (e.g., cancer).

In some embodiments, present disclosure provides methods of treating or preventing disease or disorder in a subject, the method comprising administering to the subject a pharmaceutical composition comprising a miniprotein of the present disclosure in an amount effective that modulates, binds or inhibits human Nectin-4 to treat or prevent disease or disorder in the subject. In some embodiments, the disease or disorder is cancer. In some embodiments, the cancer is treated (e.g., resolved, prevented, progression is slowed, symptoms are relieved, tumor size reduced to improve overall survival, etc.).

Methods of Modifying Uptake and/or Retention in Kidney

Decoys of the disclosure can be used to pre-emptively avoid any such off-target effects or impact that would decrease effective dosage and/or increase potential toxicity due to uptake and/or retention such as of a radionuclide in a kidney tissue. As will be understood, given context, in some embodiments, kidney tissue is biopsy tissue, e.g., from a subject, e.g., a healthy subject, e.g., a subject in need of treatment. In some embodiments, kidney tissue includes a population of cells, such as dissociated cells. In some such embodiments, cells may be biopsy cells, cells from an animal model, cells from a cell line (e.g., OK-PTC cells, etc.), engineered cells, etc. In some embodiments, a kidney tissue is in vivo, ex vivo, or in vitro. As provided herein, methods and compositions treat a disease, disorder, or condition, such as a cancer, in in a subject or group of subjects or population by mitigating or preventing off-target effects including, but not limited to blocking uptake and/or retention in kidney, while also maintaining or improving efficacy of the radiotherapeutic for treatment of the tumor by co-administration of a decoy with a therapeutic of the disclosure.

In some embodiments, the disclosure provides improved methods of reducing off-target effects of a composition as provided herein. In some such embodiments, reduction of off-target effects can be associated with a reduction in toxicity. In some embodiments, the toxicity level can be assessed by using the toxicity scale as described in, for example, "Common Terminology Criteria for Adverse Events v3.0 (CTCAE)." Toxicity scales can be graded on a scale of 1-4 as follows: Mild (Grade 1); Moderate (Grade 2); Severe (Grade 3); Potentially Life Threatening (Grade 4). Measures that can be evaluated using a toxicity scale such as described herein include, but are not limited to, pain (at a particular site, throughout the body), fever, heart rate (e.g., tachycardia, bradycardia), hypertension, respiration rate, nausea/vomiting, diarrhea, headache, fatigue, myalgia, systemic illness or clinical adverse event, laboratory abnormalities (such as in, e.g., a complete blood count including hemoglobin, white blood cells, red blood cells, precursor blood cells, platelets, fibrinogen, PTT, etc., one or more electrolyte values, liver enzyme values and/or kidney protein values, e.g., sodium, potassium, glucose, blood urea nitrogen, creatinine, calcium, magnesium, phosphorus. CPK, albumin, total protein, alkaline phosphatase, ALT, AST, bilirubin, cholesterol, pancreatic enzymes such as amylase and lipase, etc., urine measurements (e.g., protein, glucose, blood, specific gravity, etc.). Those of ordinary skill in the art will be knowledgeable about applying toxicity scales and grades to any particular symptom using clinically relevant and acceptable standards, including, such as defined in a clinical trial protocol or treatment brochure.

In some embodiments, a toxicity grade of a therapeutic (e.g., a radiotherapeutic as provided herein, a commercially available radiotherapeutic, etc.) will be reduced by one or more grade points on one or more measures in the presence of a decoy as compared to the absence of a decoy. The disclosure contemplates that one or more decoys as provided herein may be administered in conjunction with one or more radiotherapeutics including those provided herein. In some embodiments, a decoy can be provided as a standalone therapy for use in subjects being treated with one or more radiotherapeutic treatments (e.g., not limited to those provided herein). In some embodiments, administration of the decoy will enable higher dosing with one or more radiotherapeutic treatments, as compared to dosing in the absence of a decoy with no change in toxicity grade of the therapeutic.

In some embodiments, the disclosure provides methods of reducing one or more off-target effects of a composition as provided herein. In some such embodiments, reduction of one or more off-target effects includes reduced uptake and/or retention of a composition (e.g., a radiolabeled composition) as provided herein in kidney in % ID/g of tissue. In some embodiments, the reduced uptake and/or retention in kidney tissue can be determined by measuring recovered radiation (e.g. from urine).

Recovered radiation can be determined using standard methods known to those of skill in the art, including, for example, collecting urine at one or more time points after administration of a radiolabeled compound and determining the amount of radiation in the sample as compared to the amount of radiation administered. In some embodiments, if more radiation is recovered in urine in connection with administration of a decoy, less radiation is being retained in a kidney. In some embodiments, a decoy results in an increase in output of radiation by a kidney. In some embodiments, administration of a decoy results in more radiation being taken up by a tumor and less being taken up and/or retained in a kidney tissue.

In some embodiments, where a polypeptide or composition as provided herein is taken up and/or retained in the kidney, administration of a decoy (e.g., C295-C297, e.g., a miniprotein comprising an amino acid sequence of any of SEQ ID NOs: 209-211) reduces uptake of the polypeptide or composition in the kidney as compared to administration without the decoy. Administration of a decoy can be prior to, concomitant with, or after administration of a polypeptide or composition provided herein (e.g., a Nectin-4 binding polypeptide or composition). In some embodiments, cancer in a subject is treated after administration of a polypeptide or composition provided herein. In some embodiments, the cancer is characterized in that cancer cells express Nectin-4. In some embodiments, the cancer treated and one or more off-target effects and/or toxicity grade is reduced in the presence of the decoy as compared to treatment without administration of the decoy.

Among other things, the present disclosure provides a method of treating an individual with cancer comprising administering (a) a composition comprising a miniprotein (M) and a radionuclide (R); and (b) a decoy, the improvement comprising reducing one or more off-target effects or toxicity measures after administration of the composition and the decoy as compared to administration of the composition in the absence of the decoy. In some embodiments, the composition comprises an M that targets Nectin-4.

In another aspect, the disclosure provides a method of treating an individual with cancer by administering: (a) a composition comprising a miniprotein (M) and a radionuclide (R); and (b) a decoy, the improvement comprising achieving a reduction in concentration of R in a kidney tissue in the presence of the decoy as compared to the concentration of R in the kidney tissue in the absence of the decoy. In certain embodiments, the reduction in the one or more off-target effects or toxicity measures is measured as a reduction in one or more toxicity grades of each of the one or more off target effects or toxicity measures. In some embodiments, the reduction in concentration of R in the kidney tissue is measured by urine output of R. In some embodiments, the percent of administered radiation recovered in the presence of the decoy is increased as compared to radiation recovered in absence of the decoy. In some embodiments, the reduction in concentration of R in the kidney tissue is determined by maintenance of eGFR over at least the period that the subject is receiving treatment. In some embodiments, the administration of the composition can be repeated more often (e.g., (e.g., at least 2, 3, 4, 5, 6 times more, etc.) in the presence of the decoy than in the absence of the decoy before a dose limiting toxicity is reached.

In another aspect, the disclosure provides a method of reducing uptake by a kidney tissue of a composition the improvement comprising administering a composition comprising (a) a radionuclide therapeutic comprising at least a miniprotein (M) and a radionuclide (R); and (b) a decoy, such that in the presence of the decoy, the radionuclide is less concentrated in the kidney tissue than in the absence of the decoy. In some embodiments, the reduction in concentration of R in the kidney tissue is measured by urine output of R. In some embodiments, the urine output is expressed as a percent of administered radiation recovered in the presence of the decoy and is increased as compared to radiation recovered in absence of the decoy. In some embodiments, the reduction in concentration of R in the kidney tissue is determined by maintenance of eGFR over at least the period that the subject is receiving treatment. In some embodiments, the administration of the composition can be repeated more often (e.g., at least 2, 3, 4, 5, 6 times more, etc.) in the presence of the decoy than in the absence of the decoy before a dose limiting toxicity is reached. In certain embodiments, administration of a compound comprising a miniprotein is administered concomitant with the decoy. In certain embodiments, administration of a compound comprising the miniprotein (M) is administered sequentially with the decoy. In some embodiments, the sequential administering comprises administering the decoy followed by administering the composition comprising the miniprotein (M). In some embodiments, the sequential administering comprises administering the composition comprising a miniprotein followed by administering the decoy. In certain embodiments, the decoy is administered in a molar or mass excess relative to the miniprotein (M). In some embodiments, the excess is at least about 2, 10, 50, 100, 250, 500, 750, 1,000, 2,500, 5,000, 7,500, or 10,000× excess relative to the miniprotein (M). In some embodiments, the decoy comprises or consists any of compounds C295-C297 and/or an amino acid sequence comprising, consisting essentially of, or consisting of any of SEQ ID NOs: 209-211. In certain embodiments, the Nectin-4 targeting miniprotein comprises or consists of any compound or amino acid sequence selected from TABLE 2A. In certain embodiments, the decoy comprises or consists of a scaffold that is the same as the scaffold of a Nectin-4 binding miniprotein provided herein. In some embodiments, the decoy comprises or consists of an amino acid sequence of any of SEQ ID NOs: 209-211 and/or is selected from any of compounds C295-C297, and the miniprotein comprises or consists of an amino acid sequence of the miniprotein sequence of C294. In some embodiments, the decoy comprises or consists of a scaffold that is the same as a Nectin-4 binding protein as set forth in TABLE 2A and the Nectin-4 binding protein is selected from a bicyclic Nectin-4 binding protein (e.g. C294) as set forth in TABLE 21. In some embodiments, the bicyclic-binding protein is C294 and/or has an amino acid sequence comprising or consisting of that of SEQ ID NO: 238.

TABLE 21

| Compound Name | N-terminus | SEQ ID NO: Sequences | C-terminus |
|---|---|---|---|
| C294 | [TATA(1,5,15)] SCBiot-(dPEG4) | 238 CP(1Nal)(GD)CM (hR)DWSTP(hyP) WC | NH2 |

In some embodiments, the present disclosure comprises a method for treatment, comprising administering a pharmaceutical composition as provided herein in the absence of administering targeted conditioning or pre-conditioning regimens where conditioning is necessary prior to administration of therapies, e.g., adoptive cell therapies and gene therapies to ablate certain cells.

[5] "dD" refers to D-aspartic acid; "hR" refers to homo-arginine; "hyP" refers to hydroxyproline; "1Nal" refers to 1-naphthylamine; "sRme2" refers to symmetric dimethyl arginine; "Cit" refers to citrulline; "Kme" refers to methyl lysine; "Kme2" refers to dimethyl lysine; "Kme3" refers to trimethyl lysine; "Kipr" refers to Ne-isopropyl-L-Lysine.

In one aspect, the disclosure provides, in a method of improving binding affinity strength of a polypeptide to Nectin-4, the improvement comprising modifying four amino acid residues of a polypeptide, which polypeptide has at least 44 amino acids in length and has substitutions at positions corresponding to 12, 21, 26, and 32 of SEQ ID NO: 78, wherein the substitutions correspond to K12A, Y21Q, S26Kme3, and G32A.

In some aspects, the disclosure provides a method of treating cancer, the method comprising administering to a subject in need thereof, a composition comprising a conjugate comprising a polypeptide having at least 90% identity to at least 40 amino acids of an amino acid sequence as set forth in any one of SEQ ID NOs: 3-158, 161-168, 170-208, 212-237, 243-246 and 248 and a radionuclide. In some embodiments, the SEQ ID NO: is selected 3-158, 161-168, 170-208, 212-237, 243-246 and 248.

In some embodiments, the radionuclide is associated with the polypeptide with a linker and/or chelator according to a formula M-L-C-R, wherein M is the polypeptide. L is a linker, C is a chelator, and R is the radionuclide. In some embodiments, M has an amino acid sequence comprising or consisting of SEQ ID NO: 195 or SEQ ID NO: 200. In some embodiments, L comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, any linker set forth in Table 2A, or (Gly)n-(gGlu)n- or (PEG)n, wherein n is from 1 to 10, (Gly)1-10, or any fragment or combination via covalent bond thereof. In some embodiments, C comprises or consists of DOTA, Crown, NOPO, Macropa, lead specific chelator (PSC), N-succinimidyl 3-(tri-n-butylstannyl)benzoate (BuSTB), or N-succinimidyl 3-trimethylstannylbenzoate (MeSTB)

In some embodiments, R is Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. In some embodiments, R is a therapeutic agent and/or an imaging agent. In some embodiments, R is Cu-64, Ga-68, Lu-177, In-111, Cu-67, La-132, or F-18.

In one aspect, the disclosure provides a method of reducing kidney cell uptake of a composition comprising administering to a subject a Nectin-4 binding protein having an amino acid sequence comprising at least one modified lysine residue at a position corresponding to X12 and/or X26 of SEQ ID NO: 195, wherein the modification comprises at least small alkyl group attached to the nitrogen of the lysine side chain, optionally comprising a monomethyl, dimethyl, trimethyl, or isopropyl group and the reduction is as compared to administration to the subject or a control subject an otherwise identical composition but not comprising the modified lysine residue at the position corresponding to X12 and/or X26.

In one aspect, the disclosure provides, in a method of treating cancer, the improvement comprising administering a composition comprising a Nectin-4 binding protein having an amino acid sequence comprising at least one modified lysine residue at a position corresponding to X12 and/or X26 of SEQ ID NO: 195, wherein the modification comprises at least one carbon attached to the nitrogen of the lysine side chain, optionally comprising a methyl, dimethyl, trimethyl, or isopropyl group as compared to a composition not comprising a modified lysine residue at a position corresponding to X12 and/or X26.

In one aspect, the disclosure provides a method of treating a subject with refractory or recurrent cancer comprising administering a composition, compound, conjugate, or pharmaceutical composition as provided herein.

In one aspect, the disclosure provides a method of improving biodistribution of a pharmaceutical composition for a Nectin-4 positive population of cancer cells in a subject having a Nectin-4-positive cancer, comprising contacting the population with a polypeptide that has a modified lysine at a position corresponding to X12 and/or X26 of SEQ ID NO: 195, wherein the lysine is modified by adding at least one small alkyl group to a lysine side chain and wherein the biodistribution is improved as compared to contacting the population without the modified lysine at a position corresponding to X12 and/or X26 of SEQ ID NO: 195.

In one aspect, the disclosure provides a method of diagnosing presence of a Nectin-4 positive population of cancer cells comprising: contacting a population of cells with a composition, compound, conjugate, or pharmaceutical composition thereof: detecting the presence of the composition, compound, or pharmaceutical composition of step (a) by measuring a signal; and comparing the detection in step (b) to a control signal; and diagnosing cancer if the composition, compound, or pharmaceutical composition of step (a) is detected above the control.

In some embodiments, the contacting is performed by administering to a subject in need thereof.

In some embodiments, the administering is intravenous or subcutaneous. In some embodiments, the contacting is outside of the subject, optionally in vitro with a biopsy sample.

In one aspect, the disclosure provides a method of treating a cancer in a subject using an immunotherapy, the method comprising administering to the subject a composition comprising a composition, compound, pharmaceutical composition or conjugate as provided herein.

Use of a composition, compound, pharmaceutical composition, or conjugate as provided herein to treat cancer in a subject.

In one aspect, the disclosure provides a method of treating a subject in need thereof comprising administering to the subject in need thereof a composition, compound, pharmaceutical composition, or conjugate as provided herein.

In some embodiments, the subject is diagnosed as having cancer. In some embodiments, a cancer cell from the subject expresses Nectin-4, or a portion thereof.

In some embodiments, the expression of Nectin-4 is higher in the cancer cell than in a non-cancer cell, which expression can be measured by protein and/or nucleic acid levels.

In some embodiments, the composition, compound, pharmaceutical composition, or conjugate as provided herein is not taken up and/or retained in the kidney as compared to a compound that does not comprise the composition, compound, pharmaceutical composition, or conjugate as provided herein.

In some embodiments, the composition, compound, or pharmaceutical composition is internalized in a cell expressing human Nectin-4.

In some embodiments, the cancer is selected from breast cancer, ovarian cancer, melanoma, pancreatic cancer, peripheral neuroma, glioblastoma, adrenocortical carcinoma. AIDS-related lymphoma, anal cancer, urothelial cancer, bladder cancer, meningioma, glioma, astrocytoma, cervical cancer, chronic myeloproliferative disorders, colon cancer, endometrial cancer, ependymoma, esophageal cancer. Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, the composition, compound, conjugate, or pharmaceutical composition is administered intravenously or subcutaneously.

In one aspect, the disclosure provides a method of targeting cancer cells expressing Nectin-4, the method comprising: (i) determining or having determined a level of expression of Nectin-4 in a population of cancer cells; (ii) administering to a subject in need thereof a composition comprising a composition according to the composition, compound, pharmaceutical composition, or conjugate as provided herein, wherein the polypeptide of the composition, compound, or pharmaceutical composition is designed to specifically bind to human Nectin-4 and (iii) wherein the composition, compound, or pharmaceutical composition is attached to the surface and/or internalized into one or more Nectin-4 expressing cancer cells.

In some embodiments, the subject is treated after the administering as compared to prior to the administering.

In one aspect, the disclosure provides, in a method of targeting a population of cancer cells expressing Nectin-4, the improvement comprising contacting the population with the composition according to a composition, compound, pharmaceutical composition, or conjugate as provided herein, wherein X12 and/or X26 comprise a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at positions X12 and/or X26, wherein, optionally, the small alkyl group is part of a monomethyl, dimethyl, trimethyl, or isopropyl group.

In one aspect, the disclosure provides a method of evaluating locations of one or more populations of cancerous cells in a subject, the method comprising administering to the subject a composition, compound, pharmaceutical composition, or conjugate as provided herein and detecting to determine location of the composition in the subject.

In one aspect, the disclosure provides, in a method of decreasing kidney uptake of a composition administered to detect and/or treat one or more populations of cancer cells, the improvement comprising administering to a subject in need thereof the composition according to a composition, compound, pharmaceutical composition, or conjugate as provided herein, wherein X12 and/or X26 comprise a lysine with at least one additional small alkyl group attached to the nitrogen in the side chain, wherein the composition is taken up less by kidney cells than in a composition comprising a polypeptide that does not have a small alkyl group attached to a nitrogen on the side chain of a lysine at positions X12 and/or X26, wherein, optionally, the small alkyl group is part of a monomethyl, dimethyl, trimethyl, or isopropyl group.

In some embodiments, the detecting comprises an imaging procedure allows for selecting subjects, monitoring subjects, and/or treating subjects with a therapeutic comprising a miniprotein designed to bind to Nectin-4 expressed on one or more cancer cells in the one or more populations of cancer cells.

In some embodiments, the therapeutic comprises a composition, compound, pharmaceutical composition, or conjugate as provided herein.

In one aspect, the disclosure provides, in a method of a method of improving delivery of a radionuclide to a population of cancer cells in a subject, the method comprising administering a composition, compound, pharmaceutical composition, or conjugate as provided herein, wherein the amino acid sequences of the polypeptide comprise amino acids corresponding to positions X12 and/or X26 of SEQ ID NO: 195, and wherein X12 and/or X26 comprise a lysine with at least one additional small alkyl group attached to the nitrogen in the side chain, wherein uptake by kidney cells is less than with a polypeptide having an amino acid sequence that does not comprise an additional small alkyl group attached to a nitrogen on the side chain of a lysine at positions X12 and/or X26.

In some embodiments, the small alkyl group comprises a monomethyl, dimethyl, trimethyl, or isopropyl group.

In one aspect, the disclosure provides, in a method of treating an individual with cancer, the improvement comprising reducing one or more off-target effects or toxicity measures by administering a composition, compound, pharmaceutical composition, or conjugate as provided herein, wherein the amino acid sequences of the polypeptide comprise amino acids corresponding to positions X12 and/or X26 of SEQ ID NO: 195, and wherein X12 and/or X26 comprise a lysine with at least one additional small alkyl group attached to the nitrogen in the side chain, wherein uptake by kidney cells is less than with a polypeptide having an amino acid sequence that does not comprise an additional small alkyl group attached to a nitrogen on the side chain of a lysine at positions X12 and/or X26.

In one aspect, the disclosure provides, in a method of treating an individual with cancer, the improvement comprising achieving a reduction in concentration of R in a kidney tissue in the presence of a composition, compound, pharmaceutical composition, or conjugate as provided herein, wherein the amino acid sequences of the polypeptide comprise amino acids corresponding to positions X12 and/or X26 of SEQ ID NO: 195, and wherein X12 and/or X26 comprise a lysine with at least one additional small alkyl group attached to the nitrogen in the side chain, wherein uptake by kidney cells is less than with a polypeptide having an amino acid sequence that does not comprise a small alkyl group attached to a nitrogen on the side chain of a lysine at positions X12 and/or X26, as compared to the concentration of R in the kidney tissue in the absence the composition, compound, pharmaceutical composition or conjugate.

In some embodiments, the reduction in concentration of R in the kidney tissue is measured by urine output of R as measured by percent of administered radiation recovered or by detection as measured by a cell-based in vitro assay, or an in vivo detection assay.

In some embodiments, the administration of the composition can be repeated at least 2, 3, 4, 5, 6, or 7 times more in the presence of the composition having 90% identity to at least 40 amino acids of SEQ ID NO: 195 including a modified lysine at positions corresponding to X12 and/or X26 of SEQ ID NO: 195 than in the presence of an A or K at positions corresponding to X12 and/or X26.

In one aspect, the disclosure provides, in a method of reducing uptake by a kidney tissue of a composition the improvement comprising administering a composition comprising (a) a radionuclide therapeutic comprising at least a polypeptide and a radionuclide (R); wherein the polypeptide has at least 90% identity to 40 amino acids of SEQ ID NO: 195 and/or has a modified lysine at positions corresponding to X12 and/or X26 of SEQ ID NO: 195, such that in the presence of the modified lysine, the radionuclide is less concentrated in the kidney tissue than in the absence of the polypeptide.

In one aspect, the disclosure provides a method comprising administering to a subject in need thereof a compound that binds to Nectin-4 and includes one or two modified lysines at positions corresponding to X12 and/or X26, respectively, of SEQ ID NO: 195, wherein administration of the compound having a miniprotein with the one or two modified lysines reduces one or more off target effects, toxicity grades, and/or uptake and/or retention in a kidney tissue as compared to a compound having an alanine or unmodified lysine at a position corresponding to X12 and an unmodified lysine at a position corresponding to X26.

In one aspect, the disclosure provides a method of treating an individual having or suspected of having a Nectin-4-positive cancer, the method comprising administering to the individual: a means for blocking uptake of a radiotherapeutic to kidney tissue, and a linker, chelator, and, a radionuclide.

In some embodiments, the means for binding to kidney tissue binds to Nectin-4 and includes one or two modified lysines at positions corresponding to X12 and/or X26, respectively, of SEQ ID NO: 195 and/or has at least 90% identity to 40 amino acids of SEQ ID NO: 195 and/or has a modified lysine at positions corresponding to X12 and/or X26 of SEQ ID NO: 195. In some embodiments, the means for binding to kidney tissue binds to Nectin-4 and includes one or two modified lysines at positions corresponding to X12 and/or X26, respectively, of SEQ ID NO: 195 and/or has at least 90% identity to 35 contiguous amino acids of SEQ ID NO: 195 and/or has a modified lysine at positions corresponding to X12 and/or X26 of SEQ ID NO: 195.

In some embodiments, the means blocks uptake and/or retention of the radiotherapeutic into the kidney as compared to a means that does not include one or two modified lysines at positions corresponding to X12 and/or X26, respectively, of SEQ ID NO: 195 and/or has at least 90% identity to 40 amino acids of SEQ ID NO: 195 and/or has a modified lysine at positions corresponding to X12 and/or X26 of SEQ ID NO: 195.

In some embodiments, the means blocks uptake and/or retention of the radiotherapeutic into the kidney as compared to a means that does not include one or two modified lysines at positions corresponding to X12 and/or X26, respectively, of SEQ ID NO: 195 and/or has at least 90% identity to 35 contiguous amino acids of SEQ ID NO: 195 and/or has a modified lysine at positions corresponding to X12 and/or X26 of SEQ ID NO: 195.

In some embodiments, the means is a radiotherapeutic. In some embodiments, the radiotherapeutic is targeted to a tumor or a population of cancer cells. In some embodiments, the radiotherapeutic targeted to the tumor or the population of cancer cells is at a greater concentration than in the absence of the means for binding to kidney tissue. In some embodiments, the radionuclide therapeutic comprises a polypeptide that targets Nectin-4.

In some embodiments, the radionuclide therapeutic comprises or consists of a compound selected from C3-C293 or C298-C307.

In some embodiments, the radionuclide of the radiotherapeutic is selected from Ac-225, Cu-64, Ga-68, In-111, Lu-177, or Pb-212.

Formulation and Administration

In various aspects formulations of the pharmaceutical compositions of the present disclosure include parenteral e.g., subcutaneous, intravenous, intraarterial, intramuscular, intradermal, intraperitoneal, intraurethral, interperitoneal, and intrathecal administration. See for instance, Remington: The Science and Practice of Pharmacy, Lippincott Williams & Wilkins 22nd ed. (2013) described in more detail.

In some embodiments, a pharmaceutical composition comprising a miniprotein of the present disclosure is administered to a subject in need thereof. In some embodiments, the subject has or is at risk of having cancer. By way of non-limiting example, in some embodiments, the cancer is selected from breast cancer, ovarian cancer, melanoma, pancreatic cancer, peripheral neuroma, glioblastoma, adrenocortical carcinoma, AIDS-related lymphoma, anal cancer, bladder cancer (e.g., early stage bladder cancer), meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, determination of an appropriate dose and regimen of a miniprotein of the present disclosure can be made by the clinician, e.g., using parameters or factors known or suspected in the art to affect treatment or predicted to affect treatment. Actual dosage levels of the active ingredients (e.g., miniproteins as provided by compositions of the present disclosure may be vaned so as to obtain an amount of the active ingredient which is effective to achieve the desired therapeutic response for a particular patient, composition, and mode of administration, without being toxic to the patient. In some embodiments, the selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

In some embodiments, administration is by one or more routes including, but not limited to bronchial, buccal, enteral, interdermal, transdermal, intra-arterial, intradermal, intragastric, intramedullary, intramuscular, intranasal, intraperitoneal, intrathecal, intraurethral, intravenous, intraventricular, within a specific organ and/or tissue, mucosal, nasal, oral, rectal, subcutaneous, sublingual, topical, tracheal (including by intratracheal instillation), transdermal, vaginal and vitreal.

In some embodiments, administration may comprise or consist of continuous dosing (e.g., intravenous administration) for a period of time.

In some embodiments, administration may comprise or consist of intermittent dosing.

In some embodiments, administration may comprise or consist of dosing separated by a selected period of time and with one or more doses, based on clinical response and/or activity following one or more doses.

In some embodiments, administration of the decoy will enable higher dosing with one or more radiotherapeutic treatments, as compared to dosing in the absence of a decoy with no change in toxicity grade of the therapeutic.

In some embodiments, administration is to a subject is suffering from a relevant disease, disorder or condition. In some embodiments, administration is to a subject susceptible to or at risk of developing a disease, disorder, or condition. In some such embodiments, a subject displays one or more symptoms or characteristics of a disease, disorder or condition. In some embodiments, a subject does not display any symptom or characteristic of a disease, disorder, or condition. In some such embodiments, a subject is someone with one or more features characteristic of susceptibility to or at risk of developing a disease, disorder, or condition. In some embodiments, a subject has received a diagnosis of a disease, disorder, or condition.

In some embodiments, the present disclosure provides a method for modulating biological activity of Nectin-4 in a subject. In some such embodiments, the method comprises administering a pharmaceutical composition provided by the disclosure to the subject in an amount effective to modulate the biological activity of Nectin-4 in the subject.

In some embodiments, the present disclosure provides a method for treating or preventing cancer in a subject. In some embodiments, the method comprises administering to the subject a pharmaceutical composition provided by the present disclosure, wherein the miniprotein of the pharmaceutical composition selectively binds to Nectin-4 in an amount effective to treat or prevent the cancer in the subject.

In some embodiments, the present disclosure provides methods and compositions that bind target (e.g., Nectin-4) and are capable of activating or inhibiting immune cell response. In some embodiments, compositions are administered for the treatment of non-small-cell lung cancer (NSCLC), cutaneous squamous cell carcinoma, pancreatic cancer, primary hepatocellular carcinoma, colorectal carcinoma, clear cell renal carcinoma, breast cancer and prostate cancer. (Yang, S et al., Int J of Bio Sci 2020 Mar. 25 (16): 11; 1767-1773).

In some embodiments, the present disclosure provides a method for detecting the presence or extent of a cancer in a subject. In some such embodiments, the method comprises measuring a level of Nectin-4 in a sample comprising one or more cells from the subject; wherein detection of the level of Nectin-4 in the subject relative to the levels of the Nectin-4 in one or more control subjects is indicative of the presence or extent of the cancer.

In some embodiments, a composition provided by the present disclosure is used to downregulate an inhibitory immune response in a subject. For example, in some embodiments, a miniprotein the present disclosure specifically binds such that it may be used to deliver a cytotoxic payload and promote cellular cytotoxicity of T cells for specific Nectin-4-expressing (e.g., tumor) cells. (See Goodman A, Patel S P, Kurzrock R Nat Rev Clin Oncol. 2017 April; 14(4):203-220.) In some such embodiments, the miniprotein modulates IFN-γ IL-2, IL-10, and IL-13 production during T-cell activation.

Kits

In one aspect, provided herein are kits comprising a pharmaceutical composition described herein for therapeutic, imaging, or diagnostic uses. In some embodiments, kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a cancer, the kit comprising: (a) a dosage of pharmaceutical composition described herein and (b) instructions for using the in methods of therapy methods disclosed herein. In certain embodiments for treating human patients, the kit comprises a pharmaceutical composition described herein comprising a miniprotein conjugate described herein.

In some embodiments, a kit comprises a cold miniprotein conjugate as provided herein (i.e., a miniprotein conjugate that contains a cold-metal surrogate of a radionuclide), and instructions for chelation of the miniprotein conjugate to the cold-metal surrogate of a radionuclide. In some embodiments, a cold-metal surrogate is a natural isotope of an element that is not radioactive. In some embodiments, an element may have more than one natural isotope that is not radioactive. In some embodiments, the kit comprises a hot miniprotein conjugate as provided herein (i.e., a miniprotein conjugate described herein comprising the radionuclide), with instructions for administration to a subject. In some embodiments, a kit comprises a combination of cold miniprotein conjugates (i.e., a miniprotein conjugate described herein comprising a cold-metal conjugate), and hot miniprotein conjugates as provided herein (i.e., a miniprotein conjugate described herein comprising the radionuclide), with instructions for administration to a subject. In some embodiments, a kit comprises a combination of a miniprotein conjugate that is conjugated to a radionuclide as provided herein and a miniprotein conjugate that is conjugated to a cold-metal surrogate as provided herein. In some embodiments, the cold miniprotein conjugates assists in diluting the hot miniprotein conjugate. In some embodiments, a cold miniprotein conjugate is combined with a hot miniprotein conjugate so a smaller radioactive dose can be administered to a patient. In some embodiments, the kit comprises less than 5% hot miniprotein conjugates and greater than 95% cold miniprotein conjugates, less than 10% hot miniprotein conjugates and greater than 90% cold miniprotein conjugates, less than 20% hot miniprotein conjugates and greater than 80% cold miniprotein conjugates, less than 30% hot miniprotein conjugates and greater than 70% cold miniprotein conjugates, less than 40% hot miniprotein conjugates and greater than 60% cold miniprotein conjugates, less than 50% hot miniprotein conjugates and greater than 50% cold miniprotein conjugates, less than 60% hot miniprotein conjugates and greater than 40% cold miniprotein conjugates, less than 70% hot miniprotein conjugates and greater than 30% cold miniprotein conjugates, less than 80% hot miniprotein conjugates and greater than 20% cold miniprotein conjugates, or less than 90% hot miniprotein conjugates and greater than 10% cold miniprotein conjugates. In some embodiments, the percentage of hot miniprotein conjugates refers to the specific activity of the radiolabeled product.

In some embodiments, a kit comprises a combination of miniprotein conjugate that is radiolabeled as provided herein and a miniprotein that is not conjugated. In some embodiments, a kit comprises a combination of miniprotein conjugate that is radiolabeled with an alpha emitter radionuclide as provided herein and a miniprotein that is radiolabeled with a beta emitter radionuclide. In some embodiments, the kit comprises less than 5% beta emitter miniprotein conjugates and greater than 95% alpha miniprotein conjugates, less than 10% beta emitter miniprotein conjugates and greater than 90% alpha emitter miniprotein conjugates, less than 20% beta emitter miniprotein conjugates and greater than 80% alpha emitter miniprotein conjugates, less than 30% beta emitter miniprotein conjugates and greater than 70% alpha emitter miniprotein conjugates, less than 40% beta emitter miniprotein conjugates and greater than 60% alpha emitter miniprotein conjugates, less than 50% beta emitter miniprotein conjugates and greater than 50% alpha emitter miniprotein conjugates, less than 60% beta emitter miniprotein conjugates and greater than 40% alpha emitter miniprotein conjugates, less than 70% beta emitter miniprotein conjugates and greater than 30% alpha emitter miniprotein conjugates, less than 80% beta emitter miniprotein conjugates and greater than 20% alpha emitter miniprotein conjugates, or less than 90% beta emitter miniprotein conjugates and greater than 10% alpha emitter miniprotein conjugates.

In some embodiments, the present disclosure provides kits comprising a miniprotein as provided herein. In some embodiments, the kit comprises compositions for detecting the Nectin-4 miniprotein (e.g., conjugation to one or more detectable moieties).

In some embodiments, a kit comprises a label indicating the intended use of the contents of the kit and instructions for use. The term label includes any writing, or recorded material supplied on or with the kit, or which otherwise accompanies the kit.

In some embodiments, a kit provided herein has a date of certification equal to or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days. In some embodiments, a kit provided herein has a date of certification equal to or greater than 1, 2, 3, 4, 5, 6, 7, 8, 9, 10, 11, 12, 13, 14, 15, 16, 17, 18, 19, or 20 days. In some embodiments, a kit provided herein has a date of certification equal to or greater than 1, 2, 3, 4, 5, 6, 7, 8, 9, or 10 days. For example, the date of certification can refer to a regulatory certification that establishes the time range in which the kit remains efficacious and/or safe. In some embodiments, the pharmaceutical composition comprised in the kit maintains stability and/or efficacy for equal to or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days such that the pharmaceutical composition can be administered to a patient. In some embodiments, the pharmaceutical composition comprised in the kit maintains stability and/or efficacy for equal to or greater than 1, 2, 3, 4, 5, 6, 7, 8, 9, 10, 11, 12, 13, 14, 15, 16, 17, 18, 19, or 20 days such that the pharmaceutical composition can be administered to a patient. In some embodiments, the pharmaceutical composition comprised in the kit maintains stability and/or efficacy for equal to or greater than 1, 2, 3, 4, 5, 6, 7, 8, 9, or 10 days such that the pharmaceutical composition can be administered to a patient.

In some embodiments, the present disclosure provides a kit for treating, monitoring, or diagnosing a subject having or suspected of having cells overexpressing Nectin-4, the kit comprising. (a) a unit of a pharmaceutical composition described herein and (b) instructions for using the in methods of administration disclosed herein. In certain embodiments for treating human patients, the kit comprises a pharmaceutical composition described herein comprising miniprotein as provided herein.

The disclosure also provides kits comprising one or more compositions as disclosed herein. A kit of the disclosure can comprise a composition represented by the formula selected from one or more of M-L-C-R, M-L-C, M-C-R, M-L-R, M-C, M-L, and M-R, wherein M comprises a miniprotein (M), L comprises linker (L), C comprises a chelator (C), and R comprises a radionuclide (R); a decoy, wherein the decoy blocks uptake and/or retention of the composition into the kidney. In some embodiments, the decoy is the same scaffold as the scaffold of M. In certain embodiments, when R is present, it can be supplied separately from any of M. C. L, or the decoy. In some embodiments, when R is present, it can be added just prior to use. In some embodiments, a decoy can be supplied in a molar or mass excess as compared to a composition comprising a miniprotein provided herein. For example, a decoy may be supplied in a molar or mass excess.

The molar or mass excess may be enough to be administered in an excess of about 1, 2, 5, 10, 100, 250, 500, 750, 1000, 1250, 1500, 1750, 2000, 2500, 3000, 3500, 4000, 4500, 5000, 5500, 6000, 6500, 7000, 7500, 8000, 8500, 9000, 9500, 10000 or more times greater than the amount of miniprotein of a conjugate (e.g., a compound, a radiotherapeutic, etc. as provided herein). In some embodiments, a molar excess is no greater than 10,000 fold greater than the amount of miniprotein of a conjugate.

In some embodiments, the disclosure provides a kit comprising a polypeptide and instructions for use, wherein the polypeptide has an amino acid sequence as set forth in a polypeptide of any one of a composition, compound, pharmaceutical composition or conjugate as provided herein.

In some embodiments, the kit further comprises one or more of a linker, chelator, and radionuclide.

In some embodiments, the linker comprises or consists of a polyethylene glycol (PEG) linker of PEG4, PEG, PEG2, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- or (PEG)n, wherein n is from 1 to 10, (Gly)1-10, or any fragment or combination via covalent bond thereof. In some embodiments, the chelator comprises or consists of DOTA, NOPO, Crown. Macropa, lead specific chelator (PSC), N-succinimidyl 3-(tri-n-butylstannyl)benzoate (BuSTB), or N-succinimidyl 3-trimethylstannylbenzoate (MeSTB).

In some embodiments, prior to use of the kit, the compound is labeled with a radionuclide, wherein the radionuclide is chelated to the chelator to produce a composition with a formula M-L-C-R. In some embodiments, the radionuclide is selected from Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, Tb-165, or At-211. In some embodiments, the radionuclide is Ac-225, Cu-64, Ga-68, In-111, Lu-177, or Pb-212.

In some embodiments, if the polypeptide of the kit has an amino acid comprising any of those set forth in any one of SEQ ID NOs: 83, 85, 93, 99, 134, 138, 145, 155, 161-176, 195, or 200 the polypeptide further comprises a linker, wherein the linker is PEG4, and a chelator, wherein the chelator is DOTA. In some embodiments, when present, the linker is attached to the N-terminus amino acid of the polypeptide. In some embodiments, the C-terminal amino acid of the polypeptide is not cysteine. In some embodiments, when present, the chelator is attached to either the polypeptide or the linker. In some embodiments, when present, the radionuclide is attached to the chelator. In some embodiments, when present, the radionuclide is attached to the N-terminus amino acid of the polypeptide.

Certain Exemplary Embodiments

In some embodiments, the present disclosure provides compositions comprising a miniprotein (M), an optional linker (L), and one or both of a chelator (C) and a radionuclide (R), represented a formula selected from M)x-L-C-R, (M)x-L-C, (M)x-C-R, (M)x-L-R, (M)x-C, (M)x-L, and (M)x-R. In some embodiments, the miniprotein comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer. In some embodiments, the binder comprises or consists of a linear polypeptide and/or a non-disulfide sequence. In some embodiments, M is characterized in that it comprises 100 amino acids. In some preferred embodiments, the miniprotein is characterized in that it comprises (i) no more than 100 amino acids and/or 12 kDa; (ii) at least one secondary structure elements; (iii) a sequestered hydrophobic core; and/or displays cooperative folding. In some embodiments, the miniprotein comprises no more than about 100 amino acids or less, 90 amino acids, 85 amino acids, 80 amino acids, 75 amino acids, 70 amino acids, 65 amino acids, 60 amino acids, 55 amino acids, 50 amino acids, 45 amino acids, 40 amino acids, 35 amino acids, 30 amino acids, 25 amino acids, 20 amino acids, or 15 amino acids. In some embodiments, the miniprotein comprises at least one disulfide bridge.

In some embodiments, the present disclosure provides compositions represented by the formula L-C, wherein L comprises or consists of a linker, C comprises or consists of a chelator, and wherein the linker is designed to be conjugated to a polypeptide.

In some embodiments, the present disclosure provides compositions represented by the formula L-C-R, wherein L comprises or consists of a linker, C comprises or consists of a chelator, and R comprises or consists of a radionuclide, and wherein the composition is capable of being conjugated to a miniprotein. In some embodiments, L comprises or consists of a polyethylene glycol (PEG) linker of PEG4, PEG2, PEG6, PEG8, PEG12, PEG24, lys(MPB)-PEG4, PEG36, an ester linker, an amide linker, a maleimide linker, a succinimidyl-4-N-maleimidomethyl) cyclohexane-1-carboxylate (SMCC) linker, a propanoic acid linker, a dTyr-Gly-Phe (yGF) linker, a caproleic acid linker, or (Gly)n-(γGlu)n- or (PEG)n, wherein n is from 1 to 10, $(Gly)_{1-10}$ (SEQ ID NO: 240), or any fragment or combination via covalent bond thereof. In some embodiments, C comprises or consists of tetrazacyclododecane-1,4,7,10-tetraacetic acid (DOTA), Crown, NOPO, PSC, N-succinimidyl 3-(tri-n-butylstannyl)benzoate (BuSTB), N-succinimidyl 3-trimethylstannylbenzoate (MeSTB), or Macropa as set forth as follows:

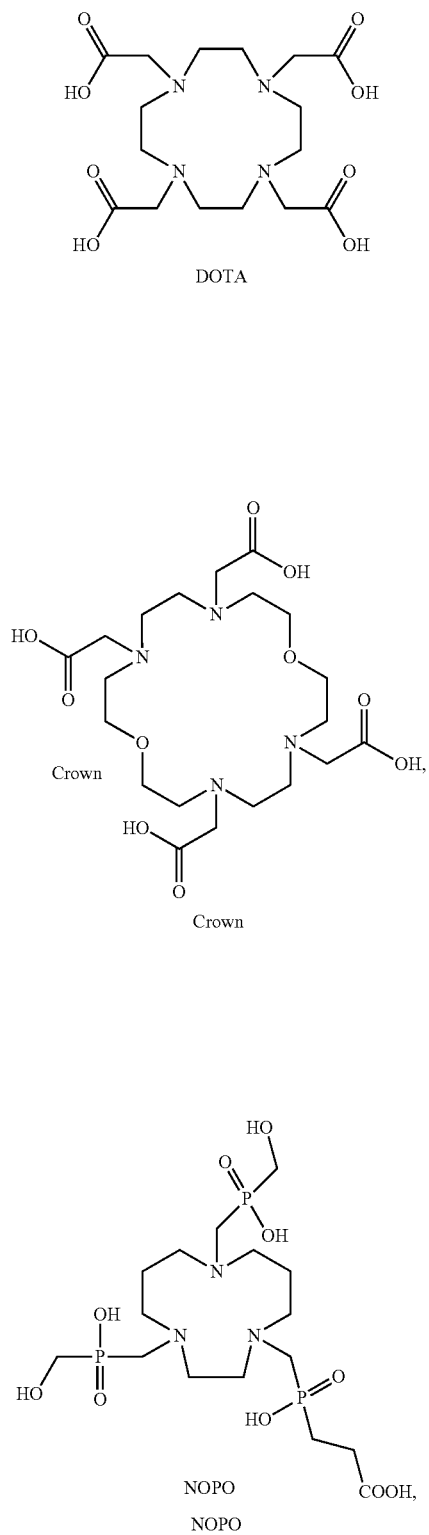

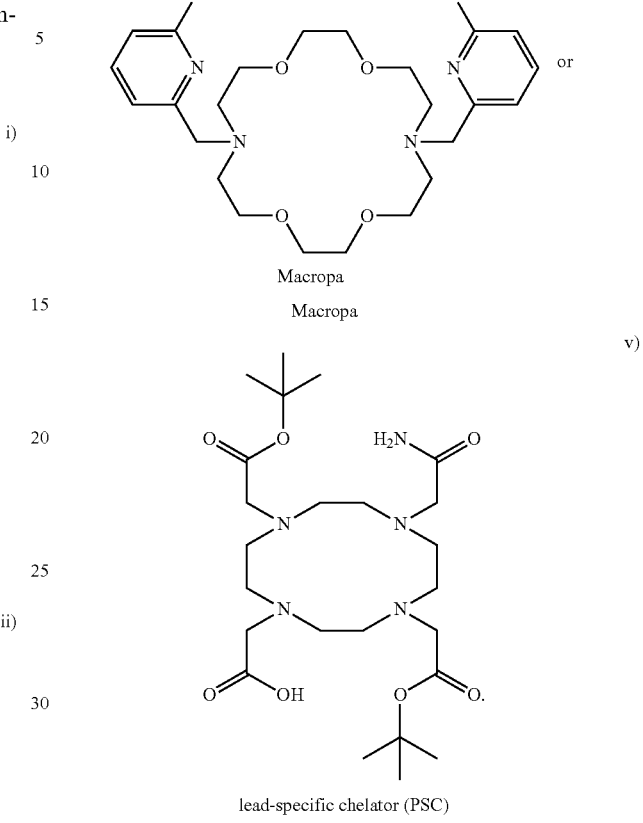

In some embodiments. C comprises or consists of tetrazacyclododecane-1,4,7,10-tetraacetic acid (DOTA), Crown, NOPO, PSC, N-succinimidyl 3-(tri-n-butylstannyl)benzoate (BuSTB), N-succinimidyl 3-trimethylstannylbenzoate (MeSTB), or Macropa, or a derivative thereof In some embodiments, the present disclosure provides isolated constructs or pharmaceutically acceptable salts thereof comprising a miniprotein, optional linker, and at least one of a chelator or radionuclide. In some embodiments. R comprises or consists of Ac-225, in-111, Ga-68, Pb-212, Lu-177, Cu-67, Cu-64, La-132, La-135, Ce-134, F-18, I-131. I-124, Pb-203, Th-232, Bi-123, or At-211. In some embodiments, the composition comprises at least one additional component. In some embodiments, the composition can penetrate tumor tissue. In some embodiments, the miniprotein specifically binds to a target. In some embodiments, the composition displays μm or nM binding affinity to the target (e.g., in an in vitro assay, e.g., in a cell isolated from a tumor e.g., in vivo, e.g., to a tumor.) In some embodiments, the composition displays μm or nM binding affinity to the target, e.g., in an in vitro assay. In some embodiments, the composition binds to the target with an affinity of 1 pM to 100 nM e.g., as measured by an in vitro binding assay. In some embodiments, the composition binds to the target with an affinity of 100 pM to 10 nM, e.g., as measured by an in vitro binding assay. In some embodiments, the miniprotein binding to the target modulates biological function. In some embodiments, the miniprotein binding to the target does not elicit an immune response. In some embodiments, the immune response includes a systemic immune response or a local immune response. In some embodiments, the target is located in, on, or near a cell. In some embodiments, the target is a protein expressed on the surface of the cell. In some embodiments, the cell is a tumor cell. In some embodiments, the tumor cell is a solid tumor cell. In some embodiments, the cell is a human cell. In some embodiments, the target is Nectin-4. In some embodiments, the miniprotein selectively binds to Nectin-4 or a portion thereof.

i) DOTA

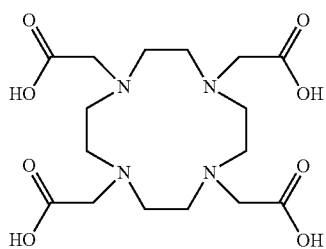

ii) Crown

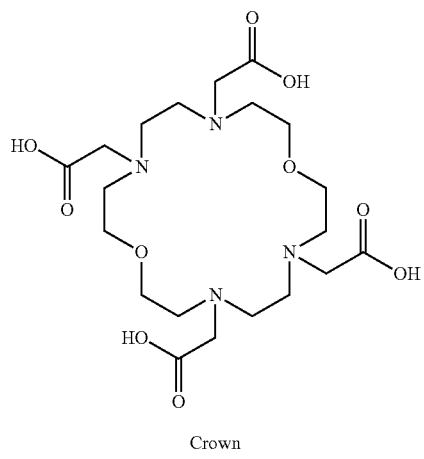

Crown iii) NOPO

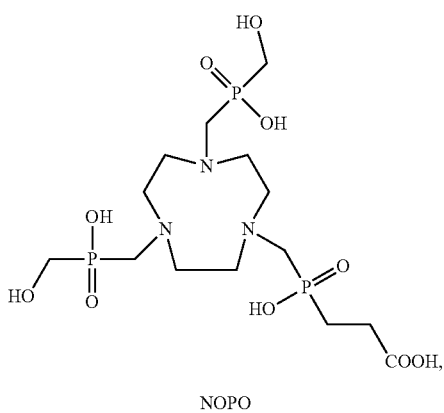

NOPO iv) Macropa

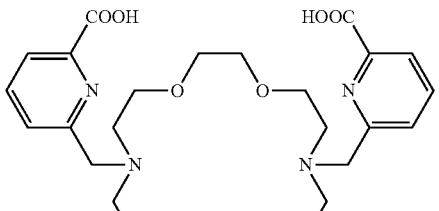

or

Macropa v) lead-specific chelator (PSC)

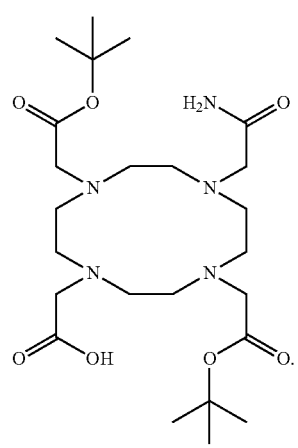

In some embodiments, the chelator covalently attaches to the miniprotein. In some embodiments, the chelation efficiency is >90%. In some embodiments, when R is present, the radionuclide is an alpha-emitter. In some embodiments, the radionuclide is Ac-225, In-111, Ga-68, Pb-212, Lu-177, Cu-67, Cu-64, La-132, La-135, Ce-134, F-18, I-131, I-124, Pb-203, Th-232, Bi-123, or At-211. In some embodiments, the miniprotein specifically binds to a target. In some embodiments, the target is Nectin-4. In some embodiments, the Nectin-4 is expressed on a cell. In some embodiments, the cell is a human cell. In some embodiments, the human cell is a tumor cell. In some embodiments, the tumor cell is a solid tumor cell. In some embodiments, the miniprotein comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer. In some embodiments, the miniprotein comprises one or more disulfide bonds. In some embodiments, the miniprotein is characterized in that it has nM or sub-nM binding affinity on the target in vivo or in a cell-based assay. In some embodiments, the miniprotein a binding affinity of 1 pM to 100 nM to Nectin-4 on a cell line expressing human Nectin-4. In some embodiments, the miniprotein a binding affinity of 100 pM to 10 nM to Nectin-4 on a cell line expressing human Nectin-4. In some embodiments, the miniprotein has an amino acid sequence no more than about 100 amino acids or less, 90 amino acids, 85 amino acids, 80 amino acids, 75 amino acids, 70 amino acids, 65 amino acids, 60 amino acids, 55 amino acids, 50 amino acids. 45 amino acids, 40 amino acids, 35 amino acids, 30 amino acids, 25 amino acids, 20 amino acids, or 15 amino acids. In some embodiments, the miniprotein does not elicit an immune response or wherein the immune response elicited is tolerable. In some embodiments, the pharmaceutical composition comprises high tumor tissue penetration. In some embodiments, the pharmaceutical composition is not taken up and/or retained in the kidney or liver. In some embodiments, the pharmaceutical composition does not bind megalin and/or cubulin. In some embodiments, the pharmaceutical composition is internalized in a cell expressing human Nectin-4.

In some embodiments, the present disclosure provides methods of treating a subject in need thereof comprising administering a composition comprising a miniprotein (M), an optional linker (L), and one or both of a chelator (C) and a radionuclide (R). In some embodiments, when L is present, L comprises or consists of a polyethylene glycol (PEG) linker, an ester linker, an amide linker, a maleimide linker, a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a dTyr-Gly-Phe (yGF) linker, a caproleic acid linker, or any fragment or combination thereof. In some embodiments, when C is present, C comprises or consists of NOPO, Crown, PSC, N-succinimidyl 3-(tri-n-butylstannyl)benzoate (BuSTB), N-succinimidyl 3-trimethylstannylbenzoate (MeSTB), Macropa or tetrazacyclododecane-1,4,7,10-tetraacetic acid (DOTA) as set forth as follows:

i)

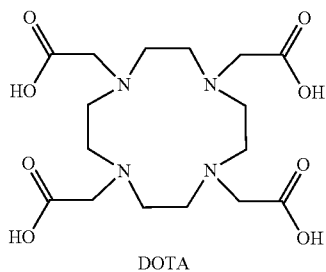

DOTA ii)

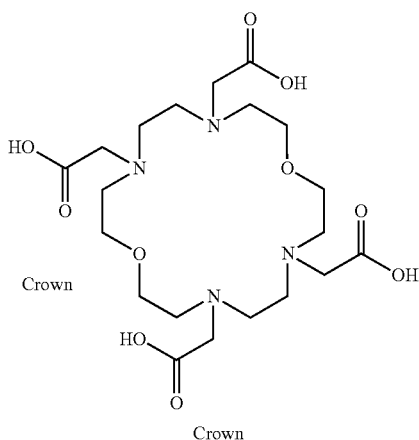

Crown

Crown iii)

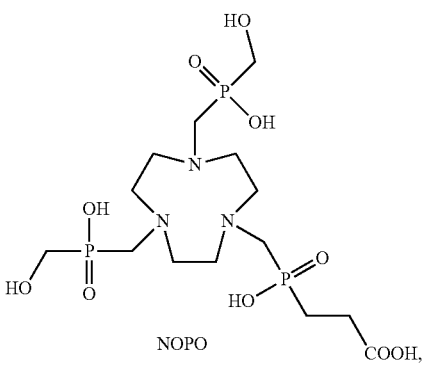

NOPO iv)

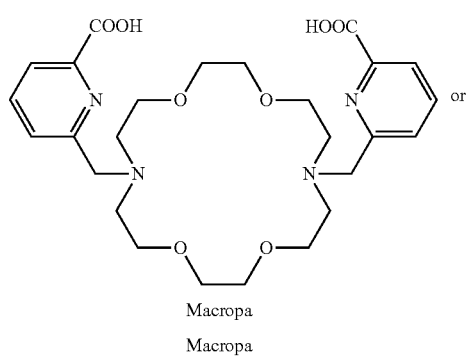

Macropa

Macropa or v)

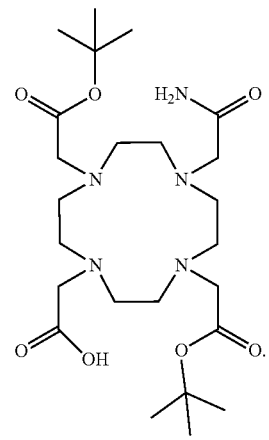

lead-specific chelator (PSC)

In some embodiments, when R is present. R comprises or consists of Ac-225, In-111, Ga-68, Pb-212, Lu-177, Cu-67, Cu-64, La-132, La-135, Ce-134, F-18, I-131, I-124, Pb-203, Th-232, Bi-123, Sm-153, Ra-225, Tb-165, or At-211. In some embodiments, M comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer. In some embodiments. M is characterized in that it comprises no more than 100 amino acids. In some preferred embodiments, M is characterized in that it comprises (i) no more than 100 amino acids and/or 12 kDa; (ii) at least two secondary structure elements; (iii) a sequestered hydrophobic core; and/or displays cooperative folding. In some embodiments, a composition comprising M, optional L, and one or both of C and R, for use in a method of the present disclosure, comprises at least one additional component. In some embodiments, the composition can penetrate tumor tissue. In some embodiments, the miniprotein comprises no more than about 100 amino acids or less. 90 amino acids, 85 amino acids, 80 amino acids, 75 amino acids, 70 amino acids, 65 amino acids, 60 amino acids, 55 amino acids, 50 amino acids, 45 amino acids, 40 amino acids, 35 amino acids, 30 amino acids, 25 amino acids, 20 amino acids, or 15 amino acids. In some embodiments, the miniprotein comprises at least one disulfide bridge. In some embodiments, the miniprotein specifically binds to a target. In some embodiments, the composition displays mm or nM binding affinity to the target in an in vitro assay. In some embodiments, the miniprotein a binding affinity of 1 pM to 100 nM to Nectin-4 on a cell line expressing human Nectin-4. In some embodiments, the composition binds to the target with an affinity of 100 pM to 10 nM, e.g., as measured by an in vitro binding assay. In some embodiments, the composition is characterized in that it has high tissue penetrating properties relative to a composition comprising a full-size protein that binds to the same target. In some embodiments, the miniprotein binding to the target modulates biological function. In some embodiments, administration of the composition does not elicit an immune response. In some embodiments, the immune response includes a systemic immune response or a local immune response. In some embodiments, the target is located in, on, or near a cell. In some embodiments, the target is a protein expressed on the surface of the cell. In some embodiments, the cell is a tumor cell. In some embodiments, the tumor cell is a solid tumor cell. In some embodiments, the cell is a human cell. In some embodiments, the target is Nectin-4. In some embodiments, the subject has or is at risk of having cancer. In some embodiments, the cancer is selected from breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors. In some embodiments, after administration of the composition, the cancer is treated. In some embodiments, the composition is administered intravenously or subcutaneously.

In some embodiments, the present disclosure provides methods of characterizing miniprotein conjugates comprising contacting a population of cells expressing Nectin-4 with a miniprotein conjugate and measuring one or more of: (i) binding affinity; (ii) internalization; (iii) binding specificity; (iv) immune response as characterize by secretion or expression of one or more cytokines.

In some embodiments, the present disclosure provides methods of detecting cancer comprising administering to a subject a composition comprising a Nectin-4-specific miniprotein, further comprising a detectable moiety, and detecting the presence and/or quantity of the composition in the subject, wherein detection of the miniprotein is associated with risk of developing or having cancer. In some embodiments, the miniprotein of the composition is designed for conjugation to one or more additional components. In some embodiments, the composition penetrates tumor tissue. In some embodiments, the miniprotein of the composition comprises less than 12 kDa. In some embodiments, the miniprotein of the composition comprises no more than about 100 amino acids or less, 90 amino acids, 85 amino acids, 80 amino acids, 75 amino acids, 70 amino acids, 65 amino acids, 60 amino acids, 55 amino acids, 50 amino acids. 45 amino acids, 40 amino acids, 35 amino acids, 30 amino acids, 25 amino acids, 20 amino acids, or 15 amino acids. In some embodiments, the miniprotein of the composition comprises at least one disulfide bond. In some embodiments, the miniprotein that does not comprise multiple cysteine residues such as, for example, a miniprotein comprising a single cysteine residue. In some such embodiments, the miniprotein may form a dimer, such as with another miniprotein (e.g., self-dimerization). In some embodiments, two miniproteins are linked together to form a dimer. In other embodiments, two miniproteins are each linked to a linker to form a dimer. In other embodiments, two different miniproteins are each linked to a linker to form a dimer.

In some embodiments, the method identifies a subject as having a cancer. In some embodiments, the cancer is selected from breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma. Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors. In some embodiments, a cancer cell from the subject expresses Nectin-4, or a portion thereof. In some embodiments, the expression of the target is higher in the cancer cell than in a non-cancer cell.

In some embodiments, the present disclosure provides methods of targeting a population of cancer cells expressing Nectin-4, the method comprising: (i) determining a level of expression of a target in a population of cancer cells; (ii) administering to a subject in need thereof a composition according to the present disclosure or a pharmaceutical composition according to the present disclosure, wherein the composition specifically binds Nectin-4; and (iii) wherein the composition targets the Nectin-4-expressing cells and is internalized into the Nectin-4 expressing cells; (iv) wherein the patient is treated after the administering as compared to prior to the administering and (v) wherein the treatment preferentially damages cells expressing Nectin-4.

In some embodiments, a composition provided herein preferentially damages (e.g., to a greater extent, e.g., kills) cells expressing Nectin-4 as compared to cells not expressing Nectin-4. In some embodiments, a composition provided herein does not damage cells not expressing Nectin-4. In some embodiments, administration comprises further administering a decoy. In some embodiments, damage to cells not expressing Nectin-4 is reduced after administration of the polypeptide or the composition in presence of a decoy as compared to the administration in the absence of a decoy.

In some embodiments, the present disclosure provides pharmaceutical compositions comprising a conjugate in accordance with the present disclosure and a pharmaceutically acceptable excipient. In some embodiments, the composition is formulated for parenteral or oral administration.

In some embodiments, the present disclosure provides methods of imaging a cell or population of cells in a subject having or suspected of having cancer comprising administering a pharmaceutical composition in accordance with the present disclosure and detecting a presence of the pharmaceutical composition in the subject.

In some embodiments, the present disclosure provides methods of treating cancer in a subject in need thereof comprising administering a pharmaceutical composition in accordance with the present disclosure to the subject, wherein the subject is treated and non-cancer cells of the subject are not killed.

In one aspect, the disclosure provides a kit comprising a composition represented by the formula selected from one or more of M-L-C-R, M-L-C, M-C-R, M-L-R, M-C, M-L, and M-R, wherein M comprises a miniprotein (M), L comprises a linker (L), C comprises a chelator (C), and R comprises a radionuclide (R); a decoy peptide, wherein the decoy peptide blocks or reduces uptake of the composition into the kidney. In some embodiments, the decoy peptide can have a higher affinity for kidney tissue than for tumor tissue. In certain embodiments, when R is present, it can be supplied separately from any of M, C, L, or the decoy. In some embodiments, when R is present, it can be added just prior to use. In some embodiments, binding affinities can be measured in vitro or in vivo, including such as by methods provided herein. In some embodiments, a decoy peptide can be supplied in a molar excess as compared to a composition comprising a miniprotein provided herein.

In another aspect, the disclosure provides a kit comprising a composition represented by the formula selected from one or more of M-L-C-R, M-L-C, M-C-R, M-L-R. M-C, M-L, and M-R, wherein M comprises a miniprotein (M), L comprises linker (L), C comprises a chelator (C), and R comprises a radionuclide (R); a decoy, wherein the decoy blocks uptake of the composition into a kidney tissue. In some embodiments, the decoy and the composition are administered to a subject in need thereof. In some embodiments, after the administration, the decoy appears in a higher concentration in the kidney tissue than in the tumor tissue as measured by % ID/g. In some embodiments, when R is present, it is supplied separately from any of M. C. L, or the decoy. In some embodiments, the decoy is selected from C295-C297 and/or a miniprotein having an amino acid sequence comprising or consisting of an amino acid sequence of any of SEQ ID NOs: 295-297. In some embodiments, the decoy is supplied in a molar excess as compared to the composition, which molar excess may optionally be selected from a 10, 100, 1000, or more molar excess. In some embodiments, the R, if present, is added just prior to use.

The present disclosure is further illustrated by the following examples which should not be construed as further limiting. The contents of all references cited throughout this application are expressly incorporated herein by reference.

Additional Embodiments

In some embodiments, the disclosure provides a polypeptide, comprising: an amino acid sequence, wherein the amino acid sequence comprises Formula III: CX2YX4X5X6FFTX10LX12X13LX15GX17DICX21Y IX24X25X26FX28X29X30X31X32 X33CIX36EIX39X40X41LGCX45 (SEQ ID NO: 216), wherein X45 is an optional amino acid or carboxy terminus comprising an —OH and wherein X2 is D or E; X4 is D or K, X5 is E or G; X6 is Q or E; X10 is A or E, X12 is A, K, E, or S; X13 is A, R, Q, K, S, or Cit; X15 is Y, R, or K, X17 is A, D, G, or S; X21 is D, Q, E, L, S, or Y; X24 is Q, L, K, or S; X25 is A, Q, E, K; X26 is A, Q, K, S, Y, T, D, R, (Kme3), (sRme2), Cit, Arg(NO2), OH-Norleu, or Norleu; X28 is A, N, Q, D, K, or S; X29 is N, T, or Y; X30 is L, Y, or V; X31 is P or E; X32 is A, D, Q, G, or K; X33 is D, Q, E, I, or L; X36 is Q, K or E; X39 is L or R; X40 is D, Q, or E; X41 is N, K or Q; and X45, when present as an amino acid is S.

In some embodiments, the amino acid sequence satisfies one or more of: wherein if X4 is K, then X26 is K and X15 is Y; wherein if X4 is D, then X26 is one of N. T, D. R, (Kme3), (sRme2), Cit, or Arg(NO2), or X26 is K, X10 is E, X36 is K, and X39 is R; or wherein one or more leucine in the amino acid sequence is Leu-13C6,15N.

In some embodiments, X2 is E; X4 is D, X5 is E; X6 is E; X10 is A, X12 is A or K; X13 is R X15 is R; X17 is G; X21 is Y; X24 is Q; X25 is A; X26 is Q. K, or S; X28 is A or Q; X29 is T or Y; X30 is L or V; X31 is P; X32 is G; X33 is L; X36 is E; X39 is L; X40 is D; X41 is N or Q; and X45 is S.

In some embodiments, the amino acid sequence shares at least 90% identity to any one of SEQ ID NOs: 3-158 or 177-215. In some embodiments, the amino acid sequence shares at least 90% identity to any one of SEQ ID NOs: 78, 83, 85, 93, 96, 99, 134, 138, 145, 155, or 178-215. In some embodiments, the amino acid sequence shares at least 90% identity to any one of SEQ ID NOs: 78, 83, 85, 93, 99, 103, 134, 138, 145, 155, 194, 195, 200, 203, or 204. In some embodiments, the amino acid sequence shares at least 90% identity to any one of SEQ ID NOs: 78, 99, 103, 195, or 200.

In some embodiments, the amino acid sequence shares 100% identity to any one of SEQ ID NOs: 3-158 or 177-215.

In some embodiments, the amino acid sequence shares 100% identity to any one of SEQ ID NOs: 78, 83, 85, 93, 99, 103, 134, 138, 145, 155, 194, 195, 200, 203, or 204.

In some embodiments, the amino acid sequence shares 100% identity to any one of SEQ ID NOs: 78, 83, 85, 99, 103, 195, or 200.

In some embodiments, the disclosure provides a polypeptide, comprising: an amino acid sequence, wherein the amino acid sequence comprises Formula IV: CX2X3X4X5X6X7X8X9X10X11X12X13X14X15X16 X17X18X19CX21X22X23X24X25 X26X27X28X29X30X31X32X33CX35X36X37X3 8X39X40X41X42X43CS (SEQ ID NO: 233) wherein X2 is E, G, A, S, T, D, N, K, R, Y, F, V, I, or W; X3 is Y, P, G, A, S, T, Q, K, H, F, W, V, M, D, E, L, or I; X4 is D, S, N, R, Y, L, M, G, T, or L X5 is E, G, D, Q, F, W, V, L, I, M, K, or R; X6 is E, P, G, D, Q, N, K, Y, F, W, or V; X7 is F, Y, or W; X8 is F, Y, W, 1, or M; X9 is T, P, A, S, D, Q, N, K, Y, F, V, M, E, R, or L; X10 is A, S, E, N, K, F, W, V, L, I, G, T, D, Q, R, or H; X11 is L, T, I, or M; X12 is K, L, G, A, S, T, N, R, H, F, W, V, I, or M; X13 is R, G, A, S, E, N, K, Y, W, L, I, or M; X14 is L, T, V, I, or M; X15 is R, T, Q, K, L, I, M, or V; X16 is G, D, N, K, R, H, Y, W, V, L, I, or M; X17 is G, P, A, S, T, D, Q, N, R, H, Y, F, W, V, L, or M; X18 is D, P, G, A, T, E, Q, N, K, Y, F, W, V, I, M, or S; X19 is I, P, A, T, D, N, Y, V, M, G, or Q; X21 is Y, S, T, D, E, K, F, W, L, I, or V; X22 is Y or E; X23 is I, A, T, Y, V, L, M, or F; X24 is Q, P, G, D, K, R, H, F, V, L, I, M, or N; X25 is A, P, S, D, E, Q, K, R, Y, F, W, V, I, M, or T; X26 is S, P, G, A, D, Q, N, R, F, V, L, I, T, E, or W; X27 is F, P, A, S, K, H, Y, W, M, E, or V; X28 is Q, P, G, A, S, D, E, K, R, H, Y, W, V, L, F, or I; X29 is Y, P, A, S, E, Q, N, K, F, W, L, I, M, T, or V; X30 is L, P, G, A, S, T, E, N, R, H, F, W, V, 1, M, Q, or K; X31 is P, G, A, T, D, E, Q, N, K, R, H, Y, V, S, W, L, or I; X32 is G, A, S, D, N, R, H, Y, L, I, or V; X33 is L, P, G, A, S, D, E, N, K, R, H, Y, F, W, V, I, or M; X35 is I, P, S, D, E, N, K, R, Y, F, W, L, or M; X36 is E, G, A, S, T, D, Q, K, R, H, Y, W, L, I, or M; X37 is E, P, G, A, S, T, N, K, R, H, Y, F, W, V, or D; X38 is I, A, S, E, Y, F, W, V, L, T, or H; X39 is L, S, T, E, N, R, H, Y, F, W, V, M, D, or I; X40 is D, G, A, S, E, Q, R, H, F, W, V, L, I, M, N, or K; X41 is N, G, A, S, D, Q, R, H, Y, F, V, L, I, M, P, or K; X42 I, L, P, G, Q, N, H, F, W, I, M, or S; and X43 is G, P, A, T, D, N, K, R, Y, F, W, V, I, or Q.

In some embodiments, X2 is E or W; X3 is Y, D, E, L, or I; X4 is D, G, T, or I; X5 is E, K, or R; X6 is E; X7 is F; X8 is F; X9 is T, E, R, or L; X10 is A, G, T, D, Q, R, or H; X11 is L or M; X12 is K, X13 is R; X14 is L or M; X15 is R or V; X16 is G; X17 is G; X18 is D or S; X19 is I, G, or Q; X21 is Y or V; X22 is Y; X23 is I or F; X24 is Q or N; X25 is A or T; X26 is S, T, E, or W; X27 is F, E, or V; X28 is Q, F, or I; X29 is Y, T, or V; X30 is L, Q, or K; X31 is P, S, W, L, or I; X32 is G or V; X33 is L or M; X35 is I; X36 is E; X37 is E or D; X38 is I, T, or H; X39 is L, D, or I; X40 is D, N, or K; X41 is N, P, or K; X42 is L or S; and X43 is G or Q.

In some embodiments the disclosure provides a polypeptide, comprising an amino acid sequence, wherein the amino acid sequence comprises Formula V: CX2X3X4X5X6X7X8X9X10X11X12X13X14X15X16 X17X18X19CX21X22X23X24X25 X26X27X28X29X30X31X32X33CX35X36X37X38X 39X40X41X42X43CS (SEQ ID NO: 234) wherein X2 is E, P, G, A, S, T, Q, N, K, R, H, Y, F, W, V, L, I, or M; X3 is Y, P, G, A, S, T, D, E, Q, N, K, R, H, F, W, V, L, I, or M; X4 is D, P, G, A, S, T, E, Q, N, K, R, H, Y, F, W, V, L, I, or M; X5 is E, P, G, S, T, D, Q, N, K, R, H, F, W, V, L, I, M, or Y; X6 is E, P, G, A, S, T, D, Q, N, K, R, H, F, W, V, L, I, M, or Y; X7 is F, Y, or W; X8 is F, T, Y, W, V, L, I, or M; X9 is T, P, G, S, D, E, N, K, R, H, Y, F, V, L, I, M, A, Q, or W; X10 is A, P, G, S, T, D, E, Q, N, K, R, H, Y, F, W, V, L, I, or M; X11 is L, A, V, I, or M; X12 is A, G, S, D, E, Q, N, K, R, H, Y, F, W, V, L, I, M, or T; X3 is R, P, S, T, D, E, Q, K, H, Y, F, V, L, M, G, A, N, W, or I; X14 is L, A, T, F, V, I, or M; X15 is R, Q, Y, F, W, V, L, I, M, or K; X16 is G, P, A, S, T, D, E, Q, N, K, R, H, Y, F, W, V, L, M, or 1; X17 is G, P, A, S, T, D, E, Q, N, K, R, H, Y, W, V, L, I, M, or F; X18 is D, P, G, A, S, T, E, Q, N, K, R, H, Y, W, V, I, M, F, or L; X19 is 1, P, G, A, S, T, D, E, Q, N, K, R, Y, F, W, V, L, M, or H; X21 is Y, P, G, A, S, T, D, E, Q, N, K, R, H, F, W, V, L, I, or M; X22 is Y, H, or F; X23 is I, G, A, S, T, Y, W, V, L, M, or F; X24 is Q, G, S, T, D, E, N, K, R, H, F, W, V, L, I, M, P, A, or Y; X25 is A, G, S, T, D, E, Q, N, K, R, H, Y, F, W, V, M, P, L, or I; X26 is K, P, G, A, S, T, D, E, Q, N, R, H, Y, F, W, V, L, I, or M; X27 is F, P, G, A, S, T, D, E, Q, N, K, R, H, Y, W, V, L, I, or M; X28 is Q, P, G, A, S, T, D, E, N, K, R, H, Y, F, W, V, L, I, or M; X29 is Y, P, G, A, S, T, D, E, N, K, R, H, F, W, V, L, I, M, or Q; X30 is L, P, G, A, S, T, D, E, Q, N, K, R, H, Y, F, W, V, 1, or M; X31 is P, G, A, S, T, D, Q, N, K, R, H, Y, F, V, I, M, E, W, or L; X32 is G, P, A, S, T, D, E, Q, N, K, R, H, Y, F, W, V, L, I, or M; X33 is L, P, G, A, S, T, D, E, Q, N, K, R, H, Y, F, W, V, I, or M; X35 is I, P, G, A, S, T, D, E, Q, N, K, R, Y, F, W, V, L, M, or H; X36 is E, P, G, A, S, D, Q, N, R, H, F, V, L, I, M, T, K, Y, or W; X37 is E, P, G, A, S, T, D, N, K, H, Y, F, W, V, L, I, M, Q, or R; X38 is I, P, G, A, S, T, E, Q, N, K, H, Y, F, W, V, L, or M; X39 is L, G, A, S, T, D, E, Q, N, K, R, H, Y, W, V, I, M, or F; X40 is D, P, G, A, S, E, Q, N, K, R, H, Y, F, W, V, L, I, M, or T; X41 is N, P, G, A, S, T, D, E, Q, K, R, H, Y, F, W, V, L, I, or M; X42 is L, G, A, S, T, E, Q, N, K, R, H, Y, F, W, V, 1, or M; and X43 is G, P, A, S, T, D, E, Q, N, K, R, H, Y, F, W, V, L, M, or I.

In some embodiments, X2 is E; X3 is Y; X4 is D; X5 is E or Y; X6 is E or Y; X7 is F; X8 is F; X9 is T, A, Q, or W; X10 is A; X11 is L; X12 is A or T; X13 is R, G, A, N, W, or I; X14 is L; X15 is R or K; X16 is G or I; X17 is G or F; X18 is D, F, or L; X19 is I or H; X21 is Y; X22 is Y; X23 is I or F; X24 is Q, P, A, or Y; X25 is A, P, L, or I; X26 is K; X27 is F; X28 is Q; X29 is Y or Q; X30 is L; X31 is P, E, W, or L; X32 is G; X33 is L; X35 is I or H; X36 is E, T, K, Y, or W; X37 is E, Q, or R; X38 is I or M X39 is L or F; X40 is D or T; X41 is N; X42 is L; and X43 is G or I.

In some embodiments, the disclosure provides a polypeptide comprising: an amino acid sequence, wherein the amino acid sequence comprises Formula VI: CX2X3X4X5X6X7X8X9X10X11X12X13X1 4X15X16X17X18X19CX21X22X23X24X25 X26X27X28X29X30X31 X32X33CX35X36X37X38X39X40X41X42X43CS (SEQ ID NO: 235) wherein X2 is E, P, G, A, S, T, D, Q, N, K, R, H, Y, W, V, L, I, M, or F; X3 is Y, P, G, A, S, T, D, E, Q, K, R, H, F, W, V, L, I, M, or N; X4 is D, P, A, S, E, Q, N, or H; X5 is E, P, G, A, T, Q, N, K, R, H, Y, F, W, V, L, I, M, S, or D; X6 is Q, P, G, A, S, T, D, E, N, K, R, H, Y, F, W, V, L, I or M, X7 is F, Y, or W; X8 is F, Y, W, V, I, or M, X9 is T, P, G, A, S, D, Q, N, R, H, Y, F, V, L, I, M, E, K, or W; X10 is A, G, T, D, E, Q, N, K, R, H, W, L, I, M, S, Y, F, or V; X11 is L, V, I, or M; X12 is A, G, S, T, D, K, R, Y, F, W, V, L, I, M, E, Q, N, or H; X13 is R, G, A, S, T, D, Q, N, K, H, Y, F, W, V, L, M, E, or I; X14 is L, T, V, I, or M; X15 is R, Q, K, I, or M; X16 is G, A, T, D, E, Q, N, K, R, H, Y, W, V, L, I, M, P, S, or F; X17 is G, P, A, S, T, D, E, Q, N, K, R, H, Y, F, W, V, L, I, or M; X18 is D, P, G, A, S, T, E, N, K, H, Y, F, L, M, Q, or K; X19 is I, G, A, S, T, E, Q, N, K, R, H, Y, F, W, V, L, or M; X21 is Y, P, G, A, S, D, E, Q, N, K, R, H, F, W, V, L, I, M, or T; X22 is Y; X23 is I, A, T, Y, F, W, V, L, or M; X24 is Q, P, A, S, D, E, N, K, H, Y, F, W, V, L, I, G, T, R, or M; X25 is E, P, G, A, S, T, D, Q, N, R, H, Y, F, W, V, L, I, M, or K; X26 is Q, G, A, S, T, E, N, K, R, H, F, W, V, L, 1, M, D, or Y; X27 is F, Y, W, L, I, M, or V; X28 is A, P, G, S, T, D, E, Q, N, K, R, H, Y, W, V, L, I, M, or F; X29 is T, P, G, A, S, D, E, Q, K, R, H, Y, F, W, V, L, I, M, or N; X30 is V, P, G, A, T, D, E, N, K, R, H, Y, F, W, I, M, S, Q, or L; X31 is P, G, A, S, T, D, E, Q, N, K, R, H, Y, F, W, V, L, I, or M; X32 is G, P, A, T, D, E, Q, N, K, R, H, Y, F, W, V, L, I, M, or S; X33 is L, P, G, A, S, T, D, E, Q, K, R, H, Y, F, W, V, I, M, or N; X35 is I, P, G, A, S, T, D, E, Q, N, K, R, H, Y, F, W, L, M, or V; X36 is E, P, G, A, S, T, D, N, R, H, F, W, V, L, I, M, K, or Y; X37 is E, P, G, A, S, T, D, N, R, H, Y, W, V, L, I, M, Q, K, or F; X38 is I, G, A, S, E, Q, H, Y, W, V, L, M, P, or F; X39 is L, G, A, S, T, D, E, Q, N, K, H, Y, F, W, V, I, M, or R; X40 is D, P, G, A, S, T, E, Q, N, R, H, Y, F, W, L, I, M, or K; X41 is Q, P, G, A, S, T, D, E, N, K, R, H, Y, F, W, V, L, I, or M; X42 is L, G, A, S, T, E, Q, R, H, Y, F, V, I, M, N, or W; and X43 is G, P, A, S, T, D, E, Q, N, K, F, W, V, L, I, M, R, H, or Y.

In some embodiments, X2 is E or F; X3 is Y or N; X4 is D; X5 is E, S, or D; X6 is Q; X7 is F; X8 is F; X9 is T. E, K, or W; X10 is A. S, Y, F, or V; X11 is L; X12 is A. E, Q, N, or H; X13 is R. E, or I; X14 is L; X15 is R; X16 is G, P. S, or F; X17 is G; X18 is D, Q, or K; X19 is 1; X21 is Y or T X22 is Y; X23 is I or M; X24 is Q, G, T, R, or M; X25 is E or K; X26 is Q, D, or Y; X27 is F or V; X28 is A or F; X29 is T or N; X30 is V. S. Q, or L; X31 is P; X32 is G or S; X33 is L or N; X35 is I or V; X36 is E, K, or Y; X37 is E, Q, K, or F; X38 is I, P, or F; X39 is L or R; X40 is D or K; X41 is Q; X42 is L, N, or W; and X43 is G, R, H, or Y.

In some embodiments, the disclosure provides a polypeptide comprising an amino acid sequence, wherein the amino acid sequence comprises Formula VII: CX2X3X4X5X6X7X8X9X10X11X12X13X14X15X16X17X18X19CX21X22X23X24X25 X26X27X28X29X30X31X32X33CX35X36X37X38X39X40X41X42X43CS (SEQ ID NO: 236) wherein X2 is E, P, G, A, S, T, D, Q, N, K, R, H, Y, W, V, L, I, M, or F; X3 is Y, P, G, A, S, T, D, E, Q, N, K, H, W, V, L, I, M, R, or F; X4 is D, P, G, A, T, Q, N, K, R, H, Y, F, W, V, L, M, S, E, or I; X5 is E, P, G, A, S, T, D, N, K, R, H, Y, F, W, V, L, Q, I or M; X6 is E, P, G, A, D, Q, N, R, H, Y, F, W, V, L, M, S, K, or 1; X7 is F, Y, or W; X8 is F, H, Y, W, V, L, I, or M; X9 is T, P, G, S, D, E, Q, N, K, R, H, Y, F, W, V, L, I, M, or A; X10 is A, P, G, T, D, E, Q, N, K, R, H, Y, F, W, V, L, M, S, or I; X11 is L, A, V, I, or M; X12 is A, P, G, S, T, D, E, K, R, H, Y, F, W, V, L, I, M, Q, or N; X13 is R, P, A, S, T, D, E, Q, N, K, H, Y, F, W, V, L, I, M, or G; X14 is L, T, F, V, M, or I; X15 is R, Q, N, K, H, F, W, V, L, I, M, or Y; X16 is G, P, A, T, D, E, Q, N, K, R, H, Y, F, W, V, L, I, M, or S; X17 is G, A, S, D, E, Q, N, K, R, H, Y, F, W, V, L, I, M, or P; X18 is D, P, G, A, S, T, E, Q, N, K, R, Y, F, W, V, L, 1, M, or H; X19 is I, P, G, A, S, T, D, E, Q, N, K, R, H, Y, F, W, V, L, or M; X21 is Q, P, G, A, S, D, E, N, R, H, Y, F, W, V, I, M, T, K, or L; X22 is Y, H, or F; X23 is 1, G, A, S, T, Y, F, V, L, or M; X24 is Q, P, G, A, S, E, N, K, R, H, Y, F, W, V, L, I, M, T, or D; X25 is A, P, G, S, T, D, E, Q, N, K, H, Y, F, W, V, L, I, M, or R; X26 is Kme3, K, P, G, S, T, D, E, Q, N, R, H, Y, F, W, V, L, M, A, or I; X27 is F, P, G, A, S, D, E, Q, N, K, R, H, Y, W, V, L, I, or M; X28 is Q, P, G, A, S, T, D, E, N, K, R, H, Y, F, W, V, L, I, or M; X29 is Y, P, G, A, S, T, D, E, Q, N, K, R, H, F, W, V, L, I or M; X30 is L, P, G, A, T, D, E, Q, N, K, R, H, Y, F, W, V, 1, M, or S; X31 is P, G, S, T, D, E, Q, N, K, R, H, Y, W, V, L, I, M, A, or F; X32 is A, P, G, S, T, D, Q, N, K, R, H, Y, F, W, V, I, M, E, or L; X33 is L, P, G, A, S, T, D, E, Q, N, K, R, H, Y, F, W, V, 1, or M; X35 is I, P, G, A, S, T, D, E, Q, N, R, H, Y, W, V, L, M, K, or F; X36 is E, P, A, S, T, D, Q, N, K, R, H, Y, F, W, V, L, I, M, or G; X37 is E, G, A, S, D, Q, N, K, R, H, Y, F, W, V, L, I, M, or T; X38 is I, P, G, A, S, T, D, E, Q, N, H, Y, F, W, V, L, M, K, or R; X39 is L, G, A, S, T, D, E, Q, N, R, H, Y, W, V, I, M, K, or F; X40 is D, P, G, A, S, T, E, Q, K, R, H, Y, W, V, L, I, M, N, or F; X41 is N, P, G, A, S, T, D, E, Q, K, R, H, Y, F, W, V, L, I, or M; X42 is L, G, A, S, D, E, Q, N, K, R, H, Y, F, W, V, I, or M; and X43 is G, P, A, S, T, D, E, Q, N, K, R, H, Y, F, W, V, L, I, or M.

In some embodiments, X2 is E or F; X3 is Y, R, or F; X4 is D, S, E, or 1; X5 is E, Q, I, or M; X6 is E, S, K, or I; X7 is F or W; X8 is F; X9 is T or A; X10 is A, S, or 1; X11 is L; X12 is A, Q, or N; X13 is R or G; X14 is L or I; X15 is R or Y; X16 is G or S; X17 is G or P; X18 is D or H; X19 is 1; X21 is Q, T, K, or L; X22 is Y; X23 is I; X24 is Q, T, or D; X25 is A or R; X26 is Kme3 or K, A, or 1; X27 is F; X28 is Q; X29 is Y; X30 is L or S; X31 is P, A, or F; X32 is A, E, or L; X33 is L; X35 is I, K, or F; X36 is E or G; X37 is E or T; X38 is I, K, or R; X39 is L, K, or F; X40 is D, N, or F; X41 is N; X42 is L or M; and X43 is G.

In some embodiments, the polypeptide comprises one or more of a linker, chelator, and radionuclide. In some embodiments, the linker comprises or consists of a polyethylene glycol (PEG) linker of PEG2, PEG, PEG4, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n- (SEQ ID NO: 239) or (PEG)n, wherein n is from 1 to 10, $(Gly)_{1-10}$ (SEQ ID NO: 240), or any fragment or combination via covalent bond thereof.

In some embodiments, the chelator comprises or consists of DOTA, NOPO, Macropa, lead specific chelator (PSC), N-succinimidyl 3-(tri-n-butylstannyl)benzoate (BuSTB), N-succinimidyl 3-trimethylstannylbenzoate (MeSTB), or Crown.

In some embodiments, a radionuclide is selected from Ac-225, Cu-64, Lu-177, Pb-212, Ga-68, In-111, Cu-67, La-132, La-135, Ce-134, F-18, I-131, I-124, Pb-203, Th-232, Bi-123, or At-211.

In some embodiments, if the polypeptide comprises any one of SEQ ID NO: 83, 85, 93, 99, 134, 138, 145, 155, then the poly peptide further comprises a linker, wherein the linker is PEG4, and a chelator, wherein the chelator is DOTA.

In some embodiments, when present, the linker is attached to the C-terminal end of the polypeptide. In some embodiments, when present, the chelator is attached to either the polypeptide or the linker. In some embodiments, when present, the radionuclide is attached to the chelator.

In some embodiments, the polypeptide comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer.

In some embodiments, the polypeptide comprises at least one disulfide bridge. In some embodiments, the polypeptide selectively binds to Nectin-4 or a portion thereof. In some embodiments, the polypeptide exhibits a binding affinity of 10 pM to 200 nM, 10 pM to 100 nM, or 10 nM to 100 nM to Nectin-4, or a portion thereof, in vivo or in a cell-based assay.

In some embodiments, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a miniprotein (M). L comprises a linker (L). C comprises a chelator (C), R comprises a radionuclide (R), and x is 1, 2, 3, or 4, wherein M comprises an amino acid sequence of any one of SEQ ID NO: 216-237.

In some embodiments, the amino acid sequence satisfies one or more of: wherein if X2 is K, then X13 is K and X8 is Y; wherein if X2 is D, then X13 is one of N. T, D, R, (Kme3), (sRme2), Cit, or Arg(NO2), or X13 is K, X5 is E. X20 is K, and X21 is R; or wherein one or more leucine in the amino acid sequence is Leu-13C6,15N.

In some embodiments, the amino acid sequence shares at least 90% identity to any one of SEQ ID NOs: 3-158 or 177-215.

In some embodiments, the amino acid sequence shares at least 90% identity to any one of SEQ ID NOs: 78, 83, 85, 93, 96, 99, 134, 138, 145, 155, or 178-215. In some embodiments, the amino acid sequence shares 100% identity to any one of SEQ ID NOs: 78, 83, 85, 93, 96, 99, 134, 138, 145, 155, or 178-215. In some embodiments the composition comprises any one of C218-C293. In some embodiments, the amino acid sequence shares 90% identity to any one of SEQ ID NOs: 78, 83, 85, 99, 103, 195, or 200. In some embodiments, the amino acid sequence shares 100% identity to any one of SEQ ID NO: 78, 83, 85, 99, 103, 195, or 200. In some embodiments, the composition comprises any one of C218-C293.

In some embodiments, the disclosure provides a composition comprising a formula selected from one or more of (M)x-L-C-R, (M)x-L-C, (M)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, wherein M comprises an amino acid sequence of any one of SEQ ID NOs: 233, 234, or 237. In some embodiments, when L is present, L comprises or consists of a polyethylene glycol (PEG) linker of PEG4, PEG, PEG2, PEG6, PEG8, PEG12, PEG24, lys(MPB)-PEG4, PEG36, an ester linker, an amide linker, a maleimide linker a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a dTyr-Gly-Phe (yGF) linker, a caproleic acid linker, or (Gly)n-(gGlu)n-(SEQ ID NO: 239) or (PEG)n, wherein n is from 1 to 10. (Gly)$_{1-10}$ (SEQ ID NO: 240), or any fragment or combination via covalent bond thereof.

In some embodiments, when C is present, C comprises or consists of:

i) DOTA

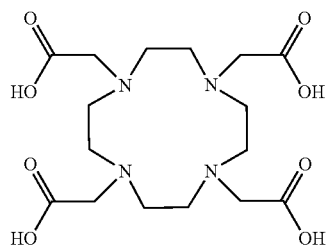

ii) Crown

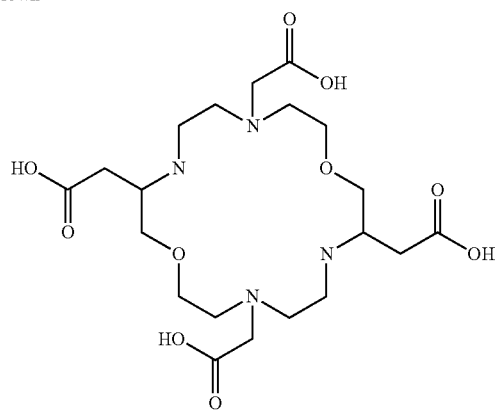

Crown iii) NOPO

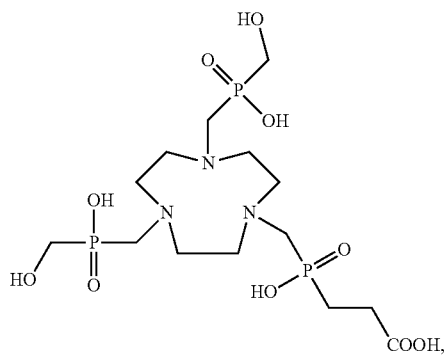

NOPO iv) Macropa

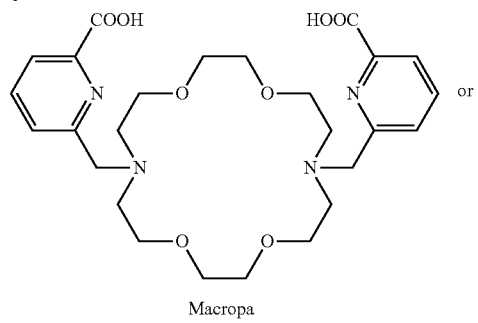

Macropa or v) lead-specific chelator (PSC)

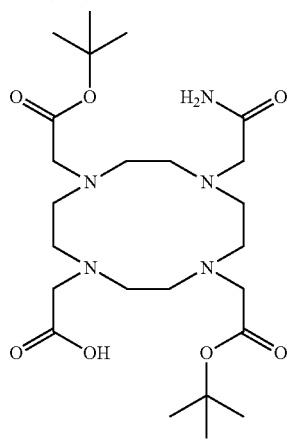

vi) N-succinimidyl 3-(tri-n-butylstannyl)benzoate (BuSTB), or
vii) N-succinimidyl 3-trimethylstannylbenzoate (MeSTB).

In some embodiments, when R is present, R comprises or consists of Ac-225, In-111, Ga-68, Pb-212, Lu-177, Cu-67, Cu-64, La-132, La-135, Ce-134, F-18, I-131, I-124, Pb-203, Th-232, Bi-123, or At-211.

In some embodiments, the linker is attached to the C-terminal end of the miniprotein. In some embodiments, the chelator is attached to either the miniprotein or the linker. In some embodiments, when present, the radionuclide is attached to the chelator. In some embodiments, the miniprotein comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer.

In some embodiments, the miniprotein comprises at least one disulfide bridge.

In some embodiments, M selectively binds to Nectin-4 or a portion thereof. In some embodiments, M exhibits a binding affinity of 10 pM to 200 nM, 10 pM to 100 nM, or 10 nM to 100 nM to Nectin-4, or a portion thereof, in vivo or in a cell-based assay.

In some embodiments, the composition further comprises a second miniprotein. In some embodiments, the second miniprotein comprises an amino acid sequence of any one of SEQ ID NOs: 3-158, 177-215, or 216-237 (including amino acid substitutions as set forth in Table 1C, Table 2C, Table 2D, Table 2E, Table 2F, or Table 2G).

In some embodiments, the radionuclide (R) comprises a hot radionuclide, and the second polypeptide is conjugated to a cold-metal surrogate. In some embodiments the radionuclide (R) comprises an alpha emitter, and wherein the second polypeptide is conjugated to a beta emitter. In some embodiments the radionuclide (R) comprises a beta emitter, and wherein the second polypeptide is conjugated to an alpha emitter.

In some embodiments, the disclosure provides a composition comprising a plurality of miniprotein conjugates, wherein each miniprotein conjugate is represented by a formula selected from one or more of (M)x-L-C-R, (M)x-L-C, (M)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, wherein M comprises an amino acid sequence of any one of SEQ ID NOs: 3-158, 177-215, or 216-237. In some embodiments, a first subset of the plurality of miniprotein conjugates comprise radionuclides (R) comprising a hot radionuclide and a second subset of the plurality of miniprotein conjugates comprise radionuclides (R) comprising a cold-metal surrogate of a radionuclide. In some embodiments the first subset accounts for less than 10%, less than 20%, less than 30%, less than 40%, less than 50%, less than 60%, less than 70%, less than 80%, or less than 90% of miniprotein conjugates in the plurality of miniprotein conjugates.

In some embodiments, the second subset accounts for less than 10%, less than 20%, less than 30%, less than 40%, less than 50%, less than 60%, less than 70%, less than 80%, or less than 90% of miniprotein conjugates in the plurality of miniprotein conjugates.

In some embodiments, a first subset of the plurality of miniprotein conjugates comprise radionuclides (R) comprising an alpha emitter and a second subset of the plurality of miniprotein conjugates comprise radionuclides (R) comprising a beta emitter. In some embodiments, the first subset accounts for less than 10%, less than 20%, less than 30%, less than 40%, less than 50%, less than 60%, less than 70%, less than 80%, or less than 90% of miniprotein conjugates in the plurality of miniprotein conjugates. In some embodiments, the second subset accounts for less than 10%, less than 20%, less than 30%, less than 40%, less than 50%, less than 60%, less than 70%, less than 80%, or less than 90% of miniprotein conjugates in the plurality of miniprotein conjugates.

In some embodiments, the composition further comprises one or more isolated polypeptides comprising an amino acid sequence of any one of SEQ ID NOs: 3-158, 177-215, or 216-237. In some embodiments, the one or more isolated polypeptides are not conjugated to a linker, a chelator, or a radionuclide.

In some embodiments, the disclosure provides a composition comprising a miniprotein-drug conjugate, comprising a miniprotein and at least one drug moiety, wherein the miniprotein comprises an amino acid sequence selected from any one of SEQ ID NOs: 3-158, 177-215, or 216-237 (including amino acid substitutions as set forth in Table 1C, Table 2C, Table 2D, Table 2E, Table 2F, or Table 2G). In some embodiments, the miniprotein comprises an amino acid sequence selected from any one of SEQ ID NOs: 78, 83, 85, 93, 96, 99, 134, 138, 145, 155, or 177-215. In some embodiments, the miniprotein comprises an amino acid sequence selected from any one of SEQ ID NOs: 78, 83, 85, 93, 99, 103, 134, 138, 145, 155, 194, 195, 200, 203, or 204. In some embodiments, the amino acid sequence comprises a sequence of SEQ ID NO: 78, 83, 85, 99, 103, 195, or 200. In some embodiments, the drug moiety is selected from a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRMI, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, a topoisomerase inhibitor, an auristatin (e.g., monomethyl auristatin E), and an immunotoxin.

In some embodiments, the disclosure provides a composition comprising an isolated compound or pharmaceutically acceptable salt thereof comprising an optional linker (L), and one or more of a miniprotein (M), chelator (C) or radionuclide (R), wherein M comprises an amino acid sequence selected from any one of SEQ ID NOs: 3-158, 177-215, or 216-237 (including amino acid substitutions as set forth in Table 1C, Table 2C, Table 2D, Table 2E, Table 2F, or Table 2G). In some embodiments, M comprises a sequence selected from any one of SEQ ID NOs: 78, 83, 85, 93, 96, 99, 134, 138, 145, 155, or 178-215. In some embodiments. M comprises a sequence selected from any one of SEQ ID NOs: 78, 83, 85, 93, 99, 103, 134, 138, 145, 155, 194, 195, 200, 203, or 204. In some embodiments, M comprises a sequence of SEQ ID NOs: 78, 83, 85, 99, 103, 195, or 200.

In some embodiments, the disclosure provides a pharmaceutical composition comprising any composition provided herein and a pharmaceutically acceptable excipient. In some embodiments, the disclosure provides a use of any composition provided herein to treat cancer in a subject.

In some embodiments, the disclosure provides a method of treating a subject in need thereof comprising administering to the subject in need thereof any polypeptide or composition provided herein. In some embodiments, the method further comprises administering a decoy. In some embodiments, the decoy can be selected from any of C295-C297. In some embodiments, the decoy can have an amino acid sequence comprising an amino acid sequence of any of SEQ ID NOs: 209-211.

In some embodiments, administration of the decoy can reduce one or more off-target effects and/or can reduce uptake and/or retention of a polypeptide or composition as provided herein in kidney tissue. In some embodiments, administration of a polypeptide or composition as provided herein, to a subject in need thereof, does not elicit an immune response, or wherein the immune response elicited is tolerable to the subject. In some embodiments, the tolerable immune response includes a systemic immune response or a local immune response. In some embodiments, the subject is diagnosed as having cancer. In some embodiments, a cancer cell from the subject expresses Nectin-4, or a portion thereof. In some embodiments, expression of Nectin-4 is higher in the cancer cell than in a non-cancer cell.

In some embodiments, the polypeptide or composition is not taken up and/or retained in the kidney. In some embodiments, the polypeptide or composition is taken up and/or retained in the kidney, but administration of the decoy reduces uptake of the polypeptide or composition in the kidney as compared to administration without the decoy.

In some embodiments, the polypeptide or composition does not bind megalin and/or cubulin. In some embodiments, the polypeptide or composition is internalized in a cell expressing human Nectin-4.

In some embodiments, the cancer is selected from breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and Sezary syndrome, myelodysplastic syndromes, nasopharyngeal cancer, neuroblastoma, non-small cell lung cancer, small cell lung cancer, head and neck cancer, skin cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilms tumor and other childhood kidney tumors.

In some embodiments, the polypeptide or composition is administered intravenously or subcutaneously. In some embodiments, the decoy is administered intravenously or subcutaneously. In some embodiments, the administration of the decoy is before, concomitant with, or after the administration of the polypeptide or composition. In some embodiments, the cancer is treated after administration of the polypeptide or composition.

In some embodiments, the cancer is treated and one or more off-target effects and/or toxicity grade is reduced in the presence of the decoy as compared to treatment without administration of the decoy.

In some embodiments, the method further comprises administering a second polypeptide.

In some embodiments, the second polypeptide is a decoy. In some embodiments, the second polypeptide comprises an amino acid sequence of any one of SEQ ID NOs: 3-158, 177-215, or 216-237 (including amino acid substitutions as set forth in Table 1C, Table 2C, Table 2D, Table 2E, Table 2F, or Table 2G). In some embodiments, the second polypeptide is conjugated to a cold-metal surrogate of a radionuclide. In some embodiments, the second polypeptide is conjugated to an alpha emitter. In some embodiments, the second polypeptide is conjugated to a beta emitter.

In some embodiments, the method further comprises administering a second therapeutic agent selected from a treatment or component for use in monoclonal antibody therapy, a DNA damage response (DDR) inhibitor, immunotherapy, chemotherapy, radiotherapy, gene therapy, or RNA therapy. In some embodiments, the second therapeutic agent comprises an immunotherapy or radiotherapy treatment. In some embodiments, the DDR inhibitor is selected from an inhibitor of Serine-protein kinase ATM (ATM), Serine/threonine-protein kinase ATR (ATR), Serine/threonine-protein kinase Chk1 (CHK1/2), DNA-dependent protein kinase catalytic subunit (DNA-PK), Poly [ADP-ribose] polymerase (PARP), Membrane-associated tyrosine- and threonine-specific CDC2-inhibitory kinase (PKMYT1), RNA-directed DNA polymerase (POLO), and DNA repair protein RAD51 homolog 1 (RAD51). In some embodiments, the polypeptide or composition achieves a tumor/kidney (T/K) ratio greater than 0.5% ID/g, 1% ID/g, 1.5% ID/g, 2% ID/g, 2.5% ID/g, 3% ID/g, 3.5% ID/g, 4% ID/g.

4.5% ID/g, 5% ID/g, 5.5% ID/g, 6% ID/g, 6.5% ID/g, 7% ID/g, 7.5% ID/g, 8% ID/g, 8.5% ID/g, 9% ID/g, 9.5% ID/g, or 10% ID/g.

In some embodiments, the disclosure provides a method of targeting a population of cancer cells expressing Nectin-4. In some embodiments, the method comprises (i) determining a level of expression of Nectin-4 in a population of cancer cells, (ii) administering to a subject in need thereof a composition comprising any polypeptide or composition provided herein, wherein the polypeptide or composition specifically binds Nectin-4, and (iii) wherein the polypeptide or composition targets the Nectin-4-expressing cells and is internalized into the Nectin-4 expressing cells. In some embodiments, administering the polypeptide or the composition comprises administering the polypeptide or the composition to a patient in need thereof, and the patient is treated after the administering as compared to prior to the administering. In some embodiments, the method further comprises administering a decoy. In some embodiments, the treatment does not damage cells not expressing Nectin-4. In some embodiments, damage to cells not expressing Nectin-4 is reduced after administration of the polypeptide or composition in presence of a decoy as compared to the administration in the absence of a decoy.

In some embodiments, the disclosure provides a miniprotein conjugate comprising (i) a miniprotein (M) that specifically binds to Nectin-4, (ii) a chelator (C) conjugated to (M) through an optional linker (L), wherein (C) comprises DOTA, and (L), when present, comprises PEG, and (iii) a radionuclide (R) chelated to (C), wherein (R) is Actinium-225.

In some embodiments, the disclosure provides a miniprotein conjugate comprising (i) a miniprotein (M) that specifically binds to Nectin-4, (ii) a chelator (C) conjugated to (M) through an optional linker (L), wherein (C) comprises DOTA, and (L), when present, comprises PEG, and (iii) a radionuclide (R) chelated to (C), wherein (R) is Indium-111.

In some embodiments, the disclosure provides a miniprotein conjugate comprising (i) a miniprotein (M) that specifically binds to Nectin-4, (ii) a chelator (C) conjugated to (M) through an optional linker (L), wherein (C) comprises DOTA, and (L), when present, comprises PEG, and (iii) a radionuclide (R) chelated to (C), wherein (R) is Gallium-68.

In some embodiments, the disclosure provides a miniprotein conjugate comprising (i) a miniprotein (M) that specifically binds to Nectin-4, (ii) a chelator (C) conjugated to (M) through an optional linker (L), wherein (C) comprises DOTA, and (L), when present, comprises PEG, and (iii) a radionuclide (R) chelated to (C), wherein (R) is Copper-64.

In some embodiments, the disclosure provides a miniprotein conjugate comprising (i) a miniprotein (M) that specifically binds to Nectin-4, (ii) a chelator (C) conjugated to (M) through an optional linker (L), wherein (C) comprises DOTA, and (L), when present, comprises PEG, and (iii) a radionuclide (R) chelated to (C), wherein (R) is Iodine-131.

In some embodiments, the disclosure provides a miniprotein conjugate comprising (i) a miniprotein (M) that specifically binds to Nectin-4, (ii) a chelator (C) conjugated to (M) through an optional linker (L), wherein (C) comprises DOTA, and (L), when present, comprises PEG, and (iii) a radionuclide (R) chelated to (C), wherein (R) is Iodine-124.

In some embodiments, the disclosure provides a miniprotein conjugate comprising (i) a miniprotein (M) that specifically binds to Nectin-4, (ii) a chelator (C) conjugated to (M) through an optional linker (L), wherein (C) comprises DOTA, and (L), when present, comprises PEG, and (iii) a radionuclide (R) chelated to (C), wherein (R) is Lead-203.

In some embodiments, the disclosure provides a miniprotein conjugate comprising (i) a miniprotein (M) that specifically binds to Nectin-4, (ii) a chelator (C) conjugated to (M) through an optional linker (L), wherein (C) comprises DOTA, and (L), when present, comprises PEG, and (iii) a radionuclide (R) chelated to (C), wherein (R) is Thorium-232.

In some embodiments, the disclosure provides a miniprotein conjugate comprising (i) a miniprotein (M) that specifically binds to Nectin-4, (ii) a chelator (C) conjugated to (M) through an optional linker (L), wherein (C) comprises DOTA, and (L), when present, comprises PEG, and (iii) a radionuclide (R) chelated to (C), wherein (R) is Bismuth-213.

In some embodiments, M of miniproteins described herein comprises an amino acid sequence selected from any one of SEQ ID NOs: 158, 177-215, or 216-236 (including amino acid substitutions as set forth in Table 1C, Table 2C, Table 2D, Table 2E, Table 2F, or Table 2G). In some embodiments, M comprises an amino acid sequence selected from any one of SEQ ID NOs: 78, 83, 85, 93, 99, 134, 138, 145, 155, or 178-215. In some embodiments. M comprises a sequence selected from any one of SEQ ID NOs: 78, 83, 85, 93, 99, 103, 134, 138, 145, 155, 194, 195, 200, 203, or 204. In some embodiments, M comprises a sequence of SEQ ID NOs: 78, 83, 85, 99, 103, 195, or 200.

In some embodiments, the disclosure provides an isolated polynucleotide comprising one or more nucleic acid sequences encoding a polypeptide selected from SEQ ID NOs: 178-215; or a nucleic acid sequence encoding a polypeptide comprising at least 90%, 95%, 96%, 97%, 98%, 99% or greater identity to any one of SEQ ID NOs: 178-215. In some embodiments, a vector comprises the isolated polynucleotide described herein. In some embodiments, a host cell is transformed with the isolated polynucleotide or the vector described herein.

In some embodiments, the disclosure provides a method of producing a composition comprising a formula selected from one or more of (M)x-L-C-R, (M)x-L-C, (M)x-C-R, (M)x-L-R, (M)x-C, (M)x-L, and (M)x-R, wherein M comprises a miniprotein (M), L comprises a linker (L), C comprises a chelator (C), R comprises a radionuclide (R), and x is 1, 2, 3, or 4, the method comprising: synthesizing a miniprotein (M) and/or linker (L), and
  optionally reacting a chelator (C) and/or a radionuclide (R), and conjugating
  one or more of the miniprotein (M) to the linker (L), one or more of the miniprotein (M) to the chelator (C), one or more of the miniprotein (M) to the radionuclide (R), one or more of the miniprotein (M) to the linker (L) to the chelator (C), one or more of the miniprotein (M) to the linker (L) to the chelator (C) and the radionuclide (R), one or more of the miniprotein (M) to the chelator (C) to the radionuclide (R), or one or more of the miniprotein (M) to the linker (L) to the radionuclide (R).

In some embodiments, the method comprises synthesizing (M)x-L-C and reacting with a radionuclide (R). In some embodiments, the method comprises synthesizing (M)x-L-C. (M)x-L, (M)x-C, or (M)x-C and reacting with a radionuclide (R). In some embodiments, reacting a chelator (C) and a radionuclide (R) is performed at a temperature of between 10° C. and 65° C. during an incubation period. In some embodiments, reacting a chelator (C) and a radionuclide (R) is performed during an incubation period of 5 minutes to 30 minutes. In some embodiments, reacting a chelator (C) and a radionuclide (R) is performed at a pH in the range of 5.0 to 7.4. In some embodiments, reacting a chelator (C) and a radionuclide (R) is performed in an aqueous solution that is substantially free of alcohol.

In some embodiments, when L is present, L comprises or consists of a polyethylene glycol (PEG) linker of PEG4, PEG, PEG2, PEG6, PEG8, PEG12, PEG24, lys(MPB)-PEG4, PEG36, an ester linker, an amide linker, a maleimide linker a valine-citrulline linker, a hydrazone linker, a N-succinimidyl-4-(2-pyridyldithio)butyrate (SPDB) linker, a succinimidyl-4-(N-maleimidomethyl)cyclohexane-1-carboxylate (SMCC) linker, a vinylsulfone-based linker, a propanoic acid linker, a dTyr-Gly-Phe (yGF) linker, a caproleic acid linker, or (Gly)n-(gGlu)n- (SEQ ID NO: 239) or (PEG)n, wherein n is from 1 to 10, (Gly)$_{1-10}$ (SEQ ID NO: 240), or any fragment or combination via covalent bond thereof.

In some embodiments, when C is present, C comprises or consists of:

i) DOTA

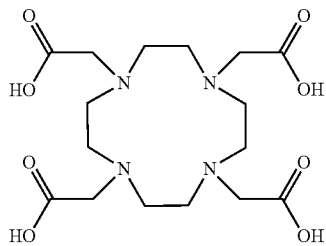

ii) Crown

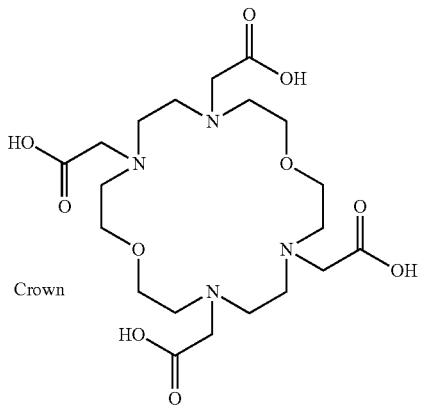

Crown iii) NOPO,

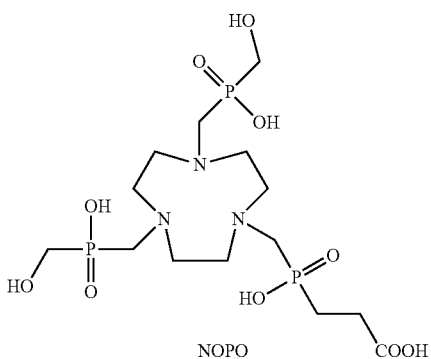

NOPO iv) Macropa

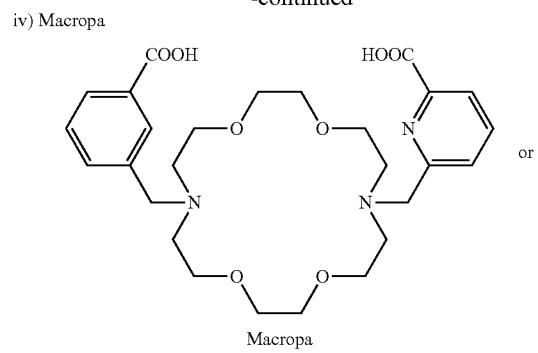

Macropa or v) lead-specific chelator (PSC)

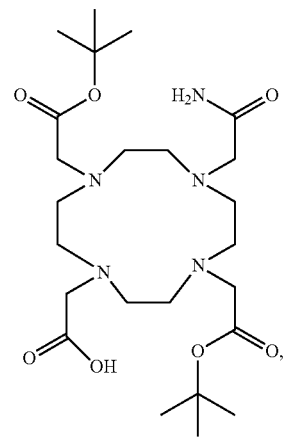

vi) N-succinimidyl 3-(tri-n-butylstannyl)benzoate (BuSTB), or vii) N-succinimidyl 3-trimethylstannylbenzoate (MeSTB).

In some embodiments, when R is present, R comprises or consists of Ac-225, In-111, Ga-68, Pb-212, Lu-177, Cu-67, Cu-64, La-132, La-135, Ce-134, F-18, I-131, I-124, Pb-203, Th-232, Bi-123, or At-211. In some embodiments, M comprises an amino acid sequence selected from any one of SEQ ID NOs: 3-158, 177-215, or 216-237 (including amino acid substitutions as set forth in Table 1C, Table 2C, Table 2D, Table 2E, Table 2F, or Table 2G). In some embodiments, if M comprises any one of SEQ ID NO: 83, 85, 93, 99, 134, 138, 145, 155, then the composition comprises the linker PEG4, the chelator DOTA, and the radionuclide In-111. In some embodiments. M comprises a sequence selected from any one of SEQ ID NOs: 78, 83, 85, 93, 99, 134, 138, 145, 155, 194, 195, 200, 203, or 204. In some embodiments, M comprises a sequence of SEQ ID NOs: 78, 83, 85, 99, 103, 195, or 200.

In some embodiments, the disclosure provides a method of delivering a radionuclide to a selected location within a patient, the method comprising administering a composition comprising a radionuclide as provided herein to the patient. In some embodiments, the radionuclide is selected from Ac-225, In-111, Ga-68, Pb-212, Lu-177, Cu-67, Cu-64, La-132, La-135, Ce-134, F-18, I-131, I-124, Pb-203, Th-232. Bi-123, or At-211. In some embodiments, the method further comprises carrying out an imaging procedure to evaluate the localization of the radionuclide within the body, wherein the imaging procedure optionally comprises positron emission tomography (PET) imaging or single-photon emission computerized tomography (SPECT) imaging. In some embodiments, the imaging procedure allows for selecting patients.

In some embodiments, the imaging procedure allows for monitoring patients. In some embodiments, the imaging procedure allows for determining an appropriate dose for treating a patient in need of a pharmaceutical composition as provided herein.

In some embodiments, the disclosure provides a kit comprising a polypeptide and instructions for use, wherein the polypeptide comprises an amino acid sequence of Formula III: CX2YX4X5X6FFTX10LX12X13LX15GX17DICX21YX24X25X26FX28X29X30X31X32X33CIX36E1X39X40X41 LGCX45 (SEQ ID NO: 216) wherein X45 is an optional amino acid or carboxy terminus comprising an —OH and wherein X2 is D or E; X4 is D or K, X5 is E or G; X6 is Q or E; X10 is A or E, X12 is A, K, E, or S; X13 is A, R, Q, K, S, or Cit; X15 is Y, R, or K, X17 is A, D, G, or S; X21 is D, Q, E, L, S, or Y; X24 is Q, L, K, or S; X25 is A, Q, E, K; X26 is A, Q, K, S, Y, T, D, R, (Kme3), (sRme2), Cit, Arg(NO2), OH-Norleu, or Norleu; X28 is A, N, Q, D, K, or S; X29 is N, T, or Y; X30 is L, Y, or V; X31 is P or E; X32 is A, D, Q, G, or K; X33 is D, Q, E, I, or L; X36 is Q, K or E; X39 is L or R; X40 is D, Q, or E; X41 is N, K or Q; and X45, when present as an amino acid is S.

In some embodiments, the amino acid sequence satisfies one or more of: wherein if X4 is K, then X26 is K and X15 is Y; wherein if X4 is D, then X26 is one of N, T, D, R, (Kme3), (sRme2), Cit, or Arg(NO2), or X26 is K, X10 is E, X36 is K, and X39 is R; or wherein one or more leucine in the amino acid sequence is Leu-13C6,15N.

In some embodiments, X2 is E; X4 is D, X5 is E; X6 is E; X10 is A, X12 is A or K; X13 is R; X1 is R; X17 is G; X21 is Y; X24 is Q; X25 is A; X26 is Q. K, or S; X28 is A or Q; X29 is T or Y; X30 is L or V; X31 is P; X32 is G; X33 is L; X36 is E; X39 is L; X40 is D; X41 is N or Q; and X45 is S. In some embodiments, the amino acid sequence shares at least 90% identity to any one of SEQ ID NOs: 3-158 or 177-215. In some embodiments, the amino acid sequence shares at least 90% identity to any one of SEQ ID NOs: 78, 83, 85, 93, 96, 99, 134, 138, 145, 155, or 178-215. In some embodiments, the amino acid sequence shares at least 90% identity to any one of SEQ ID NOs: 78, 83, 85, 93, 99, 103, 134, 138, 145, 155, 194, 195, 200, 203, or 204. In some embodiments, the amino acid sequence shares at least 90% identity to any one of SEQ ID NOs: 78, 99, 103, 195, or 200. In some embodiments, the amino acid sequence shares 100% identity to any one of SEQ ID NOs: 3-158 or 177-215. In some embodiments, the amino acid sequence shares 100% identity to any one of SEQ ID NOs: 78, 83, 85, 93, 99, 103, 134, 138, 145, 155, 194, 195, 200, 203, or 204. In some embodiments, the amino acid sequence shares 100% identity to any one of SEQ ID NOs: 78, 83, 85, 99, 103, 195, or 200.

In some embodiments, the disclosure provides a kit comprising a polypeptide and instructions for use, wherein the polypeptide comprises an amino acid sequence of Formula IV: CX2X3X4X5X6X7X8X9X10X11X12X13X14X15X16X17X18X19CX21X22X23X24X25X26X27X28X29X30X31X32X33CX35X36X37X38X39X40X41X42X43CS (SEQ ID NO: 233) wherein X2 is E, G, A, S, T, D, N, K, R, Y, F, V, I, or W; X3 is Y, P, G, A, S, T, Q, K, H, F, W, V, M, D, E, L, or I; X4 is D, S, N, R, Y, L, M, G, T, or I; X5 is E, G, D, Q, F, W, V, L, I, M, K, or R; X6 is E, P, G, D, Q, N, K, Y, F, W, or V; X7 is F, Y, or W; X8 is F, Y, W, I, or M; X9 is T, P, A, S, D, Q, N, K, Y, F, V, M, E, R, or L; X10 is A, S, E, N, K, F, W, V, L, 1, G, T, D, Q, R, or H; X11 is L, T, I, or M; X12 is K, L, G, A, S, T, N, R, H, F, W, V, I, or M; X13 is R, G, A, S, E, N, K, Y, W, L, I, or M; X14 is L, T, V, I, or M; X15 is R, T, Q, K, L, I, M, or V; X16 is G, D, N, K, R, H, Y, W, V, L, I, or M; X17 is G, P, A, S, T, D, Q, N, R, H, Y, F, W, V, L, or M; X18 is D, P, G, A, T, E, Q, N, K, Y, F, W, V, I, M, or S; X19 is I, P, A, T, D, N, Y, V, M, G, or Q; X21 is Y, S, T, D, E, K, F, W, L, I, or V; X22 is Y or E; X23 is 1, A, T, Y, V, L, M, or F; X24 is Q, P, G, D, K, R, H, F, V, L, I, M, or N; X25 is A, P, S, D, E, Q, K, R, H, Y, F, W, V, I, M, or T; X26 is S, P, G, A, D, Q, N, R, F, V, L, I, T, E, or W; X27 is F, P, A, S, K, H, Y, W, M, E, or V; X28 is Q, P, G, A, S, D, E, K, R, H, Y, W, V, L, F, or I; X29 is Y, P, A, S, E, Q, N, K, F, W, L, I, M, T, or V; X30 is L, P, G, A, S, T E, N, R, H, F, W, V, I, M, Q, or K; X31 is P, G, A, T, D, E, Q, N, K, R, H, Y, V, S, W, L, or I; X32 is G, A, S, D, N, R, H, Y, L, I, or V; X33 is L, P, G, A, S, D, E, N, K, R, H, Y, F, W, V, I, or M; X35 is I, P, S, D, E, N, K, R, Y, F, W, L, or Mg X36 is E, G, A, S, T, D, Q, K, R, H, Y, W, L, I, or M; X37 is E, P, G, A, S, T, N, K, R, H, Y, F, W, V, or D; X38 is I, A, S, E, Y, F, W, V, L, T, or H; X39 is L, S, T, E, N, R, H, Y, F, W, V, M, D, or I; X40 is D, G, A, S, E, Q, R, H, F, W, V, L, I, M, N, or K; X41 is N, G, A, S, D, Q, R, H, Y, F, V, L, I, M, P, or K; X42 I, L, P, G, Q, N, H, F, W, 1, M, or S; and X43 is G, P, A, T, D, N, K, R, Y, F, W, V, 1, or Q.

In some embodiments, X2 is E or W; X3 is Y, D, E, L, or I; X4 is D, G, T, or I; X5 is E, K, or R; X6 is E; X7 is F; X8 is F; X9 is T, E, R, or L; X10 is A, G, T, D, Q, R, or H; X11 is L or M; X12 is K; X13 is R; X14 is L or M; X15 is R or V; X16 is G; X17 is G; X18 is D or S; X19 is I, G, or Q; X21 is Y or V; X22 is Y; X23 is I or F; X24 is Q or N; X25 is A or T; X26 is S. T, E, or W; X27 is F, E, or V; X28 is Q, F, or L X29 is Y, T, or V; X30 is L. Q, or K; X31 is P, S, W, L, or I; X32 is G or V; X33 is L or M; X35 is I; X36 is E; X37 is E or D; X38 is I, T, or H; X39 is L, D, or I; X40 is D, N, or K; X41 is N, P, or K; X42 is L or S; and X43 is G or Q.

In some embodiments, the disclosure provides a kit comprising a polypeptide and instructions for use, wherein the polypeptide comprises an amino acid sequence of Formula V: CX2X3X4X5X6X7X8X9X10X11X12X13X14X15X16X17X18X19CX21X22X23X24X25X26X27X28X29X30X31X32X33CX35X36X37X38X39X40X41X42X43CS (SEQ ID NO: 234) wherein X2 is E, P, G, A, S, T, Q, N, K, R, H, Y, F, W, V, L, I, or M; X3 is Y, P, G, A, S, T, D, E, Q, N, K, R, H, F, W, V, L, I, or M; X4 is D, P, G, A, S, T, E, Q, N, K, R, H, Y, F, W, V, L, I, or M; X5 is E, P, G, S, T, D, Q, N, K, R, H, F, W, V, L, I, M, or Y; X6 is E, P, G, A, S, T, D, Q, N, K, R, H, F, W, V, L, I, M, or Y; X7 is F, Y, or W, X8 is F, T, Y, W, V, L, I, or M; X9 is T, P, G, S, D, E, N, K, R, H, Y, F, V, L, I, M, A, Q, or W; X10 is A, P, G, S, T, D, E, Q, N, K, R, H, Y, F, W, V, L, I, or M; X11 is L, A, V, 1, or M; X12 is A, G, S, D, E, Q, N, K, R, H, Y, F, W, V, L, I, M, or T; X13 is R, P, S, T, D, E, Q, K, H, Y, F, V, L, M G, A, N, W, or I; X14 is L, A, T, F, V, 1, or M; X15 is R, Q, Y, F, W, V, L, I, M, or K; X16 is G, P, A, S, T, D, E, Q, N, K, R, H, Y, F, W, V, L, M, or I; X17 is G, P, A, S, T, D, E, Q, N, K, R, H, Y, W, V, L, I, M, or F; X18 is D, P, G, A, S, T, E, Q, N, K, R, H, Y, W, V, I, M, F, or L; X19 is I, P, G, A, S, T, D, E, Q, N, K, R, Y, F, W, V, L, M, or H; X21 is Y, P, G, A, S, T, D, E, Q, N, K, R, H, F, W, V, L, I, or M; X22 is Y, H, or F; X23 is I, G, A, S, T, Y, W, V, L, M, or F; X24 is Q, G, S, T, D, E, N, K, R, H, F, W, V, L, I, M, P, A, or Y; X25 is A, G, S, T, D, E, Q, N, K, R, H, Y, F, W, V, M, P, L, or I; X26 is K, P, G, A, S, T, D, E, Q, N, R, H, Y, F, W, V, L, I, or M; X27 is F, P, G, A, S, T, D, E, Q, N, K, R, H, Y, W, V, L, I, or M; X28 is Q, P, G, A, S, T, D, E, N, K, R, H, Y, F, W, V, L, I, or M; X29 is Y, P, G, A, S, T, D, E, N, K, R, H, F, W, V, L, I, M, or Q; X30 is L, P, G, A, S, T, D, E, Q, N, K, R, H, Y, F, W, V, 1, or M; X31 is P, G, A, S, T, D, Q, N, K, R, H, Y, F, V, I, M, E, W, or L; X32 is G, P, A, S, T, D, E, Q, N, K, R, H, Y, F, W, V, L, I, or M; X33 is L, P, G, A, S, T, D, E, Q, N, K, R, H, Y, F, W, V, I, or M; X35 is I, P, G, A, S, T, D, E, Q, N, K, R, Y, F, W, V, L, M, or H; X36 is E, P, G, A, S, D, Q, NR, H, F, V, L, I, M, T, K, Y, or W; X37 is E, P, G, A, S, T, D, N, K, H, Y, F, W, V, L, I, M, Q, or R; X38 is I, P, G, A, S, T, E, Q, N, K, H, Y, F, W, V, L, or M; X39 is L, G, A, S, T, D, E, Q, N, K, R, H, Y, W, V, I, M, or F; X40 is D, P, G, A, S, E, Q, N, K, R, H, Y, F, W, V, L, I, M, or T; X41 is N, P, G, A, S, T, D, E, Q, K, R, H, Y, F, W, V, L, I, or M; X42 is L, G, A, S, T, E, Q, N, K, R, H, Y, F, W, V, 1, or M; and X43 is G, P, A, S, T, D, E, Q, N, K, R, H, Y, F, W, V, L, M, or I.

In some embodiments, X2 is E, X3 is Y; X4 is D; X5 is E or Y; X6 is E or Y; X7 is F; X8 is F; X9 is T, A, Q, or W; X10 is A; X11 is L; X12 is A or T; X13 is R, G, A, N, W, or I; X14 is L; X15 is R or K; X16 is G or 1; X17 is G or F; X18 is D, F, or L; X19 is I or H; X21 is Y; X22 is Y; X23 is I or F; X24 is Q, P, A, or Y; X25 is A, P, L, or I; X26 is K; X27 is F; X28 is Q; X29 is Y or Q; X30 is L; X31 is P, E, W, or L; X32 is G; X33 is L; X35 is I or H; X36 is E, T, K, Y, or W; X37 is E, Q, or R; X38 is I or M; X39 is L or F; X40 is D or T; X41 is N; X42 is L; and X43 is G or I.

In some embodiments, the disclosure provides a kit comprising a polypeptide and instructions for use, wherein the polypeptide comprises an amino acid sequence of Formula VI; CX2X3X4X5X6X7X8X9X10X11X12X13 X14X15X16X17X18X19CX21X22X23X24X25 X26X27X28X29X30X31X32X33CX35X36X37X 38X39X40X41X42X43CS (SEQ ID NO: 235) wherein X2 is E, P, G, A, S, T, D, Q, N, K, R, H, Y, W, V, L, I, M, or F; X3 is Y, P, G, A, S, T, D, E, Q, K, R, H, F, W, V, L, I, M, or N; X4 is D, P, A, S, E, Q, N, or H; X5 is E, P, G, A, T, Q, N, K, R, H, Y, F, W, V, L, I, M, S, or D; X6 is Q, P, G, A, S, T, D, E, N, K, R, H, Y, F, W, V, L, I, or M; X7 is F, Y, or W; X8 is F, Y, W, V, I, or M; X9 is T, P, G, A, S, D, Q, N, R, H, Y, F, V, L, I, M, E, K, or W; X10 is A, G, T, D, E, Q, N, K, R, H, W, L, I, M, S, Y, F, or V; X11 is L, V, I, or M; X12 is A, G, S, T, D, K, R, Y, F, W, V, L, I, M, E, Q, N, or H; X13 is R, G, A, S, T, D, Q, N, K, H, Y, F, W, V, L, M, E, or I; X14 is L, T, V, I, or M; X15 is R, Q, K, I, or M; X16 is G, A, T, D, E, Q, N, K, R, H, Y, W, V, L, I, M, P, S, or F; X17 is G, P, A, S, T, D, E, Q, N, K, R, H, Y, F, W, V, L, I, or M; X18 is D, P, G, A, S, T, E, N, K, H, Y, F, L, M, Q, or K; X19 is I, G, A, S, T, E, Q, N, K, R, H, Y, F, W, V, L, or M; X21 is Y, P, G, A, S, D, E, Q, N, K, R, H, F, W, V, L, I, M, or T; X22 is Y; X23 is I, A, T, Y, F, W, V, L, or M; X24 is Q, P, A, S, D, E, N, K, H, Y, F, W, V, L, I, G, T, R, or M, X25 is E, P, G, A, S, T, D, Q, N, R, H, Y, F, W, V, L, I, M, or K; X26 is Q, G, A, S, T, E, N, K, R, H, F, W, V, L, 1, M, D, or Y; X27 is F, Y, W, L, I, M, or V; X28 is A, P, G, S, T, D, E, Q, N, K, R, H, Y, W, V, L, I, M, or F; X29 is T, P, G, A, S, D, E, Q, K, R, H, Y, F, W, V, L, I, M, or N; X30 is V, P, G, A, T, D, E, N, K, R, H, Y, F, W, I, M, S, Q, or L; X31 is P, G, A, S, T, D, E, Q, N, K, R, H, Y, F, W, V, L, I, or M; X32 is G, P, A, T, D, E, Q, N, K, R, H, Y, F, W, V, L, I, M, or S; X33 is L, P, G, A, S, T, D, E, Q, K, R, H, Y, F, W, V, I, M, or N; X35 is I, P, G, A, S, T, D, E, Q, N, K, R, H, Y, F, W, L, M, or V; X36 is E, P, A, S, T, D, N, R, H, F, W, V, L, I, M, K, or Y; X37 is E, P, G, A, S, T, D, N, R, H, Y, W, V, L, I, M, Q, K, or F; X38 is I, G, A, S, E, Q, H, Y, W, V, L, M, P, or F; X39 is L, G, A, S, T, D, E, Q, N, K, H, Y, F, W, V, I, M, or K; X40 is D, P, G, A, S, T, E, Q, N, R, H, Y, F, W, L, M, or K; X41 is Q, P, G, A, S, T, D, E, N, K, R, H, Y, F, W, V, L, I, or M; X42 is L, G, A, S, T, E, Q, R,
H, Y, F, V, I, M, N, or W; and X43 is G, P, A, S, T, D, E, Q, N, K, F, W, V, L, I, M, R, H, or Y.

In some embodiments, X2 is E or F; X3 is Y or N; X4 is D; X5 is E, S, or D; X6 is Q; X7 is F; X8 is F; X9 is T, E, K, or W; X1 is A, S, Y, F, or V; X11 is L; X12 is A, E, Q, N, or H; X13 is R, E, or; X14 is L; X15 is R; X16 is G, P, S, or F; X17 is G; X18 is D, Q, or K; X19 is I; X21 is Y or T; X22 is Y; X23 is I or M; X24 is Q, G, T, R, or M X25 is E or K; X26 is Q, D, or Y; X27 is F or V; X28 is A or F; X29 is T or N; X30 is V, S, Q, or L; X31 is P; X32 is G or S; X33 is L or N; X35 is I or V; X36 is E, K, or Y; X37 is E, Q, K, or F; X38 is I, P, or F; X39 is L or R; X40 is D or K; X41 is Q; X42 is L, N, or W; and X43 is G, R, H, or Y.

In some embodiments, the disclosure provides a kit comprising a polypeptide and instructions for use, wherein the polypeptide comprises an amino acid sequence of Formula VII; CX2X3X4X5X6X7X8X9X10X11X12X13X 14X15X16X17X18X19CX21X22X23X24X25 X26X27X28X29X30X31X32X33CX35X36X37X 38X39X40X41X42X43CS (SEQ ID NO: 236) wherein X2 is E, P, G, A, S, T, D, Q, N, K, R, H, Y, W, V, L, I, M, or F; X3 is Y, P, G, A, S, T, D, E, Q, N, K, H, W, V, L, I, M, R, or F; X4 is D, P, G, A, T, Q, N, K, R, H, Y, F, W, V, L, M, S, E, or I; X5 is E, P, G, A, S, T, D, N, K, R, H, Y, F, W, V, L, Q, I, or M; X6 is E, P, G, A, D, Q, N, R, H, Y, F, W, V, L, M, S, K, or I; X7 is F, Y, or W; X8 is F, H, Y, W, V, L, I, or M; X9 is T, P, G, S, D, E, Q, N, K, R, H, Y, F, W, V, L, I, M, or A; X10 is A, P, G, T, D, E, Q, N, K, R, H, Y, F, W, V, L, M, S, or I; X11 is L, A, V, I, or M; X12 is A, P, G, S, T, D, E, K, R, H, Y, F, W, V, L, I, M, Q, or N; X13 is R, P, A, S, T, D, E, Q, N, K, H, Y, F, W, V, L, I, M, or G; X14 is L, T, F, V, M, or I; X15 is R, Q, N, K, H, F, W, V, L, I, M, or Y; X16 is G, P, A, T, D, E, Q, N, K, R, H, Y, F, W, V, L, I, M, or S; X17 is G, A, S, D, E, Q, N, K, R H, Y, F, W, V, L, I, M, or P; X18 is D, P, G, A, S, T, E, Q, N, K, R, Y, F, W, V, L, I, M, or H; X19 is I, P, G, A, S, T, D, E, Q, N, K, R, H, Y, F, W, V, L, or M; X21 is Q, P, G, A, S, D, E, N, R, H, Y, F, W, V, I, M, T, K, or L; X22 is Y, H, or F; X23 is I, G, A, S, T, Y, F, V, L, or M; X24 is Q, P, G, A, S, E, N, K, R, H, Y, F, W, V, L, I, M, T, or D; X25 is A, P, G, S, T, D, E, Q, N, K, H, Y, F, W, V, L, I, M, or R; X26 is Kme3 or K, P, G, S, T, D, E, Q, N, R, H, Y, F, W, V, L, M, A, or I; X27 is F, P, G, A, S, D, E, Q, N, K, R, H, Y, W, V, L, I, or M; X28 is Q, P, G, A, S, T, D, E, N, K, R, H, Y, F, W, V, L, I, or M; X29 is Y, P, G, A, S, T, D, E, Q, N, K, R, H, F, W, V, L, I, or M; X30 is L, P, G, A, T, D, E, Q, N, K, R, H, Y, F, W, V, I, M, or S; X31 is P, G, S, T, D, E, Q, N, K, R, H, Y, W, V, L, I, M, A, or F; X32 is A, P, G, S, T, D, Q, N, K, R, H, Y, F, W, V, I, M, E, or L; X33 is L, P, G, A, S, T, D, E, Q, N, K, R, H, Y, F, W, V, I, or M; X35 is I, P, G, A, S, T, D, E, Q, N, R, H, Y, W, V, L, M, K, or F; X36 is E, P, A, S, T, D, Q, N, K, R, H, Y, F, W, V, L, I, M, or G; X37 is E, G, A, S, D, Q, N, K, R, H, Y, F, W, V, L, I, M, or T; X38 is I, P, G, A, S, T, D, E, Q, N, H, Y, F, W, V, L, M, K, or R; X39 is L, G, A, S, T, D, E, Q, N, R, H, Y, W, V, I, M, K, or F; X40 is D, P, G, A, S, T, E, Q, K, R, H, Y, W, V, L, I, M, N, or F; X41 is N, P, G, A, S, T, D, E, Q, K, R, H, Y, F, W, V, L, I, or M; X42 is L, G, A, S, D, E, Q, N, K, R, H, Y, F, W, V, I, or M; and X43 is G, P, A, S, T, D, E, Q, N, K, R, H, Y, F, W, V, L, I, or M.

In some embodiments, X2 is E or F; X3 is Y, R, or F; X4 is D, S, E, or I; X5 is E, Q, I, or M; X6 is E, S, K, or I; X7 is F or W; X8 is F; X9 is T or A; X10 is A, S, or 1; X11 is L; X12 is A, Q, or N; X13 is R or G; X14 is L or I; X15 is R or Y; X16 is G or S; X17 is G or P; X18 is D or H; X19 is I; X21 is Q, T, K, or L; X22 is Y; X23 is I; X24 is Q. T, or D; X25 is A or R; X26 is Kme3 or K, A, or I; X27 is F;

X28 is Q; X29 is Y; X30 is L or S; X31 is P, A, or F; X32 is A, E, or L; X33 is L; X35 is I, K, or F; X36 is E or G; X37 is E or T; X38 is I, K. or R; X39 is L, K, or F; X40 is D, N, or F; X41 is N; X42 is L or M; and X43 is G.

In some embodiments, any one of the kits described herein further comprise one or more of a linker, chelator, and radionuclide. In some embodiments, the linker comprises or consists of a polyethylene glycol (PEG) linker of PEG2, PEG, PEG4, PEG6, PEG8, PEG12, PEG24, PEG36, lys (MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, or (Gly)n-(gGlu)n-(SEQ ID NO: 239) or (PEG)n, wherein n is from 1 to 10, (Gly)$_{1-10}$ (SEQ ID NO: 240), or any fragment or combination via covalent bond thereof. In some embodiments, the chelator comprises or consists of DOTA, NOPO, Macropa, lead specific chelator (PSC), N-succinimidyl 3-(tri-n-butylstannyl)benzoate (BuSTB), N-succinimidyl 3-trimethylstannylbenzoate (MeSTB), or Crown. In some embodiments, the radionuclide is selected from Ac-225, Ga-68, In-111, Pb-212, Lu-177, Cu-67, Cu-64, La-132, La-135, Ce-134, F-18, I-131, I-124, Pb-203, Th-232, Bi-123, or At-211.

In some embodiments, if the polypeptide comprises any one of SEQ ID NOs: 83, 85, 93, 99, 134, 138, 145, and 155, then the polypeptide further comprises a linker, wherein the linker is PEG4, and a chelator, wherein the chelator is DOTA. In some embodiments, when present, the linker is attached to the C-terminal end of the polypeptide. In some embodiments, when present, the chelator is attached to either the polypeptide or the linker. In some embodiments, when present, the radionuclide is attached to the chelator. In some embodiments, when present, the radionuclide is attached to the C-terminal end of the polypeptide. In some embodiments, the polypeptide comprises or consists of a linear polypeptide, a folded polypeptide (e.g., covalently linked polypeptide, non-covalently linked polypeptide, or polypeptide include a di-sulfide linkage), cysteine-dense peptide, a knottin peptide, a binder, an affibody, an engineered Kunitz domain, a monobody, an anticalin, a designed ankyrin repeat domain (DARPin), or an avimer. In some embodiments, the polypeptide comprises at least one disulfide bridge. In some embodiments, the polypeptide selectively binds to Nectin-4 or a portion thereof. In some embodiments, the polypeptide exhibits a binding affinity of 10 pM to 200 nM, 10 pM to 100 nM, or 10 nM to 100 nM to Nectin-4, or a portion thereof, in vivo or in a cell-based assay.

In some embodiments, the kit described herein further comprises a second polypeptide, wherein the second polypeptide comprises an amino acid sequence of any one of SEQ ID NOs: 3-158, 177-215, or 216-237 (including amino acid substitutions as set forth in Table 1C, Table 2C, Table 2D, Table 2E, Table 2F, or Table 2G). In some embodiments, the second polypeptide is conjugated to a cold-metal surrogate of a radionuclide. In some embodiments, the second polypeptide is conjugated to an alpha emitter. In some embodiments, the second polypeptide is conjugated to a beta emitter. In some embodiments, a second therapeutic agent is selected from a treatment or component for use in monoclonal antibody therapy, a DNA damage response (DDR) inhibitor, immunotherapy, chemotherapy, radiotherapy, gene therapy, or RNA therapy. In some embodiments, the second therapeutic agent is an immunotherapy or radiotherapy treatment or component. In some embodiments, the DNA damage response (DDR) inhibitor is selected from an inhibitor of Serine-protein kinase ATM (ATM). Serine/threonine-protein kinase ATR (ATR). Serine/threonine-protein kinase Chk1 (CHK1/2), DNA-dependent protein kinase catalytic subunit (DNA-PK), Poly [ADP-ribose] polymerase (PARP). Membrane-associated tyrosine- and threonine-specific CDC2-inhibitory kinase (PKMYT1). RNA-directed DNA polymerase (POLO), and DNA repair protein RAD51 homolog 1 (RAD51). In some embodiments, the kit achieves a regulatory certification date of equal to or greater than 1, 2, 3, 4, 5, 6, 7, 8, 9, 10, 11, 12, 13, 14, 15, 16, 17, 18, 19, or 20 days.

In some embodiments, the disclosure provides a kit comprising: a composition represented by the formula selected from one or more of M-L-C-R, M-L-C, M-C-R, M-L-R. M-C, M-L, and M-R, wherein M comprises a miniprotein (M), L comprises a linker (L), C comprises a chelator (C), and R comprises a radionuclide (R); and a decoy, wherein the decoy blocks uptake and/or retention of the composition into kidney tissue.

In some embodiments, the disclosure provides a kit comprising: (a) (i) a polypeptide described herein or (ii) a composition described herein, and (b) a decoy, wherein the decoy molecule blocks uptake and/or retention of the polypeptide or the composition into a kidney tissue.

In some embodiments, the polypeptide or composition further comprises a radionuclide (R). In some embodiments, when R is present, R is supplied separately from any other components (e.g., M, C, L) of the polypeptide or composition or the decoy. In some embodiments, R, if present, is added just prior to use. In some embodiments, the decoy and the polypeptide or the composition are administered to a subject in need thereof. In some embodiments, after the administration, the decoy appears in a higher concentration in the kidney tissue than in the tumor tissue as measured by % ID/g. In some embodiments, the decoy is selected from any C295-C297 and/or has an amino acid sequence comprising SEQ ID NOs: 209-211. In some embodiments, the miniprotein has an amino acid sequence comprising any of SEQ ID NOs: 3-158 or 177-215. In some embodiments, the decoy is supplied in a molar or mass excess as compared to the composition, which molar or mass excess is optionally selected from a 10, 100, 1000, or more molar or mass excess.

In some embodiments, the disclosure provides that in a method of treating an individual with cancer comprising administering (a) a composition comprising a miniprotein (M) and a radionuclide (R); and (b) a decoy, the improvement comprising reducing one or more off-target effects or toxicity measures after administration of the composition and the decoy as compared to administration of the composition in the absence of the decoy.

In some embodiments, the composition comprises an M that targets Nectin-4.

In some embodiments, the disclosure provides that in a method of treating an individual with cancer by administering: (a) a composition comprising a miniprotein (M) and a radionuclide (R); and (b) a decoy, the improvement comprising achieving a reduction in concentration of R in a kidney tissue in the presence of the decoy as compared to the concentration of R in the kidney tissue in the absence of the decoy. In some embodiments, the miniprotein has an amino acid sequence comprising a sequence selected from any of SEQ ID NOs: 3-158 or 177-215. In some embodiments, the decoy has an amino acid sequence comprising the amino acid sequence of any of SEQ ID NOs: 209-211. In some embodiments, the reduction in the one or more off-target effects or toxicity measures is measured as a reduction in one or more toxicity grades of each of the one or more off-target effects or toxicity measures. In some embodiments, the reduction in concentration of R in the kidney tissue is measured by urine output of R as measured by percent of administered radiation recovered. In some embodiments, the percent of administered radiation recovered in the presence of the decoy is increased as compared to radiation recovered in absence of the decoy. In some embodiments, the reduction in concentration of R in the kidney tissue is determined by maintenance of eGFR over at least the period that the subject is receiving treatment. In some embodiments, the administration of the composition can be repeated more often (e.g., at least 2, 3, 4, 5, 6 times more, etc.) in the presence of the decoy than in the absence of the decoy before a dose limiting toxicity is reached.

In some embodiments, the disclosure provides a method of reducing uptake of a composition by a kidney tissue. In some embodiments, the method comprises an improvement comprising administering a composition comprising (a) a radionuclide therapeutic comprising at least a miniprotein (M) and a radionuclide (R); and (b) a decoy, such that in the presence of the decoy, the radionuclide is less concentrated in the kidney tissue than in the absence of the decoy. In some embodiments, the reduction in concentration of R in the kidney tissue is measured by urine output of R. In some embodiments, the urine output is expressed as a percent of administered radiation recovered in the presence of the decoy and is increased as compared to radiation recovered in absence of the decoy. In some embodiments, the reduction in concentration of R in the kidney tissue is determined by maintenance of eGFR over at least the period that the subject is receiving treatment. In some embodiments, the administration of the composition can be repeated more often (e.g., at least 2, 3, 4, 5, 6 times more, etc.) in the presence of the decoy than in the absence of the decoy before a dose limiting toxicity is reached. In some embodiments, administration of a compound comprising a miniprotein is administered concomitant with the decoy. In some embodiments, administration of a compound comprising the miniprotein (M) is administered sequentially with the decoy. In some embodiments, the sequential administering comprises administering the decoy, followed by administering the composition comprising the miniprotein (M). In some embodiments, the sequential administering comprises administering the composition comprising a miniprotein followed by administering the decoy. In some embodiments, the decoy is administered in a molar or mass excess relative to the miniprotein (M). In some embodiments, the molar or mass excess is at least about 2, 10, 50, 100, 250, 500, 750, 1,000, 2,500, 5,000, 7,500, or 10,000× molar or mass excess relative to the miniprotein (M). In some embodiments, the decoy comprises or consists of an amino acid sequence comprising that of any of SEQ ID NOs: 209-211. In some embodiments, the decoy is selected from any of C295-C297. In some embodiments, the miniprotein comprises or consists of any compound or amino acid sequence selected from TABLE 2A. In some embodiments, the decoy comprises or consists of an amino acid sequence comprising that of any of SEQ ID NOs: 209-211. In some embodiments, the decoy is selected from any of C295-C297. In some embodiments, the decoy comprises or consists of a decoy having an amino acid sequence comprising any of those of SEQ ID NOs: 209-211 and the miniprotein comprises or consists of a miniprotein selected from Table 2A. In some embodiments, the decoy is selected from any of C295-C297 and the miniprotein comprises or consists of miniprotein selected from Table 2A.

In some embodiments, the disclosure provides a method comprising administering to a subject in need thereof a compound that binds to Nectin-4 and a decoy, wherein administration of the decoy reduces one or more off-target effects, toxicity grades, and/or uptake and/or retention in a kidney tissue. In some embodiments, the compound comprises or consists of an amino acid sequence comprising or consisting of any of SEQ ID NOs: 3-158 or 177-215. In some embodiments, the decoy comprises or consists of an amino acid sequence selected any of SEQ ID NOs: 209-211. In some embodiments, the decoy comprises or consists of C295-C297.

In some embodiments, the disclosure provides a combination composition comprising: (i) a radionuclide therapeutic comprising a composition represented by the formula selected from one or more of M-L-C-R, M-L-C, M-C-R, M-L-R, M-C, M-L, and M-R, wherein M comprises a miniprotein (M). L comprises a linker (L). C comprises a chelator (C), and R comprises a radionuclide (R), wherein the M is of a particular scaffold; and (ii) a decoy comprising or consisting of an amino acid sequence selected from SEQ ID NOs: 209-211. In some embodiments, the decoy and the miniprotein M have the same scaffold.

In some embodiments, the disclosure provides a method comprising treating an individual with a cancer, the method comprising administering to the individual: a means for blocking uptake of a radiotherapeutic to kidney tissue, and a radionuclide therapeutic comprising a composition represented by the formula selected from one or more of M-L-C-R, M-L-C, M-C-R, M-L-R, M-C, M-L, and M-R, wherein M comprises a miniprotein (M), L comprises a linker (L). C comprises a chelator (C), and R comprises a radionuclide (R), wherein the M is of a particular scaffold.

In some embodiments, the means for blocking uptake of a radiotherapeutic to kidney tissue blocks uptake and/or retention of the radiotherapeutic into the kidney. In some embodiments, the radiotherapeutic is targeted to a tumor or a population of cancer cells. In some embodiments, the radiotherapeutic targeted to the tumor or the population of cancer cells is at a greater concentration than in the absence of the means for binding to kidney tissue.

In some embodiments, the disclosure provides a combination composition comprising a miniprotein or compound that binds to Nectin-4 and a decoy. In some embodiments, the miniprotein or compound is selected from Table 2A. In some embodiments, the decoy is selected from C295-C297 and/or has an amino acid sequence comprising, consisting essentially of, or consisting of any of SEQ ID NOs: 209-211. In some embodiments, the decoy is administered together or separately from the miniprotein or compound that binds to Nectin-4. In some embodiments, the decoy is administered sequentially with (prior to or after) the miniprotein or compound that binds to Nectin-4. In some embodiments, administration of the miniprotein or compound that binds to Nectin-4 is administered concomitant with the decoy. In some embodiments, sequential administering comprises administering the decoy followed by administering the composition comprising the miniprotein or compound that binds to Nectin-4. In some embodiments, the sequential administering comprises administering the composition comprising a miniprotein followed by administering the decoy.

In some embodiments, the disclosure provides a method of improving a cancer treatment. In some embodiments, the method comprises improving cancer treatment in an individual experiencing one or more off-target effects, the method comprising administering: (a) a decoy; and (b) a radionuclide therapeutic, wherein the one or more off-target effects is prevented or reduced as compared to administering the radiotherapeutic in the absence of the decoy. In some embodiments, the radionuclide therapeutic comprises a miniprotein that targets Nectin-4. In some embodiments, the radionuclide therapeutic comprises a compound selected from Table 2A. In some embodiments, the decoy is selected from C295-C297 and/or has an amino acid sequence comprising, consisting essentially of, or consisting of any of SEQ ID NOs: 209-211.

EXAMPLES

Example 1: Screening Scaffold Libraries to Identify Nectin-4 Specific Miniproteins This Example describes an exemplary library screen for initial identification of miniproteins that bind to Nectin-4 or a portion or fragment thereof.

Using a phage display library, a panning experiment was carried out to bind a phage displayed miniprotein scaffold to a Nectin-4 target linked to a solid support. Tissue culture grade plates were coated with recombinant Nectin-4 and a buffer. Through the first round of panning, colonies were allowed to bind on the plate for 2 h at 37° C. The plate was washed ~20 times, and the bound phage were eluted with HCl. The bound phage was used to infect E coil cells to produce additional phage used in additional rounds of panning. To measure the binding of the phage to Nectin-4, an ELISA assay was performed. The positive clones were sequenced.

Using yeast surface display, a miniprotein polypeptide library was generated and genetically fused to the yeast mating agglutinin protein Aga2p. Aga2p attaches by two disulfide bonds to Aga1p, a yeast cell wall protein. Expression of this construct was put under the control of a galactose-inducible promoter, and the N-terminus of the miniprotein polypeptide was fused to Aga2p.

Library Construction

To construct a miniprotein library, mutants were created by varying disulfide-constrained CDP loop regions. The library included variations in the loop length along with sequence diversity. In some cases, a larger surface contact area was necessary to achieve high-affinity binding to the Nectin-4 target. To mutate any miniprotein loop regions at the DNA level, degenerate codons were introduced by oligonucleotide assembly using overlap extension PCR. The degenerate portion was flanked by sufficient sequence homology with neighboring oligonucleotides to design primers to allow for specific annealing. The genetic material was amplified with flanking primers that had sufficient overlap with the yeast display vector for homologous recombination in yeast.

Two-color FACS was used for yeast library screening, using APC and FITC fluorophores. The c-myc epitope was measured using APC, and the other (FITC) measured the interaction of the miniprotein mutant against the Nectin-4 target. Nectin-4 was incubated with the yeast library and allowed to come to equilibrium prior to FACS sorting.

Example 2: Engineering Miniproteins for Improved Nectin-4 Binding

This Example describes exemplary engineering of miniproteins that bind to Nectin-4 to achieve, among other things, improved binding affinity to Nectin-4 or a portion or fragment thereof as compared to proteins that are not engineered as provided herein.

To improve the binding affinity of the engineered miniproteins to Nectin-4, an SAR approach was used, wherein various amino acid residues within the engineered structure were replaced with optimal substitutions, resulting in improved binding affinity. These substitutions included natural and non-natural amino acids, conjugated chemical moieties, and other small molecule attachments. Chemical crosslinking was used to provide proper structural conformation and stability, which are key features to retention of binding affinity. Miniproteins in accordance with the present disclosure can be generally characterized by having small disulfide-rich peptide scaffolds and can have difficulty folding. Using techniques known to those of ordinary skill in the art, optimized conditions for folding and purification via reverse-phase HPLC were developed to ensure final compounds with correct structure, conformation, and purity. Improved miniproteins were generated and are provided herein (see, e.g., TABLES 2A and 2B).

Example 3: Direct Binding Assay Against Nectin-4

This Example describes exemplary binding assays of miniproteins that bind to Nectin-4.

A direct binding assay was utilized to measure the affinity of miniproteins to the Nectin-4 expressed on the surface of mammalian cells. An equilibrium binding constant was measured ($K_D$) using a miniprotein conjugated to a fluorophore or radioisotope. A miniprotein that possessed an N- or C-terminal epitope tag for detection by a labeled antibody was also used in an assay such as performed herein.

For the direct binding assay utilizing fluorescence, aliquots of mammalian cells expressing Nectin-4 were pelleted in polypropylene tubes. The cells were resuspended in an appropriate binding buffer with a range of miniprotein concentration of at least 100-fold above and below the expected $K_D$ (e.g., one set of dilutions for each miniprotein being tested). The culture media contained BSA to prevent nonspecific binding, and binding was measured at several volumes ranging from 50 µL to 5 mL. Cells expressing Nectin-4 were incubated with Nectin-4-specific miniproteins until equilibrium was reached (several hours). Miniproteins labeled with an N- or C-terminal epitope tag were washed and resuspended in fluorescently labeled anti-epitope tag antibody. After incubation, cells were analyzed with a flow cytometer and the mean fluorescence signal at each miniprotein concentration was determined using data analysis software. For the negative control, the assay was performed with cells that did not express Nectin-4. Expression of Nectin-4 was confirmed using commercially available antibodies. In order to differentiate between live and dead cells to properly analyze the data, instrument scatter patterns or propidium iodide were used to prevent nonspecific binding of dead cells. Moore, Sarah J., and Jennifer R Cochran. "Chapter Nine—Engineering CDPs as Novel Binding Agents." Methods in Enzymology, edited by K. Dane Wittrup and Gregory L. Verdine, vol. 503, Academic Press, 2012, pp. 223-51. ScienceDirect, doi:10.1016/B978-0-12-396962-0,00009-4.

Example 4A: Affinity Maturation of Miniproteins

This Example describes exemplary affinity maturation of miniproteins that bind to Nectin-4, including to enrich for and produce proteins that bind to Nectin-4 with higher affinity than proteins prior to affinity maturation.

Yeast codon-optimized DNA encoding for a Nectin-4 miniprotein (e.g., a linear polypeptide, a folded polypeptide (e.g., covalently linked polypeptide, non-covalently linked polypeptide, or polypeptide including a disulfide linkage), cysteine-dense peptide, a knottin peptide, a binder, an affibody, an engineered Kunitz domain, a monobody, an anticalin, a designed ankyrin repeat domain (DARPin), or an avimer) sequences was amplified using an error-prone DNA polymerase to introduce random mutations. This amplified pool of DNA was transformed into yeast for cell surface display of the mutated Nectin-4 miniprotein(s).

The yeast library displaying the miniprotein variants was then subjected to cell sorting. Cell sorting was first performed using magnetic based approaches and then subsequently by fluorescent-based sorting using flow cytometry/FACS analysis.

In each round, the yeast was incubated with Nectin-4 protein at decreasing concentrations, and the yeast bound to Nectin-4 was isolated. Subsequent rounds of sorting were performed to enrich for higher affinity miniproteins. Individual yeast clones harboring a single peptide miniprotein sequence were isolated after multiple round of selection. Plasmid DNA was isolated and Sanger sequencing was performed to determine the affinity matured miniprotein sequence.

Resulting engineered Nectin-4 miniproteins developed using this assay were synthesized and have amino acid sequences as set forth in TABLE 2A (see, e.g., SEQ ID NOs: 3-158, 161, and 177-215; note that amino acid sequences containing non-natural amino acids were further engineered using chemical synthesis as provided herein after initial development using natural amino acids in a yeast-based assay).

Example 4B: Further Engineering of Affinity Matured Miniproteins

Certain engineered Nectin-4 miniproteins developed in Example 4A were further modified. Starting with a miniprotein having an amino acid sequence of SEQ ID NO: 195, amino acid residues at positions corresponding to 12, and/or 26 along the length of SEQ ID NO: 195 were substituted with K, Kme, Kme2, Kme3, or Kipr. The modified sequences are set forth in SEQ ID NOs: 162-168 (see TABLE 2A) and identified as compounds C298-C304.

Example 5: Synthesis of Nectin-4 Miniprotein-PEG4-DOTA Conjugates

This Example describes synthesis of exemplary Nectin-4 miniprotein-PEG4-DOTA conjugates, which can also be labeled with radiolabels or cold-metal surrogates thereof.

Synthesis of Polypeptide and Conjugation of Chelator

Polypeptides were synthesized on a peptide synthesizer, such as a Chorus peptide synthesizer (Gyros Protein Technologies Inc., Tucson, AZ) by solid-phase methods using Fmoc strategy with N-[(dimethylamino)-1H-1,2,3-triazolo-[4,5-b]pyridin-1-ylmethylene]-N-methylmethanaminium hexafluorophosphate N-oxide (HATU) (0.4 M, 5-fold molar excess to amino acid) in N,N-dimethylformamide (DMF) as the activator, and N'N-diisopropylethylamine (DIEA), 0.8 M, was used as the base. A 20% piperidine/DMF solution was used for Fmoc deprotection. The resin was Fmoc-Ser (tbu)-Wang resin (CEM Corp.) with loading of (0.30 mmol/g) or Rink Amide MBHA LL (Novabiochem) with loading of (0.30-0.40) mmol/g on a (20-40) μmol scale. Fmoc-protected amino acids were coupled sequentially, using 15-minute double-couple cycles, at ambient temperature. Upon completion of the synthesis, the n-terminal Fmoc-protecting group was removed using a 20% solution of Piperidine/DMF.

Metal-chelating motifs were covalently attached to polypeptide chains at the end of the linear SPPS. First, orthogonally protected linkers (e.g., amino-discrete polyethylene glycols, amino-hexanoic acids, and amino acids) were coupled to either the N-terminal amine or alternatively, the ε-amino side chain of a lysine. After an appropriate deprotection step (20% piperidine in dimethylformamide for Fmoc), metal chelators were coupled to the linker-polypeptide chain with conventional HATU activation in DMF containing 2% N,N-diisopropylethylamine (DIEA). Chelators such as tri-t-butyl-DOTA, bis-t-butyl-NOTA, tetra-t-butyl-DTPA, or CROWN were coupled to the linker also using HATU activation in DMF containing 2% N,N-diisopropylethylamine (DIEA). Finally, polypeptides were cleaved from solid support and acid-labile protecting groups were removed with a cocktail of TFA. Incorporation of the PEG4 linker was done using standard SPPS methods and Fmoc-(PEG4)-OH as the coupling partner to the free amine of the resin-bound peptide. Upon completion, the Fmoc-protecting group was removed, and the DOTA chelator was attached using standard SPPS methods mentioned above using (2-(4,7,10-Tris(2-(tert-butoxy)-2-oxoethyl)-1,4,7,10-tetraazacyclododecan-1-yl)acetic acid) as the coupling partner.

Final deprotection and cleavage of the peptide from the solid support was performed by treatment of the resin with 95% TFA. 2% thioanisole. 2% water and 1% triisopropylsilane for 2-3 h.

The cleaved peptide was precipitated using cold diethyl ether. The diethyl ether was decanted, and the solids were triturated with cold diethyl ether and pelleted by centrifugation to yield a white solid.

Disulfide bridge formation was accomplished via natural folding cyclization. The white solid was dissolved in 10-15 ml of (6 M Guanidine/HCl) in water, and allowed to stir. The pH of the solution was adjusted to 7.5 using a 1 M solution of ammonium bicarbonate in water. Next, a 0.2 M solution of Disulfiram in acetonitrile was added to the solution and the mixture allowed to stir overnight at room temperature. A small sample was tested by HPLC/MS to confirm disulfide formation reaction completion. The pH of the reaction solution was adjusted to 4-5 using TFA, and filtered to give a clear, off-white solution. The solution was purified via a Gilson preparative HPLC system using the 30×250 Waters XBridge Protein BEH C4 OBD™ Prep 300 Å 5 μm column at 25° C. A gradient was used within the ranges of 10-50% acetonitrile/water with 0.1% TFA over 30-45 minutes at a flow rate of 30 mL/min, λ −215 nm. The appropriate fractions containing the desired product were combined and lyophilized to give a white solid, which was confirmed to be the desired product by HPLC/MS.

Formation of Metal Complex with Polypeptide

Peptides with covalently attached metal chelators were complexed with either their cold-metal surrogates (e.g., indium, lanthanum, gallium, copper, or europium) or radionuclides (e.g., 111-In or 225-Ac). See, e.g., TABLE 2A. Metalation reactions were carried out in slightly alkaline aqueous buffers. Peptides were dissolved in buffers comprised of 100 mM ammonium acetate, pH 7-8 with 3 molar equivalents of metal. Additional weakly coordinating formulants were also used to avoid oxidation of some metals. Metalation reactions were monitored by RP-HPLC under neutral mobile phases such as 10 mM triethylammonium acetate as a modifier. Ultra-violet signals were used to identify analytes and their shifting retention times were indicative of metalated peptides. Elevated temperatures of 60-90° C. were used, as appropriate, for efficient complexation. After the completion of the metal complexation, excess metal was separated from metalated peptide by semi-prep HPLC under neutral conditions. Mass spectroscopy was used to confirm the metalated peptide species. Radioactive species were characterized for radiochemical yield and purity with either radio-HPLC or radio-TLC.

Example 6A: Radiolabeling of Nectin-4-PEG4-DOTA with Ac$^{225}$

This Example describes radiolabeling of exemplary Nectin-4 miniprotein-PEG4-DOTA conjugates with Ac-225.

Ac-225, in the form of [$^{225}$Ac]actinium chloride, is prepared from reconstitution of dried [$^{225}$Ac]actinium nitrate residue in hydrochloric acid (100 mM), and added to a solution of DOTA containing miniprotein, prepared at 5 mg/mL in sodium acetate buffer or ethanol, with various amounts of sodium acetate buffer (250 mM, pH 6), in a 1.5 mL Eppendorf vial and heated at 75° C. for 30 minutes. Ac-225 radiolabeled products are purified using a PD-10 column and eluted with sodium ascorbate in saline (2 mg/mL), and passed through a 0.22 µm filter. The radiochemical purity is determined as the ratio of the main product peak to other peaks. The radiochemical yield is determined as the ratio of final activity of the product over the starting activity used for the reaction adjusted for the radioactive decay.

Example 6B: Labeling of Nectin-4-PEG4-DOTA with $^{nat}$In

This Example describes metalation of exemplary Nectin-4 miniprotein-PEG4-DOTA conjugates with $^{nat}$In (see, e.g., TABLE 2A for exemplary PEG4-DOTA conjugates; note that the $^{nat}$In-PEG4-DOTA conjugates disclosed in TABLE 2A, such as, e.g., C I10, etc. are labeled using natural abundance Indium, which can be a combination of 113-In and 115-In, and may be seen, for example, as $^{nat}$In. Radioactive Indium is used to label exemplary PEG4-DOTA conjugates such as, e.g., C109, etc.)

Labeling of polypeptide binder-PEG4-DOTA with natural abundance In ($^{nat}$In): 1 mg of miniprotein DOTA conjugate was dissolved in 100 µl of pH 6 ammonium acetate solution (0.1 M) (or pH 5 sodium acetate solution (0.1 M)) and 2 molar equivalents of InCl$_3$ in separated reaction buffer solution were added. Reaction mixture was heated at 70° C., or 60° C. for 30-40 minutes and mass spec analysis showed completion of indium chelation to DOTA. Metalated product was purified using semi-prep system (10 mm×250 mm, 5 µm, gradient: 5-50%-10 min and hold at 50% for 5 min-4.0 mL/min (or 5-60%-10 min and hold at 60% for 5 min-4.0 ml/min depending on the peptide hydrophobicity), column temperature: RT or 60° C. (depending on the peptide stickiness), mobile phase: A: pH 6.5 100 mM TEAA, B: 10% pH 6.5 100 mM TEAA in acetonitrile).

Example 7A: Peptide Binding Assay to Nectin-4 Via Surface Plasma Resonance (SPR)

This Example describes SPR analysis to measure Nectin-4 miniprotein binding affinity.

Peptide binding affinity to the target protein was measured by SPR using an SPR machine, such as a Biacore T200 instrument. The target protein was covalently coupled to a Biacore chip surface using free amine-coupling chemistry (NHS/EDC) and all uncoupled sites were blocked with ethanolamine. Free peptides were flowed over the target protein surface in increasing concentrations to measure association ($K_a$, 1/Ms$^{-1}$)) and dissociation ($K_d$, s$^{-1}$) to calculate the dissociation equilibrium constant ($K_D$) using an appropriate binding model (see, e.g., Nikolas Stroth, J Biol Methods. 2016; 3 (1)).

Figure 1B:
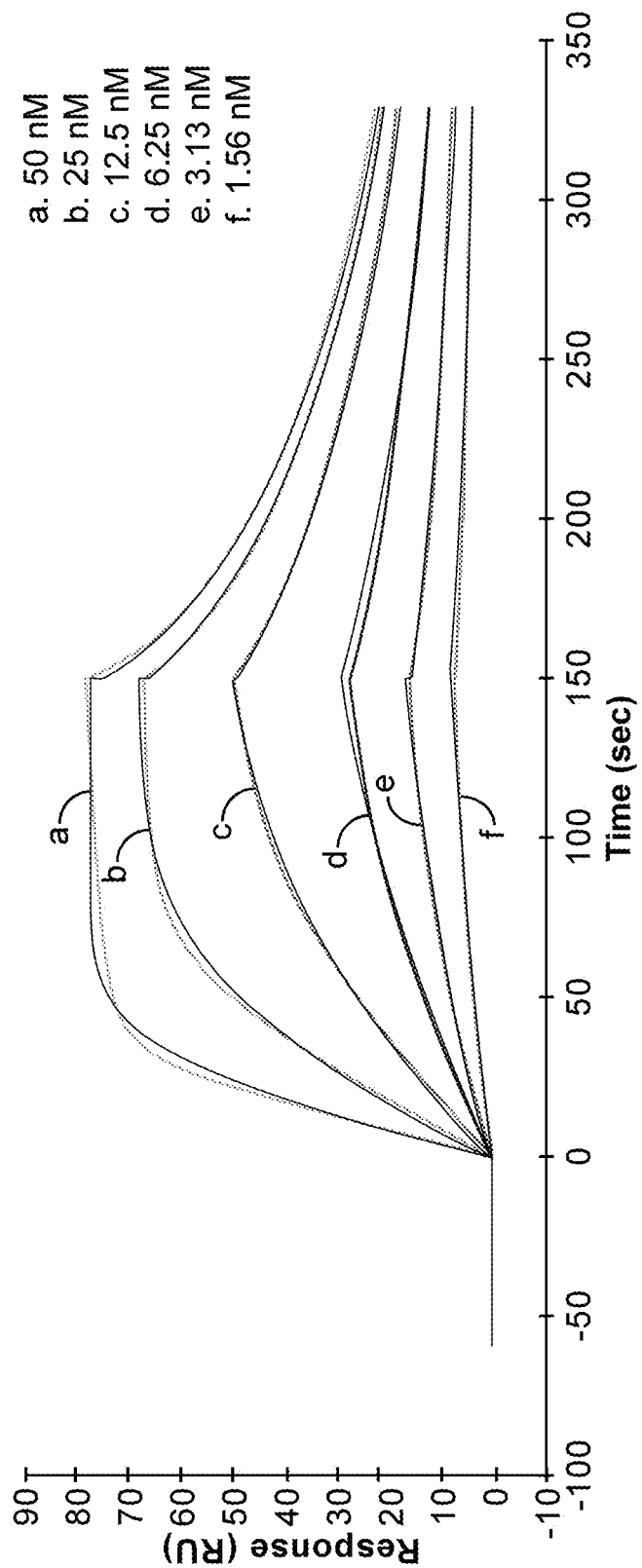
Figure 2A:
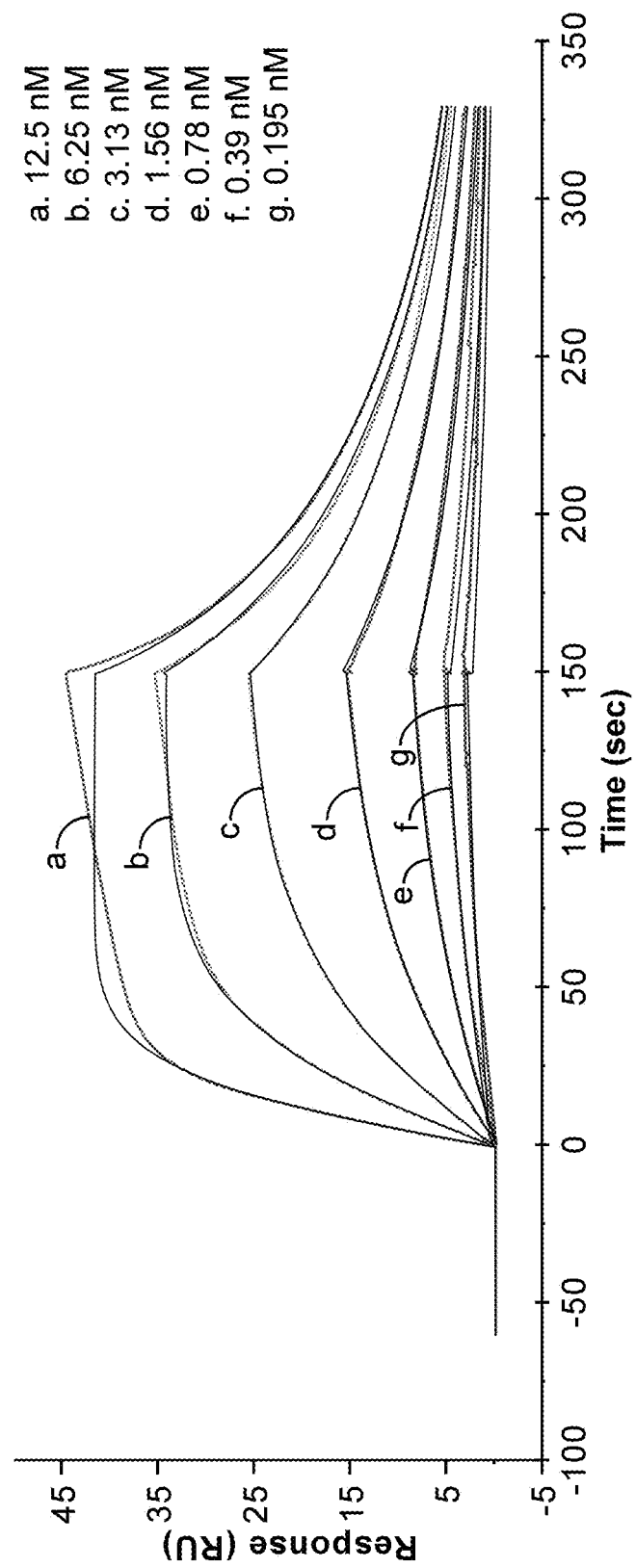
FIGS. 2A and 2B are fitted sensorgrams (SPR) of an exemplary Nectin-4 peptide binding to mouse and human Nectin-4, respectively.
Figure 2B:
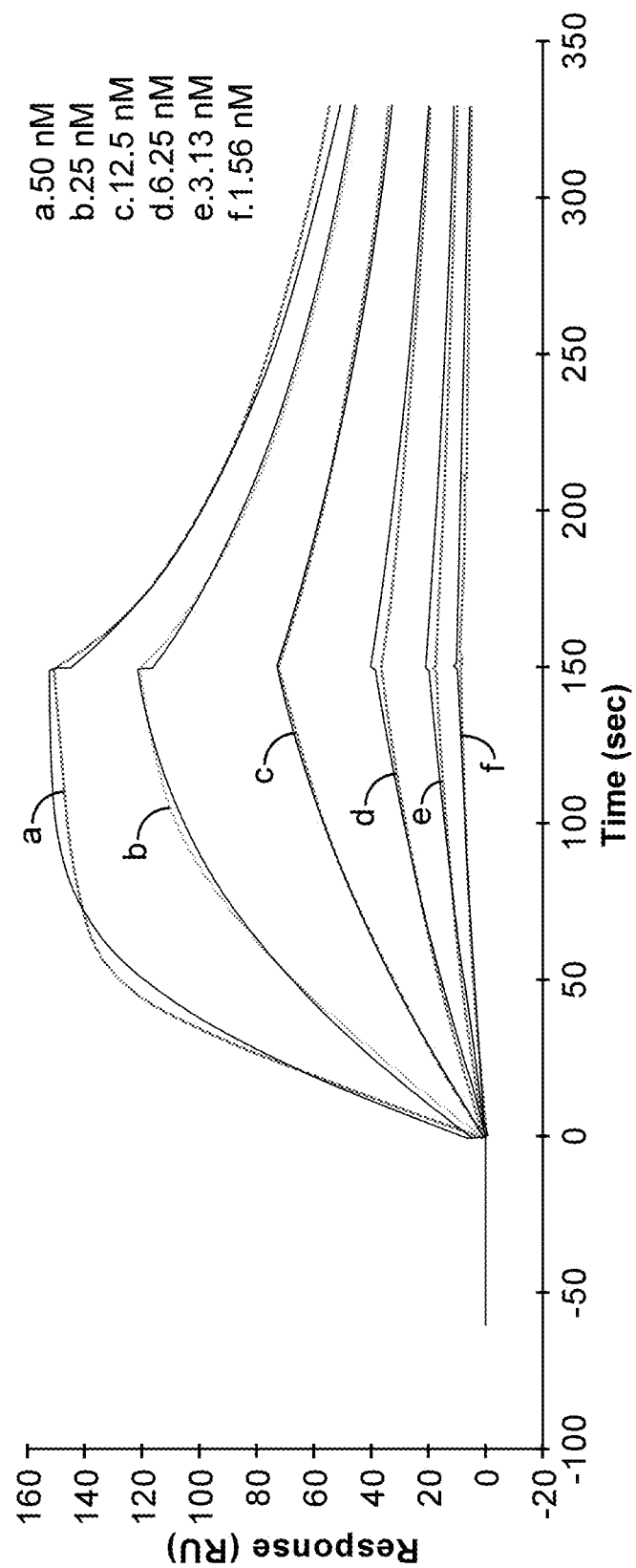

FIGS. 1A and 1B show fitted sensorgrams (SPR) from the BIACORE machine, demonstrating the affinity of an exemplary Nectin-4 compound, C9, with a miniprotein with an amino acid sequence according to SEQ ID NO: 5 and TABLE 2A. TABLE 2B shows SPR data from the BIACORE, demonstrating the affinity of an exemplary Nectin-4 compound, C12, with a miniprotein with an amino acid sequence according to SEQ ID NO: 5. In this example, affinity for mouse Nectin-4 (FIGS. 1A and 2A) and human Nectin-4 (FIGS. 1B and 2B) were measured using a 1:1 binding model at 25° C. In FIGS. 1A, 1B, 2A, and 2B, lines on graphs are labeled from top to bottom, beginning with letter "a." and the corresponding concentration is noted to the right of the figure. As demonstrated by the SPR measurements on the BIACORE machine, C9 had a $K_D$ of 7.825 nM (Chi$^2$=0.130; $k_d$=0.02134 s$^{-1}$) for mouse Nectin-4 (FIG. 1A) and 7.496 nM (Chi$^2$=0.560; $k_d$=0.02271 s$^{-1}$) for human Nectin-4 (FIG. 1B), and C12 had a $K_D$ of 2.942 nM (Chi$^2$=0.230; $k_d$=0.02625 s$^{-1}$) for mouse Nectin-4 (FIG. 2A) and 10.5 nM (Chi$^2$=2.68; $k_d$=0.01697 s$^{-1}$) for human Nectin-4 (FIG. 2B).

Example 7B: Peptide Binding Assays

This Example describes peptide binding assays using exemplary Nectin-4 miniproteins and conjugates thereof.

Surface plasmon resonance (SPR) analyses were performed using Biacore T200 (GE Healthcare). Target protein ("ligand") was immobilized to a CM5 Series S sensor chip (Cytiva) using amine-coupling chemistry. Running buffer was 0.05% surfactant P20 in HEPES buffered saline (HBS-P), pH 7.4 (Cytiva). Immobilization was performed at 25° C. Carboxyl groups in each flow cell were activated using a 1:1 mixture of 0.4 M 1-ethyl-3-(3-dimethylaminopropyl)-carbodiimide in water (EDC) and 0.1 M N-hydroxysuccinimide in water (NHS) for 7 minutes. The ligand was prepared in 10 mM sodium acetate pH 5 (Cytiva). Pulsatile injections were made to target a specific immobilization level. Any remaining amine-reactive esters on the chip surface were blocked with a 7-minute injection of 1 M ethanolamine, pH 8.5. Three 10-second pulses of 50 mM sodium hydroxide were then made to remove any unbound ligand. Reference cells were modified using amine coupling chemistry, omitting ligand injection.

Exemplary compounds set forth in TABLE 2A ("analyte") were injected to the prepared ligand surface and blank reference surface in increasing concentrations to cover 0.1- 10× the expected $K_D$ range at 25° C. Increase in signal (RU) is proportional to an increase in binding events between the analyte and ligand surface. The injection was then stopped, and dissociation was measured. The resulting sensorgram has reference surface and blank injection subtracted prior to curve fitting. Measured association ($k_a$, 1/Ms$^{-1}$) and dissociation ($k_d$, s$^{-1}$) were fit to a 1:1 binding model to calculate a dissociation equilibrium constant, $K_D$ (M) for each analyte. Binding affinity, as estimated from DELFIA® binding assays for exemplary compounds, is set forth in TABLE 2B.

Additional binding affinity measurements, as estimated from surface plasmon resonance (SPR), are summarized in TABLE 3.

TABLE 3

Binding Affinities of Exemplary Compounds to Nectin-4

| SEQ ID NO: OF POLYPEPTIDE TESTED | Compound Name | Binding Affinity ($K_D$, nM) |
|---|---|---|
| 93 | C143 | 0.238 |
| 99 | C149 | 0.297 |
| 134 | C185 | 0.371 |
| 138 | C190 | 0.318 |
| 145 | C197 | 0.212 |
| 155 | C208 | 0.302 |
| 194 | C247 | 0.283 |
| 195 | C253 | 0.255 |
| 200 | C259 | 0.226 |
| 203 | C264 | 0.476 |
| 204 | C267 | 0.586 |

Example 8A: Binding Affinity Assay of Radiolabeled Conjugates

This Example describes measurements of binding affinity using radiolabeled Nectin-4 miniproteins, cold-labeled surrogates, and conjugates thereof.

To measure binding affinity of miniproteins conjugated to Ac-225, La-138, and DOTA to the N-terminus to determine if the miniprotein affects Nectin-4 binding specificity, a binding assay as provided in Example 3 was performed. The positive control was a Nectin-4 miniprotein not conjugated to DOTA and Ac$^{225}$ (or its cold metal surrogate). It was expected that the miniprotein alone would bind to Nectin-4. Binding affinity with cells that do not express Nectin-4 was also measured as a negative control.

Figure 3A:
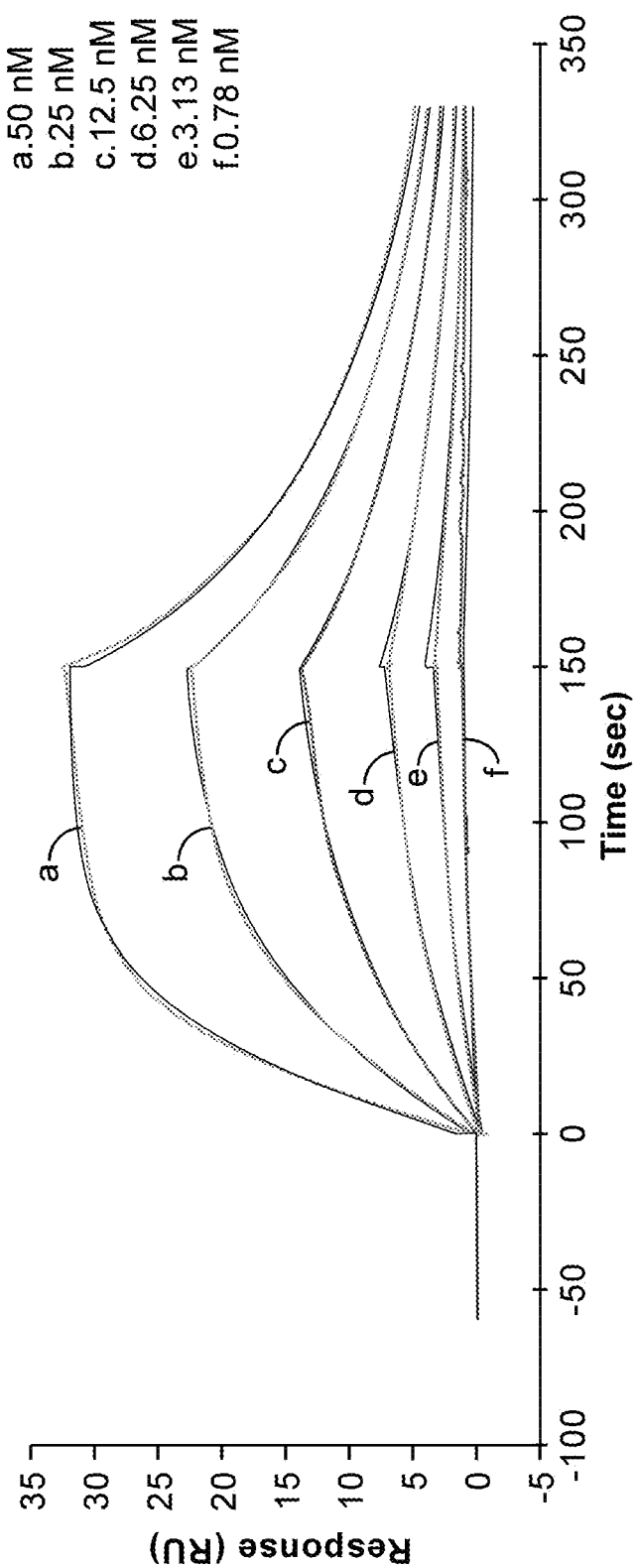
FIGS. 3A and 3B are fitted sensorgrams (SPR) of an exemplary conjugate comprising an exemplary Nectin-4 peptide binding to mouse and human Nectin-4, respectively.
Figure 3B:
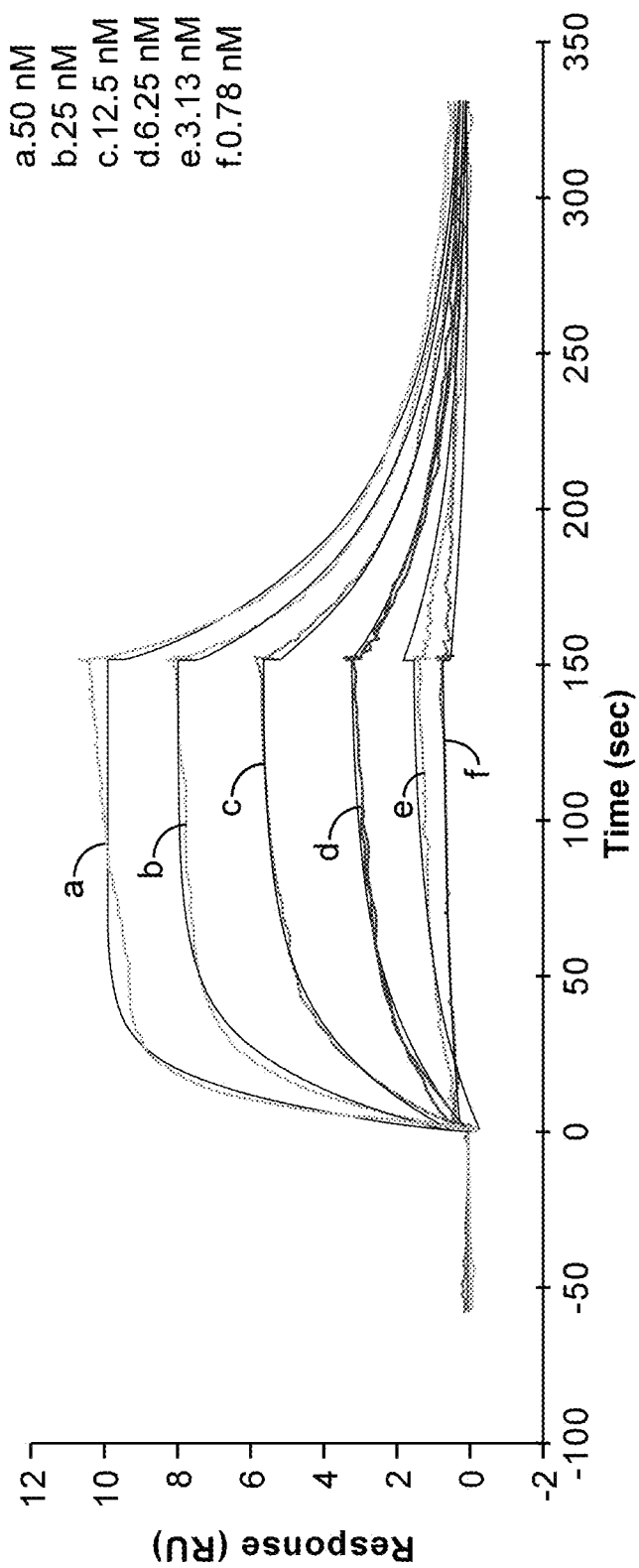
Figures 4A, 4B:
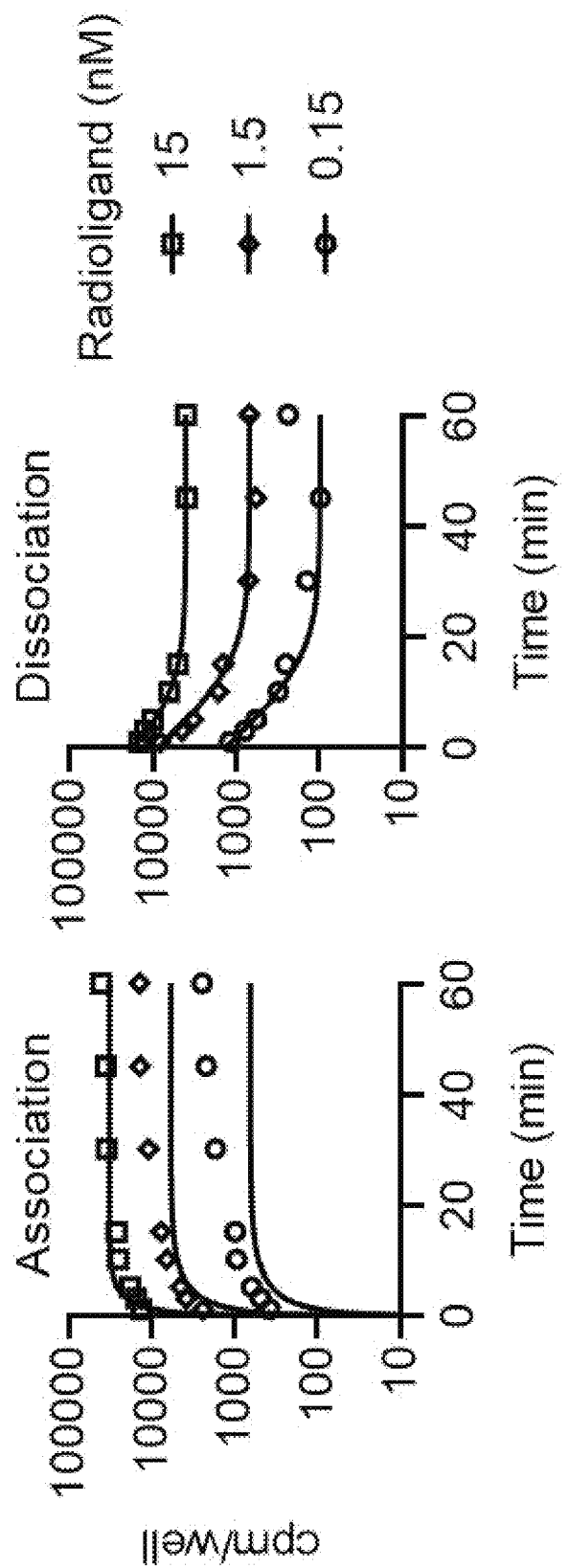
FIGS. 4A and 4B are graphs showing association (FIG. 4A) and dissociation (FIG. 4B) kinetics for an exemplary compound comprising a radioconjugate miniprotein provided herein, on a human Nectin-4-expressing cancer line.
Figures 5A, 5B:
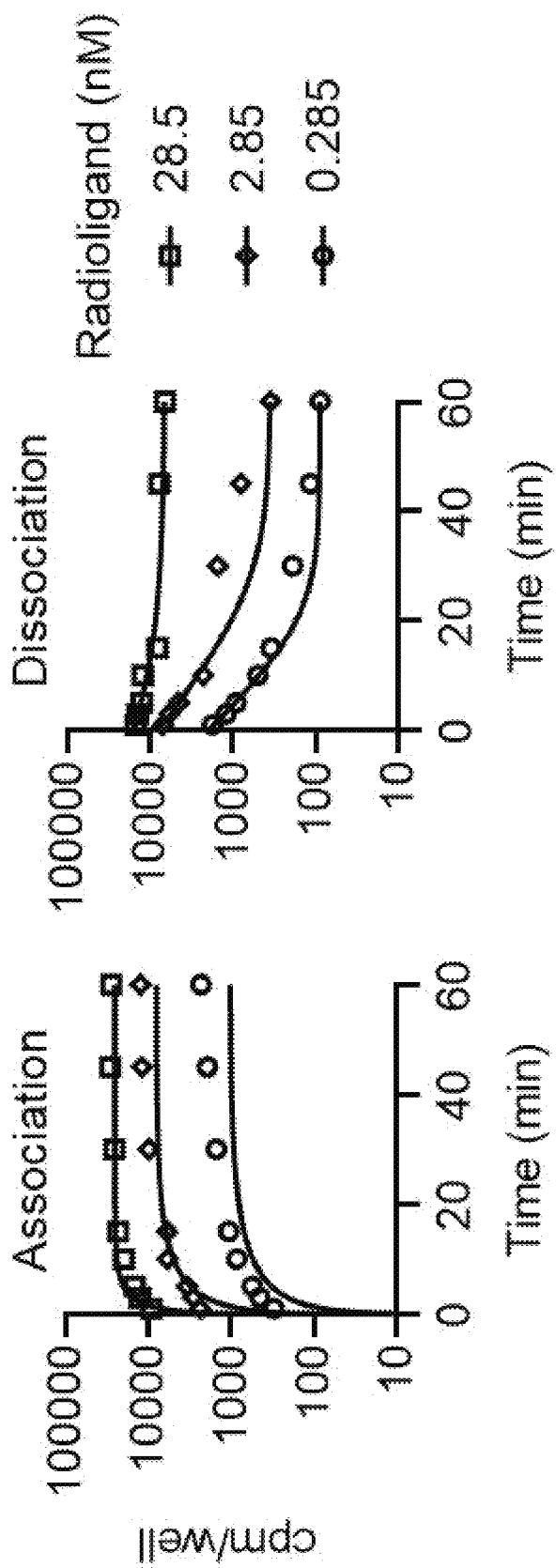
FIGS. 5A and 5B are graphs showing association (FIG. 5A) and dissociation (FIG. 5B) kinetics of an exemplary compound comprising a radioconjugate miniprotein provided herein, on a human Nectin-4-expressing cancer line.

FIGS. 3A and 3B show fitted sensorgrams (SPR) from the BIACORE machine, demonstrating the affinity of an exemplary Nectin-4 compound, C91. (i.e., a conjugate comprising a Nectin-4 peptide of SEQ ID NO: 5 and arranged having an N-terminus comprising $^{138}$La-DOTA-PEG4 and a C-terminus comprising OH). In this example, affinity for mouse Nectin-4 (FIG. 3A) and human Nectin-4 (FIG. 3B) were measured using a 1:1 binding model at 25° C. In both FIGS. 3A and 3B, lines on graphs were labeled from top to bottom, beginning with letter a, and the corresponding concentration was noted to the right of the figure. As demonstrated by the SPR measurements from the BIACORE machine, C91 had a $K_D$ of 24.65 nM (Chi$^2$=0.0634; k$_d$=0.02817 s$^{-1}$) for mouse Nectin-4 (FIG. 3A) and 17.91 nM (Chi$^2$=0.0281; k$_d$=0.02966 s$^{-1}$) for human Nectin-4 (FIG. 3B).

Example 8B: Radioligand Binding Assays

Radioligand binding was performed in HT-1376 urothelial cancer cells by method of saturation. Cells were seeded at 20,000 cells per well in 96-well format 48 h prior to assay. Lutetium-177-labeled radioconjugates of C215 and C117 were incubated with cells at 4° C. for 1 h at various increasing concentrations of radioligand. At the end of incubation, cells were washed three times with PBS and radioactivity was quantified by gamma counting as shown in FIGS. 4A-5B.

Radioligand binding was performed in HT-1376 urothelial cancer cells by method of kinetic analysis. Cells were seeded at 20,000 cells per well in 96-well format 48 h prior to assay. On the day of assay, culture medium was removed and PBS was added to cells. Association kinetics were measured at three concentrations of radioligand, and this was performed by the addition of lutetium-177 radioconjugates to cells at various time points from 1 to 60 minutes. Dissociation kinetics were measured by method of forced dissociation at three concentrations of radioligand by first incubating cells with radioligand until equilibrium was reached at 1 h, followed by the addition of 1000 times excess non-radioactive competitor ligand at time points from 1 to 60 minutes. Data were fitted to measure association (FIGS. 4A and 5A) and dissociation (FIGS. 4B and 5B) by global fit for all concentrations evaluated and the $K_a$, $K_d$, and $K_D$ were determined. The $K_D$ values and confidence intervals are provided in TABLE 4.

TABLE 4

$K_D$ of Exemplary Compounds Prior to Radiolabeling

| Compound (PEG4-DOTA prior to radiolabeling) | $K_D$ (nM) | Confidence Interval (CI) |
|---|---|---|
| C215 | 5.01 | 4.17 to 6.08 |
| C82 | 14.08 | 0.78 to 1.03 |
| C214 | 3.03 | 2.42 to 3.77 |
| C109 | 8.72 | 5.2 to 15.86 |
| C117 | 2.64 | 1.73 to 3.9 |

Example 8C: Competitive Binding Assay

This Example describes the results of competitive binding assays on exemplary Nectin-4 miniproteins.

A competition binding assay was utilized to determine the $K_i$ for miniproteins bound to Nectin-4 expressed on the surface of cancer cells. To accomplish this, Nectin-4-expressing HT-1376 cells were plated in 384-well plates and incubated with a fixed concentration (10 nM) of C307, a compound with a well-characterized Nectin-4-binding miniprotein (SEQ ID NO: 48), and varying concentrations (3-fold dilutions from 5 µM in a 12-point dose-response curve) of non-metalated miniproteins (e.g. biotin-labeled). Miniprotein incubations occurred for 90 min to reach binding equilibrium. During this period, unlabeled miniprotein displaced C307 binding to Nectin-4 and indirectly impacted the fluorescent signal derived from the Nectin-4-bound, Eu-labeled miniprotein, C307. After miniprotein incubations, the wells were washed to remove unbound ligand and treated according to manufacturer instructions for a DELFIA® (dissociation-enhanced lanthanide fluorescent immunoassay, Revvity Health Sciences). In brief, washed wells were incubated with 15 µL of 2 M HCl for 2 h at 37° C., after which 17 µL of 2 M NaOH and 30 µL of DELFIA® enhancement solution were added to each well and incubated for an additional 30 min. The remaining Eu reacted with the DELFIA® enhancer solution to generate fluorescence measured on the Envision instrument. Relative fluorescence units (RFUs) were measured as a function of test article concentration in order to calculate an IC50. The Ki can then be calculated using the Cheng-Prusoff equation for converting a measured IC50 to Ki:

$$Ki=IC50/(1+([C307]/K_D))$$

where IC50 was calculated from the DELFIA® data using a one binding site fit model, the concentration of Eu-labeled C307 was 10 nM (i.e. [C3071], and the previously determined equilibrium binding constant ($K_D$) for C307 was 5.2 nM.

Additionally, HT-1376 human urothelial cancer cells were used to determine the on-cell binding affinity of C253 in a competitive binding assay, by testing the test article over 12 concentrations ranging from 28 pM to 5 µM in the presence of 10 nM of C307. The $K_i$ for C253 was determined to be 0.82 nM (95% confidence interval [CI]: 0.70-0.91)]

Figure 21:
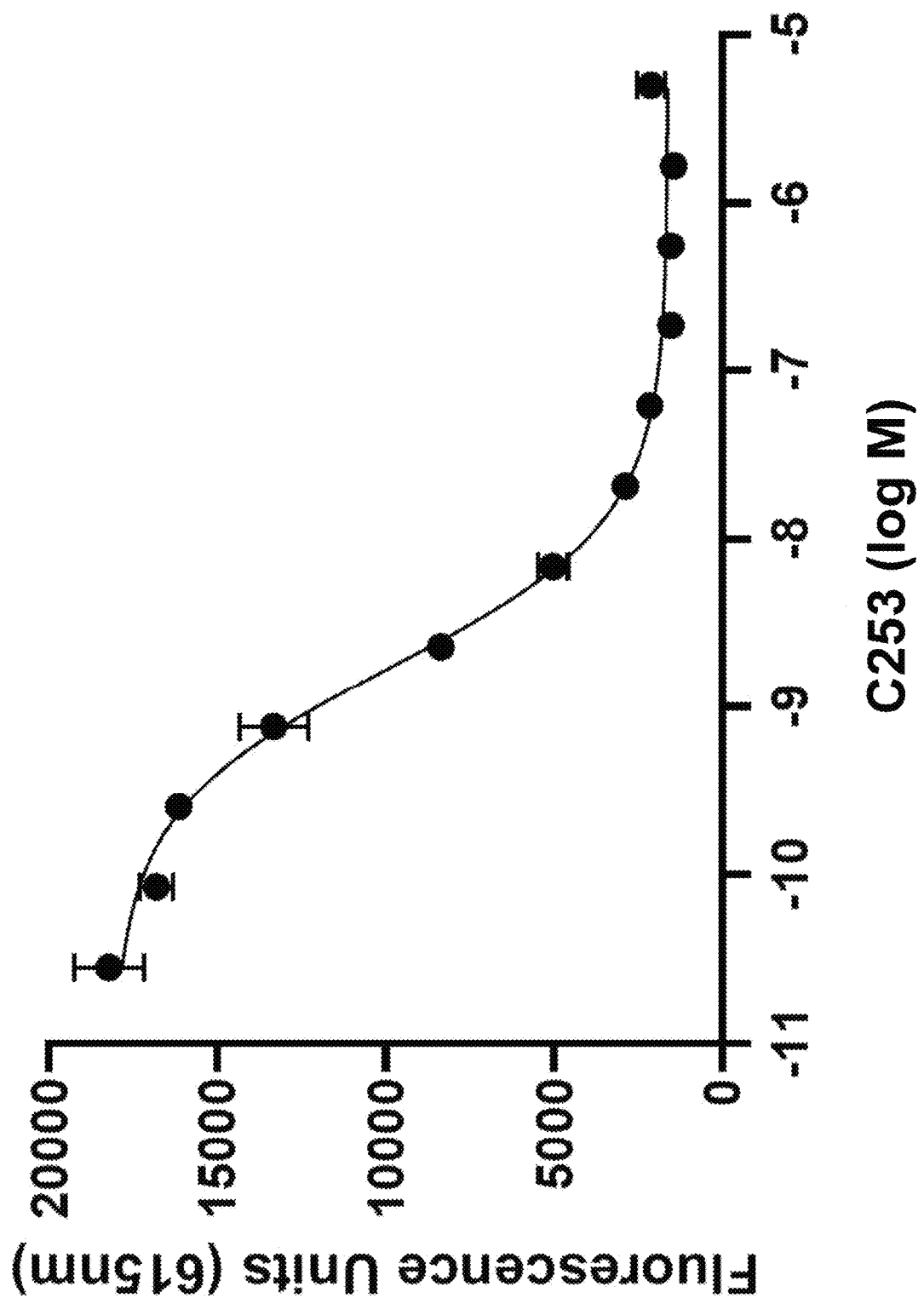
FIG. 21 is a graph showing high binding affinity of a biotin-labeled exemplary Nectin-4-targeting miniprotein (C253) to endogenous Nectin-4 expressed on HT-1376 human urothelial cancer cells in the presence of a europium-labeled Nectin-4 binder (C307). The dose-response curve depicts fluorescence units as a measurement of the binding of biotin-labeled exemplary Nectin-4-binding miniprotein C253, evaluated over 12 concentrations ranging from 28 pM to 5 µM (x-axis; expressed in log M).

The dose-response curve for C253 is provided in FIG. 21.

Example 9: $^{111}$In Labeling of Miniproteins for Use in Biodistribution Assays This Example describes radiolabeling of exemplary compounds for use in biodistribution assays.

In-111 labeling of miniproteins with MES buffer: In-111 was neutralized with 0.5 M MES buffer pH 5.5. This mixture was added to miniproteins prepared at 2 mg/mL in water with an equivalent amount of 0.5 M MES buffer pH 5.5, in a 1.5 mL Eppendorf vial and heated at 37° C. for 60 mi. After the reaction, an HPLC sample was taken and an equivalent amount of 10 mM DTPA in 0.1 M ammonium acetate pH 5 was added and incubated for at least 15 minutes. The sample was then used for HPLC analysis.

In-111 labeling of miniproteins with sodium acetate buffer: In-111 was neutralized with 0.1 M sodium acetate buffer pH 5. This mixture was added to a vessel with an exemplary compound, C188 (which has a miniprotein of SEQ ID NO: 136), prepared at 5 mg/mL in sodium acetate buffer, with various amounts of 0.1 M sodium acetate buffer pH 5, in a 1.5 mL Eppendorf vial and heated at 75° C. for 45 minutes. After the reaction, an HPLC sample was taken and an equivalent amount of 10 mM DTPA in 0.1 M ammonium acetate pH 5 was added and incubated for at least 15 min. The sample was then used for HPLC analysis.

Purification of $^{111}$In-miniproteins: Purification was done on two of the crude reaction mixtures mixed with 10 mM DTPA in 0.1 M ammonium acetate pH 5 and incubated for 15 minutes. A 3 kDa 0.5 mL Amicon filter was used for purification and the filter was spun at 15,000 RCF for 9 minutes. Saline was used as a formulation buffer.

Labeling of polypeptide binder-PEG4-DOTA with natural abundance In ($^{nat}$In): 1 mg of miniprotein DOTA conjugate was dissolved in 100 µl of pH 6 ammonium acetate solution (0.1 M) (or pH 5 sodium acetate solution (0.1 M)) and 2 molar equivalents of InCl$_3$ in separated reaction buffer solution were added. Reaction mixture was heated at 70° C., or 60° C. for 30-40 minutes and mass spec analysis showed completion of indium chelation to DOTA. Metalated product was purified using semi-prep system (10 mm×250 mm, 5 µm, gradient: 5-50%-10 min and hold at 50% for 5 min-4.0 mL/min (or 5-60%-10 min and hold at 60% for 5 min-4.0 ml/min depending on the peptide hydrophobicity), column temperature: RT or 60° C. (depending on the peptide stickiness), mobile phase: A: pH 6.5 100 mM TEAA, B: 10% pH 6.5 100 mM TEAA in acetonitrile).

Example 10: In Vivo Biodistribution Involving $^{111}$In-Labeled Miniproteins

This Example describes biodistribution assays using radiolabeled miniproteins and conjugates thereof as provided herein.

Animals: Female athymic nude mice (6-8 weeks of age) were purchased from Charles River Laboratories and housed according to IACUC guidelines with ad libitum feeding. Biodistribution imaging experiments were performed on both null and tumor-bearing athymic nude mice. Tumor xenograft models were generated by inoculating mice subcutaneously with 3×10$^6$ HT-1376 cells in 200 µL (50:50 PBS/Matrigel) in either the right shoulder or right flank. HT-1376 is a human cell line that expresses Nectin-4. Tumors were monitored for 14 days prior to SPECT/CT imaging dates. Mice with tumor volumes between 150 mm$^3$ and 250 mm$^3$ were selected for study inclusion and randomized to treatment arms. An excess of 60% of required imaging study mice were inoculated with tumor cells to ensure enough mice with appropriate tumor ranges were generated.

Animal grouping and Treatment: Animals were monitored for body weight bi-weekly and at the time of experimentation, grouped into groups of n=3. Animals were administered test-agents (TAs) that were prepared as described above. Animals received one of two standard injected dose activates and mass dose injections, depending at which site imaging studies were performed.

Site-1: 350 µCi of activity ($^{111}$In) at approximately 3-5 µg of total peptide per mouse.

Site-2: 30 MBq (810 Ci) of activity ($^{111}$In) at approximately 1 nM (4-6 µg) of total peptide per mouse.

Animal imaging: Animals were sedated using isoflurane gas and imaged in a 3 bed hotel using a NanoScan SPECT/CT scanner. Animals were imaged at timepoints between 10 min and 72 h post-dosing via SPECT scan, followed by CT scans. Details of the image process and analysis are described in Example 11.

Humane endpoints: All animals were euthanized following the final imaging time point and carcasses were discarded according to IACUC protocols.

Results of the biodistribution assay with exemplary miniproteins are shown in TABLE 5A and TABLE 5B. A relationship between target affinity and tumor uptake was observed, confirming that exemplary Nectin-4 miniprotein compounds specifically target and bind to tumors with high affinity and do not accumulate in non-target organs as compared to Nectin-4 miniproteins with less binding affinity.

TABLE 5A

Biodistribution Data for Exemplary Nectin-4 Miniprotein Compounds, Tumor

| Compound Name | Data of Biodistribution (+4 h Tumor~% ID/g) |
|---|---|
| C101 | 1.62 |
| C105 | 1.55 |
| C109 | 2.25 |
| C113 | 1.65 |
| C117 | 2.29 |
| C121 | 2.03 |
| C129 | 1.77 |
| C133 | 1.29 |
| C137 | 1.12 |

TABLE 5B

Biodistribution Data for Exemplary Nectin-4 Miniprotein Compounds, Kidneys

| Compound Name | 4 h (% ID/g) | | 24 h (% ID/g) | |
|---|---|---|---|---|
| | Average | StDev | Average | StDev |
| C82 | 144.57 | 14.35 | 104.05 | 21.11 |
| C100 | 111.82 | 2.20 | 61.79 | 7.29 |
| C104 | 69.63 | 6.39 | 40.56 | 9.58 |
| C109 | 77.43 | 17.72 | 36.88 | 5.48 |
| C117 | 149.73 | 13.22 | 93.33 | 9.39 |
| C113 | 87.90 | 3.86 | 42.66 | 5.00 |
| C121 | 100.39 | 15.82 | 60.42 | 12.74 |
| C129 | 43.45 | 24.17 | 19.94 | 11.05 |
| C133 | 43.83 | 0.15 | 20.94 | 2.26 |

TABLE 5B-continued

Biodistribution Data for Exemplary Nectin-4 Miniprotein Compounds, Kidneys

| Compound Name | 4 h (% ID/g) | | 24 h (% ID/g) | |
|---|---|---|---|---|
| | Average | StDev | Average | StDev |
| C137 | 78.82 | 9.08 | 42.86 | 5.65 |
| C293 | 55.78 | 6.10 | 32.60 | 2.06 |
| C250 | 67.48 | 20.71 | 34.85 | 8.14 |
| C241 | 60.07 | 8.96 | 38.28 | 17.31 |
| C244 | 27.72 | 13.57 | 15.88 | 7.45 |
| C236 | 65.14 | 6.38 | 42.08 | 5.73 |
| C271 | 59.10 | 5.34 | 34.34 | 0.72 |
| C245 | 61.02 | 18.99 | 33.54 | 9.39 |
| C251 | 16.58 | 4.00 | 10.19 | 2.63 |
| C260 | 12.82 | 3.36 | 7.36 | 1.43 |

Example 11: Image Analysis Methods

This Example describes imaging analysis methods for use with biodistribution assays such as in Example 10.

Image Processing: Images were generated as SPECT/CT pairs with the SPECT reported in units of activity. Namely, the values assigned to the voxels (volume elements) comprising the SPECT images were in units of μCi. SPECT images were co-registered to the CT scan for anatomical reference, resampled to 0.2 mm$^3$ voxels, masked to remove the CT background, and cropped to a uniform size prior to analysis.

Estimating tissue uptake: Regions of interest (ROIs) were defined using VivoQuant software. The kidneys and bladder were segmented as fixed volume phantoms and registered using the CT for anatomical reference. Two fixed volume spheres were used to create the liver ROI. Spheres were placed at appropriate anatomical locations based on CT and SPECT signal. Group and individual master spreadsheets were generated which included the volume, activity, and concentration (Activity/Volume) at each time point for each ROI generated. Additionally, plots of activity were generated using Matplotlib based python tools to highlight trends in the data. Outputs of each region were plotted and reported in percent injected dose per gram (% ID/g) and regions which were fully segmented were additionally presented in percent injected dose (% ID). Plots of body weights and tumor volumes measured manually in the lab were also created in the same manner.

Uptake unit definitions: Results were presented in units of percent injected dose (% ID) and percent injected dose per gram (% ID/g). The definition of these units can be found in the equations below: The % ID for each analyzed region from the in vivo imaging data can be defined as stated in Equation 1:

$$\% \, ID = \frac{Uptake}{Injected \, Dose} * 100$$

where Uptake=Radioactivity (μCi) in a particular ROI, decay-corrected to the time of injection and imaging timepoint; and Injected dose=Radioactivity (μCi) injected into the subject.

The % ID/g for each analyzed region from the in vivo imaging data can be defined as stated in Equation 2:

$$\frac{ID}{g} = \frac{\frac{Uptake}{Injected \, Dose} * 100}{ROI \, weight}$$

where Uptake=Radioactivity (μCi) in a particular ROI, decay-corrected to the time of injection and imaging timepoint; Injected dose=Radioactivity (μCi) injected into the subject; and Weight=For in vivo, this is the volume of the particular ROI in mL.

Image generation: After the preprocessing described in A, individual maximum intensity projections (MIPs) were created with VivoQuant software for each subject at each time point and scaled in percent injected dose per gram (% ID/g). The CT for each image was windowed from −500 to 4500 Hounsfield Units (HU). The SPECT was windowed at various ranges to highlight different regions of uptake. Images were then stitched together using Image Magick based python tools to create montages of subjects over time and time points over groups.

ROIs for quantitative analysis were generated from CT scans in order to quantify the injected dose per gram (% ID/g) in tissues of mice as shown in TABLE 5A, TABLE 5B, and Example 10. A relationship between binding affinity and tumor uptake was observed, showing that increased affinity for Nectin-4 resulted in increased tumor uptake. This supports specificity and improvement in targeting over miniproteins with lower binding affinity.

Example 12: Plasma Pharmacokinetic Analysis in Sprague Dawley Rats

This Example describes plasma pharmacokinetic analysis of compounds provided herein using plasma analysis in Sprague Dawley rats.

To begin, double jugular vein-cannulated Sprague Dawley rats were dosed with bolus intravenous injections of miniproteins (0.03-0.3 mg/kg) and FITC-sinistrin. Nine blood collection timepoints were taken from 0-2 h, processed to plasma with $K_2$ EDTA, and were frozen for subsequent bioanalysis. Plasma miniprotein concentrations were measured by LC-MS/MS. To control for inter-animal renal clearance differences, and to compare with glomerular filtration rate (GFR), the miniprotein was co-formulated with a molecular marker of GFR, FITC-sinistrin (FS) (Pill et al., 2005). Plasma FITC-sinistrin was measured fluorometrically. All unknown sample measurements were interpolated against known authentic standards spiked into normal rat plasma to calculate concentration. Finally, non-compartmental analysis was performed to estimate plasma pharmacokinetic parameters.

Exemplary plasma terminal half-lives and averages of controls are reported in TABLE 6. Additionally, plasma half-life data of a GFR control and previously published (see Challita-Eid et al Cancer Res (2016) 76 (10):3003-3013) measurements for enfortumab vedotin are also shown in TABLE 6.

TABLE 6

Plasma terminal half-life

| Compound | Plasma terminal half-life (min) |
|---|---|
| C102 | 28.9 |
| C110 | 26.8 |
| C217 | 31.4 |
| C216 | 31.4 |
| C97 | 27.3 |
| C102 | 28.9 |
| C109 | 30.5 |
| C110 | 24.1 |
| C114 | 25.5 |
| C118 | 19.7 |
| C219 | 25.4 |
| C237 | 28.4 |
| C240 | 29.7 |
| C242 | 29.7 |
| C246 | 38 |
| C251 | 28.7 |
| C254 | 23.9 |
| C261 | 28.7 |
| C270 | 28.3 |
| Compound Average | 28.2 |
| GFR Control | 26.7 |
| enfortumab vedotin | 2,476.8 (1.72 days) |

Figure 22:
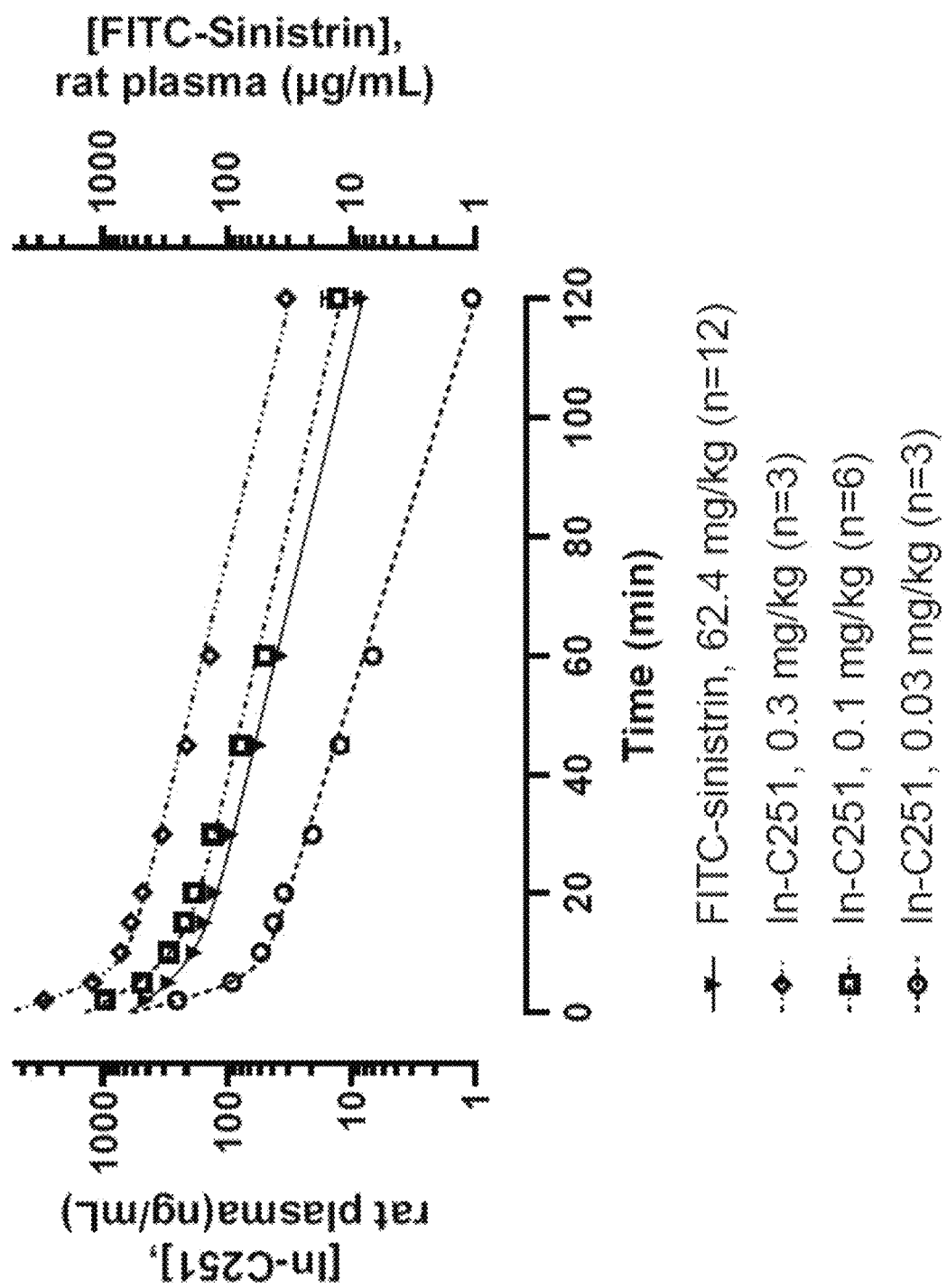
FIG. 22 is a graph showing the plasma profile and clearance of an indium-labeled exemplary Nectin-4-targeting conjugate ($^{nat}$In-C251) intravenously administered at 0.03 mg/kg (circles), 0.1 mg/kg (squares), or 0.3 mg/kg (diamonds) in rats, compared to FITC-Sinistrin, (FS; inverted triangles), a molecule known to be cleared at the glomerular filtration rate (GFR), at 62.4 mg/kg. The plot shows the concentration of $^{111}$In-C251 and FITC-Sinistrin over a 2 h period.

The plasma profile for C251 is provided in FIG. 22 and the plasma pharmacokinetic values from the noncompartmental analysis are provided in TABLE 7.

TABLE 7

Noncompartmental Analysis Reported Values (±SE)

| Dose (mg/kg) | N | $C_{max}$ (ng/mL) | $AUC_{INF}$ (min*ng/mL) | CL (mL/min/kg) | $V_{ss}$ (mL/kg) |
|---|---|---|---|---|---|
| 0.03 | 3 | 253 (28) | 2850 (229) | 10.6 (0.9) | 202 (24) |
| 0.1 | 6 | 964 (34) | 15009 (1263) | 6.9 (0.5) | 182 (8.3) |
| 0.3 | 3 | 2963 (352) | 41017 (2015) | 7.3 (0.4) | 199 (24) |

$AUC_{INF}$ = area under the curve from zero to infinity; CL = clearance; $C_{max}$ = maximum concentration; SE = standard error; $V_{ss}$ = volume of distribution at steady-state.

Overall plasma clearance of indium-111 radiolabeled C251 was estimated at 7.93 mL/kg (SE 0.57) compared with FS clearance of 7.44 mL/kg (SE 0.44). The terminal plasma half-lives of indium-111 radiolabeled C251 and FS were reported as 25 min (SE 1.9) and 27 min (SE 1.7), respectively.

Example 13A: Binding and Internalization Assays of Miniproteins

Figure 23A:
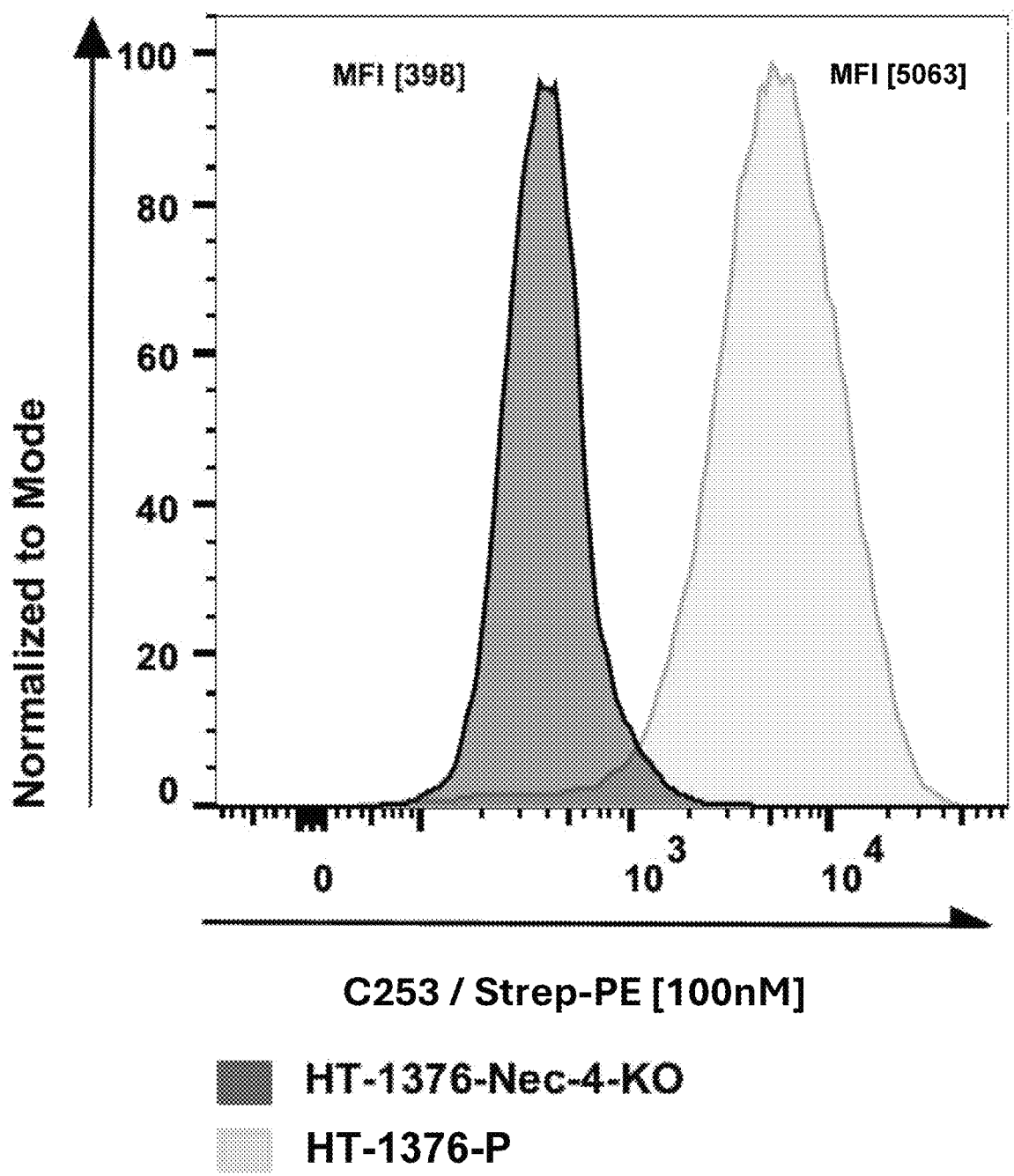
FIGS. 23A and 23B are graphs showing selective target binding of a biotin-labeled exemplary Nectin-4-targeting miniprotein (C253), as measured by flow cytometry (FIG. 23A), and a dose-response curves (FIG. 23B) in Nectin-4-expressing (HT-1376-Parental or "HT-1376-P") or knockout (HT-1376-KO) cells.
Figure 23B:
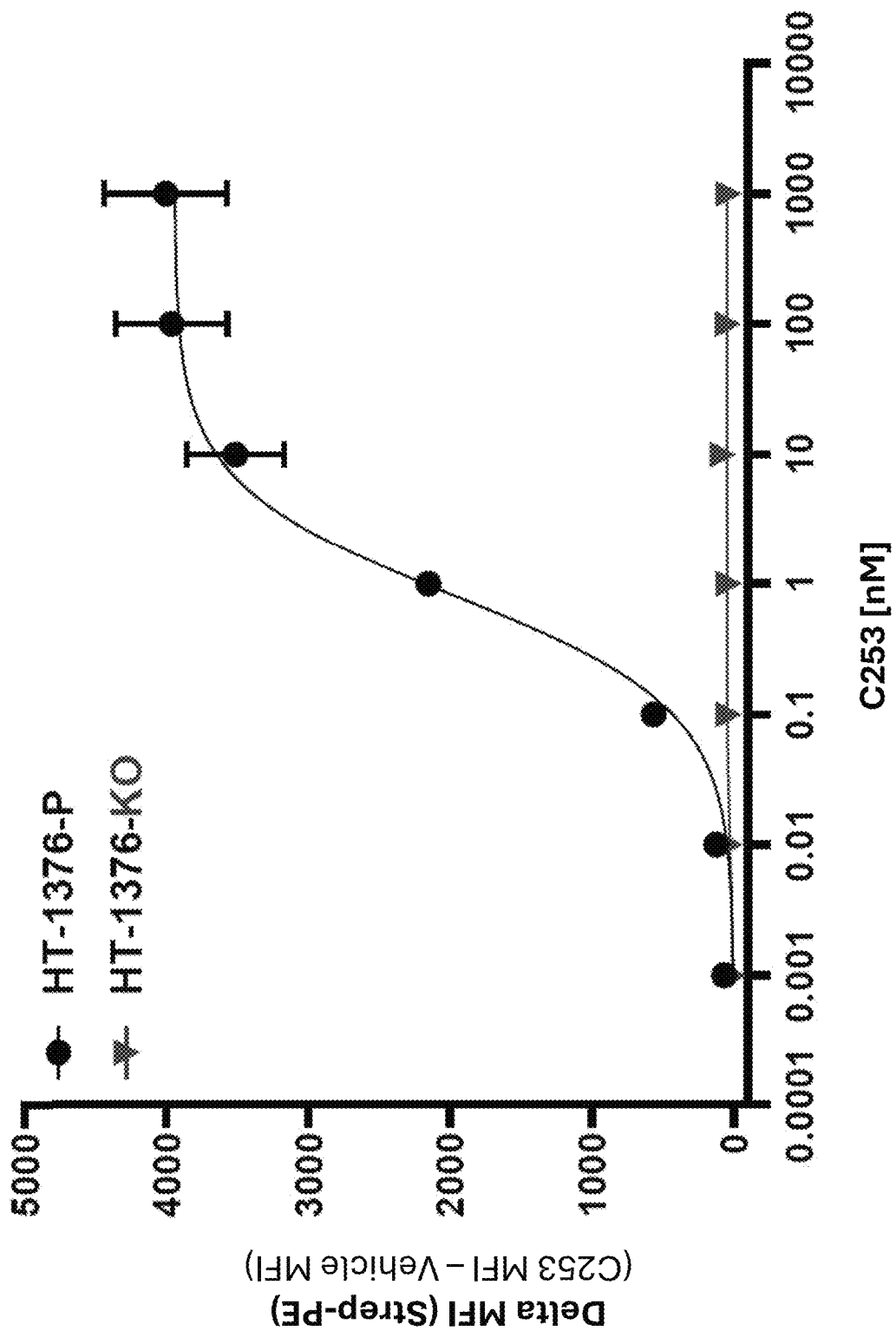

This Example describes binding knockout and internalization assays of Nectin-4 miniproteins.
Binding in Endogenous and Knockout Cells:
Fluorescent imaging for Nectin-4 binding was conducted using assays as described in Example 3. Briefly. Nectin-4 knockout HT-1376 cells were generated via CRISPR/Cas9 mediated gene deletion followed by single cell cloning. Cells were probed with anti-Nectin-4 antibody to confirm protein expression or knockdown and then binding of a biotinylated exemplary Nectin-4-targeting miniprotein (C253) was examined. Flow cytometry was performed to measure on-target binding to cell surface Nectin-4. The results, as shown in FIGS. 23A and 23B, confirmed a potent and highly selective Nectin-4 targeting agent.
Internalization Assay:
HT-1376 cells that endogenously express Nectin-4 or HT-1376 Nectin-4 knockout cells were plated and treated for 30 min at 37° C. with phycoerythrin (PE)-labeled C251. After 30 min, the cells were fixed and analyzed by fluorescence microscopy for binding to cells.

On cells endogenously expressing Nectin-4, C251 bound to the surface of cells, and was seen internalized in intracellular punctae (data not shown). No such signal was observed in the knockout cells.

The results showed that C251 potently and selectively binds Nectin-4 on the cell surface and rapidly internalizes in a target-dependent fashion.

Example 13B: Internalization Assay of Radiolabeled Conjugate

This Example describes internalization assays of radiolabeled conjugates of Nectin-4 miniproteins.

Internalization was assessed for indium-111 radiolabeled C215 in HT-1376 and MCF7 cells. Cells were incubated in the presence of radioligand or radioligand plus 1000 times excess unlabeled compound (C215) at 37° C., or 4° C. for 1 h. At the end of incubation cells were washed four times with PBS and membrane bound radioligand was removed by three 0.5% trypsin washes. Cell suspensions were washed three times by method of centrifugation and removal of supernatant. Internalized radioactivity was measured by gamma counting cell pellets and cell number was determined by counting cells on an automatic cell counter. The binding assay confirmed that radiolabeled conjugates were successfully internalized into cells, as shown in FIGS. 6A and 6B, which depict internalization of an exemplary indium-111 radioconjugate. C215, in HT-1376 (FIG. 6A) and MCF7 cell lines (FIG. 6B).

Example 13C: In Vitro Cell Cytotoxicity Assay

Cytotoxicity to $^{225}$Ac-radioconjugates was assessed in HT-1376 urothelial cancer cells. Cells were seeded in 96-well plates at densities of 250 to 1000 cells per well two days prior to treatment. On the day of treatment $^{225}$Ac-radioconjugates were diluted in culture medium to concentrations ranging from 0,0001 to 100 μCi/mL and treatment solutions were incubated with cells for 24 h. At the end of the treatment period, the treatment solution was removed, and fresh culture medium was replenished for the regrowth period of the assay that lasted 4-5 day's. At the end of the regrowth period the culture medium was removed and viability was assessed by CellTiter-Glo (Promega, Waltham MA) luminescent assay and the plates were read on a Perkin Elmer Enspire multimode plate reader. Data were normalized to treatment controls and plotted as non-linear sigmoidal dose response curves to determine the effective concentration for 50% reduction in cell viability. EC50 values for these exemplary radioconjugates are shown in TABLE 8.

TABLE 8

EC50 values for $^{225}$Ac radioconjugates

| Compound radiolabeled with $^{225}$Ac | EC50 (microcurie/milliliter) for $^{225}$Ac radioconjugates |
|---|---|
| C215 | 0.086 |
| C214 | 0.014 |
| C109 | 0.029 |
| C113 | 0.042 |
| C117 | 0.014 |

Example 14: Thermal Stability Assay

This Example shows thermal stability of an exemplary Nectin-4 miniprotein.

Figure 7:
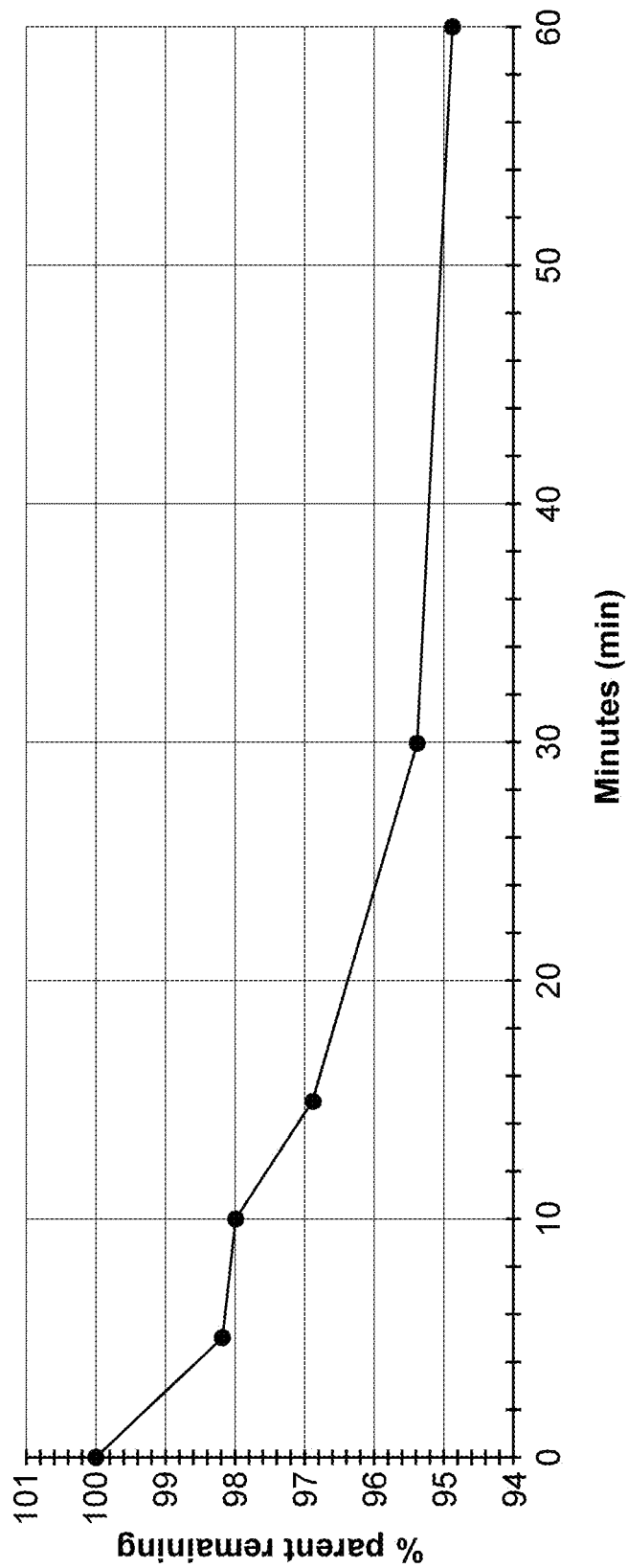
FIG. 7 is a graph showing thermostability of an exemplary compound, expressed as percentage of parent remaining over 60 minutes while heated at 75° C.
Figure 8:
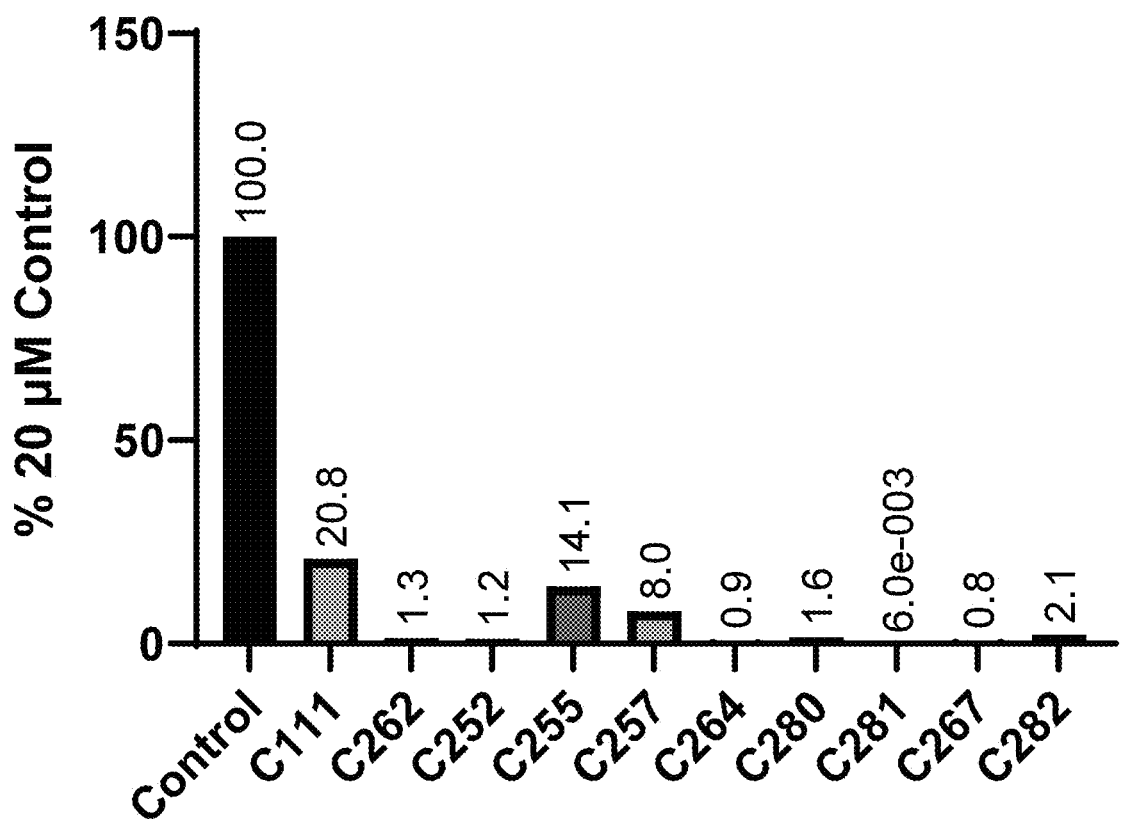
FIG. 8 is a bar graph of the percent uptake of exemplary miniproteins tested at 20 M in a proximal tubule epithelial cell assay vs 20 μM control peptide set at 100%.

The thermal stability of an exemplary compound, C215, was analyzed at a concentration of 1 mg/mL at 75° C., in 0.9% saline solution. A heating plate was set to 75° C. and the sample was heated for a period of one h. The vial was shaken prior to collecting 10 µL aliquots at 5, 10, 15, 30, and 60 minute time intervals. The % parent remaining was analyzed by HPLC using the following system and method: Analytical Agilent 1100 HPLC system using a 4.6×250 mm, 300 Angstrom. BEH300, 5 µm, Xbridge C18 column at 1.0 mL/min. The solvent system consisted of A=Water+0.1% TFA, B=Acetonitrile+0.1% TFA. The gradient consisted of 5% to 70% B over 15 minutes, then the column was washed and equilibrated to initial conditions. C215 was determined to remain stable over 60 min (see FIG. 7).

Example 15: In Vitro Cell Killing Assay

This Example describes in vitro cell killing assays using exemplary Nectin-4 miniproteins or conjugates thereof.

KT-1376 cells (a urothelial cancer cell line), MCF-7 cells (a breast cancer cell line), or NCI-H358 cells (a human non-small cell lung cancer cell line) are incubated with serially diluted unconjugated miniprotein, miniprotein-Ac$^{225}$ conjugate, or miniprotein-Lu$^{177}$ conjugate. Cells are plated in black, 96-well Corning Costar 3603 plates at densities to allow for Log phase growth throughout the experiment. On Day 0, cells are allowed to settle and attach overnight. Cells are plated in triplicate for each concentration and controls examined. On Day 1, media is removed and replaced with RPMI-1640+10% Dialyzed FBS (Gibco 26400-044) with the indicated concentration of control non-conjugated miniprotein, miniprotein-Ac$^{225}$ conjugate, or miniprotein-Lu$^{177}$ conjugate (starting concentration 100 nM, serially diluted 1:3 to a final of concentration of 0.045 nM), 0.01% DMSO or 1 µM Staurosporine as positive control for cell death. On Day 4 (72 h after treatment) cells are analyzed by Cell Titer Glo (Promega G7573) per manufacturer's instructions. Plates are read in luminescence mode on a PheraStarFS plate reader. Data are collected, replicates averaged, and standard deviations are calculated and analyzed through nonlinear regression analysis with 4 parameters to generate IC50s for each cell line tested.

Example 16: Potency of Radiolabeled Conjugates

This Example describes measurement of potency of radiolabeled conjugates of Nectin-4 miniproteins.

Measuring Potency of Ac-Binder Conjugates

The alkaline comet assay involves measurement of DNA damage in SSB and DSB. Similar to the binding assay of Example 3, aliquots of mammalian tumor cells expressing Nectin-4 are pelleted in polypropylene tubes. The cells are resuspended in an appropriate binding buffer with a range of miniprotein concentration of at least 100-fold above and below the expected $K_D$. The culture media contains BSA to prevent nonspecific binding, and binding should be measured at several volumes ranging from 50 mL to 5 mL. The cells expressing Nectin-4 are incubated with the miniprotein-Actinium conjugate until equilibrium is reached, which will take several hours.

The cells incubated with the conjugate are embedded in a thin layer of agarose on a thin glass slide. The cells are lysed in a solution containing detergent and NaCl, releasing the DNA from the proteins bound to it, but leaving DNA fragments still attached to the nuclear membrane. Then, the plate is incubated in an alkaline solution, an electrophoresis is run, and DNA is stained with ethidium bromide. DNA fragments travel to the anode forming a comet-like image when viewed by fluorescence microscopy. The image of the comet head denotes DNA content, and the tail denotes frequency of DNA breaks. Software programs designed to analyze the comet image allow measurement of DNA content and tail length. The length of the comet tail correlates with the level of DNA damage. Tumor cells that do not express Nectin-4 are used for a negative control to measure DNA damage.

Measuring DNA Damage Via H2AX Chromatin Staining

Cells expressing Nectin-4 are incubated with the miniprotein-Ac conjugate. After incubation, cells are fixed at different time points to study γ-H2AX induction and loss kinetics. Cells are fixed in ice cold 50% CH$_3$OH and 50% (CH$_3$)$_2$CO for 20 minutes at room temperature. After fixation cells are permeabilized with 0.5% Triton X100:PBS and then blocked with 0.2% skimmed milk, 0.1% TritonX—100, 5% FBS in Phosphate Saline Buffer (PBS). Cells are then stained with anti-γ-H2AX antibody (Upstate) and anti-mouse AlexaFluor-488 secondary antibody (Molecular Probes) for the kinetics experiments and with anti-mouse AlexaFluor 568 (Molecular Probes) for the 53BP1/γ-H2AX colocalization experiments. Coverslips are mounted with VECTASHIELD™ Mounting Medium containing DAPI, to counterstain cellular nuclei. γ-H2AX foci are scored manually by the same operator throughout the cell nuclei using a Zeiss Apotome fluorescence microscope with 63× objective and the average number of foci per cell are calculated from a minimum of 250 cells per dose/time point.

Example 17A: Estimating Peptide Binding Affinity of Exemplary Miniproteins on Live Cells: DELFIA Binding Assay A whole cell binding assay was used to estimate the equilibrium binding affinity ($K_D$) or binding inhibition constant ($K_i$) of miniprotein ligands to cells expressing a target of interest. Cells were dispensed into a 384-well plate and incubated at 37° C., in 5% CO$_2$ overnight. The next day cells were gently washed once in assay buffer prior to addition of europium chelated ligand. For $K_D$ determination, a miniprotein conjugated with europium chelate (DOTA or DTPA) in the presence or absence of 100-fold excess un-conjugated ligand was incubated with cells over 12 different concentrations ranging from 100 times below and above expected $K_D$ values. For $K_i$ determination, a single concentration ($K_D$ equivalent concentration) of europium-chelate miniprotein was added to each well followed immediately by the addition of unconjugated competing ligand over 12 different concentrations ranging from 100 times below and above expected $K_i$ values as before. The plate was incubated for 1.5 h at room temperature to reach binding equilibrium. Cells were then washed three times at room temperature with 1×PBS followed by the addition of 2 M HCl and incubated for two h at 37° C. Following this step, 2 M NaOH and fluorescent inducer solution were added to each well and incubated for 30 minutes at room temperature according to the manufacturer's protocol (Perkin-ELMER DELFIA assay). Plates were read on an Envision plate reader and a curve-fitting model was applied to estimate $K_D$ and $K_i$ values using GraphPad Prism software. Mean DELFIA $K_i$ values for exemplary miniproteins are recorded in TABLE 9A.

TABLE 9A

| Mean DELFIA $K_i$ | |
|---|---|
| Compound Name | Mean DELFIA $K_i$ +/− SD (M) |
| C262 | 1.04E−09 ± 0.53B-09 (n = 5) |
| C252 | 0.76E−09 ± 0.15E-09 (n = 5) |
| C255 | 0.66E−09 ± 0.23E-09 (n = 2) |
| C257 | 0.66E−09 ± 0.33B-09 (n = 2) |
| C264 | 0.53E−09 ± 0.09E-09 (n = 3) |
| C280 | 0.54E−09 ± 0.08E-09 (n = 5) |
| C267 | 0.76E−09 ± 0.15E-09 (n = 3) |

Example 17B: Estimating Peptide Binding Affinity of Exemplary Miniproteins with Modified Lysine Residues on Live Cells: DELFIA Binding Assay Engineered Nectin-4 miniproteins with further modified lysine residues (C298-C304; as described in Example 4B) were evaluated for their ability to bind to Nectin-4. Binding inhibition constants ($K_i$) for these exemplary Nectin-4-targeting miniproteins and C251 were estimated using a whole cell binding assay to cells expressing Nectin-4 (as described in Example 17A). $K_i$ values estimated using the DELFIA assay are provided in TABLE 9B. These data demonstrate that modification of lysine residues (e.g., by methylation) does not affect the binding kinetics of Nectin-4-targeting miniproteins and confirm that such modified miniproteins still bind strongly to Nectin-4 expressed on cells.

TABLE 9B

| Mean $K_i$ for Exemplary Nectin-4-targeting Miniproteins | |
|---|---|
| Compound Name | Mean DELFIA Ki (M) |
| C251 (Control) | 0.819 |
| C298 | 0.95 |
| C299 | 0.86 |
| C300 | 1.042 |
| C301 | 1.066 |
| C302 | 0.876 |
| C303 | 1.103 |
| C304 | 1.565 |

Example 18A: Proximal Tubule Epithelial Cell Uptake Assay Methods

Opossum kidney proximal tubule cells were plated in the upper chamber of 24-well transwell plates containing 600 μL of growth media in the lower chamber and were incubated overnight at 37° C., in 5% $CO_2$. The following day, the media was changed, and cells were incubated an additional 24 h with orbital shaking at 146 RPM. Next, cells were washed and treated in duplicates with biotinylated exemplary miniproteins pre-complexed with streptavidin-AF647 for 1 h at 37° C., and 5% C02 with continuous orbital shaking. Following incubation, cells were washed three times with 1×PBS and lysed with RIPA buffer containing protease and phosphatase inhibitor cocktail and a universal nuclease for 30 minutes. Uptake was measured on 100 μL of lysates using a fluorimeter. Mean % uptake values of control miniprotein C306 in the presence of exemplary miniproteins are provided in TABLE 10A and summarized in FIG. 8.

TABLE 10A

| Mean Percent Uptake in Opossum Kidney Cells | |
|---|---|
| Compound Name | % Uptake of C306 (Control) |
| C306 (Control) | 100 |
| C111 | 20.8 ± 4.08 (n = 19) |
| C262 | 1.27 ± 0.214 (n = 4) |
| C252 | 1.24 ± 1.09 (n = 4) |
| C255 | 14.1 ± 4.24 (n = 5) |
| C257 | 7.99 ± 1.64 (n = 5) |
| C264 | 0.859 ± 0.393 (n = 3) |
| C280 | 1.56 ± 0.875 (n = 4) |
| C281 | 0.006 ± 0.392 (n = 2) |
| C267 | 0.800 ± 0.692 (n = 3) |
| C282 | 2.14 (n = 1) |

Example 18B: Additional Proximal Tubule Epithelial Cell Uptake Assay Methods

Uptake of engineered Nectin-4 miniproteins with further modified lysine residues (C298-C304, as described in Example 4B) was evaluated. Percent uptake of these exemplary Nectin-4-targeting miniproteins and C251 were determined against a control miniprotein, C306, using opossum kidney proximal tubule cells as described in Example 18A. Percent uptake of the control miniprotein in the presence of exemplary Nectin-4-targeting miniproteins is provided in TABLE 10B. Percent uptake of C298, which has an unmodified lysine (K) at amino acid position 26 (along the length of the miniprotein sequence. SEQ ID NO: 162), was 37% in the presence of C298. All other miniproteins having a modified lysine (modified with one or more small alkyl groups of monomethyl, dimethyl, trimethyl, or isopropyl group) had (i) kidney uptake similar to that of C251 and (ii) reduced uptake as compared to C298, which has an unmodified lysine at position 26. These data demonstrate that modification of lysine residues (e.g., by addition of one or more small alkyl groups) at position 26 decreases uptake of Nectin-4-targeting miniproteins by kidney cells as compared to Nectin-4 targeting miniproteins without a modified lysine residue at position 26.

TABLE 10B

| Percent Uptake Data for Exemplary Nectin-4-targeting Miniproteins | | |
|---|---|---|
| SEQ ID NO: of miniprotein | Compound Name | % Uptake of C306 |
| 195 | C251 | 2 |
| 162 | C298 | 37 |
| 163 | C299 | 3 |
| 164 | C300 | 3 |
| 165 | C301 | 3 |
| 166 | C302 | 2 |
| 167 | C303 | 3 |
| 168 | C304 | 2 |

Example 19: Evaluating In Vitro Metabolic Stability of Test Articles

Exemplary miniproteins were spiked into biological matrices at initial concentration between 1-2 μM. Tested matrices were varied by species (mouse, rat, human) and type (plasma, serum, and kidney brush border membrane (kBBM) preparations tested each from 0.625-100 μg/mL protein content). Tested conditions were incubated with miniproteins at 37° C. for 4 h. At collection points of 0, 15, 30, 60, 120, 240 minutes, 50 μL of each condition were quenched by organic solvent (methanol or acetonitrile) or the addition of 4% phosphoric acid solution followed by solid-phase extraction. Fractions of each quenched timepoint were subsequently assayed for parent miniproteins concentration by high resolution LC-MS. Percent-parent-remaining-time plots were constructed from the ratio of each given time collection to the time-zero parent miniprotein. Percent-parent-remaining in mouse serum and plasma for exemplary miniproteins are recorded in TABLE 11.

TABLE 11

Percent Parent Remaining in Serum/Plasma

| SEQ ID NO: OF POLYPEPTIDE | Compound Name | mkBBM ($t_{1/2}$ h) | mPlasma ($t_{1/2}$ h) | hkBBM ($t_{1/2}$ h) | h Plasma ($t_{1/2}$ h) |
|---|---|---|---|---|---|
| 78 | C109 | >12 | >12 | >12 | >12 |
| 145 | C236 | >12 | >12 | | |
| 138 | C241 | >12 | >12 | | |
| 99 | C244 | >12 | >12 | | |
| 194 | C245 | >12 | >12 | | |
| 134 | C250 | >12 | >12 | | |
| 195 | C251 | >12 | >12 | >12 | >12 |
| 195 | C254 | ND | ND | >12 | >12 |
| 200 | C260 | 11.2 | >12 | | |
| 203 | C265 | >12 | >12 | | |
| 204 | C268 | >12 | >12 | | |
| 155 | C271 | >12 | >12 | | |
| 93 | C293 | >12 | >12 | | |

Example 20A: Evaluating Efficacy in Mice

This Example describes measuring the effect of exemplary miniproteins on a tumor in mice.

Animals: Female athymic nude mice (6-8 weeks of age) were purchased from Charles River Laboratories and housed according to IACUC guidelines with ad libitum feeding. In vivo efficacy study experiments were performed in tumor bearing athymic nude mice. Tumor xenograft models were generated by inoculating mice subcutaneously with $3 \times 10^6$ HT-1376-OE cells in 200 μL (50:50 PBS/Matrigel) in either the right shoulder or right flank. HT-1376-OE is a human-derived cell line engineered to overexpress ("OE") Nectin-4. Tumors were monitored for a minimum of 14 days prior to group stratification and study initiation dates. Mice with tumor volumes between 150 mm³ and 250 mm³ were selected for study inclusion and randomized to treatment arms. An excess of 60% of required study mice were inoculated with tumor cells to ensure enough mice with appropriate tumor ranges were generated.

Animal grouping and Treatment One day prior to treatment, $^{225}$Ac-labeled test articles were prepared as described above at a specific activity of approximately 1 μCi/μg, with activity measurements made at secular equilibrium on a dose calibrator. On the day of treatment, dose measurements for a sample injected dose were measured and confirmed on a gamma counter and corrected for decay. Indicated doses of vehicle or radiolabeled test article were prepared corresponding to the indicated administered dose levels per group. Doses were administered via tail vein injection while the mice were restrained and awake. Syringes with prepared doses were weighed pre and post injection and the weights were recorded.

Animal monitoring: Tumor volume, measured by calipers, and body weight measurements for enrolled mice were performed twice a week for an initial planned monitoring period of 8 weeks. More frequent gross observations of mice were performed as needed.

Humane endpoints: Mice remained on the study until they reached the end of the 8-week monitoring period or a number of pre-defined humane endpoints, including:

1. An increase in tumor volume size that exceeds >1500 mm³, or 20 mm in one dimension, or the tumor becomes ulcerated or necrotic.
2. A decrease in body weight ≥20% from maximum recorded weight.
3. Any signs of pain or distress (i.e., consistent hunched posture, rough coat, squinted eyes, slowed gait).
4. Tumors that compromise mobility or ability to eat or drink.
5. BCS score ≤2.

For an exemplary experiment, there were three study arms varying in treatment and dose that the mice were grouped into, which are summarized below in TABLE 12. Group 1 received a vehicle, or control, as treatment. Group 2 and Group 3 received $^{225}$Ac-C251. All groups received a total of one dose. Group 3 received twice the level of the dose as Group 2.

TABLE 12

Study Arms

| Group | Treatment | Dose (nCi) | Route | Schedule | Monitoring |
|---|---|---|---|---|---|
| 1 (n = 8) | Vehicle | n/a | IV | Single Dose | 8-weeks |
| 2 (n = 8) | $^{225}$Ac-C251 | 500 | IV | Single Dose | 8-weeks |
| 3 (n = 8) | $^{225}$Ac-C251 | 1,000 | IV | Single Dose | 8-weeks |

Figure 9A:
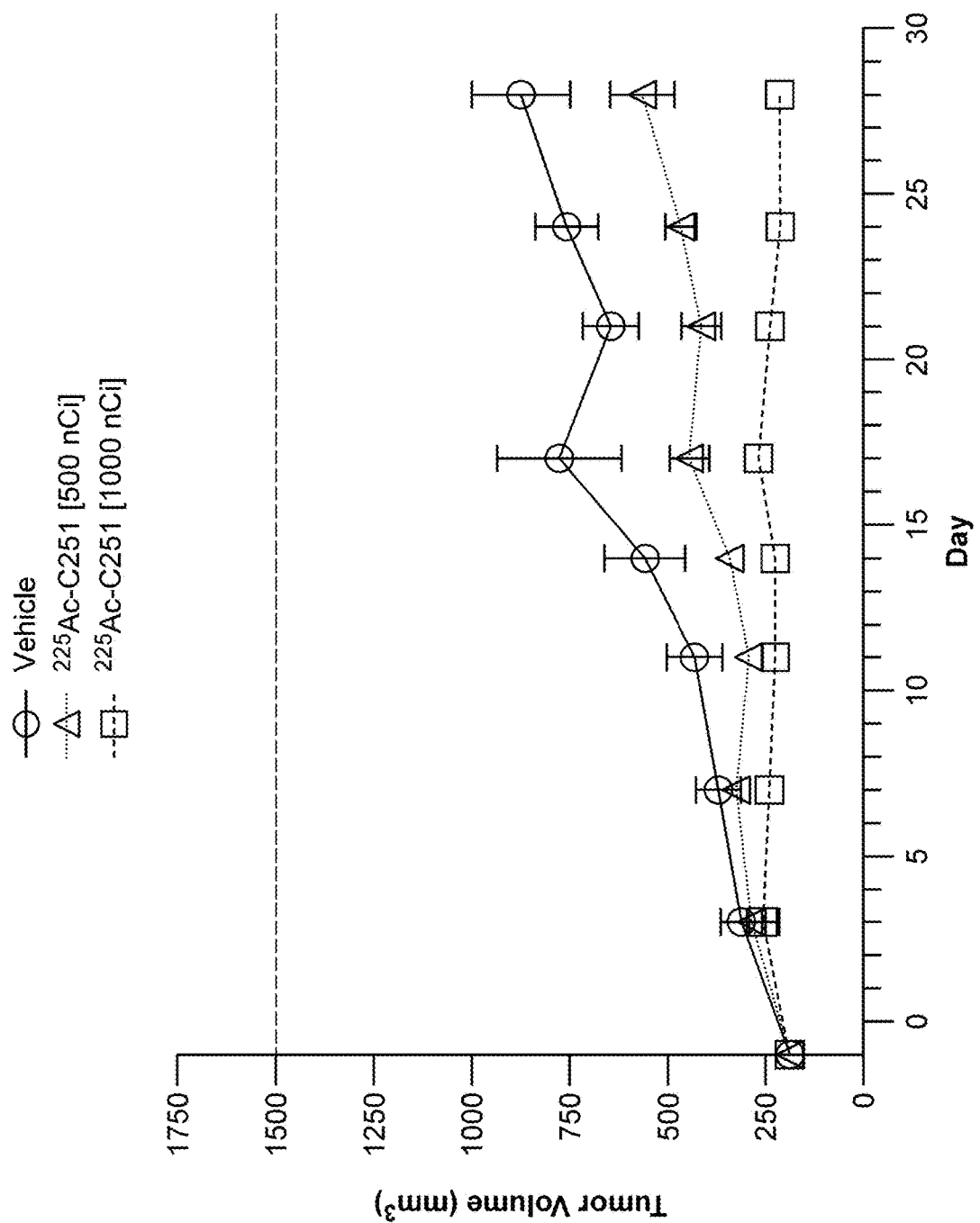
FIG. 9A is a graph showing tumor volume (mm$^3$) over time in mice treated with 500 nCi of $^{225}$Ac-C251 (triangles), 1000 nCi of $^{225}$Ac-C251 (squares) or vehicle (circles). Mice were dosed at Day 0.
Figure 9B:
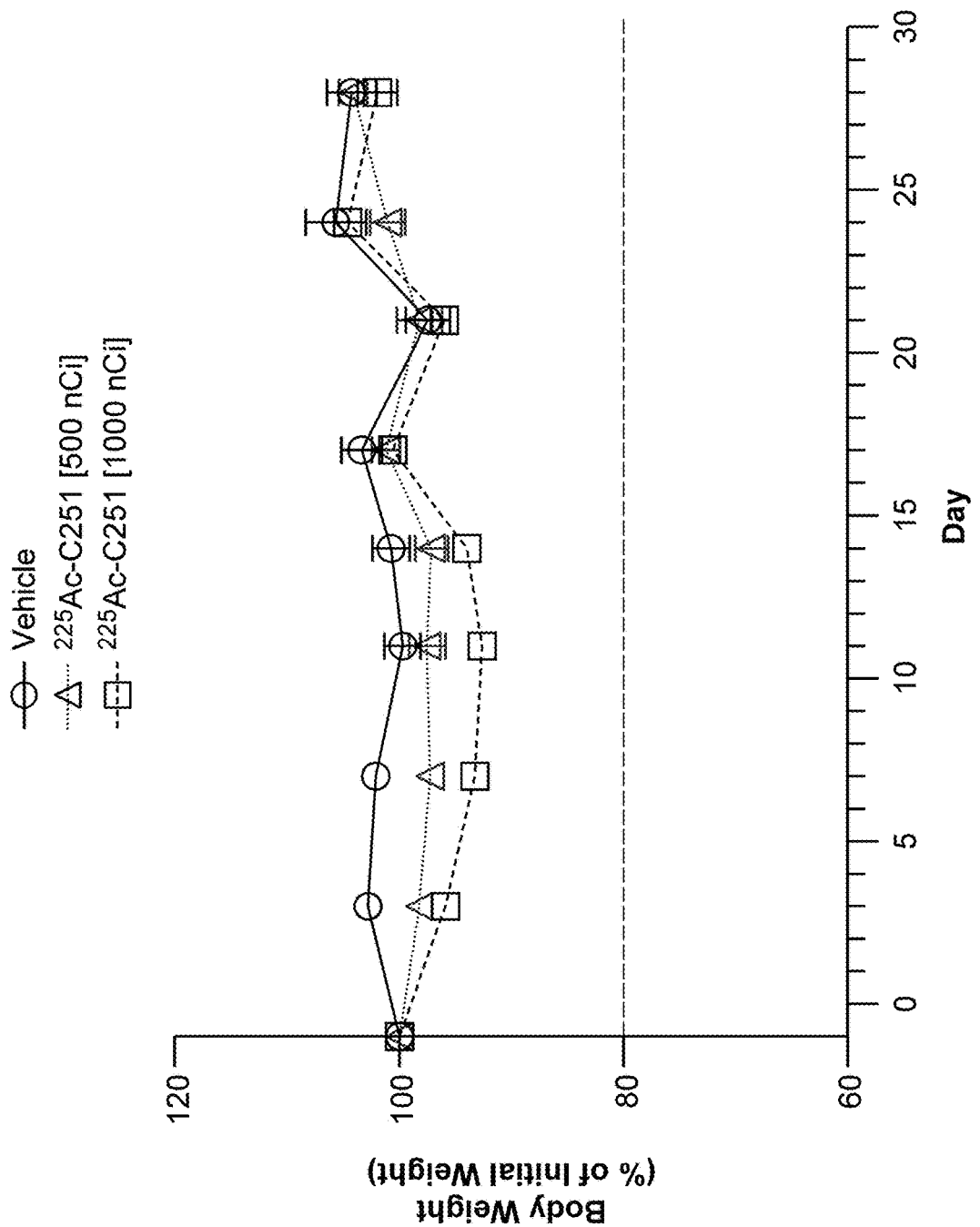
FIG. 9B is a graph showing body weight as a percentage relative to initial body weight over time of mice undergoing the treatments described in FIG. 9A.

The results of the first four weeks of monitoring are summarized in FIG. 9A and FIG. 9B. Overtime, the tumor volume in Group 1 increased more than the tumor volume in Group 2 and Group 3 (FIG. 9A). Additionally, body weight was generally maintained over time in all three groups over the observed time period (FIG. 9B).

In another exemplary experiment, a similar treatment plan was followed where Group 2 and Group 3 received $^{225}$Ac-C244 as summarized in TABLE 13.

TABLE 13

Study Arms

| Group | Treatment | Dose (nCi) | Route | Schedule | Monitoring |
|---|---|---|---|---|---|
| 1 (n = 8) | Vehicle | n/a | IV | Single Dose | 8-weeks |
| 2 (n = 8) | $^{225}$Ac-C244 | 500 | IV | Single Dose | 8-weeks |
| 3 (n = 8) | $^{225}$Ac-C244 | 1,000 | IV | Single Dose | 8-weeks |

Figure 10A:
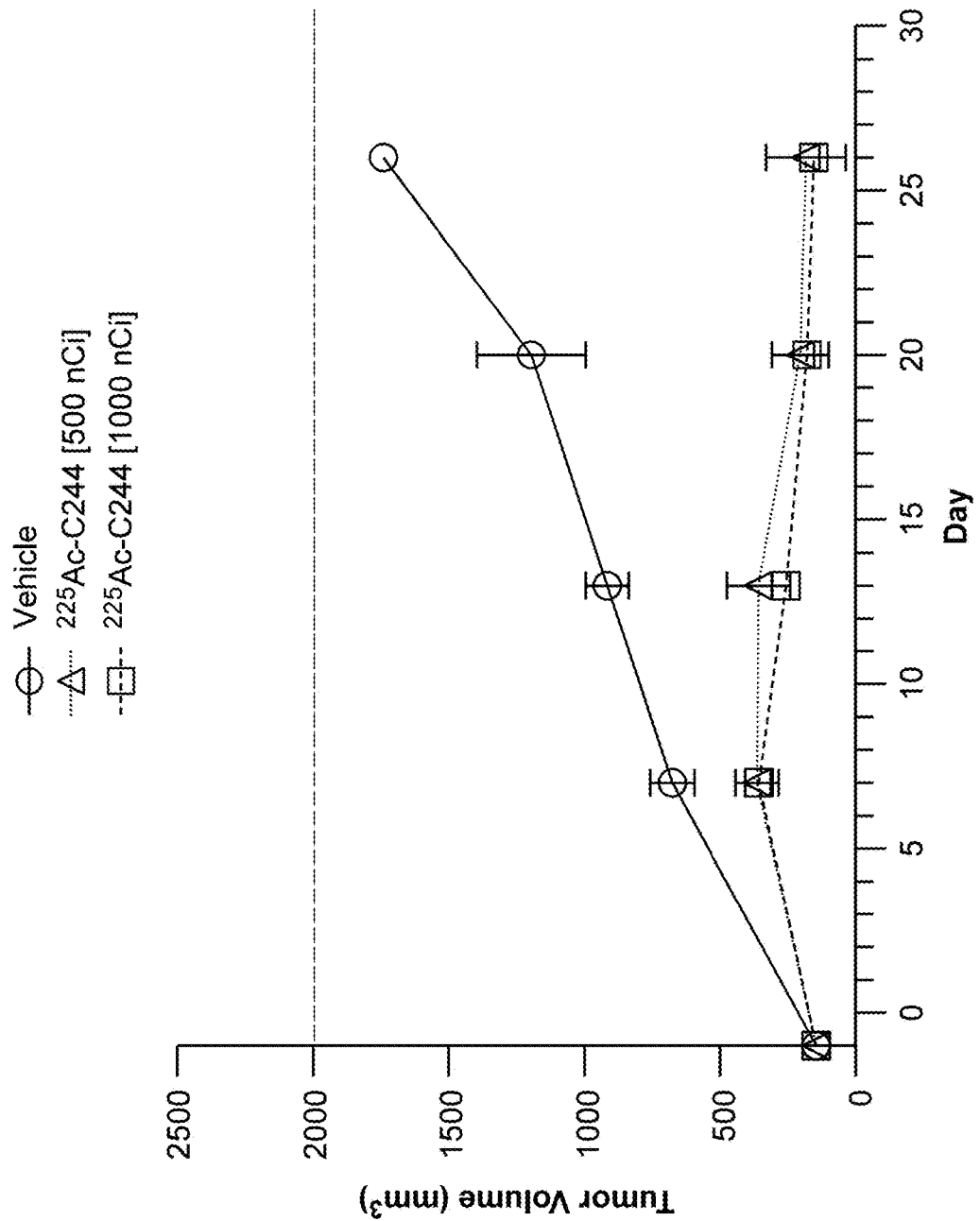
FIG. 10A is a graph showing tumor volume over time in mice treated with 500 nCi of $^{225}$Ac-C244 (triangles), I000 nCi (squares) of $^{225}$Ac-C244 or vehicle (circles). Mice were dosed at Day 0.
Figure 10B:
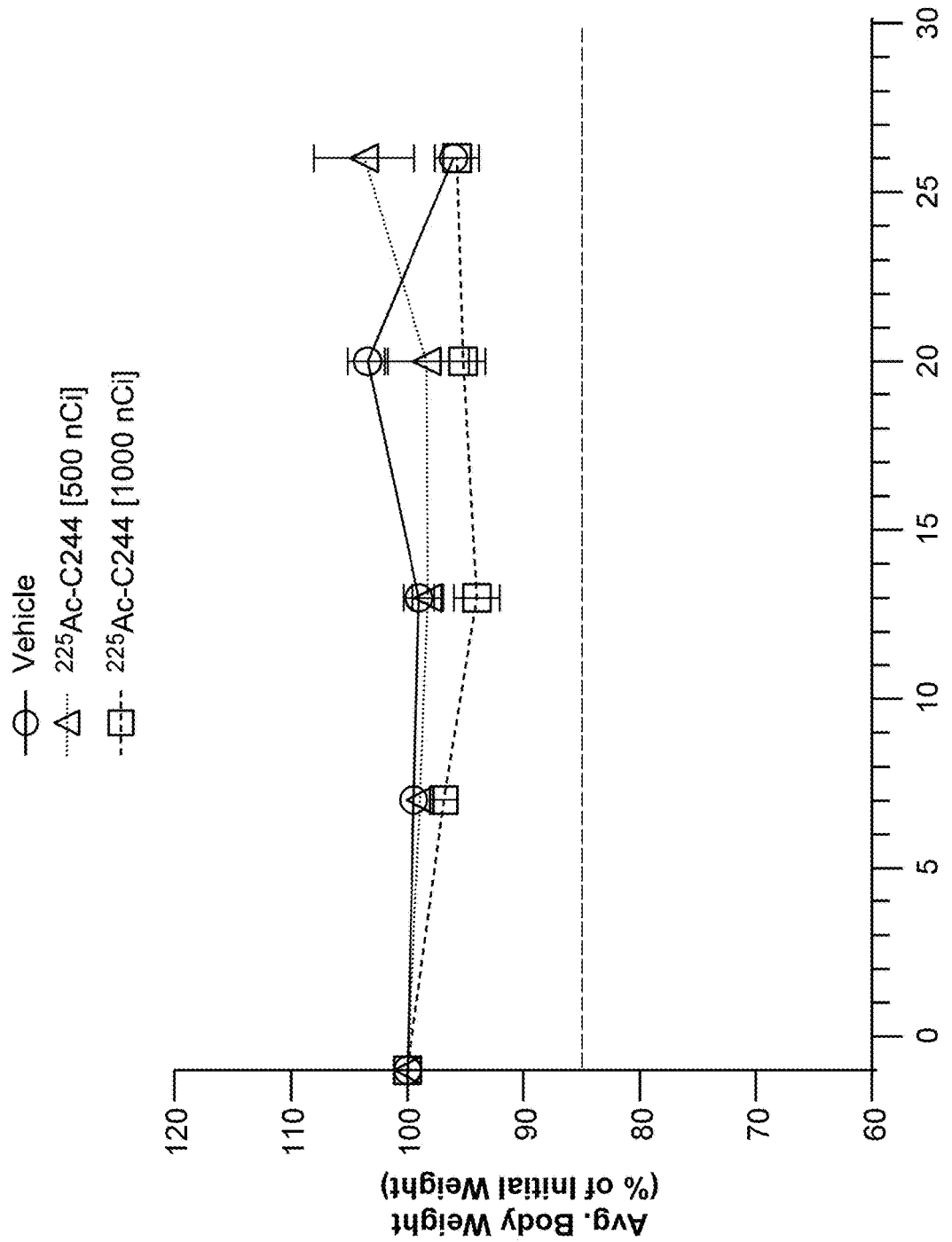
FIG. 10B is a graph showing body weight as a percentage relative to initial body weight over time of mice undergoing the treatments described in FIG. 10A.

The results of the first four weeks of monitoring are summarized in FIG. 10A and FIG. 10B. Over time, the tumor volume in Group 1 increased more than the tumor volume in Group 2 and Group 3 (FIG. 10A). Additionally, body weight was generally maintained over time in all three groups over the observed time period (FIG. 10B).

In another exemplary experiment, a similar treatment plan was followed where Group 2 and Group 3 received $^{225}$Ac-C200 as summarized in TABLE 14.

TABLE 14

Study Arms

| Group | Treatment | Dose (nCi) | Route | Schedule | Monitoring |
|---|---|---|---|---|---|
| 1 (n = 8) | Vehicle | n/a | IV | Single Dose | 8-weeks |
| 2 (n = 8) | $^{225}$Ac-C260 | 500 | IV | Single Dose | 8-weeks |
| 3 (n = 8) | $^{225}$Ac-C260 | 1,000 | IV | Single Dose | 8-weeks |

Figure 11A:
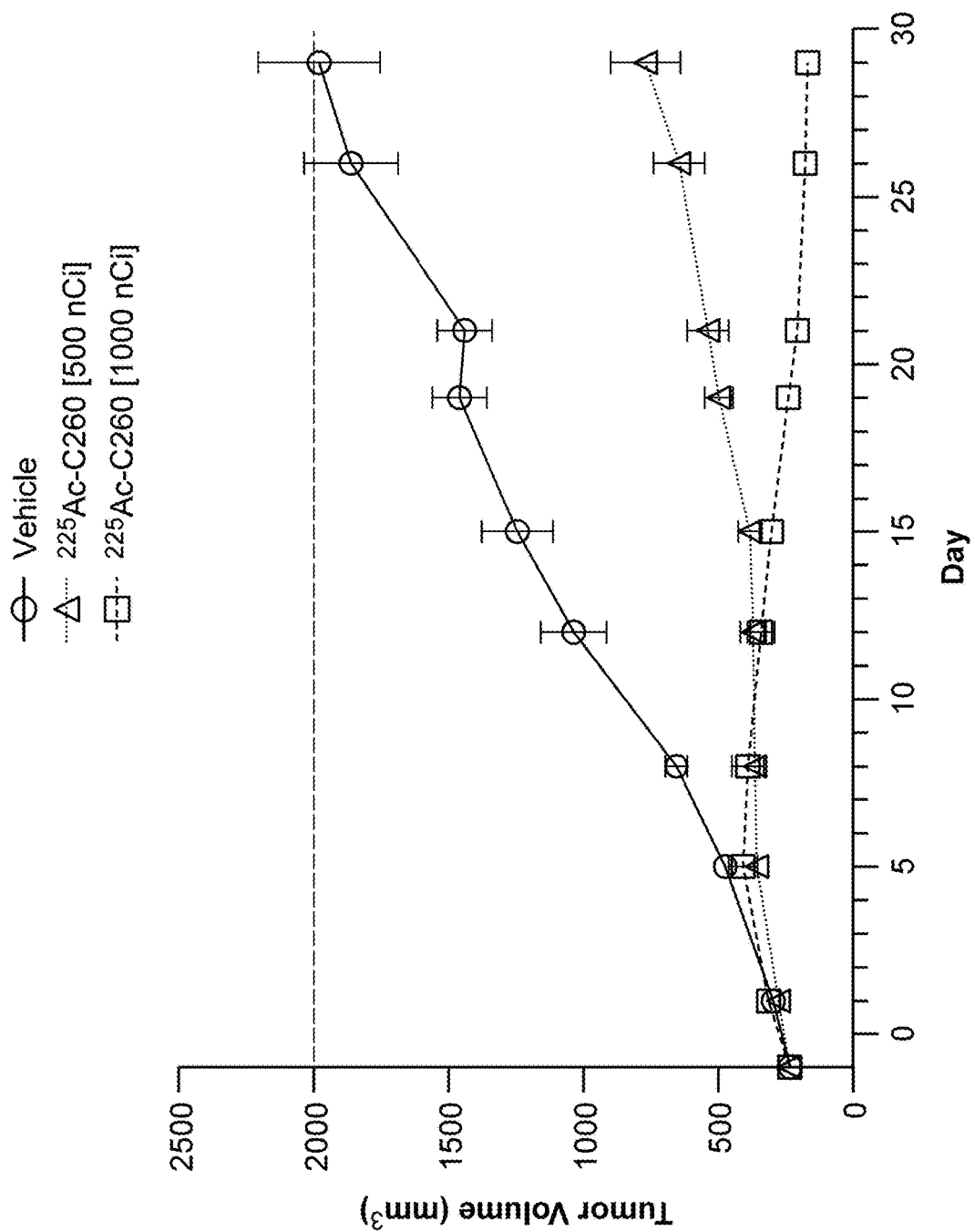
FIG. 11A is a graph showing tumor volume over time in mice treated with 500 nCi of $^{225}$Ac-C260 (triangles), 1000 nCi of $^{225}$Ac-C260 (squares), or vehicle (circles). Mice were dosed at Day 0.
Figure 11B:
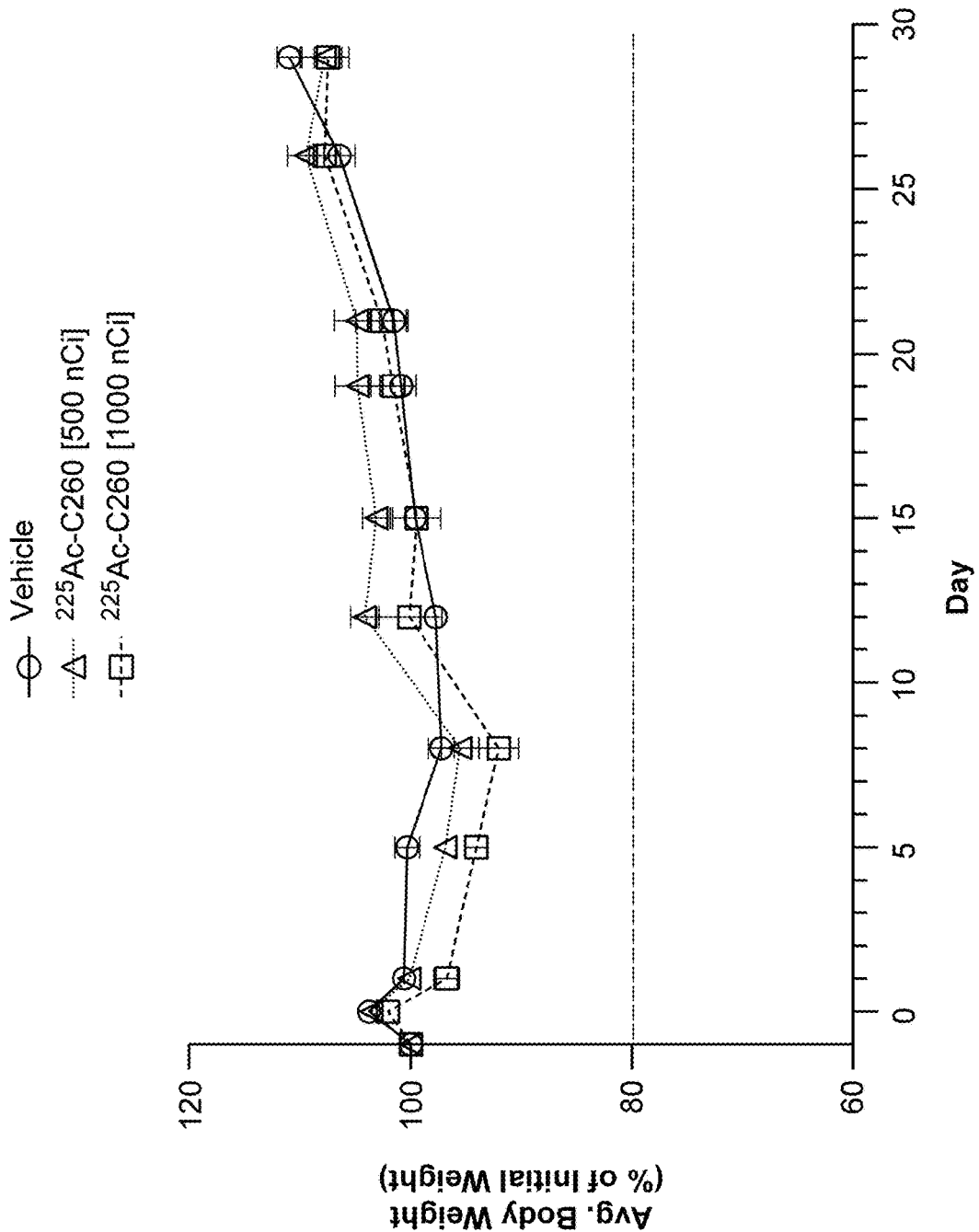
FIG. 11B is a graph showing body weight as a percentage relative to initial body weight over time of mice undergoing the treatments described in FIG. 11A.

The results of the first four weeks of monitoring are summarized in FIG. 11A and FIG. 11B. Over time, the tumor volume in Group 1 increased more than the tumor volume in Group 2 and Group 3 (FIG. 11A). Additionally, body weight was generally maintained over time in all three groups over the observed time period (FIG. 11B).

Histology: To ensure translational relevance of the animals models, subcutaneous tumors were established for both models, then tissues were resected and examined for membranous Nectin-4 expression via immunohistochemistry analysis, comparing staining/H-scoring to representative tumor biopsies collected from patients, as well as published surveys of Nectin-4 expression in metastatic urothelial carcinoma patients. The models ranged from low/medium (H-score of 175) in the HT-1376 "low expression" model to high (H-score of 291) in the HT-1376 Representative model (data not shown).

Example 20B: Survival Study in Cell-Line Derived Xenograft Model

This Example shows survival impact of an exemplary Nectin-4-binding tumor-targeting compound.

Animals: Female athymic nude mice (6-8 weeks of age) were purchased from Charles River Laboratories and housed according to IACUC guidelines with ad libitum feeding. In vivo efficacy study experiments were performed in tumor bearing athymic nude mice. Tumor xenograft models were generated by inoculating mice subcutaneously with $3 \times 10^6$ of HT-1376-Parental ("HT-1376-P") cells or HT-1376-OE cells (cells engineered to overexpress Nectin-4), in 200 μL (50:50 PBS/Matrigel) in either the right shoulder or right flank. Tumors were monitored for a minimum of 14 days prior to group stratification and study initiation dates. Mice with tumor volumes between 150 mm$^3$ and 250 mm$^3$ were selected for study inclusion and randomized to treatment arms.

Animal grouping and treatment: One day prior to treatment, $^{225}$Ac-labeled Nectin-4 binding compounds were prepared as described above in Example 6A at a specific activity of approx. 1 μCi/μg, with activity measurements made at secular equilibrium on a dose calibrator. On the day of treatment, dose measurements for a sample injected dose were measured and confirmed on a gamma counter and corrected for decay. Indicated doses of vehicle or radiolabeled test article were prepared corresponding to the indicated administered dose levels per group. Doses were administered via tail vein injection while restrained and awake. Syringes with prepared doses were weighed pre and post injection and weights recorded.

Animal monitoring: Frequent gross observations of mice were performed over an extended 8-week observation period. Subject survival was monitored over the duration of the study.

Humane endpoints: Mice remained on study until they reached the end of the 8-week monitoring period or a number of pre-defined humane endpoints, including:

(1) increase in tumor volume size that exceeded >2,000 mm$^3$, or 20 mm in one dimension, or tumor became ulcerated or necrotic;
(2) decrease in body weight ≥20% from maximum recorded weight;
(3) any signs of pain or distress (e.g. consistent hunched posture, rough coat, squinted eyes, slowed gait, etc.);
(4) tumors that compromised mobility and/or ability to eat or drink; and/or.
(5) BCS score ≤2.

Descriptions of the study arms and in vivo study design are described in TABLE 15A. Eight animals were analyzed in each of the four groups. All animals were given a single dose of treatment (see TABLE 15), administered intravenously and monitored for eight weeks.

TABLE 15A

Study Arms For Survival Study

| Group (n = 8/group) | Treatment | $^{225}$Ac-C251 Administered Dose [nCi] (Single Dose) | Model |
|---|---|---|---|
| 1 | Vehicle | n/a | HT-1376-P |
| 2 | $^{225}$Ac-C251 | 1,000 | HT-1376-P |
| 3 | Vehicle | n/a | HT-1376-OE |
| 4 | $^{225}$Ac-C251 | 1,000 | HT-1376-OE |

Figure 9C:
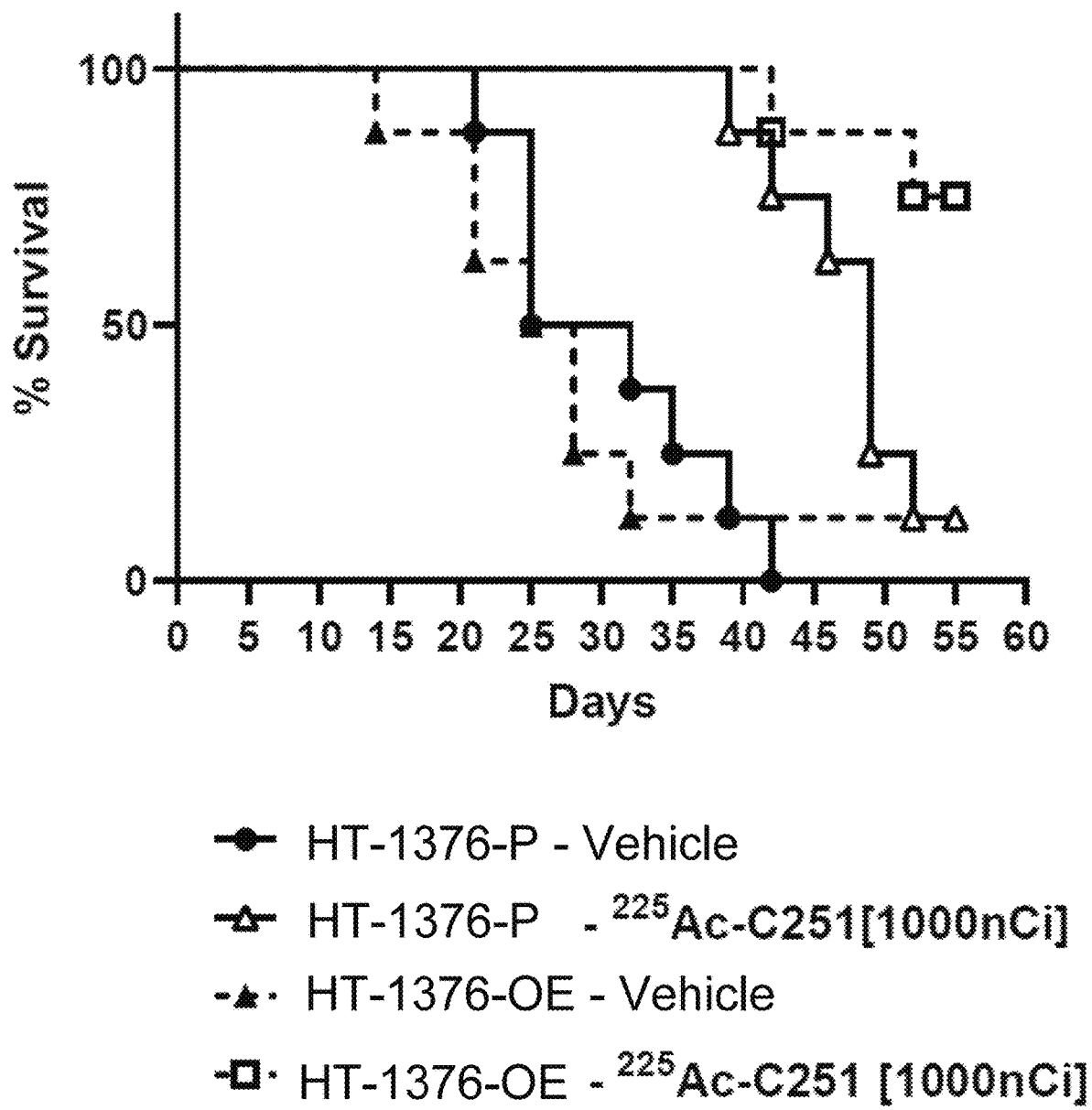
FIG. 9C is a graph showing proportion of survival in a mouse xenograft model over an 8-week period. Xenografts were generated with HT-1376-Parental Nectin-4-Expressing Cells (P) or HTI376-Nectin-4-Overexpressing (OE) cells. Mice were treated with vehicle (P, closed circles; OE, closed triangles) or 1000 nCi of $^{225}$Ac-C251 (P, open triangles; OE, open squares).

A survival benefit was observed in groups administered the $^{225}$Ac-labeled exemplary Nectin-4-targeting radionuclide conjugate ($^{125}$Ac-C251) as compared to those treated with vehicle (FIG. 9C and TABLE 15B). FIG. 9C shows the survival proportions for mice in groups 1-4. Higher survival proportions were observed in the groups treated with $^{225}$Ac-C251 and the highest median survival was observed in the HT-1376-|OE| model that received 225Ac-C251 (TABLE 15B).

TABLE 15B

Mean survival in an HT-1376-P and HT1376-OE generated CDX model.

| Model | Treatment | Median Survival (Days) | Significance (GBW Test) |
|---|---|---|---|
| HT-1376-[P] | Vehicle | 28.5 | p = 0.0006 |
|  | $^{225}$Ac-C251 | 49 |  |
| HT-1376-[OE] | Vehicle | 26.5 | p = 0.0017 |
|  | $^{225}$Ac-C251 | NR |  |

Example 21: Biodistribution of Miniprotein Conjugates

This example describes an assay to observe the biodistribution profile of radiolabeled miniproteins disclosed herein.

6-8 week old female mice were engrafted through subcutaneous injection with cultured $3.0 \times 10^6$ HT-1376-OE cells (1:1—Cells:Matrigel). HT-1376-OE is a model cell line that highly expresses Nectin-4. Fourteen (14) days later, the mice were each dosed with a radiolabeled miniprotein, for example at a dose of ~350 μCi/3.5 μg miniprotein. SPECT and/or CT imaging of the mice was done at timepoints between 15 min to 24 h after the administration of the injected dose, such as 4 h and 22 h (static scanning). Initial SPECT and/or CT rapid dynamic scanning was done at time points between 15 min and 75 min after the administration of the injected dose. For each miniprotein tested, a group of three mice were used, as summarized below in TABLE 16A.

TABLE 16A

Biodistribution Testing Groups and Details

| Group (N) | Imaging Tracer (Injected Dose [µCi ± SD], Volume, Route) | Average Injected Mass (µg = SD) |
|---|---|---|
| A (n = 3) | $^{111}$In-C109 (359.8 ± 12.0 170 µL, IV) | 3.64 ± 0.12 |
| B (n = 3) | $^{111}$In-C244 (351.7 ± 1.7, 160 µL, IV) | 3.56 ± 0.02 |
| C (n = 3) | $^{111}$In-C251 (344.6 ± 5.7, 170 µL, IV) | 3.58 ± 0.06 |
| D (n = 3) | $^{111}$In-C260 (347.7 ± 11.1, 180 µL, IV) | 3.55 ± 0.11 |

Figure 15:
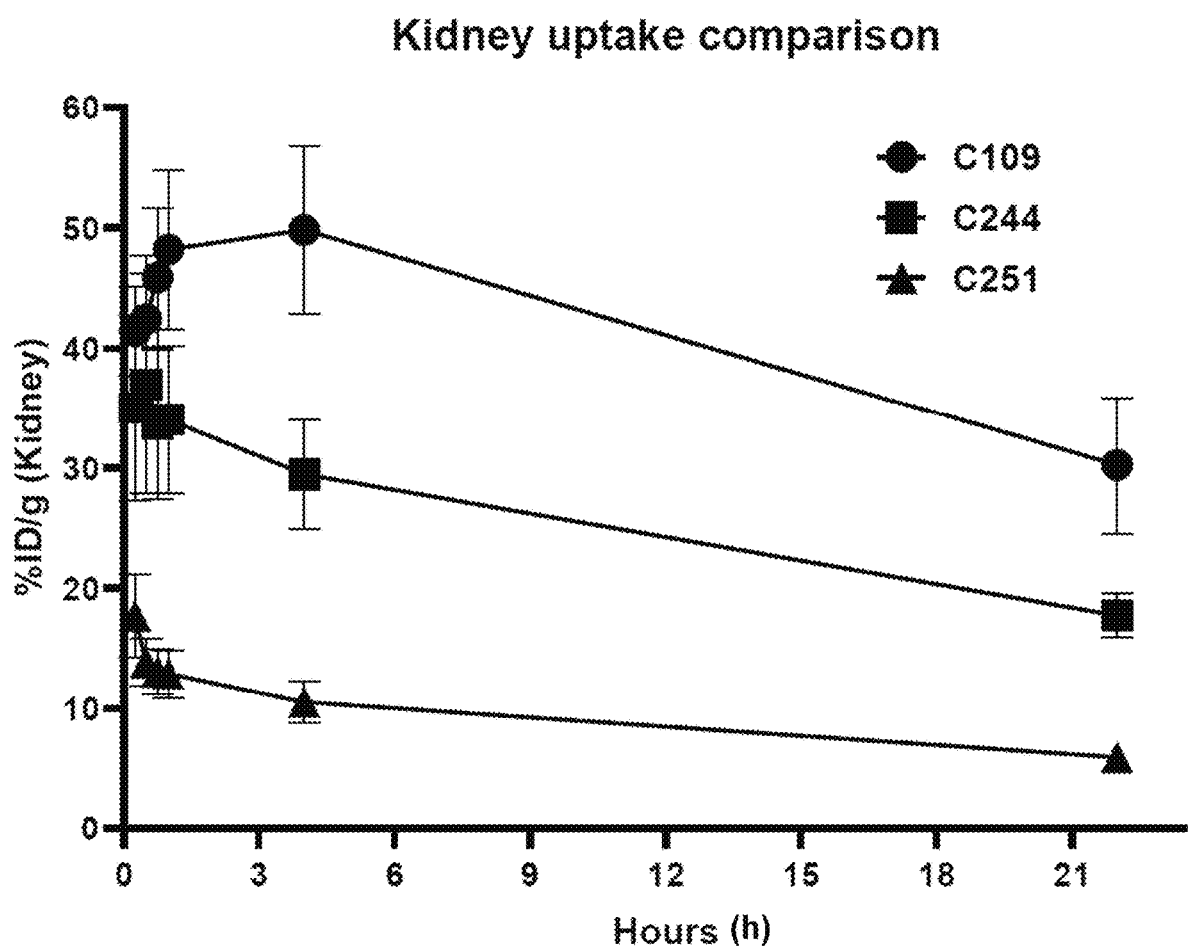
FIG. 15 is a graph showing kidney uptake (% ID/g) comparisons for $^{111}$In-radiolabeled miniproteins (C109, C244, and C251).

The observed images suggest increased tumor target expression improves tumor deposition with all tested radiolabeled miniproteins, for example the tested miniproteins were observed to have a positive tumor/kidney (T/K) ratio. Kidney uptake comparisons for indicated $^{111}$In-radiolabeled miniproteins are shown in FIG. 15B. $^{111}$In-C251 (as well as other representatives of this series) accumulated in the tumor, and cleared through the kidney, but was not observed elsewhere in the animals, suggesting an optimal biodistribution profile.

Quantitative results of the biodistribution study are shown below in TABLES 16B and 16C.

TABLE 16B

Biodistribution Data for Exemplary Nectin-4 Miniprotein Compounds, Tumor

| Compound Name | Data of Biodistribution (+4 h Tumor-% ID/g) |
|---|---|
| C109 | 6.27 |
| C244 | 5.64 |
| C251 | 6.61 |
| C260 | 7.12 |

TABLE 16C

Biodistribution Data for Exemplary Nectin-4 Miniprotein Compounds, Kidneys

| Compound Name | 4 h (% ID/g) Average | 4 h (% ID/g) StDev | 22 h (% ID/g) Average | 22 h (% ID/g) StDev |
|---|---|---|---|---|
| C109 | 49.84 | 12.07 | 30.2 | 9.83 |
| C244 | 29.46 | 7.93 | 17.75 | 3.21 |
| C251 | 10.54 | 3.04 | 5.96 | 1.20 |
| C260 | 11.61 | 2.43 | 6.92 | 1.93 |

For $^{225}$Ac-containing Nectin-4 binders, the predicted absorbed dose to kidneys was 0.16 RBE5Gy/MBq, the estimated maximum administered activity 140. 6 MBq, and estimated absorbed dose to kidney after 4 to 6 administrations was 4.8 to 7.2 RBE5G.

Overall, C251 was expected to have a wide therapeutic margin, given predictions of absorbed dose to the kidney from allometric scaling of predicted absorbed doses.

Example 22: Synthesis of an Exemplary Compound

Compound C251 was synthesized and characterized as follows.

SPPS Experimental Conditions (High Temperature)

Synthesis was carried out on a Chorus Peptide Synthesizer with heating at 90° C. for couplings and 75° C. deprotections. DIC/Oxyma Pure was used as the activation/coupling system, with each being used in concentrations of 0.4 M and the Fmoc-Amino Acid conc. 0.2 M.

Resin/loading: 0.32 mmol/g; Fmoc-Ser(trt)-OH, Wang resin DIC: 0.75 M

Oxyma Pure: 0.3 M Fmoc-AA: 0.2 M

Reaction Set-up: 80 µM scale

Fmoc Deprotection: 2 min/75° C., after deprotection resin wash (3×5000 µL×30 s)

Coupling conditions: 2 min/90° C.

Double-Couple conditions: 2×2 min/90° C.

*All residues were single-coupled at 90° C., except for Ile and Leu residues, which were double-coupled.

SPPS Experimental Conditions (Ambient Temp. (DIEA-HATU):

Compound 251 with Disulfide Connectivity at (1,34) and (20,44) was synthesized as follows.

Resin/Loading: Fmoc-Ser(tbu)-Wang (0.32 mmol/g)

HATU: 0.4 M in DMF

DIEA: 0.8 M in DMF

Piperdine: 20% in DMF

Double-Couple conditions: 2×15 min, Ambient temperature

Synthesis was carried out on a Symphony X peptide synthesizer under normal SPPS conditions on an 80 µM scale. DIEA (0.8 M)/HATU (0.4 M) were used as the Base/Activator pair and Fmoc-Amino Acid concentrations were 0.2 M. Each residue was subjected to 15-min double-couplings. The Trimethyl Lysine residue at position 26 was added using Fmoc-Lys(Me)3-OH Chloride under normal SPPS conditions. Upon completion of the synthesis, the N-terminal Fmoc-protecting group was removed using a 20% solution of Piperidine/DMF (2×3000 µL×5 min). The resin was then washed with DMF (6×3000 µL×30 s). Next, attachment of the PEG4 spacer group proceeded under standard SPPS coupling conditions (as mentioned above) using Fmoc-(PEG-4)-OH as the coupling partner, with a single 45 min coupling step. The Fmoc-protecting group was next removed, using conditions mentioned above, and washed with DMF (6×3000 µL×30 s) to give the free amine, ready for coupling with the DOTA chelator.

Addition of DOTA-PEG4

Addition of the DOTA-PEG4 occurred in two steps. First, addition of the PEG-4 spacer was afforded via single-couple reaction using Fmoc-(PEG-4)-OH under standard SPPS conditions. DIPEA and HATU were used as the Base/Activator pair in concentrations of 0.8 M and 0.4 M respectively. The PEG-4 reagent was used in a concentration of 0.2 M. Next, deprotection of the Fmoc group was afforded via (2×3000 µL×2 min). The resin was then washed with DMF (6×3000 µL×30 s).

DOTA was next attached using (2-(4,7,10-Tris(2-(tert-butoxy)-2-oxoethyl)-1,4,7,10-tetraazacyclododecan-1-yl) acetic acid). This reagent was dissolved to a concentration of 0.2 M and coupled to the PEG4 linker under standard SPPS conditions in the same manner as above. Upon completion, the resin was washed with DMF (6×3000 µL×30 s) and DCM (6×3000 µL×30 s). Finally, it was dried under vacuum for 2 h.

Cleavage from Resin

Final deprotection and cleavage of the peptide from the solid support was performed by treatment of the resin with (95% TFA. 2.0% thioanisole, 2.0% water and 1% triisopropylsilane) for 2-6 h at room temperature. Complete deprotection of the t-butyl esters on DOTA requires additional time. Heating at 50° C. for 15-20 min can be used also for complete removal of the t-butyl protecting groups. The cleaved peptide was precipitated using cold diethyl ether. The diethyl ether was decanted, and the solids triturated again with cold diethyl ether and pelleted by centrifugation.

Folding Conditions for Disulfide Formation

The crude product from above was dissolved in 25 mL of 6 M Guanidine/HCl and allowed to stir for 30 min. Next, the pH was adjusted to 8.0-8.5 using a 1 M solution of Ammonium Bicarbonate. Next, 250 µL of a 0.2 M solution of Disulfiram in acetonitrile was added to the solution and the mixture allowed to stir overnight at room temperature. A small sample was tested by HPLC/MS to confirm reaction completion. Next, neat TFA was used to quench the reaction by addition until the pH was adjusted to a pH range of 4-5. The reaction mixture was filtered using a syringe filter (Whatman, 0.45 µM, PTFE w/GMF) glass media, 0.45 µM) and the resulting solution purified via reverse-phase chromatography.

Figure 12:
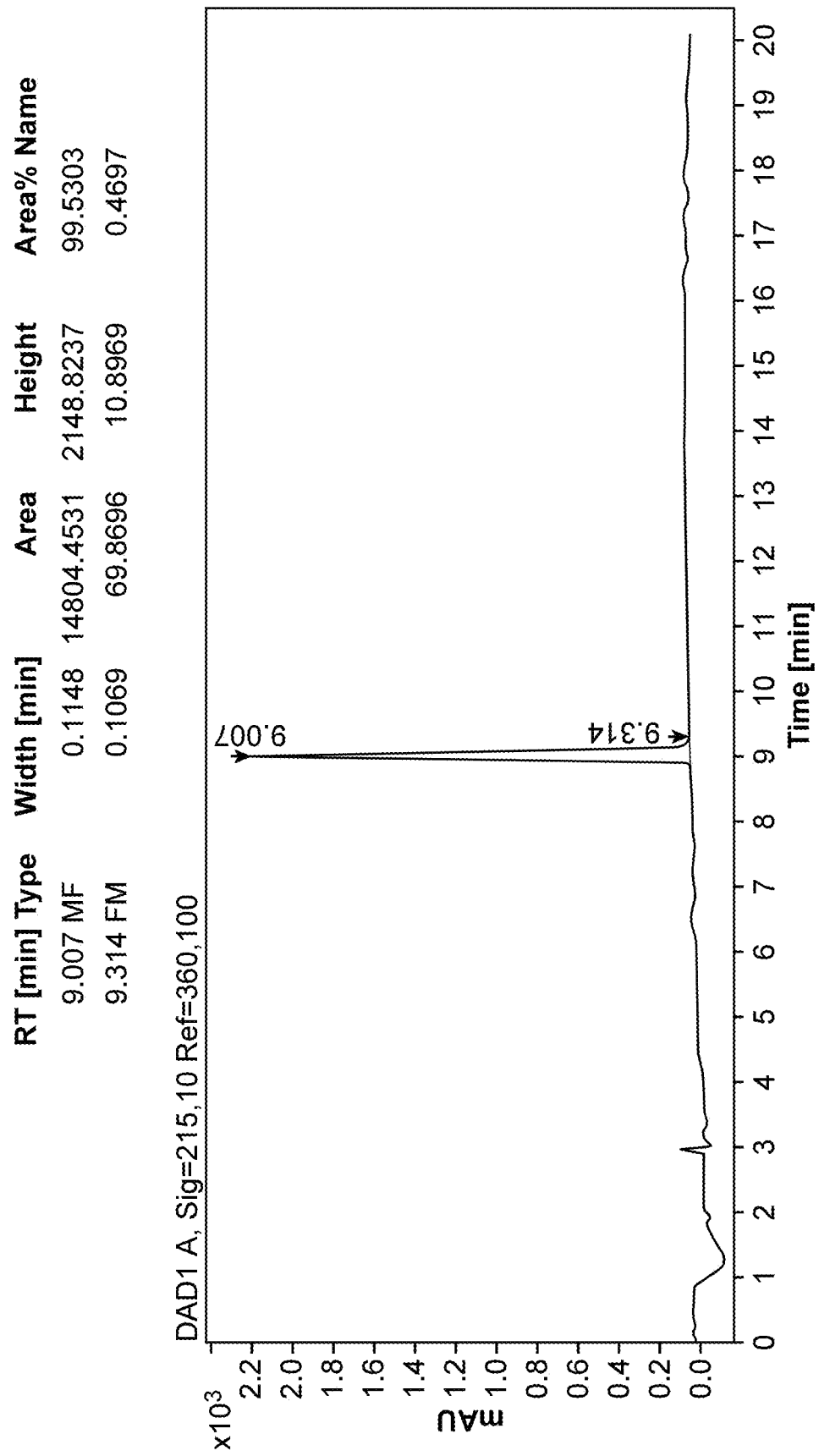
FIG. 12 is an exemplary HPLC trace for exemplary miniprotein C251, showing the milli-absorbance unit (mAU) over time (mm).
Figure 13:
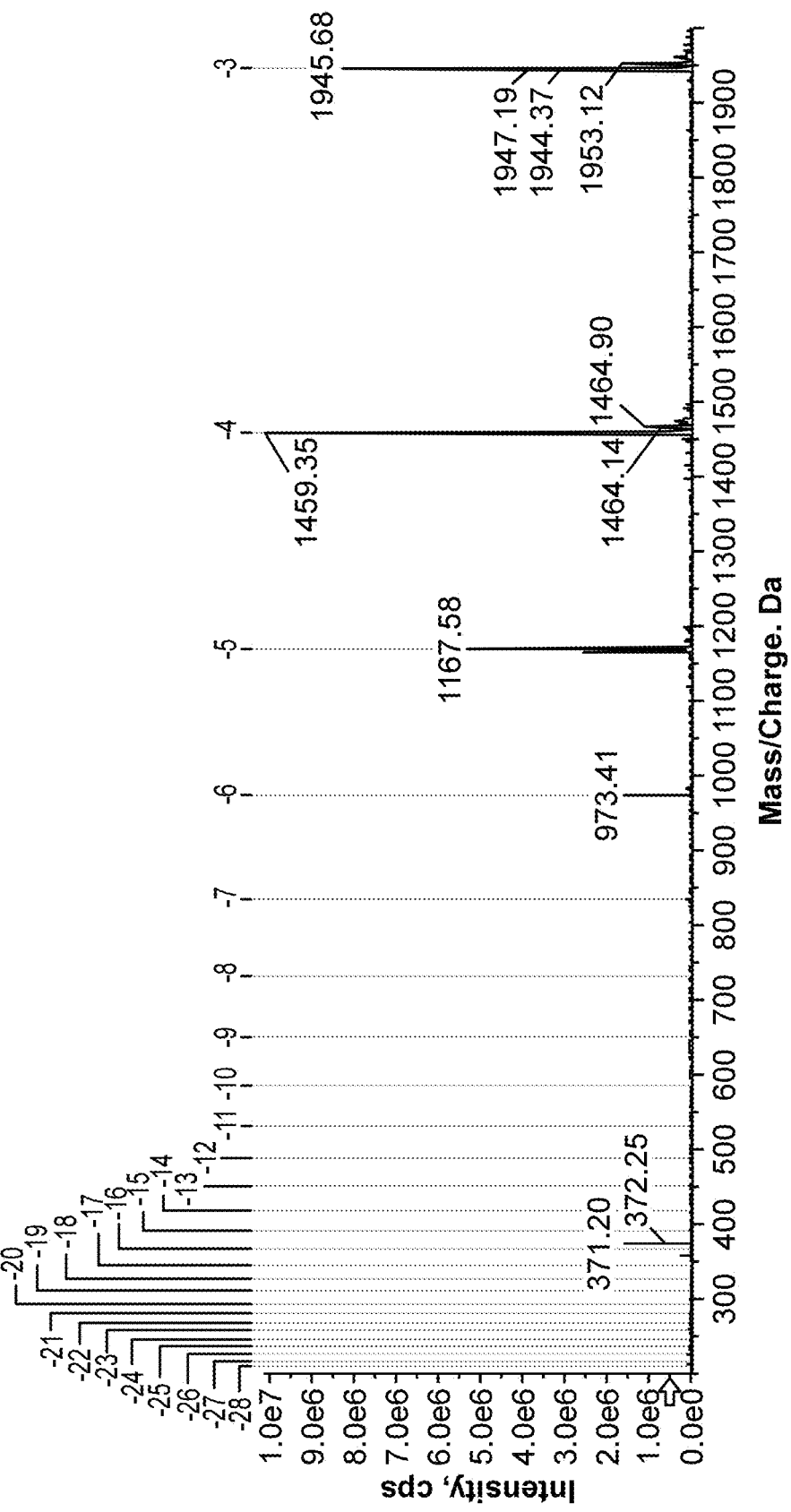
FIG. 13 is an exemplary mass spectrum for exemplary miniprotein C251.
Figure 14A:
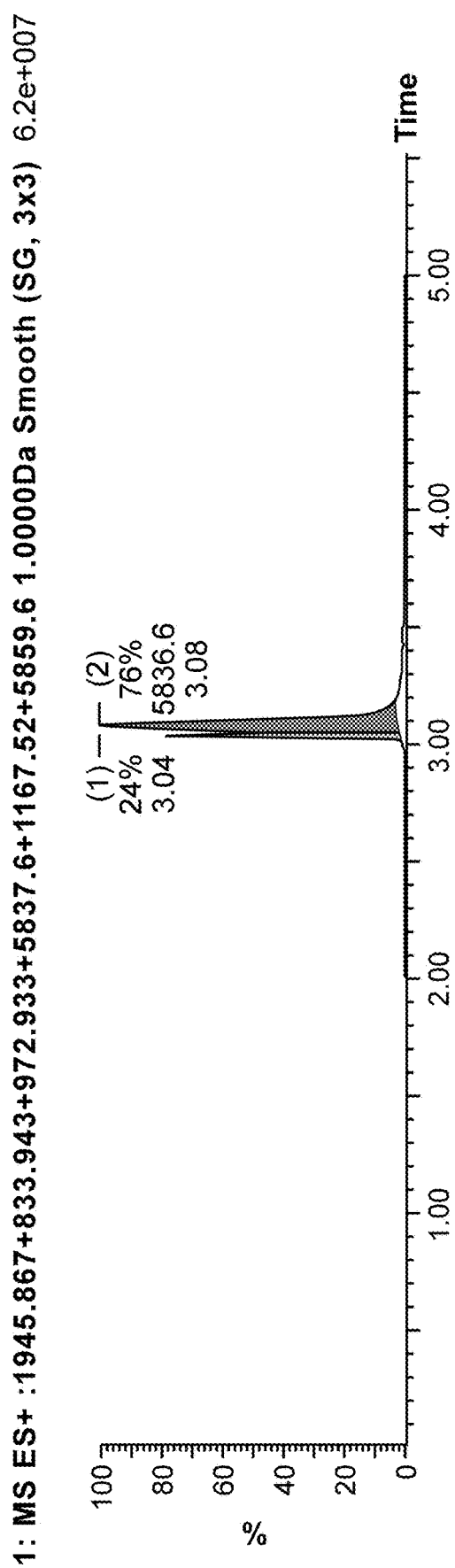
FIGS. 14A-14C are graphs showing exemplary UPLC-MS data for C251.
Figure 14B:
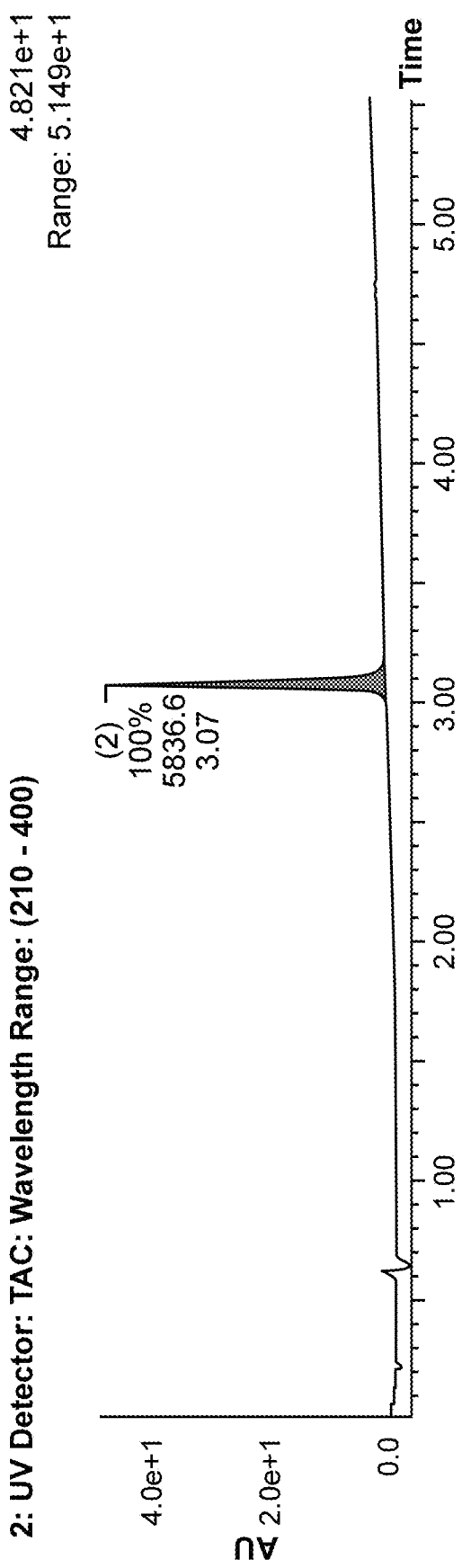
Figure 14C:
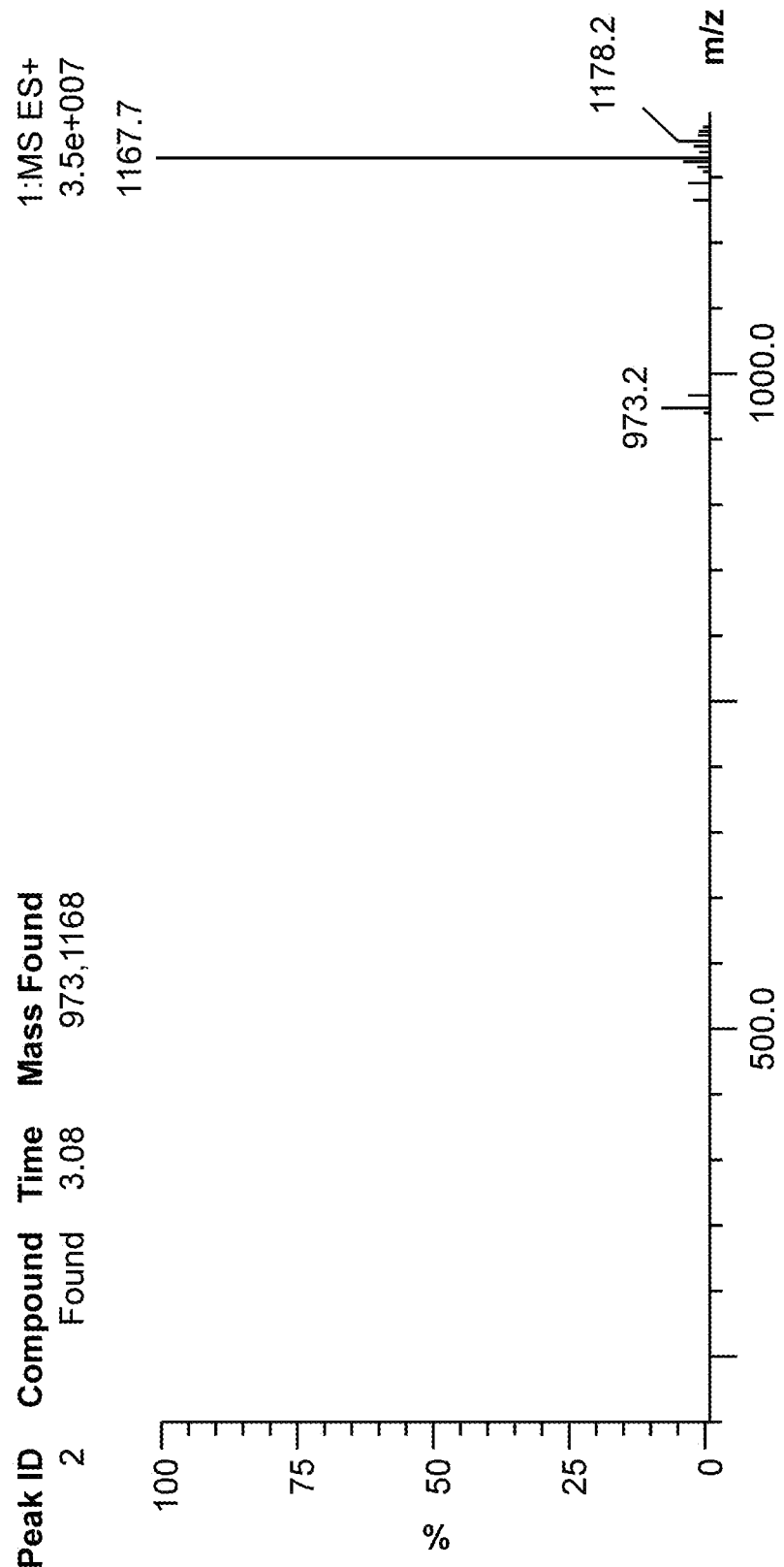

Compound 251 (C251) was characterized and measured, including as seen via HPLC (FIG. 12), mass spectral analysis (FIG. 13), and UPLC-MS (FIGS. 14A-14C).

TABLE 17

Compound C251.

| | | |
|---|---|---|
| MW | 5836.7 Da | |
| Batch Number | 1 | |
| Purity | HPLC | 99.5% |
| | UPLC-MS | 100.0% |
| Chemical form | Lyo powder | |
| Storage conditions | Freezer | |
| | Thermal Stability no issues observed | |
| | Solubility soluble 20% MeCN | |
| | Notes | |

TABLE 18

Analytical HPLC Conditions-Compound C251
ANALYTICAL HPLC CONDITIONS

| | | |
|---|---|---|
| Column | Waters XBridge BEH130, C18, 4.6 × 250 mm 5 µm, 130Å | |
| Solvent A | 0.1% TFA in H₂O | |
| Solvent B | 0.1% TFA in MeCN | |
| Method Type | Gradient | |
| Method | Time (min) | % Solvent B |
| | 0 | 5 |
| | 15 | 60 |
| | 17 | 95 |
| | 17.2 | 5 |
| | 20 | 5 |
| Flow rate | 1.5 mL/min | |
| UV-1 | 215 nm | |
| UV-2 | 280 nm | |
| Column heater | 40° C. | |
| Standard solution | 2000 µg/mL | |
| Std. Injection Vol. | 15 µL | |
| Retention time | 9.07 min | |

TABLE 19

UPLC-MS Conditions-Compound C251
UPLC-MS CONDITIONS

| | | |
|---|---|---|
| Column | Waters Acquity Protein, C4, 2.1X100 | |
| Solvent A | 0.1% Formic acid in H₂O | |
| Solvent B | 0.1% Formic in MeCN | |
| Method Type | Gradient | |
| Method | Time (min) | % Solvent B |
| | 0 | 10 |
| | 0.5 | 10 |
| | 4 | 60 |
| | 4.5 | 95 |
| | 5 | 10 |
| | 5.5 | 10 |
| Flow rate | 0.5 mL/min | |
| UV-1 | 215 nm | |
| UV-2 | 280 nm | |
| Column heater | 40° C. | |
| Standard solution | 2000 µg/mL | |
| Std. Injection Vol. | 2 µL | |

Example 23: Single Amino Acid Substitutions on Nectin-4 Miniproteins

This Example describes exemplary library screening for identification of single amino acid substitutions in miniproteins described herein that preserve Nectin-4 binding.

Using a Yeast Display Library

A miniprotein polypeptide library was generated and genetically fused to the yeast mating agglutinin protein Aga2p. Aga2p attaches by two disulfide bonds to Aga1p, a yeast cell wall protein. Expression of these constructs was put under the control of a galactose-inducible promoter and the N-terminal of the miniproteins was fused to Aga2p.

Library Construction

Oligos that encode the miniprotein library consisting of every possible single amino acid substitutions for each position in the miniprotein sequence, except for the four cysteine residues, in the DNA sequence of the miniprotein were synthesized. Specifically, beginning with SEQ ID NO: 78, every possible single amino acid substitutions at every position except for the cysteine at positions 1, 20, 34, and 44 were introduced. Additionally, beginning with SEQ ID NO: 83, every possible single amino acid substitutions at every position except for the cysteine at positions 1, 20, 34, and 44 were introduced. Additionally, beginning with SEQ ID NO: 85, every possible single amino acid substitutions at every position except for the cysteine at positions 1, 20, 34, and 44 were introduced. Additionally, beginning with SEQ ID NO: 103, every possible single amino acid substitutions at every position except for the cysteine at positions 1, 20, 34, and 44 were introduced.

The oligos were amplified and converted to double-stranded DNA by using PCR. An additional round of overlap extension PCR was employed to append a nucleotide sequence for homologous recombination with a yeast plasmid that permits expression and display of encoded exemplary miniproteins on a yeast surface. The DNAs were cloned into yeast cells using a PEG-based method.

Library Analysis

Two-color FACS was used for screening the yeast miniprotein library. Display of a miniprotein was measured via an anti-c-myc epitope antibody, followed by labeling using an anti-anti-epitope tag fluorescently conjugated antibody. To detect Nectin-4 binding, yeast cells displaying a miniprotein library were incubated with 10 nM biotinylated Nectin-4 and allowed to come to equilibrium. The extent of Nectin-4 binding was detected by a fluorescently conjugated anti-biotin molecule. The labeled yeast cells were analyzed using a fluorescence activated cell sorter. Yeast cell showing simultaneous display of epitope and Nectin-4 binding were captured by cell sorter. The captured yeast cells were analyzed by next generation sequencing.

Figure 16:
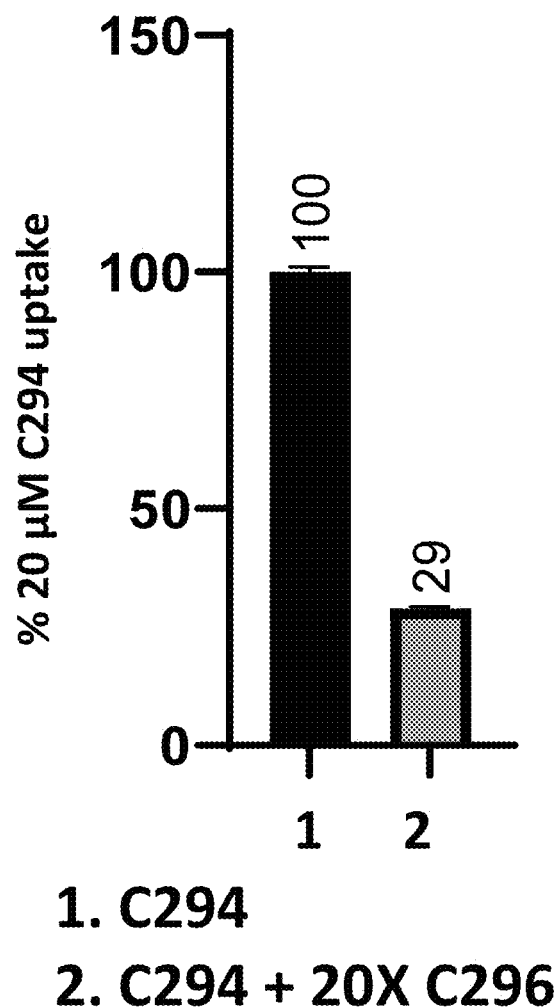
FIG. 16 is a graph showing reduction in cellular uptake of exemplary target-binding miniprotein compound, C294, when combined with an exemplary decoy, C296, in vitro. The bar graph depicts percent uptake of an exemplary Nectin-4-targeting miniprotein (C294) alone/without a decoy peptide (20 µM) or in combination with a 20-fold molar excess of an exemplary decoy (C296). Error bars represent standard error of the mean (SEM).

For each amino acid position, the allowed substitutions were the amino acid substitutions that still resulted in Nectin-4 binding. Allowed substitutions did not disrupt the binding of the miniprotein to 10 nM Nectin-4. TABLE 2C shows the allowed amino acid substitutions at various positions across a miniprotein of SEQ ID NO: 78. TABLE 2D shows the allowed amino acid substitutions at various positions across a miniprotein of SEQ ID NO: 83. TABLE 2E shows the allowed amino acid substitutions at various positions across a miniprotein of SEQ ID NO: 85. TABLE 2G shows the allowed amino acid substitutions at various positions across a miniprotein of SEQ ID NO: 103. To evaluate whether or not each amino acid substitution was allowed and/or preferred, the ratio was calculated between the frequency in a population enriched for miniproteins that bind to Nectin-4 and the frequency of the same sequence in the initial library. All such ratios were normalized by dividing them by the ratio observed for a substitution to the same amino acid. Substitutions with a normalized ratio larger than 0.5 and lower than 1.5 were designated as "allowed substitutions." Substitutions with a normalized ratio of 1.5 or higher were designated as "preferred substitutions." Preferred substitutions improved the level of binding of the miniprotein to 10 nM Nectin-4. TABLE 2C shows the preferred amino acid substitutions at various positions across a miniprotein of SEQ ID NO: 78. TABLE 2D shows the preferred amino acid substitutions at various positions across a miniprotein of SEQ ID NO: 83. TABLE 2E shows the preferred amino acid substitutions at various positions across a miniprotein of SEQ ID NO: 85. TABLE 2G shows the preferred amino acid substitutions at various positions across a miniprotein of SEQ ID NO: 103.

Example 24: Multiple Amino Acid Substitutions on Nectin-4 Miniproteins

This Example describes exemplary library screening for identification of two or more amino acid substitutions in a miniprotein described herein that preserve Nectin-4 binding.

Using a Vast Display Library

A miniprotein polypeptide library is generated and genetically fused to the yeast mating agglutinin protein Aga2p. Aga2p attaches by two disulfide bonds to Aga1p, a yeast cell wall protein. Expression of these constructs is put under the control of a galactose-inducible promoter and the N-terminal of the miniproteins is fused to Aga2p.

Library Construction

Oligos that encode the miniprotein library consisting of two or more amino acid substitutions in the sequence of the miniprotein, except for the four cysteine residues, in the DNA sequence of the miniprotein are synthesized. Specifically, oligos are designed to introduce two or more (e.g., two, three, four, five, six, seven, eight, nine, or ten or more) amino acid substitutions shown in TABLE 2C at their respectively indicated positions across a miniprotein of SEQ ID NO: 78. Additionally, oligos are designed to introduce two or more (e.g., two, three, four, five, six, seven, eight, nine, or ten or more) amino acid substitutions shown in TABLE 2D at their respectively indicated positions across a miniprotein of SEQ ID NO: 83. Additionally, oligos are designed to introduce two or more (e.g., two, three, four, five, six, seven, eight, nine, or ten or more) amino acid substitutions shown in TABLE 2E at their respectively indicated positions across a miniprotein of SEQ ID NO: 85. Additionally, oligos are designed to introduce two or more (e.g., two, three, four, five, six, seven, eight, nine, or ten or more) amino acid substitutions shown in TABLE 2F at their respectively indicated positions across a miniprotein of SEQ ID NO: 195. Additionally, oligos are designed to introduce two or more (e.g., two, three, four, five, six, seven, eight, nine, or ten or more) amino acid substitutions shown in TABLE 2G at their respectively indicated positions across a miniprotein of SEQ ID NO: 103.

The oligos are amplified and converted to double-stranded DNA using PCR. An additional round of overlap extension PCR is employed to append a nucleotide sequence for homologous recombination with a yeast plasmid that permits expression and display of encoded exemplary miniproteins on a yeast surface. The DNAs are cloned into yeast cells using a PEG-based method.

Library Analysis

Two-color FACS is used for screening the yeast miniprotein library. Display of a miniprotein is measured via an anti-c-myc epitope antibody, followed by labeling using an anti-anti-epitope tag fluorescently conjugated antibody. To detect Nectin-4 binding, yeast cells displaying a miniprotein library are incubated with 10 nM biotinylated Nectin-4 and allowed to come to equilibrium. The extent of Nectin-4 binding is detected by a fluorescently conjugated anti-biotin molecule. The labeled yeast cells are analyzed using a fluorescence activated cell sorter. Yeast cell showing simultaneous display of epitope and Nectin-4 binding are captured by cell sorter. The captured yeast cells are analyzed by next generation sequencing. For each amino acid position, the allowed substitutions are the amino acid substitutions that maintain Nectin-4 binding. Allowed substitutions do not disrupt the binding of a miniprotein to 10 nM Nectin-4. To identify preferred substitutions, the ratio is calculated between the frequency in a population enriched for miniproteins that bind to Nectin-4 and the frequency of the same sequence in the initial library. All such ratios are normalized by dividing them by the ratio observed for a substitution to the same amino acid. Substitutions with a normalized ratio larger than 0.5 and lower than 1.5 are designated as "allowed substitutions." Substitutions with a normalized ratio of 1.5 or higher are designated as "preferred substitutions." Preferred substitutions improve the level of binding of a miniprotein to 10 nM Nectin-4.

Example 25: In Vitro Reduction of Exemplary Comparator Miniprotein Compound by an Exemplary Decoy in OK-PTC Cells This Example shows reduction in exemplary comparator molecule uptake by kidney cells in vitro when combined with an exemplary decoy as compared to no decoy. Uptake of exemplary comparator compound C294, a Nectin-4 targeting bicyclic miniprotein, at 20 μM was evaluated in OK-PTC cells in vitro (as described in Examples 23A and 23B; here, cells were treated with a compound alone or were co-incubated with a compound and a decoy (of a different scaffold) that were added together or at substantially the same time) and measured after incubation in presence or absence of a 20-fold molar excess of exemplary decoy. C296.

Comparator compound details are provided in TABLE 20 and FIG. 16. FIG. 16 shows reduction in cellular uptake of an exemplary target-binding miniprotein compound when combined with an exemplary decoy in vitro. FIG. 16 depicts percent uptake (on the y-axis) of an exemplary Nectin-4-targeting bicyclic miniprotein (C294) alone (20 μM; column 1, x-axis) or in combination (column 2, x-axis) with a 20-fold molar excess of an exemplary decoy (C296). Uptake of the Nectin-4 targeting bicyclic miniprotein (C294) was reduced by co-treatment with a 20-fold molar excess of the decoy peptide C296 as shown in FIG. 16. These results show that a Nectin-4 bicyclic compound can be decoyed by decoys of a different scaffold.

TABLE 20

Exemplary Comparator Compound Sequences And Structures

| Compound ID NO[6] | N-Term. | Sequence[7] | SEQ NO:[8] | C-Term. |
|---|---|---|---|---|
| C294 | [TATA (15,15)] SCBiot-(dPEG4) | CP(1Nal)(dD)CM(hR) DWSTP(hyP)WC | 238 | NH2 |

[6] Each compound is identified via a compound # (e.g., "C1", "C2", "C3", etc.) and refers to the combination of the N-terminal. Linker (if present), Sequence, and C-terminal
[7] Lowercase amino acid residues "f" and "w" refer to D-amino acids (D-phenylalanine and D-tryptophan, respectively); "dD" refers to D-aspartic acid; "hR" refers to homo-arginine; "hyP" refers to hydroxyproline; "1Nal" refers to 1-naphthylamine
[8] Refer, to sequences in the "Sequence" column Example 26: In Vivo Decoy of a Miniprotein Monomer in Presence of an Exemplary Decoy This Example shows measurements of kidney and tumor retention (in % ID/g) with an $^{111}$In-labeled exemplary miniprotein (C109) compound in presence or absence of an exemplary decoy (C295) of the same scaffold as the miniprotein. Biodistribution in kidney tissue and tumor tissue was determined in mouse xenograft model using SPECT/CT analysis as described herein and evaluated using methods similar to those described in Examples 10, 11, and 21.

Mice were administered: (1) an $^{111}$In-labeled exemplary Nectin-4 binding compound, C109 ([111]In-C109), or (2) [111]In-C109 at 3.7 μg peptide/mouse (+/−0.0 μg)/Activity dose—359.6 μCi+/−4.5 μCi; or (2) [111]In-C67 at 3.7 μg of peptide/mouse (+/−0.1 μg)/Activity dose—362.9 μCi+/−12.6 μCi and an exemplary decoy of the same scaffold, C295. Kidney and tumor uptake were measured between 0.25 and 32 h post-injection. Kidney (FIG. 17A) and tumor (FIG. 17B) uptake (in % ID/g) were both reduced at all time points measured in mice co-administered [11]In-C109 and C295 as compared to those receiving [111]In-C109 alone (without any decoy).

Figure 17A:
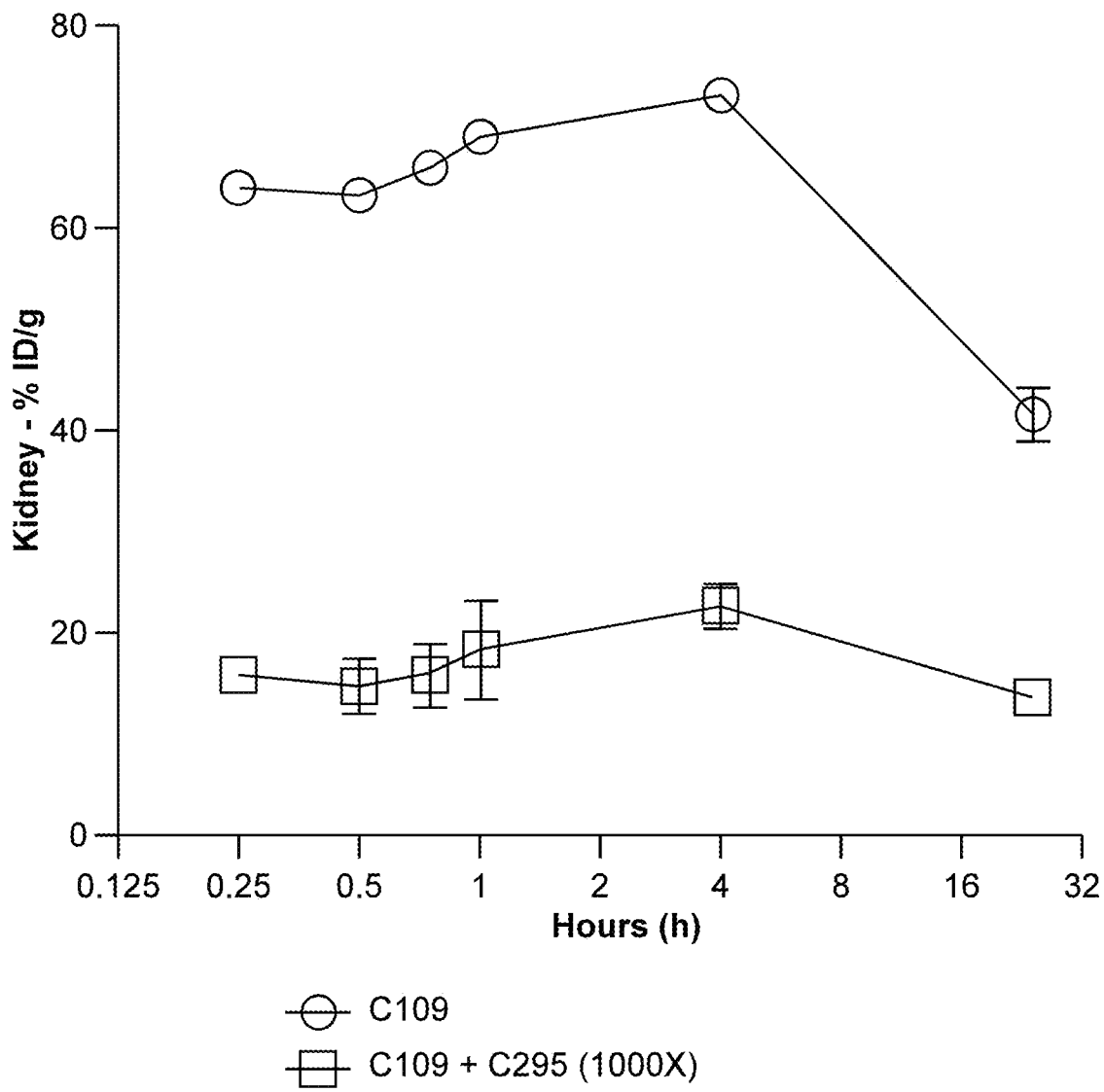
FIGS. 17A-17D are graphs showing in vivo kidney (FIGS. 17A and 17C) or tumor (FIGS. 17B and 17D) retention, in an exemplary mouse xenograft model, shown as % ID/g from 0.25-32 h post-injection of an $^{111}$In-labeled exemplary Nectin-4-targeting miniprotein conjugate ($^{111}$In-C109 in FIGS. 17A and 17B; $^{111}$In-C251 in FIGS. 17C and 17D) alone/without a decoy or co-administered with a 1,000-fold molar excess of an exemplary decoy (C295 in FIGS. 17A and 17B; C296 in FIGS. 17C and 17D).
Figure 17B:
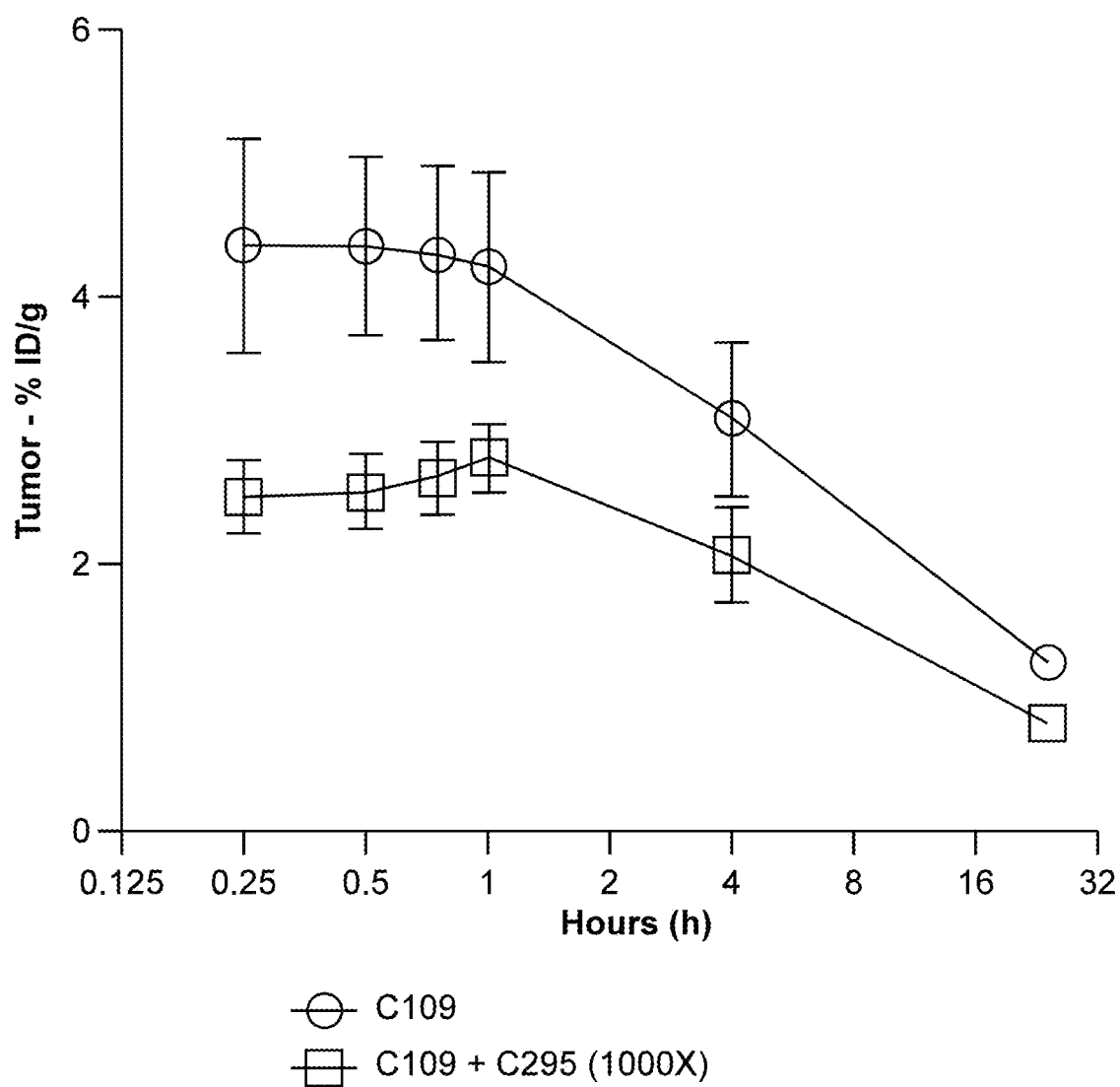

FIG. 17A shows % ID/g in kidney of an $^{111}$In-labeled exemplary Nectin-4-targeting miniprotein ([111]In-C109) alone (solid circles) or in combination with an exemplary decoy (of the same scaffold) at 1000-fold excess (solid squares). FIG. 17B shows % ID/g in tumor of an $^{111}$In-labeled exemplary Nectin-4-targeting miniprotein ([111]In-C109) alone (solid circles) or in combination with an exemplary decoy (solid squares) of the same scaffold as the miniprotein. TABLE 21 shows quantification of biodistribution in kidneys in the decoy ([111]In-C109 and C295) and no decoy ([111]In-C109 alone) conditions at 4 and 22 h. These results show that an exemplary Nectin-4-binding monomer can be successfully decoyed (by a decoy of the same scaffold) without impacting efficacy, by reducing kidney uptake but not impacting the ability of the exemplary monomer to reach the tumor.

TABLE 21

Exemplary In Vivo Kidney Biodistribution Analysis Of An Exemplary Nectin-4 Binding Compound Co-Administered With Exemplary Decoy

| Compound ID | Decoy/Scaffold | 4 h (% ID/g) | | 22 h (% ID/g) | |
|---|---|---|---|---|---|
| NO/Scaffold | (fold excess) | Average | StDev | Average | StDev |
| $^{111}$In-labeled C109 (A) | — | 73.2 | 0.7 | 41.7 | 4.5 |
| $^{111}$In-labeled C109 (A) | C295/A (1,000) | 22.7 | 3.8 | 13.7 | 1.0 |

Example 27: In Vivo Reduction in Uptake and Retention in Kidney of a Miniprotein Compound in Presence of a Decoy Peptide This Example shows reduction in kidney uptake and retention (in % ID/g) in kidney of an exemplary Nectin-4-binding miniprotein (C251) compound in presence or absence of exemplary decoys of the same scaffold as the miniprotein (C296, C295, and C297). Biodistribution in kidney tissue was determined in a non-tumor bearing mouse model with methods similar to those described in Examples 10 and 11.

Figure 17C:
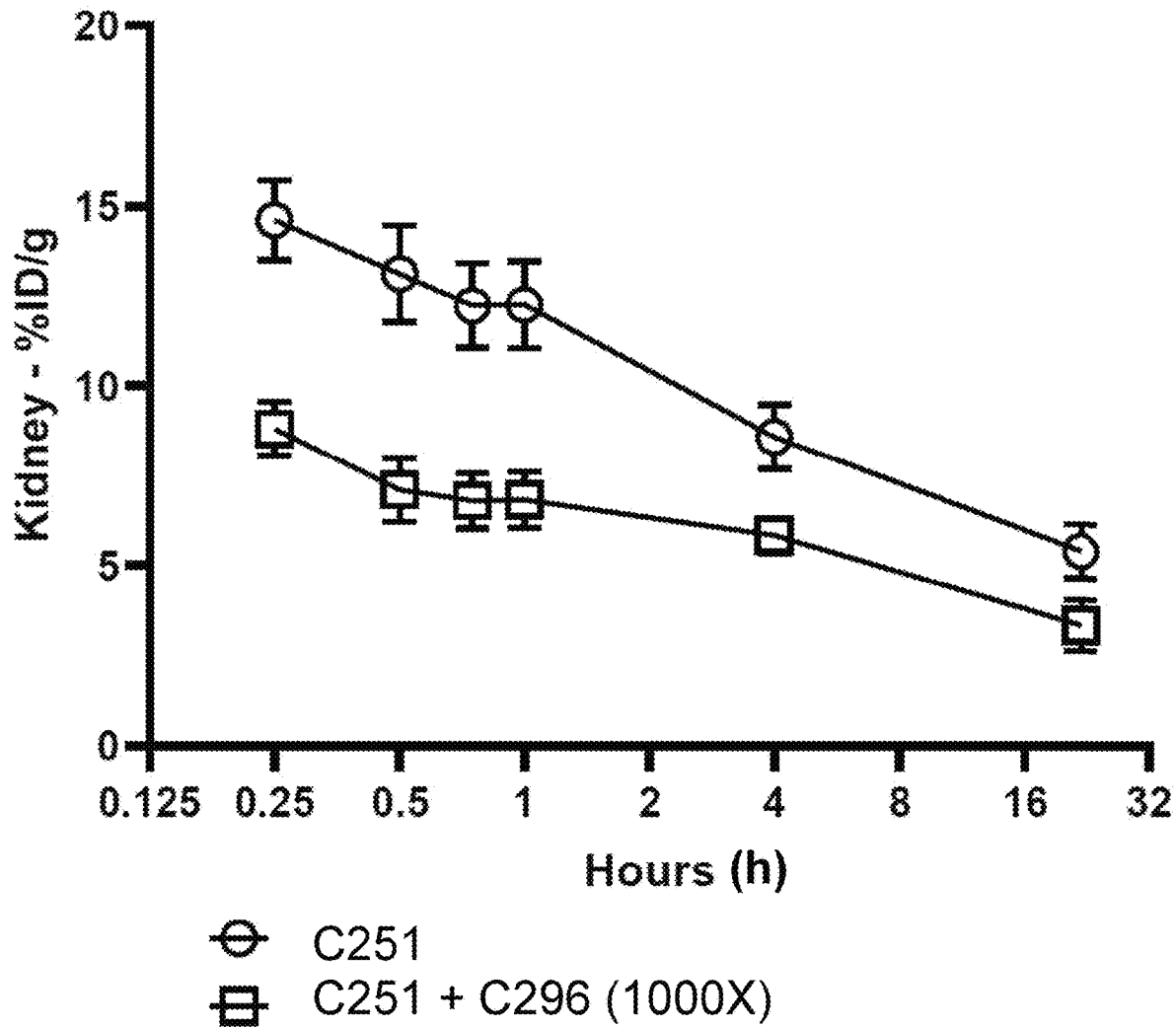
Figure 17D:
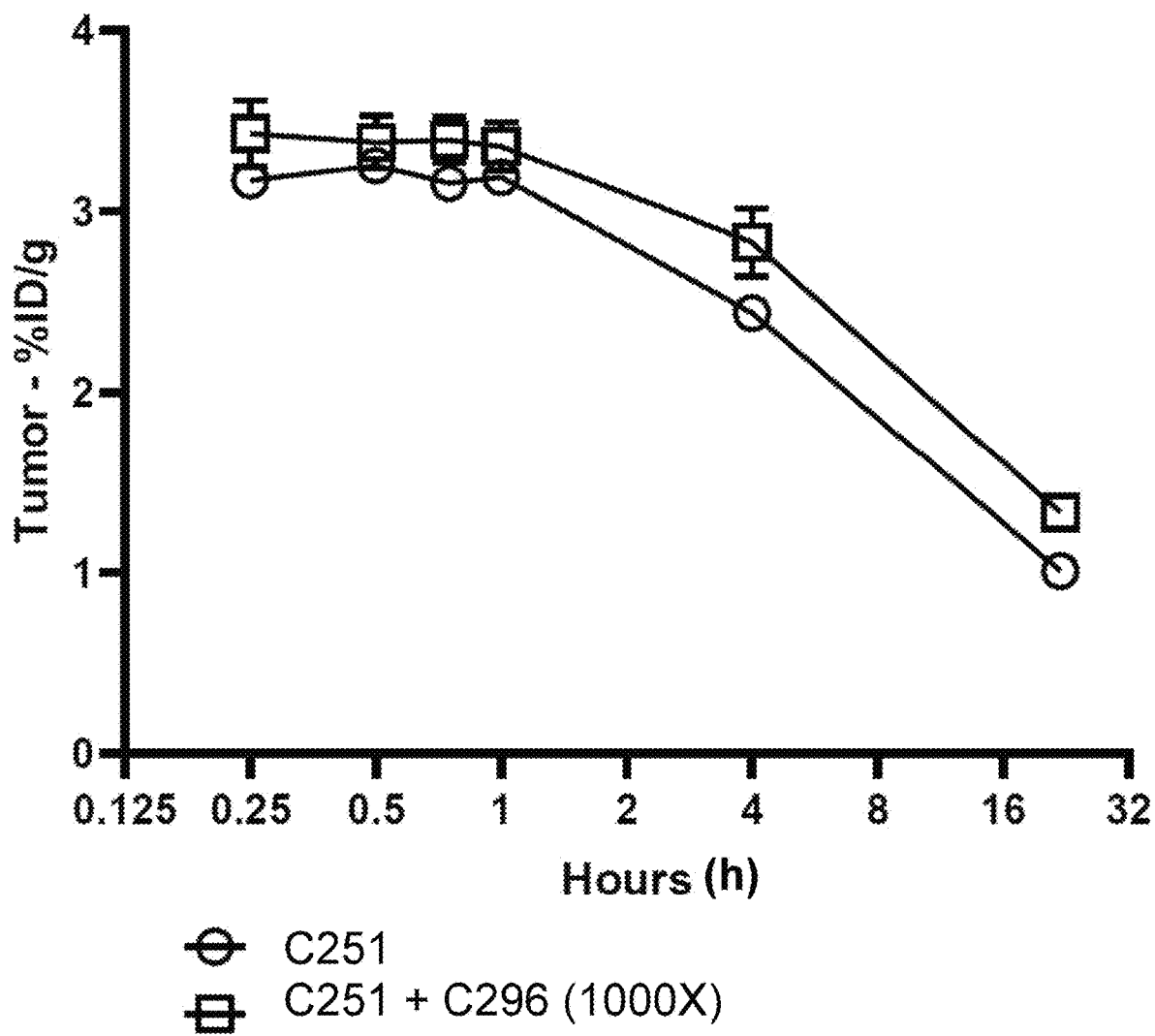

Mice were administered: (1) an exemplary compound. C251, labeled with [111]In ([111]In-C251) or (2) [111]In-C251 and an exemplary decoy, C296, C295, or C297. Kidney uptake (in % ID/g) was reduced at both 4 and 22 h post-injection in mice co-administered [111]In-C251 and any of the three decoys as compared to those receiving [111]In-C251 alone (TABLE 22). In addition, a change in localization of the [111]In-C251 compound was observed in kidney tissue in presence of decoy versus no decoy (data not shown). Specifically, co-administration of [111]In-C251 and any of C296, C295, and C297 (as determined by SPECT/CT analysis) showed a difference in the anatomical profile of the detected signal of [111]In-C251, particularly between 15-75 minutes post-injection. After decoy administration, images showed that [111]In-C251 was detected in the medulla of the kidney, whereas without decoy administration [111]In-C251 was detected in the proximal tubule section of the kidney cortex (data not shown). Localization to the medulla is considered to indicate active clearance and lack of retention (including as compared to [111]In-C251 in the absence of the decoy). TABLE 22 shows quantification of biodistribution in kidneys in the no decoy ([111]In-C251 alone) or decoy ([111]In-C251 plus C2%, C295, or C297) conditions at 4 and 22 h. FIGS. 17C and 17D show % ID/g in kidney (FIG. 17C) and tumor (FIG. 17D) of an exemplary Nectin-4-targeting miniprotein conjugate ([111]In-C251) alone/without a decoy or in combination with an exemplary decoy (C296). These results show that Nectin-4-binding compounds can be successfully decoyed by various decoys of the same scaffold as the Nectin-4-binding miniprotein, reducing uptake and retention in kidney tissue.

TABLE 22

Exemplary In Vivo Kidney Biodistribution Analysis Of An Exemplary Nectin-4 Binding Compound Co-Administered With Exemplary Decoys Of the Same Scaffold

| Compound ID NO/Scaffold | Decoy/Scaffold (fold excess) | 4 h (% ID/g) Average | StDev | 22 (% ID/g) Average | StDev |
|---|---|---|---|---|---|
| $^{111}$In-labeled C251 (A) | — | 8.6 | 1.6 | 5.4 | 1.3 |
| $^{111}$In-labeled C251 (A) | C295/A (1,000) | 6.0 | 0.3 | 3.9 | 0.2 |
| $^{111}$In-labeled C251 (A) | C297/A (1,000) | 3.9 | 1.8 | 2.1 | 0.9 |
| $^{111}$In-labeled C251 (A) | C296 A/(1,000) | 5.8 | 0.8 | 3.3 | 1.2 |

Example 28: In Vivo Reduction in Uptake and Retention in Kidney of a Nectin-4 Binding Miniprotein Compound in Presence of Decoys without Impacting Efficacy of the Miniprotein Against Tumor Volume Reduction This Example shows efficacy of an exemplary Nectin-4-binding tumor-targeting compound in presence and absence of a co-administered decoy (of the same scaffold). This Example shows that uptake and retention in kidney of a the miniprotein was reduced with administration of a decoy, but the decoy administration did not reduce efficacy of the miniprotein against tumor volume in vivo. Biodistribution in kidney tissue was determined in a mouse xenograft model as described herein (including below).

Animals: Female athymic nude mice (6-8 weeks of age) were purchased from Charles River Laboratories and housed according to IACUC guidelines with ad libitum feeding. In vivo efficacy study experiments were performed in tumor bearing athymic nude mice. Tumor xenograft models were generated by inoculating mice subcutaneously with $3 \times 10^6$ HT-1376 cells engineered to overexpress Nectin-4, in 200 µL (50:50 PBS/Matrigel) in either the right shoulder or right flank. Tumors were monitored for a minimum of 14 days prior to group stratification and study initiation dates. Mice with tumor volumes between 150 mm$^3$ and 250 mm$^3$ were selected for study inclusion and randomized to treatment arms 1, 2, 3, or 4, as set out in TABLE 23.

Animal grouping and treatment: One day prior to treatment, $^{225}$Ac-labeled Nectin-4 binding compounds were prepared as described above in Example 6A at a specific activity of approx. 1 µCi/µg, with activity measurements made at secular equilibrium on a dose calibrator. On the day of treatment, dose measurements for a sample injected dose were measured and confirmed on a gamma counter and corrected for decay. Indicated doses of vehicle or radiolabeled test article were prepared corresponding to the indicated administered dose levels per group. Doses were administered via tail vein injection while restrained and awake. Syringes with prepared doses were weighed pre and post injection and weights recorded.

Animal monitoring: Tumor volume (caliper measurement) and body weight measurements for enrolled mice were performed twice a week for an initial planned monitoring period of 8 weeks. More frequent gross observations of mice were performed.

Humane endpoints: Mice remained on study until they reached the end of the 8-week monitoring period or a number of pre-defined humane endpoints, including:
(1) increase in tumor volume size that exceeded >2,000 mm$^3$, or 20 mm in one dimension, or tumor became ulcerated or necrotic;
(2) decrease in body weight ≥20% from maximum recorded weight;
(3) any signs of pain or distress (e.g., consistent hunched posture, rough coat, squinted eyes, slowed gait, etc.);
(4) tumors that compromised mobility and/or ability to eat or drink; and/or.
(5) BCS score ≤2.

Descriptions of the study arms and in vivo study design with exogenously expressed target protein are described in TABLE 23. Eight animals were analyzed in each of the four groups. All animals were given a single dose of treatment (see TABLE 23), administered intravenously and monitored for eight weeks. Measurements of tumor volumes (FIG. 18A) and body weights (FIG. 18B) were compared in mice treated according to the study arms described in TABLE 23.

TABLE 23

Study Arms For In Vivo Studies Of Exemplary $^{225}$Ac-Labeled Test Articles with Co-Administration Of Decoys in Xenografted Tumors from an HT-1376 Target-Expressing Cell Line

| Group | Treatment | $^{225}$Ac-C251 Administered Dose [nCi] | Decoy Mass Dose |
|---|---|---|---|
| 1 | Vehicle | n/a | n/a |
| 2 | C296 | n/a | 1,000X |
| 3 | $^{225}$Ac-C251 | 1,000 | n/a |
| 4 | $^{225}$Ac-C251 + C296 | 1,000 | 1,000X |

Figure 18A:
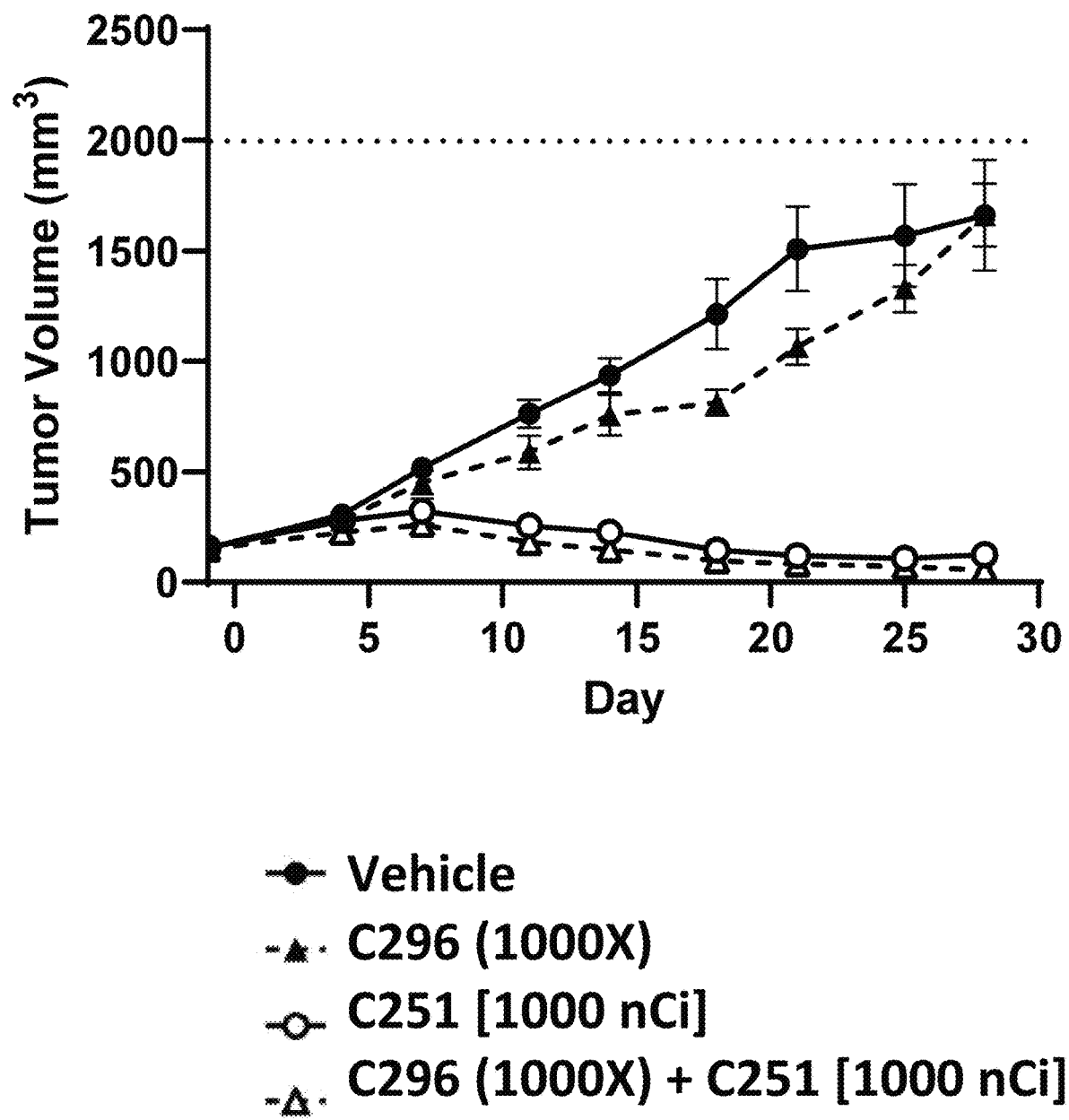
FIGS. 18A and 18B are graphs showing in vivo tumor volume (mm$^3$.
Figure 18B:
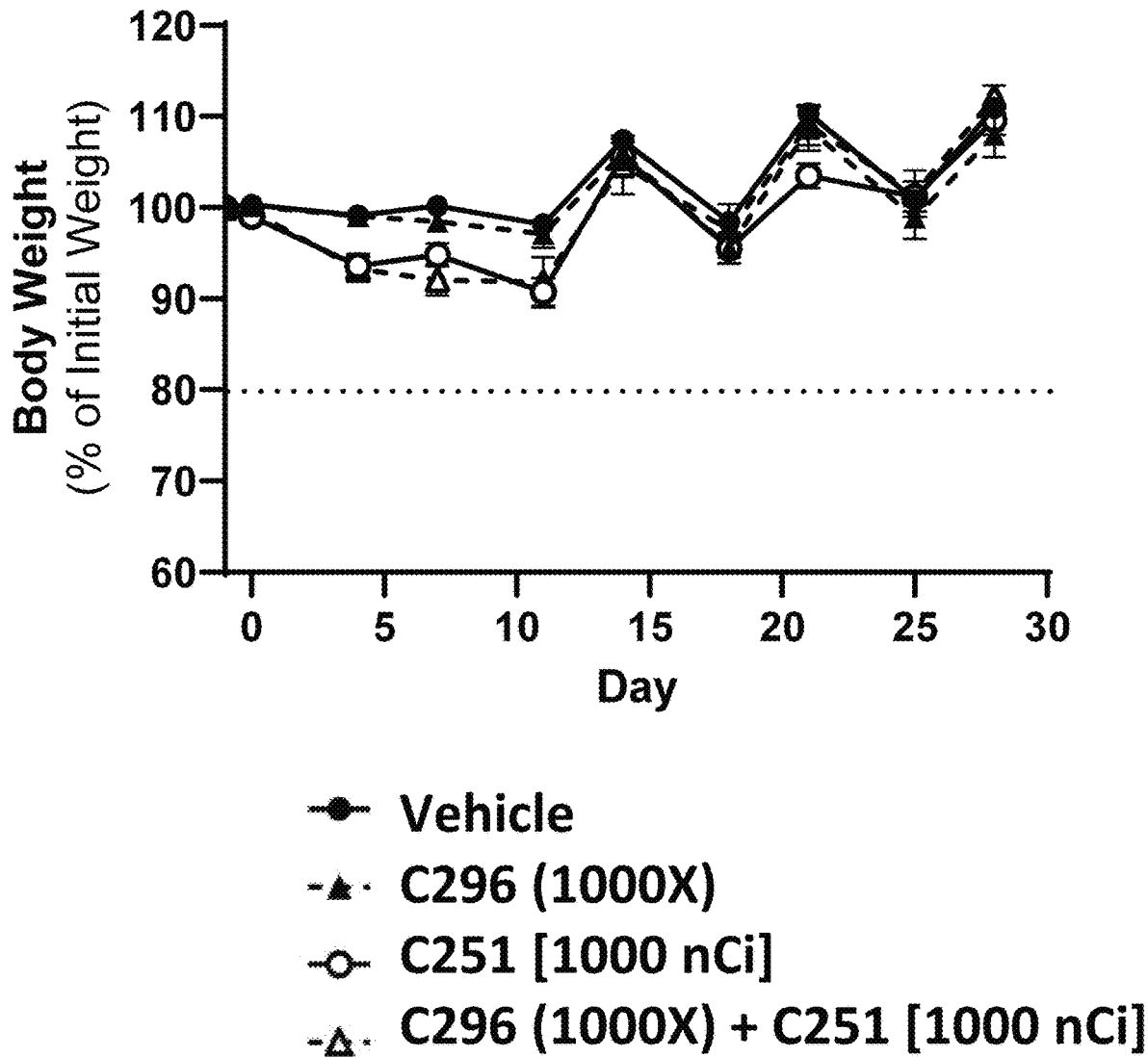

FIGS. 18A and 18B show results of analyses of the tumor volume (mm$^3$; FIG. 18A) and body weight (% of initial weight; FIG. 18B) measurements between days 0 and 30. Within each of the four groups, mice were treated with: (1) a non-binding, non-radiolabeled control (vehicle) (solid circles); (2) an exemplary decoy (C296; 1000× of C251 dose, solid triangles); (3) an exemplary Nectin-4-targeting radionuclide ($^{225}$Ac-C251; approx. 1 µg of peptide/mouse; 1,00) nCi; open circles); and (4) a combination of the exemplary decoy peptide (C296; approx. 1 mg of decoy/mouse; 1000×; open triangles) and the exemplary Nectin-4-targeting radionuclide ($^{225}$Ac C251; 1,000 nCi). In FIG. 18A, the dotted line at 2,000 mm$^3$ marks the maximum tumor growth threshold for the pre-defined humane endpoint of experimental mice. In FIG. 18B, the dotted line at 80% of initial body weight marks the body weight decrease threshold for the pre-defined humane endpoint for the experimental mice.

Reduction in tumor volume in mouse efficacy studies was observed in Group 3 and Group 4 (each administered the exemplary Nectin-4 binding miniprotein test article radionuclide, $^{225}$Ac-C251) (FIG. 18A). Groups 1 (vehicle) and 2 (decoy alone) both showed growth in tumor volume over the period of time tracked. As shown in FIG. 18A, both Groups 3 and 4 tumor volumes (radionuclide-labeled compound or radionuclide-labeled compound plus decoy, respectively) were reduced compared to Groups 1 and 2 (vehicle or decoy alone, respectively). Furthermore, as shown by reduction in tumor volume, efficacy of C251 was not reduced in the presence of the exemplary decoy. C296, demonstrating that co-administration of a decoy did not reduce efficacy of tumor treatment

Example 29: In Vivo Efficacy Study Involving Actinium-Labeled Miniproteins in Cell-Line Derived Xenograft Model This Example shows in vivo efficacy of an exemplary Nectin-4-binding tumor-targeting compound, evaluated in a cell-line derived xenograft ("CDX") model.

Animals: Female athymic nude mice (6-8 weeks of age) were purchased from Charles River Laboratories and housed according to IACUC guidelines with ad libitum feeding. In vivo efficacy study experiments were performed in tumor bearing athymic nude mice. Tumor xenograft models were generated by inoculating mice subcutaneously with $3 \times 10^6$ HT-1376-cells ("Parental", which express Nectin-4), in 200 µL (50:50 PBS/Matrigel) in either the right shoulder or right flank. Tumors were monitored for a minimum of 14 days prior to group stratification and study initiation dates. Mice with tumor volumes between 150 mm³ and 250 mm³ were selected for study inclusion and randomized to treatment arms. An excess of 60% of required study mice were inoculated with tumor cells to ensure enough mice with appropriate tumor ranges were generated.

Animal grouping and treatment: On study dosing day, $^{225}$Ac-C251 was prepared as described at a specific activity of approximately 1 µCi/µg, with activity measurements for the labeled product made at secular equilibrium on a dose calibrator. Dose measurements for a sample injected dose were measured and confirmed on a gamma counter and corrected for decay. EV doses were calculated based on mouse weights and liquid concentration of prepared material. Indicated doses of vehicle, EV or radiolabeled C251 were prepared corresponding to the indicated administered dose levels per group. Doses were administered via tail vein injection while restrained and awake.

Animal monitoring: Tumor volume (caliper measurement) and body weight measurements for enrolled mice were performed twice a week for an initial planned monitoring period of 8 weeks. More frequent gross observations of mice were performed.

Hunan endpoints: Mice remained on study until they reached the end of the 8-week monitoring period or a number of pre-defined humane endpoints, including:

1. An increase in tumor volume size that exceeds >1500 mm³, or 20 mm in one dimension, or tumor becomes ulcerated or necrotic.
2. A decrease in body weight ≥20% from maximum recorded weight.
3. Any signs of pain or distress (i.e., consistent hunched posture, rough coat, squinted eyes, slowed gait).
4. Tumors that compromise mobility or ability to eat or drink.
5. BCS score ≤2.

TABLE 24

Study arms for CDX efficacy studies of exemplary $^{225}$Ac-labeled Nectin-4 binding compounds vs. EV

| Group | PDX model | Treatment | Administered activity dose (nCi/mouse) | Mass Dose | Route | Schedule | Monitoring |
|---|---|---|---|---|---|---|---|
| 1 (n = 8) | HT-1376-Target expressing | Vehicle | n/a | n/a | IV | Single Dose | 8-weeks |
| 2 (n = 8) | HT-1376-Target expressing | $^{225}$Ac-C251 | 1000 | 0.5 µg/kg | IV | Single Dose | 8-weeks |
| 3 (n = 8) | HT-1376-Target expressing | $^{225}$Ac-C251 | 2000 | 1 µg/kg | IV | Single Dose | 8-weeks |

TABLE 24-continued

Study arms for CDX efficacy studies of exemplary $^{225}$Ac-labeled Nectin-4 binding compounds vs. EV

| Group | PDX model | Treatment | Administered activity dose (nCi/mouse) | Mass Dose | Route | Schedule | Monitoring |
|---|---|---|---|---|---|---|---|
| 4 (n = 8) | HT-1376-Target expressing | enfortumab vedotin | — | 3 mg/kg | IV | Multi Dose (QWx3) | 8-weeks |

Figure 19A:
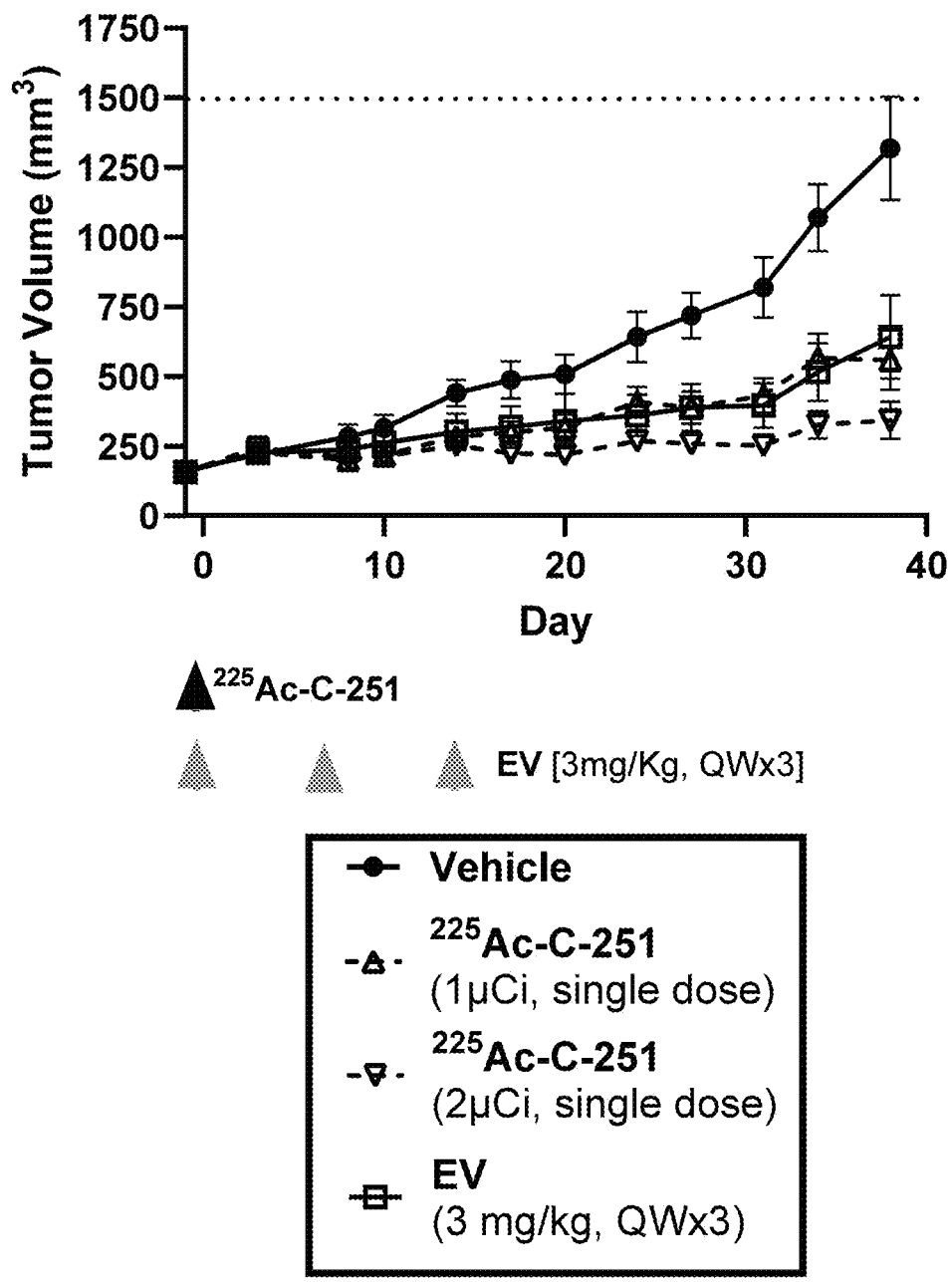
FIGS. 19A and 19B are graphs showing in vivo tumor volume (mm$^3$.
Figure 19B:
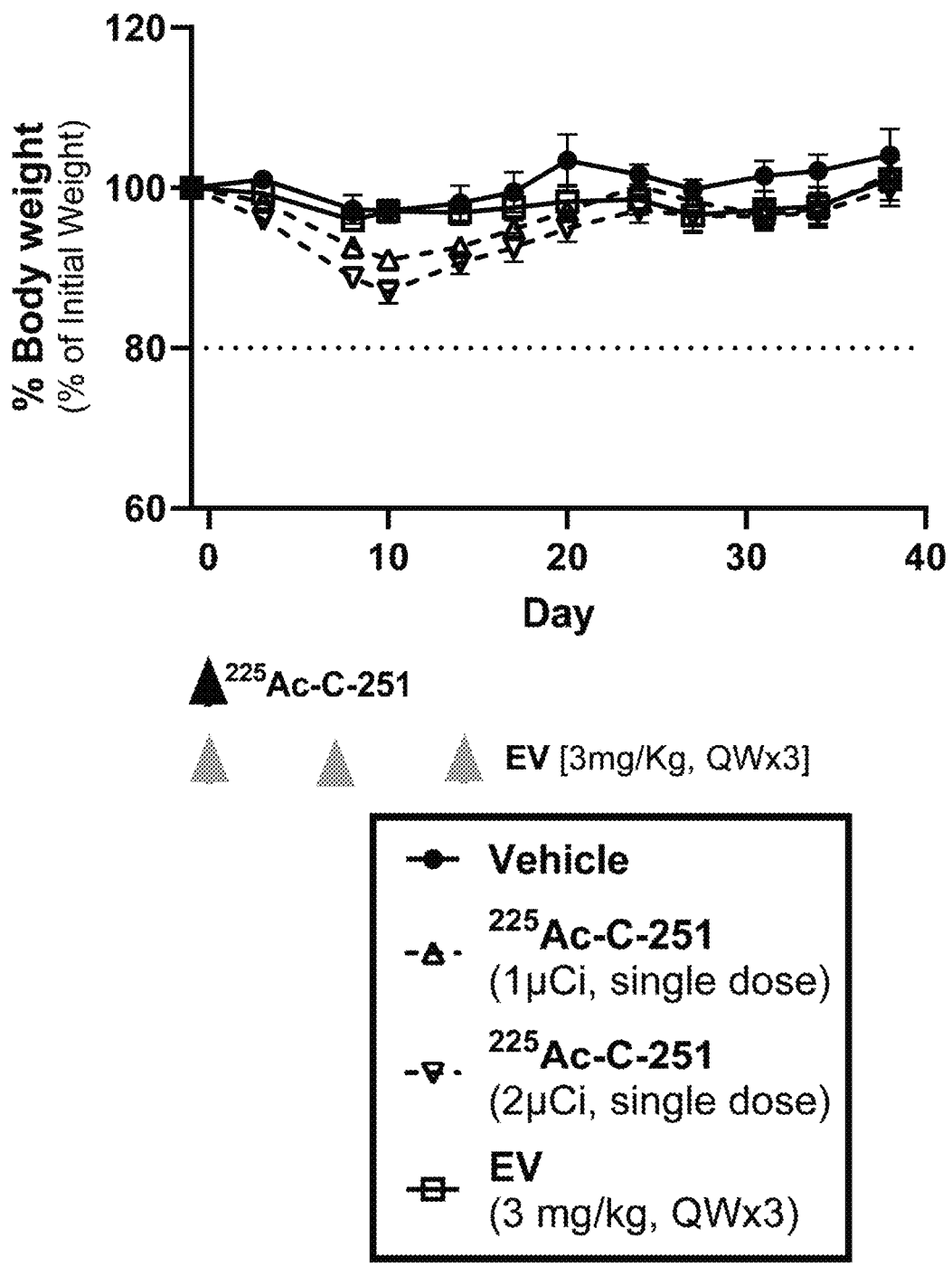

FIGS. 19A and 19B shows the tumor volume (mm³; FIG. 19A) and body weight (% of initial weight; FIG. 19B) measurements in the mice administered (1) a non-binding, non-radiolabeled control (vehicle) (solid circles); (2) an $^{225}$Ac-labeled exemplary Nectin-4-targeting radionuclide conjugate ($^{221}$Ac-C251) at 0.5 sg/kg; 1,000 nCi; single dose (open triangles); (3) an $^{225}$Ac-labeled exemplary Nectin-4-targeting radionuclide conjugate ($^{225}$Ac-C251) at 1 µg/kg; 2,000 nCi; single dose (inverted open triangles); and (4) an anti-Nectin-4 ADC control (enfortumab vedotin (EV)) at 3 mg/kg; three doses (open squares). In FIG. 19A, the dotted line at 1,500 mm³ marks the maximum tumor growth threshold for the pre-defined humane endpoint of experimental mice. In FIG. 19B, the dotted line at 80% of initial body weight marks the body weight decrease threshold for the pre-defined humane endpoint of experimental mice.

Some reduction in tumor volume was observed in Group 2 and Group 3 (each administered the exemplary Nectin-4 binding miniprotein radionuclide conjugate, $^{225}$Ac-C251, at 1000 nCi and 2000 nCi, respectively) and Group 4 (administered EV) (FIG. 19A). As shown in FIG. 19A, tumor volume growth in Groups 2-4 was reduced compared to Group 1, demonstrating efficacy of tumor treatment by Nectin-4 binding miniprotein test article radionuclides.

Example 30: In Vivo Efficacy Study Involving Actinium-Labeled Miniproteins in Patient-Derived Xenograft Model This Example shows in vivo efficacy of an exemplary Nectin-4-binding tumor-targeting compound, evaluated in a patient-derived xenograft ("PDX") model.

Animals: Female NMRI nude mice (6-8 weeks of age) were purchased from Janvier and housed according to IACUC guidelines with ad libitum feeding of altromin 1324 pellets (Brogaarden). In vivo efficacy study experiments were performed in tumor bearing NMRI nude mice. Patient derived xenograft (PDX) models for study dosing were generated through serial tumor transplantation (×2) in mice post recovery from cryo-storage.

Tumor recover and transplantation: Recipient animals were anesthetized (Isoflurane gas) and placed in a prone position on a sterile surface. Initial tumors were recovered from liquid nitrogen storage ($LN_2$) and inoculated subcutaneously at the right flank. The surgical site was sterilized, and an incision cut in the skin. A tumor piece was inserted, and the incision will be closed using sutures. The animals were returned to their cages and monitored until fully recovered from the anesthesia. Tumor growth was monitored using calipers and volumes calculated using the following calculation–Tumor volume=0.52(length×width²). When tumors reached approx. 750-1000 mm³, donor mice were euthanized via cervical dislocation, the skin surrounding the tumor site sterilized and tumor resected. The tumor was dissected into smaller sections for serial transplantation into recipient mice (×5). Mice used in study dosing (×30 mice) were inoculated with PDX tumor pieces from 2 donor mice, as described previously. Tumors were monitored for approximately 28 days prior to group stratification and study initiation dates. Mice (×20) with tumor volumes between 100 mm³ and 400 mm³ were selected for study inclusion and randomized to treatment arms.

Animal grouping and treatment: On study dosing day, $^{225}$Ac-labeled C251 was prepared as described at a specific activity of approx. 1 μCi/μg, with activity measurements for the labeled product made at secular equilibrium on a dose calibrator. Dose measurements for a sample injected dose were measured and confirmed on a gamma counter and corrected for decay. EV doses were calculated based on mouse weights and liquid concentration of prepared material. Indicated doses of vehicle, EV or radiolabeled C251 were prepared corresponding to the indicated administered dose levels per group. Doses were administered via tail vein injection while restrained and awake.

Animal monitoring: Tumor volume (caliper measurement) and body weight measurements for enrolled mice were performed twice a week for an initial planned monitoring period of 8 weeks. More frequent gross observations of mice were performed.

Humane endpoints: Mice remained on study, until they reached the end of the 8-week monitoring period or a number of pre-defined humane endpoints, including:
1. An increase in tumor volume size that exceeds >1500 mm³, or 20 mm in one dimension, or tumor becomes ulcerated or necrotic.
2. A decrease in body weight ≥20% from maximum recorded weight.
3. Any signs of pain or distress (i.e., consistent hunched posture, rough coat, squinted eyes, slowed gait).
4. Tumors that compromise mobility or ability to eat or drink.
5. BCS score ≤2.

TABLE 25

Study arms for PDX efficacy studies of exemplary $^{225}$Ac-labeled Nectin-4 binding compounds vs. EV

| Group | Treatment | Administered activity dose (nCi/mouse) | Mass Dose | Route | Schedule | Monitoring |
|---|---|---|---|---|---|---|
| 1 (n = 5) | Vehicle | n/a | n/a | IV | Single Dose | 8-weeks |
| 2 (n = 5) | $^{225}$Ac-C251 | 2000 | 1 μg/kg | IV | Single Dose | 8-weeks |
| 3 (n = 5) | enfortumab vedotin | — | 3 mg/kg | IV | Multi Dose (QWx3) | 8-weeks |

Figure 20A:
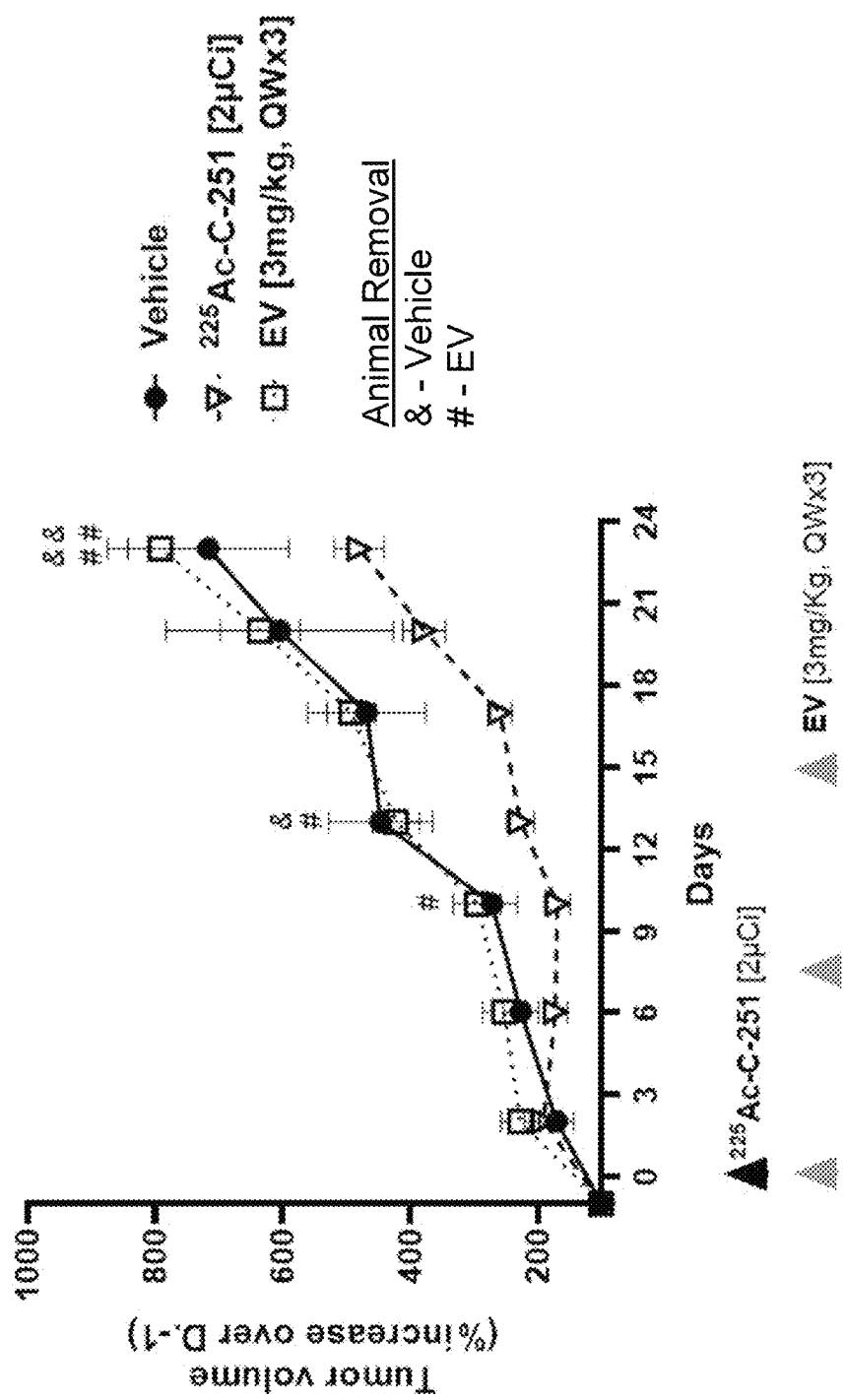
FIGS. 20A and 20B are graphs showing in vivo tumor volume (mm$^3$.
Figure 20B:
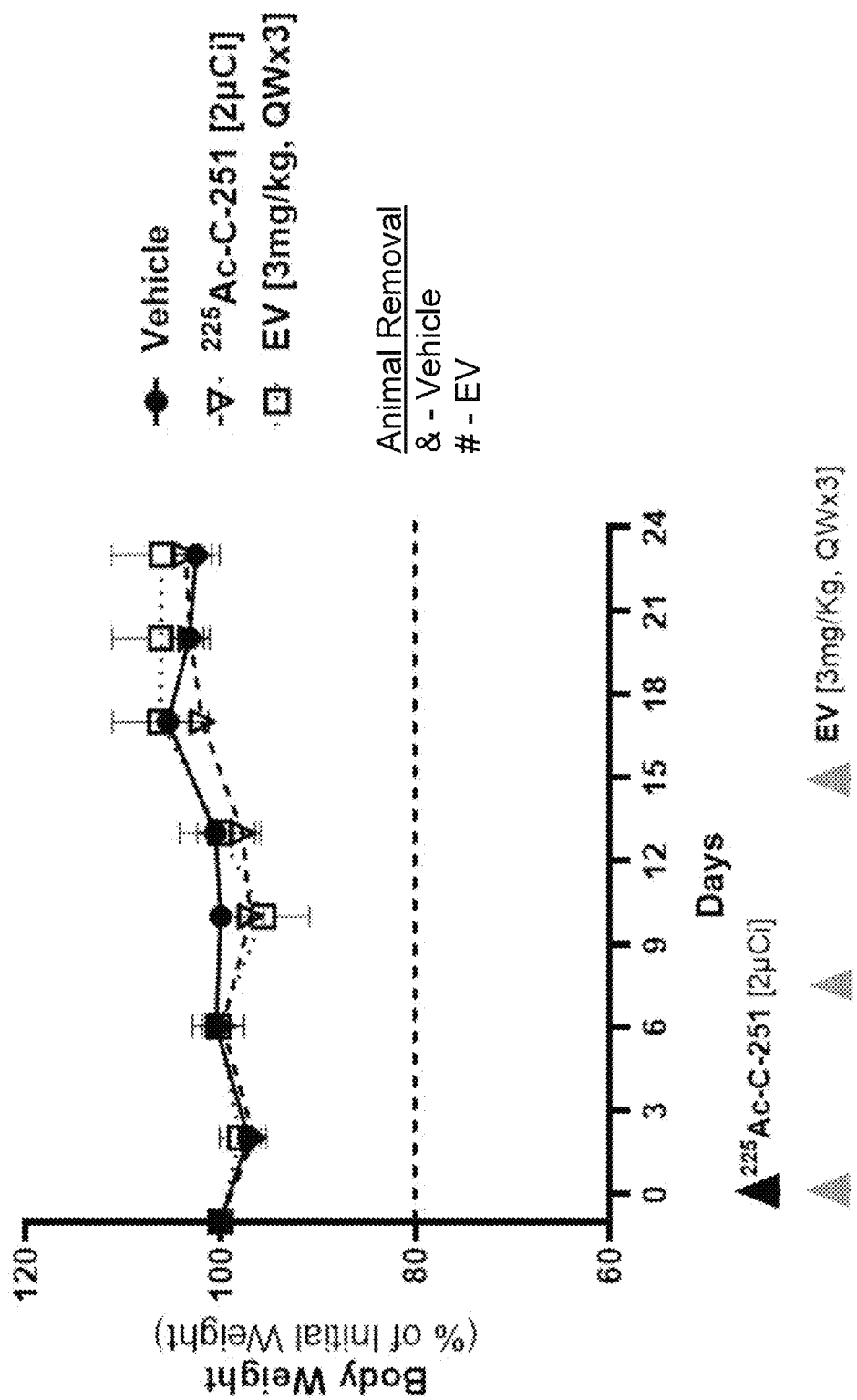

FIGS. 20A and 20B are graphs showing in vivo tumor volume (mm³; FIG. 20A) and body weight (% of initial weight; FIG. 20B) measurements in an exemplary patient-derived mouse xenograft model, treated at Day 0 with: (i) vehicle (circles); (ii) an $^{225}$Ac-labeled exemplary Nectin-4-targeting radionuclide conjugate ($^{225}$Ac-C251; 1 mg; 2,000 nCi; single dose; inverted triangles), or (iii) an anti-Nectin-4 ADC control (enfortumab vedotin (EV); 3 mg/kg; three doses; squares). In FIG. 20A, animal removal from the study is identified with symbols at relevant timepoints ("&" for the vehicle treatment group and "#" for the EV treatment group), with each symbol representing one animal being removed. In FIG. 20B, the dotted line at 80% of initial body weight marks the body weight decrease threshold for the pre-defined humane endpoint of experimental mice.

As shown in FIG. 20A, tumor volume growth of Group 2 (radionuclide-labeled compound) was reduced compared to Groups 1 and 3 (vehicle and EV, respectively), demonstrating the efficacy of the exemplary radionucleotide-labeled Nectin-4-binding miniprotein in tumor treatment.

Example 31: Evaluation of Off-Target Binding of Exemplary Nectin-4-Targeting Miniproteins This Example describes the evaluation of off-target binding of six exemplary Nectin-4-binding miniproteins relative to other human proteins.

To evaluate potential off-target binding, six biotin-labeled molecules were tested in a cell microarray platform having 6,416 different human proteins spanning diverse functions and subcellular locations. All exemplary miniproteins evaluated (C190, C197, C208, C247, C253, and C259) were found to have low-background binding to un-transfected HEK293 cells and were deemed suitable for this assay.

Initially, two pools of compounds were tested. Pool #1 consisted of C190. C197, and C208, and pool #2 consisted of C247, C253, and C259 at 2 μg/mL for each molecule. To perform this assay. HEK293 cells were plated on a dish and localized spots of cells were transiently over-expressed with a single cDNA encoding for GFP and one of the 6,416 targets. Included in this library were multiple clones for the Nectin family members, including plasma membrane, non-tethered secreted, and tethered secreted forms of Nectin-1, 2, 3, and 4. Secreted protein targets were tethered to the plasma membrane to aid in detection. The molecule pools were incubated on the fixed, over-expressing cell microarrays (n=2 per protein), and binding was visualized using Alexa Fluor 647 streptavidin fluorescence. All transfection efficiencies exceeded minimum thresholds for the microarray expression targets. In total. 18 library preliminary interactions (including some target clone duplicates) were identified, including Nectin-4, but no other Nectin family members were identified.

To specifically confirm these preliminary interactions, vectors encoding the 18 interaction proteins were spotted in duplicates, and each of the 6 molecules were tested individually (n=2) at 2 μg/mL against these targets as described above. All positive control interactions were strong and passed quality control. The only specific interactions observed (medium to strong intensity) confirmed on-target Nectin-4 binding in two different clones (membrane-bound and tethered secreted form) for each of the 6 test molecules. These interactions with the primary target occurred after fixation and in the absence of fixation. The remaining 16 preliminary interactions identified with the pooled molecules (PLPP3, GLP2R, SLC22A23, SPNS2, IGFBP4, IGFBP3, IGF2, EDN2, IGF1, PAPPA, MFSD2B, EGF. TRPV5, TRPV4, CXCL12, IGFBP5) were all found to be weak to very weak or non-specific interactions for each of the test molecules, with comparable intensity as the PBS (secondary antibody only) control. Thus no significant interactions were identified for any test molecules outside of Nectin-4, indicating high specificity for the primary target (data not shown).

Example 32: Allometric Scaling of Preclinical Dosimetry Accurately Predicts Human Absorbed Dose to Major Organs This Example describes the evaluation of the utility of an optimized allometric scaling method in predicting the therapeutic index for exemplary miniprotein binders to Nectin-4.

Among the many allometric scaling methods that account for differences in surface area, organ mass, and physiology between species, the selected method was based on the molecular characteristics of exemplary Nectin-4-binding miniproteins.

C109 and C251 have miniproteins that are structurally similar. They have each been observed to also rapidly clear, and be efficacious with a single administration in a preclinical model. Both Nectin-4-binding miniproteins exhibited selectivity. They bound to HT-1376 cells and had no binding to the isogenic HT-1376 Nectin-4 KO cells. They also displayed no off-target binding, as determined by a cell microarray platform having 6,416 different human proteins spanning diverse functions and subcellular locations. Both displayed clearance at the glomerular filtration rate (GFR) and target and dose-dependent efficacy. Due its lower uptake in the in vitro kidney assay and higher affinity for Nectin-4, C251 was predicted to deliver a lower absorbed dose to kidneys in humans.

Figure 24A:
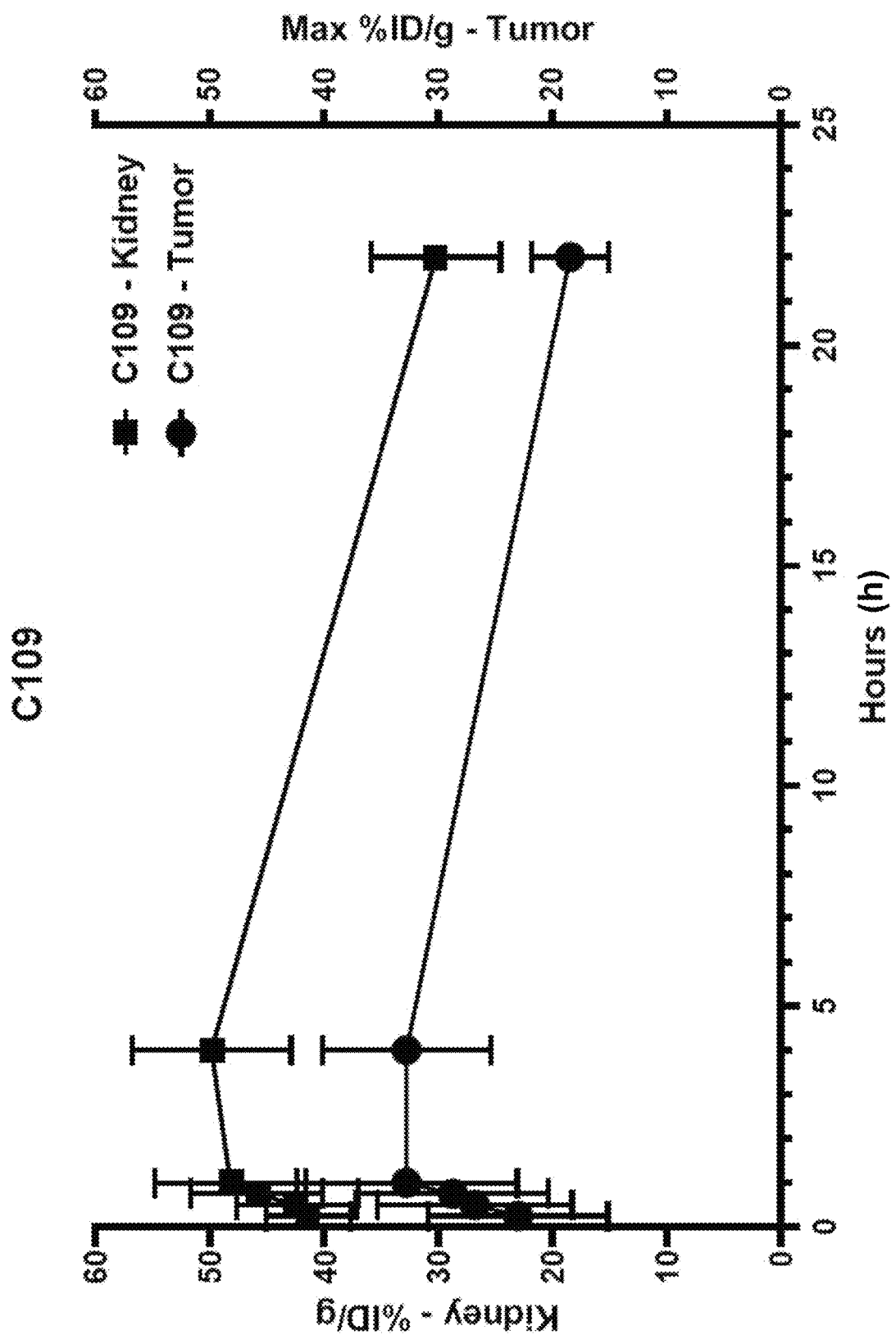
FIGS. 24A and 24B are graphs showing in vivo retention of $^{111}$In-labeled exemplary Nectin-4-targeting miniprotein conjugates $^{111}$In-C109 (FIG. 24A) and $^{111}$In-C251 (FIG. 24B) in kidney (squares) and tumor (circles) in an exemplary mouse isogenic xenograft model observed from 10 min through 22 h post-injection.
Figure 24B:
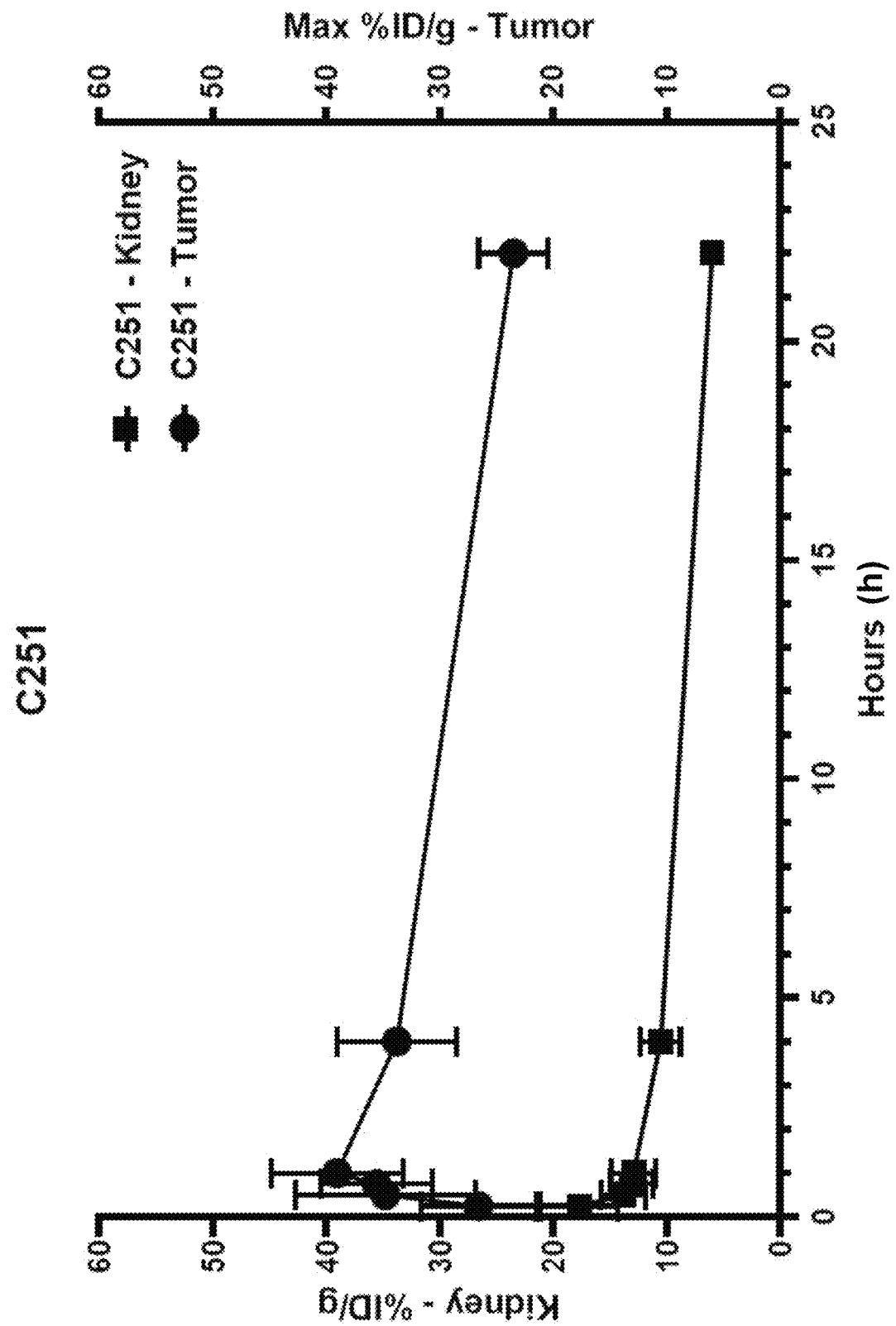

Predicted doses for $^{225}$Ac were derived from $^{111}$In (mice) by extrapolating the initial results to account for the longer half-life of $^{225}$Ac and the increased relative biologic effectiveness. Isogenic xenograft models were generated using HT-1376 (human urinary bladder carcinoma) cells endogenously or exogenously expressing Nectin-4. Intravenous injection of $^{111}$In-C109 or $^{111}$In-C251 was followed by SPECT/CT imaging from 10 min through 22 h for whole-body image reconstruction and generation of time-activity curves for various ROIs as described above. Preclinical biodistribution for C109 (FIG. 24A) and C251 (FIG. 24B) showed similar uptake and retention in tumor tissue, with a marked decrease in renal uptake with C251.

To calculate predicted absorbed doses to kidneys in humans, a mass-to-organ weight scaling method was applied to preclinical $^{111}$In-C109 and $^{111}$In-C251 SPECT imaging data using the following equation:

$$\text{Human organ exposure} = \text{Mouse organ exposure} \times \frac{\left(\frac{\text{organ mass}}{\text{whole body mass}}\right)_{\text{human}}}{\left(\frac{\text{organ mass}}{\text{whole body mass}}\right)_{\text{mouse}}},$$

and corrected for (i) the $^{225}$Ac activity constant or (ii) $^{177}$Lu for direct comparison with human dosimetry.

TABLE 26 shows the comparison of estimated absorbed doses in mouse kidney for C109 and C251. Scaling of time-activity curves in mice predicted an approximately 85% reduction in the total absorbed dose to the kidney with $^{225}$Ac-C251 versus $^{225}$Ac-C109. The absorbed doses in mouse kidney for $^{225}$Ac-C251 versus $^{225}$Ac-C109 were 0.16 RBE$_5$Gy/MBq and 1.06 RBE$_5$Gy/MBq, respectively. The estimated absorbed dose to kidney was significantly lower for C251.

TABLE 26

Comparison of estimated absorbed doses of exemplary Nectin-4-binding miniproteins in mouse kidney.

| | C109 Characteristics | | C251 Characteristics | |
| --- | --- | --- | --- | --- |
| Location | Absorbed Dose per MBq (RBE5 Gy/MBq) | Estimated Absorbed Dose after 4 to 6 Administrations of 7.4 Gy (RBE5 Gy) | Absorbed Dose per MBq (RBE5 Gy/MBq) | Estimated Absorbed Dose after 4 to 6 Administrations of 7.4 Gy (RBE5 Gy) |
| Kidney | 1.06 | 31.38-47.06 | 0.16 | 4.74-7.10 |

Next, a small group of patients with metastatic cancers underwent SPECT/CT for dosimetry with $^{177}$Lu-C109 or $^{177}$Lu-C251. SPECT/CTs were obtained 3, 24, and 48 h post-injection and reconstructed using ordered subset MLEM with CT-based attenuation correction (AC), effective scatter correction using CT-based AC, and resolution recovery. Kidney dosimetry was performed using OLINDA, EXM v1. PET/CT scanning with $^{68}$Ga-C109 or $^{68}$Ga-C251 was used for imaging. One patient received $^{68}$Ga-C109 and $^{177}$Lu-C109 as well as $^{68}$Ga-C251 and $^{177}$Lu-C251 approximately two months apart.

Intrapatient comparison confirmed tumor uptake of both $^{68}$Ga-C109 and $^{68}$Ga-C251. Additionally, C251-uptake consistently appeared increased in representative lesions as assessed by SUV$_{max}$ (TABLE 27).

TABLE 27

Representative lesions that could be identified on both C109 and C251 images from the same patient dosed two months apart were selected for evaluation of SUV$_{max}$ at the 1- and 3-h timepoints.

| | Lesion | | | |
| --- | --- | --- | --- | --- |
| | C109 SUV$_{max}$ | | C251 SUV$_{max}$ | |
| Time (h) | 1 h | 3 h | 1 h | 3 h |
| Bony (right scapula) | 10.83 | 11.57 | 27.74 | 27.75 |
| Lung lesion | 7.78 | 12.61 | 10.34 | 16.22 |
| Liver lesion | 15.06 | 21.41 | 38.47 | 49.32 |
| Lymph node (left para-aortic) | 24.73 | 31.49 | 28.39 | 29.44 |

TABLE 28 shows the comparison of absorbed dose to the kidneys of $^{177}$Lu-labeled exemplary Nectin-4 miniproteins based on preclinical models and human dosimetry in a patient receiving both C109 and C251. Taken together, the data shown in TABLES 26 and 28 demonstrate a clear differentiation in the predicted absorbed dose to the kidneys between C109 and C251 in both mice and humans. The relative reduction in absorbed dose between C109 and C251 in both mice and humans was considered consistent.

TABLE 28

Comparison of absorbed dose to the kidneys with C109 and C251 based on preclinical models and human dosimetry.

| Compound | Absorbed Dose per GBq of $^{177}$Lu (Gy/GBq) | Relative Reduction |
|---|---|---|
| Mouse | | |
| C109 | 0.86 | 74% |
| C251 | 0.22 | |
| Human | | |
| C109 | 1.41 | 80% |
| C251 | 0.28 | |

Based on this translational evaluation, differences in preclinical scaled dosimetry for radiolabeled miniproteins appear useful for comparing compounds and predicting therapeutic indices in patients. Overall, a clinically meaningful reduction in absorbed dose to kidneys was predicted over a full course of treatment with C251. Further studies with larger patient cohorts are essential to validate dosimetry findings and optimize treatment protocols to balance efficacy and safety.

Example 33: In Vivo, First in-Human Administration of Exemplary Nectin-4 Radionuclide Conjugate in Nectin-4-Expressing Tumors Including Metastatic Urothelial Carcinoma This Example describes a first-in-human biodistribution and dosimetry study for exemplary Nectin-4-binding miniprotein radionuclide C251 to evaluate its potential for the treatment of patients with Nectin-4 expressing tumors.

This assessment was conducted in 20 patients. The patients' diagnoses were metastatic urothelial cancer (mUC) (n=9), metastatic breast cancer (mBC) (n=3), cervical carcinoma (n=3), colorectal cancer (CRC) (n=2) and non-small cell lung cancer (NSCLC) (n=3). Patients received a single bolus injection of about 5 mCi of $^{68}$Ga-C251 (n=20) and images were acquired at 1 h, 2 h, and 3 h via PET-CT. Patients who were candidates for kidney dosimetry received about 10 mCi of $^{177}$Lu-C251 (n=9; 2 patients received more than mCi but data are scaled to 10 mCi) and were imaged at 3 h, 24 h, and 48 h via SPECT-CT. A total of 15 patients were evaluable for biodistribution and tumor uptake analysis and 8 patients were evaluable for kidney dosimetry. Tumor uptake was assessed using standardized uptake value (SUV) and dosimetry was analyzed using OLINDA.

There were no adverse events attributable to the administration of $^{68}$Ga-C251 or $^{177}$Lu-C251. Biodistribution analyses showed a favorable profile with no appreciable uptake of C251 in skin and transient uptake in salivary glands not expected to result in clinically meaningful exposure. As expected, the kidneys were identified as the potentially dose-limiting organ. Significant tumor uptake was observed across primary and metastatic lesions.

Where available, longitudinal imaging showed retention of tumor uptake at 3 h, 24 h, and 48 h coupled with rapid washout in normal tissues, such as lacrimal glands and salivary glands, and the gastrointestinal tract.

These data on C251 support desirable biodistribution and kidney dosimetry with transient normal tissue uptake. These data also provide evidence that Nectin-4-targeted miniprotein radiopharmaceuticals demonstrate substantial tumor uptake across several solid tumor types.

INCORPORATION BY REFERENCE

All publications and patents cited throughout the text of this specification (including all patents, patent applications, scientific publications, manufacturer's specifications, instructions, etc.), whether supra or infra, are hereby incorporated by reference in their entirety for all purposes. To the extent the material incorporated by reference contradicts or is inconsistent with this specification, the specification will supersede any such material.

EQUIVALENTS

The disclosure may be embodied in other specific forms without departing from the spirit or essential characteristics thereof. The foregoing embodiments are therefore to be considered in all respects illustrative rather than limiting the disclosure described herein. Furthermore, the headings and sections throughout the present disclosure are non-not meant to be limiting in any way. Scope of the disclosure is thus indicated by the appended claims rather than by the foregoing description, and all changes that come within the meaning and range of equivalency of the claims are intended to be embraced therein.

What is claimed is:

1. A composition, comprising a Nectin-4-binding miniprotein with an amino acid sequence comprising at least 44 amino acids, wherein the amino acids comprise (i) a cysteine at each of four positions corresponding to 1, 20, 34, and 44 of SEQ ID NO: 195; (ii) TALX12RLR at positions corresponding to positions 9-15 of SEQ ID NO: 195, wherein X12 is A, Kme, Kme2, Kme3, or Kipr; (iii) QAX26, at positions corresponding to positions 24, 25, and 26 of SEQ ID NO: 195, wherein X26 is Kme3, Kme2, Kme, or Kipr and (iv) QYL at positions corresponding to positions 28, 29, and 30 of SEQ ID NO: 195.

2. The composition of claim 1, wherein the miniprotein binds to Nectin-4 with an affinity of stronger than 10 nM in a cell-based assay.

3. The composition of claim 1, wherein the C-terminus of the miniprotein has an —OH or an —NH2.

4. The composition of claim 1, wherein a binding affinity for Nectin-4 is stronger than 100 nM.

5. The composition of claim 1, wherein an inhibition constant is no greater than 100 nM.

6. The composition of claim 1, further comprising a modified N-terminus.

7. The composition of claim 6, wherein the modified N-terminus comprises one or more of an NH2-, Acetyl-, PEGn-, wherein n=O-10, DOTA-, or Biotin-.

8. The composition of claim 1, further comprising one or more of a linker, chelator, and radionuclide.

9. The composition of claim 8, wherein, when present, the linker is attached to the N-terminus of the miniprotein.

10. The composition of claim 8, wherein, when present, the linker is attached to the N-terminus of the miniprotein and the linker comprises a polyethylene glycol (PEG) linker selected from PEG4, PEG2, PEG, PEG6, PEG8, PEG12, PEG24, PEG36, lys(MPB)-PEG4, an ester linker, an amide linker, a maleimide linker, a succinimidyl-4-(N-maleimidomethyl) cyclohexane-1-carboxylate (SMCC) linker, a propanoic acid linker, a dTyr-Gly-Phe (yGF) linker, a caproleic acid linker, and (Gly)n-(gGlu)n- or (PEG)n, wherein n is from 1 to 36, (Gly)1-10, or any fragment or combination via covalent bond thereof.

11. The composition of claim 8, wherein, when present, the chelator is attached to either the miniprotein or the linker.

12. The composition of claim 8, wherein, when present, the chelator comprises DOTA, Crown, NOPO, Macropa, lead specific chelator (PSC), N-succinimidyl 3-(tri-n-butyl-stannyl)benzoate (BuSTB), or N-succinimidyl 3-trimethyl-stannylbenzoate (MeSTB).

13. The composition of claim 8, wherein, when present, the radionuclide is attached to the chelator.

14. The composition of claim 8, wherein, when present, the radionuclide comprises Ac-225, Cu-64, Ga-68, Lu-177, Pb-212, In-111, Cu-67, La-132, La-135, Ce-134, F-18, I-131, I-124, Pb-203, Bi-123, Sm-153, Ra-225, or At-211.

15. A composition, comprising a polypeptide having an amino acid sequence comprising SEQ ID NO: 195.

16. The composition of claim 15, further comprising a linker comprising PEG4 and a chelator comprising DOTA.

17. A conjugate comprising a polypeptide (M) that specifically binds to Nectin-4 and a chelator (C) conjugated to the N-terminus of (M) through a linker (L), wherein the polypeptide has an amino acid sequence comprising:
   (i) at least 44 amino acids, wherein the amino acids comprise (a) a cysteine at each of four positions corresponding to 1, 20, 34, and 44 of SEQ ID NO: 195; (b) TALX12RLR at positions corresponding to positions 9-15 of SEQ ID NO: 195, wherein X12 is A, Kme, Kme2, Kme3, or Kipr; (c) QAX26 at positions corresponding to positions 24, 25, and 26 of SEQ ID NO: 195, wherein X26 is Kme3, Kme2, Kme, or Kipr; and (d) QYL at positions corresponding to positions 28, 29, and 30 of SEQ ID NO: 195; or
   (ii) SEQ ID NO: 195.

18. The conjugate of claim 17, wherein (C) comprises DOTA and (L) comprises PEG-4.

19. The conjugate of claim 18, further comprising a radionuclide (R) chelated to (C).

20. The conjugate of claim 17, wherein M is a miniprotein that has an amino acid sequence comprising SEQ ID NO: 195.

21. The conjugate of claim 19, wherein R comprises Ac-225, Cu-64, Ga-68, Lu-177, Pb-212, In-111, Cu-67, La-132, La-135, Ce-134, F-18, I-131, I-124, Pb-203, Th-232, Bi-123, Sm-153, Ra-225, or At-211.

22. The conjugate of claim 21, wherein R is Ac-225 or Cu-64.

23. A method, comprising contacting at least one population of cells with the composition of claim 1.

24. The method of claim 23, wherein the at least one population of cells includes kidney cells or cancer cells.

25. The method of claim 24, wherein after the contacting, the composition is taken up by the kidney cells in a lower amount than a composition comprising an amino acid sequence that comprises (i) a cysteine at each of four positions corresponding to 1, 20, 34, and 44 of SEQ ID NO: 195; (ii) SEQ ID NO: 169 at positions corresponding to positions 9-15 of SEQ ID NO: 195; (iii) QAK at positions corresponding to positions 24, 25, and 26 of SEQ ID NO: 195; and (iv) QYL at positions corresponding to positions 28, 29, and 30 of SEQ ID NO: 195.

26. A method of treating a cancer that expresses Nectin-4, the method comprising administering to a subject in need thereof, a composition comprising a miniprotein that has an amino acid sequence comprising (i) at least 44 amino acids, wherein the amino acids comprise (a) a cysteine at each of four positions corresponding to 1, 20, 34, and 44 of SEQ ID NO: 195; (b) TALX12RLR at positions corresponding to positions 9-15 of SEQ ID NO: 195, wherein X12 is A, Kme, Kme2, Kme3, or Kipr; (c) QAX26 at positions corresponding to positions 24, 25, and 26 of SEQ ID NO: 195, wherein X26 is Kme3, Kme2, Kme, or Kipr; and (d) QYL at positions corresponding to positions 28, 29, and 30 of SEQ ID NO: 195; or (ii) SEQ ID NO: 195.

27. The method of claim 26, wherein the subject is diagnosed as having cancer.

28. The method of claim 26, wherein the cancer is metastatic.

29. The method of claim 26, wherein the cancer comprises urothelial, breast, cervical, colorectal, or non-small cell lung cancer.

30. The method of claim 29, wherein the cancer is metastatic.

* * * * *

SEQUENCE LISTING

```
Sequence total quantity: 248
SEQ ID NO: 1            moltype = AA  length = 44
FEATURE                 Location/Qualifiers
source                  1..44
                        mol_type = protein
                        organism = synthetic construct
SEQUENCE: 1
CEDDGEYFAG LQRLYGGDIC YYIKLKFPKV PDLCIKEILD KLGC            44

SEQ ID NO: 2            moltype = AA  length = 44
FEATURE                 Location/Qualifiers
source                  1..44
                        mol_type = protein
                        organism = synthetic construct
SEQUENCE: 2
CEDDEEFFAD LKRLRGGDIC YYIKLKFDKV PDLCIKEILD KLGC            44

SEQ ID NO: 3            moltype = AA  length = 44
FEATURE                 Location/Qualifiers
source                  1..44
                        mol_type = protein
```

```
                                 organism = synthetic construct
SEQUENCE: 3
CEYDEEFFAG LKRLRGGDIC YYIKKKFDKV PDLCIKEILD KLGC                           44

SEQ ID NO: 4              moltype = AA   length = 44
FEATURE                   Location/Qualifiers
source                    1..44
                          mol_type = protein
                          organism = synthetic construct
SEQUENCE: 4
CEDDFQFFAD LKRLRGGDIC YYIRLKFDKV PDLCIKEILD KLGC                           44

SEQ ID NO: 5              moltype = AA   length = 44
FEATURE                   Location/Qualifiers
source                    1..44
                          mol_type = protein
                          organism = synthetic construct
SEQUENCE: 5
CEYDEEFFAG LKRLRGGDIC YYIKKKFDKV PDLCIEEILD KLGC                           44

SEQ ID NO: 6              moltype = AA   length = 44
FEATURE                   Location/Qualifiers
source                    1..44
                          mol_type = protein
                          organism = synthetic construct
SEQUENCE: 6
CEYDEEFFNG LKRLRGGDIC YYIKKKFDKV PDLCIEEILD KLGC                           44

SEQ ID NO: 7              moltype = AA   length = 44
FEATURE                   Location/Qualifiers
source                    1..44
                          mol_type = protein
                          organism = synthetic construct
SEQUENCE: 7
CEYDEEFFAG LKRLRRGDIC YYIKKKFDKV PDLCIEEILD KLGC                           44

SEQ ID NO: 8              moltype = AA   length = 44
FEATURE                   Location/Qualifiers
source                    1..44
                          mol_type = protein
                          organism = synthetic construct
SEQUENCE: 8
CEYDEEFFNG LKRLRRGDIC YYIKKKFDKV PDLCIEEILD KLGC                           44

SEQ ID NO: 9              moltype = AA   length = 44
FEATURE                   Location/Qualifiers
source                    1..44
                          mol_type = protein
                          organism = synthetic construct
SEQUENCE: 9
CEYDEEFFAG LKRLRGGDIC YYIKKKFKKV PDLCIEEILD KLGC                           44

SEQ ID NO: 10             moltype = AA   length = 44
FEATURE                   Location/Qualifiers
source                    1..44
                          mol_type = protein
                          organism = synthetic construct
SEQUENCE: 10
CEYDEEFFNG LKRLRGGDIC YYIKKKFKKV PDLCIEEILD KLGC                           44

SEQ ID NO: 11             moltype = AA   length = 44
FEATURE                   Location/Qualifiers
source                    1..44
                          mol_type = protein
                          organism = synthetic construct
SEQUENCE: 11
CEYDEEFFNG LHRLRRGDIC YYIKKKFKKV PDLCIEEILD KLGC                           44

SEQ ID NO: 12             moltype = AA   length = 44
FEATURE                   Location/Qualifiers
source                    1..44
                          mol_type = protein
                          organism = synthetic construct
SEQUENCE: 12
CEYDEEFFAG LKRLRGGDIC YYIKKKFPKV PDLCIEEILD KLGC                           44

SEQ ID NO: 13             moltype = AA   length = 44
FEATURE                   Location/Qualifiers
source                    1..44
```

```
                                mol_type = protein
                                organism = synthetic construct
SEQUENCE: 13
CEYDEEFFAG LHRLRGGDIC YYIKKKFDKV PDLCIEEILD KLGC                         44

SEQ ID NO: 14           moltype = AA   length = 44
FEATURE                 Location/Qualifiers
source                  1..44
                                mol_type = protein
                                organism = synthetic construct
SEQUENCE: 14
CEYDEEFFAG LHRLRGGDIC YYIKKKFPKV PDLCIEEILD KLGC                         44

SEQ ID NO: 15           moltype = AA   length = 44
FEATURE                 Location/Qualifiers
source                  1..44
                                mol_type = protein
                                organism = synthetic construct
SEQUENCE: 15
CEYDEEFFAG LKRLRGTDIC YYIKKKFDKV PDLCIEEILD KLGC                         44

SEQ ID NO: 16           moltype = AA   length = 44
FEATURE                 Location/Qualifiers
source                  1..44
                                mol_type = protein
                                organism = synthetic construct
SEQUENCE: 16
CEYDEEFFAG LHRLRGTDIC YYIKKKFDKV PDLCIEEILD KLGC                         44

SEQ ID NO: 17           moltype = AA   length = 44
FEATURE                 Location/Qualifiers
source                  1..44
                                mol_type = protein
                                organism = synthetic construct
SEQUENCE: 17
CEYDEEFFAG LHRLRGTDIC YYIKKKFPKV PDLCIEEILD KLGC                         44

SEQ ID NO: 18           moltype = AA   length = 44
FEATURE                 Location/Qualifiers
source                  1..44
                                mol_type = protein
                                organism = synthetic construct
SEQUENCE: 18
CEYDEEFFKG LKRLRGGDIC YYIKKKFKKV PDLCIEEILD KLGC                         44

SEQ ID NO: 19           moltype = AA   length = 44
FEATURE                 Location/Qualifiers
source                  1..44
                                mol_type = protein
                                organism = synthetic construct
SEQUENCE: 19
CEYDEEFFEG LKRLRGGDIC YYIKKKFKKV PDLCIEEILD KLGC                         44

SEQ ID NO: 20           moltype = AA   length = 44
FEATURE                 Location/Qualifiers
source                  1..44
                                mol_type = protein
                                organism = synthetic construct
SEQUENCE: 20
CEYDEEFFDG LKRLRGGDIC YYIKKKFKKV PDLCIEEILD KLGC                         44

SEQ ID NO: 21           moltype = AA   length = 44
FEATURE                 Location/Qualifiers
source                  1..44
                                mol_type = protein
                                organism = synthetic construct
SEQUENCE: 21
CEYDEEFFSG LKRLRGGDIC YYIKKKFKKV PDLCIEEILD KLGC                         44

SEQ ID NO: 22           moltype = AA   length = 44
FEATURE                 Location/Qualifiers
source                  1..44
                                mol_type = protein
                                organism = synthetic construct
SEQUENCE: 22
CEYDEEFFTG LKRLRGGDIC YYIKKKFKKV PDLCIEEILD KLGC                         44

SEQ ID NO: 23           moltype = AA   length = 44
FEATURE                 Location/Qualifiers
```

```
source                    1..44
                          mol_type = protein
                          organism = synthetic construct
SEQUENCE: 23
CEYDEEFFEG LKKLRGGDIC YYIKKKFKKV PDLCIEEILD KLGC              44

SEQ ID NO: 24             moltype = AA  length = 44
FEATURE                   Location/Qualifiers
source                    1..44
                          mol_type = protein
                          organism = synthetic construct
SEQUENCE: 24
CEYDEEFFTG LKRLRGGDIC YYIKKKFKKV PKLCIEEILD KLGC              44

SEQ ID NO: 25             moltype = AA  length = 44
FEATURE                   Location/Qualifiers
source                    1..44
                          mol_type = protein
                          organism = synthetic construct
SEQUENCE: 25
CEYDEEFFTG LKRLRGGDIC YYIKKKFKKV PELCIEEILD KLGC              44

SEQ ID NO: 26             moltype = AA  length = 44
FEATURE                   Location/Qualifiers
source                    1..44
                          mol_type = protein
                          organism = synthetic construct
SEQUENCE: 26
CEYDEEFFQG LKRLRGGDIC YYIKKKFKKV PDLCIEEILD KLGC              44

SEQ ID NO: 27             moltype = AA  length = 44
FEATURE                   Location/Qualifiers
source                    1..44
                          mol_type = protein
                          organism = synthetic construct
SEQUENCE: 27
CEYDEEFFLG LKRLRGGDIC YYIKKKFKKV PDLCIEEILD KLGC              44

SEQ ID NO: 28             moltype = AA  length = 44
FEATURE                   Location/Qualifiers
source                    1..44
                          mol_type = protein
                          organism = synthetic construct
SEQUENCE: 28
CEYKEEFFTG LKRLRGGDIC YYIKKKFKKV PDLCIEEILD KLGC              44

SEQ ID NO: 29             moltype = AA  length = 44
FEATURE                   Location/Qualifiers
source                    1..44
                          mol_type = protein
                          organism = synthetic construct
SEQUENCE: 29
CEYEEEFFTG LKRLRGGDIC YYIKKKFKKV PDLCIEEILD KLGC              44

SEQ ID NO: 30             moltype = AA  length = 44
FEATURE                   Location/Qualifiers
source                    1..44
                          mol_type = protein
                          organism = synthetic construct
SEQUENCE: 30
CEYDEEFFTG LKRLRGGKIC YYIKKKFKKV PDLCIEEILD KLGC              44

SEQ ID NO: 31             moltype = AA  length = 44
FEATURE                   Location/Qualifiers
source                    1..44
                          mol_type = protein
                          organism = synthetic construct
SEQUENCE: 31
CEYDEEFFTG LKRLRGGEIC YYIKKKFKKV PDLCIEEILD KLGC              44

SEQ ID NO: 32             moltype = AA  length = 44
FEATURE                   Location/Qualifiers
source                    1..44
                          mol_type = protein
                          organism = synthetic construct
SEQUENCE: 32
CEYDEEFFTG LKRLRGGNIC YYIKKKFKKV PDLCIEEILD KLGC              44

SEQ ID NO: 33             moltype = AA  length = 44
```

```
FEATURE                 Location/Qualifiers
source                  1..44
                        mol_type = protein
                        organism = synthetic construct
SEQUENCE: 33
CEYDEEFFTG LKRLRGGSIC YYIKKKFKKV PDLCIEEILD KLGC                         44

SEQ ID NO: 34           moltype = AA  length = 44
FEATURE                 Location/Qualifiers
source                  1..44
                        mol_type = protein
                        organism = synthetic construct
SEQUENCE: 34
CEYDEEFFTG LKRLRGGTIC YYIKKKFKKV PDLCIEEILD KLGC                         44

SEQ ID NO: 35           moltype = AA  length = 44
FEATURE                 Location/Qualifiers
source                  1..44
                        mol_type = protein
                        organism = synthetic construct
SEQUENCE: 35
CEYDEEFFTG LKRLRGGQIC YYIKKKFKKV PDLCIEEILD KLGC                         44

SEQ ID NO: 36           moltype = AA  length = 44
FEATURE                 Location/Qualifiers
source                  1..44
                        mol_type = protein
                        organism = synthetic construct
SITE                    9
                        note = 2,3-Diaminopropionic acid
SEQUENCE: 36
CEYDEEFFXG LKRLRGGDIC YYIKKKFKKV PDLCIEEILD KLGC                         44

SEQ ID NO: 37           moltype = AA  length = 44
FEATURE                 Location/Qualifiers
source                  1..44
                        mol_type = protein
                        organism = synthetic construct
SEQUENCE: 37
CEYDEEFFTG LKRLRGGDIC YYIKKKFKKV PDLCIEEILK KLGC                         44

SEQ ID NO: 38           moltype = AA  length = 44
FEATURE                 Location/Qualifiers
source                  1..44
                        mol_type = protein
                        organism = synthetic construct
SEQUENCE: 38
CEYDEEFFTG LKRLRGGDIC YYIKKKFKKV PDLCIEEILE KLGC                         44

SEQ ID NO: 39           moltype = AA  length = 44
FEATURE                 Location/Qualifiers
source                  1..44
                        mol_type = protein
                        organism = synthetic construct
SEQUENCE: 39
CEYDEKFFTG LKRLRGGDIC YYIKKKFKKV PDLCIEEILD KLGC                         44

SEQ ID NO: 40           moltype = AA  length = 44
FEATURE                 Location/Qualifiers
source                  1..44
                        mol_type = protein
                        organism = synthetic construct
SEQUENCE: 40
CEYDKEFFTG LKRLRGGDIC YYIKKKFKKV PDLCIEEILD KLGC                         44

SEQ ID NO: 41           moltype = AA  length = 44
FEATURE                 Location/Qualifiers
source                  1..44
                        mol_type = protein
                        organism = synthetic construct
SEQUENCE: 41
CKYDEEFFTG LKRLRGGDIC YYIKKKFKKV PDLCIEEILD KLGC                         44

SEQ ID NO: 42           moltype = AA  length = 44
FEATURE                 Location/Qualifiers
source                  1..44
                        mol_type = protein
                        organism = synthetic construct
SEQUENCE: 42
```

```
CEYDEQFFTG LKRLRGGDIC YYIKKKFKKV PDLCIEEILD KLGC                              44

SEQ ID NO: 43           moltype = AA   length = 44
FEATURE                 Location/Qualifiers
source                  1..44
                        mol_type = protein
                        organism = synthetic construct
SEQUENCE: 43
CEYDEEFFTD LKRLRGGDIC YYIKKKFKKV PKLCIEEILD KLGC                              44

SEQ ID NO: 44           moltype = AA   length = 44
FEATURE                 Location/Qualifiers
source                  1..44
                        mol_type = protein
                        organism = synthetic construct
SEQUENCE: 44
CEYDEEFFTE LKRLRGGDIC YYIKKKFKKV PKLCIEEILD KLGC                              44

SEQ ID NO: 45           moltype = AA   length = 44
FEATURE                 Location/Qualifiers
source                  1..44
                        mol_type = protein
                        organism = synthetic construct
SEQUENCE: 45
CEYDEEFFTK LKRLRGGDIC YYIKKKFKKV PKLCIEEILD KLGC                              44

SEQ ID NO: 46           moltype = AA   length = 44
FEATURE                 Location/Qualifiers
source                  1..44
                        mol_type = protein
                        organism = synthetic construct
SEQUENCE: 46
CEYDEEFFTT LKRLRGGDIC YYIKKKFKKV PKLCIEEILD KLGC                              44

SEQ ID NO: 47           moltype = AA   length = 44
FEATURE                 Location/Qualifiers
source                  1..44
                        mol_type = protein
                        organism = synthetic construct
SEQUENCE: 47
CEYDEEFFTL LKRLRGGDIC YYIKKKFKKV PKLCIEEILD KLGC                              44

SEQ ID NO: 48           moltype = AA   length = 44
FEATURE                 Location/Qualifiers
source                  1..44
                        mol_type = protein
                        organism = synthetic construct
SEQUENCE: 48
CEYDEEFFTA LKRLRGGDIC YYIKKKFKKV PKLCIEEILD KLGC                              44

SEQ ID NO: 49           moltype = AA   length = 44
FEATURE                 Location/Qualifiers
source                  1..44
                        mol_type = protein
                        organism = synthetic construct
SEQUENCE: 49
CEYDEEFFLG LKRLRGGDIC YYIKKKFKKV PKLCIEEILD KLGC                              44

SEQ ID NO: 50           moltype = AA   length = 44
FEATURE                 Location/Qualifiers
source                  1..44
                        mol_type = protein
                        organism = synthetic construct
SEQUENCE: 50
CEYDEEFFTG LKRLRGGDIC YYIKKKFKKV PKLCIEEILE KLGC                              44

SEQ ID NO: 51           moltype = AA   length = 44
FEATURE                 Location/Qualifiers
source                  1..44
                        mol_type = protein
                        organism = synthetic construct
SEQUENCE: 51
CEYDEEFFLG LKRLRGGDIC YYIKKKFKKV PDLCIEEILE KLGC                              44

SEQ ID NO: 52           moltype = AA   length = 44
FEATURE                 Location/Qualifiers
source                  1..44
                        mol_type = protein
                        organism = synthetic construct
```

```
SEQUENCE: 52
CEYDEEFFLG LKRLRGGDIC YYIKKKFKKV PKLCIEEILE KLGC              44

SEQ ID NO: 53             moltype = AA  length = 44
FEATURE                   Location/Qualifiers
source                    1..44
                          mol_type = protein
                          organism = synthetic construct
SEQUENCE: 53
CEYDEEFFTG LKRLRGGDIC YYIKKKFKKV PKLCIEEILK KLGC              44

SEQ ID NO: 54             moltype = AA  length = 44
FEATURE                   Location/Qualifiers
source                    1..44
                          mol_type = protein
                          organism = synthetic construct
SEQUENCE: 54
CEYDEEFFLG LKRLRGGDIC YYIKKKFKKV PKLCIEEILK KLGC              44

SEQ ID NO: 55             moltype = AA  length = 44
FEATURE                   Location/Qualifiers
source                    1..44
                          mol_type = protein
                          organism = synthetic construct
SEQUENCE: 55
CEYDEEFFLG LKRLRGGDIC YYIKKKFKKV PDLCIEEILK KLGC              44

SEQ ID NO: 56             moltype = AA  length = 44
FEATURE                   Location/Qualifiers
source                    1..44
                          mol_type = protein
                          organism = synthetic construct
SEQUENCE: 56
CEYDEEFFTG LKRLRGGDIC YYIKKKFKKV PELCIEEILK KLGC              44

SEQ ID NO: 57             moltype = AA  length = 44
FEATURE                   Location/Qualifiers
source                    1..44
                          mol_type = protein
                          organism = synthetic construct
SEQUENCE: 57
CEYDEEFFTG LKRLRGGDIC YYIKKKFKKV PELCIEEILE KLGC              44

SEQ ID NO: 58             moltype = AA  length = 44
FEATURE                   Location/Qualifiers
source                    1..44
                          mol_type = protein
                          organism = synthetic construct
SEQUENCE: 58
CEYDEEFFLG LKRLRGGDIC YYIKKKFKKV PELCIEEILK KLGC              44

SEQ ID NO: 59             moltype = AA  length = 44
FEATURE                   Location/Qualifiers
source                    1..44
                          mol_type = protein
                          organism = synthetic construct
SEQUENCE: 59
CEYDEEFFLG LKRLRGGDIC YYIKKKFKKV PELCIEEILE KLGC              44

SEQ ID NO: 60             moltype = AA  length = 44
FEATURE                   Location/Qualifiers
source                    1..44
                          mol_type = protein
                          organism = synthetic construct
SEQUENCE: 60
CEYDEEFFKG LKRLRGGDIC YYIKKKFKKV PKLCIEEILE KLGC              44

SEQ ID NO: 61             moltype = AA  length = 44
FEATURE                   Location/Qualifiers
source                    1..44
                          mol_type = protein
                          organism = synthetic construct
SEQUENCE: 61
CEYDEKFFTG LKRLRGGDIC YYIKKKFKKV PKLCIEEILD KLGC              44

SEQ ID NO: 62             moltype = AA  length = 44
FEATURE                   Location/Qualifiers
source                    1..44
                          mol_type = protein
```

```
                        organism = synthetic construct
SEQUENCE: 62
CEYDEQFFTG LKRLRGGDIC YYIKKKFKKV PKLCIEEILD KLGC                    44

SEQ ID NO: 63           moltype = AA  length = 44
FEATURE                 Location/Qualifiers
source                  1..44
                        mol_type = protein
                        organism = synthetic construct
SEQUENCE: 63
CEYDEKFFLG LKRLRGGDIC YYIKKKFKKV PKLCIEEILK KLGC                    44

SEQ ID NO: 64           moltype = AA  length = 44
FEATURE                 Location/Qualifiers
source                  1..44
                        mol_type = protein
                        organism = synthetic construct
SEQUENCE: 64
CEYDEQFFLG LKRLRGGDIC YYIKKKFKKV PKLCIEEILK KLGC                    44

SEQ ID NO: 65           moltype = AA  length = 44
FEATURE                 Location/Qualifiers
source                  1..44
                        mol_type = protein
                        organism = synthetic construct
SEQUENCE: 65
CEYDEKFFTG LKRLRGGDIC YYIKKKFKKV PKLCIEEILK KLGC                    44

SEQ ID NO: 66           moltype = AA  length = 44
FEATURE                 Location/Qualifiers
source                  1..44
                        mol_type = protein
                        organism = synthetic construct
SEQUENCE: 66
CEYDEQFFTG LKRLRGGDIC YYIKKKFKKV PKLCIEEILK KLGC                    44

SEQ ID NO: 67           moltype = AA  length = 44
FEATURE                 Location/Qualifiers
source                  1..44
                        mol_type = protein
                        organism = synthetic construct
SEQUENCE: 67
CEYDEEFFKA LKRLRGGDIC YYIKKKFKKV PKLCIEEILE KLGC                    44

SEQ ID NO: 68           moltype = AA  length = 44
FEATURE                 Location/Qualifiers
source                  1..44
                        mol_type = protein
                        organism = synthetic construct
SEQUENCE: 68
CEYDEEFFLA LKRLRGGDIC YYIKKKFKKV PKLCIEEILE KLGC                    44

SEQ ID NO: 69           moltype = AA  length = 44
FEATURE                 Location/Qualifiers
source                  1..44
                        mol_type = protein
                        organism = synthetic construct
SEQUENCE: 69
CEYDEEFFLA LKRLRGGDIC YYIKKKFKKV PKLCIEEILD KLGC                    44

SEQ ID NO: 70           moltype = AA  length = 44
FEATURE                 Location/Qualifiers
source                  1..44
                        mol_type = protein
                        organism = synthetic construct
SEQUENCE: 70
CEYDEEFFTA LKRLRGGDIC YYIKKKFKKV PKLCIEEILE KLGC                    44

SEQ ID NO: 71           moltype = AA  length = 44
FEATURE                 Location/Qualifiers
source                  1..44
                        mol_type = protein
                        organism = synthetic construct
SEQUENCE: 71
CEYDEEFFKG LKRLRGGDIC YYIKKKFKKV PKLCIEEILD KLGC                    44

SEQ ID NO: 72           moltype = AA  length = 44
FEATURE                 Location/Qualifiers
source                  1..44
```

```
                        mol_type = protein
                        organism = synthetic construct
SEQUENCE: 72
CEYDEEFFKA LKRLRGGDIC YYIKKKFKKV PKLCIEEILD KLGC                    44

SEQ ID NO: 73           moltype = AA   length = 44
FEATURE                 Location/Qualifiers
source                  1..44
                        mol_type = protein
                        organism = synthetic construct
SITE                    12
                        note = Acetylated Lysine
SITE                    13
                        note = Citrulline
SITE                    15
                        note = Citrulline
SITE                    41
                        note = Acetylated Lysine
SEQUENCE: 73
CEYDEEFFTA LKXLXGGDIC YYIKKKFKKV PKLCIEEILD KLGC                    44

SEQ ID NO: 74           moltype = AA   length = 44
FEATURE                 Location/Qualifiers
source                  1..44
                        mol_type = protein
                        organism = synthetic construct
SITE                    12
                        note = Acetylated Lysine
SITE                    13
                        note = Citrulline
SITE                    15
                        note = Citrulline
SITE                    24
                        note = Acetylated Lysine
SITE                    25
                        note = Acetylated Lysine
SITE                    26
                        note = Acetylated Lysine
SITE                    28
                        note = Acetylated Lysine
SITE                    29
                        note = Acetylated Lysine
SITE                    32
                        note = Acetylated Lysine
SITE                    41
                        note = Acetylated Lysine
SEQUENCE: 74
CEYDEEFFTA LKXLXGGDIC YYIKKKFKKV PKLCIEEILD KLGC                    44

SEQ ID NO: 75           moltype = AA   length = 44
FEATURE                 Location/Qualifiers
source                  1..44
                        mol_type = protein
                        organism = synthetic construct
SITE                    24
                        note = Acetylated Lysine
SITE                    25
                        note = Acetylated Lysine
SITE                    26
                        note = Acetylated Lysine
SITE                    28
                        note = Acetylated Lysine
SITE                    29
                        note = Acetylated Lysine
SITE                    32
                        note = Acetylated Lysine
SEQUENCE: 75
CEYDEEFFTA LKRLRGGDIC YYIKKKFKKV PKLCIEEILD KLGC                    44

SEQ ID NO: 76           moltype = AA   length = 44
FEATURE                 Location/Qualifiers
source                  1..44
                        mol_type = protein
                        organism = synthetic construct
SEQUENCE: 76
CEYDEQFFTA LKRLRGGDIC YYISAQFNTL PDLCIEEILE NLGC                    44

SEQ ID NO: 77           moltype = AA   length = 44
FEATURE                 Location/Qualifiers
```

```
                         -continued source                   1..44
                         mol_type = protein
                         organism = synthetic construct
SEQUENCE: 77
CEYDEEFFTA LKKLRGGDIC YYIQQAFNYL PGICIEEILD NLGC                  44

SEQ ID NO: 78            moltype = AA  length = 45
FEATURE                  Location/Qualifiers
source                   1..45
                         mol_type = protein
                         organism = synthetic construct
SEQUENCE: 78
CEYDEEFFTA LKRLRGGDIC YYIQASFQYL PGLCIEEILD NLGCS                 45

SEQ ID NO: 79            moltype = AA  length = 44
FEATURE                  Location/Qualifiers
source                   1..44
                         mol_type = protein
                         organism = synthetic construct
SEQUENCE: 79
CEYDEQFFTA LKALRGGDIC YYIQASFNYL PDLCIEEILD NLGC                  44

SEQ ID NO: 80            moltype = AA  length = 45
FEATURE                  Location/Qualifiers
source                   1..45
                         mol_type = protein
                         organism = synthetic construct
SEQUENCE: 80
CEYDEQFFTA LKALRGGDIC YYIQASFNYL PDLCIEEILD NLGCS                 45

SEQ ID NO: 81            moltype = AA  length = 45
FEATURE                  Location/Qualifiers
source                   1..45
                         mol_type = protein
                         organism = synthetic construct
SEQUENCE: 81
CEYDEEFFTA LKRLRGGDIC YYIQAKFQYL PKLCIEEILD NLGCS                 45

SEQ ID NO: 82            moltype = AA  length = 45
FEATURE                  Location/Qualifiers
source                   1..45
                         mol_type = protein
                         organism = synthetic construct
SEQUENCE: 82
CEYDEEFFTA LKRLRGGDIC YYIQKAFQYL PGLCIEEILD NLGCS                 45

SEQ ID NO: 83            moltype = AA  length = 45
FEATURE                  Location/Qualifiers
source                   1..45
                         mol_type = protein
                         organism = synthetic construct
SEQUENCE: 83
CEYDEEFFTA LARLRGGDIC YYIQAKFQYL PGLCIEEILD NLGCS                 45

SEQ ID NO: 84            moltype = AA  length = 44
FEATURE                  Location/Qualifiers
source                   1..44
                         mol_type = protein
                         organism = synthetic construct
SEQUENCE: 84
CEYDEQFFTA LARLRGGDIC YYIQEQFATV PGLCIEEILD QLGC                  44

SEQ ID NO: 85            moltype = AA  length = 45
FEATURE                  Location/Qualifiers
source                   1..45
                         mol_type = protein
                         organism = synthetic construct
SEQUENCE: 85
CEYDEQFFTA LARLRGGDIC YYIQEQFATV PGLCIEEILD QLGCS                 45

SEQ ID NO: 86            moltype = AA  length = 44
FEATURE                  Location/Qualifiers
source                   1..44
                         mol_type = protein
                         organism = synthetic construct
SEQUENCE: 86
CEYDEEFFTA LSRLRGGDIC YYIQQAFQYL PGLCIEEILD NLGC                  44

SEQ ID NO: 87            moltype = AA  length = 45
```

```
FEATURE                 Location/Qualifiers
source                  1..45
                        mol_type = protein
                        organism = synthetic construct
SEQUENCE: 87
CEYDEEFFTA LSRLRGGDIC YYIQQAFQYL PGLCIEEILD NLGCS              45

SEQ ID NO: 88           moltype = AA  length = 44
FEATURE                 Location/Qualifiers
source                  1..44
                        mol_type = protein
                        organism = synthetic construct
SEQUENCE: 88
CEYDEQFFTA LSSLRGGDIC YYIQEQFANV PGICIEEILD NLGC               44

SEQ ID NO: 89           moltype = AA  length = 45
FEATURE                 Location/Qualifiers
source                  1..45
                        mol_type = protein
                        organism = synthetic construct
SEQUENCE: 89
CEYDEQFFTA LSSLRGGDIC YYIQEQFANV PGICIEEILD NLGCS              45

SEQ ID NO: 90           moltype = AA  length = 45
FEATURE                 Location/Qualifiers
source                  1..45
                        mol_type = protein
                        organism = synthetic construct
SEQUENCE: 90
CEYDEEFFTA LARLRGADIC YYIQAKFQYL PGDCIEEILD NLGCS              45

SEQ ID NO: 91           moltype = AA  length = 45
FEATURE                 Location/Qualifiers
source                  1..45
                        mol_type = protein
                        organism = synthetic construct
SEQUENCE: 91
CDYDEEFFTA LARLRGGDIC EYIQAKFQYL PGLCIEEILD NLGCS              45

SEQ ID NO: 92           moltype = AA  length = 45
FEATURE                 Location/Qualifiers
source                  1..45
                        mol_type = protein
                        organism = synthetic construct
SEQUENCE: 92
CEYDEEFFTA LARLRGGDIC YYIQAKFQYL PGECIEEILQ NLGCS              45

SEQ ID NO: 93           moltype = AA  length = 45
FEATURE                 Location/Qualifiers
source                  1..45
                        mol_type = protein
                        organism = synthetic construct
SEQUENCE: 93
CEYDEEFFTA LARLRGDDIC SYIQAKFQYL PGLCIEEILD NLGCS              45

SEQ ID NO: 94           moltype = AA  length = 45
FEATURE                 Location/Qualifiers
source                  1..45
                        mol_type = protein
                        organism = synthetic construct
SEQUENCE: 94
CEYDGEFFTA LARLRGADIC EYIQAKFQYY PGLCIEEILD NLGCS              45

SEQ ID NO: 95           moltype = AA  length = 45
FEATURE                 Location/Qualifiers
source                  1..45
                        mol_type = protein
                        organism = synthetic construct
SEQUENCE: 95
CEYDEEFFTA LARLRGGDIC YYILAKFQYL PGECIEEILD NLGCS              45

SEQ ID NO: 96           moltype = AA  length = 45
FEATURE                 Location/Qualifiers
source                  1..45
                        mol_type = protein
                        organism = synthetic construct
SEQUENCE: 96
CEYDEQFFTA LARLRGGDIC EYIQAKFQYL PGLCIEEILD NLGCS              45
```

```
SEQ ID NO: 97           moltype = AA   length = 45
FEATURE                 Location/Qualifiers
source                  1..45
                        mol_type = protein
                        organism = synthetic construct
SEQUENCE: 97
CEYDEEFFTA LARLRGADIC DYIQAKFQYL PGLCIEEILD NLGCS               45

SEQ ID NO: 98           moltype = AA   length = 45
FEATURE                 Location/Qualifiers
source                  1..45
                        mol_type = protein
                        organism = synthetic construct
SEQUENCE: 98
CEYDEEFFTA LARLRGGDIC EYIQAKFQYL PGLCIQEILD NLGCS               45

SEQ ID NO: 99           moltype = AA   length = 45
FEATURE                 Location/Qualifiers
source                  1..45
                        mol_type = protein
                        organism = synthetic construct
SEQUENCE: 99
CEYDEEFFTA LARLRGGDIC QYIQAKFQYL PGQCIEEILD NLGCS               45

SEQ ID NO: 100          moltype = AA   length = 45
FEATURE                 Location/Qualifiers
source                  1..45
                        mol_type = protein
                        organism = synthetic construct
SEQUENCE: 100
CEYDEEFFTA LARLRGGDIC EYIQAKFQYL EGLCIEEILD NLGCS               45

SEQ ID NO: 101          moltype = AA   length = 45
FEATURE                 Location/Qualifiers
source                  1..45
                        mol_type = protein
                        organism = synthetic construct
SEQUENCE: 101
CEYDEAFFTA LARLRGGDIC QYIQAKFQYL PGLCIEEILD NLGCS               45

SEQ ID NO: 102          moltype = AA   length = 45
FEATURE                 Location/Qualifiers
source                  1..45
                        mol_type = protein
                        organism = synthetic construct
SEQUENCE: 102
CEYDEQFFTA LARLRGGDIC YYILAKFQYL PGLCIEEILD NLGCS               45

SEQ ID NO: 103          moltype = AA   length = 45
FEATURE                 Location/Qualifiers
source                  1..45
                        mol_type = protein
                        organism = synthetic construct
SEQUENCE: 103
CEYDEEFFTA LARLRGGDIC QYIQAKFQYL PALCIEEILD NLGCS               45

SEQ ID NO: 104          moltype = AA   length = 45
FEATURE                 Location/Qualifiers
source                  1..45
                        mol_type = protein
                        organism = synthetic construct
SEQUENCE: 104
CEYDEEFFTA LARLRGGDIC YYIQAKFAYL PALCIEEILD NLGCS               45

SEQ ID NO: 105          moltype = AA   length = 45
FEATURE                 Location/Qualifiers
source                  1..45
                        mol_type = protein
                        organism = synthetic construct
SEQUENCE: 105
CEYDEEFFTA LARLRGGDIC QYIQAKFAYV PGLCIEEILD NLGCS               45

SEQ ID NO: 106          moltype = AA   length = 45
FEATURE                 Location/Qualifiers
source                  1..45
                        mol_type = protein
                        organism = synthetic construct
SEQUENCE: 106
CEYDEEFFTA LARLRGSDIC LYIQAKFQYL PGLCIEEILD NLGCS               45
```

```
SEQ ID NO: 107          moltype = AA  length = 45
FEATURE                 Location/Qualifiers
source                  1..45
                        mol_type = protein
                        organism = synthetic construct
SEQUENCE: 107
CEYDEEFFTA LARLRGGDIC DYIQAKFQYL PGLCIAEILD NLGCS               45

SEQ ID NO: 108          moltype = AA  length = 45
FEATURE                 Location/Qualifiers
source                  1..45
                        mol_type = protein
                        organism = synthetic construct
SEQUENCE: 108
CEYDGEFFTA LARLRGGDIC QYIQAKFQYL PGLCIEEILD NLGCS               45

SEQ ID NO: 109          moltype = AA  length = 45
FEATURE                 Location/Qualifiers
source                  1..45
                        mol_type = protein
                        organism = synthetic construct
SEQUENCE: 109
CDYDEEFFTA LARLRGGDIC YYIQAKFSYL PGLCIEEILD NLGCS               45

SEQ ID NO: 110          moltype = AA  length = 45
FEATURE                 Location/Qualifiers
source                  1..45
                        mol_type = protein
                        organism = synthetic construct
SEQUENCE: 110
CDYDEEFFTA LARLRGGDIC QYIQAKFQYL PGLCIEEILD NLGCS               45

SEQ ID NO: 111          moltype = AA  length = 45
FEATURE                 Location/Qualifiers
source                  1..45
                        mol_type = protein
                        organism = synthetic construct
SEQUENCE: 111
CEYDEEFFTA LASLRGGDIC YYIQAKFQYL PGLCIEEILD NLGCS               45

SEQ ID NO: 112          moltype = AA  length = 45
FEATURE                 Location/Qualifiers
source                  1..45
                        mol_type = protein
                        organism = synthetic construct
SEQUENCE: 112
CEYDEEFFTA LAQLRGGDIC YYIQAKFQYL PGLCIEEILD NLGCS               45

SEQ ID NO: 113          moltype = AA  length = 45
FEATURE                 Location/Qualifiers
source                  1..45
                        mol_type = protein
                        organism = synthetic construct
SITE                    13
                        note = Citrulline
SEQUENCE: 113
CEYDEEFFTA LAXLRGGDIC YYIQAKFQYL PGLCIEEILD NLGCS               45

SEQ ID NO: 114          moltype = AA  length = 45
FEATURE                 Location/Qualifiers
source                  1..45
                        mol_type = protein
                        organism = synthetic construct
SITE                    26
                        note = hydroxy-norleucine
SEQUENCE: 114
CEYDEEFFTA LARLRGGDIC YYIQAXFQYL PGLCIEEILD NLGCS               45

SEQ ID NO: 115          moltype = AA  length = 45
FEATURE                 Location/Qualifiers
source                  1..45
                        mol_type = protein
                        organism = synthetic construct
SEQUENCE: 115
CEYDEEFFTA LARLRGGDIC YYIQAYFQYL PGLCIEEILD NLGCS               45

SEQ ID NO: 116          moltype = AA  length = 45
FEATURE                 Location/Qualifiers
```

```
source                  1..45
                        mol_type = protein
                        organism = synthetic construct
SEQUENCE: 116
CEYDEEFFTA LARLRGGDIC YYIQAKFQYL PKLCIEEILD NLGCS                    45

SEQ ID NO: 117          moltype = AA  length = 45
FEATURE                 Location/Qualifiers
source                  1..45
                        mol_type = protein
                        organism = synthetic construct
SEQUENCE: 117
CEYDEEFFTA LARLRGGDIC EYIQAKFQYL PKLCIEEILD NLGCS                    45

SEQ ID NO: 118          moltype = AA  length = 45
FEATURE                 Location/Qualifiers
source                  1..45
                        mol_type = protein
                        organism = synthetic construct
SEQUENCE: 118
CEYDEEFFTA LARLRGGDIC SYIQAKFQYL PKLCIEEILD NLGCS                    45

SEQ ID NO: 119          moltype = AA  length = 45
FEATURE                 Location/Qualifiers
source                  1..45
                        mol_type = protein
                        organism = synthetic construct
SEQUENCE: 119
CEYDEEFFTA LARLRGGDIC DYIQAKFQYL PKLCIEEILD NLGCS                    45

SEQ ID NO: 120          moltype = AA  length = 45
FEATURE                 Location/Qualifiers
source                  1..45
                        mol_type = protein
                        organism = synthetic construct
SITE                    13
                        note = Citrulline
SITE                    26
                        note = hydroxy-norleucine
SEQUENCE: 120
CEYDEEFFTA LAXLRGDDIC SYIQAXFQYL PGLCIEEILD NLGCS                    45

SEQ ID NO: 121          moltype = AA  length = 45
FEATURE                 Location/Qualifiers
source                  1..45
                        mol_type = protein
                        organism = synthetic construct
SITE                    13
                        note = Citrulline
SEQUENCE: 121
CEYDEEFFTA LAXLRGGDIC EYIQAKFQYL PGLCIEEILD NLGCS                    45

SEQ ID NO: 122          moltype = AA  length = 45
FEATURE                 Location/Qualifiers
source                  1..45
                        mol_type = protein
                        organism = synthetic construct
SITE                    13
                        note = Citrulline
SEQUENCE: 122
CEYDEEFFTA LAXLRGDDIC SYIQAKFQYL PGLCIEEILD NLGCS                    45

SEQ ID NO: 123          moltype = AA  length = 45
FEATURE                 Location/Qualifiers
source                  1..45
                        mol_type = protein
                        organism = synthetic construct
SITE                    26
                        note = hydroxy-norleucine
SEQUENCE: 123
CEYDEEFFTA LARLRGGDIC YYIQAXFQYL PGLCIEEILD NLGCS                    45

SEQ ID NO: 124          moltype = AA  length = 45
FEATURE                 Location/Qualifiers
source                  1..45
                        mol_type = protein
                        organism = synthetic construct
SITE                    13
                        note = Citrulline
```

```
SEQUENCE: 124
CEYDEEFFTA LAXLRGGDIC SYIQAKFQYL PGLCIEEILD NLGCS                    45

SEQ ID NO: 125            moltype = AA   length = 45
FEATURE                   Location/Qualifiers
source                    1..45
                          mol_type = protein
                          organism = synthetic construct
SITE                      13
                          note = Citrulline
SEQUENCE: 125
CDYDEEFFTA LAXLRGGDIC EYIQAKFQYL PGLCIEEILD NLGCS                    45

SEQ ID NO: 126            moltype = AA   length = 45
FEATURE                   Location/Qualifiers
source                    1..45
                          mol_type = protein
                          organism = synthetic construct
SEQUENCE: 126
CEYDEEFFTA LKRLRGGDIC YYIQASFQYL PGECIEEILD NLGCS                    45

SEQ ID NO: 127            moltype = AA   length = 45
FEATURE                   Location/Qualifiers
source                    1..45
                          mol_type = protein
                          organism = synthetic construct
SEQUENCE: 127
CEYDEEFFTA LKRLRGGDIC EYIQASFQYL PGLCIEEILD NLGCS                    45

SEQ ID NO: 128            moltype = AA   length = 45
FEATURE                   Location/Qualifiers
source                    1..45
                          mol_type = protein
                          organism = synthetic construct
SEQUENCE: 128
CEYDEEFFTA LKRLRGGDIC SYIQASFQYL PGLCIEEILD NLGCS                    45

SEQ ID NO: 129            moltype = AA   length = 45
FEATURE                   Location/Qualifiers
source                    1..45
                          mol_type = protein
                          organism = synthetic construct
SEQUENCE: 129
CEYDEEFFTA LKRLRGDDIC YYIQASFQYL PGLCIEEILD NLGCS                    45

SEQ ID NO: 130            moltype = AA   length = 45
FEATURE                   Location/Qualifiers
source                    1..45
                          mol_type = protein
                          organism = synthetic construct
SEQUENCE: 130
CEYDEEFFTA LKRLRGDDIC EYIQASFQYL PGLCIEEILD NLGCS                    45

SEQ ID NO: 131            moltype = AA   length = 45
FEATURE                   Location/Qualifiers
source                    1..45
                          mol_type = protein
                          organism = synthetic construct
SEQUENCE: 131
CEYDEEFFTA LKRLRGDDIC SYIQASFQYL PGLCIEEILD NLGCS                    45

SEQ ID NO: 132            moltype = AA   length = 45
FEATURE                   Location/Qualifiers
source                    1..45
                          mol_type = protein
                          organism = synthetic construct
SEQUENCE: 132
CEYDEQFFTA LKRLRGADIC EYIQASFQYL PGLCIEEILD NLGCS                    45

SEQ ID NO: 133            moltype = AA   length = 45
FEATURE                   Location/Qualifiers
source                    1..45
                          mol_type = protein
                          organism = synthetic construct
SEQUENCE: 133
CEYDEQFFTA LKRLRGGDIC SYIQASFQYL PGLCIEEILD NLGCS                    45

SEQ ID NO: 134            moltype = AA   length = 45
FEATURE                   Location/Qualifiers
```

```
source                       1..45
                             mol_type = protein
                             organism = synthetic construct
SEQUENCE: 134
CEYDEQFFTA LKRLRGADIC SYIQASFQYL PGLCIEEILD NLGCS                    45

SEQ ID NO: 135               moltype = AA  length = 45
FEATURE                      Location/Qualifiers
source                       1..45
                             mol_type = protein
                             organism = synthetic construct
SEQUENCE: 135
CEYDEQFFTA LKRLRGDDIC SYIQASFQYL PGLCIEEILD NLGCS                    45

SEQ ID NO: 136               moltype = AA  length = 45
FEATURE                      Location/Qualifiers
source                       1..45
                             mol_type = protein
                             organism = synthetic construct
SEQUENCE: 136
CDYDEEFFTA LKRLRGGDIC EYIQASFQYL PGLCIEEILD NLGCS                    45

SEQ ID NO: 137               moltype = AA  length = 45
FEATURE                      Location/Qualifiers
source                       1..45
                             mol_type = protein
                             organism = synthetic construct
SEQUENCE: 137
CDYDEEFFTA LKRLRGGDIC SYIQASFQYL PGLCIEEILD NLGCS                    45

SEQ ID NO: 138               moltype = AA  length = 45
FEATURE                      Location/Qualifiers
source                       1..45
                             mol_type = protein
                             organism = synthetic construct
SEQUENCE: 138
CDYDEQFFTA LKRLRGGDIC EYIQASFQYL PGLCIEEILD NLGCS                    45

SEQ ID NO: 139               moltype = AA  length = 45
FEATURE                      Location/Qualifiers
source                       1..45
                             mol_type = protein
                             organism = synthetic construct
SEQUENCE: 139
CDYDEEFFTA LKRLRGDDIC EYIQASFQYL PGLCIEEILD NLGCS                    45

SEQ ID NO: 140               moltype = AA  length = 45
FEATURE                      Location/Qualifiers
source                       1..45
                             mol_type = protein
                             organism = synthetic construct
SEQUENCE: 140
CDYDEEFFTA LKRLRGDDIC SYIQASFQYL PGLCIEEILD NLGCS                    45

SEQ ID NO: 141               moltype = AA  length = 45
FEATURE                      Location/Qualifiers
source                       1..45
                             mol_type = protein
                             organism = synthetic construct
SEQUENCE: 141
CDYDEQFFTA LKRLRGDDIC EYIQASFQYL PGLCIEEILD NLGCS                    45

SEQ ID NO: 142               moltype = AA  length = 45
FEATURE                      Location/Qualifiers
source                       1..45
                             mol_type = protein
                             organism = synthetic construct
SEQUENCE: 142
CEYDEQFFTA LKRLRGADIC DYIQASFQYL PGLCIEEILD NLGCS                    45

SEQ ID NO: 143               moltype = AA  length = 45
FEATURE                      Location/Qualifiers
source                       1..45
                             mol_type = protein
                             organism = synthetic construct
SEQUENCE: 143
CEYDEEFFTA LKRLRGADIC DYIQASFQYL PGLCIEEILD NLGCS                    45

SEQ ID NO: 144               moltype = AA  length = 45
```

```
FEATURE              Location/Qualifiers
source               1..45
                     mol_type = protein
                     organism = synthetic construct
SEQUENCE: 144
CEYDEQFFTA LKRLRGGDIC DYIQASFQYL PGLCIEEILD NLGCS                     45

SEQ ID NO: 145       moltype = AA   length = 45
FEATURE              Location/Qualifiers
source               1..45
                     mol_type = protein
                     organism = synthetic construct
SEQUENCE: 145
CEYDEQFFTA LKRLRGDDIC DYIQASFQYL PGLCIEEILD NLGCS                     45

SEQ ID NO: 146       moltype = AA   length = 45
FEATURE              Location/Qualifiers
source               1..45
                     mol_type = protein
                     organism = synthetic construct
SEQUENCE: 146
CEYDEEFFTA LKRLRGGDIC EYIQAAFQYL PGLCIEEILD NLGCS                     45

SEQ ID NO: 147       moltype = AA   length = 45
FEATURE              Location/Qualifiers
source               1..45
                     mol_type = protein
                     organism = synthetic construct
SITE                 26
                     note = Norleucine
SEQUENCE: 147
CEYDEEFFTA LKRLRGGDIC EYIQAXFQYL PGLCIEEILD NLGCS                     45

SEQ ID NO: 148       moltype = AA   length = 45
FEATURE              Location/Qualifiers
source               1..45
                     mol_type = protein
                     organism = synthetic construct
SEQUENCE: 148
CEYDEEFFTA LKRLRGGDIC DYIQASFQYL PGLCIEEILD NLGCS                     45

SEQ ID NO: 149       moltype = AA   length = 45
FEATURE              Location/Qualifiers
source               1..45
                     mol_type = protein
                     organism = synthetic construct
SITE                 26
                     note = trimethyllysine
SEQUENCE: 149
CEYDEEFFTA LKRLRGGDIC EYIQAKFQYL PGLCIEEILD NLGCS                     45

SEQ ID NO: 150       moltype = AA   length = 45
FEATURE              Location/Qualifiers
source               1..45
                     mol_type = protein
                     organism = synthetic construct
SEQUENCE: 150
CEYDEEFFTA LKRLRGGDIC EYIQASFQYL PGECIEEILD NLGCS                     45

SEQ ID NO: 151       moltype = AA   length = 45
FEATURE              Location/Qualifiers
source               1..45
                     mol_type = protein
                     organism = synthetic construct
SEQUENCE: 151
CEYDEEFFTA LKRLRGGDIC DYIQASFQYL PGECIEEILD NLGCS                     45

SEQ ID NO: 152       moltype = AA   length = 45
FEATURE              Location/Qualifiers
source               1..45
                     mol_type = protein
                     organism = synthetic construct
SEQUENCE: 152
CEYDEEFFTA LKRLRGGDIC EYIQASFQYL PGECIEEILQ NLGCS                     45

SEQ ID NO: 153       moltype = AA   length = 45
FEATURE              Location/Qualifiers
source               1..45
                     mol_type = protein
```

```
                              -continued organism = synthetic construct
SEQUENCE: 153
CEYDEEFFTA LKRLRGGDIC DYIQASFQYL PGECIEEILQ NLGCS              45

SEQ ID NO: 154            moltype = AA   length = 45
FEATURE                   Location/Qualifiers
source                    1..45
                          mol_type = protein
                          organism = synthetic construct
SEQUENCE: 154
CDYDEQFFTA LKRLRGADIC EYIQASFQYL PGLCIEEILD NLGCS              45

SEQ ID NO: 155            moltype = AA   length = 45
FEATURE                   Location/Qualifiers
source                    1..45
                          mol_type = protein
                          organism = synthetic construct
SEQUENCE: 155
CDYDEQFFTA LKRLRGADIC EYIQASFQYL PGECIEEILD NLGCS              45

SEQ ID NO: 156            moltype = AA   length = 45
FEATURE                   Location/Qualifiers
source                    1..45
                          mol_type = protein
                          organism = synthetic construct
SEQUENCE: 156
CDYDEQFFTA LKRLRGADIC EYIQASFQYL PGQCIEEILD NLGCS              45

SEQ ID NO: 157            moltype = AA   length = 45
FEATURE                   Location/Qualifiers
source                    1..45
                          mol_type = protein
                          organism = synthetic construct
SEQUENCE: 157
CDYDEQFFTA LKRLRGGDIC EYIQASFQYL PGECIEEILD NLGCS              45

SEQ ID NO: 158            moltype = AA   length = 45
FEATURE                   Location/Qualifiers
source                    1..45
                          mol_type = protein
                          organism = synthetic construct
SEQUENCE: 158
CDYDEQFFTA LKRLRGGDIC EYIQASFQYL PGQCIEEILD NLGCS              45

SEQ ID NO: 159            moltype = AA   length = 510
FEATURE                   Location/Qualifiers
source                    1..510
                          mol_type = protein
                          organism = Homo sapiens
SEQUENCE: 159
MPLSLGAEMW GPEAWLLLLL LLASFTGRCP AGELETSDVV TVVLGQDAKL PCFYRGDSGE   60
QVGQVAWARV DAGEGAQELA LLHSKYGLHV SPAYEGRVEQ PPPPRNPLDG SVLLRNAVQA  120
DEGEYECRVS TFPAGSFQAR LRLRVLVPPL PSLNPGPALE EGQGLTLAAS CTAEGSPAPS  180
VTWDTEVKGT TSSRSFKHSR SAAVTSEFHL VPSRSMNGQP LTCVVSHPGL LQDQRITHIL  240
HVSFLAEASV RGLEDQNLWH IGREGAMLKC LSEGQPPPSY NWTRLDGPLP SGVRVDGDTL  300
GFPPLTTEHS GIYVCHVSNE FSSRDSQVTV DVLDPQEDSG KQVDLVSASV VVVGVIAALL  360
FCLLVVVVVL MSRYHRRKAQ QMTQKYEEEL TLTRENSIRR LHSHHTDPRS QPEESVGLRA  420
EGHPDSLKDN SSCSVMSEEP EGRSYSTLTT VREIETQTEL LSPGSGRAEE EEDQDEGIKQ  480
AMNHFVQENG TLRAKPTGNG IYINGRGHLV                                  510

SEQ ID NO: 160            moltype = AA   length = 508
FEATURE                   Location/Qualifiers
source                    1..508
                          mol_type = protein
                          organism = Mus musculus
SEQUENCE: 160
MPLSLGAEMW GPEAWLRLLF LASFTGQYSA GELETSDVVT VVLGQDAKLP CFYRGDPDEQ   60
VGQVAWARVD PNEGIRELAL LHSKYGLHVN PAYEDRVEQP PPPRDPLDGS VLLRNAVQAD  120
EGEYECRVST FPAGSFQARM RLRVLVPPLP SLNPGPPLEE GQGLTLAASC TAEGSPAPSV  180
TWDTEVKGTQ SSRSFTHPRS AAVTSEFHLV PSRSMNGQPL TCVVSHPGLL QDRRITHTLQ  240
VAFLAEASVR GLEDQNLWQV GREGATLKCL SEGQPPPKYN WTRLDGPLPS GVRVKGDTLG  300
FPPPLTTEHSG VYVCHVSNEL SSRDSQVTVE VLDPEDPGKQ VDLVSASVII VGVIAALLFC  360
LLVVVVVLMS RYHRRKAQQM TQKYEEELTL TRENSIRRLH SHHSDPRSQP EESVGLRAEG  420
HPDSLKDNSS CSVMSEEPEG RSYSTLTTVR EIETQTELLS PGSGRTEEDD DQDEGIKQAM  480
NHFVQENGTL RAKPTGNGIY INGRGHLV                                    508

SEQ ID NO: 161            moltype = AA   length = 45
FEATURE                   Location/Qualifiers
source                    1..45
```

```
                        mol_type = protein
                        organism = synthetic construct
SITE                    26
                        note = Trimethyl Lysine
SEQUENCE: 161
CEYDEEFFTA LARLRGADIC QYIQAKFQYL PALCIEEILD NLGCS                    45

SEQ ID NO: 162          moltype = AA  length = 45
FEATURE                 Location/Qualifiers
source                  1..45
                        mol_type = protein
                        organism = synthetic construct
SEQUENCE: 162
CEYDEEFFTA LARLRGGDIC QYIQAKFQYL PALCIEEILD NLGCS                    45

SEQ ID NO: 163          moltype = AA  length = 45
FEATURE                 Location/Qualifiers
source                  1..45
                        mol_type = protein
                        organism = synthetic construct
SITE                    26
                        note = Methyl Lysine
SEQUENCE: 163
CEYDEEFFTA LARLRGGDIC QYIQAKFQYL PALCIEEILD NLGCS                    45

SEQ ID NO: 164          moltype = AA  length = 45
FEATURE                 Location/Qualifiers
source                  1..45
                        mol_type = protein
                        organism = synthetic construct
SITE                    26
                        note = Dimethyl Lysine
SEQUENCE: 164
CEYDEEFFTA LARLRGGDIC QYIQAKFQYL PALCIEEILD NLGCS                    45

SEQ ID NO: 165          moltype = AA  length = 45
FEATURE                 Location/Qualifiers
source                  1..45
                        mol_type = protein
                        organism = synthetic construct
SITE                    26
                        note = N-epsilon-isopropyl-L-Lysine
SEQUENCE: 165
CEYDEEFFTA LARLRGGDIC QYIQAKFQYL PALCIEEILD NLGCS                    45

SEQ ID NO: 166          moltype = AA  length = 45
FEATURE                 Location/Qualifiers
source                  1..45
                        mol_type = protein
                        organism = synthetic construct
SITE                    12
                        note = Methyl Lysine
SITE                    26
                        note = Trimethyl Lysine
SEQUENCE: 166
CEYDEEFFTA LKRLRGGDIC QYIQAKFQYL PALCIEEILD NLGCS                    45

SEQ ID NO: 167          moltype = AA  length = 45
FEATURE                 Location/Qualifiers
source                  1..45
                        mol_type = protein
                        organism = synthetic construct
SITE                    12
                        note = Dimethyl Lysine
SITE                    26
                        note = Trimethyl Lysine
SEQUENCE: 167
CEYDEEFFTA LKRLRGGDIC QYIQAKFQYL PALCIEEILD NLGCS                    45

SEQ ID NO: 168          moltype = AA  length = 45
FEATURE                 Location/Qualifiers
source                  1..45
                        mol_type = protein
                        organism = synthetic construct
SITE                    12
                        note = N-epsilon-isopropyl-L-Lysine
SITE                    26
                        note = Trimethyl Lysine
SEQUENCE: 168
```

CEYDEEFFTA LKRLRGGDIC QYIQAKFQYL PALCIEEILD NLGCS                45

```
SEQ ID NO: 169          moltype = AA   length = 7
FEATURE                 Location/Qualifiers
source                  1..7
                        mol_type = protein
                        organism = synthetic construct
SEQUENCE: 169
TALARLR                                                          7

SEQ ID NO: 170          moltype = AA   length = 45
FEATURE                 Location/Qualifiers
source                  1..45
                        mol_type = protein
                        organism = synthetic construct
VARIANT                 2
                        note = E or D
VARIANT                 6
                        note = E or Q
VARIANT                 17
                        note = G or A
SITE                    21
                        note = Q or Y or E
SITE                    26
                        note = Trimethyllysine
VARIANT                 32
                        note = A or G or D
VARIANT                 41
                        note = N or K
VARIANT                 45
                        note = S or deleted
SEQUENCE: 170
```
CXYDEXFFTA LARLRGXDIC KYIQKKFQYL PXLCIEEILD XLGCX                45

```
SEQ ID NO: 171          moltype = AA   length = 45
FEATURE                 Location/Qualifiers
source                  1..45
                        mol_type = protein
                        organism = synthetic construct
VARIANT                 2
                        note = E or D
VARIANT                 6
                        note = E or Q
VARIANT                 17
                        note = G or A
VARIANT                 21
                        note = Q or Y or E
VARIANT                 26
                        note = trimethyllysine or dimethyl lysine or K or
                         Nepsilon-isopropyl-L-Lysine or methyl lysine or S
VARIANT                 32
                        note = A or G or D
VARIANT                 41
                        note = N or K
VARIANT                 45
                        note = S or deleted
SEQUENCE: 171
```
CXYDEXFFTA LARLRGXDIC XYIQKXFQYL PXLCIEEILD XLGCX                45

```
SEQ ID NO: 172          moltype = AA   length = 45
FEATURE                 Location/Qualifiers
source                  1..45
                        mol_type = protein
                        organism = synthetic construct
VARIANT                 2
                        note = E or D
VARIANT                 6
                        note = E or Q
VARIANT                 12
                        note = A or trimethyllysine or dimethyl lysine or
                         Nepsilon-isopropyl-L-Lysine or methyl lysine or K
VARIANT                 17
                        note = G or A
VARIANT                 21
                        note = Q or Y or E
VARIANT                 26
                        note = trimethyllysine or dimethyl lysine or K or
                         Nepsilon-isopropyl-L-Lysine or methyl lysine or S
VARIANT                 32
```

```
                        note = A or G or D
VARIANT                 41
                        note = N or K
VARIANT                 45
                        note = S or deleted
SEQUENCE: 172
CXYDEXFFTA LXRLRGXDIC XYIQKXFQYL PXLCIEEILD XLGCX              45

SEQ ID NO: 173          moltype = AA  length = 45
FEATURE                 Location/Qualifiers
source                  1..45
                        mol_type = protein
                        organism = synthetic construct
VARIANT                 26
                        note = trimethyllysine or dimethyl lysine or K or
                         Nepsilon-isopropyl-L-Lysine or methyl lysine or S
SEQUENCE: 173
CEYDEEFFTA LARLRGGDIC QYIQAXFQYL PALCIEEILD NLGCS              45

SEQ ID NO: 174          moltype = AA  length = 45
FEATURE                 Location/Qualifiers
source                  1..45
                        mol_type = protein
                        organism = synthetic construct
VARIANT                 12
                        note = A or trimethyllysine or dimethyl lysine or
                         Nepsilon-isopropyl-L-Lysine or methyl lysine or K
SEQUENCE: 174
CEYDEEFFTA LXRLRGGDIC QYIQAKFQYL PALCIEEILD NLGCS              45

SEQ ID NO: 175          moltype = AA  length = 45
FEATURE                 Location/Qualifiers
source                  1..45
                        mol_type = protein
                        organism = synthetic construct
VARIANT                 12
                        note = A or trimethyllysine or dimethyl lysine or
                         Nepsilon-isopropyl-L-Lysine or methyl lysine or K
VARIANT                 26
                        note = trimethyllysine or dimethyl lysine or K or
                         Nepsilon-isopropyl-L-Lysine or methyl lysine or S
SEQUENCE: 175
CEYDEEFFTA LXRLRGGDIC QYIQAXFQYL PALCIEEILD NLGCS              45

SEQ ID NO: 176          moltype = AA  length = 45
FEATURE                 Location/Qualifiers
source                  1..45
                        mol_type = protein
                        organism = synthetic construct
VARIANT                 2
                        note = E or D
VARIANT                 6
                        note = E or Q
VARIANT                 9
                        note = T or A
VARIANT                 10
                        note = A or G
VARIANT                 12
                        note = A or trimethyllysine or dimethyl lysine or
                         Nepsilon-isopropyl-L-Lysine or methyl lysine or K
VARIANT                 13
                        note = R or citrulline
VARIANT                 17
                        note = G or A
VARIANT                 21
                        note = Q or Y or E
VARIANT                 24
                        note = Q or K
VARIANT                 25
                        note = A or K
VARIANT                 26
                        note = trimethyllysine or dimethyl lysine or K or
                         Nepsilon-isopropyl-L-Lysine or methyl lysine or S
VARIANT                 28
                        note = Q or K
VARIANT                 29
                        note = Y or K
VARIANT                 30
                        note = L or V
```

```
VARIANT                     32
                            note = A or G or D
VARIANT                     41
                            note = N or K
VARIANT                     45
                            note = S or deleted
SEQUENCE: 176
CXYDEXFFXX LXXLRGXDIC XYIXXXFXXX PXLCIEEILD XLGCX                                45

SEQ ID NO: 177              moltype = AA  length = 44
FEATURE                     Location/Qualifiers
source                      1..44
                            mol_type = protein
                            organism = synthetic construct
SEQUENCE: 177
CEYDEEFFTA LKRLRGGDIC YYIKKKFDYL PKLCIEEILD NLGC                                 44

SEQ ID NO: 178              moltype = AA  length = 45
FEATURE                     Location/Qualifiers
source                      1..45
                            mol_type = protein
                            organism = synthetic construct
SEQUENCE: 178
CEYDEEFFTA LKRLRGGDIC QYIQASFQYL PGQCIEEILD NLGCS                                45

SEQ ID NO: 179              moltype = AA  length = 45
FEATURE                     Location/Qualifiers
source                      1..45
                            mol_type = protein
                            organism = synthetic construct
SEQUENCE: 179
CEYDEQFFTA LKRLRGGDIC QYIQASFQYL PGQCIEEILD NLGCS                                45

SEQ ID NO: 180              moltype = AA  length = 45
FEATURE                     Location/Qualifiers
source                      1..45
                            mol_type = protein
                            organism = synthetic construct
SEQUENCE: 180
CDYDEQFFTA LKRLRGGDIC QYIQASFQYL PGQCIEEILD NLGCS                                45

SEQ ID NO: 181              moltype = AA  length = 45
FEATURE                     Location/Qualifiers
source                      1..45
                            mol_type = protein
                            organism = synthetic construct
SEQUENCE: 181
CEYDEEFFTA LKRLRGADIC QYIQASFQYL PGQCIEEILD NLGCS                                45

SEQ ID NO: 182              moltype = AA  length = 45
FEATURE                     Location/Qualifiers
source                      1..45
                            mol_type = protein
                            organism = synthetic construct
SEQUENCE: 182
CDYDEEFFTA LKRLRGADIC QYIQASFQYL PGQCIEEILD NLGCS                                45

SEQ ID NO: 183              moltype = AA  length = 45
FEATURE                     Location/Qualifiers
source                      1..45
                            mol_type = protein
                            organism = synthetic construct
SEQUENCE: 183
CEYDEQFFTA LKRLRGGDIC EYIQASFQYL PGLCIEEILD NLGCS                                45

SEQ ID NO: 184              moltype = AA  length = 45
FEATURE                     Location/Qualifiers
source                      1..45
                            mol_type = protein
                            organism = synthetic construct
SEQUENCE: 184
CDYDEQFFTA LKRLRGADIC SYIQASFQYL PGLCIEEILD NLGCS                                45

SEQ ID NO: 185              moltype = AA  length = 45
FEATURE                     Location/Qualifiers
source                      1..45
                            mol_type = protein
                            organism = synthetic construct
SEQUENCE: 185
```

CEYDEQFFTA LARLRGGDIC EYIQASFQYL PGLCIEEILD NLGCS    45

SEQ ID NO: 186          moltype = AA   length = 45
FEATURE                 Location/Qualifiers
source                  1..45
                        mol_type = protein
                        organism = synthetic construct
SEQUENCE: 186
CEYDEQFFTA LARLRGADIC EYIQASFQYL PGLCIEEILD NLGCS    45

SEQ ID NO: 187          moltype = AA   length = 45
FEATURE                 Location/Qualifiers
source                  1..45
                        mol_type = protein
                        organism = synthetic construct
SEQUENCE: 187
CDYDEQFFTA LARLRGGDIC EYIQASFQYL PGLCIEEILD NLGCS    45

SEQ ID NO: 188          moltype = AA   length = 45
FEATURE                 Location/Qualifiers
source                  1..45
                        mol_type = protein
                        organism = synthetic construct
SITE                    13
                        note = Citrulline
SEQUENCE: 188
CDYDEQFFTA LAXLRGGDIC YYIQAKFQYL PGLCIEEILD NLGCS    45

SEQ ID NO: 189          moltype = AA   length = 45
FEATURE                 Location/Qualifiers
source                  1..45
                        mol_type = protein
                        organism = synthetic construct
SITE                    13
                        note = Citrulline
SEQUENCE: 189
CDYDEQFFTA LAXLRGGDIC EYIQAKFQYL PGLCIEEILD NLGCS    45

SEQ ID NO: 190          moltype = AA   length = 45
FEATURE                 Location/Qualifiers
source                  1..45
                        mol_type = protein
                        organism = synthetic construct
SITE                    13
                        note = Citrulline
SEQUENCE: 190
CDYDEQFFTA LAXLRGADIC EYIQAKFQYL PGLCIEEILD NLGCS    45

SEQ ID NO: 191          moltype = AA   length = 45
FEATURE                 Location/Qualifiers
source                  1..45
                        mol_type = protein
                        organism = synthetic construct
SITE                    13
                        note = Citrulline
SEQUENCE: 191
CDYDEQFFTA LAXLRGADIC YYIQAKFQYL PGLCIEEILD NLGCS    45

SEQ ID NO: 192          moltype = AA   length = 45
FEATURE                 Location/Qualifiers
source                  1..45
                        mol_type = protein
                        organism = synthetic construct
SITE                    13
                        note = Citrulline
SITE                    26
                        note = hydroxy-norleucine
SEQUENCE: 192
CDYDEQFFTA LAXLRGGDIC EYIQAXFQYL PGLCIEEILD NLGCS    45

SEQ ID NO: 193          moltype = AA   length = 45
FEATURE                 Location/Qualifiers
source                  1..45
                        mol_type = protein
                        organism = synthetic construct
SITE                    13
                        note = Citrulline
SEQUENCE: 193
CDYDEQFFTA LAXLRGGDIC EYIQAYFQYL PGLCIEEILD NLGCS    45

```
SEQ ID NO: 194         moltype = AA  length = 45
FEATURE                Location/Qualifiers
source                 1..45
                       mol_type = protein
                       organism = synthetic construct
SEQUENCE: 194
CDYDEQFFTA LARLRGADIC EYIQASFQYL PGECIEEILD NLGCS                    45

SEQ ID NO: 195         moltype = AA  length = 45
FEATURE                Location/Qualifiers
source                 1..45
                       mol_type = protein
                       organism = synthetic construct
SITE                   26
                       note = trimethyllysine
SEQUENCE: 195
CEYDEEFFTA LARLRGGDIC QYIQAKFQYL PALCIEEILD NLGCS                    45

SEQ ID NO: 196         moltype = AA  length = 45
FEATURE                Location/Qualifiers
source                 1..45
                       mol_type = protein
                       organism = synthetic construct
SITE                   26
                       note = trimethyllysine
SEQUENCE: 196
CDYDEQFFTA LKRLRGGDIC EYIQAKFQYL PGECIEEILD NLGCS                    45

SEQ ID NO: 197         moltype = AA  length = 45
FEATURE                Location/Qualifiers
source                 1..45
                       mol_type = protein
                       organism = synthetic construct
SITE                   26
                       note = trimethyllysine
SEQUENCE: 197
CDYDEQFFTA LKRLRGGDIC EYIQAKFQYL PGLCIEEILD NLGCS                    45

SEQ ID NO: 198         moltype = AA  length = 45
FEATURE                Location/Qualifiers
source                 1..45
                       mol_type = protein
                       organism = synthetic construct
SITE                   26
                       note = trimethyllysine
SEQUENCE: 198
CDYDEQFFTA LKRLRGADIC EYIQAKFQYL PGECIEEILD NLGCS                    45

SEQ ID NO: 199         moltype = AA  length = 45
FEATURE                Location/Qualifiers
source                 1..45
                       mol_type = protein
                       organism = synthetic construct
SITE                   26
                       note = trimethyllysine
SEQUENCE: 199
CDYDEQFFTA LKRLRGADIC EYIQAKFQYL PGLCIEEILD NLGCS                    45

SEQ ID NO: 200         moltype = AA  length = 45
FEATURE                Location/Qualifiers
source                 1..45
                       mol_type = protein
                       organism = synthetic construct
SITE                   13
                       note = Citrulline
SITE                   26
                       note = trimethyllysine
SEQUENCE: 200
CDYDEQFFTA LAXLRGGDIC EYIQAKFQYL PGLCIEEILD NLGCS                    45

SEQ ID NO: 201         moltype = AA  length = 45
FEATURE                Location/Qualifiers
source                 1..45
                       mol_type = protein
                       organism = synthetic construct
SITE                   26
                       note = trimethyllysine
SEQUENCE: 201
```

```
CEYDEQFFTA LARLRGADIC EYIQAKFQYL PGLCIEEILD NLGCS            45

SEQ ID NO: 202           moltype = AA   length = 45
FEATURE                  Location/Qualifiers
source                   1..45
                         mol_type = protein
                         organism = synthetic construct
SITE                     26
                         note = trimethyllysine
SEQUENCE: 202
CEYDEQFFTA LARLRGGDIC EYIQAKFQYL PGLCIEEILD NLGCS            45

SEQ ID NO: 203           moltype = AA   length = 45
FEATURE                  Location/Qualifiers
source                   1..45
                         mol_type = protein
                         organism = synthetic construct
SEQUENCE: 203
CEYDEQFFTA LARLRGGDIC EYIQARFQYL PGLCIEEILD NLGCS            45

SEQ ID NO: 204           moltype = AA   length = 45
FEATURE                  Location/Qualifiers
source                   1..45
                         mol_type = protein
                         organism = synthetic construct
SITE                     26
                         note = dimethylated arginine
SEQUENCE: 204
CEYDEQFFTA LARLRGGDIC EYIQARFQYL PGLCIEEILD NLGCS            45

SEQ ID NO: 205           moltype = AA   length = 45
FEATURE                  Location/Qualifiers
source                   1..45
                         mol_type = protein
                         organism = synthetic construct
SEQUENCE: 205
CEYDEQFFTA LKRLRGGDIC EYIQANFQYL PGLCIEEILD NLGCS            45

SEQ ID NO: 206           moltype = AA   length = 45
FEATURE                  Location/Qualifiers
source                   1..45
                         mol_type = protein
                         organism = synthetic construct
SEQUENCE: 206
CEYDEQFFTA LKRLRGGDIC EYIQATFQYL PGLCIEEILD NLGCS            45

SEQ ID NO: 207           moltype = AA   length = 45
FEATURE                  Location/Qualifiers
source                   1..45
                         mol_type = protein
                         organism = synthetic construct
SEQUENCE: 207
CEYDEQFFTA LKRLRGGDIC EYIQADFQYL PGLCIEEILD NLGCS            45

SEQ ID NO: 208           moltype = AA   length = 45
FEATURE                  Location/Qualifiers
source                   1..45
                         mol_type = protein
                         organism = synthetic construct
SEQUENCE: 208
CEYDEQFFTA LKRLRGGDIC EYIQARFQYL PGLCIEEILD NLGCS            45

SEQ ID NO: 209           moltype = AA   length = 44
FEATURE                  Location/Qualifiers
source                   1..44
                         mol_type = protein
                         organism = synthetic construct
SEQUENCE: 209
CEYDEEFFTE LERLKGGDIC YYIKKKFDKV PRLCIKEIRD KLGC             44

SEQ ID NO: 210           moltype = AA   length = 44
FEATURE                  Location/Qualifiers
source                   1..44
                         mol_type = protein
                         organism = synthetic construct
SEQUENCE: 210
CEYKEEFFTE LKRLYGGDIC YYIKKKFKKV PDLCIEEILD KLGC             44

SEQ ID NO: 211           moltype = AA   length = 44
```

```
FEATURE              Location/Qualifiers
source               1..44
                     mol_type = protein
                     organism = synthetic construct
SEQUENCE: 211
CEYDEEFFTE LERLKGGDIC YYIKKKFDKV PDLCIKEIRD KLGC                          44

SEQ ID NO: 212       moltype = AA  length = 45
FEATURE              Location/Qualifiers
source               1..45
                     mol_type = protein
                     organism = synthetic construct
SEQUENCE: 212
CEYDEQFFTA LARLRGADIC EYIQARFQYL PGLCIEEILD NLGCS                         45

SEQ ID NO: 213       moltype = AA  length = 45
FEATURE              Location/Qualifiers
source               1..45
                     mol_type = protein
                     organism = synthetic construct
SITE                 26
                     note = Citrulline
SEQUENCE: 213
CEYDEQFFTA LARLRGGDIC EYIQAXFQYL PGLCIEEILD NLGCS                         45

SEQ ID NO: 214       moltype = AA  length = 45
FEATURE              Location/Qualifiers
source               1..45
                     mol_type = protein
                     organism = synthetic construct
SITE                 26
                     note = Arg-NO2
SEQUENCE: 214
CEYDEQFFTA LARLRGGDIC EYIQARFQYL PGLCIEEILD NLGCS                         45

SEQ ID NO: 215       moltype = AA  length = 45
FEATURE              Location/Qualifiers
source               1..45
                     mol_type = protein
                     organism = synthetic construct
SITE                 11
                     note = Leu-13C6,15N
SITE                 14
                     note = Leu-13C6,15N
SITE                 30
                     note = Leu-13C6,15N
SITE                 33
                     note = Leu-13C6,15N
SITE                 39
                     note = Leu-13C6,15N
SITE                 42
                     note = Leu-13C6,15N
SEQUENCE: 215
CEYDEEFFTA LKRLRGGDIC YYIQASFQYL PGLCIEEILD NLGCS                         45

SEQ ID NO: 216       moltype = AA  length = 45
FEATURE              Location/Qualifiers
source               1..45
                     mol_type = protein
                     organism = synthetic construct
VARIANT              2
                     note = D or E
VARIANT              4
                     note = D or K
VARIANT              5
                     note = E or G
VARIANT              6
                     note = Q or E
VARIANT              10
                     note = A or E
VARIANT              12
                     note = A or K or E or S
VARIANT              13
                     note = A or R or Q or K or S or citrulline
VARIANT              15
                     note = Y or R or K
VARIANT              17
                     note = A or D or G or S
VARIANT              21
```

```
VARIANT             note = D or Q or E or L or S or Y
                    24
VARIANT             note = Q or L or K or S
                    25
                    note = A or Q or E or K
VARIANT             26
                    note = A or Q or K or S or Y or T or D or R or
                     trimethyllysine or dimethylated arginine or citrulline or
                     Arg-NO2 or OH-Norleu or Norleu
VARIANT             28
                    note = A or N or Q or D or K or S
VARIANT             29
                    note = N or T or Y
VARIANT             30
                    note = L or Y or V
VARIANT             31
                    note = P or E
VARIANT             32
                    note = A or D or Q or G or K
VARIANT             33
                    note = D or Q or E or I or L
VARIANT             36
                    note = Q or K or E
VARIANT             39
                    note = L or R
VARIANT             40
                    note = D or Q or E
VARIANT             41
                    note = N or K or Q
VARIANT             45
                    note = S or deleted
SEQUENCE: 216
CXYXXXFFTX LXXLXGXDIC XYIXXXFXXX XXXCIXEIXX XLGCX

```
VARIANT              39
                     note = L or R
VARIANT              40
                     note = D or Q or E
VARIANT              41
                     note = N or K or Q
SEQUENCE: 217
CEYXXXFFTX LXXLXGXDIC XYIXXXFXXX XXXCIXEIXX XLGCS                          45

SEQ ID NO: 218       moltype = AA  length = 45
FEATURE              Location/Qualifiers
source               1..45
                     mol_type = protein
                     organism = synthetic construct
VARIANT              4
                     note = D or K
VARIANT              5
                     note = E or G
VARIANT              6
                     note = Q or E
VARIANT              10
                     note = A or E
VARIANT              12
                     note = A or K or E or S
VARIANT              13
                     note = A or R or Q or K or S or citrulline
VARIANT              15
                     note = Y or R or K
VARIANT              17
                     note = A or D or G or S
VARIANT              21
                     note = D or Q or E or L or S or Y
VARIANT              24
                     note = Q or L or K or S
VARIANT              25
                     note = A or Q or E or K
VARIANT              26
                     note = A or Q or K or S or Y or T or D or R or
                      trimethyllysine or dimethylated arginine or citrulline or
                      Arg-NO2 or OH-Norleu or Norleu
VARIANT              28
                     note = A or N or Q or D or K or S
VARIANT              29
                     note = N or T or Y
VARIANT              30
                     note = L or Y or V
VARIANT              31
                     note = P or E
VARIANT              32
                     note = A or D or Q or G or K
VARIANT              33
                     note = D or Q or E or I or L
VARIANT              36
                     note = Q or K or E
VARIANT              39
                     note = L or R
VARIANT              40
                     note = D or Q or E
VARIANT              41
                     note = N or K or Q
SEQUENCE: 218
CDYXXXFFTX LXXLXGXDIC XYIXXXFXXX XXXCIXEIXX XLGCS                          45

SEQ ID NO: 219       moltype = AA  length = 45
FEATURE              Location/Qualifiers
source               1..45
                     mol_type = protein
                     organism = synthetic construct
VARIANT              4
                     note = D or K
VARIANT              5
                     note = E or G
VARIANT              6
                     note = Q or E
VARIANT              10
                     note = A or E
VARIANT              12
                     note = A or K or E or S
VARIANT              13
```

```
                         note = A or R or Q or K or S or citrulline
VARIANT                  15
                         note = Y or R or K
VARIANT                  21
                         note = D or Q or E or L or S or Y
VARIANT                  24
                         note = Q or L or K or S
VARIANT                  25
                         note = A or Q or E or K
VARIANT                  26
                         note = A or Q or K or S or Y or T or D or R or
                          -trimethyllysine or -dimethylated arginine or citrulline
                          or Arg-NO2 or OH-Norleu or Norleu
VARIANT                  28
                         note = A or N or Q or D or K or S
VARIANT                  29
                         note = N or T or Y
VARIANT                  30
                         note = L or Y or V
VARIANT                  31
                         note = P or E
VARIANT                  32
                         note = A or D or Q or G or K
VARIANT                  33
                         note = D or Q or E or I or L
VARIANT                  36
                         note = Q or K or E
VARIANT                  39
                         note = L or R
VARIANT                  40
                         note = D or Q or E
VARIANT                  41
                         note = N or K or Q
SEQUENCE: 219
CEYXXXFFTX LXXLXGGDIC XYIXXXFXXX XXXCIXEIXX XLGCS                         45

SEQ ID NO: 220           moltype = AA  length = 45
FEATURE                  Location/Qualifiers
source                   1..45
                         mol_type = protein
                         organism = synthetic construct
VARIANT                  5
                         note = E or G
VARIANT                  6
                         note = Q or E
VARIANT                  10
                         note = A or E
VARIANT                  12
                         note = A or K or E or S
VARIANT                  13
                         note = A or R or Q or K or S or citrulline
VARIANT                  15
                         note = Y or R or K
VARIANT                  21
                         note = D or Q or E or L or S or Y
VARIANT                  24
                         note = Q or L or K or S
VARIANT                  25
                         note = A or Q or E or K
VARIANT                  26
                         note = A or Q or K or S or Y or T or D or R or
                          -trimethyllysine or -dimethylated arginine or citrulline
                          or Arg-NO2 or OH-Norleu or Norleu
VARIANT                  28
                         note = A or N or Q or D or K or S
VARIANT                  29
                         note = N or T or Y
VARIANT                  30
                         note = L or Y or V
VARIANT                  31
                         note = P or E
VARIANT                  32
                         note = A or D or Q or G or K
VARIANT                  33
                         note = D or Q or E or I or L
VARIANT                  36
                         note = Q or K or E
VARIANT                  39
                         note = L or R
```

```
VARIANT                 40
                        note = D or Q or E
VARIANT                 41
                        note = N or K or Q
SEQUENCE: 220
CDYDXXFFTX LXXLXGGDIC XYIXXXFXXX XXXCIXEIXX XLGCS               45

SEQ ID NO: 221          moltype = AA  length = 45
FEATURE                 Location/Qualifiers
source                  1..45
                        mol_type = protein
                        organism = synthetic construct
VARIANT                 5
                        note = E or G
VARIANT                 6
                        note = Q or E
VARIANT                 10
                        note = A or E
VARIANT                 12
                        note = A or K or E or S
VARIANT                 13
                        note = A or R or Q or K or S or citrulline
VARIANT                 15
                        note = Y or R or K
VARIANT                 21
                        note = D or Q or E or L or S or Y
VARIANT                 24
                        note = Q or L or K or S
VARIANT                 25
                        note = A or Q or E or K
VARIANT                 26
                        note = A or Q or K or S or Y or T or D or R or
                         -trimethyllysine or -dimethylated arginine or citrulline
                         or Arg-NO2 or OH-Norleu or Norleu
VARIANT                 28
                        note = A or N or Q or D or K or S
VARIANT                 29
                        note = N or T or Y
VARIANT                 30
                        note = L or Y or V
VARIANT                 31
                        note = P or E
VARIANT                 32
                        note = A or D or Q or G or K
VARIANT                 33
                        note = D or Q or E or I or L
VARIANT                 36
                        note = Q or K or E
VARIANT                 39
                        note = L or R
VARIANT                 40
                        note = D or Q or E
SEQUENCE: 221
CEYDXXFFTX LXXLXGADIC XYIXXXFXXX XXXCIXEIXX NLGCS               45

SEQ ID NO: 222          moltype = AA  length = 44
FEATURE                 Location/Qualifiers
source                  1..44
                        mol_type = protein
                        organism = synthetic construct
VARIANT                 4
                        note = D or K
VARIANT                 5
                        note = E or G
VARIANT                 6
                        note = Q or E
VARIANT                 10
                        note = A or E
VARIANT                 12
                        note = A or K or E or S
VARIANT                 13
                        note = A or R or Q or K or S or citrulline
VARIANT                 15
                        note = Y or R or K
VARIANT                 21
                        note = D or Q or E or L or S or Y
VARIANT                 24
                        note = Q or L or K or S
VARIANT                 25
```

```
                        note = A or Q or E or K
VARIANT                 26
                        note = A or Q or K or S or Y or T or D or R or
                         -trimethyllysine or -dimethylated arginine or citrulline
                         or Arg-NO2 or OH-Norleu or Norleu
VARIANT                 28
                        note = A or N or Q or D or K or S
VARIANT                 29
                        note = N or T or Y
VARIANT                 30
                        note = L or Y or V
VARIANT                 31
                        note = P or E
VARIANT                 32
                        note = A or D or Q or G or K
VARIANT                 33
                        note = D or Q or E or I or L
VARIANT                 39
                        note = L or R
VARIANT                 40
                        note = D or Q or E
SEQUENCE: 222
CEYXXXFFTX LXXLXGGDIC XYIXXXFXXX XXXCIKEIXX DKGC                        44

SEQ ID NO: 223          moltype = AA  length = 45
FEATURE                 Location/Qualifiers
source                  1..45
                        mol_type = protein
                        organism = synthetic construct
VARIANT                 5
                        note = E or G
VARIANT                 6
                        note = Q or E
VARIANT                 13
                        note = A or R or Q or K or S or citrulline
VARIANT                 15
                        note = Y or R or K
VARIANT                 24
                        note = Q or L or K or S
VARIANT                 25
                        note = A or Q or E or K
VARIANT                 26
                        note = A or Q or K or S or Y or T or D or R or
                         -trimethyllysine or -dimethylated arginine or citrulline
                         or Arg-NO2 or OH-Norleu or Norleu
VARIANT                 28
                        note = A or N or Q or D or K or S
VARIANT                 29
                        note = N or T or Y
VARIANT                 30
                        note = L or Y or V
VARIANT                 31
                        note = P or E
VARIANT                 32
                        note = A or D or Q or G or K
VARIANT                 33
                        note = D or Q or E or I or L
VARIANT                 39
                        note = L or R
VARIANT                 40
                        note = D or Q or E
SEQUENCE: 223
CEYDXXFFTA LKXLXGGDIC EYIXXXFXXX XXXCIEEIXX NLGCS                       45

SEQ ID NO: 224          moltype = AA  length = 45
FEATURE                 Location/Qualifiers
source                  1..45
                        mol_type = protein
                        organism = synthetic construct
VARIANT                 5
                        note = E or G
VARIANT                 6
                        note = Q or E
VARIANT                 13
                        note = A or R or Q or K or S or citrulline
VARIANT                 15
                        note = Y or R or K
VARIANT                 24
                        note = Q or L or K or S
```

```
VARIANT             25
                    note = A or Q or E or K
VARIANT             26
                    note = A or Q or K or S or Y or T or D or R or
                     -trimethyllysine or -dimethylated arginine or citrulline
                     or Arg-NO2 or OH-Norleu or Norleu
VARIANT             28
                    note = A or N or Q or D or K or S
VARIANT             29
                    note = N or T or Y
VARIANT             30
                    note = L or Y or V
VARIANT             31
                    note = P or E
VARIANT             32
                    note = A or D or Q or G or K
VARIANT             33
                    note = D or Q or E or I or L
VARIANT             39
                    note = L or R
VARIANT             40
                    note = D or Q or E
SEQUENCE: 224
CEYDXXFFTA LKXLXGGDIC YYIXXXFXXX XXXCIEEIXX NLGC

```
                     note = D or Q or E or I or L
VARIANT              40
                     note = D or Q or E
SEQUENCE: 226
CEYDXXFFTA LKXLXGGDIC YYIQASFQXX XXXCIEEILX NLGCS          45

SEQ ID NO: 227       moltype = AA  length = 45
FEATURE              Location/Qualifiers
source               1..45
                     mol_type = protein
                     organism = synthetic construct
VARIANT              5
                     note = E or G
VARIANT              6
                     note = Q or E
VARIANT              10
                     note = A or E
VARIANT              12
                     note = A or K or E or S
VARIANT              13
                     note = A or R or Q or K or S or citrulline
VARIANT              15
                     note = Y or R or K
VARIANT              21
                     note = D or Q or E or L or S or Y
VARIANT              24
                     note = Q or L or K or S
VARIANT              25
                     note = A or Q or E or K
VARIANT              26
                     note = A or Q or K or S or Y or T or D or R or
                       -trimethyllysine or -dimethylated arginine or citrulline
                       or Arg-NO2 or OH-Norleu or Norleu
VARIANT              28
                     note = A or N or Q or D or K or S
VARIANT              29
                     note = N or T or Y
VARIANT              30
                     note = L or Y or V
VARIANT              31
                     note = P or E
VARIANT              32
                     note = A or D or Q or G or K
VARIANT              33
                     note = D or Q or E or I or L
SEQUENCE: 227
CDYDXXFFTX LXXLXGGDIC XYIXXXFXXX XXXCIEEILD NLGCS          45

SEQ ID NO: 228       moltype = AA  length = 44
FEATURE              Location/Qualifiers
source               1..44
                     mol_type = protein
                     organism = synthetic construct
VARIANT              5
                     note = E or G
VARIANT              6
                     note = Q or E
VARIANT              12
                     note = A or K or E or S
VARIANT              13
                     note = A or R or Q or K or S or citrulline
VARIANT              15
                     note = Y or R or K
VARIANT              24
                     note = Q or L or K or S
VARIANT              25
                     note = A or Q or E or K
VARIANT              26
                     note = A or Q or K or S or Y or T or D or R or
                       -trimethyllysine or -dimethylated arginine or citrulline
                       or Arg-NO2 or OH-Norleu or Norleu
VARIANT              28
                     note = A or N or Q or D or K or S
VARIANT              29
                     note = N or T or Y
VARIANT              30
                     note = L or Y or V
VARIANT              31
                     note = P or E
```

-continued

```
VARIANT                 32
                        note = A or D or Q or G or K
VARIANT                 33
                        note = D or Q or E or I or L
SEQUENCE: 228
CEYKXXFFTE LXXLXGGDIC YYIXXXFXXX XXXCIEEILD NLGC              44

SEQ ID NO: 229          moltype = AA  length = 45
FEATURE                 Location/Qualifiers
source                  1..45
                        mol_type = protein
                        organism = synthetic construct
VARIANT                 6
                        note = Q or E
VARIANT                 12
                        note = A or K or E or S
VARIANT                 24
                        note = Q or L or K or S
VARIANT                 26
                        note = A or Q or K or S or Y or T or D or R or
                        -trimethyllysine or -dimethylated arginine or citrulline
                        or Arg-NO2 or OH-Norleu or Norleu
VARIANT                 29
                        note = N or T or Y
VARIANT                 30
                        note = L or Y or V
VARIANT                 31
                        note = P or E
VARIANT                 32
                        note = A or D or Q or G or K
VARIANT                 33
                        note = D or Q or E or I or L
VARIANT                 40
                        note = D or Q or E
SEQUENCE: 229
CEYDEXFFTA LXRLRGGDIC EYIXAXFQXX XXXCIEEILX NLGCS             45

SEQ ID NO: 230          moltype = AA  length = 45
FEATURE                 Location/Qualifiers
source                  1..45
                        mol_type = protein
                        organism = synthetic construct
VARIANT                 6
                        note = Q or E
VARIANT                 13
                        note = A or R or Q or K or S or citrulline
VARIANT                 15
                        note = Y or R or K
VARIANT                 21
                        note = D or Q or E or L or S or Y
VARIANT                 24
                        note = Q or L or K or S
VARIANT                 25
                        note = A or Q or E or K
VARIANT                 26
                        note = A or Q or K or S or Y or T or D or R or
                        -trimethyllysine or -dimethylated arginine or citrulline
                        or Arg-NO2 or OH-Norleu or Norleu
VARIANT                 28
                        note = A or N or Q or D or K or S
VARIANT                 29
                        note = N or T or Y
VARIANT                 30
                        note = L or Y or V
VARIANT                 31
                        note = P or E
VARIANT                 32
                        note = A or D or Q or G or K
SEQUENCE: 230
CDYDEXFFTA LAXLXGGDIC XYIXXXFXXX XXLCIEEILD NLGCS             45

SEQ ID NO: 231          moltype = AA  length = 45
FEATURE                 Location/Qualifiers
source                  1..45
                        mol_type = protein
                        organism = synthetic construct
VARIANT                 12
                        note = A or K or E or S
VARIANT                 26
```

```
                                note = A or Q or K or S or Y or T or D or R or
                                -trimethyllysine or -dimethylated arginine or citrulline
                                or Arg-NO2 or OH-Norleu or Norleu
VARIANT                         30
                                note = L or Y or V
VARIANT                         31
                                note = P or E
VARIANT                         32
                                note = A or D or Q or G or K
SEQUENCE: 231
CEYDEQFFTA LXRLRGGDIC EYIQAXFQYX XXLCIEEILD NLGCS                                        45

SEQ ID NO: 232                  moltype = AA  length = 45
FEATURE                         Location/Qualifiers
source                          1..45
                                mol_type = protein
                                organism = synthetic construct
VARIANT                         12
                                note = A or K or E or S
VARIANT                         26
                                note = A or Q or K or S or Y or T or D or R or
                                -trimethyllysine or -dimethylated arginine or citrulline
                                or Arg-NO2 or OH-Norleu or Norleu
VARIANT                         30
                                note = L or Y or V
VARIANT                         31
                                note = P or E
VARIANT                         32
                                note = A or D or Q or G or K
SEQUENCE: 232
CEYDEEFFTA LXRLRGGDIC EYIQAXFQYX XXLCIEEILD NLGCS                                        45

SEQ ID NO: 233                  moltype = AA  length = 45
FEATURE                         Location/Qualifiers
source                          1..45
                                mol_type = protein
                                organism = synthetic construct
VARIANT                         2
                                note = E or G or A or S or T or D or N or K or R or Y or F
                                or V or I or W
VARIANT                         3
                                note = Y or P or G or A or S or T or Q or K or H or F or W
                                or V or M or D or E or L or I
VARIANT                         4
                                note = D or S or N or R or Y or L or M or G or T or I
VARIANT                         5
                                note = E or G or D or Q or F or W or V or L or I or M or K
                                or R
VARIANT                         6
                                note = E or P or G or D or Q or N or K or Y or F or W or V
VARIANT                         7
                                note = F or Y or W
VARIANT                         8
                                note = F or Y or W or I or M
VARIANT                         9
                                note = T or P or A or S or D or Q or N or K or Y or F or V
                                or M or E or R or L
VARIANT                         10
                                note = A or S or E or N or K or F or W or V or L or I or G
                                or T or D or Q or R or H
VARIANT                         11
                                note = L or T or I or M
VARIANT                         12
                                note = K or L or G or A or S or T or N or R or H or F or W
                                or V or I or M
VARIANT                         13
                                note = R or G or A or S or E or N or K or Y or W or L or I
                                or M
VARIANT                         14
                                note = L or T or V or I or M
VARIANT                         15
                                note = R or T or Q or K or L or I or M or V
VARIANT                         16
                                note = G or D or N or K or R or H or Y or W or V or L or I
                                or M
VARIANT                         17
                                note = G or P or A or S or T or D or Q or N or R or H or Y
                                or F or W or V or L or M
VARIANT                         18
```

```
                    note = D or P or G or A or T or E or Q or N or K or Y or F
                    or W or V or I or M or S
VARIANT             19
                    note = I or P or A or T or D or N or Y or V or M or G or Q
VARIANT             21
                    note = Y or S or T or D or E or K or F or W or L or I or V
VARIANT             22
                    note = Y or E
VARIANT             23
                    note = I or A or T or Y or V or L or M or F
VARIANT             24
                    note = Q or P or G or D or K or R or H or F or V or L or I
                    or M or N
VARIANT             25
                    note = A or P or S or D or E or Q or K or R or H or Y or F
                    or W or V or I or M or T
VARIANT             26
                    note = S or P or G or A or D or Q or N or R or F or V or L
                    or I or T or E or W
VARIANT             27
                    note = F or P or A or S or K or H or Y or W or M or E or V
VARIANT             28
                    note = Q or P or G or A or S or D or E or K or R or H or Y
                    or W or V or L or F or I
VARIANT             29
                    note = Y or P or A or S or E or Q or N or K or F or W or L
                    or I or M or T or V
VARIANT             30
                    note = L or P or G or A or S or T or E or N or R or H or F
                    or W or V or I or M or Q or K
VARIANT             31
                    note = P or G or A or T or D or E or Q or N or K or R or H
                    or Y or V or S or W or L or I
VARIANT             32
                    note = G or A or S or D or N or R or H or Y or L or I or V
VARIANT             33
                    note = L or P or G or A or S or D or E or N or K or R or H
                    or Y or F or W or V or I or M
VARIANT             35
                    note = I or P or S or D or E or N or K or R or Y or F or W
                    or L or M
VARIANT             36
                    note = E or G or A or S or T or D or Q or K or R or H or Y
                    or W or L or I or M
VARIANT             37
                    note = E or P or G or A or S or T or N or K or R or H or Y
                    or F or W or V or D
VARIANT             38
                    note = I or A or S or E or Y or F or W or V or L or T or H
VARIANT             39
                    note = L or S or T or E or N or R or H or Y or F or W or V
                    or M or D or I
VARIANT             40
                    note = D or G or A or S or E or Q or R or H or F or W or V
                    or L or I or M or N or K
VARIANT             41
                    note = N or G or A or S or D or Q or R or H or Y or F or V
                    or L or I or M or P or K
VARIANT             42
                    note = L or P or G or Q or N or H or F or W or I or M or S
VARIANT             43
                    note = G or P or A or T or D or N or K or R or Y or F or W
                    or V or I or Q
SEQUENCE: 233
CXXXXXXXX XXXXXXXXC XXXXXXXXX XXXCXXXXX XXXCS                             45

SEQ ID NO: 234      moltype = AA  length = 45
FEATURE             Location/Qualifiers
source              1..45
                    mol_type = protein
                    organism = synthetic construct
VARIANT             2
                    note = E or P or G or A or S or T or Q or N or K or R or H
                    or Y or F or W or V or L or I or M
VARIANT             3
                    note = Y or P or G or A or S or T or D or E or Q or N or K
                    or R or H or F or W or V or L or I or M
VARIANT             4
                    note = D or P or G or A or S or T or E or Q or N or K or R
```

-continued

```
                   or H or Y or F or W or V or L or I or M
VARIANT            5
                   note = E or P or G or S or T or D or Q or N or K or R or H
                   or F or W or V or L or I or M or Y
VARIANT            6
                   note = E or P or G or A or S or T or D or Q or N or K or R
                   or H or F or W or V or L or I or M or Y
VARIANT            7
                   note = F or Y or W
VARIANT            8
                   note = F or T or Y or W or V or L or I or M
VARIANT            9
                   note = T or P or G or S or D or E or N or K or R or H or Y
                   or F or V or L or I or M or A or Q or W
VARIANT            10
                   note = A or P or G or S or T or D or E or Q or N or K or R
                   or H or Y or F or W or V or L or I or M
VARIANT            11
                   note = L or A or V or I or M
VARIANT            12
                   note = A or G or S or D or E or Q or N or K or R or H or Y
                   or F or W or V or L or I or M or T
VARIANT            13
                   note = R or P or S or T or D or E or Q or K or H or Y or F
                   or V or L or M or G or A or N or W or I
VARIANT            14
                   note = L or A or T or F or V or I or M
VARIANT            15
                   note = R or Q or Y or F or W or V or L or I or M or K
VARIANT            16
                   note = G or P or A or S or T or D or E or Q or N or K or R
                   or H or Y or F or W or V or L or M or I
VARIANT            17
                   note = G or P or A or S or T or D or E or Q or N or K or R
                   or H or Y or W or V or L or I or M or F
VARIANT            18
                   note = D or P or G or A or S or T or E or Q or N or K or R
                   or H or Y or W or V or I or M or F or L
VARIANT            19
                   note = I or P or G or A or S or T or D or E or Q or N or K
                   or R or Y or F or W or V or L or M or H
VARIANT            21
                   note = Y or P or G or A or S or T or D or E or Q or N or K
                   or R or H or F or W or V or L or I or M
VARIANT            22
                   note = Y or H or F
VARIANT            23
                   note = I or G or A or S or T or Y or W or V or L or M or F
VARIANT            24
                   note = Q or G or S or T or D or E or N or K or R or H or F
                   or W or V or L or I or M or P or A or Y
VARIANT            25
                   note = A or G or S or T or D or E or Q or N or K or R or H
                   or Y or F or W or V or M or P or L or I
VARIANT            26
                   note = K or P or G or A or S or T or D or E or Q or N or R
                   or H or Y or F or W or V or L or I or M
VARIANT            27
                   note = F or P or G or A or S or T or D or E or Q or N or K
                   or R or H or Y or W or V or L or I or M
VARIANT            28
                   note = Q or P or G or A or S or T or D or E or N or K or R
                   or H or Y or F or W or V or L or I or M
VARIANT            29
                   note = Y or P or G or A or S or T or D or E or N or K or R
                   or H or F or W or V or L or I or M or Q
VARIANT            30
                   note = L or P or G or A or S or T or D or E or Q or N or K
                   or R or H or Y or F or W or V or I or M
VARIANT            31
                   note = P or G or A or S or T or D or Q or N or K or R or H
                   or Y or F or V or I or M or E or W or L
VARIANT            32
                   note = G or P or A or S or T or D or E or Q or N or K or R
                   or H or Y or F or W or V or L or I or M
VARIANT            33
                   note = L or P or G or A or S or T or D or E or Q or N or K
                   or R or H or Y or F or W or V or I or M
VARIANT            35
```

```
                        note = I or P or G or A or S or T or D or E or Q or N or K
                        or R or Y or F or W or V or L or M or H
VARIANT                 36
                        note = E or P or G or A or S or D or Q or N or R or H or F
                        or V or L or I or M or T or K or Y or W
VARIANT                 37
                        note = E or P or G or A or S or T or D or N or K or H or Y
                        or F or W or V or L or I or M or Q or R
VARIANT                 38
                        note = I or P or G or A or S or T or E or Q or N or K or H
                        or Y or F or W or V or L or M
VARIANT                 39
                        note = L or G or A or S or T or D or E or Q or N or K or R
                        or H or Y or W or V or I or M or F
VARIANT                 40
                        note = D or P or G or A or S or E or Q or N or K or R or H
                        or Y or F or W or V or L or I or M or T
VARIANT                 41
                        note = N or P or G or A or S or T or D or E or Q or K or R
                        or H or Y or F or W or V or L or I or M
VARIANT                 42
                        note = L or G or A or S or T or E or Q or N or K or R or H
                        or Y or F or W or V or I or M
VARIANT                 43
                        note = G or P or A or S or T or D or E or Q or N or K or R
                        or H or Y or F or W or V or L or M or I
SEQUENCE: 234
CXXXXXXXXX XXXXXXXXXC XXXXXXXXXX XXXCXXXXXX XXXCS                              45

SEQ ID NO: 235          moltype = AA  length = 45
FEATURE                 Location/Qualifiers
source                  1..45
                        mol_type = protein
                        organism = synthetic construct
VARIANT                 2
                        note = E or P or G or A or S or T or D or Q or N or K or R
                        or H or Y or W or V or L or I or M or F
VARIANT                 3
                        note = Y or P or G or A or S or T or D or E or Q or K or R
                        or H or F or W or V or L or I or M or N
VARIANT                 4
                        note = D or P or A or S or E or Q or N or H
VARIANT                 5
                        note = E or P or G or A or T or Q or N or K or R or H or Y
                        or F or W or V or L or I or M or S or D
VARIANT                 6
                        note = Q or P or G or A or S or T or D or E or N or K or R
                        or H or Y or F or W or V or L or I or M
VARIANT                 7
                        note = F or Y or W
VARIANT                 8
                        note = F or Y or W or V or I or M
VARIANT                 9
                        note = T or P or G or A or S or D or Q or N or R or H or Y
                        or F or V or L or I or M or E or K or W
VARIANT                 10
                        note = A or G or T or D or E or Q or N or K or R or H or W
                        or L or I or M or S or Y or F or V
VARIANT                 11
                        note = L or V or I or M
VARIANT                 12
                        note = A or G or S or T or D or K or R or Y or F or W or V
                        or L or I or M or E or Q or N or H
VARIANT                 13
                        note = R or G or A or S or T or D or Q or N or K or H or Y
                        or F or W or V or L or M or E or I
VARIANT                 14
                        note = L or T or V or I or M
VARIANT                 15
                        note = R or Q or K or I or M
VARIANT                 16
                        note = G or A or T or D or E or Q or N or K or R or H or Y
                        or W or V or L or I or M or P or S or F
VARIANT                 17
                        note = G or P or A or S or T or D or E or Q or N or K or R
                        or H or Y or F or W or V or L or I or M
VARIANT                 18
                        note = D or P or G or A or S or T or E or N or K or H or Y
                        or F or L or M or Q or K
```

| | | |
|---|---|---|
| VARIANT | 19 | |
| | note = I or G or A or S or T or E or Q or N or K or R or H or Y or F or W or V or L or M | |
| VARIANT | 21 | |
| | note = Y or P or G or A or S or D or E or Q or N or K or R or H or F or W or V or L or I or M or T | |
| VARIANT | 23 | |
| | note = I or A or T or Y or F or W or V or L or M | |
| VARIANT | 24 | |
| | note = Q or P or A or S or D or E or N or K or H or Y or F or W or V or L or I or G or T or R or M | |
| VARIANT | 25 | |
| | note = E or P or G or A or S or T or D or Q or N or R or H or Y or F or W or V or L or I or M or K | |
| VARIANT | 26 | |
| | note = Q or G or A or S or T or E or N or K or R or H or F or W or V or L or I or M or D or Y | |
| VARIANT | 27 | |
| | note = F or Y or W or L or I or M or V | |
| VARIANT | 28 | |
| | note = A or P or G or S or T or D or E or Q or N or K or R or H or Y or W or V or L or I or M or F | |
| VARIANT | 29 | |
| | note = T or P or G or A or S or D or E or Q or K or R or H or Y or F or W or V or L or I or M or N | |
| VARIANT | 30 | |
| | note = V or P or G or A or T or D or E or N or K or R or H or Y or F or W or I or M or S or Q or L | |
| VARIANT | 31 | |
| | note = P or G or A or S or T or D or E or Q or N or K or R or H or Y or F or W or V or L or I or M | |
| VARIANT | 32 | |
| | note = G or P or A or T or D or E or Q or N or K or R or H or Y or F or W or V or L or I or M or S | |
| VARIANT | 33 | |
| | note = L or P or G or A or S or T or D or E or Q or K or R or H or Y or F or W or V or I or M or N | |
| VARIANT | 34 | |
| | note = I or P or G or A or S or T or D or E or Q or N or K or R or H or Y or F or W or L or M or V | |
| VARIANT | 35 | |
| | note = E or P or G or A or S or T or D or N or R or H or F or W or V or L or I or M or K or Y | |
| VARIANT | 36 | |
| | note = E or P or G or A or S or T or D or N or R or H or Y or W or V or L or I or M or Q or K or F | |
| VARIANT | 38 | |
| | note = I or G or A or S or E or Q or H or Y or W or V or L or M or P or F | |
| VARIANT | 39 | |
| | note = L or G or A or S or T or D or E or Q or N or K or H or Y or F or W or V or I or M or R | |
| VARIANT | 40 | |
| | note = D or P or G or A or S or T or E or Q or N or R or H or Y or F or W or L or I or M or K | |
| VARIANT | 41 | |
| | note = Q or P or G or A or S or T or D or E or N or K or R or H or Y or F or W or V or L or I or M | |
| VARIANT | 42 | |
| | note = L or G or A or S or T or E or Q or R or H or Y or F or V or I or M or N or W | |
| VARIANT | 43 | |
| | note = G or P or A or S or T or D or E or Q or N or K or F or W or V or L or I or M or R or H or Y | |
| SEQUENCE: 235 | | |
| CXXXXXXXXX XXXXXXXXXC XYXXXXXXXX XXXCXXXXXX XXXCS | | 45 |
| | | |
| SEQ ID NO: 236 | moltype = AA  length = 45 | |
| FEATURE | Location/Qualifiers | |
| source | 1..45 | |
| | mol_type = protein | |
| | organism = synthetic construct | |
| VARIANT | 2 | |
| | note = E or P or G or A or S or T or D or Q or N or K or R or H or Y or W or V or L or I or M or F | |
| VARIANT | 3 | |
| | note = Y or P or G or A or S or T or D or E or Q or N or K or H or W or V or L or I or M or R or F | |
| VARIANT | 4 | |

-continued

```
                    note = D or P or G or A or T or Q or N or K or R or H or Y
                      or F or W or V or L or M or S or E or I
VARIANT             5
                    note = E or P or G or A or S or T or D or N or K or R or H
                      or Y or F or W or V or L or Q or I or M
VARIANT             6
                    note = E or P or G or A or D or Q or N or R or H or Y or F
                      or W or V or L or M or S or K or I
VARIANT             7
                    note = F or Y or W
VARIANT             8
                    note = F or H or Y or W or V or L or I or M
VARIANT             9
                    note = T or P or G or S or D or E or Q or N or K or R or H
                      or Y or F or W or V or L or I or M or A
VARIANT             10
                    note = A or P or G or T or D or E or Q or N or K or R or H
                      or Y or F or W or V or L or M or S or I
VARIANT             11
                    note = L or A or V or I or M
VARIANT             12
                    note = A or P or G or S or T or D or E or K or R or H or Y
                      or F or W or V or L or I or M or Q or N
VARIANT             13
                    note = R or P or A or S or T or D or E or Q or N or K or H
                      or Y or F or W or V or L or I or M or G
VARIANT             14
                    note = L or T or F or V or M or I
VARIANT             15
                    note = R or Q or N or K or H or F or W or V or L or I or M
                      or Y
VARIANT             16
                    note = G or P or A or T or D or E or Q or N or K or R or H
                      or Y or F or W or V or L or I or M or S
VARIANT             17
                    note = G or A or S or D or E or Q or N or K or R or H or Y
                      or F or W or V or L or I or M or P
VARIANT             18
                    note = D or P or G or A or S or T or E or Q or N or K or R
                      or Y or F or W or V or L or I or M or H
VARIANT             19
                    note = I or P or G or A or S or T or D or E or Q or N or K
                      or R or H or Y or F or W or V or L or M
VARIANT             21
                    note = Q or P or G or A or S or D or E or N or R or H or Y
                      or F or W or V or I or M or T or K or L
VARIANT             22
                    note = Y or H or F
VARIANT             23
                    note = I or G or A or S or T or Y or F or V or L or M
VARIANT             24
                    note = Q or P or G or A or S or E or N or K or R or H or Y
                      or F or W or V or L or I or M or T or D
VARIANT             25
                    note = A or P or G or S or T or D or E or Q or N or K or H
                      or Y or F or W or V or L or I or M or R
VARIANT             26
                    note = trimethyllysine or K or P or G or S or T or D or E
                      or Q or N or R or H or Y or F or W or V or L or M or A or I
VARIANT             27
                    note = F or P or G or A or S or D or E or Q or N or K or R
                      or H or Y or W or V or L or I or M
VARIANT             28
                    note = Q or P or G or A or S or T or D or E or N or K or R
                      or H or Y or F or W or V or L or I or M
VARIANT             29
                    note = Y or P or G or A or S or T or D or E or Q or N or K
                      or R or H or F or W or V or L or I or M
VARIANT             30
                    note = L or P or G or A or T or D or E or Q or N or K or R
                      or H or Y or F or W or V or I or M or S
VARIANT             31
                    note = P or G or S or T or D or E or Q or N or K or R or H
                      or Y or W or V or L or I or M or A or F
VARIANT             32
                    note = A or P or G or S or T or D or Q or N or K or R or H
                      or Y or F or W or V or I or M or E or L
VARIANT             33
                    note = L or P or G or A or S or T or D or E or Q or N or K
```

```
                              or R or H or Y or F or W or V or I or M
VARIANT                       35
                              note = I or P or G or A or S or T or D or E or Q or N or R
                              or H or Y or W or V or L or M or K or F
VARIANT                       36
                              note = E or P or A or S or T or D or Q or N or K or R or H
                              or Y or F or W or V or L or I or M or G
VARIANT                       37
                              note = E or G or A or S or D or Q or N or K or R or H or Y
                              or F or W or V or L or I or M or T
VARIANT                       38
                              note = I or P or G or A or S or T or D or E or Q or N or H
                              or Y or F or W or V or L or M or K or R
VARIANT                       39
                              note = L or G or A or S or T or D or E or Q or N or R or H
                              or Y or W or V or I or M or K or F
VARIANT                       40
                              note = D or P or G or A or S or T or E or Q or K or R or H
                              or Y or W or V or L or I or M or N or F
VARIANT                       41
                              note = N or P or G or A or S or T or D or E or Q or K or R
                              or H or Y or F or W or V or L or I or M
VARIANT                       42
                              note = L or G or A or S or D or E or Q or N or K or R or H
                              or Y or F or W or V or I or M
VARIANT                       43
                              note = G or P or A or S or T or D or E or Q or N or K or R
                              or H or Y or F or W or V or L or I or M
SEQUENCE: 236
CXXXXXXXXX XXXXXXXXXC XXXXXXXXXX XXXCXXXXXX XXXCS                      45

SEQ ID NO: 237                moltype = AA  length = 45
FEATURE                       Location/Qualifiers
source                        1..45
                              mol_type = protein
                              organism = synthetic construct
VARIANT                       2
                              note = E or P or G or A or S or T or D or Q or N or K or R
                              or H or Y or W or V or L or I or M or F
VARIANT                       3
                              note = Y or P or G or A or S or T or D or E or Q or N or K
                              or H or W or V or L or I or M or R or F
VARIANT                       4
                              note = D or P or G or A or T or Q or N or K or R or H or Y
                              or F or W or V or L or M or S or E or I
VARIANT                       5
                              note = E or P or G or A or S or T or D or N or K or R or H
                              or Y or F or W or V or L or Q or I or M
VARIANT                       6
                              note = E or P or G or A or D or Q or N or R or H or Y or F
                              or W or V or L or M or S or K or I
VARIANT                       7
                              note = F or Y or W
VARIANT                       8
                              note = F or H or Y or W or V or L or I or M
VARIANT                       9
                              note = T or P or G or S or D or E or Q or N or K or R or H
                              or Y or F or W or V or L or I or M or A
VARIANT                       10
                              note = A or P or G or T or D or E or Q or N or K or R or H
                              or Y or F or W or V or L or M or S or I
VARIANT                       11
                              note = L or A or V or I or M
VARIANT                       12
                              note = A or P or G or S or T or D or E or K or R or H or Y
                              or F or W or V or L or I or M or Q or N
VARIANT                       13
                              note = R or P or A or S or T or D or E or Q or N or K or H
                              or Y or F or W or V or L or I or M or G
VARIANT                       14
                              note = L or T or F or V or M or I
VARIANT                       15
                              note = R or Q or N or K or H or F or W or V or L or I or M
                              or Y
VARIANT                       16
                              note = G or P or A or T or D or E or Q or N or K or R or H
                              or Y or F or W or V or L or I or M or S
VARIANT                       17
                              note = G or A or S or D or E or Q or N or K or R or H or Y
```

|         |                                                                                                                      |
|---------|----------------------------------------------------------------------------------------------------------------------|
|         | or F or W or V or L or I or M or P                                                                                   |
| VARIANT | 18                                                                                                                   |
|         | note = D or P or G or A or S or T or E or Q or N or K or R or Y or F or W or V or L or I or M or H                   |
| VARIANT | 19                                                                                                                   |
|         | note = I or P or G or A or S or T or D or E or Q or N or K or R or H or Y or F or W or V or L or M                   |
| VARIANT | 21                                                                                                                   |
|         | note = Q or P or G or A or S or D or E or N or R or H or Y or F or W or V or I or M or T or K or L                   |
| VARIANT | 22                                                                                                                   |
|         | note = Y or H or F                                                                                                   |
| VARIANT | 23                                                                                                                   |
|         | note = I or G or A or S or T or Y or F or V or L or M                                                                |
| VARIANT | 24                                                                                                                   |
|         | note = Q or P or G or A or S or E or N or K or R or H or Y or F or W or V or L or I or M or T or D                   |
| VARIANT | 25                                                                                                                   |
|         | note = A or P or G or S or T or D or E or Q or N or K or H or Y or F or W or V or L or I or M or R                   |
| VARIANT | 26                                                                                                                   |
|         | note = K or P or G or S or T or D or E or Q or N or R or H or Y or F or W or V or L or M or A or I                   |
| VARIANT | 27                                                                                                                   |
|         | note = F or P or G or A or S or D or E or Q or N or K or R or H or Y or W or V or L or I or M                        |
| VARIANT | 28                                                                                                                   |
|         | note = Q or P or G or A or S or T or D or E or N or K or R or H or Y or F or W or V or L or I or M                   |
| VARIANT | 29                                                                                                                   |
|         | note = Y or P or G or A or S or T or D or E or Q or N or K or R or H or F or W or V or L or I or M                   |
| VARIANT | 30                                                                                                                   |
|         | note = L or P or G or A or T or D or E or Q or N or K or R or H or Y or F or W or V or I or M or S                   |
| VARIANT | 31                                                                                                                   |
|         | note = P or G or S or T or D or E or Q or N or K or R or H or Y or W or V or L or I or M or A or F                   |
| VARIANT | 32                                                                                                                   |
|         | note = A or P or G or S or T or D or Q or N or K or R or H or Y or F or W or V or I or M or E or L                   |
| VARIANT | 33                                                                                                                   |
|         | note = L or P or G or A or S or T or D or E or Q or N or K or R or H or Y or F or W or V or I or M                   |
| VARIANT | 35                                                                                                                   |
|         | note = I or P or G or A or S or T or D or E or Q or N or R or H or Y or W or V or L or M or K or F                   |
| VARIANT | 36                                                                                                                   |
|         | note = E or P or A or S or T or D or Q or N or K or R or H or Y or F or W or V or L or I or M or G                   |
| VARIANT | 37                                                                                                                   |
|         | note = E or G or A or S or D or Q or N or K or R or H or Y or F or W or V or L or I or M or T                        |
| VARIANT | 38                                                                                                                   |
|         | note = I or P or G or A or S or T or D or E or Q or N or H or Y or F or W or V or L or M or K or R                   |
| VARIANT | 39                                                                                                                   |
|         | note = L or G or A or S or T or D or E or Q or N or R or H or Y or W or V or I or M or K or F                        |
| VARIANT | 40                                                                                                                   |
|         | note = D or P or G or A or S or T or E or Q or K or R or H or Y or W or V or L or I or M or N or F                   |
| VARIANT | 41                                                                                                                   |
|         | note = N or P or G or A or S or T or D or E or Q or K or R or H or Y or F or W or V or L or I or M                   |
| VARIANT | 42                                                                                                                   |
|         | note = L or G or A or S or D or E or Q or N or K or R or H or Y or F or W or V or I or M                             |
| VARIANT | 43                                                                                                                   |
|         | note = G or P or A or S or T or D or E or Q or N or K or R or H or Y or F or W or V or L or I or M                   |
| SEQUENCE: 237 |                                                                                                                |
| CXXXXXXXXX XXXXXXXXC XXXXXXXXX XXXCXXXXXX XXXCS        45                                                                  |
|         |                                                                                                                      |
| SEQ ID NO: 238 | moltype = AA   length = 15                                                                                    |
| FEATURE | Location/Qualifiers                                                                                                  |
| source  | 1..15                                                                                                                |
|         | mol_type = protein                                                                                                   |
|         | organism = synthetic construct                                                                                       |

```
SITE                    3
                        note = 1-naphthylamine
SITE                    4
                        note = D-aspartic acid
SITE                    7
                        note = homo-arginine
SITE                    13
                        note = hydroxyproline
SEQUENCE: 238
CPXDCMRDWS TPPWC                                                        15

SEQ ID NO: 239          moltype = AA  length = 20
FEATURE                 Location/Qualifiers
source                  1..20
                        mol_type = protein
                        organism = synthetic construct
VARIANT                 2..10
                        note = Residue may be deleted
SITE                    11..20
                        note = gamma-Glu
VARIANT                 12..20
                        note = Residue may be deleted
SEQUENCE: 239
GGGGGGGGGG EEEEEEEEEE                                                   20

SEQ ID NO: 240          moltype = AA  length = 10
FEATURE                 Location/Qualifiers
source                  1..10
                        mol_type = protein
                        organism = synthetic construct
VARIANT                 2..10
                        note = Residue may be deleted
SEQUENCE: 240
GGGGGGGGGG                                                              10

SEQ ID NO: 241          moltype = AA  length = 81
FEATURE                 Location/Qualifiers
source                  1..81
                        mol_type = protein
                        organism = synthetic construct
VARIANT                 2..16
                        note = Any amino acid or deleted
VARIANT                 18..32
                        note = Any amino acid or deleted
VARIANT                 34..48
                        note = Any amino acid or deleted
VARIANT                 50..64
                        note = Any amino acid or deleted
VARIANT                 66..80
                        note = Any amino acid or deleted
SEQUENCE: 241
CXXXXXXXX XXXXXXCXXX XXXXXXXXX XXCXXXXXXX XXXXXXXCX XXXXXXXXX           60
XXXXCXXXXX XXXXXXXXXX C                                                 81

SEQ ID NO: 242          moltype = AA  length = 13
FEATURE                 Location/Qualifiers
source                  1..13
                        mol_type = protein
                        organism = synthetic construct
SITE                    3
                        note = 1-naphthylamine
SITE                    4
                        note = D-aspartic acid
SITE                    7
                        note = homo-arginine
SITE                    13
                        note = hydroxyproline
SEQUENCE: 242
CPXDCMRDWS TPP                                                          13

SEQ ID NO: 243          moltype = AA  length = 45
FEATURE                 Location/Qualifiers
source                  1..45
                        mol_type = protein
                        organism = synthetic construct
VARIANT                 2
                        note = E or D
VARIANT                 6
                        note = E or Q
```

```
VARIANT              9
                     note = T or A or N
VARIANT              10
                     note = A or G
VARIANT              12
                     note = A or trimethyllysine or dimethyl lysine or
                      Nepsilon-isopropyl-L-Lysine or K or Q or S or methyl
                      lysine or Acetylated Lysine
VARIANT              13
                     note = R or citrulline, or K
VARIANT              15
                     note = R or citrulline
VARIANT              17
                     note = G or A
VARIANT              21
                     note = Q or Y or E
VARIANT              24
                     note = Q or K
VARIANT              25
                     note = A or Q or K
VARIANT              26
                     note = trimethyllysine or dimethyl lysine or methyl lysine
                      or Nepsilon-isopropyl-L-Lysine or K or S
VARIANT              28
                     note = Q or K or D
VARIANT              29
                     note = Y or K
VARIANT              30
                     note = L or V
VARIANT              32
                     note = A or D or G or K
VARIANT              33
                     note = L or E
VARIANT              36
                     note = E or K
VARIANT              41
                     note = N or K
VARIANT              45
                     note = S or deleted
SEQUENCE: 243
CXYDEXFFXX LXXLXGXDIC XYIXXXFXXX PXXCIXEILD XLGCX                       45

SEQ ID NO: 244       moltype = AA   length = 45
FEATURE              Location/Qualifiers
source               1..45
                     mol_type = protein
                     organism = synthetic construct
VARIANT              2
                     note = E or D
VARIANT              6
                     note = E or Q
VARIANT              9
                     note = T or A or N
VARIANT              10
                     note = A or G
VARIANT              12
                     note = A or trimethyllysine or dimethyl lysine or
                      Nepsilon-isopropyl-L-Lysine or K or Q or S or methyl
                      lysine or Kac
VARIANT              13
                     note = R or citrulline, or K
VARIANT              15
                     note = R or citrulline
VARIANT              17
                     note = G or A
VARIANT              21
                     note = Q or Y or E
VARIANT              24
                     note = Q or K
VARIANT              25
                     note = A or Q or K
VARIANT              26
                     note = trimethyllysine or dimethyl lysine or methyl lysine
                      or Nepsilon-isopropyl-L-Lysine or K or S
VARIANT              28
                     note = Q or K or D
VARIANT              29
                     note = Y or K
VARIANT              30
```

```
                        note = L or V
VARIANT                 32
                        note = A or D or G or K
VARIANT                 33
                        note = L or E
VARIANT                 36
                        note = E or K
VARIANT                 41
                        note = N or K
VARIANT                 45
                        note = S or deleted
SEQUENCE: 244
CXYDEXFFXX LXXLXGXDIC XYIXXXFXXX PXXCIXEILD XLGCX                    45

SEQ ID NO: 245          moltype = AA  length = 45
FEATURE                 Location/Qualifiers
source                  1..45
                        mol_type = protein
                        organism = synthetic construct
VARIANT                 2
                        note = E or D or K
VARIANT                 3
                        note = Y or D
VARIANT                 6
                        note = E or Q or K
VARIANT                 9
                        note = T or A or N or K or L
VARIANT                 10
                        note = A or G or D or E
VARIANT                 12
                        note = A or trimethyllysine or dimethyl lysine or
                         Nepsilon-isopropyl-L-Lysine or K or Q or S or Kac or
                         methyl lysine or H
VARIANT                 13
                        note = R or citrulline, K or A or S
VARIANT                 15
                        note = R or citrulline
VARIANT                 17
                        note = G or A or D
VARIANT                 21
                        note = Q or Y or E or S or D
VARIANT                 24
                        note = Q or K or Acetylated Lysine, or S
VARIANT                 25
                        note = A or Q or K or Acetylated Lysine, L or E
VARIANT                 26
                        note = trimethyllysine or dimethyl lysine or methyl lysine
                         or Nepsilon-isopropyl-L-Lysine or K or  Acetylated Lysine,
                         S or Q or hydroxynorleucine
VARIANT                 28
                        note = Q or K or D or Acetylated Lysine or N
VARIANT                 29
                        note = Y or K or Acetylated Lysine, T or N
VARIANT                 30
                        note = L or V
VARIANT                 32
                        note = A or D or G or K or E or Acetylated Lysine
VARIANT                 33
                        note = L or E or I or Q
VARIANT                 36
                        note = E or K
VARIANT                 40
                        note = D or K or E
VARIANT                 41
                        note = N or K or Acetylated Lysine, or Q
VARIANT                 45
                        note = S or deleted
SEQUENCE: 245
CXXDEXFFXX LXXLXGXDIC XYIXXXFXXX PXXCIXEILX XLGCX                    45

SEQ ID NO: 246          moltype = AA  length = 45
FEATURE                 Location/Qualifiers
source                  1..45
                        mol_type = protein
                        organism = synthetic construct
VARIANT                 2
                        note = E or D or K
VARIANT                 3
                        note = Y or D
```

```
VARIANT             4
                    note = D or K or E
VARIANT             5
                    note = E or G or F or K
VARIANT             6
                    note = E or Q or K or A
VARIANT             7
                    note = F or Y
VARIANT             9
                    note = T or A or N or K or L or E or D or S or Dap or Q
VARIANT             10
                    note = A or G or D or E or K or T or L
VARIANT             11
                    note = L or Leu-13C6,15N
VARIANT             12
                    note = A or trimethyllysine or dimethyl lysine or methyl
                     lysine or Nepsilon-isopropyl-L-Lysine or K or Q or S or
                     Acetylated Lysine, E or H
VARIANT             13
                    note = R or citrulline, K or A or  S or Q
VARIANT             14
                    note = L or Leu-13C6,15N
VARIANT             15
                    note = R or citrulline, Y or K
VARIANT             16
                    note = G or R
VARIANT             17
                    note = G or A or D or T or S
VARIANT             18
                    note = D or K or E or N or S or T or Q
VARIANT             21
                    note = Q or Y or E or S or  D or L
VARIANT             24
                    note = Q or K or Acetylated Lysine, S or R or L
VARIANT             25
                    note = A or Q or K or Acetylated Lysine, L or E
VARIANT             26
                    note = trimethyllysine or dimethyl lysine or methyl lysine
                     or Nepsilon-isopropyl-L-Lysine or K or  K (Ac), S or Q or
                     R or hydroxynorleucine or Norleucine or T or D or
                     dimethylated arginine or citrulline or Arg(NO2) or A or N
VARIANT             28
                    note = Q or K or D or Acetylated Lysine, N or P or S or A
VARIANT             29
                    note = Y or K or Acetylated Lysine, T or N
VARIANT             30
                    note = L or V or Y or Leu-13C6,15N
VARIANT             31
                    note = P or E
VARIANT             32
                    note = A or D or G or K or E or Acetylated Lysine, Q or R
VARIANT             33
                    note = L or E or I or Q or D or Leu-13C6,15N
VARIANT             36
                    note = E or K or Q or A
VARIANT             39
                    note = L or R or Leu-13C6,15N
VARIANT             40
                    note = D or K or E or Q
VARIANT             41
                    note = N or K or Acetylated Lysine or Q
VARIANT             42
                    note = L or Leu-13C6,15N
VARIANT             45
                    note = S or deleted
SEQUENCE: 246
CXXXXXXFXX XXXXXXXXIC XYIXXXFXXX XXXCIXEIXX XXGCX                        45

SEQ ID NO: 247       moltype = AA  length = 7
FEATURE              Location/Qualifiers
source               1..7
                     mol_type = protein
                     organism = synthetic construct
SITE                 5
                     note = Citrulline
SEQUENCE: 247
TALAXLR                                                                   7

SEQ ID NO: 248       moltype = AA  length = 45
```

```
FEATURE             Location/Qualifiers
source              1..45
                    mol_type = protein
                    organism = synthetic construct
SITE                11
                    note = Leu-13C6,15N
SITE                14
                    note = Leu-13C6,15N
SITE                26
                    note = Trimethyllysine
SITE                30
                    note = Leu-13C6,15N
SITE                33
                    note = Leu-13C6,15N
SITE                39
                    note = Leu-13C6,15N
SITE                42
                    note = Leu-13C6,15N
SEQUENCE: 248
CEYDEEFFTA LARLRGGDIC QYIQAKFQYL PALCIEEILD NLGCS                       45
```